United States Patent
Lanquar et al.

(10) Patent No.: US 12,241,109 B2
(45) Date of Patent: *Mar. 4, 2025

(54) HOST CELLS COMPRISING A RECOMBINANT CASEIN PROTEIN AND A RECOMBINANT KINASE PROTEIN

(71) Applicant: Nobell Foods, Inc., South San Francisco, CA (US)

(72) Inventors: Viviane Lanquar, San Carlos, CA (US); Magi El-Richani, San Francisco, CA (US); Leyla Hathwaik, South San Francisco, CA (US); Yaxin Wang, South San Francisco, CA (US)

(73) Assignee: Nobell Foods, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/886,925

(22) Filed: Sep. 16, 2024

(65) Prior Publication Data

US 2025/0011828 A1 Jan. 9, 2025

Related U.S. Application Data

(60) Division of application No. 18/463,864, filed on Sep. 8, 2023, now Pat. No. 12,139,737, which is a continuation of application No. 18/064,199, filed on Dec. 9, 2022, now Pat. No. 11,840,717, which is a continuation of application No. PCT/US2021/053002, filed on Sep. 30, 2021.

(60) Provisional application No. 63/240,621, filed on Sep. 3, 2021, provisional application No. 63/221,642, filed on Jul. 14, 2021, provisional application No. 63/189,547, filed on May 17, 2021, provisional application No. 63/174,244, filed on Apr. 13, 2021, provisional application No. 63/152,694, filed on Feb. 23, 2021, provisional application No. 63/138,089, filed on Jan. 15, 2021, provisional application No. 63/129,720, filed on Dec. 23, 2020, provisional application No. 63/121,468, filed on Dec. 4, 2020, provisional application No. 63/116,528, filed on Nov. 20, 2020, provisional application No. 63/085,899, filed on Sep. 30, 2020.

(51) Int. Cl.
*C12P 21/06* (2006.01)
*A23C 20/00* (2006.01)
*A23J 3/10* (2006.01)
*C07K 14/47* (2006.01)
*C12N 9/64* (2006.01)

(52) U.S. Cl.
CPC ............. *C12P 21/06* (2013.01); *A23C 20/00* (2013.01); *A23J 3/10* (2013.01); *C07K 14/4732* (2013.01); *C12N 9/6424* (2013.01); *C12N 9/6483* (2013.01); *C12Y 304/21009* (2013.01); *C07K 2319/00* (2013.01)

(58) Field of Classification Search
CPC ........................................................ A23J 3/10
See application file for complete search history.

(56) References Cited

U.S. PATENT DOCUMENTS

| | | |
|---|---|---|
| 4,518,616 A | 5/1985 | Czulak |
| 5,068,118 A | 11/1991 | Strandholm |
| 5,650,554 A | 7/1997 | Moloney |
| 5,741,957 A | 4/1998 | Deboer et al. |
| 5,767,366 A | 6/1998 | Sathasivan et al. |
| 5,891,433 A | 4/1999 | Silver |
| 5,959,171 A | 9/1999 | Hyttinen et al. |
| 5,968,830 A | 10/1999 | Dan et al. |
| 6,100,447 A | 8/2000 | Wu et al. |
| 6,127,145 A | 10/2000 | Sutliff et al. |
| 6,222,094 B1 | 4/2001 | Hansson et al. |
| 6,225,105 B1 | 5/2001 | Sathasivan et al. |
| 6,245,974 B1 | 6/2001 | Michalowski et al. |
| 6,388,066 B1 | 5/2002 | Bruce et al. |
| 6,455,759 B1 | 9/2002 | Vierstra et al. |
| 6,569,831 B1 | 5/2003 | Legrand et al. |
| 6,632,468 B2 | 10/2003 | Morgan et al. |
| 6,642,437 B1 | 11/2003 | Lemaux et al. |
| 6,781,044 B2 | 8/2004 | Rodriguez et al. |
| 6,991,824 B2 | 1/2006 | Huang et al. |
| 7,138,150 B2 | 11/2006 | Huang et al. |
| 7,157,629 B2 | 1/2007 | Cho et al. |
| 7,217,858 B2 | 5/2007 | Falco et al. |
| 7,270,989 B2 | 9/2007 | Kappeler et al. |

(Continued)

FOREIGN PATENT DOCUMENTS

| | | |
|---|---|---|
| CN | 106591404 A | 4/2017 |
| EP | 3202899 A1 | 8/2017 |

(Continued)

OTHER PUBLICATIONS

U.S. Appl. No. 15/947,596, filed Apr. 6, 2018.

(Continued)

*Primary Examiner* — Suzanne M Noakes

(74) *Attorney, Agent, or Firm* — COOLEY LLP

(57) ABSTRACT

Provided herein are compositions and methods for producing milk proteins, which allow for safe, sustainable and humane production of milk proteins for commercial use, such as use in food compositions. The disclosure provides recombinant fusion proteins comprising at least first protein and a second protein, wherein at least one of the first protein and the second protein is a milk protein, or fragment thereof. The disclosure also provides methods for producing the recombinant fusions proteins, and food compositions comprising the same.

30 Claims, 30 Drawing Sheets

Specification includes a Sequence Listing.

(56) References Cited

U.S. PATENT DOCUMENTS

| | | |
|---|---|---|
| 7,304,208 B2 | 12/2007 | Huang et al. |
| 7,354,902 B2 | 4/2008 | Legrand et al. |
| 7,365,240 B2 | 4/2008 | Verbsky et al. |
| 7,390,936 B1 | 6/2008 | Van Rooijen et al. |
| 7,417,178 B2 | 8/2008 | Huang et al. |
| 7,428,875 B2 | 9/2008 | Orvar |
| 7,501,265 B1 | 3/2009 | Moloney et al. |
| 7,531,325 B2 | 5/2009 | Van Rooijen et al. |
| 7,575,898 B2 | 8/2009 | Ludevid et al. |
| 7,589,252 B2 | 9/2009 | Huang et al. |
| 7,718,851 B2 | 5/2010 | Huang et al. |
| 7,854,952 B2 | 12/2010 | Carr et al. |
| 7,960,614 B2 | 6/2011 | Chang et al. |
| 8,017,400 B2 | 9/2011 | Toriyama et al. |
| 8,158,857 B2 | 4/2012 | Huang et al. |
| 8,163,880 B2 | 4/2012 | Heifetz et al. |
| 8,273,954 B1 | 9/2012 | Rogers et al. |
| 8,293,533 B2 | 10/2012 | Falco et al. |
| 8,334,139 B1 | 12/2012 | Fraley et al. |
| 8,334,254 B2 | 12/2012 | Legrand et al. |
| 8,362,317 B2 | 1/2013 | Calabotta et al. |
| 8,609,416 B2 | 12/2013 | Barnett |
| 8,637,316 B2 | 1/2014 | Migiwa et al. |
| 8,686,225 B2 | 4/2014 | Huang et al. |
| 8,802,825 B2 | 8/2014 | Gica et al. |
| 8,809,630 B2 | 8/2014 | Kumimoto et al. |
| 8,822,181 B2 | 9/2014 | Torrent et al. |
| 8,927,809 B2 | 1/2015 | Meyer et al. |
| 9,006,513 B2 | 4/2015 | Calabotta et al. |
| 9,011,949 B2 | 4/2015 | Brown et al. |
| 9,024,114 B2 | 5/2015 | Carlson et al. |
| 9,321,828 B2 | 4/2016 | Zhang et al. |
| 9,555,097 B2 | 1/2017 | Rybicki et al. |
| 9,637,751 B2 | 5/2017 | Gica et al. |
| 9,650,640 B2 | 5/2017 | Kumar et al. |
| 9,700,067 B2 | 7/2017 | Fraser et al. |
| 9,700,071 B2 | 7/2017 | Silver et al. |
| 9,725,731 B2 | 8/2017 | Abbitt |
| 9,737,875 B2 | 8/2017 | Brown et al. |
| 9,738,694 B2 | 8/2017 | Yeo et al. |
| 9,790,512 B2 | 10/2017 | Calabotta et al. |
| 9,808,029 B2 | 11/2017 | Fraser et al. |
| 9,826,772 B2 | 11/2017 | Fraser et al. |
| 9,833,768 B2 | 12/2017 | Brown et al. |
| 9,924,728 B2 | 3/2018 | Pandya et al. |
| 9,938,327 B2 | 4/2018 | Shankar et al. |
| 9,943,096 B2 | 4/2018 | Fraser et al. |
| 10,039,306 B2 | 8/2018 | Vrljic et al. |
| 10,087,434 B2 | 10/2018 | Kale et al. |
| 10,093,913 B2 | 10/2018 | Kale et al. |
| 10,106,806 B2 | 10/2018 | Ko et al. |
| 10,125,373 B2 | 11/2018 | Mason et al. |
| 10,172,380 B2 | 1/2019 | Varadan et al. |
| 10,172,381 B2 | 1/2019 | Vrljic et al. |
| 10,273,492 B2 | 4/2019 | Shankar et al. |
| 10,287,568 B2 | 5/2019 | Kale et al. |
| 10,294,485 B2 | 5/2019 | Gupta et al. |
| 10,314,325 B2 | 6/2019 | Fraser et al. |
| 10,327,464 B2 | 6/2019 | Fraser et al. |
| 10,595,545 B2 | 3/2020 | Pandya et al. |
| 10,618,951 B1 | 4/2020 | Pettit et al. |
| 10,689,656 B2 | 6/2020 | Shankar et al. |
| 10,757,955 B2 | 9/2020 | Yang et al. |
| 10,759,758 B2 | 9/2020 | Thaler et al. |
| 10,760,062 B2 | 9/2020 | Naesby et al. |
| 10,765,116 B2 | 9/2020 | Kausch-Busies et al. |
| 10,765,125 B2 | 9/2020 | Gunes et al. |
| 10,765,318 B2 | 9/2020 | Hockings |
| 10,768,169 B2 | 9/2020 | Rezzi et al. |
| 10,772,332 B2 | 9/2020 | Mosrin et al. |
| 10,781,263 B2 | 9/2020 | Kahnert et al. |
| 10,781,427 B2 | 9/2020 | Barouch et al. |
| 10,781,432 B1 | 9/2020 | Cameron et al. |
| 10,785,976 B2 | 9/2020 | Vandock et al. |
| 10,785,977 B2 | 9/2020 | Vandock et al. |
| 10,793,850 B2 | 10/2020 | Wiessenhaan et al. |
| 10,793,872 B2 | 10/2020 | Poree et al. |
| 10,798,958 B2 | 10/2020 | Varadan et al. |
| 10,798,963 B2 | 10/2020 | Maynard et al. |
| 10,801,045 B2 | 10/2020 | Fischer et al. |
| 10,806,170 B2 | 10/2020 | Braun |
| 10,806,699 B2 | 10/2020 | Burbidge et al. |
| 10,807,968 B2 | 10/2020 | Jansen et al. |
| 10,815,500 B2 | 10/2020 | Juillerat et al. |
| 10,815,514 B2 | 10/2020 | Olsson et al. |
| 10,863,761 B2 | 12/2020 | Brown et al. |
| 10,870,861 B2 | 12/2020 | Noda et al. |
| 10,894,812 B1 | 1/2021 | Lanquar et al. |
| 10,947,552 B1 | 3/2021 | Lanquar et al. |
| 10,981,974 B2 | 4/2021 | Pettit et al. |
| 10,986,848 B2 | 4/2021 | Holz-Schietinger et al. |
| 10,988,521 B1 | 4/2021 | Lanquar et al. |
| 10,993,462 B2 | 5/2021 | Vrljic et al. |
| 11,013,250 B2 | 5/2021 | Vrljic et al. |
| 11,034,743 B1 | 6/2021 | Lanquar et al. |
| 11,051,532 B2 | 7/2021 | Henderson, Jr. et al. |
| 11,072,797 B1 | 7/2021 | Lanquar et al. |
| 11,076,615 B2 | 8/2021 | Pandya et al. |
| 11,142,555 B1 | 10/2021 | Lanquar et al. |
| 11,160,299 B2 | 11/2021 | Mahadevan et al. |
| 11,219,232 B2 | 1/2022 | Fraser et al. |
| 11,224,241 B2 | 1/2022 | Fraser et al. |
| 11,326,176 B2 | 5/2022 | Tobin |
| 11,401,526 B2 | 8/2022 | Lanquar et al. |
| 11,457,649 B2 | 10/2022 | Pandya et al. |
| 11,492,389 B1 | 11/2022 | Pettit et al. |
| 11,518,797 B2 | 12/2022 | Anchel |
| 11,685,928 B2 | 6/2023 | Lanquar et al. |
| 11,718,856 B2 | 8/2023 | Tobin |
| 11,771,104 B2 | 10/2023 | Geistlinger et al. |
| 11,771,105 B2 | 10/2023 | Radman |
| 11,800,887 B2 | 10/2023 | Mahadevan et al. |
| 11,840,717 B2 | 12/2023 | Lanquar et al. |
| 11,952,606 B2 | 4/2024 | Lanquar et al. |
| 12,077,798 B2 | 9/2024 | Lanquar et al. |
| 2002/0002714 A1 | 1/2002 | Ikegami et al. |
| 2002/0073448 A1 | 6/2002 | Michalowski et al. |
| 2002/0108149 A1 | 8/2002 | Gruis et al. |
| 2002/0155998 A1 | 10/2002 | Young et al. |
| 2002/0192813 A1 | 12/2002 | Conner et al. |
| 2003/0044503 A1 | 3/2003 | Morgan et al. |
| 2003/0056244 A1 | 3/2003 | Huang et al. |
| 2003/0074700 A1 | 4/2003 | Huang et al. |
| 2003/0166162 A1 | 9/2003 | Van Rooijen et al. |
| 2003/0172403 A1 | 9/2003 | Huang et al. |
| 2003/0221223 A1 | 11/2003 | Huang et al. |
| 2003/0229925 A1 | 12/2003 | Legrand et al. |
| 2004/0022918 A1 | 2/2004 | McCarthy et al. |
| 2004/0023257 A1 | 2/2004 | Barton et al. |
| 2004/0063617 A1 | 4/2004 | Huang et al. |
| 2004/0078851 A1 | 4/2004 | Huang et al. |
| 2004/0088754 A1 | 5/2004 | Cho et al. |
| 2004/0111766 A1 | 6/2004 | Huang et al. |
| 2004/0143857 A1 | 7/2004 | Young et al. |
| 2004/0241791 A1 | 12/2004 | Edens et al. |
| 2005/0158832 A1 | 7/2005 | Young et al. |
| 2005/0181482 A1 | 8/2005 | Meade et al. |
| 2005/0229273 A1 | 10/2005 | Huang et al. |
| 2005/0283854 A1 | 12/2005 | Krumm et al. |
| 2007/0150976 A1 | 6/2007 | Yang et al. |
| 2008/0010697 A1 | 1/2008 | Yang et al. |
| 2008/0029003 A1 | 2/2008 | Orvar |
| 2008/0050503 A1 | 2/2008 | Huang et al. |
| 2008/0092252 A1 | 4/2008 | Cammue et al. |
| 2008/0313776 A1 | 12/2008 | Li |
| 2008/0318277 A1 | 12/2008 | Huang et al. |
| 2009/0023212 A1 | 1/2009 | Zhong et al. |
| 2009/0133159 A1 | 5/2009 | Li |
| 2009/0156486 A1 | 6/2009 | Huang et al. |
| 2009/0258004 A1 | 10/2009 | Huang et al. |
| 2010/0003235 A1 | 1/2010 | Hagie et al. |
| 2010/0015713 A1 | 1/2010 | Deeter et al. |
| 2010/0031394 A1 | 2/2010 | Huang et al. |
| 2010/0064383 A1 | 3/2010 | Bogs et al. |

(56) References Cited

U.S. PATENT DOCUMENTS

| | | |
|---|---|---|
| 2010/0119691 A1 | 5/2010 | Huang et al. |
| 2010/0183589 A1 | 7/2010 | Huang et al. |
| 2010/0223682 A1 | 9/2010 | Katz et al. |
| 2010/0329995 A1 | 12/2010 | Deeter et al. |
| 2011/0092411 A1 | 4/2011 | Legrand et al. |
| 2011/0117131 A1 | 5/2011 | Huang et al. |
| 2011/0189751 A1 | 8/2011 | Barnett |
| 2011/0243975 A1 | 10/2011 | Terakawa et al. |
| 2011/0293813 A1 | 12/2011 | Cavallini et al. |
| 2011/0302672 A1 | 12/2011 | Merlo et al. |
| 2012/0088729 A1 | 4/2012 | Zhang et al. |
| 2012/0195883 A1 | 8/2012 | Huang et al. |
| 2012/0208198 A1 | 8/2012 | Bogs et al. |
| 2012/0315697 A1 | 12/2012 | Pettit et al. |
| 2013/0129899 A1 | 5/2013 | Ummadi et al. |
| 2013/0157356 A1 | 6/2013 | Barnett et al. |
| 2013/0243932 A1 | 9/2013 | Brackenridge et al. |
| 2013/0340114 A1 | 12/2013 | Albert et al. |
| 2014/0161958 A1 | 6/2014 | Brackenridge et al. |
| 2014/0237688 A1 | 8/2014 | Chang et al. |
| 2015/0080296 A1 | 3/2015 | Silver et al. |
| 2015/0087532 A1 | 3/2015 | Brown et al. |
| 2015/0150822 A1 | 6/2015 | Perumal et al. |
| 2015/0197764 A1 | 7/2015 | Aasen et al. |
| 2015/0203530 A1 | 7/2015 | Yang et al. |
| 2015/0289541 A1 | 10/2015 | Brown et al. |
| 2015/0299726 A1 | 10/2015 | McElver et al. |
| 2015/0305361 A1 | 10/2015 | Holz-Schietinger et al. |
| 2015/0305390 A1 | 10/2015 | Vrljic et al. |
| 2015/0351435 A1 | 12/2015 | Fraser et al. |
| 2015/0361446 A1 | 12/2015 | Beatty et al. |
| 2015/0361447 A1 | 12/2015 | Beatty et al. |
| 2015/0366233 A1 | 12/2015 | Brown et al. |
| 2016/0076048 A1 | 3/2016 | Zhang et al. |
| 2016/0160232 A1 | 6/2016 | Ruiter |
| 2016/0213766 A1 | 7/2016 | Huang et al. |
| 2016/0220622 A1 | 8/2016 | Park et al. |
| 2016/0222054 A1 | 8/2016 | Brown et al. |
| 2016/0298129 A1 | 10/2016 | Ruiter |
| 2016/0340411 A1 | 11/2016 | Fraser et al. |
| 2016/0369291 A1 | 12/2016 | Mayfield et al. |
| 2017/0081676 A1 | 3/2017 | Gupta et al. |
| 2017/0112175 A1 | 4/2017 | Fraser et al. |
| 2017/0164632 A1 | 6/2017 | Pandya et al. |
| 2017/0172169 A1 | 6/2017 | Grzanich et al. |
| 2017/0188612 A1 | 7/2017 | Varadan et al. |
| 2017/0273328 A1 | 9/2017 | Pandya et al. |
| 2017/0290363 A1 | 10/2017 | Fraser et al. |
| 2017/0295833 A1 | 10/2017 | Fraser et al. |
| 2017/0298337 A1 | 10/2017 | Kale et al. |
| 2017/0320041 A1 | 11/2017 | Brown et al. |
| 2017/0321203 A1 | 11/2017 | Kale et al. |
| 2017/0321204 A1 | 11/2017 | Kale et al. |
| 2017/0342131 A1 | 11/2017 | Fraser et al. |
| 2017/0342132 A1 | 11/2017 | Fraser et al. |
| 2017/0349637 A1 | 12/2017 | Shankar et al. |
| 2017/0349906 A1 | 12/2017 | Shankar et al. |
| 2018/0027851 A1 | 2/2018 | Vrljic et al. |
| 2018/0127764 A1 | 5/2018 | Shankar et al. |
| 2018/0142248 A1 | 5/2018 | Martin-Ortigosa et al. |
| 2018/0168209 A1 | 6/2018 | Fraser et al. |
| 2018/0192680 A1 | 7/2018 | Fraser et al. |
| 2018/0195081 A1 | 7/2018 | Shintaku et al. |
| 2018/0199605 A1 | 7/2018 | Fraser et al. |
| 2018/0199606 A1 | 7/2018 | Fraser et al. |
| 2018/0237793 A1 | 8/2018 | Aasen et al. |
| 2018/0243408 A1 | 8/2018 | Fanger et al. |
| 2018/0250369 A1 | 9/2018 | Macmanus et al. |
| 2018/0271111 A1 | 9/2018 | Pandya et al. |
| 2018/0291392 A1 | 10/2018 | El-Richani et al. |
| 2018/0371469 A1 | 12/2018 | Shankar et al. |
| 2019/0008192 A1 | 1/2019 | Brown et al. |
| 2019/0032066 A1 | 1/2019 | Noda et al. |
| 2019/0040404 A1 | 2/2019 | Gupta et al. |
| 2019/0048330 A1 | 2/2019 | Aharoni et al. |
| 2019/0062766 A1 | 2/2019 | Hamada et al. |
| 2019/0070287 A1 | 3/2019 | Fanger et al. |
| 2019/0116855 A1 | 4/2019 | Vrljic et al. |
| 2019/0133162 A1 | 5/2019 | Varadan et al. |
| 2019/0133163 A1 | 5/2019 | Varadan et al. |
| 2019/0200658 A1 | 7/2019 | Vrljic et al. |
| 2019/0203214 A1 | 7/2019 | Sorokin et al. |
| 2019/0216106 A1 | 7/2019 | Geistlinger et al. |
| 2019/0292217 A1 | 9/2019 | Davis et al. |
| 2019/0292555 A1 | 9/2019 | Davis et al. |
| 2019/0336595 A1 | 11/2019 | Ciaramella |
| 2019/0336596 A1 | 11/2019 | Mason et al. |
| 2020/0123556 A1 | 4/2020 | El-Richani et al. |
| 2020/0138066 A1 | 5/2020 | Anchel |
| 2020/0172584 A1 | 6/2020 | Fishman et al. |
| 2020/0247871 A1 | 8/2020 | Pettit et al. |
| 2020/0268026 A1 | 8/2020 | Khare et al. |
| 2020/0268027 A1 | 8/2020 | Gaspard et al. |
| 2020/0269161 A1 | 8/2020 | Kompala |
| 2020/0275660 A1 | 9/2020 | Sudau et al. |
| 2020/0275674 A1 | 9/2020 | Napolitano et al. |
| 2020/0277202 A1 | 9/2020 | Patey |
| 2020/0277588 A1 | 9/2020 | Cameron et al. |
| 2020/0277631 A1 | 9/2020 | Doudna et al. |
| 2020/0281224 A1 | 9/2020 | Kizer et al. |
| 2020/0282341 A1 | 9/2020 | Kompala |
| 2020/0288710 A1 | 9/2020 | Füßlein |
| 2020/0291043 A1 | 9/2020 | Hager et al. |
| 2020/0291060 A1 | 9/2020 | Singh et al. |
| 2020/0291370 A1 | 9/2020 | Chavez |
| 2020/0291408 A1 | 9/2020 | Jessen et al. |
| 2020/0291442 A1 | 9/2020 | Douchin et al. |
| 2020/0296960 A1 | 9/2020 | Curtis et al. |
| 2020/0296981 A1 | 9/2020 | Barnes et al. |
| 2020/0299412 A1 | 9/2020 | Liu et al. |
| 2020/0305481 A1 | 10/2020 | Carlson et al. |
| 2020/0308597 A1 | 10/2020 | Gray |
| 2020/0308599 A1 | 10/2020 | Church et al. |
| 2020/0308613 A1 | 10/2020 | Louie et al. |
| 2020/0308617 A1 | 10/2020 | Mikkelsen et al. |
| 2020/0315212 A1 | 10/2020 | Watson et al. |
| 2020/0315236 A1 | 10/2020 | Thakkar et al. |
| 2020/0316094 A1 | 10/2020 | Horcajada et al. |
| 2020/0318088 A1 | 10/2020 | Donohoue et al. |
| 2020/0318090 A1 | 10/2020 | Donovan et al. |
| 2020/0318108 A1 | 10/2020 | Allocca et al. |
| 2020/0323227 A1 | 10/2020 | Capronnier et al. |
| 2020/0323231 A1 | 10/2020 | Schelle et al. |
| 2020/0323237 A1 | 10/2020 | Pibarot et al. |
| 2020/0323904 A1 | 10/2020 | Sands et al. |
| 2020/0325462 A1 | 10/2020 | Brouns et al. |
| 2020/0325517 A1 | 10/2020 | Houghton-Larsen et al. |
| 2020/0329685 A1 | 10/2020 | Qimron et al. |
| 2020/0329726 A1 | 10/2020 | Waksman et al. |
| 2020/0329735 A1 | 10/2020 | Cully et al. |
| 2020/0329751 A1 | 10/2020 | Thakkar et al. |
| 2020/0330378 A1 | 10/2020 | Friedman |
| 2020/0331988 A9 | 10/2020 | Manceur et al. |
| 2020/0332248 A1 | 10/2020 | Zhou et al. |
| 2020/0332267 A1 | 10/2020 | Hoyt et al. |
| 2020/0332276 A1 | 10/2020 | Buie et al. |
| 2020/0332286 A1 | 10/2020 | Gibson et al. |
| 2020/0332288 A1 | 10/2020 | Kantardzhieva et al. |
| 2020/0332293 A1 | 10/2020 | Thess |
| 2020/0332564 A1 | 10/2020 | Baum et al. |
| 2020/0337336 A1 | 10/2020 | Rouskey et al. |
| 2020/0340000 A1 | 10/2020 | Roy-Chaudhuri et al. |
| 2020/0397021 A1 | 12/2020 | Henderson, Jr. et al. |
| 2020/0407741 A1 | 12/2020 | Mason et al. |
| 2021/0010017 A1 | 1/2021 | El-Richani et al. |
| 2021/0030014 A1 | 2/2021 | Brown et al. |
| 2021/0037848 A1 | 2/2021 | Pandya et al. |
| 2021/0037849 A1 | 2/2021 | Pandya et al. |
| 2021/0037851 A1 | 2/2021 | Fraser et al. |
| 2021/0051976 A1 | 2/2021 | Fraser et al. |
| 2021/0051977 A1 | 2/2021 | Vrljic et al. |
| 2021/0070842 A1 | 3/2021 | Fraser et al. |
| 2021/0115456 A1 | 4/2021 | Mason et al. |
| 2021/0198693 A1 | 7/2021 | Mason et al. |

(56) References Cited

U.S. PATENT DOCUMENTS

| | | |
|---|---|---|
| 2021/0221870 A1 | 7/2021 | Pettit et al. |
| 2021/0222186 A1 | 7/2021 | El-Richani et al. |
| 2021/0227849 A1 | 7/2021 | Kiayei et al. |
| 2021/0235714 A1 | 8/2021 | Geistlinger et al. |
| 2021/0251251 A1 | 8/2021 | Holz-Schietinger et al. |
| 2021/0259290 A1 | 8/2021 | Ajami et al. |
| 2021/0289804 A1 | 9/2021 | Stiles et al. |
| 2021/0289824 A1 | 9/2021 | Brown et al. |
| 2021/0307358 A1 | 10/2021 | Henderson, Jr. et al. |
| 2021/0329941 A1 | 10/2021 | Geistlinger et al. |
| 2021/0386085 A1 | 12/2021 | Ray et al. |
| 2021/0386086 A1 | 12/2021 | Ray et al. |
| 2021/0388310 A1 | 12/2021 | Geistlinger et al. |
| 2022/0007667 A1 | 1/2022 | Ray et al. |
| 2022/0007668 A1 | 1/2022 | Ray et al. |
| 2022/0033788 A1 | 2/2022 | Geistlinger et al. |
| 2022/0061365 A1 | 3/2022 | Vrljic et al. |
| 2022/0071250 A1 | 3/2022 | Brown et al. |
| 2022/0087286 A1 | 3/2022 | Henderson, Jr. et al. |
| 2022/0095654 A1 | 3/2022 | Varadan et al. |
| 2022/0098259 A1 | 3/2022 | Lanquar et al. |
| 2022/0098608 A1 | 3/2022 | Lanquar et al. |
| 2022/0117258 A1 | 4/2022 | Pandya et al. |
| 2022/0117285 A1 | 4/2022 | Mahadevan et al. |
| 2022/0169690 A1 | 6/2022 | Lanquar et al. |
| 2022/0174972 A1 | 6/2022 | Gibson et al. |
| 2022/0192239 A1 | 6/2022 | Geistlinger et al. |
| 2022/0211061 A1 | 7/2022 | Geistlinger et al. |
| 2022/0290167 A1 | 9/2022 | Tobin et al. |
| 2022/0325292 A1 | 10/2022 | Tobin |
| 2022/0372504 A1 | 11/2022 | Lanquar et al. |
| 2022/0378058 A1 | 12/2022 | Ghandi et al. |
| 2023/0034320 A1 | 2/2023 | Aharoni et al. |
| 2023/0041191 A1 | 2/2023 | Fima |
| 2023/0086338 A1 | 3/2023 | Mahadevan et al. |
| 2023/0106635 A1 | 4/2023 | Bhatt et al. |
| 2023/0135484 A1 | 5/2023 | Anchel |
| 2023/0141532 A1 | 5/2023 | Gibson et al. |
| 2023/0146346 A1 | 5/2023 | Lanquar et al. |
| 2023/0151380 A1 | 5/2023 | Morimoto et al. |
| 2023/0189857 A1 | 6/2023 | Mahadevan et al. |
| 2023/0192811 A1 | 6/2023 | Zhong et al. |
| 2023/0203556 A1 | 6/2023 | Lanquar et al. |
| 2023/0212594 A1 | 7/2023 | Tobin |
| 2023/0227882 A1 | 7/2023 | Phan et al. |
| 2023/0265139 A1 | 8/2023 | Lanquar et al. |
| 2023/0329294 A1 | 10/2023 | Mahadevan et al. |
| 2024/0002824 A1 | 1/2024 | Hurst et al. |
| 2024/0035041 A1 | 2/2024 | El-Richani et al. |
| 2024/0043900 A1 | 2/2024 | Lanquar et al. |
| 2024/0102072 A1 | 3/2024 | Lanquar et al. |
| 2024/0177797 A1 | 5/2024 | Lanquar et al. |
| 2024/0251810 A1 | 8/2024 | El-Richani et al. |

FOREIGN PATENT DOCUMENTS

| | | |
|---|---|---|
| EP | 1957110 B1 | 9/2020 |
| EP | 3069123 B1 | 9/2020 |
| EP | 3702463 A1 | 9/2020 |
| EP | 3708565 A1 | 9/2020 |
| EP | 2597969 B1 | 10/2020 |
| EP | 3307091 B1 | 10/2020 |
| EP | 3409767 B1 | 10/2020 |
| EP | 3718418 A1 | 10/2020 |
| EP | 3721894 A1 | 10/2020 |
| EP | 3722322 A1 | 10/2020 |
| EP | 3722408 A1 | 10/2020 |
| EP | 3722431 A1 | 10/2020 |
| EP | 3725788 A1 | 10/2020 |
| EP | 4017287 A1 | 6/2022 |
| EP | 4027797 A2 | 7/2022 |
| EP | 4192850 A1 | 6/2023 |
| WO | WO-9844139 A1 | 10/1998 |
| WO | WO-9849326 A1 | 11/1998 |
| WO | WO-9907866 A1 | 2/1999 |
| WO | WO-9924592 A1 | 5/1999 |
| WO | WO-9966054 A2 | 12/1999 |
| WO | WO-0006757 A1 | 2/2000 |
| WO | WO-0011200 A2 | 3/2000 |
| WO | WO-0168822 A2 | 9/2001 |
| WO | WO-0183792 A2 | 11/2001 |
| WO | WO-02063975 A2 | 8/2002 |
| WO | WO-02064750 A2 | 8/2002 |
| WO | WO-02064814 A2 | 8/2002 |
| WO | WO-03064613 A2 | 8/2003 |
| WO | WO-2004069848 A2 | 8/2004 |
| WO | WO-2005017168 A1 | 2/2005 |
| WO | WO-2005055944 A9 | 7/2005 |
| WO | WO-2005079232 A2 | 9/2005 |
| WO | WO-2006016381 A2 | 2/2006 |
| WO | WO-2013138793 A2 | 9/2013 |
| WO | WO-2015038796 A2 | 3/2015 |
| WO | WO-2015042405 A1 | 3/2015 |
| WO | WO-2015127388 A1 | 8/2015 |
| WO | WO-2015153666 A1 | 10/2015 |
| WO | WO-2016029193 A1 | 2/2016 |
| WO | WO-2016054375 A1 | 4/2016 |
| WO | WO-2016099568 A1 | 6/2016 |
| WO | WO-2016131000 A2 | 8/2016 |
| WO | WO-2016142394 A1 | 9/2016 |
| WO | WO-2016183163 A1 | 11/2016 |
| WO | WO-2016195814 A1 | 12/2016 |
| WO | WO-2016197584 A1 | 12/2016 |
| WO | WO-2017025590 A1 | 2/2017 |
| WO | WO-2017040577 A1 | 3/2017 |
| WO | WO-2017139558 A1 | 8/2017 |
| WO | WO-2017180180 A2 | 10/2017 |
| WO | WO-2017219046 A1 | 12/2017 |
| WO | WO-2018042346 A2 | 3/2018 |
| WO | WO-2018043219 A1 | 3/2018 |
| WO | WO-2018081590 A1 | 5/2018 |
| WO | WO-2018081592 A2 | 5/2018 |
| WO | WO-2018187754 A1 | 10/2018 |
| WO | WO-2018220188 A1 | 12/2018 |
| WO | WO-2018220929 A1 | 12/2018 |
| WO | WO-2019081346 A1 | 5/2019 |
| WO | WO-2019081396 A1 | 5/2019 |
| WO | WO-2019081398 A1 | 5/2019 |
| WO | WO-2019081400 A1 | 5/2019 |
| WO | WO-2019083940 A1 | 5/2019 |
| WO | WO-2019086565 A1 | 5/2019 |
| WO | WO-2019089333 A1 | 5/2019 |
| WO | WO-2019089796 A1 | 5/2019 |
| WO | WO-2019089820 A1 | 5/2019 |
| WO | WO-2019090148 A2 | 5/2019 |
| WO | WO-2019092069 A2 | 5/2019 |
| WO | WO-2019092086 A1 | 5/2019 |
| WO | WO-2019092505 A1 | 5/2019 |
| WO | WO-2019093957 A1 | 5/2019 |
| WO | WO-2019101490 A1 | 5/2019 |
| WO | WO-2019101700 A1 | 5/2019 |
| WO | WO-2019102381 A1 | 5/2019 |
| WO | WO-2019104184 A1 | 5/2019 |
| WO | WO-2019105908 A1 | 6/2019 |
| WO | WO-2019105972 A1 | 6/2019 |
| WO | WO-2019106147 A1 | 6/2019 |
| WO | WO-2019110684 A1 | 6/2019 |
| WO | WO-2019113132 A1 | 6/2019 |
| WO | WO-2019115280 A1 | 6/2019 |
| WO | WO-2019115735 A1 | 6/2019 |
| WO | WO-2019116182 A1 | 6/2019 |
| WO | WO-2019116183 A1 | 6/2019 |
| WO | WO-2019116349 A1 | 6/2019 |
| WO | WO-2019118480 A1 | 6/2019 |
| WO | WO-2019118935 A1 | 6/2019 |
| WO | WO-2019118984 A2 | 6/2019 |
| WO | WO-2019121698 A1 | 6/2019 |
| WO | WO-2019121852 A1 | 6/2019 |
| WO | WO-2019121855 A1 | 6/2019 |
| WO | WO-2019121856 A1 | 6/2019 |
| WO | WO-2019122116 A1 | 6/2019 |
| WO | WO-2019122123 A1 | 6/2019 |
| WO | WO-2019122135 A1 | 6/2019 |
| WO | WO-2019122336 A1 | 6/2019 |

(56) References Cited

FOREIGN PATENT DOCUMENTS

| | | |
|---|---|---|
| WO | WO-2019122388 A1 | 6/2019 |
| WO | WO-2019123430 A1 | 6/2019 |
| WO | WO-2019125804 A1 | 6/2019 |
| WO | WO-2019126562 A1 | 6/2019 |
| WO | WO-2019144124 A1 | 7/2019 |
| WO | WO-2019169409 A1 | 9/2019 |
| WO | WO-2019170899 A1 | 9/2019 |
| WO | WO-2019213155 A1 | 11/2019 |
| WO | WO-2020061503 A1 | 3/2020 |
| WO | WO-2020081789 A1 | 4/2020 |
| WO | WO-2020089383 A1 | 5/2020 |
| WO | WO-2020089384 A1 | 5/2020 |
| WO | WO-2020089385 A1 | 5/2020 |
| WO | WO-2020089444 A1 | 5/2020 |
| WO | WO-2020089445 A1 | 5/2020 |
| WO | WO-2020117927 A1 | 6/2020 |
| WO | WO-2019161141 A9 | 8/2020 |
| WO | WO-2020160187 A2 | 8/2020 |
| WO | WO-2020168368 A1 | 8/2020 |
| WO | WO-2020169389 A1 | 8/2020 |
| WO | WO-2020169577 A1 | 8/2020 |
| WO | WO-2020172143 A1 | 8/2020 |
| WO | WO-2020126610 A9 | 9/2020 |
| WO | WO-2020173860 A1 | 9/2020 |
| WO | WO-2020173861 A1 | 9/2020 |
| WO | WO-2020174070 A1 | 9/2020 |
| WO | WO-2020176224 A1 | 9/2020 |
| WO | WO-2020176389 A1 | 9/2020 |
| WO | WO-2020176547 A1 | 9/2020 |
| WO | WO-2020178307 A1 | 9/2020 |
| WO | WO-2020180506 A1 | 9/2020 |
| WO | WO-2020181101 A1 | 9/2020 |
| WO | WO-2020181102 A1 | 9/2020 |
| WO | WO-2020182929 A1 | 9/2020 |
| WO | WO-2020183414 A2 | 9/2020 |
| WO | WO-2020183419 A1 | 9/2020 |
| WO | WO-2020185861 A1 | 9/2020 |
| WO | WO-2020186059 A2 | 9/2020 |
| WO | WO-2020190993 A1 | 9/2020 |
| WO | WO-2020190998 A1 | 9/2020 |
| WO | WO-2020191293 A1 | 9/2020 |
| WO | WO-2020191369 A1 | 9/2020 |
| WO | WO-2020193291 A1 | 10/2020 |
| WO | WO-2020193385 A1 | 10/2020 |
| WO | WO-2020193493 A1 | 10/2020 |
| WO | WO-2020193495 A1 | 10/2020 |
| WO | WO-2020202157 A1 | 10/2020 |
| WO | WO-2020206385 A1 | 10/2020 |
| WO | WO-2020208104 A1 | 10/2020 |
| WO | WO-2020208190 A1 | 10/2020 |
| WO | WO-2020208548 A1 | 10/2020 |
| WO | WO-2020209959 A1 | 10/2020 |
| WO | WO-2020210122 A1 | 10/2020 |
| WO | WO-2020210160 A2 | 10/2020 |
| WO | WO-2020210508 A1 | 10/2020 |
| WO | WO-2020210810 A1 | 10/2020 |
| WO | WO-2020212145 A1 | 10/2020 |
| WO | WO-2020212235 A1 | 10/2020 |
| WO | WO-2020212798 A1 | 10/2020 |
| WO | WO-2020214542 A1 | 10/2020 |
| WO | WO-2020214940 A1 | 10/2020 |
| WO | WO-2020215017 A1 | 10/2020 |
| WO | WO-2020219595 A1 | 10/2020 |
| WO | WO-2020219596 A1 | 10/2020 |
| WO | WO-2020219972 A1 | 10/2020 |
| WO | WO-2020223700 A1 | 11/2020 |
| WO | WO-2021007565 A1 | 1/2021 |
| WO | WO-2021034980 A1 | 2/2021 |
| WO | WO-2021050759 A2 | 3/2021 |
| WO | WO-2021101647 A1 | 5/2021 |
| WO | WO-2021130758 A1 | 7/2021 |
| WO | WO-2021154806 A1 | 8/2021 |
| WO | WO-2021168343 A2 | 8/2021 |
| WO | WO-2021174226 A1 | 9/2021 |
| WO | WO-2021191914 A1 | 9/2021 |
| WO | WO-2022031941 A1 | 2/2022 |
| WO | WO-2022055513 A1 | 3/2022 |
| WO | WO-2022072718 A1 | 4/2022 |
| WO | WO-2022072833 A2 | 4/2022 |
| WO | WO-2022072846 A2 | 4/2022 |
| WO | WO-2022076615 A1 | 4/2022 |
| WO | WO-2022098835 A1 | 5/2022 |
| WO | WO-2022098853 A1 | 5/2022 |
| WO | WO-2022104227 A1 | 5/2022 |
| WO | WO-2022117916 A1 | 6/2022 |
| WO | WO-2022182799 A1 | 9/2022 |
| WO | WO-2022190045 A1 | 9/2022 |
| WO | WO-2022251263 A1 | 12/2022 |
| WO | WO-2022251691 A2 | 12/2022 |
| WO | WO-2022269549 A2 | 12/2022 |
| WO | WO-2023023195 A1 | 2/2023 |
| WO | WO-2023037366 A1 | 3/2023 |
| WO | WO-2023044396 A1 | 3/2023 |
| WO | WO-2023092005 A1 | 5/2023 |
| WO | WO-2023119200 A1 | 6/2023 |
| WO | WO-2023122770 A1 | 6/2023 |
| WO | WO-2023133417 A2 | 7/2023 |
| WO | WO-2023141256 A2 | 7/2023 |
| WO | WO-2023166491 A1 | 9/2023 |
| WO | WO-2023172201 A1 | 9/2023 |
| WO | WO-2023192711 A1 | 10/2023 |
| WO | WO-2023197002 A2 | 10/2023 |
| WO | WO-2023197003 A2 | 10/2023 |
| WO | WO-2023201355 A2 | 10/2023 |
| WO | WO-2023212654 A2 | 11/2023 |
| WO | WO-2023220191 A1 | 11/2023 |
| WO | WO-2023220362 A2 | 11/2023 |
| WO | WO-2023242273 A1 | 12/2023 |
| WO | WO-2024006951 A2 | 1/2024 |
| WO | WO-2024013749 A1 | 1/2024 |
| WO | WO-2024015365 A1 | 1/2024 |
| WO | WO-2024020514 A1 | 1/2024 |
| WO | WO-2024020592 A1 | 1/2024 |
| WO | WO-2024038201 A1 | 2/2024 |
| WO | WO-2024038202 A1 | 2/2024 |
| WO | WO-2024038204 A1 | 2/2024 |
| WO | WO-2024038447 A1 | 2/2024 |
| WO | WO-2024040180 A1 | 2/2024 |

OTHER PUBLICATIONS

U.S. Appl. No. 16/423,654, filed May 28, 2019.
U.S. Appl. No. 16/862,011, filed Apr. 29, 2020.
U.S. Appl. No. 17/171,646, filed Feb. 9, 2021.
U.S. Appl. No. 18/066,604, filed Dec. 15, 2022.
U.S. Appl. No. 17/039,759, filed Sep. 30, 2020, U.S. Pat. No. 10,947,552, Mar. 16, 2021.
U.S. Appl. No. 17/039,760, filed Sep. 30, 2020, U.S. Pat. No. 10,894,812, Jan. 19, 2021.
U.S. Appl. No. 17/127,090, filed Dec. 18, 2020, U.S. Pat. No. 11,034,743, Jun. 15, 2021.
U.S. Appl. No. 17/127,418, filed Dec. 18, 2020, U.S. Pat. No. 10,988,521, Apr. 27, 2021.
U.S. Appl. No. 17/157,105, filed Jan. 25, 2021, U.S. Pat. No. 11,072,797, Jul. 27, 2021.
U.S. Appl. No. 17/326,785, filed May 21, 2021, U.S. Pat. No. 11,142,555, Oct. 12, 2021.
U.S. Appl. No. 17/374,125, filed Jul. 13, 2021 Aug. 2, 2022.
U.S. Appl. No. 17/493,100, filed Oct. 4, 2021.
U.S. Appl. No. 17/590,774, filed Feb. 1, 2022.
U.S. Appl. No. 17/851,624, filed Jun. 28, 2022, U.S. Pat. No. 11,685,928, Jun. 27, 2023.
U.S. Appl. No. 18/157,337, filed Jan. 20, 2023.
U.S. Appl. No. 17/183,117, filed Feb. 23, 2021.
U.S. Appl. No. 17/183,131, filed Feb. 23, 2021.
U.S. Appl. No. 18/064,199, filed Dec. 9, 2022, U.S. Pat. No. 11,840,717, Dec. 12, 2023.
U.S. Appl. No. 18/192,519, filed Mar. 29, 2023, U.S. Pat. No. 11,952,606, Apr. 9, 2024.
U.S. Appl. No. 18/463,864, filed Sep. 8, 2023.

(56) References Cited

OTHER PUBLICATIONS

U.S. Appl. No. 18/538,150, filed Dec. 13, 2023, U.S. Pat. No. 12,077,798, Sep. 3, 2024.
U.S. Appl. No. 18/779,458, filed Jul. 22, 2024.
U.S. Appl. No. 18/886,942, filed Sep. 16, 2024.
U.S. Appl. No. 18/519,995, filed Nov. 27, 2023.
U.S. Appl. No. 18/514,264, filed Nov. 20, 2023.
U.S. Appl. No. 18/598,187, filed Mar. 7, 2024.
Ahmed et al., "Interrelationship of milk acute-phase proteins and casein percentage in cows and buffaloes subclinical mastitis," Vet Res Forum Dec. 2021;12(4):409-414.
Altschul, S. F., et al., "Basic local alignment search tool", Journal of Molecular Biology (1990); 215(3): 403-410.
Altschul, S. F., et al., "Gapped BLAST and PSI-BLAST: a new generation of protein database search programs", Nucleic Acids Research (1997); 25(17): 3389-3402.
Alvarez et al., "Higher accumulation of F1-V fusion recombinant protein in plants after induction of protein body formation," Plant Mol Biol 72:75-89 (2010).
Author Unknown) Prevention, "Foods For Bone Health: Get Your Calcium Here," May 2012, Retrieved from the Internet: URL: https://www.prevention.com/health/a20446986/dietary-sources-of-calcium/ , 3 pages.
Batt, C. A. et al., "Expression of recombinant bovine beta-lactoglobulin in *Escherichia coli*", Agricultural and biological chemistry, 54(4): 949-955 (1990).
Bauman et al. "Major advances associated with the biosynthesis of milk." Journal of Dairy Science 89(4):1235-1243 (2006).
Benchabane et al., "Preventing Unintended Proteolysis in Plant Protein Biofactories," Plant Biotechnology Journal 6:633:648 (2008).
Berry D., "Acid Makes Milk Much More," Dairy Foods, Jan. 2007, Retrieved from the Internet: URL: https://www.dairyfoods.com/articles/82509-%20all-about-acid, 4 pages.
Bovine Fam20C Uni Prot F1 MXQ3. Retrieved from https://www.uniprot.org/uniprotkb/F1MXQ3/entry on Jun. 9, 2023, pp. 1-5.
Bradley and Vanderwarn, "Determination of moisture in cheese and cheese products," J. Aoac 84:570-592 (2001).
Breene, "Application of texture profile analysis to instrumental food texture evaluation," J. Texture Stud. 6:53-82 (1975).
Chavan et al. Cheese substitutes: an alternative to natural cheese—a review. (2007) Int. J. of Food Science, Technology & Nutrition ; vol. 2; pp. 25-39 (Year: 2007).
Chen et al., "Textural analysis of cheese," J. Dairy Sci. 62:901-907 (1979).
Chiera et al., "Isolation of two highly active soybean (*Glycine max* (L.) Merr.) promoters and their characterization using a new automated image collection and analysis system," Plant Cell Reports,26(9):1501-1509 (2007).
Chikpah et al. Potentials of Sodom apple (*Calotropis procera*) extract as a coagulant to substitute alum in soy cheese production Ghana. (2015) Elixir Food Science; vol. 79; pp. 30166-30170 (Year: 2015).
Chong et al., "Expression of full-length bioactive antimicrobial human lactoferrin in potato plants," Transgenic Res. 9(1):71-78 (2000).
Chong et al., "Expression of the human milk protein beta-casein in transgenic potato plants," Transgenic Res. 6(4):289-296 (1997).
Coleman et al., "The maize gamma-zein sequesters alpha-zein and stabilizes its accumulation in protein bodies of transgenic tobacco endosperm.," The Plant Cell, vol. 8, Issue 12, Dec. 1996, pp. 2335-2345,.
Cramer et al., "Transgenic Plants for Therapeutic Proteins: Linking Upstream and Downstream Strategies," J. Hammond et al.(eds.), Plant Biotechnology, pp. 95-118 (2000).
Creamer 1974; Beta casein degradation in Gouda and cheddar cheese. Journal of Dairy Science 58(3): 287-292.
De La Torre et al., "The intron and 5' distal region of the soybean Gmubi promoter contribute to very high levels of gene expression in transiently and stably transformed tissues," Plant Cell Reports 34:111-120 (2015).

Definition "Cheese" (2023) Free Dictionary Online; downloaded from https://www.thefreedictionary.com/cheese on Jan. 12, 2023, 1 page.
Definition "Gelate" (2023) Free Dictionary Online; downloaded from https://www.thefreedictionary.com/gelate on Jan. 12, 2023, 1 page.
Deiss et al., "Functional Domains within the a Sequence Involved in the Cleavage-Packaging of Herpes Simplex Virus DNA," Journal of Virology, Sep. 1986, vol. 59, No. 3, pp. 605-618.
Devereux et al. "A comprehensive set of sequence analysis programs for the VAX" Nucleic Acids Research 12(1):387-395 (Jan. 11, 1984).
Diamos et al. "Chimeric 3' flanking regions strongly enhance gene expression in plants," Plant Biotechnology Journal 16(12):1971-1982 (2018).
Drake et al., "Relationship between instrumental and sensory measurements of cheese texture," J. Texture Stud. 30:451-476 (1999).
Dunwell, "Transgenic Crops: The Next Generation, or an Example of 2020 Vision," Annals of Botany 84:269-277 (1999).
EMS-McClung et al., "Expression of Maize Gamma Zein C-Terminus in *Escherichia coli*," Protein Expression and Purification 13, pp. 1-8 (1998), Article No. PT980858.
Ferrer-Miralles et al., "Bacterial cell factories for recombinant protein production; expanding the catalogue," Microb Cell Fact. 12:113, pp. 1-4 (2013).
Fife et al., "Test for measuring the stretchability of melted cheese," J. Dairy Sci. 85(12):3539-3545 (2002).
Finer et al., "Transformation of soybean via particle bombardment of embryogenic suspension culture tissue," In Vitro Cell and Develop Biol—Plant 27P:175-182 (1991).
Galeaz. K, "Soy Cheese, Indiana Soybean Board," pp. 1-3, 1998.
Geli et al., "Two Structural Domains Mediate Two Sequential Events in [gamma]-Zein Targeting: Protein Endoplasmic Reticulum Retention and Protein Body Formation.," The Plant Cell, vol. 6, Issue 12, Dec. 1994, pp. 1911-192.
GenBank Accession No. CAA25231, dated Jan. 31, 2003, 1 page.
GenBank accession No. Glyma.02G012600: Retrieved Oct. 14, 2020, from http://soykb.org/gene_card.php?gene=Glyma.02G012600. 1, 4 pages.
GenBank accession No. J01263.1, dated Jun. 17, 1998, 3 pages.
GenBank accession No. L22576.1, dated Dec. 28, 2007, 2 pages.
GenBank Accession No. M15132.1, dated Apr. 26, 1993, 1 page.
GenBank accession No. X14712.1, dated Mar. 13, 1995, 2 pages.
GenBank accession No. X51514.1 dated Apr. 18, 2005, 2pages.
GenBank Accession No. X59836.1, dated Jul. 20, 1992, 2 pages.
GenBank accession No. Z50202.1, dated Aug. 21, 1998, 3 pages.
GenBank No. ABP64791, dated Jun. 5, 2012, 1 page.
Ghag et al., Heterologous protein production in plant systems, GM Crops & Food, DOI: 10.1080/21645698.2016.1244599, 49 pages (2016).
Greenberg et al., "Human beta-casein. Amino acid sequence and identification of phosphorylation sites," J. Biol. Chem. 259(8):5132-5138 (1984).
Herman, "Soybean seed proteome rebalancing," Frontiers in plant science, 5, 437, 8 pages (2014).
Hernandez-Garcia, "A soybean (*Glycine max*) polyubiquitin promoter gives strong constitutive expression in transgenic soybean," Plant cell reports,28(5):837-849 (2009).
Hernandez-Garcia et al., "High level transgenic expression of soybean (*Glycine max*) GmERF and Gmubi gene promoters isolated by a novel promoter analysis pipeline," BMC plant biology, 10(1), 237, 16 pages (2010).
Horvath et al., "The production of recombinant proteins in transgenic barley grains," Proc. Natl. Acad. Sci. USA, 97:1914-1919 (2000).
Hudson et al., "Optimizing Recombinant Protein Expression in Soybean," Soybean—Molecular Aspects of Breeding, 24 pages (2011).
Hussein et al. Chemical composition and sensory qualities of West African soft cheese (*Warankashi*) produced from blends of cow milk and soy milk. (2016) Nigerian Journal of Tropical Agriculture; vol. 16; pp. 79-89 (Year: 2016).

(56) References Cited

OTHER PUBLICATIONS

Imafidon et al., "Isolation, purification, and alteration of some functional groups of major milk proteins: a review," Crit. Rev. Food. Sci. Nutr. 37(7):663-689, (1997).

International Search Report and Written Opinion for International Application No. PCT/US2021/053002 dated Jan. 25, 2022, 18 pages.

International Search Report and Written Opinion for International Application No. PCT/US2022/030788 dated Oct. 5, 2022, 17 pages.

International Search Report and Written Opinion issued by The International Searching Authority for Application No. PCT/US2018/026572, dated Jul. 20, 2018, 20 pages.

International Search Report and Written Opinion issued by The International Searching Authority for Application No. PCT/US22/77440, dated Jan. 31, 2023, 18 pages.

Jana et al., "Functional properties of Mozzarella cheese for its end use application," J. Food Sci Technol 54(12):3776-3778 (2017).

Jimenez-Flores, et al. Cloning and Sequence Analysis of Bovine Beta-casein cDNA. (1987) Biochemical and Biophysical Research Communications; vol. 142; pp. 617-621.

Kaminski et al., "Polymorphism of bovine beta-casein and its potential effect on human health," Journal of applied genetics, 48(3), 189-198 (2007).

Kapoor et al., "Comparison of pilot scale and rapid visco analyzer process cheese manufacture," J. Dairy Sci. 87:2813-2821 (2004).

Kapoor et al., "Small-scale manufacture of process cheese using arapid visco analyzer," J. Dairy Sci. 88:3382-3391 (2005).

Karki. U, et al., "Cellular engineering of plant cells for improved therapeutic protein production", Plant Cell Reports, 2021, 40:1087-1099.

Karlin, S., et al.; "Applications and statistics for multiple high-scoring segments in molecular sequences," PNAS USA; 90(12):5873-5877 (1993).

K-Casein (2018) download from "wikipedia.org/w/index.php?title=K-Casein&oldid=845015288"; pp. 1-5 (Year: 2018).

Kim, et al., Genetic modification of the soybean to enhance the—carotene content through seed-specific expression. PLoS One, 7(10), e48287, 12 pages (2012).

Kinney, "Development of genetically engineered soybean oils for food applications. Journal of Food Lipids," 3(4), 273-292 (1996).

Klemaszewski, J. et al., "Formation and Coalescence Stability of Emulsions Stabilized by Different Milk Proteins," J. Food Sci., 57(2):366-371 (1992).

Klemaszewski, J. et al., "Stabilization of cultured dairy products and cheeses. Chapter in Hydrocolloids in Food Processing," Laaman, T. (ed.) Blackwell-Wiley, publisher. ISBN 9780813820767, 30 pages (2011).

Klemaszewski, J.L. and Kinsella, J.E., "Sulfitolysis of Whey Proteins: Effects on emulsion properties," J. Agric. Food Chem. 39:1033-1036 (1991).

Klemaszewski, J.L., Das, K.P., Kang, Y.J. and Kinsella, J.E., "Effects of controlled sulfitolysis of Bovine Serum Albumin on droplet size and surface area of emulsions," J. Agric. Food Chem.38(3):647-650 (1990).

Klemaszewski, J.L., Haque, Z., and Kinsella, J.E., "An Electronic Imaging System for Determining Droplet Size and Dynamic Breakdown of Protein Stabilized Emulsions," Journal of Food Science 54(2):440-445 (1989).

Kuhn et al., "The baculovirus expression vector pBSV-8His directs secretion of histidine-tagged proteins," Gene, 162 225-229 (1995).

Lee et al. Physiochemical and microbiological properties of yogurt-cheese manufactured with ultrafiltrated cow's milk and soy milk blends. (2015) Korean J. Food Sci. An.; vol. 35; pp. 205-210.

Li et al., Secretion of Active Recombinant Phytase from Soybean Cell-Suspension Cultures, Plant Physiol 114(3):1103-1111 (Jul. 1997).

Lin et al., "FAM20C directly binds to and phosphorylates Periostin," SciRep 10:17155, 11 pages (2020).

Loch, J. I. et al., "Engineered β-Lactoglobulin Produced in *E. coli*: Purification, Biophysical and Structural Characterisation", Molecular Biotechnology; 58:605-618 (2016).

Lohner et al., "A Milk-Curdling Activity," Science Buddies, 2017, 7 Pages.

Manninen, "Protein Hydrolysates in Sports Nutrition," Nutr Metab (Lond) 6:38, pp. 1-5 (2009).

Maughan et al., "Biolistic transformation, expression, and inheritance of bovine—casein in soybean (*Glycine max*)," In Vitro Cellular & Developmental Biology—Plant, 35(4):344-349 (1999).

Metzger et al., "RVA: Process cheese manufacture," Aust. J. Dairy Technol. 57:136 (2002).

Morison et al., "Viscosity and Non-Newtonian Behaviour of Concentrated Milk and Cream," International Journal of Food Properties 16(4):882-894 (2013).

Needleman, S. B., et al., "A general method applicable to the search for similarities in the amino acid sequence of two proteins", Journal of Molecular Biology (1970); 48(3): 443-453.

Nishizawa & Ishimoto, "Maturation of somatic embryos as a model for soybean seed development," Plant biotechnology, 26(5), 543-550 (2009).

Old Europe Cheese; A lactose intolerant's guide to cheese. (2022) downloaded from https://oldeuropecheese.com/blog/a-lactose-intolerants-guide-to-cheese/ on Jun. 1, 2022; pp. 1-6.

Pearson & Lipman, "Improved tools for biological sequence comparison," Proc. Natl. Acad. Sci. USA 85, 24442-448 (1988).

Philip, et al., "Processing and localization of bovine-casein expressed in transgenic soybean seeds under control of a soybean lectin expression cassette," Plant Science 161:323-335 (2001).

Pierce et al., "Ketocarotenoid production in soybean seeds through metabolic engineering," PloS one, 10(9), e0138196, 15 pages (2015).

Prow et al., "Melt analysis of process cheese spread or product using a rapid visco analyzer," J. Dairy Sci. 88:1277-1287 (2005).

Salmon et al., "Production of human lactoferrin in transgenic tobacco," Protein Expression and Purification 13:127-135 (1998).

Sanders.G.P., et al., "Curd tension of Milk and its Relationship to Firmness of Curd in Cheesemaking," Journal of Dairy Science; pp. 395-404, 1936.

Sathasivan et al., "Nucleotide sequence of a mutant acetolactate synthase gene from an imidazolinone-resistant *Arabidopsis thaliana* var. *Columbia*," Nucleic Acids Research 18(8):2188, 1 page (1990).

Tablibracci. V. S, et al., "A single kinase generates the majority of the secreted phosphoproteome", Cell, 2015, 161 (7): 1619-1632. doi:10.1016/j.cell.2015.05.028.

Tagliabracci et al., "Secreted Kinase Phosphorylates Extracellular Proteins that Regulate Biomineralization", ScienceXpress, http://www.sciencemag.org/content/early/recent May 10, 2012, DOI: 10.1126/science.1217817. 4 pages, 30 supplemental pages.

Takaiwa et al., "Compensatory rebalancing of rice prolamins by production of recombinant prolamin/bioactive peptide fusion proteins within ER-derived protein bodies," Plant Cell Rep 37:209-223 (2018).

Takase et al., "Expression of human alpha-lactalbumin in transgenic tobacco," Journal of Biochemistry (Tokyo) 123:440-444 (1998).

Thurmond et al. "Expression and Characterization of Phosphorylated Recombinant Human b-Casein in *Escherichia coli*," Protein Expression and Purification, 1997, vol. 10, pp. 202-208.

Torrent et al., "Lysine-rich modified γ-zeins accumulate in protein bodies of transiently transformed maize endosperms," Plant Molecular Biology 34:139-149 (1997).

Torrent et al., "Role of structural domains for maize γ-zein retention in Xenopus oocytes," Planta 192, 512-518 (1994).

Truong et al., "Influence of carbon to nitrogen ratios on soybean somatic embryo (cv. Jack) growth and composition," Journal of experimental botany, 64(10), 2985-2995 (2013).

Uniprot Accession No. P02662, dated Aug. 12, 2020, 5 pages.
Uniprot Accession No. P02663.2, dated Aug. 12, 2020, 3 pages.
Uniprot Accession No. P02666.2, dated Oct. 7, 2020, 6 pages.
Uniprot Accession No. P02668.1, dated Aug. 12, 2020, 6 pages.
Uniprot Accession No. P33049.1, dated Dec. 11, 2019, 3 pages.
UniprotKB/Swiss-Prot Ref. 5 No. P04706, created Aug. 13, 1987, updated Nov. 8, 2023, 3 pages.

(56) References Cited

OTHER PUBLICATIONS

Webpage for AB-BLAST Basic Local Alignment Search Tool, dated Jun. 2, 2020: Retrieved Oct. 12, 2020, at http://blast.wustl/edu/blast/README.html, 22 pages.

West 2017; 6 dairy foods that are naturally low in lactose. Healthline, on the world wide web at healthline.com/nutrition/ dairy-foods-low-in-lactose, pp. 1-14.

Wong et al., "Improved co-expression of multiple genes in vectors containing internal ribosome entry sites (IRESes) from human genes," Gene Therapy 9:337-344 (2002).

Wongkhalaung et al., Development of a Yogurt-type Product from Saccharified Rice. (2000) Kasetsart J.; vol. 34; pp. 107-116.

Worley et al., "Engineering in vivo Instability of Firefly Luciferase and *Escherichia coli*-Glucuronidase in Higher Plants Using Recognition Elements from the Ubiquitin Pathway," Plant Molecular Biology 37:337-347 (1998).

Xu et al., "High-Yields and Extended Serum Half-Life of Human Interferon a2b Expressed in Tobacco Cells as Arabinogalactan-Protein Fusions," Biotechnol Bioeng 97(5):997-1008 (Aug. 1, 2007).

Yang et al., "Comparative studies of the serum half-life extension of a protein via site-specific conjugation to a species-matched or -mismatched albumin," Biomaterials Science 6(8):2092-2100 (2018).

Yun et al. "Role of the Phosphoryl Group of B-Casein in Milk Curdling" Agricultural and Biological Chemistry 46(6):1505-1511 (1982).

Zhang et al., "Isolation and characterization of "GmScream" promoters that regulate highly expressing soybean (*Glycine max* Merr.) genes," Plant Science 241:189-198 (2015).

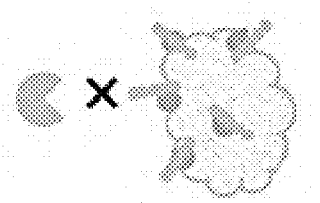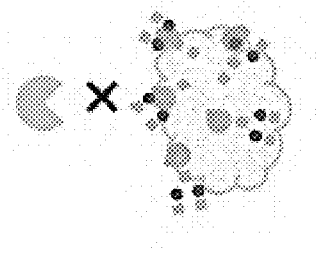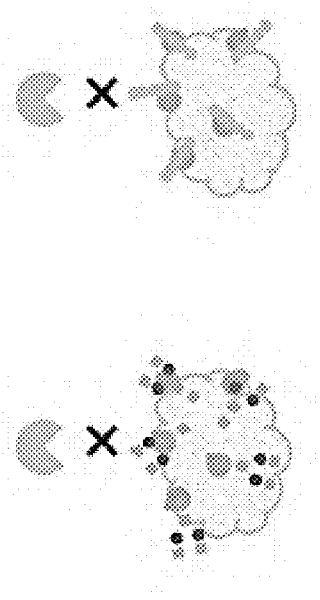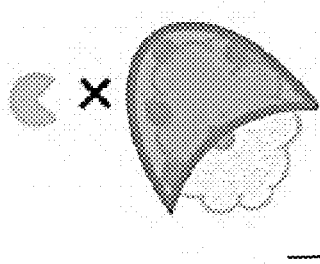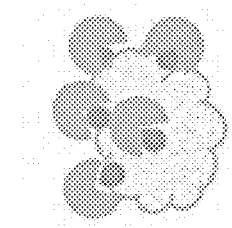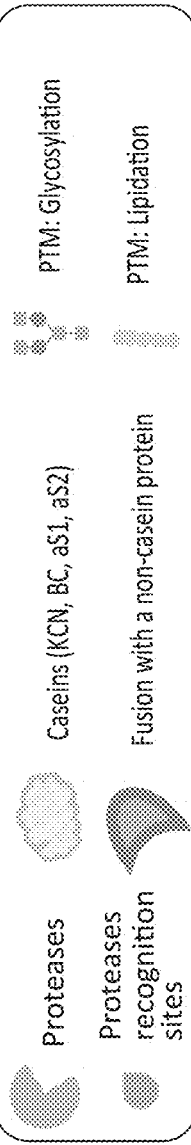

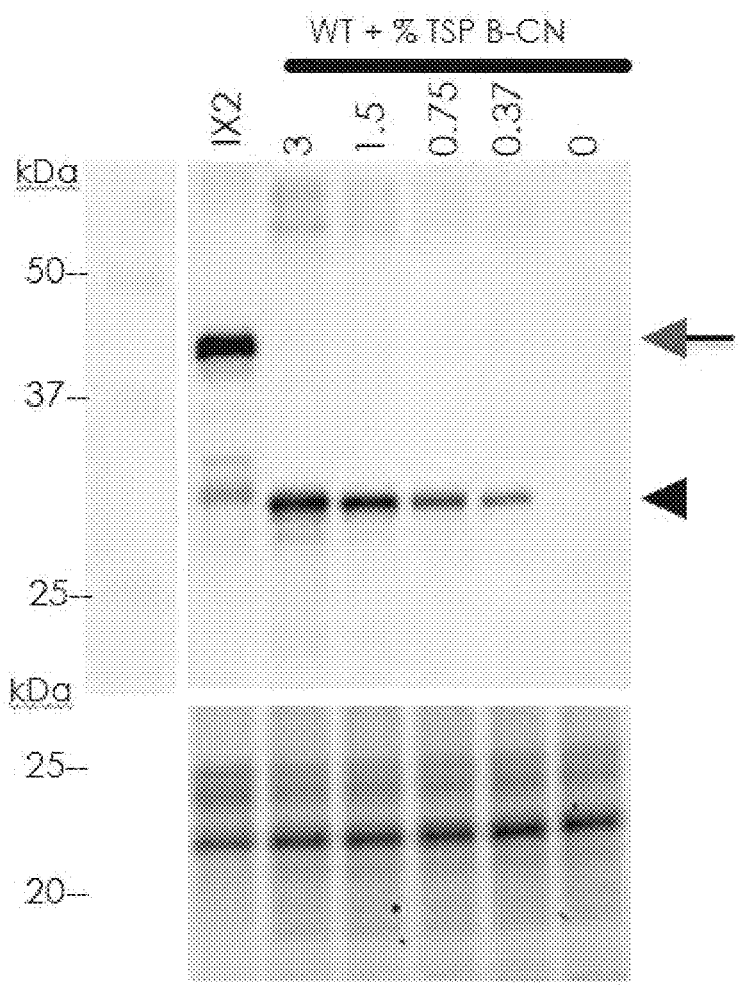

Molecular Weight

Hydrophobocity

FIG. 18

Wild type seeds

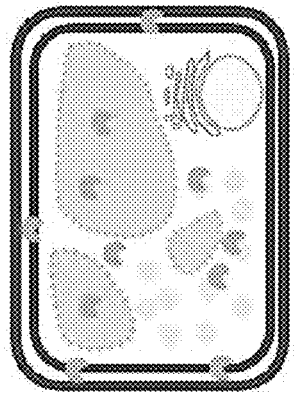
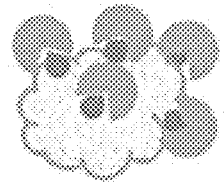

The proteases present in the different cell compartments have full access to casein.

Caseins do not accumulate at high levels.

Seeds wherein one or more proteases is knocked-down or knocked-out

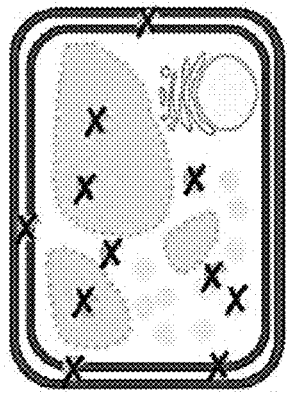
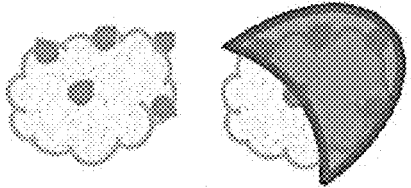

The absence of protease activity prevents casein degradation.

Caseins and/or casein fusion proteins can accumulate.

- Proteases
- Protease recognition sites
- Caseins (KCN, BC, aS1, aS2)
- Fusion with a partner protein A: 75% Kappa, 25% Beta. Melt =2
B: 100% Kappa. Melt =0
C: 50% Kappa, 50% Beta. Melt= 3
D: 100% Beta. Melt =4

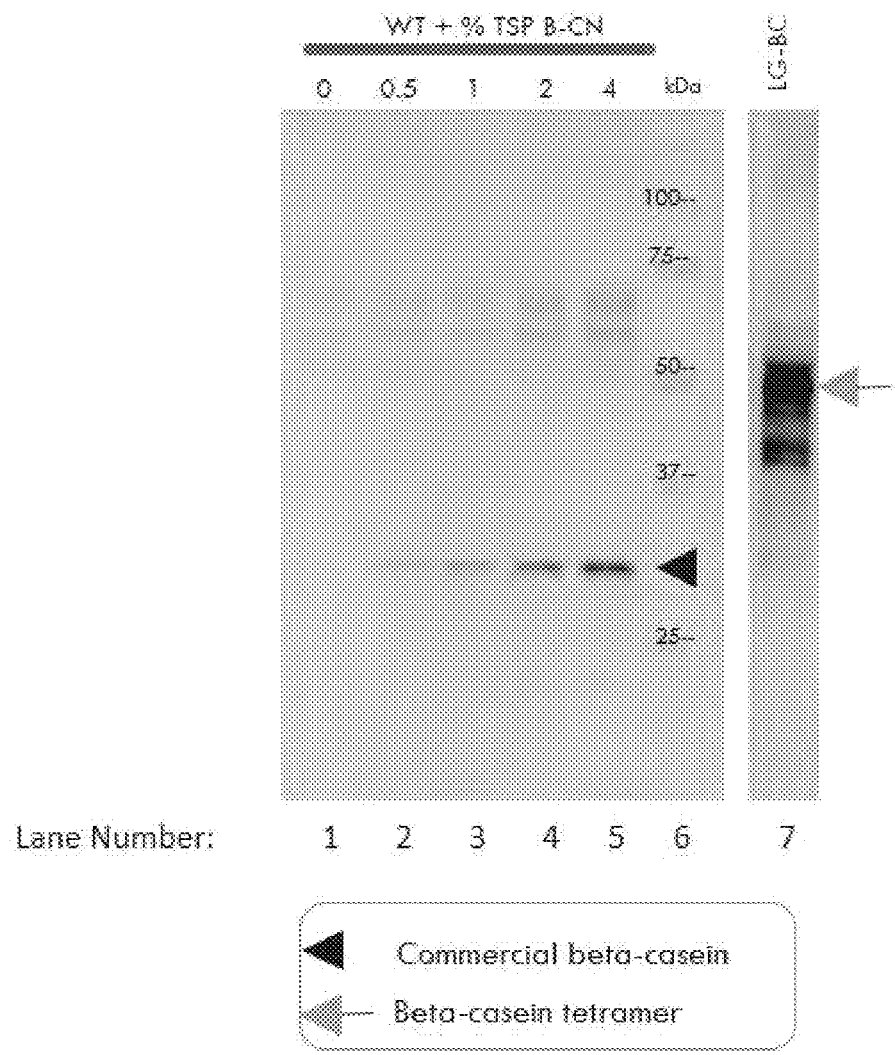

HOST CELLS COMPRISING A RECOMBINANT CASEIN PROTEIN AND A RECOMBINANT KINASE PROTEIN

CROSS-REFERENCE TO RELATED APPLICATIONS

This application is a divisional of U.S. application Ser. No. 18/463,864 filed Sep. 8, 2023, which is a continuation of U.S. application Ser. No. 18/064,199 filed Dec. 9, 2022, now U.S. Pat. No. 11,840,717, which is a continuation of International Application No. PCT/US2021/053002, filed Sep. 30, 2021, which claims priority to U.S. Application Nos. 63/240,621 filed on Sep. 3, 2021; 63/221,642, filed on Jul. 14, 2021; 63/189,547, filed on May 17, 2021; 63/174,244, filed on Apr. 13, 2021; 63/152,694, filed on Feb. 23, 2021; 63/138,089, filed on Jan. 15, 2021; 63/129,720, filed on Dec. 23, 2020; 63/121,468, filed on Dec. 4, 2020; 63/116,528, filed on Nov. 20, 2020; and 63/085,899, filed on Sep. 30, 2020, each of which is incorporated by reference herein in its entirety for all purposes.

DESCRIPTION OF THE TEXT FILE SUBMITTED ELECTRONICALLY

The contents of the electronic sequence listing (ALRO_008_11US_SeqList_ST26.xml; Size: 1,100,118 bytes; and Date of Creation: Sep. 16, 2024) are herein incorporated by reference in its entirety.

FIELD OF THE DISCLOSURE

The present disclosure generally relates to recombinant milk proteins, and methods of production, extraction, and purification thereof. The present disclosure also relates to food compositions (e.g., cheese compositions) comprising one or more recombinant milk proteins.

BACKGROUND

Globally, more than 7.5 billion people consume milk and milk products, and it is estimated that cow milk accounts for 83% of global milk production. Demand for cow milk and dairy products is expected to continue rising due to increased reliance on these products in developing countries as well as growth in the human population, which is expected to exceed 9 billion people by 2050. Relying on animal agriculture to meet the growing demand for food is not a sustainable solution. According to the Food & Agriculture Organization of the United Nations, animal agriculture is responsible for 18% of all greenhouse gases, more than the entire transportation sector combined. Dairy cows alone account for 3% of this total.

In addition to impacting the environment, animal agriculture poses a serious risk to human health. A startling 80% of antibiotics used in the United States go towards treating animals, resulting in the development of antibiotic resistant microorganisms, also known as superbugs. For years, food companies and farmers have administered antibiotics not only to sick animals, but also to healthy animals, to prevent illness. In September 2016, the United Nations announced the use of antibiotics in the food system as a crisis on par with Ebola and HIV.

For at least these reasons, alternative dairy compositions produced without the use of mammalian milk have become increasingly popular. However, such compositions often fail to achieve the same organoleptic properties as their milk-derived counterparts. For example, some alternative dairy compositions on the market today are known to have an off-putting texture or taste, poor melt characteristics and/or lack of stretch. These compositions may also have reduced nutritional value compared to their milk-derived counterparts. For example, some "vegan" cheeses, typically made from oils and starch, may contain little to no protein.

Accordingly, there is an urgent need to provide bovine milk and/or essential high-quality proteins from bovine milk in a more sustainable and humane manner, instead of solely relying on animal farming. Also, there is a need for selectively producing the specific milk proteins that confer nutritional and clinical benefits, and/or do not provoke allergic responses, and a need to prepare improved alternative dairy compositions which comparable nutritional value and similar organoleptic properties as their milk-derived counterparts.

BRIEF SUMMARY

Provided herein are recombinant fusion proteins comprising (i) a first milk protein, and (ii) a second milk protein. At least one of the first milk protein and the second milk protein may be, for example, α-S1 casein, α-S2 casein, β-casein, κ-casein, para-κ-casein, β-lactoglobulin, α-lactalbumin, lysozyme, lactoferrin, lactoperoxidase, serum albumin, or an immunoglobulin. In some embodiments, at least one of the first milk protein and the second milk protein is β-lactoglobulin. In some embodiments, at least one of the first milk protein and the second milk protein is α-S1 casein, α-S2 casein, β-casein, κ-casein, or para-κ-casein. In some embodiments, i) the first milk protein is α-S1 casein, α-S2 casein, β-casein, κ-casein, or para-κ-casein; and ii) the second milk protein is α-S1 casein, α-S2 casein, β-casein, κ-casein, or para-κ-casein. In some embodiments, at least one of the first milk protein and the second milk protein is κ-casein and comprises the sequence of SEQ ID NO: 4, or a sequence at least 90% identical thereto. In some embodiments, at least one of the first milk protein and the second milk protein is para-κ-casein and comprises the sequence of SEQ ID NO: 2, or a sequence at least 90% identical thereto. In some embodiments, at least one of the first milk protein and the second milk protein is β-casein and comprises the sequence of SEQ ID NO: 6, or a sequence at least 90% identical thereto. In some embodiments, at least one of the first milk protein and the second milk protein is α-S1 casein and comprises the sequence SEQ ID NO: 8, or a sequence at least 90% identical thereto. In some embodiments, at least one of the first milk protein and the second milk protein is α-S2 casein and comprises the sequence SEQ ID NO: 84, or a sequence at least 90% identical thereto. In some embodiments, the first milk protein and the second milk protein are different proteins. In some embodiments, the first milk protein and the second milk protein are the same proteins. In some embodiments, the fusion protein is plant-expressed. In some embodiments, the fusion protein is expressed in soybean plant. In some embodiments, the fusion protein comprises a protease cleavage site. In some embodiments, the protease cleavage site is a chymosin cleavage site.

Also provided herein are nucleic acids encoding one or more of the recombinant fusion proteins of the disclosure, and expression vectors comprising the same. In some embodiments, the nucleic acids are codon-optimized for expression in a plant, such as a soybean.

Additionally, provided herein are host cells comprising a nucleic acid or an expression vector of the disclosure; i.e., a nucleic acid or expression vector encoding a fusion protein.

The host cells may be, for example, plant cells, bacterial cells, fungal cells, or mammalian cells. In some embodiments, the host cells are soybean cells.

Also provided herein are plants stably transformed with a nucleic acid or an expression vector of the disclosure. In some embodiments, the fusion protein is expressed in the plant in an amount of 1% or higher per total protein weight of soluble protein extractable from the plant.

Also provided herein are methods for making a fusion protein, the methods comprising: (a) transforming a host cell with a nucleic acid or an expression vector described herein; and (b) growing the transformed host cell under conditions wherein the fusion protein is expressed. In some embodiments, the method comprises co-expressing in the host cell a protein capable of forming a protein body, such as a prolamin selected from a gliadin, a hordein, a secalin, a zein, a kafirin, or an avenin. In some embodiments, the method comprises expressing a kinase in the host cell. In some embodiments, expression of one or more proteases is knocked down or knocked out in the cell.

Also provided herein are transgenic plants comprising a recombinant fusion protein, or a nucleic acid or expression vector comprising the same. In some embodiments, the transgenic plant is a soybean plant. In some embodiments, the fusion protein is expressed in the plant in an amount of 1% or higher per total protein weight of soluble protein extractable from the plant.

Also provided herein are methods for stably expressing a recombinant fusion protein in a plant, the methods comprising: (i) transforming a plant with a plant transformation vector comprising an expression cassette comprising a nucleic acid molecule encoding the fusion protein; and (ii) growing the transformed plant under conditions wherein the recombinant fusion protein is expressed. In some embodiments, the fusion protein is expressed in an amount of 1% or higher per total protein weight of soluble protein extractable from the plant.

Also provided herein are seed processing compositions comprising a fusion protein of the disclosure.

Also provided herein are food compositions comprising a fusion protein of the disclosure. In some embodiments, the food composition is selected from the group consisting of cheese and processed cheese products, yogurt and fermented dairy products, directly acidified counterparts of fermented dairy products, cottage cheese dressing, frozen dairy products, frozen desserts, desserts, baked goods, toppings, icings, fillings, low-fat spreads, dairy-based dry mixes, soups, sauces, salad dressing, geriatric nutrition, creams and creamers, analog dairy products, follow-up formula, baby formula, infant formula, milk, dairy beverages, acid dairy drinks, smoothies, milk tea, butter, margarine, butter alternatives, growing up milks, low-lactose products and beverages, medical and clinical nutrition products, protein/nutrition bar applications, sports beverages, confections, meat products, analog meat products, meal replacement beverages, weight management food and beverages, cultured buttermilk, sour cream, yogurt, skyr, leben, lassi, kefir, powder containing a milk protein, and low-lactose products. In some embodiments, the food composition comprises a total amount of casein protein; wherein about 32% to 100% by weight of the total amount of casein protein in the food composition is beta-casein. In some embodiments, the food composition is a cheese composition. In some embodiments, the cheese composition has the ability to stretch to at least 3 cm in length without breaking, as determined by heating a 100 gram mass of the composition at a temperature of 225° C. for 4 minutes and cooling to about 90° C. and pulling with a fork placed beneath the mass.

Also provided herein is method of making a food composition, comprising combining a fusion protein disclosed herein into a food composition.

Also provided herein is an alternative dairy food composition comprising i) a recombinant fusion protein described herein; and ii) at least one lipid. In some embodiments, the recombinant fusion protein confers on the alternative dairy food composition one or more characteristics of a dairy food product selected from the group consisting of: taste, aroma, appearance, handling, mouthfeel, density, structure, texture, elasticity, springiness, coagulation, binding, leavening, aeration, foaming, creaminess and emulsification. In some embodiments, the alternative dairy food composition does not comprise any other milk proteins. In some embodiments, the alternative dairy food composition comprises calcium at a concentration of about 0.01 to about 2% by weight. In some embodiments, the alternative dairy food composition comprises a total amount of casein protein; wherein about 32% to 100% by weight of the total amount of casein protein in the food composition is beta-casein. In some embodiments, the alternative diary food composition has a pH of about 5.2 to about 5.9. In some embodiments, the alternative dairy food composition is selected from the group consisting of cheese and processed cheese products, yogurt and fermented dairy products, directly acidified counterparts of fermented dairy products, cottage cheese dressing, frozen dairy products, frozen desserts, desserts, baked goods, toppings, icings, fillings, low-fat spreads, dairy-based dry mixes, soups, sauces, salad dressing, geriatric nutrition, creams and creamers, analog dairy products, follow-up formula, baby formula, infant formula, milk, dairy beverages, acid dairy drinks, smoothies, milk tea, butter, margarine, butter alternatives, growing up milks, low-lactose products and beverages, medical and clinical nutrition products, protein/nutrition bar applications, sports beverages, confections, meat products, analog meat products, meal replacement beverages, weight management food and beverages, cultured buttermilk, sour cream, yogurt, skyr, leben, lassi, kefir, powder containing a milk protein, and low-lactose products. In some embodiments, the alternative diary food composition is a cheese composition.

Also provided herein are solid phase, protein-stabilized emulsions comprising a fusion protein described herein, wherein the emulsions have the ability to stretch to at least 3 cm in length without breaking, as determined by heating a 100 gram mass of the emulsion to a temperature of about 225° C. for 4 minutes and cooling to about 90° C. and pulling with a fork placed beneath the mass.

Also provided herein are colloidal suspensions comprising a fusion protein described herein, wherein the colloidal suspension has at least one, at least two, or at least three characteristics that are substantially similar to bovine milk selected from taste, appearance, mouthfeel, structure, texture, density, elasticity, springiness, coagulation, binding, leavening, aeration, foaming, creaminess, and emulsification.

These and other embodiments are described in detail below.

BRIEF DESCRIPTION OF THE DRAWINGS

The accompanying figures, which are incorporated herein and form a part of the specification, illustrate some, but not the only or exclusive, example embodiments and/or features.

It is intended that the embodiments and figures disclosed herein are to be considered illustrative rather than limiting.

FIGS. 1A, 1B, 1C, 1D, 1E, 1F, 1G, 1H, 1I, 1J, 1K, 1L, 1M, 1N, 1O, and 1P show expression cassettes having different combinations of fusions between sequences encoding structured and intrinsically unstructured proteins (not to scale). Coding regions and regulatory sequences are indicated as blocks (not to scale). As used in the figures, "L" refers to linker; "Sig" refers to a signal sequence that directs foreign proteins to protein storage vacuoles, "5' UTR" refers to the 5' untranslated region, and "KDEL" refers to an endoplasmic reticulum retention signal (SEQ ID NO: 23).

FIGS. 2A, 2B, 2C, 2D, 2E, 2F, 2G, 2H, 2I, 2J, 2K, 2L, 2M, 2N, 2O, and 2P show expression cassettes having different combinations of fusions between sequences encoding a first protein and a second protein (not to scale), wherein the first and/or second protein is a milk protein (not shown). Coding regions and regulatory sequences are indicated as blocks (not to scale). As used in the figures, "L" refers to linker; "Sig" refers to a signal sequence that directs foreign proteins to protein storage vacuoles, "5' UTR" refers to the 5' untranslated region, and "KDEL" refers to an endoplasmic reticulum retention signal (SEQ ID NO: 23).

FIG. 10A shows detection of the fusion protein using a primary antibody raised against κ-casein (kCN). The kCN commercial protein is detected at an apparent MW of ~26 kDa (theoretical: 19 kDa—arrow). The fusion protein is detected at an apparent MW of ~40 kDa (theoretical: 38 kDa—arrowhead). FIG. 10B shows detection of the fusion protein using a primary antibody raised against β-lactoglobulin (LG). The LG commercial protein is detected at an apparent MW of ~18 kDa (theoretical: 18 kDa—arrow). The fusion protein is detected at an apparent MW of ~40 kDa (theoretical: 38 kDa—arrowhead). FIG. 10C and FIG. 10D show protein gels as control for equal lane loading (image is taken at the end of the SDS run).

FIG. 11A-11E provides a series of illustrations showing potential mechanisms by which casein proteins may be degraded in plant cells, and how fusion of a casein protein with a second protein (i.e., a fusion partner) may lead to accumulation thereof. KCN stands for kappa-casein, BC stands for beta casein, aS1 stands for alpha-S1 casein, aS2 stands for alpha-S2 casein, PTM stands for post-translational modification.

In FIG. 12A, a κ-casein protein is fused to a β-lactoglobulin protein. The κ-casein comprises a natural chymosin cleavage site (arrow 1). Cleavage of the fusion protein with rennet (or chymosin) yields two fragments: a para-kappa casein fragment, and a fragment comprising a κ-casein macropeptide fused to β-lactoglobulin. In some embodiments, a second protease cleavage site may be added at the C-terminus of the κ-casein protein (i.e., at arrow 2), in order to further allow separation of the κ-casein macropeptide and the β-lactoglobulin. The second protease cleavage site may be a rennet cleavage site (e.g., a chymosin cleavage site), or it may be a cleavage site for a different protease. In FIG. 12B, a para-κ-casein protein is fused directly to β-lactoglobulin. A protease cleavage site (e.g., a chymosin cleavage site) is added between the para-κ-casein and the β-lactoglobulin to allow for separation thereof. By fusing the para-κ-casein directly to the β-lactoglobulin, no κ-casein macropeptide is produced upon cleavage of the fusion by chymosin (or other protease).

FIG. 14A shows protein detected using a primary antibody raised against KCN. FIG. 14B shows total protein, as a loading control (Stain-Free detection by Bio-Rad®).

FIGS. 15A and 15B are images that show protein detection by western blotting. FIG. 15A shows detection of a fusion protein comprising β-casein and β-lactoglobulin using a primary antibody raised against β-casein (B-CN). Commercial protein was detected at an apparent MW of ~30 kDa (arrowhead; theoretical: 23.5 kDa). The fusion protein was detected at an apparent MW of ~40 kDa (arrow; theoretical: 42 kDa). FIG. 15B shows a protein gel as a control for equal lane loading, visualized using stain-free detection by Bio Rad® (image is taken at the end of the SDS run). 5 μg of total protein extracts were loaded per lane.

FIG. 18 is a schematic that shows how knocking-down or knocking-out the expression and/or activity of one or more proteases in a plant seed may prevent degradation of a casein protein expressed therein. As shown in the schematic, the casein accumulates in the seed at a higher level than in a seed with wildtype levels of protease expression and/or activity.

FIG. 34 is a western blot showing expression of a fusion protein comprising beta-casein and beta-lactoglobulin in tobacco leaves. Commercial beta-casein, in monomeric form, was detected at an apparent molecular weight of ~30 kDa (theoretical: 23.5 kDa—arrowhead). The fusion protein was detected at an apparent MW of ~48 kDa (theoretical: 42 kDa—arrow).

DETAILED DESCRIPTION

Figures 1A, 1P:
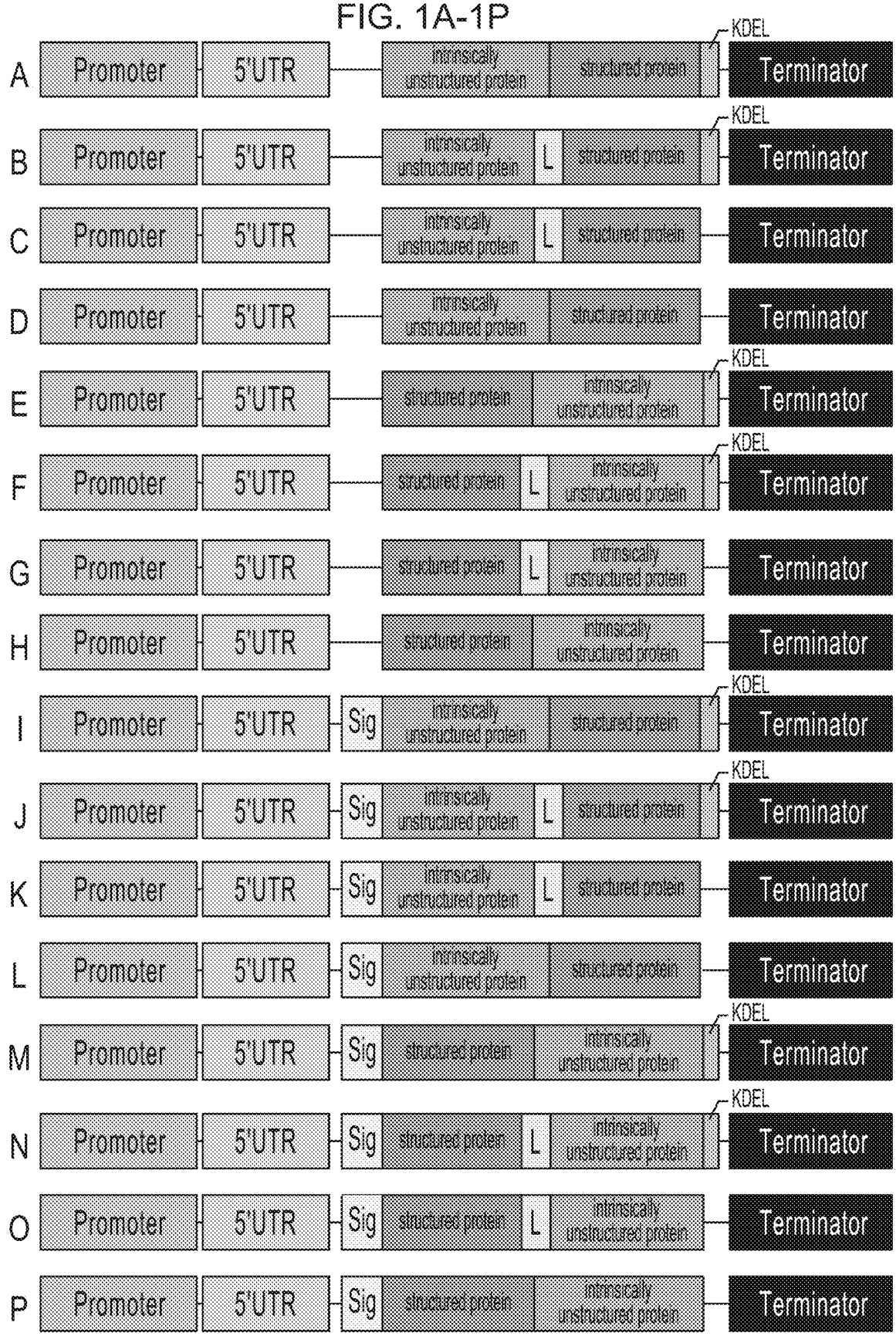

Provided herein are compositions and methods for producing milk proteins, which allow for safe, sustainable and humane production of milk proteins for commercial use, such as use in food compositions. The disclosure provides recombinant fusion proteins comprising at least first protein and a second protein, wherein at least one of the first protein and the second protein is a milk protein, or fragment thereof. The disclosure also provides methods for producing the recombinant fusions proteins, and food compositions comprising the same.

Also provided herein are alternative dairy compositions, solid phase protein-stabilized emulsions, cheese compositions, and colloidal suspensions, comprising one or more casein proteins, wherein the casein proteins are isolated or recombinant, and are selected from the group consisting of kappa-casein, para-kappa-casein, beta-casein, alpha-S1-casein and alpha-S2-casein. The compositions, emulsions, or suspensions may be used to produce food compositions that have organoleptic properties similar to traditional dairy compositions.

The following description includes information that may be useful in understanding the present disclosure. It is not an admission that any of the information provided herein is prior art or relevant to the presently claimed disclosures, or that any publication specifically or implicitly referenced is prior art.

Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art.

Any ranges listed herein are intended to be inclusive of endpoints. For example, a range of 2-4 includes 2 and 4.

As used herein, the singular forms "a," "an," and "the: include plural referents unless the content clearly dictates otherwise.

The term "about" or "approximately" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example, in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

As used herein, "mammalian milk" can refer to milk derived from any mammal, such as bovine, human, goat, sheep, camel, buffalo, water buffalo, dromedary, llama and any combination thereof. In some embodiments, a mammalian milk is a bovine milk.

As used herein, "structured" refers to those proteins having a well-defined secondary and tertiary structure, and "unstructured" refers to proteins that do not have well defined secondary and/or tertiary structures. An unstructured protein may also be described as lacking a fixed or ordered three-dimensional structure. "Disordered" and "intrinsically disordered" are synonymous with unstructured.

Figure 12A:
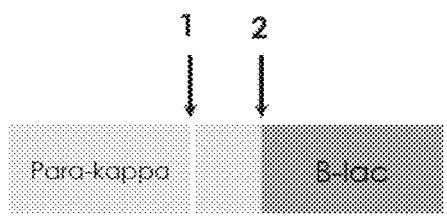
FIGS. 12A and 12B show two illustrative fusion proteins.
Figure 12B:
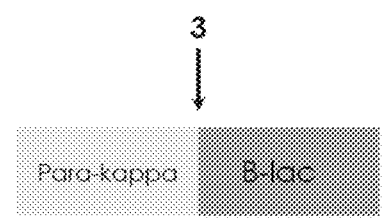

As used herein, "rennet" refers to a set of enzymes typically produced in the stomachs of ruminant mammals. Chymosin, its key component, is a protease enzyme that cleaves κ-casein (to produce para-κ-casein and a macropeptide (see e.g., FIG. 12)). In addition to chymosin, rennet contains other enzymes, such as pepsin and lipase. Rennet is used to separate milk into solid curds (for cheesemaking) and liquid whey. Rennet or rennet substitutes are used in the production of many cheeses.

As used herein "whey" refers to the liquid remaining after milk has been curdled and strained, for example during cheesemaking. Whey comprises a collection of globular proteins, typically a mixture of β-lactoglobulin, α-lactalbumin, bovine serum albumin, and immunoglobulins.

The term "plant" includes reference to whole plants, plant organs, plant tissues, and plant cells and progeny of same, but is not limited to angiosperms and gymnosperms such as *Arabidopsis*, potato, tomato, tobacco, alfalfa, lettuce, carrot, strawberry, sugar beet, cassava, sweet potato, soybean, lima bean, pea, chick pea, maize (corn), turf grass, wheat, rice, barley, sorghum, oat, oak, eucalyptus, walnut, palm and duckweed as well as fern and moss. Thus, a plant may be a monocot, a dicot, a vascular plant reproduced from spores such as fern or a nonvascular plant such as moss, liverwort, hornwort and algae. The word "plant," as used herein, also encompasses plant cells, seeds, plant progeny, propagule whether generated sexually or asexually, and descendants of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent.

The term "vascular plant" refers to a large group of plants that are defined as those land plants that have lignified tissues (the xylem) for conducting water and minerals throughout the plant and a specialized non-lignified tissue (the phloem) to conduct products of photosynthesis. Vascular plants include the clubmosses, horsetails, ferns, gymnosperms (including conifers) and angiosperms (flowering plants). Scientific names for the group include Tracheophyta and Tracheobionta. Vascular plants are distinguished by two primary characteristics. First, vascular plants have vascular tissues which distribute resources through the plant. This feature allows vascular plants to evolve to a larger size than non-vascular plants, which lack these specialized conducting tissues and are therefore restricted to relatively small sizes. Second, in vascular plants, the principal generation phase is the sporophyte, which is usually diploid with two sets of chromosomes per cell. Only the germ cells and gametophytes are haploid. By contrast, the principal generation phase in non-vascular plants is the gametophyte, which is haploid with one set of chromosomes per cell. In these plants, only the spore stalk and capsule are diploid.

The term "non-vascular plant" refers to a plant without a vascular system consisting of xylem and phloem. Many non-vascular plants have simpler tissues that are specialized for internal transport of water. For example, mosses and leafy liverworts have structures that look like leaves, but are not true leaves because they are single sheets of cells with no stomata, no internal air spaces and have no xylem or phloem. Non-vascular plants include two distantly related groups. The first group are the bryophytes, which is further categorized as three separate land plant Divisions, namely Bryophyta (mosses), Marchantiophyta (liverworts), and Anthocerotophyta (hornworts). In all bryophytes, the primary plants are the haploid gametophytes, with the only diploid portion being the attached sporophyte, consisting of a stalk and sporangium. Because these plants lack lignified water-conducting tissues, they can't become as tall as most vascular plants. The second group is the algae, especially the green algae, which consists of several unrelated groups. Only those groups of algae included in the Viridiplantae are still considered relatives of land plants.

The term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots".

The term "plant tissue" refers to any part of a plant, such as a plant organ. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

The term "seed" is meant to encompass the whole seed and/or all seed components, including, for example, the coleoptile and leaves, radicle and coleorhiza, scutellum, starchy endosperm, aleurone layer, pericarp and/or testa, either during seed maturation and seed germination.

"Microorganism" and "microbe" mean any microscopic unicellular organism and can include bacteria, algae, yeast, or fungi.

The term "transgenic" means an organism that has been transformed with one or more exogenous nucleic acids from another species. "Transformation" refers to a process by which a nucleic acid is introduced into a cell, either transiently or stably. Transformation may rely on any known method for the insertion of nucleic acid sequences into a prokaryotic or eukaryotic host cell, including *Agrobacterium*-mediated transformation protocols, viral infection, whiskers, electroporation, heat shock, lipofection, polyethylene glycol treatment, micro-injection, and particle bombardment.

"Stably integrated" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, heat shock, lipofection, polyethylene glycol treatment, micro-injection, and particle bombardment.

As used herein, the terms "stably expressed" or "stable expression" refer to expression and accumulation of a protein in a plant cell. In some embodiments, a protein may accumulate because it is not degraded by endogenous plant proteases. In some embodiments, a protein is considered to be stably expressed in a plant if it is present in the plant in an amount of 1% or higher per total protein weight of soluble protein extractable from the plant.

As used herein, the term "fusion protein" refers to a protein comprising at least two constituent proteins (or fragments or variants thereof) that are encoded by separate genes, and that have been joined so that they are transcribed and translated as a single polypeptide. In some embodiments, a fusion protein may be separated into its constituent proteins, for example by cleavage with a protease.

The term "recombinant" refers to nucleic acids or proteins formed by laboratory methods of genetic recombination (e.g., molecular cloning) to bring together genetic material from multiple sources, creating sequences that would not otherwise be found in the genome. A recombinant fusion protein is a protein created by combining sequences encoding two or more constituent proteins, such that they are expressed as a single polypeptide. Recombinant fusion proteins may be expressed in vivo in various types of host cells, including plant cells, bacterial cells, fungal cells, mammalian cells, etc. Recombinant fusion proteins may also be generated in vitro.

The term "promoter" or a "transcription regulatory region" refers to nucleic acid sequences that influence and/or promote initiation of transcription. Promoters are typically considered to include regulatory regions, such as enhancer or inducer elements. The promoter will generally be appropriate to the host cell in which the target gene is being expressed. The promoter, together with other transcriptional and translational regulatory nucleic acid sequences (also termed "control sequences"), is necessary to express any given gene. In general, the transcriptional and translational regulatory sequences include, but are not limited to, promoter sequences, ribosomal binding sites, transcriptional start and stop sequences, translational start and stop sequences, and enhancer or activator sequences.

The term signal peptide—also known as "signal sequence", "targeting signal", "localization signal", "localization sequence", "transit peptide", "leader sequence", or "leader peptide", is used herein to refer to an N-terminal peptide which directs a newly synthesized protein to a specific cellular location or pathway. Signal peptides are often cleaved from a protein during translation or transport, and are therefore not typically present in a mature protein.

The term "proteolysis" or "proteolytic" or "proteolyze" means the breakdown of proteins into smaller polypeptides or amino acids. Uncatalyzed hydrolysis of peptide bonds is extremely slow. Proteolysis is typically catalyzed by cellular enzymes called proteases, but may also occur by intramolecular digestion. Low pH or high temperatures can also cause proteolysis non-enzymatically. Limited proteolysis of a polypeptide during or after translation in protein synthesis often occurs for many proteins. This may involve removal of the N-terminal methionine, signal peptide, and/or the conversion of an inactive or non-functional protein to an active one.

The term "2A peptide", used herein, refers to nucleic acid sequence encoding a 2A peptide or the 2A peptide itself. The average length of 2A peptides is 18-22 amino acids. The designation "2A" refers to a specific region of picornavirus polyproteins and arose from a systematic nomenclature adopted by researchers. In foot-and-mouth disease virus (FMDV), a member of Picornaviridae family, a 2A sequence appears to have the unique capability to mediate cleavage at its own C-terminus by an apparently enzyme-independent, novel type of reaction. This sequence can also mediate cleavage in a heterologous protein context in a range of eukaryotic expression systems. The 2A sequence is inserted between two genes of interest, maintaining a single open reading frame. Efficient cleavage of the polyprotein can lead to co-ordinate expression of active two proteins of interest. Self-processing polyproteins using the FMDV 2A sequence could therefore provide a system for ensuring coordinated, stable expression of multiple introduced proteins in cells including plant cells.

The term "purifying" is used interchangeably with the term "isolating" and generally refers to the separation of a particular component from other components of the environment in which it was found or produced. For example, purifying a recombinant protein from plant cells in which it was produced typically means subjecting transgenic protein containing plant material to biochemical purification and/or column chromatography.

When referring to expression of a protein in a specific amount per the total protein weight of the soluble protein extractable from the plant ("TSP"), it is meant an amount of a protein of interest relative to the total amount of protein that may reasonably be extracted from a plant using standard methods. Methods for extracting total protein from a plant are known in the art. For example, total protein may be extracted from seeds by bead beating seeds at about 15000 rpm for about 1 min. The resulting powder may then be resuspended in an appropriate buffer (e.g., 50 mM Carbonate-Bicarbonate pH 10.8, 1 mM DTT, 1× Protease Inhibitor Cocktail). After the resuspended powder is incubated at about 4° C. for about 15 minutes, the supernatant may be collected after centrifuging (e.g., at 4000 g, 20 min, 4° C.). Total protein may be measured using standard assays, such as a Bradford assay. The amount of protein of interest may be measured using methods known in the art, such as an ELISA or a Western Blot.

When referring to a nucleic acid sequence or protein sequence, the term "identity" is used to denote similarity between two sequences. Sequence similarity or identity may be determined using standard techniques known in the art, including, but not limited to, the local sequence identity algorithm of Smith & Waterman, Adv. Appl. Math. 2, 482 (1981), by the sequence identity alignment algorithm of Needleman & Wunsch, J Mol. Biol. 48,443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12, 387-395 (1984), or by inspection. Another suitable algorithm is the BLAST algorithm, described in Altschul et al., J Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altschul et al., Methods in Enzymology, 266, 460-480 (1996); blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity. Further, an additional useful algorithm is gapped BLAST as reported by Altschul et al, (1997) Nucleic Acids Res. 25, 3389-3402. Unless otherwise indicated, percent identity is determined herein using the algorithm available at the world wide web address: blast.ncbi.nlm.nih.gov/Blast.cgi.

As used herein, the terms "dicot" or "dicotyledon" or "dicotyledonous" refer to a flowering plant whose embryos have two seed leaves or cotyledons. Examples of dicots include, but are not limited to, *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus.

The terms "monocot" or "monocotyledon" or "monocotyledonous" refer to a flowering plant whose embryos have one cotyledon or seed leaf. Examples of monocots include, but are not limited to turf grass, maize (corn), rice, oat, wheat, barley, sorghum, orchid, iris, lily, onion, palm, and duckweed.

As used herein, a "low lactose product" is any food composition considered by the FDA to be "lactose reduced", "low lactose", or "lactose free".

As used herein, a "milk protein" is any protein, or fragment or variant thereof, that is typically found in one or more mammalian milks. In some embodiments, the milk proteins described herein are casein proteins, such as kappa-casein, para-kappa-casein, beta-casein, alpha-S1-casein, and alpha-S2-casein.

As used herein, a "non-milk" protein is any protein that is not typically found in any mammalian milk composition. One non-limiting example of a non-milk protein is green fluorescent protein (GFP).

As used herein, a "caseinate" is a compound derived from casein. Caseinates may be produced by adding acid to skim milk to reduce the pH to about 4.6, which causes the casein proteins to be precipitated. The resulting curd is rinsed and dried to produce acid casein. Acid casein is typically insoluble without further treatment, such as pH adjustment. Acid casein either before or after drying can be mixed with a base such as sodium hydroxide to produce sodium caseinate, or calcium hydroxide to produce calcium caseinate.

As used herein, an "alternative dairy composition" is a composition that comprises an isolated, or recombinant, casein protein, and may also comprise variations of the composition, such as a low-fat alternative dairy composition.

As used herein, the phrase "solid phase, protein-stabilized emulsion" refers to a homogenous and stable emulsion that is a solid at room temperature. The solid-phase, protein stabilized emulsions described herein is formed by the protein reducing the interfacial tension between the continuous aqueous phase and discontinuous lipid phase by aligning and/or unfolding at the interface. The amphiphilic nature of proteins allows them to interact with both phases and association between proteins in the aqueous phase results in decreased mobility of water in the form of increased viscosity and/or solid like behavior at different temperatures. The presence of "emulsifying salts" can enhance the emulsifying properties of the proteins.

As used herein, "cheese" refers to a food that is produced by curdling animal-derived milk. The milk may be curdled using, for example, enzymes (e.g., rennet), or using acid.

As used herein, "cheese composition" refers to a food that is produced by combining one or more milk proteins, optionally with other ingredients, as described herein. For example, cheese compositions may be produced using one or more recombinant milk proteins, or one or more milk proteins isolated from bovine milk. The cheese compositions may, in some embodiments, include only one milk protein. In some embodiments, the cheese compositions may comprise 2, 3, or 4 milk proteins. In some embodiments, the cheese compositions may comprise one or more milk proteins in a ratio that does not occur in the milk produced by any mammal (i.e., a non-naturally occurring ratio).

As used herein, the term "melt", "melting", or "meltability" refers to the liquefaction of cheese or a cheese composition by heat.

As used herein, the term "viscosity" or "flow" refers to the tendency of cheese (or a cheese composition) to spread and flow when completely melted.

As used herein, the term "stretch", "stretching", or "stretchability" refers to the formation of fibrous strands of cheese (or a cheese composition) that elongate without breaking.

As used herein, the term "oiling-off" refers to the tendency of free oil separation from melted cheese or a cheese composition (also known as fat leakage).

As used herein, the term "browning" or "blistering" refers to the trapped pockets of heated air and steam that may be scorched during baking with cheese (or a cheese composition).

As used herein, the term "whitening" or "decolorization" refers to the bleaching of cheese (or a cheese composition).

As used herein, the term "spread", "spreading" or "spreadability" refers to the ability of cheese or a cheese composition to spread over a surface on application of slight force to form a layer, thin enough to form a coating.

The term "ash" is used herein as it is well known in the art, and means one or more ions, elements, minerals and/or compounds that may be found in mammalian produced milk. Ash may comprise one or more of sodium, potassium, calcium, magnesium, phosphorus, iron, copper, zinc, chloride, manganese, selenium, iodine, phosphate, citrate, sulfate, and carbonate. In some embodiments, ash may comprise calcium carbonate and/or sodium citrate.

Milk Proteins

The fusion proteins described herein may comprise one or more milk proteins. In some embodiments, the fusion proteins described herein may comprise a first protein and a second protein, wherein the first protein and/or second protein is a milk protein. In some embodiments, the first protein and the second protein are both milk proteins. As used herein the term "milk protein" refers to any protein, or fragment or variant thereof, that is typically found in one or more mammalian milks. Examples of mammalian milk include, but are not limited to, milk produced by a cow, human, goat, sheep, camel, horse, donkey, dog, cat, elephant, monkey, mouse, rat, hamster, guinea pig, whale, dolphin, seal, sheep, buffalo, water buffalo, dromedary, llama, yak, zebu, reindeer, mole, otter, weasel, wolf, raccoon, walrus, polar bear, rabbit, or giraffe. Some representative examples of milk protein species of the disclosure can be found in Table 34.

The composition of milk varies depending on the mammal. For example, as shown below in Table 1, cow milk comprises β-lactoglobulin, α-S1-casein, and α-S2-casein, whereas human milk does not. However, for the purposes of this disclosure, β-lactoglobulin, α-S1-casein, and α-S2-casein are considered milk proteins.

TABLE 1

Protein composition of human and cow milk

| Protein | Human milk (mg/mL) | Bovine (cow) milk (mg/mL) |
|---|---|---|
| α-lactalbumin | 2.2 | 1.2 |
| α-s1-casein | 0 | 11.6 |
| α-s2-casein | 0 | 3.0 |
| β-casein | 2.2 | 9.6 |
| κ-casein | 0.4 | 3.6 |
| γ-casein | 0 | 1.6 |
| Immunoglobulins | 0.8 | 0.6 |
| Lactoferrin | 1.4 | 0.3 |
| β-lactoglobulin | 0 | 3.0 |
| Lysozyme | 0.5 | Traces |
| Serum albumin | 0.4 | 0.4 |
| Other | 0.8 | 0.6 |

Illustrative milk proteins that may be used in the fusion proteins of the disclosure include, but are not limited to, α-S1 casein, α-S2 casein, β-casein, κ-casein, para-κ-casein, β-lactoglobulin, α-lactalbumin, lysozyme, lactoferrin, lactoperoxidase, serum albumin, and immunoglobulins (e.g., IgA, IgG, IgM, IgE).

Milk proteins may be further classified as structured or unstructured proteins. An "unstructured milk protein" is a milk protein that lacks a defined secondary structure, a defined tertiary structure, or a defined secondary and tertiary structure. Whether a milk protein is unstructured may be determined using a variety of biophysical and biochemical methods known in the art, such as small angle X-ray scattering, Raman optical activity, circular dichroism, nuclear magnetic resonance (NMR) and protease sensitivity.

In some embodiments, a milk protein is considered to be unstructured if it is unable to be crystallized using standard techniques.

Illustrative unstructured milk proteins that may be used in the fusion proteins of the disclosure includes members of the casein family of proteins, such as α-S1 casein, α-S2 casein, β-casein, and κ-casein. The caseins are phosphoproteins, and make up approximately 80% of the protein content in bovine milk and about 20-45% of the protein in human milk. Caseins form a multi-molecular, granular structure called a casein micelle in which some enzymes, water, and salts, such as calcium and phosphorous, are present. The micellar structure of casein in milk is significant in terms of a mode of digestion of milk in the stomach and intestine and a basis for separating some proteins and other components from cow milk. In practice, casein proteins in bovine milk can be separated from whey proteins by acid precipitation of caseins, by breaking the micellar structure by partial hydrolysis of the protein molecules with proteolytic enzymes, or microfiltration to separate the smaller soluble whey proteins from the larger casein micelle. Caseins are relatively hydrophobic, making them poorly soluble in water.

In some embodiments, the casein proteins described herein (e.g., α-S1 casein, α-S2 casein, β-casein, and/or κ-casein) are isolated or derived from cow (*Bos taurus*), goat (*Capra hircus*), sheep (*Ovis aries*), water buffalo (*Bubalus bubalis*), dromedary camel (*camelus* dromedaries), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*vicugna pacos*), zebu (*Bos indicus*), llama (*Lama glama*), or human (*Homo sapiens*). In some embodiments, a casein protein (e.g., α-S1 casein, α-S2 casein, β-casein, or κ-casein) has at least 80%, at least 85%, at least 90%, at least 95%, at least 96%, at least 97%, at least 98%, or at least 99% identity with a casein protein from one or more of cow (*Bos taurus*), goat (*Capra hircus*), sheep (*Ovis aries*), water buffalo (*Bubalus bubalis*), dromedary camel (*camelus* dromedaries), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*vicugna pacos*), zebu (*Bos indicus*), llama (*Lama glama*), or human (*Homo sapiens*).

As used herein, the term "α-S1 casein" refers to not only the α-S1 casein protein, but also fragments or variants thereof. α-S1 casein is found in the milk of numerous different mammalian species, including cow, goat, and sheep. The sequence, structure and physical/chemical properties of α-S1 casein derived from various species is highly variable. An illustrative sequence for bovine α-S1 casein can be found at Uniprot Accession No. P02662, and an illustrative sequence for goat α-S1 casein can be found at GenBank Accession No. X59836.1. The terms "α-S1 casein" and "alpha-S1-casein" (and similar terms) are used interchangeably herein.

As used herein, the term "α-S2 casein" refers to not only the α-S2 casein protein, but also fragments or variants thereof. α-S2 is known as epsilon-casein in mouse, Gamma-casein in rat, and casein-A in guinea pig. The sequence, structure and physical/chemical properties of α-S2 casein derived from various species is highly variable. An illustrative sequence for bovine α-S2 casein can be found at Uniprot Accession No. P02663, and an illustrative sequence for goat α-S2 casein can be found at Uniprot Accession No. P33049. The terms "α-S2 casein" and "alpha-S2-casein" (and similar terms) are used interchangeably herein.

As used herein, the term "β-casein" refers to not only the β-casein protein, but also fragments or variants thereof. For example, A1 and A2 β-casein are genetic variants of the β-casein milk protein that differ by one amino acid (at amino acid 67, A2 β-casein has a proline, whereas A1 has a histidine). Other genetic variants of β-casein include the A3, B, C, D, E, F, H1, H2, I and G genetic variants. The sequence, structure and physical/chemical properties of β-casein derived from various species is highly variable. Exemplary sequences for bovine β-casein can be found at Uniprot Accession No. P02666 and GenBank Accession No. M15132.1. The terms "β-casein", "beta-casein" and "β-casein" (and similar terms) are used interchangeably herein.

As used herein, the term "κ-casein" refers to not only the κ-casein protein, but also fragments or variants thereof. κ-casein is cleaved by rennet, which releases a macropeptide from the C-terminal region. The remaining product with the N-terminus and approximately two-thirds of the original peptide chain is referred to as para-κ-casein. The sequence, structure and physical/chemical properties of κ-casein derived from various species is highly variable. Illustrative sequences for bovine κ-casein can be found at Uniprot Accession No. P02668 and GenBank Accession No. CAA25231. The terms "κ-casein", "κ-casein" and "kappa-casein" (and similar terms) are used interchangeably herein.

In some embodiments, the milk protein is a casein protein, for example, α-S1 casein, α-S2 casein, β-casein, and or κ-casein. In some embodiments, the milk protein is κ-casein and comprises the sequence of SEQ ID NO: 4, or a sequence at least 90%, at least 95%, at least 96%, at least 97%, at least 98%, or at least 99% identical thereto. In some embodiments, the milk protein is para-κ-casein and comprises the sequence of SEQ ID NO: 2, or a sequence at least 90%, at least 95%, at least 96%, at least 97%, at least 98%, or at least 99% identical thereto. In some embodiments, the milk protein is β-casein and comprises the sequence of SEQ ID NO: 6, or a sequence at least 90%, at least 95%, at least 96%, at least 97%, at least 98%, or at least 99% identical thereto. In some embodiments, the milk protein is α-S1 casein and comprises the sequence SEQ ID NO: 8, or a sequence at least 90%, at least 95%, at least 96%, at least 97%, at least 98%, or at least 99% identical thereto. In some embodiments, milk protein is α-S2 casein and comprises the sequence SEQ ID NO: 84, or a sequence at least 90%, at least 95%, at least 96%, at least 97%, at least 98%, or at least 99% identical thereto.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 4. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 2. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 6. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 8. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 84.

In some embodiments, α-S1 casein is encoded by the sequence of SEQ ID NO: 7, or a sequence at least 90%, at least 95%, at least 96%, at least 97%, at least 98%, or at least 99% identical thereto. In some embodiments, α-S2 casein is encoded by the sequence of SEQ ID NO: 83, or a sequence at least 90%, at least 95%, at least 96%, at least 97%, at least 98%, or at least 99% identical thereto. In some embodiments, β-casein is encoded by the sequence of SEQ ID NO: 5, or a sequence at least 90%, at least 95%, at least 96%, at least 97%, at least 98%, or at least 99% identical thereto. In some embodiments, κ-casein is encoded by the sequence of SEQ ID NO: 3, or a sequence at least 90%, at least 95%, at least 96%, at least 97%, at least 98%, or at least 99% identical thereto. In some embodiments, para-κ-casein is encoded by the sequence of SEQ ID NO: 1, or a sequence at least 90%, at least 95%, at least 96%, at least 97%, at least 98%, or at least 99% identical thereto.

In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 7. In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 83. In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 3. In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1. In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 5.

In some embodiments, the milk protein is a casein protein, and comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 85-133, or 148-563. In some embodiments, the milk protein is a casein protein and comprises the sequence of any one of SEQ ID NO: 85-133 or 148-563.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 85-98 or 148-340. In some embodiments, the milk protein comprises the sequence of any one of SEQ ID NO: 85-98 or 148-340.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 99-109 or 341-440. In some embodiments, the milk protein comprises the sequence of any one of SEQ ID NO: 99-109 or 341-440.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 110-120 or 441-494. In some embodiments, the milk protein comprises the sequence of any one of SEQ ID NO: 110-120 or 441-494.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 121-133 or 495-563. In some embodiments, the milk protein comprises the sequence of any one of SEQ ID NO: 121-133 or 495-563 or 495-563.

In some embodiments, the milk protein is a structured protein. Examples of structured milk proteins include, for example, β-lactoglobulin, α-lactalbumin, lysozyme, lactoferrin, lactoperoxidase, serum albumin, or an immunoglobulin.

In some embodiments, the milk protein is β-lactoglobulin and comprises the sequence of SEQ ID NO: 10, or a sequence at least 90%, at least 95%, at least 96%, at least 97%, at least 98%, or at least 99% identical thereto. In some embodiments, the milk protein is β-lactoglobulin and is encoded by the sequence of any one of SEQ ID NO: 9, 11, 12, or 13, or a sequence at least 90%, at least 95%, at least 96%, at least 97%, at least 98%, or at least 99% identical to any one of SEQ ID NO: 9, 11, 12, or 13. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 9-13 or 564-614. In some embodiments, the milk protein comprises the sequence of any one of SEQ ID NO: 10 or 564-614.

Fusion Partners

The fusion proteins described herein comprise a first protein and a second protein, wherein at least one of the first protein and the second protein is a milk protein. Accordingly, in addition to the milk protein, the fusion proteins described herein comprise a "fusion partner" (i.e., the second protein)—a protein that is fused the milk protein in a fusion protein.

In some embodiments, fusion partner is a protein with a molecular weight of about 5 to about 100 kDa. For example, the fusion partner may have a molecular weight of at least 5 kDa, at least 10 kDa, at least 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, or about 100 kDa. In some embodiments, the fusion partner is a protein with a molecular weight of about 15 kDa, or more.

In some embodiments, fusion partner is a protein with about 10% to about 90% hydrophobic amino acids, e.g., about 10% to about 20%, about 20% to about 30%, about 30% to about 40%, about 40% to about 50%, about 50% to about 60%, about 60% to about 70%, about 70% to about 80%, or about 80% to about 90%. In some embodiments, the fusion partner may comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% hydrophobic amino acids. In some embodiments, the fusion partner is a protein with about 25% or more hydrophobic amino acids. In some embodiments, the fusion partner is a protein with about 30% or more hydrophobic amino acids. In some embodiments, the fusion partner is a protein with about 35% or more hydrophobic amino acids. In some embodiments, the fusion partner is a protein with about 40% or more hydrophobic amino acids. A hydrophobic amino acid is an amino acid with a hydrophobic side chain, such as alanine (A), valine (V), isoleucine (I), leucine (L), methionine (M), phenylalanine (F), tryptophan (W), tyrosine (Y), or proline.

In some embodiments, the fusion partner is a flexible protein. In general, proteins with fewer disulfide bonds are more flexible. In some embodiments, the fusion partner comprises less than about 5 disulfide bonds per 10 kDa molecular weight. In some embodiments, the fusion partner comprises less than about 4.5 disulfide bonds per 10 kDa molecular weight. In some embodiments, the fusion partner comprises less than about 4.0 disulfide bonds per 10 kDa molecular weight. In some embodiments, the fusion partner comprises less than about 3.5 disulfide bonds per 10 kDa molecular weight. In some embodiments, the fusion partner comprises less than about 3.0 disulfide bonds per 10 kDa molecular weight. In some embodiments, the fusion partner comprises less than about 2.5 disulfide bonds per 10 kDa molecular weight. In some embodiments, the fusion partner comprises less than about 2.0 disulfide bonds per 10 kDa molecular weight. In some embodiments, the fusion partner comprises less than about 1.5 disulfide bonds per 10 kDa molecular weight. In some embodiments, the fusion partner comprises less than about 1 disulfide bond per 10 kDa molecular weight. Number of disulfide bonds may be predicted using one or more computer algorithms known to those of skill in the art. For example, the software SnapGene® or the Prot Pi tool (available on the Internet by placing https://in front of www.protpi.ch/Calculator) may be useful for making such predictions. Notably, as understood by those of skill in the art, the number of cysteines in a protein, on its own, is not necessarily predictive of the number of disulfide bonds in that protein. The secondary and tertiary structure of the protein must also be considered, to determine whether a given cysteine is in appropriate proximity to another cysteine in order to form a bond.

In some embodiments, the fusion partner comprises at least one of the following characteristics: (i) a molecular weight of 15 kDa or higher, (ii) at least 30% hydrophobic amino acids, (iii) less than about 2.5 disulfide bonds per 10 kDa molecular weight. In some embodiments, the fusion partner comprises at least two of the following characteristics: (i) a molecular weight of 15 kDa or higher, (ii) at least 30% hydrophobic amino acids, (iii) less than about 2.5 disulfide bonds per 10 kDa molecular weight. In some embodiments, the fusion partner comprises all three of the following characteristics: (i) a molecular weight of 15 kDa or higher, (ii) at least 30% hydrophobic amino acids, and (iii) less than about 2.5 disulfide bonds per 10 kDa molecular weight.

In some embodiments, the fusion partner comprises at least one of the following characteristics: (i) a molecular weight of 10 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 11 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 12 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 13 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 14 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 15 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 16 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 17 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 18 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 19 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 20 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 21 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 22 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 23 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 24 kDa or higher, (ii) at least 30% hydrophobic amino acids, (iii) less than about 2.5 disulfide bonds per 10 kDa molecular weight. In some embodiments, the fusion partner comprises at least one of the following characteristics: (i) a molecular weight of 25 kDa or higher, (ii) at least 30% hydrophobic amino acids, (iii) less than about 2.5 disulfide bonds per 10 kDa molecular weight.

In some embodiments, the fusion partner comprises a molecular weight of 15 kDa or higher and at least 30% hydrophobic amino acids. In some embodiments, the fusion partner comprises a molecular weight of 15 kDa or higher and less than about 2.5 disulfide bonds per 10 kDa molecular weight. In some embodiments, the fusion partner comprises at least 30% hydrophobic amino acids and less than about 2.5 disulfide bonds per 10 kDa molecular weight.

In some embodiments, the fusion partner is kappa-casein. In some embodiments, the fusion partner is beta-casein. In some embodiments, the fusion partner is alpha-casein. In some embodiments, the fusion partner is beta-lactoglobulin. In some embodiments, the fusion partner is green fluorescent protein. In some embodiments the fusion partner is lysozyme. In some embodiments, fusion partner is 2S globulin. In some embodiments, the fusion partner is oleosin A. In some embodiments, the fusion partner is oleosin B. In some embodiments, the fusion partner is the Kunitz-Trypsin inhibitor. In some embodiments the fusion partner is the Bowman-Birk inhibitor. In some embodiments, the fusion partner is Hydrophobin II.

Non-Milk Proteins

In some embodiments, the fusion partner is a non-milk protein. Accordingly, in some embodiments, the fusion proteins described herein may comprise one or more non-milk proteins, including any fragment or variant thereof. As used herein, the term "non-milk protein" refers to any protein that is not typically present in any mammalian milk composition. In some embodiments, the fusion proteins described herein may comprise a first protein and a second protein, wherein the first protein is a milk protein and the second protein (i.e., the fusion partner) is a non-milk protein. The non-milk protein may be, for example, an animal protein or a plant protein. In some embodiments, the animal protein is a mammalian protein. In some embodiments, the animal protein is an avian protein. The non-milk proteins described herein may be classified as structured or unstructured. In some embodiments, the non-milk protein is a structured protein. In some embodiment, the non-milk protein is an unstructured protein.

Whether a protein is structured may be determined using a variety of biophysical and biochemical methods known in the art, such as small angle X-ray scattering, Raman optical activity, circular dichroism, and protease sensitivity. In some embodiments, a protein is considered to be structured if it has been crystallized or if it may be crystallized using standard techniques.

In some embodiments, the non-milk protein is a protein that is typically used as a marker. As used herein, the term "marker" refers to a protein that produces a visual or other signal and is used to detect successful delivery of a vector (e.g., a DNA sequence) into a cell. Proteins typically used as a marker may include, for example, fluorescent proteins (e.g., green fluorescent protein (GFP)). Other examples include yellow fluorescent protein (YFP), orange fluorescent protein, blue fluorescent protein (BFP), cyan fluorescent protein (CFP), or red fluorescent protein (RFP). Non-limiting examples of proteins within these color classes are shown below in Table 2 (See also, Schaner, N. et al., A guide to choosing fluorescent proteins, 2005, Nature, 2:12, 905-909).

TABLE 2

Examples of fluorescent proteins

| Color class | Protein |
| --- | --- |
| Far-red | mPlum |
| Red | mCherry |
|  | tdTomato |
|  | mStrawberry |
|  | J-Red |
|  | DsRed-monomer |
| Orange | mOrange |
|  | mKO |
| Yellow-green | mCitrine |
|  | Venus |
|  | YPet |
|  | EYFP |
| Green | Emerald |
|  | EGFP |
| Color class | Protein |
|  | GFP |
| Cyan | CyPet |
|  | mCFPm |
|  | Cerulean |
| UV-excitable green | T-Sapphire |

Other examples of marker proteins include, but are not limited to, bacterial or other enzymes (e.g., β-glucuronidase (GUS), β-galactosidase, luciferase, chloramphenicol acetyltransferase).

Additional non-limiting examples of non-milk proteins that may be used in the fusion proteins described herein are provided in Table 3. In some embodiments, a fragment or variant of any one of the proteins listed in Table 3 may be used.

TABLE 3

Non-milk proteins for use as fusion partners

| Categories | Protein or Protein family | Native Species | Exemplary Uniprot Accession No. |
| --- | --- | --- | --- |
| Mammalian | Collagen family | Human (*Homo sapiens*) | Q02388, P02452, P08123, P02458 |
|  | Hemoglobin | Bovine (*Bos taurus*) | P02070 |
| Avian proteins | Ovalbumin | Chicken (*Gallus gallus*) | P01012 |
|  | Ovotransferrin | Chicken (*Gallus gallus*) | P02789 |
|  | Ovoglobulin | Chicken (*Gallus gallus*) | I0J170 |
|  | Lysozyme | Chicken (*Gallus gallus*) | P00698 |
| Plant Proteins | Oleosins | Soybean (*Glycine max*) | P29530, P29531 |
|  | Leghemoglobin | Soybean (*Glycine max*) | Q41219 |

TABLE 3-continued

Non-milk proteins for use as fusion partners

| Categories | Protein or Protein family | Native Species | Exemplary Uniprot Accession No. |
|---|---|---|---|
| | Extensin-like protein family | Soybean (*Glycine soja*) | A0A445JU93 |
| | Prolamin | Rice (*Oryza sativa*) | Q0DJ45 |
| | Glutenin | Wheat (*Sorghum bicolor*) | P10388 |
| | Gamma-kafirin preprotein | Wheat (*Sorghum bicolor*) | Q41506 |
| | Alpha globulin | Rice (*Oryza sativa*) | P29835 |
| | Basic 7S globulin precursor | Soybean (*Glycine max*) | P13917 |
| | 2S albumin | Soybean (*Glycine max*) | P19594 |
| | Beta-conglycinins | Soybean (*Glycine max*) | P0DO16, P0DO15, P0DO15 |
| | Glycinins | Soybean (*Glycine max*) | P04347, P04776, P04405 |
| | Canein | Sugar cane (*Saccharum officinarum*) | ABP64791.1 |
| | Zein | Corn (*Zea Mays*) | ABP64791.1 |
| | Patatin | Tomato (*Solanum lycopersicum*) | P07745 |
| | Kunitz-Trypsin inhibitor | Soybean (*Glycine max*) | Q39898 |
| | Bowman-Birk inhibitor | Soybean (*Glycine max*) | I1MQD2 |
| | Cystatine | Tomato (*Solanum lycopersicum*) | Q9SE07 |
| Fungal proteins | Hydrophobin I | Fungus (*Trichoderma reesei*) | P52754 |
| | Hydrophobin II | Fungus (*Trichoderma reesei*) | P79073 |

In some embodiments, the non-milk protein may be an animal protein. For example, in some embodiments, the non-milk protein may be a mammalian protein. The mammalian protein may be, for example, hemoglobin or collagen. In some embodiments, the non-milk protein is an avian protein, such as ovalbumin, ovotransferrin, lysozyme or ovoglobulin.

In some embodiments, the non-milk protein is a plant protein. In some embodiments, the non-milk protein is a protein that is typically expressed in a seed. In some embodiments, the plant protein is a protein that is not typically expressed in a seed. In some embodiments, the plant protein is a storage protein, e.g., a protein that acts as a storage reserve for nitrogen, carbon, and/or sulfur. In some embodiments, the plant protein may inhibit one or more proteases. In some embodiments, the non-milk protein is a plant protein selected from: oleosins, leghemoglobin, extension-like protein family, prolamin, glutenin, gamma-kafirin preprotein, α-globulin, basic 7S globulin precursor, 2S albumin, β-conglycinins, glycinins, canein, zein, patatin, kunitz-trypsin inhibitor, bowman-birk inhibitor, and cystatine. Illustrative plant proteins that may be used to inhibit one or more proteases are shown below in Table 4. In some embodiments, the non-milk protein comprises the sequence of any one of SEQ ID NO: 840, 842, 844, 846, 848 or 850. In some embodiments, the non-milk protein comprises a sequence having at least 85%, at least 90%, at least 91%, at least 92%, at least 93%, at least 94%, at least 95%, at least 96%, at least 97%, at least 98%, or at least 99% identity to any one of SEQ ID NO: 840, 842, 844, 846, 848 or 850. In some embodiments, the non-milk protein comprises a sequence having the sequence of any one of SEQ ID NO: 840, 842, 844, 846, 848 or 850 plus at least 1, at least 2, at least 3, at least 4, at least 5, at least 6, at least 7, at least 8, at least 9, at least 10, at least 11, at least 12, at least 13, at least 14, at least 15, or more amino acid substitutions.

TABLE 4

Proteins capable of inhibiting plant proteases

| Protein Name | Short Name | Accession No. (Uniprot) | DNA Sequence | Protein Sequence |
|---|---|---|---|---|
| Bowman-Birk serine protease inhibitor D-II | GmBBID-II | Glyma16g33400 | 839 | 840 |
| Bowman-Birk serine protease inhibitor A1 | GMBBI-A1 | Glyma14g26410 | 841 | 842 |
| Kunitz-type trypsin inhibitor gene 1 | GmKTi1 | Glyma01g10900 | 843 | 844 |
| Kunitz-type trypsin inhibitor gene 2 | GmKTi2 | AAB23483 | 845 | 846 |
| Kunitz-type trypsin inhibitor gene 3 | GmKTi3 | Glyma08g45531 | 847 | 848 |
| Cystatine proteinase inhibitor (Cystatin) | SlCYS8 | | 849 | 850 |

In some embodiments, the structured protein is a fungal protein. For example, the fungal protein may be selected from hydrophobin I and hydrophobin II.

Fusion Proteins

Described herein are fusion proteins comprising at least first protein and a second protein. In some embodiments, at least one of the first protein and the second protein is a milk protein. In some embodiments, a fusion protein comprises at least two proteins, such as three, four, five, six, seven, eight, nine, or ten proteins, or more. In some embodiments, the proteins in the fusion proteins are linked via a linker. In some embodiments, the fusion proteins comprise one or more protease cleavage sites, such as one or more chymosin cleavage sites. Various illustrative embodiments of the fusion proteins of the disclosure are described in further detail below.

Fusion Protein Comprising a Milk Protein and a Non-Milk Protein

In some embodiments, a fusion protein comprises at least first protein and a second protein, wherein at least one of the first protein and the second protein is a milk protein, and at least one of the first protein and the second protein is a non-milk protein. In some embodiments, a fusion protein comprises at least two proteins, such as three, four, five, six, seven, eight, nine, or ten proteins, or more.

In some embodiments, the first protein is a milk protein and the second protein is a non-milk protein. In some embodiments, the non-milk protein is an avian protein. For example, the non-milk protein may be an avian protein selected from: ovalbumin, ovotransferrin, and ovoglobulin. In some embodiments, the non-milk protein is a protein capable of inhibiting one or more proteases, such as the proteins shown above in Table 4, or variants thereof.

In some embodiments, the fusion protein comprises α-S1 casein, or fragment thereof; and ovalbumin. In some embodiments, the fusion protein comprises α-S2 casein, or fragment thereof; and ovalbumin. In some embodiments, the fusion protein comprises β-casein, or fragment thereof; and ovalbumin. In some embodiments, the fusion protein comprises κ-casein, or fragment thereof; and ovalbumin. In some embodiments, the recombinant fusion protein comprises para-κ-casein, or fragment thereof; and ovalbumin.

In some embodiments, the fusion protein comprises α-S1 casein, or fragment thereof; and ovotransferrin. In some embodiments, the fusion protein comprises α-S2 casein, or fragment thereof; and ovotransferrin. In some embodiments, the fusion protein comprises β-casein, or fragment thereof; and ovotransferrin. In some embodiments, the fusion protein comprises κ-casein, or fragment thereof; and ovotransferrin. In some embodiments, the fusion protein comprises para-κ-casein, or fragment thereof; and ovotransferrin.

In some embodiments, the fusion protein comprises α-S1 casein, or fragment thereof; and ovoglobulin. In some embodiments, the fusion protein comprises α-S2 casein, or fragment thereof; and ovoglobulin. In some embodiments, the fusion protein comprises β-casein, or fragment thereof; and ovoglobulin. In some embodiments, the fusion protein comprises κ-casein, or fragment thereof; and ovoglobulin. In some embodiments, the fusion protein comprises para-k-casein, or fragment thereof; and ovoglobulin.

In some embodiments, the fusion protein comprises a non-milk protein that functions as a marker, such as green fluorescent protein (GFP). In some embodiments, the fusion protein comprises α-S1-casein, or fragment thereof; and GFP. In some embodiments, the fusion protein comprises α-S2-casein, or fragment thereof; and GFP. In some embodiments, the fusion protein comprises β-casein, or fragment thereof; and GFP. In some embodiments, the fusion protein comprises κ-casein, or fragment thereof; and GFP. In some embodiments, the fusion protein comprises para-κ-casein, or fragment thereof; and GFP.

In some embodiments, the fusion protein comprises a non-milk protein that is a plant protein. In some embodiments, the fusion protein comprises α-S1 casein, or fragment thereof; and a plant protein selected from the group consisting of hydrophobin I, hydrophobin II, oleosins, leghemoglobin, extension-like protein family, prolamin, glutenin, gamma-kafirin preprotein, α-globulin, basic 7S globulin precursor, 2S albumin, β-conglycinins, glycinins, canein, zein, patatin, kunitz-trypsin inhibitor, bowman-birk inhibitor, and cystatine.

In some embodiments, the fusion protein comprises α-S2-casein, or fragment thereof; and a plant protein selected from the group consisting of hydrophobin I, hydrophobin II, oleosins, leghemoglobin, extension-like protein family, prolamin, glutenin, gamma-kafirin preprotein, α-globulin, basic 7S globulin precursor, 2S albumin, β-conglycinins, glycinins, canein, zein, patatin, kunitz-trypsin inhibitor, bowman-birk inhibitor, and cystatine.

In some embodiments, the fusion protein comprises β-casein, or fragment thereof; and a plant protein selected from the group consisting of hydrophobin I, hydrophobin II, oleosins, leghemoglobin, extension-like protein family, prolamin, glutenin, gamma-kafirin preprotein, α-globulin, basic 7S globulin precursor, 2S albumin, β-conglycinins, glycinins, canein, zein, patatin, kunitz-trypsin inhibitor, bowman-birk inhibitor, and cystatine.

In some embodiments, the fusion protein comprises κ-casein, or fragment thereof; and a plant protein selected from the group consisting of hydrophobin I, hydrophobin II, oleosins, leghemoglobin, extension-like protein family, prolamin, glutenin, gamma-kafirin preprotein, α-globulin, basic 7S globulin precursor, 2S albumin, β-conglycinins, glycinins, canein, zein, patatin, kunitz-trypsin inhibitor, bowman-birk inhibitor, and cystatine.

In some embodiments, the fusion protein comprises para-κ-casein, or fragment thereof; and a plant protein selected from the group consisting of hydrophobin I, hydrophobin II, oleosins, leghemoglobin, extension-like protein family, prolamin, glutenin, gamma-kafirin preprotein, α-globulin, basic 7S globulin precursor, 2S albumin, β-conglycinins, glycinins, canein, zein, patatin, kunitz-trypsin inhibitor, bowman-birk inhibitor, and cystatine.

Fusion Proteins Comprising a Milk Protein and an Animal (e.g., Mammalian) Protein In some embodiments, the fusion proteins described herein comprise (i) a milk protein (which may be unstructured or structured), and (ii) an animal protein. In some embodiments, the fusion proteins described herein comprise (i) an unstructured milk protein, and (ii) a mammalian protein. In some embodiments, the fusion proteins described herein comprise (i) an unstructured milk protein, and (ii) an avian protein. In some embodiments, the fusion proteins described herein comprise (i) an unstructured milk protein, and (ii) a fungal protein.

In some embodiments, the fusion proteins comprise a milk protein, such as a casein protein. In some embodiments, the fusion protein comprises a milk protein selected from α-S1 casein, α-S2 casein, β-casein, and κ-casein. In some embodiments, the fusion protein comprises a milk protein isolated or derived from cow (*Bos taurus*), goat (*Capra hircus*), sheep (*Ovis aries*), water buffalo (*Bubalus bubalis*), dromedary camel (*camelus dromedaries*), bactrian camel (*camelus bactrianus*), wild yak (*Bos mutus*), horse (*Equus caballus*), donkey (*Equus asinus*), reindeer (*Rangifer tarandus*), eurasian elk (*Alces alces*), alpaca (*Vicugna pacos*), zebu (*Bos indicus*), llama (*Lama glama*), or human (*Homo sapiens*). In some embodiments, the fusion protein comprises a casein protein (e.g., α-S1 casein, α-S2 casein, β-casein, para-κ-casein or κ-casein) from cow (*Bos taurus*), goat (*Capra hircus*), sheep (*Ovis aries*), water buffalo (*Bubalus bubalis*), dromedary camel (*camelus dromedaries*), bactrian camel (*Camelus bactrianus*), wild yak (*Bos mutus*), horse (*Equus caballus*), donkey (*Equus asinis*), reindeer (*Rangifer tarandus*), eurasian elk (*Alces alces*), alpaca (*Vicugna pacos*), zebu (*Bos indicus*), llama (*Lama glama*), or human (*Homo sapiens*).

In some embodiments, the fusion protein comprises a milk protein found in Table 34. In some embodiments, the fusion protein comprises a milk protein that is a variant of a protein found in Table 34. In some embodiments, the fusion protein comprises a casein protein as found in Table 34 and/or a variant thereof. In some embodiments, the fusion protein comprises a beta-lactoglobulin as found in Table 34 and/or a variant thereof. One of skill in the art would be able to utilize the numerous milk proteins taught in Table 34, along with their associated SEQ ID NO and/or accession number and find such other milk proteins as encompassed by the disclosure.

In some embodiments, the fusion protein comprises a milk protein that shares at least 50%, at least 55%, at least 60%, at least 65%, at least 70%, at least 75%, at least 80%, at least 85%, at least 90%, at least 95%, or at least 100% sequence identity to a protein in Table 34 and/or a variant thereof. In some embodiments, the fusion protein comprises a milk protein that shares at least from about 70% to about 100% sequence identity to a protein in Table 34 and/or a variant thereof. In some embodiments, the fusion protein comprises a milk protein that shares at least from about 80% to about 100% sequence identity to a protein in Table 34 and/or a variant thereof. In some embodiments, the fusion protein comprises a milk protein that shares at least from about 90% to about 100% sequence identity to a protein in Table 34 and/or a variant thereof. In some embodiments, the fusion protein comprises a milk protein that shares at least 50%, 55%, 60%, 65%, 70%, 75%, 80%, 85%, 90%, 95%, or 100% sequence identity with any one of SEQ ID NO: 148-614. In some embodiments, the fusion protein comprises a milk protein that comprises a sequence of any one of SEQ ID NO: 148-614.

In some embodiments, the fusion protein is α-S1 casein. In some embodiments, the α-S1 casein comprises the sequence SEQ ID NO: 8, or a sequence at least 70%, 80%, 90%, at least 95%, at least 96%, at least 97%, at least 98%, or at least 99% identical thereto. In some embodiments, the α-S1 casein comprises the sequence of any one of SEQ ID NO: 99-109, or a sequence at least 90%, at least 95%, at least 96%, at least 97%, at least 98%, or at least 99% identical thereto.

In some embodiments, the fusion protein comprises α-S2 casein. In some embodiments, the α-S2 casein comprises the sequence SEQ ID NO: 84, or a sequence at least 70%, 80%, 90%, at least 95%, at least 96%, at least 97%, at least 98%, or at least 99% identical thereto. In some embodiments, the α-S2 casein comprises the sequence of any one of SEQ ID NO: 110-120, or a sequence at least 90%, at least 95%, at least 96%, at least 97%, at least 98%, or at least 99% identical thereto.

In some embodiments, the fusion protein comprises β-casein. In some embodiments, the β-casein comprises the sequence of SEQ ID NO: 6, or a sequence at least 70%, 80%, 90%, at least 95%, at least 96%, at least 97%, at least 98%, or at least 99% identical thereto. In some embodiments, the β-casein comprises the sequence of any one of SEQ ID NO: 121-133, or a sequence at least 90%, at least 95%, at least 96%, at least 97%, at least 98%, or at least 99% identical thereto.

In some embodiments, the fusion protein comprises κ-casein. In some embodiments, the κ-casein comprises the sequence of SEQ ID NO: 4, or a sequence at least 70%, 80%, 90%, at least 95%, at least 96%, at least 97%, at least 98%, or at least 99% identical thereto. In some embodiments, the κ-casein comprises the sequence of any one of SEQ ID NO: 85-98, or a sequence at least 90%, at least 95%, at least 96%, at least 97%, at least 98%, or at least 99% identical thereto.

In some embodiments, the fusion protein comprises para-κ-casein. In some embodiments, the para-κ-casein comprises the sequence of SEQ ID NO: 2, or a sequence at least 70%, 80%, 90%, at least 95%, at least 96%, at least 97%, at least 98%, or at least 99% identical thereto.

In some embodiments, the fusion protein comprises β-lactoglobulin, α-lactalbumin, albumin, lysozyme, lactoferrin, lactoperoxidase, or an immunoglobulin (e.g., IgA, IgG, IgM, or IgE).

In some embodiments, the fusion protein comprises β-lactoglobulin. In some embodiments, the β-lactoglobulin comprises the sequence of SEQ ID NO: 10, or a sequence at least 70%, 80%, 90%, at least 95%, at least 96%, at least 97%, at least 98%, or at least 99% identical thereto.

In some embodiments, the fusion protein comprises a mammalian protein selected from hemoglobin and collagen. In some embodiments, the fusion protein comprises an avian protein selected from ovalbumin, ovotransferrin, lysozyme and ovoglobulin.

In some embodiments, a fusion protein comprises a casein protein (e.g., κ-casein, para-κ-casein, β-casein, or α-S1 casein) and β-lactoglobulin. In some embodiments, a fusion protein comprises κ-casein and β-lactoglobulin (see, e.g., FIG. 4, FIG. 9, FIG. 12A-12B). In some embodiments, a fusion protein comprises para-κ-casein and β-lactoglobulin (see, e.g., FIG. 7, FIG. 8, FIG. 12A-12B). In some embodiments, a fusion protein comprises β-casein and β-lactoglobulin. In some embodiments, a fusion protein comprises α-S1 casein and β-lactoglobulin.

In some embodiments, a plant-expressed recombinant fusion protein comprises κ-casein, or fragment thereof; and β-lactoglobulin, or fragment thereof. In some embodiments, the fusion protein comprises, in order from N-terminus to C-terminus, the κ-casein and the β-lactoglobulin.

In some embodiments, a plant-expressed recombinant fusion protein comprises β-casein, or fragment thereof; and β-lactoglobulin, or fragment thereof. In some embodiments, the fusion protein comprises, in order from N-terminus to C-terminus, the β-casein and the β-lactoglobulin.

Fusion Proteins Comprising a Milk Protein and a Plant Protein

In some embodiments, the fusion proteins described herein comprise (i) a milk protein (which may be unstructured or structured), and (ii) a plant protein. In some embodiments, the milk protein is a casein protein, such as α-S1 casein, α-S2 casein, β-casein, or κ-casein. In some embodiments, the milk protein is β-lactoglobulin, α-lactalbumin, albumin, lysozyme, lactoferrin, lactoperoxidase, or an immunoglobulin (e.g., IgA, IgG, IgM, or IgE). In some embodiments, the plant protein is selected from the group consisting of: hydrophobin I, hydrophobin II, oleosins, leghemoglobin, extension-like protein family, prolamin, glutenin, gamma-kafirin preprotein, α-globulin, basic 7S globulin precursor, 2S albumin, β-conglycinins, glycinins, canein, zein, patatin, kunitz-trypsin inhibitor, bowman-birk inhibitor, and cystatine. In some embodiments, the plant protein is a protein that is capable of forming a protein body (PB), such as a prolamin. In some embodiments, the protein that is capable of forming a protein body comprises one or more repeat sequences, such as a repeat sequence selected from PPPPVHL (SEQ ID NO: 828); PPPPVXS, wherein X=S, Y, Q, or F (SEQ ID NO: 829); PPPV (SEQ ID NO: 830); PPVHX, wherein X=S or F (SEQ ID NO: 831); PPPVHS (SEQ ID NO: 832); PPPVXS, wherein X=Y, H, or F (SEQ ID NO: 833); PPPVXL, wherein X=H, or D (SEQ ID NO: 834); PPPVHL (SEQ ID NO: 835); PPPPPVYS (SEQ ID NO: 836); PPPPVHS (SEQ ID NO: 837); and PPPVHL (SEQ ID NO: 838). In some the repeat sequence repeats at least 2, at least 3, at least 4, at least 5, at least 6, at least 7, at least 8, at least 9 or at least 10 times.

Fusion Protein Comprising a Milk Protein and Prolamin

In some embodiments, the fusion protein comprises a prolamin protein, or a fragment or derivative thereof. Prolamins are a group of plant storage proteins having a high proline and glutamine amino acid content, and have poor solubility in water. They are found in plants, mainly in the seeds of cereal grants such as wheat (e.g., the gliadin class of proteins), barley (e.g., the hordein class of proteins), rye (e.g., the secalin class of proteins), corn (e.g., the zein class of proteins), sorghum (e.g., the kafirin class of proteins), and oats (e.g., the avenin class of proteins).

In some embodiments, a fusion protein comprises a canein, such as a gamma canein. For example, the canein may be a 27 kD gamma canein (gCan27), or a fragment or derivative thereof. gCan27 is a zein-like protein, known to be resident in the endoplasmic reticulum. An illustrative sequence for gCAN27 from sugar cane (*Saccharum officinarum*) can be found at Uniprot Ref. No. ABP64791.1 (SEQ ID NO: 800).

In some embodiments, the fusion protein comprises a canein, wherein the canein has the sequence of SEQ ID NO: 800, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises a canein, wherein the canein has the sequence of SEQ ID NO: 800 with 1-5, 5-10, 10-20, 20-30, or 30-50 amino acid substitutions relative thereto. In some embodiments, the fusion protein comprises a canein, wherein the canein has a sequence corresponding to amino acids 42-237 of SEQ ID NO: 800, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises a canein, wherein the canein has a sequence corresponding to amino acids 42-237 of SEQ ID NO: 800 with 1-5, 5-10, 10-20, 20-30, or 30-50 amino acid substitutions relative thereto. In some embodiments, the fusion protein comprises a canein, wherein the canein has the sequence of SEQ ID NO: 805, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises a canein, wherein the canein has the sequence of SEQ ID NO: 805 with 1-5, 5-10, 10-20, 20-30, or 30-50 amino acid substitutions relative thereto. In some embodiments, the canein is encoded by the DNA sequence of SEQ ID NO: 804.

In some embodiments, the fusion protein comprises a milk protein and canein, or a fragment thereof. In some embodiments, the fusion protein comprises a casein protein and canein, or a fragment thereof. In some embodiments, the fusion protein comprises α-S1 casein and canein. In some embodiments, the fusion protein comprises α-S2-casein and canein. In some embodiments, the fusion protein comprises β-casein and canein. In some embodiments, the fusion protein comprises κ-casein and canein. In some embodiments, the fusion protein comprises para-κ-casein and canein. In some embodiments, the fusion protein comprises β-lactoglobulin and canein. In some embodiments, the fusion protein comprises the sequence of SEQ ID NO: 803, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises the sequence of SEQ ID NO: 803, or a sequence with 1-5, 5-10, 10-20, 20-30, or 30-50 amino acid substitutions relative thereto. In some embodiments, the fusion protein is encoded by the DNA sequence of SEQ ID NO: 802.

In some embodiments, the fusion protein comprises a zein, such as gamma zein (γZein or glutenin 2). Zein is a storage protein of the prolamin class. It is found in the seeds of cereal plants and is able to accumulate within the endoplasmic reticulum (ER). In maize, for example, there are our classes of zeins (α, β, δ, γ). During endosperm development, γ- and β-zeins are synthesized first, forming a polymer termed protein bodies (PBs) where α- and δ-zein will later accumulate (Mainieri et al, 2018). Proteins in the ER lumen usually have a tetrapeptide at the C terminus (KDEL (SEQ ID NO: 23) or variations), which is necessary and sufficient for ER localization; however, zeins do not have this signal. The interactions that retain zeins in the ER are not well understood, but γ-zein is able to form ER-located PBs when expressed in storage (Coleman et al., 1996) or vegetative (Geli et al., 1994, Torrent et al., 2009, Marques et al 2020) tissues of transgenic plants in the absence of its partner zein subunits, indicating that no tissue-specific helper factors are required.

The γ-zein sequence (including the 27 kDa form of the protein) contains a signal peptide for translocation to the ER (co-translationally removed) followed by a region containing eight repeats of the hexapeptide PPPVHL (SEQ ID NO: 812), the prox domain and seven Cys residues involved in inter-chain bonds that make the protein insoluble in non-reducing conditions, and finally a second region (C-term) homologous to 2S albumins, which are vacuolar storage proteins present in various amounts in all land plants.

An illustrative sequence for γ-zein from corn (*Zea mays*) can be found at Uniprot Ref. No. P04706 (SEQ ID NO: 801). In some embodiments, the fusion protein comprises γ-zein, wherein the γ-zein has the sequence of SEQ ID NO: 801, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises a γ-zein, wherein the for γ-zein has the sequence of SEQ ID NO: 801 with 1-5, 5-10, 10-20, 20-30, or 30-50 amino acid substitutions relative thereto. In some embodiments, the fusion protein comprises γ-zein, wherein the γ-zein has a sequence corresponding to amino acids 17-112 of SEQ ID NO: 801, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises γ-zein, wherein the γ-zein has a sequence corresponding to amino acids 17-112 of SEQ ID NO: 801 with 1-5, 5-10, 10-20, 20-30, or 30-50 amino acid substitutions relative thereto. In some embodiments, the fusion protein comprises a γ-zein, wherein the γ-zein has a sequence corresponding to amino acids 20-223 of SEQ ID NO: 801, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises a γ-zein, wherein the γ-zein has a sequence corresponding to amino acids 20-223 of SEQ ID NO: 801 with 1-5, 5-10, 10-20, 20-30, or 30-50 amino acid substitutions relative thereto. In some embodiments, the fusion protein comprises a γ-zein, wherein the γ-zein has the sequence of SEQ ID NO: 809, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises a γ-zein, wherein the γ-zein has the sequence of SEQ ID NO: 809 with 1-5, 5-10, 10-20, 20-30, or 30-50 amino acid substitutions relative thereto. In some embodiments, the γ-zein is encoded by the DNA sequence of SEQ ID NO: 808. In some embodiments, the fusion protein comprises a γ-zein, wherein the γ-zein has the sequence of SEQ ID NO: 811, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises a γ-zein, wherein the γ-zein has the sequence of SEQ ID NO: 811 with 1-5, 5-10, 10-20, 20-30, or 30-50 amino acid substitutions relative thereto. In some embodiments, the γ-zein is encoded by the DNA sequence of SEQ ID NO: 810.

In some embodiments, the fusion protein comprises a milk protein and γ-zein, or a fragment thereof. In some embodiments, the fusion protein comprises a casein protein and γ-zein, or a fragment thereof. In some embodiments, the fusion protein comprises α-S1 casein and γ-zein. In some embodiments, the fusion protein comprises α-S2-casein and γ-zein. In some embodiments, the fusion protein comprises β-casein and γ-zein. In some embodiments, the fusion protein comprises κ-casein and γ-zein. In some embodiments, the fusion protein comprises para-κ-casein and γ-zein. In some embodiments, the fusion protein comprises β-lactoglobulin and γ-zein. In some embodiments, the fusion protein comprises the sequence of SEQ ID NO: 807, or a sequence at least 80%, at least 85%, at least 90%, at least 91%, at least 92%, at least 93%, at least 94%, at least 95%, at least 96%, at least 97%, at least 98%, or at least 99% identical thereto. In some embodiments, the fusion protein comprises the sequence of SEQ ID NO: 807, or a sequence with 1-5, 5-10, 10-20, 20-30, or 30-50 amino acid substitutions relative thereto. In some embodiments, the fusion protein is encoded by the DNA sequence of SEQ ID NO: 806.

Fusion Protein Comprising Two or More Milk Proteins

In some embodiments, the fusion proteins described herein comprise at least first protein and a second protein, wherein the first protein and/or second protein is a milk protein. In some embodiments, the first protein and the second protein are milk proteins. In some embodiments, each of the first protein and the second protein are independently selected from α-S1 casein, α-S2 casein, β-casein, κ-casein, para-κ-casein, β-lactoglobulin, α-lactalbumin, lysozyme, lactoferrin, lactoperoxidase, serum albumin, and immunoglobulins.

In some embodiments, the recombinant fusion protein comprises α-S1 casein, or fragment thereof; and β-lactoglobulin. In some embodiments, the recombinant fusion protein comprises α-S2 casein, or fragment thereof; and β-lactoglobulin. In some embodiments, the recombinant fusion protein comprises β-casein, or fragment thereof; and β-lactoglobulin. In some embodiments, the recombinant fusion protein comprises κ-casein, or fragment thereof; and β-lactoglobulin. In some embodiments, the recombinant fusion protein comprises para-κ-casein, or fragment thereof; and β-lactoglobulin.

In some embodiments, the recombinant fusion protein comprises α-S1 casein, or fragment thereof; and α-lactalbumin. In some embodiments, the recombinant fusion protein comprises α-S2 casein, or fragment thereof; and α-lactalbumin. In some embodiments, the recombinant fusion protein comprises β-casein, or fragment thereof; and α-lactalbumin. In some embodiments, the recombinant fusion protein comprises κ-casein, or fragment thereof; and α-lactalbumin. In some embodiments, the recombinant fusion protein comprises para-κ-casein, or fragment thereof; and α-lactalbumin.

In some embodiments, the recombinant fusion protein comprises α-S1 casein, or fragment thereof; and lysozyme. In some embodiments, the recombinant fusion protein comprises α-S2 casein, or fragment thereof; and lysozyme. In some embodiments, the recombinant fusion protein comprises β-casein, or fragment thereof; and lysozyme. In some embodiments, the recombinant fusion protein comprises κ-casein, or fragment thereof; and lysozyme. In some embodiments, the recombinant fusion protein comprises para-κ-casein, or fragment thereof; and lysozyme.

In some embodiments, the recombinant fusion protein comprises α-S1 casein, or fragment thereof; and lactoferrin. In some embodiments, the recombinant fusion protein comprises α-S2 casein, or fragment thereof; and lactoferrin. In some embodiments, the recombinant fusion protein comprises β-casein, or fragment thereof; and lactoferrin. In some embodiments, the recombinant fusion protein comprises κ-casein, or fragment thereof; and lactoferrin. In some embodiments, the recombinant fusion protein comprises para-κ-casein, or fragment thereof; and lactoferrin.

In some embodiments, the recombinant fusion protein comprises α-S1 casein, or fragment thereof; and lactoperoxidase. In some embodiments, the recombinant fusion protein comprises α-S2 casein, or fragment thereof; and lactoperoxidase. In some embodiments, the recombinant fusion protein comprises β-casein, or fragment thereof; and lactoperoxidase. In some embodiments, the recombinant fusion protein comprises κ-casein, or fragment thereof; and lactoperoxidase. In some embodiments, the recombinant fusion protein comprises para-κ-casein, or fragment thereof; and lactoperoxidase.

In some embodiments, the recombinant fusion protein comprises α-S1 casein, or fragment thereof; and an immunoglobulin. In some embodiments, the recombinant fusion protein comprises α-S2 casein, or fragment thereof; and an immunoglobulin. In some embodiments, the recombinant fusion protein comprises β-casein, or fragment thereof; and an immunoglobulin. In some embodiments, the recombinant fusion protein comprises κ-casein, or fragment thereof; and an immunoglobulin. In some embodiments, the recombinant fusion protein comprises para-κ-casein, or fragment thereof; and an immunoglobulin.

In some embodiments, the first protein and the second protein are casein proteins. In some embodiments, the fusion protein comprises κ-casein and para-κ-casein. In some embodiments, the fusion protein comprises κ-casein and β-casein. In some embodiments, the fusion protein comprises κ-casein and α-S1-casein. In some embodiments, the fusion protein comprises κ-casein and α-S2-casein. In some embodiments, the fusion protein comprises para-κ-casein and β-casein. In some embodiments, the fusion protein comprises para-κ-casein and α-S1-casein. In some embodiments, the fusion protein comprises para-κ-casein and α-S2-casein. In some embodiments, the fusion protein comprises β-casein and α-S1-casein. In some embodiments, the fusion protein comprises β-casein and α-S2-casein. In some embodiments, the fusion protein comprises α-S1-casein and α-S2-casein.

In some embodiments, the fusion protein comprises two of the same casein proteins. In some embodiments, the fusion protein comprises a first protein and a second protein, wherein each of the first and second proteins are κ-casein. In some embodiments, the fusion protein comprises a first protein and a second protein, wherein each of the first and second proteins are β-casein. In some embodiments, the fusion protein comprises a first protein and a second protein, wherein each of the first and second proteins are para-κ-casein. In some embodiments, the fusion protein comprises a first protein and a second protein, wherein each of the first and second proteins are α-S1-casein. In some embodiments, the fusion protein comprises a first protein and a second protein wherein each of the first and second proteins are α-S2-casein.

In some embodiments, the fusion protein comprises, form N-terminus to C-terminus, a para-kappa-casein and a beta-lactoglobulin. In some embodiments, the fusion protein comprises, from N-terminus to C-terminus, a beta-lactoglobulin and a para-kappa-casein. In some embodiments, the fusion protein comprises, from N-terminus to C-terminus, an alpha-S1-casein and a beta-lactoglobulin. In some embodiments, the fusion protein comprises, from N-terminus to C-terminus, a beta-lactoglobulin and an alpha-S1-casein. In some embodiments, the fusion protein comprises, from N-terminus to C-terminus, a beta-casein and a beta-lactoglobulin. In some embodiments, the fusion protein comprises from N-terminus to C-terminus, a beta-lactoglobulin and a beta-casein.

Fusion Proteins Comprising a Milk Protein and a Fusion Partner

In some embodiments, a fusion protein comprises a milk protein and a fusion partner having one or more desirable characteristics. For example, in some embodiments, a fusion protein comprises a first protein and a second protein, wherein the first protein is a milk protein, and the second protein comprises at least one of the following characteristics: (i) a molecular weight of 15 kDa or higher; (ii) at least 30% hydrophobic amino acids; and/or (iii) less than about 2.5 disulfide bonds per 10 kDa molecular weight. In some embodiments, the second protein comprises at least two of the characteristics (i), (ii) and (iii). In some embodiments, the second protein comprises all three of the characteristics (i), (ii) and (iii).

In some embodiments, a fusion protein comprises a milk protein and a fusion partner, wherein the fusion partner has a molecular weight of 15 kDa or higher. In some embodiments, a fusion protein comprises a milk protein and a fusion partner, wherein the fusion partner has at least 30% hydrophobic amino acids. In some embodiments, a fusion protein comprises a milk protein and a fusion partner, wherein the fusion partner has less than about 2.5 disulfide bonds per 10 kDa molecular weight. In some embodiments, a fusion protein comprises a milk protein and a fusion partner, wherein the fusion partner has a molecular weight of 15 kDa or higher, and at least 30% hydrophobic amino acids. In some embodiments, a fusion protein comprises a milk protein and a fusion partner, wherein the fusion partner has at least 30% hydrophobic amino acids, and less than about 2.5 disulfide bonds per 10 kDa molecular weight. In some embodiments, a fusion protein comprises a milk protein and a fusion partner, wherein the fusion partner has a molecular weight of 15 kDa or higher, and less than about 2.5 disulfide bonds per 10 kDa molecular weight. In some embodiments, a fusion protein comprises a milk protein and a fusion partner, wherein the fusion partner has a molecular weight of 15 kDa or higher, at least 30% hydrophobic amino acids, and less than about 2.5 disulfide bonds per 10 kDa molecular weight.

In some embodiments, the fusion protein comprises a protease cleavage site located between the first protein and the second protein. In some embodiments, the protease cleavage site is a chymosin cleavage site. In some embodiments, cleavage of the fusion protein with a protease separates the first protein from the second protein. In some embodiments, after being separated from one another, the first protein and/or the second protein optionally comprise at their N-terminus or C-terminus one or more amino acids that do not occur in the native form of the first protein or the second protein and that are derived from the protease cleavage site.

Fusion Proteins Comprising More than Two Proteins

Fusion proteins may also be created that comprise more than two proteins, such as at least 3, at least 4, at least 5, at least 6, at least 7, at least 8, at least 9, or at least 10, or more proteins. In some embodiments, a fusion protein comprising more than two proteins may comprise at least one milk protein. In some embodiments, a fusion protein comprising more than two proteins may comprise at least one casein protein. In some embodiments, each of the proteins in a fusion protein comprising more than two proteins may be a milk protein. In some embodiments, each of the proteins in a fusion protein comprising more than two proteins may be a casein protein.

In some embodiments, a fusion protein comprising more than two proteins may comprise at least one structured protein and at least one structured protein. In some embodiments, a fusion protein comprising more than two proteins may comprise at least one milk protein (e.g., a casein) and at least one non-milk protein. In some embodiments, a fusion protein comprising more than two proteins may comprise at least one milk protein (e.g., a casein) and at least one plant protein. In some embodiments, a fusion protein comprising more than two proteins may comprise at least one milk protein (e.g., a casein) and at least one animal (e.g., mammalian) protein.

In some embodiments, a fusion protein comprises three proteins, wherein each protein is individually selected from α-S1 casein, α-S2 casein, β-casein, κ-casein, para-κ-casein, β-lactoglobulin, α-lactalbumin, lysozyme, lactoferrin, lactoperoxidase, serum albumin, and an immunoglobulin. In some embodiments, a fusion protein comprises four proteins, wherein each protein is individually selected from α-S1 casein, α-S2 casein, β-casein, κ-casein, para-κ-casein, β-lactoglobulin, α-lactalbumin, lysozyme, lactoferrin, lactoperoxidase, serum albumin, and an immunoglobulin. In some embodiments, a fusion protein comprises five proteins, wherein each protein is individually selected from α-S1 casein, α-S2 casein, β-casein, κ-casein, para-κ-casein, β-lactoglobulin, α-lactalbumin, lysozyme, lactoferrin, lactoperoxidase, serum albumin, and an immunoglobulin. In some embodiments, a fusion protein comprises six proteins, wherein each protein is individually selected from α-S1 casein, α-S2 casein, β-casein, κ-casein, para-κ-casein, β-lactoglobulin, α-lactalbumin, lysozyme, lactoferrin, lactoperoxidase, serum albumin, and an immunoglobulin. In some embodiments, a fusion protein comprises seven proteins, wherein each protein is individually selected from α-S1 casein, α-S2 casein, β-casein, κ-casein, para-κ-casein, β-lactoglobulin, α-lactalbumin, lysozyme, lactoferrin, lactoperoxidase, serum albumin, and an immunoglobulin. In some embodiments, a fusion protein comprises eight proteins, wherein each protein is individually selected from α-S1 casein, α-S2 casein, β-casein, κ-casein, para-κ-casein, β-lactoglobulin, α-lactalbumin, lysozyme, lactoferrin, lactoperoxidase, serum albumin, and an immunoglobulin. In some embodiments, a fusion protein comprises nine proteins, wherein each protein is individually selected from α-S1 casein, α-S2 casein, β-casein, κ-casein, para-κ-casein, β-lactoglobulin, α-lactalbumin, lysozyme, lactoferrin, lactoperoxidase, serum albumin, and an immunoglobulin. In some embodiments, a fusion protein comprises ten proteins, wherein each protein is individually selected from α-S1 casein, α-S2 casein, β-casein, κ-casein, para-κ-casein, β-lactoglobulin, α-lactalbumin, lysozyme, lactoferrin, lactoperoxidase, serum albumin, and an immunoglobulin.

In some embodiments, a fusion protein comprises three proteins, wherein each protein is individually selected from α-S1 casein, α-S2 casein, β-casein, κ-casein, and para-κ-casein. In some embodiments, a fusion protein comprises four proteins, wherein each protein is individually selected from α-S1 casein, α-S2 casein, β-casein, κ-casein, and para-κ-casein. In some embodiments, a fusion protein comprises five proteins, wherein each protein is individually selected from α-S1 casein, α-S2 casein, β-casein, κ-casein, and para-κ-casein. In some embodiments, a fusion protein comprises six proteins, wherein each protein is individually selected from α-S1 casein, α-S2 casein, β-casein, κ-casein, and para-κ-casein. In some embodiments, a fusion protein comprises seven proteins, wherein each protein is individually selected from α-S1 casein, α-S2 casein, β-casein, κ-casein, and para-κ-casein. In some embodiments, a fusion protein comprises eight proteins, wherein each protein is individually selected from α-S1 casein, α-S2 casein, β-casein, κ-casein, and para-κ-casein. In some embodiments, a fusion protein comprises nine proteins, wherein each protein is individually selected from α-S1 casein, α-S2 casein, β-casein, κ-casein, and para-κ-casein. In some embodiments, a fusion protein comprises ten proteins, wherein each protein is individually selected from α-S1 casein, α-S2 casein, β-casein, κ-casein, and para-κ-casein.

In some embodiments, a fusion protein comprises between 3 and 10 proteins, wherein each protein is different. In some embodiments, a fusion protein comprises between 3 and 10 proteins, wherein each protein is the same. In some embodiments, a fusion protein comprises between 3 and 10 proteins, wherein each protein is a milk protein. In some embodiments, a fusion protein comprises between 3 and 10 proteins, wherein each protein is a casein.

In some embodiments, a fusion protein comprises a first, a second, and a third protein, wherein the first protein is beta casein, the second protein is kappa casein, and the third protein is beta-lactoglobulin. See, e.g., SEQ ID NO: 652.

In some embodiments, a fusion protein comprises a first, second, a third, and a fourth protein, wherein the first protein is kappa casein, the second protein is beta casein, the third protein is alpha-S1-casein, and the fourth protein is beta-lactoglobulin. In some embodiments, a fusion protein comprises a first, second, and third protein, wherein the first protein is kappa casein, the second protein is beta casein, the third protein is beta-lactoglobulin. In some embodiments, a fusion protein comprises a first, second, and third protein, wherein the first protein is kappa casein, the second protein is alpha-S1-casein, the third protein is beta-lactoglobulin. In some embodiments, a fusion protein comprises a first, second, and third protein, wherein the first protein is beta-casein, the second protein is alpha-S1-casein, the third protein is beta-lactoglobulin. In some embodiments, a fusion protein comprises a first, second, and third protein, wherein the first protein is kappa-casein, the second protein is beta-casein, the third protein is alpha-S1-casein.

In some embodiments, a fusion protein comprising a first, second, third, and fourth protein, wherein the third protein is kappa-casein. In some embodiments, a fusion protein comprising a first, second, third, and fourth protein, wherein the third protein is kappa-casein and the fourth protein is beta-lactoglobulin. In some embodiments, the kappa-casein comprises a chymosin cleavage site. In some embodiments, cleavage of the fusion protein with chymosin produces the following polypeptides: (a) a first polypeptide comprising the first protein, the second protein, and para-kappa-casein; (b) a second polypeptide comprising a kappa-casein macropeptide and the fourth protein.

In some embodiments, a fusion protein comprises a first, second, third, and fourth protein, wherein the first protein is beta-casein, the second protein is beta-casein, the third protein is kappa-casein, and the fourth protein is beta-lactoglobulin. See, e.g., SEQ ID NO: 652.

In some embodiments, a fusion protein comprises a first, second, third, fourth, and fifth protein wherein the first protein is beta-casein, the second protein is beta-casein, the third protein is beta-casein, the fourth protein is kappa-casein, and the fifth protein is beta-lactoglobulin. See, e.g., SEQ ID NO: 654.

In some embodiments, a fusion protein comprises a first, second, third, fourth, fifth, and sixth protein wherein the first protein is beta-casein, the second protein is beta-casein, the third protein is beta-casein, the fourth protein is beta-casein, the fifth protein is kappa-casein, and the sixth protein is beta-lactoglobulin. See, e.g., SEQ ID NO: 656.

In some embodiments, a fusion protein comprises a first, second, third, fourth, and fifth protein wherein the first protein is beta-casein, the second protein is beta-casein, the third protein is beta-casein, the fourth protein is beta-casein, and the fifth protein is beta-lactoglobulin. See, e.g., SEQ ID NO: 658 and 662.

In some embodiments, a fusion protein comprises a first, second, third, and fourth protein, wherein the first protein is beta-casein, the second protein is beta-casein, the third protein is beta-casein, and the fourth protein is beta-lactoglobulin. See, e.g., SEQ ID NO: 660.

In some embodiments, a fusion protein comprises a first, second, third, and fourth protein, wherein the first protein is beta-casein, the second protein is beta-casein, the third protein is beta-casein, and the fourth protein is beta-casein. See, e.g., SEQ ID NO: 664.

Table 5 lists illustrative fusion proteins contemplated by the instant disclosure. The fusion proteins comprise the listed constituent proteins in order from N-terminus to C-terminus. As will be understood by those of skill in the art, in some embodiments, a fusion protein may comprise the constituent proteins in order from C-terminus to N-terminus. In some embodiments, one or more of the fusion proteins may comprise a protease cleavage site, such as a protease cleavage site located between two of the constituent proteins.

TABLE 5

Illustrative Fusion Proteins

| Fusion Protein No. | First Protein | Second Protein | Third Protein | Fourth Protein | Fifth Protein | Sixth Protein |
|---|---|---|---|---|---|---|
| 1 | BC | LG | | | | |
| 2 | BC | BC | LG | | | |
| 3 | BC | BC | KCN | LG | | |
| 4 | BC | BC | BC | KCN | LG | |
| 5 | BC | BC | BC | BC | BC | |
| 6 | BC | aS1 | aS1 | BC | | |

TABLE 5-continued

Illustrative Fusion Proteins

| Fusion Protein No. | First Protein | Second Protein | Third Protein | Fourth Protein | Fifth Protein | Sixth Protein |
|---|---|---|---|---|---|---|
| 7 | BC | aS1 | aS1 | BC | LG | |
| 8 | BC | aS1 | BC | | | |
| 9 | ZN | BC | | | | |
| 10 | ZN27 | BC | | | | |
| 11 | BC | BC | | | | |
| 12 | BC | BC | BC | | | |
| 13 | BC | BC | BC | LG | | |
| 14 | BC | BC | BC | BC | LG | |
| 15 | KCN | BC | BC | BC | | |
| 16 | KCN | BC | BC | | | |
| 17 | KCN | BC | aS1 | LG | | |
| 18 | BC | BC | aS1 | aS1 | BC | BC |
| 19 | paraKCN | paraKCN | paraKCN | BC | BC | |
| 20 | BC | aS1 | KCN | | | |
| 21 | aS1 | LG | | | | |
| 22 | KCN | LG | | | | |
| 23 | paraKCN | LG | | | | |
| 24 | aS1 | aS1 | aS1 | aS1 | | |
| 25 | KCN | KCN | KCN | KCN | | |
| 26 | aS1 | aS1 | aS1 | aS1 | LG | |
| 27 | KCN | KCN | KCN | KCN | LG | |
| 28 | paraKCN | paraKCN | paraKCN | paraKCN | LG | |
| 29 | paraKCN | paraKCN | paraKCN | paraKCN | | |
| 30 | KCN | BC | aS1 | LG | | |
| 31* | KCN | BC | aS1 | | | |
| 32* | KCN | BC | | | | |
| 33* | BC | BC | BC | BC | | |

BC = beta-casein, LG = beta-lactoglobulin, KCN = kappa-casein; paraKCN = para-kappa-casein, aS1 = alpha-S1-casein, ZN = truncated zein, ZN27 = full-length zein
*indicates that the vector used to express the listed fusion protein also comprises a sequence encoding a Fam kinase, wherein the Fam kinase is expressed under the control of a different promoter.

Fusion Protein Structure

The fusion proteins described herein may have various different structures, in order to increase expression and/or accumulation in a plant or other host organism or cell. The designation of "first protein", "second protein", "third protein", and/or "fourth protein" is not intended to imply any order.

In some embodiments, the fusion protein may comprise, from N-terminus to C-terminus, the first protein and the second protein. In some embodiments, the fusion protein may comprise, from N-terminus to C-terminus, the second protein and the first protein. In some embodiments, a fusion protein comprises, in order from N-terminus to C-terminus, a first protein and a second protein, wherein the first protein and/or the second protein is a milk protein. In some embodiments, a fusion protein comprises, in order from N-terminus to C-terminus, a second protein and a first protein, wherein the first protein and/or the second protein is a milk protein. For example, in some embodiments, a fusion protein comprises, in order from N-terminus to C-terminus, κ-casein and β-lactoglobulin. In some embodiments, a fusion protein comprises, in order from N-terminus to C-terminus, β-lactoglobulin and κ-casein. In some embodiments, a fusion protein comprises, in order from N-terminus to C-terminus, para-κ-casein and β-lactoglobulin. In some embodiments, a fusion protein comprises, in order from N-terminus to C-terminus, β-lactoglobulin and para-k-casein. In some embodiments, a fusion protein comprises, in order from N-terminus to C-terminus, β-casein and β-lactoglobulin. In some embodiments, a fusion protein comprises, in order from N-terminus to C-terminus, β-lactoglobulin and β-casein. In some embodiments, a fusion protein comprises, in order from N-terminus to C-terminus, α-S1 casein and β-lactoglobulin. In some embodiments, a fusion protein comprises, in order from N-terminus to C-terminus, β-lactoglobulin and α-S1 casein.

In some embodiments, a fusion protein comprises, in order from N-terminus to C-terminus, a milk protein and a plant protein. In some embodiments, a fusion protein comprises, in order from N-terminus to C-terminus, a plant protein and a milk protein. In some embodiments, a fusion protein comprises, in order from N-terminus to C-terminus, a casein protein and a plant protein. In some embodiments, a fusion protein comprises, in order from N-terminus to C-terminus, a plant protein and a casein protein.

Cleavable Fusion Proteins

In some embodiments, it may be desirable to cleave the fusion protein to separate its constituent proteins. For example, it may be desirable to cleave the fusion protein to separate its constituent proteins so that the proteins may individually be used in one or more food compositions.

In some embodiments, a fusion protein comprises a protease cleavage site. For example, in some embodiments, the fusion protein comprises an endoprotease, endopeptidase, and/or endoproteinase cleavage site. In some embodiments, the fusion protein comprises a rennet cleavage site. In some embodiments, the fusion protein comprises a chymosin cleavage site. In some embodiments, the fusion protein comprises a trypsin cleavage site.

The protease cleavage site may be located between the first protein and the second protein. In some embodiments, the protease cleavage site may be located between a milk protein and the non-milk protein. For example, the protease cleavage site may be located between the milk protein and the animal (e.g., mammalian or avian) protein, or between the milk protein and the plant protein, such that cleavage of the protein at the protease cleavage site will separate the two proteins. In some embodiments, the protease cleavage site may be located between a first milk protein and a second milk protein. In some embodiments, the protease cleavage site may be located between a first casein protein and a second casein protein.

In some embodiments, the protease cleavage site may be contained within the sequence of the first protein or the second protein. In some embodiments, the protease cleavage site may be located in either the milk protein or the non-milk protein, for example, the animal (e.g., mammalian or animal) or plant protein. In some embodiments, the protease cleavage site may be added separately, for example, between the two proteins.

In some embodiments, a fusion protein comprises a chymosin cleavage site. In some embodiments, a fusion protein comprises a chymosin cleavage site selected from any one of the sequences shown in Table 6, below. In some embodiments, a fusion protein comprises a chymosin cleavage site that is not shown in Table 6, below. In some embodiments, a fusion protein comprises a chymosin cleavage site having at least 1, at least 2, at least 3 or at least 4 amino acid substitutions relative to any one of the sequences shown in Table 6. In some embodiments, a fusion protein comprises a chymosin cleavage site with a sequence of any one of SEQ ID NO: 665-668, or a sequence having 1, 2, 3, 4, or more amino acid substitutions relative thereto. In the sequences of Table 6, cleavage typically occurs after the underlined residue.

TABLE 6

Chymosin cleavage sites

| Chymosin Cleavage Site | SEQ ID NO: |
|---|---|
| RHPHPHLSFMAIPPKK | 665 |
| HPHPHLSFMAIPPK | 666 |
| RHPHPHLSFM | 667 |
| EDFLQKQQYGISSKFR | 668 |
| RHPHPHLSFMAIPPKK | 669 |
| HHPHPHLSFMAIPPKK | 670 |
| RHPHPRLSFMAIPPKK | 671 |
| RRPRPHLSFMAIPPKK | 672 |
| HQTFQHASFIATPPQK | 673 |
| RRPNLHPSFIAIPPKK | 674 |
| PYAIPNPSFLAMPTNE | 675 |
| PHPIPNPSFLAIPTNE | 676 |
| RHPCPHPSFIAIPPKK | 677 |
| ARRPPHASFIAIPPKK | 678 |
| VGRHSHPFFMAILPNK | 679 |
| RRPRPRPSFIAIPPKK | 680 |
| RHPRPHPSFIAIPPKX | 681 |
| RHPYRRPSFIAIPPKK | 682 |
| RHPHLPASFIVIPPKK | 683 |
| CRRPHPSFLAIPPXK | 684 |
| HRPNLHPSFIAIPPKK | 685 |
| HRPQLHPSFIAIPPKK | 686 |
| HRPHIHPSFIAIPPKK | 687 |
| HRPHLHPSFIAIPPKK | 688 |
| HRPHLHPSFIAIPAKK | 689 |
| HHPHPCPSFLAIPPKK | 690 |
| HRPHLHPSFTAIPAKK | 691 |
| HHPHPRPSFTAIPPKK | 692 |
| HHPHPRPSFLAIPPKK | 693 |
| HRPHLHPSFIAIPTKK | 694 |
| HHKYLKPSFIVIPPTK | 695 |
| RHPRPHPSFIAIPPKK | 696 |
| YHQAKHPSFMAILSKK | 697 |
| PHTYLKPPFIVIPPKK | 698 |
| HRPKLHPSFIAVPPKK | 699 |
| RRPHPRLSFMAIPPKK | 700 |
| KPAEFFRL | 701 |
| KPAEFKRL | 702 |
| KPAEFERL | 703 |
| KPAEFTRL | 704 |
| KPAEFGRL | 705 |
| KPAEFARL | 706 |
| KPAEFVRL | 707 |
| KPAEFLRL | 708 |
| KPAEFIRL | 709 |
| HPHLSFMAI | 710 |
| HPHLSFEAI | 711 |
| YGIFLRF | 712 |
| YGIFKRF | 713 |
| YGAFLRF | 714 |
| KYSSWYVAL | 715 |
| KYSSWKVAL | 716 |
| KYSSWEVAL | 717 |
| KYSSWLVAL | 718 |
| RPKPQQFFGLM | 719 |
| RPKPQQFKGLM | 720 |
| AFPLEFKREL | 721 |
| AFPLEFKREL | 722 |
| AFPLEFEREL | 723 |
| AFPLEFEREL | 724 |
| AFPLEFIREL | 725 |
| AFPLEFFREL | 726 |
| KIPYILKRQL | 727 |
| KIPYILRRQL | 728 |
| KIPYILERQL | 729 |
| KIPYILSRQL | 730 |
| KIPYILARQL | 731 |
| KIPYILIRQL | 732 |
| KIPYILFRQL | 733 |
| KIPYILFRQL | 734 |
| KIPYILWRQL | 735 |
| EDFLQKQQYGISSKYSGFG | 736 |
| EDFLQKQQYGISSKFM | 737 |
| EDFLQKQQYGISSKFA | 738 |
| EDFLQKQQYGISSKFC | 739 |
| EDFLQKQQYGISSKFF | 740 |

TABLE 6-continued

Chymosin cleavage sites

| Chymosin Cleavage Site | SEQ ID NO: |
|---|---|
| EDFLQKQQYGISSKFH | 741 |
| EDFLQKQQYGISSKFI | 742 |
| EDFLQKQQYGISSKFK | 743 |
| EDFLQKQQYGISSKFL | 744 |
| EDFLQKQQYGISSKFN | 745 |
| EDFLQKQQYGISSKFR | 746 |
| EDFLQKQQYGISSKFT | 747 |
| EDFLQKQQYGISSKFV | 748 |
| EDFLQKQQYGISSKFW | 749 |
| EDFLQKQQYGISSKYSGFV | 750 |
| EDFLQKQQYGISSKYSGFV | 751 |
| EDFLQKQQYGISSKYSGFM | 752 |
| EDFLQKQQYGISSKYSGFM | 753 |
| EDFLQKQQYGISSKYSGFS | 754 |
| EDFLQKQQYGISSKSSGFV | 755 |
| EDFLQKQQYGISSKSSGFV | 756 |
| EDFLQKQQYGISSKSSGFV | 757 |
| EDFLQKQQYGISSKYV | 758 |
| EDFLQKQQYGISSKFS | 759 |

In some embodiments, a fusion protein comprises a cleavage site recognized by an endoprotease. For example, in some embodiments, a fusion protein comprises a cleavage site selected from any one of the sequences shown in Table 7, below. In some embodiments, a fusion protein comprises a cleavage site having at least 1, at least 2, at least 3 or at least 4 amino acid substitutions relative to any one of the sequences shown in Table 7. In the sequences of Table 7, cleavage typically occurs after the underlined residue.

TABLE 7

Endoprotease Cleavage Sites

| Cleavage Site | SEQ ID NO: | Endoprotease |
|---|---|---|
| DDDDK | 760 | Enterokinase |
| HPHLSFMAI | 761 | Pepsin A |
| HPHLSFEAI | 762 | Pepsin A |
| LVPRG | 763 | Thrombin |
| ELSLSRLRDSA | 764 | Thrombin |
| ELSLSRLR | 765 | Thrombin |
| DNYTRLRK | 766 | Thrombin |
| YTRLRKQM | 767 | Thrombin |
| APSGRVSM | 768 | Thrombin |

TABLE 7-continued

Endoprotease Cleavage Sites

| Cleavage Site | SEQ ID NO: | Endoprotease |
|---|---|---|
| VSMIKNLQ | 769 | Thrombin |
| RIRPKLKW | 770 | Thrombin |
| AMAPRERK | 771 | Thrombin |
| NFFWKTFT | 772 | Thrombin |
| KMYPRGNH | 773 | Thrombin |
| QTYPRTNT | 774 | Thrombin |
| IQGR | 775 | Factor Xa |
| IEGR | 776 | Factor Xa |
| ENLYFQ(G/S) (G/S = G or S) | 777 | TEV protease |
| EXXYXQ(G/S) (x = any amino acid, G/S = G or S) | 778 | TEV protease |
| VDVADX (x = any amino acid) | 779 | Caspase 2 |
| RXXR (x = any amino acid) | 780 | Furin |
| XX(T/A/S/V)XX (x = any amino acid) | 781 | Alpha-lytic protease |

In some embodiments, a fusion protein comprises a cleavage site that is sensitive to cleavage by one or more chemical agents, such as nickel, formic acid, or hydroxylamine. For example, in some embodiments, a fusion protein comprises a chemical cleavage site selected from any one of the sequences shown in Table 8, below. In the sequences of Table 8, cleavage typically occurs after the underlined residue.

TABLE 8

Chemical Cleavage Sites

| Chemical Cleavage Site | SEQ ID NO: | Chemical agent |
|---|---|---|
| GSHHW | 782 | Nickel |
| DP | — | Formic Acid |
| NG | — | Hydroxylamine |

In some embodiments, the fusion protein comprises a protease cleavage site that comprises the amino acids residues F and M (phenylalanine and methionine). Without being bound by any theory, it is believed that one or more enzymes (e.g., chymosin) and cleave between the F and the M. When a protease, such as chymosin, is used to cleave a fusion protein comprising an FM cleavage site, the first protein comprises the F at its C terminus and the second protein comprises a M at its N terminus when liberated from the fusion protein. For example, a protein separated from a fusion protein by cleavage of an FM site may comprise the sequence of any one of SEQ ID NO: 782-791. Thus, in some embodiments, a protein derived from (i.e., separated from) a fusion protein may comprise at least one non-native amino acid. In some embodiments, the non-native amino acid is derived from a protease cleavage site.

In some embodiments, a fusion protein comprises a linker between the first protein and the second protein. In some embodiments, the linker is between the milk protein and the animal (e.g., mammalian or avian) protein, or between the milk protein and the plant protein. In some embodiments, the linker is between a first milk protein and a second milk protein. In some embodiments, the linker is between a first casein protein and a second casein protein. In some embodiments, the linker may comprise a peptide sequence recognizable by an endoprotease. In some embodiments, the linker may comprise a protease cleavage site. In some embodiments, the linker may comprise a self-cleaving peptide, such as a 2A peptide.

In some embodiments, a fusion protein may comprise a signal peptide. The signal peptide may be cleaved from the fusion protein, for example, during processing or transport of the protein within the cell. In some embodiments, the signal peptide is located at the N-terminus of the fusion protein. In some embodiments, the signal peptide is located at the C-terminus of the fusion protein.

In some embodiments, the signal peptide is selected from the group consisting of GmSCB1, StPat21, 2Sss, Sig2, Sig12, Sig8, Sig10, Sig11, and Coixss. In some embodiments, the signal peptide is Sig10 and comprises SEQ ID NO: 15, or a sequence at least 90%, at least 95%, at least 96%, at least 97%, at least 98%, or at least 99% identical thereto. In some embodiments, the signal peptide is Sig2 and comprises SEQ ID NO: 17, or a sequence at least 90%, at least 95%, at least 96%, at least 97%, at least 98%, or at least 99% identical thereto.

In some embodiments, the fusion protein comprises the sequence of SEQ ID NO: 71. In some embodiments, the fusion protein comprises the sequence of SEQ ID NO: 73. In some embodiments, the fusion protein comprises the sequence of SEQ ID NO: 75. In some embodiments, the fusion protein comprises the sequence of SEQ ID NO: 77. In some embodiments, the fusion protein comprises the sequence of SEQ ID NO: 79. In some embodiments, the fusion protein comprises the sequence of SEQ ID NO: 81. In some embodiments, the fusion protein comprises the sequence of SEQ ID NO: 135. In some embodiments, the fusion protein comprises the sequence of SEQ ID NO: 137. In some embodiments, the fusion protein comprises the sequence of SEQ ID NO: 616. In some embodiments, the fusion protein comprises the sequence of SEQ ID NO: 618. In some embodiments, the fusion protein comprises the sequence of SEQ ID NO: 620. In some embodiments, the fusion protein comprises the sequence of SEQ ID NO: 622. In some embodiments, the fusion protein comprises the sequence of SEQ ID NO: 624. In some embodiments, the fusion protein comprises the sequence of SEQ ID NO: 626. In some embodiments, the fusion protein comprises the sequence of SEQ ID NO: 628. In some embodiments, the fusion protein comprises the sequence of SEQ ID NO: 630. In some embodiments, the fusion protein comprises the sequence of SEQ ID NO: 632. In some embodiments, the fusion protein comprises the sequence of SEQ ID NO: 634. In some embodiments, the fusion protein comprises the sequence of SEQ ID NO: 636. In some embodiments, the fusion protein comprises the sequence of SEQ ID NO: 638. In some embodiments, the fusion protein comprises the sequence of SEQ ID NO: 640. In some embodiments, the fusion protein comprises the sequence of SEQ ID NO: 642. In some embodiments, the fusion protein comprises the sequence of SEQ ID NO: 644. In some embodiments, the fusion protein comprises the sequence of SEQ ID NO: 646. In some embodiments, the fusion protein comprises the sequence of SEQ ID NO: 648. In some embodiments, the fusion protein comprises the sequence of SEQ ID NO: 650. In some embodiments, the fusion protein comprises the sequence of SEQ ID NO: 652. In some embodiments, the fusion protein comprises the sequence of SEQ ID NO: 654. In some embodiments, the fusion protein comprises the sequence of SEQ ID NO: 656. In some embodiments, the fusion protein comprises the sequence of SEQ ID NO: 658. In some embodiments, the fusion protein comprises the sequence of SEQ ID NO: 660. In some embodiments, the fusion protein comprises the sequence of SEQ ID NO: 662. In some embodiments, the fusion protein comprises the sequence of SEQ ID NO: 664. In some embodiments, the fusion protein comprises the sequence of SEQ ID NO: 793. In some embodiments, the fusion protein comprises the sequence of SEQ ID NO: 795. In some embodiments, the fusion protein comprises the sequence of SEQ ID NO: 797. In some embodiments, the fusion protein comprises the sequence of SEQ ID NO: 799.

In some embodiments, the fusion protein comprises the sequence of SEQ ID NO: 71, with 1, 2, 3, 4, 5, 6, 7, 8, 9, 10, or more amino acid substitutions. In some embodiments, the fusion protein comprises the sequence of SEQ ID NO: 73, with 1, 2, 3, 4, 5, 6, 7, 8, 9, 10, or more amino acid substitutions. In some embodiments, the fusion protein comprises the sequence of SEQ ID NO: 75, with 1, 2, 3, 4, 5, 6, 7, 8, 9, 10, or more amino acid substitutions. In some embodiments, the fusion protein comprises the sequence of SEQ ID NO: 77, with 1, 2, 3, 4, 5, 6, 7, 8, 9, 10, or more amino acid substitutions. In some embodiments, the fusion protein comprises the sequence of SEQ ID NO: 79, with 1, 2, 3, 4, 5, 6, 7, 8, 9, 10, or more amino acid substitutions. In some embodiments, the fusion protein comprises the sequence of SEQ ID NO: 81, with 1, 2, 3, 4, 5, 6, 7, 8, 9, 10, or more amino acid substitutions. In some embodiments, the fusion protein comprises the sequence of SEQ ID NO: 135, with 1, 2, 3, 4, 5, 6, 7, 8, 9, 10, or more amino acid substitutions. In some embodiments, the fusion protein comprises the sequence of SEQ ID NO: 137, with 1, 2, 3, 4, 5, 6, 7, 8, 9, 10, or more amino acid substitutions. In some embodiments, the fusion protein comprises the sequence of SEQ ID NO: 616, with 1, 2, 3, 4, 5, 6, 7, 8, 9, 10, or more amino acid substitutions. In some embodiments, the fusion protein comprises the sequence of SEQ ID NO: 618, with 1, 2, 3, 4, 5, 6, 7, 8, 9, 10, or more amino acid substitutions. In some embodiments, the fusion protein comprises the sequence of SEQ ID NO: 620, with 1, 2, 3, 4, 5, 6, 7, 8, 9, 10, or more amino acid substitutions. In some embodiments, the fusion protein comprises the sequence of SEQ ID NO: 622, with 1, 2, 3, 4, 5, 6, 7, 8, 9, 10, or more amino acid substitutions. In some embodiments, the fusion protein comprises the sequence of SEQ ID NO: 624, with 1, 2, 3, 4, 5, 6, 7, 8, 9, 10, or more amino acid substitutions. In some embodiments, the fusion protein comprises the sequence of SEQ ID NO: 626, with 1, 2, 3, 4, 5, 6, 7, 8, 9, 10, or more amino acid substitutions. In some embodiments, the fusion protein comprises the sequence of SEQ ID NO: 628, with 1, 2, 3, 4, 5, 6, 7, 8, 9, 10, or more amino acid substitutions. In some embodiments, the fusion protein comprises the sequence of SEQ ID NO: 630, with 1, 2, 3, 4, 5, 6, 7, 8, 9, 10, or more amino acid substitutions. In some embodiments, the fusion protein comprises the sequence of SEQ ID NO: 632, with 1, 2, 3, 4, 5, 6, 7, 8, 9, 10, or more amino acid substitutions. In some embodiments, the fusion protein comprises the sequence of SEQ ID NO: 634, with 1, 2, 3, 4, 5, 6, 7, 8, 9, 10, or more amino acid substitutions. In some embodiments, the fusion protein comprises the sequence of SEQ ID NO: 636, with 1, 2, 3, 4, 5, 6, 7, 8, 9, 10, or more amino acid substitutions. In some embodiments, the fusion protein comprises the sequence of SEQ ID NO: 638, with 1, 2, 3, 4, 5, 6, 7, 8, 9, 10, or more amino acid substitutions. In some embodiments, the fusion protein comprises the sequence of SEQ ID NO: 640, with 1, 2, 3, 4, 5, 6, 7, 8, 9, 10, or more amino acid substitutions. In some embodiments, the fusion protein comprises the sequence of SEQ ID NO: 642, with 1, 2, 3, 4, 5, 6, 7, 8, 9, 10, or more amino acid substitutions. In some embodiments, the fusion protein comprises the sequence of SEQ ID NO: 644, with 1, 2, 3, 4, 5, 6, 7, 8, 9, 10, or more amino acid substitutions. In some embodiments, the fusion protein comprises the sequence of SEQ ID NO: 646, with 1, 2, 3, 4, 5, 6, 7, 8, 9, 10, or more amino acid substitutions. In some embodiments, the fusion protein comprises the sequence of SEQ ID NO: 648, with 1, 2, 3, 4, 5, 6, 7, 8, 9, 10, or more amino acid substitutions. In some embodiments, the fusion protein comprises the sequence of SEQ ID NO: 650, with 1, 2, 3, 4, 5, 6, 7, 8, 9, 10, or more amino acid substitutions. In some embodiments, the fusion protein comprises the sequence of SEQ ID NO: 652, with 1, 2, 3, 4, 5, 6, 7, 8, 9, 10, or more amino acid substitutions. In some embodiments, the fusion protein comprises the sequence of SEQ ID NO: 654, with 1, 2, 3, 4, 5, 6, 7, 8, 9, 10, or more amino acid substitutions. In some embodiments, the fusion protein comprises the sequence of SEQ ID NO: 656, with 1, 2, 3, 4, 5, 6, 7, 8, 9, 10, or more amino acid substitutions. In some embodiments, the fusion protein comprises the sequence of SEQ ID NO: 658, with 1, 2, 3, 4, 5, 6, 7, 8, 9, 10, or more amino acid substitutions. In some embodiments, the fusion protein comprises the sequence of SEQ ID NO: 660, with 1, 2, 3, 4, 5, 6, 7, 8, 9, 10, or more amino acid substitutions. In some embodiments, the fusion protein comprises the sequence of SEQ ID NO: 662, with 1, 2, 3, 4, 5, 6, 7, 8, 9, 10, or more amino acid substitutions. In some embodiments, the fusion protein comprises the sequence of SEQ ID NO: 664, with 1, 2, 3, 4, 5, 6, 7, 8, 9, 10, or more amino acid substitutions. In some embodiments, the fusion protein comprises the sequence of SEQ ID NO: 793, with 1, 2, 3, 4, 5, 6, 7, 8, 9, 10, or more amino acid substitutions. In some embodiments, the fusion protein comprises the sequence of SEQ ID NO: 795, with 1, 2, 3, 4, 5, 6, 7, 8, 9, 10, or more amino acid substitutions. In some embodiments, the fusion protein comprises the sequence of SEQ ID NO: 797, with 1, 2, 3, 4, 5, 6, 7, 8, 9, 10, or more amino acid substitutions. In some embodiments, the fusion protein comprises the sequence of SEQ ID NO: 799, with 1, 2, 3, 4, 5, 6, 7, 8, 9, 10, or more amino acid substitutions.

In some embodiments, the fusion protein comprises the sequence of SEQ ID NO: 71, or a sequence at least 90%, at least 95%, at least 96%, at least 97%, at least 98%, or at least 99% identical thereto. In some embodiments, the fusion protein comprises the sequence of SEQ ID NO: 73, or a sequence at least 90%, at least 95%, at least 96%, at least 97%, at least 98%, or at least 99% identical thereto. In some embodiments, the fusion protein comprises the sequence of SEQ ID NO: 75, or a sequence at least 90%, at least 95%, at least 96%, at least 97%, at least 98%, or at least 99% identical thereto. In some embodiments, the fusion protein comprises the sequence of SEQ ID NO: 77, or a sequence at least 90%, at least 95%, at least 96%, at least 97%, at least 98%, or at least 99% identical thereto. In some embodiments, the fusion protein comprises the sequence of SEQ ID NO: 79, or a sequence at least 90%, at least 95%, at least 96%, at least 97%, at least 98%, or at least 99% identical thereto. In some embodiments, the fusion protein comprises the sequence of SEQ ID NO: 81, or a sequence at least 90%, at least 95%, at least 96%, at least 97%, at least 98%, or at least 99% identical thereto. In some embodiments, the fusion protein comprises the sequence of SEQ ID NO: 135, or a sequence at least 90%, at least 95%, at least 96%, at least 97%, at least 98%, or at least 99% identical thereto. In some embodiments, the fusion protein comprises the sequence of SEQ ID NO: 137, or a sequence at least 90%, at least 95%, at least 96%, at least 97%, at least 98%, or at least 99% identical thereto. In some embodiments, the fusion protein comprises the sequence of SEQ ID NO: 616, or a sequence at least 90%, at least 95%, at least 96%, at least 97%, at least 98%, or at least 99% identical thereto. In some embodiments, the fusion protein comprises the sequence of SEQ ID NO: 618, or a sequence at least 90%, at least 95%, at least 96%, at least 97%, at least 98%, or at least 99% identical thereto. In some embodiments, the fusion protein comprises the sequence of SEQ ID NO: 620, or a sequence at least 90%, at least 95%, at least 96%, at least 97%, at least 98%, or at least 99% identical thereto. In some embodiments, the fusion protein comprises the sequence of SEQ ID NO: 622, or a sequence at least 90%, at least 95%, at least 96%, at least 97%, at least 98%, or at least 99% identical thereto. In some embodiments, the fusion protein comprises the sequence of SEQ ID NO: 624, or a sequence at least 90%, at least 95%, at least 96%, at least 97%, at least 98%, or at least 99% identical thereto. In some embodiments, the fusion protein comprises the sequence of SEQ ID NO: 626, or a sequence at least 90%, at least 95%, at least 96%, at least 97%, at least 98%, or at least 99% identical thereto. In some embodiments, the fusion protein comprises the sequence of SEQ ID NO: 628, or a sequence at least 90%, at least 95%, at least 96%, at least 97%, at least 98%, or at least 99% identical thereto. In some embodiments, the fusion protein comprises the sequence of SEQ ID NO: 630, or a sequence at least 90%, at least 95%, at least 96%, at least 97%, at least 98%, or at least 99% identical thereto. In some embodiments, the fusion protein comprises the sequence of SEQ ID NO: 632, or a sequence at least 90%, at least 95%, at least 96%, at least 97%, at least 98%, or at least 99% identical thereto. In some embodiments, the fusion protein comprises the sequence of SEQ ID NO: 634, or a sequence at least 90%, at least 95%, at least 96%, at least 97%, at least 98%, or at least 99% identical thereto. In some embodiments, the fusion protein comprises the sequence of SEQ ID NO: 636, or a sequence at least 90%, at least 95%, at least 96%, at least 97%, at least 98%, or at least 99% identical thereto. In some embodiments, the fusion protein comprises the sequence of SEQ ID NO: 638, or a sequence at least 90%, at least 95%, at least 96%, at least 97%, at least 98%, or at least 99% identical thereto. In some embodiments, the fusion protein comprises the sequence of SEQ ID NO: 640, or a sequence at least 90%, at least 95%, at least 96%, at least 97%, at least 98%, or at least 99% identical thereto. In some embodiments, the fusion protein comprises the sequence of SEQ ID NO: 642, or a sequence at least 90%, at least 95%, at least 96%, at least 97%, at least 98%, or at least 99% identical thereto. In some embodiments, the fusion protein comprises the sequence of SEQ ID NO: 644, or a sequence at least 90%, at least 95%, at least 96%, at least 97%, at least 98%, or at least 99% identical thereto. In some embodiments, the fusion protein comprises the sequence of SEQ ID NO: 646, or a sequence at least 90%, at least 95%, at least 96%, at least 97%, at least 98%, or at least 99% identical thereto. In some embodiments, the fusion protein comprises the sequence of SEQ ID NO: 648, or a sequence at least 90%, at least 95%, at least 96%, at least 97%, at least 98%, or at least 99% identical thereto. In some embodiments, the fusion protein comprises the sequence of SEQ ID NO: 650, or a sequence at least 90%, at least 95%, at least 96%, at least 97%, at least 98%, or at least 99% identical thereto. In some embodiments, the fusion protein comprises the sequence of SEQ ID NO: 652, or a sequence at least 90%, at least 95%, at least 96%, at least 97%, at least 98%, or at least 99% identical thereto. In some embodiments, the fusion protein comprises the sequence of SEQ ID NO: 654, or a sequence at least 90%, at least 95%, at least 96%, at least 97%, at least 98%, or at least 99% identical thereto. In some embodiments, the fusion protein comprises the sequence of SEQ ID NO: 656, or a sequence at least 90%, at least 95%, at least 96%, at least 97%, at least 98%, or at least 99% identical thereto. In some embodiments, the fusion protein comprises the sequence of SEQ ID NO: 658, or a sequence at least 90%, at least 95%, at least 96%, at least 97%, at least 98%, or at least 99% identical thereto. In some embodiments, the fusion protein comprises the sequence of SEQ ID NO: 660, or a sequence at least 90%, at least 95%, at least 96%, at least 97%, at least 98%, or at least 99% identical thereto. In some embodiments, the fusion protein comprises the sequence of SEQ ID NO: 662, or a sequence at least 90%, at least 95%, at least 96%, at least 97%, at least 98%, or at least 99% identical thereto. In some embodiments, the fusion protein comprises the sequence of SEQ ID NO: 664, or a sequence at least 90%, at least 95%, at least 96%, at least 97%, at least 98%, or at least 99% identical thereto. In some embodiments, the fusion protein comprises the sequence of SEQ ID NO: 793, or a sequence at least 90%, at least 95%, at least 96%, at least 97%, at least 98%, or at least 99% identical thereto. In some embodiments, the fusion protein comprises the sequence of SEQ ID NO: 795, or a sequence at least 90%, at least 95%, at least 96%, at least 97%, at least 98%, or at least 99% identical thereto. In some embodiments, the fusion protein comprises the sequence of SEQ ID NO: 797, or a sequence at least 90%, at least 95%, at least 96%, at least 97%, at least 98%, or at least 99% identical thereto. In some embodiments, the fusion protein comprises the sequence of SEQ ID NO: 799, or a sequence at least 90%, at least 95%, at least 96%, at least 97%, at least 98%, or at least 99% identical thereto.

In some embodiments, the fusion proteins have a molecular weight in the range of about 1 kDa to about 500 kDa, about 1 kDa to about 250 kDa, about 1 to about 100 kDa, about 10 to about 50 kDa, about 1 to about 10 kDa, about 10 to about 200 kDa, about 30 to about 150 kDa, about 30 kDa to about 50 kDa, or about 20 to about 80 kDa.

Nucleic Acids Encoding Fusion Proteins and Vectors Comprising the Same

Also provided herein are nucleic acids encoding the fusion proteins of the disclosure. In some embodiments, the nucleic acids are DNAs. In some embodiments, the nucleic acids are RNAs.

Also provided herein are examples of expression cassettes for the expression of casein proteins in non-mammalian systems, such as plants and microorganisms, to produce recombinant casein proteins. The expression cassette may comprise, for example, a promoter, a 5' untranslated region (UTR), a sequence encoding one or more casein proteins, and a terminator. The expression cassette may further comprise a selectable marker and retention signal.

In some embodiments, a nucleic acid comprises a sequence encoding a fusion protein. In some embodiments, a nucleic acid comprises a sequence encoding a fusion protein, which is operably linked to a promoter. In some embodiments, a nucleic acid comprises, in order from 5' to 3', a promoter, a 5' untranslated region (UTR), a sequence encoding a fusion protein, and a terminator.

The promoter may be a plant promoter. A "plant promoter" is a promoter capable of initiating transcription in plant cells. Examples of promoters under developmental control include promoters that preferentially initiate transcription in certain organs, such as leaves, roots, flowers, seeds and tissues such as fibers, xylem vessels, tracheids, or sclerenchyma. Such promoters are referred to as "tissue-preferred." Promoters which initiate transcription only in certain tissue are referred to as "tissue-specific." A "cell-type" specific promoter primarily drives expression in certain cell types in one or more organs, for example, vascular cells in leaves, roots, flowers, or seeds. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter which is active under most environmental conditions.

In some embodiments, the promoter is a plant promoter derived from, for example soybean, lima bean, *Arabidopsis*, tobacco, rice, maize, barley, sorghum, wheat, pea, and/or oat. In some embodiments, the promoter is a constitutive or an inducible promoter. Exemplary constitutive promoters include, but are not limited to, the promoters from plant viruses such as the 35S promoter from CaMV and the promoters from such genes as rice actin; ubiquitin; pEMU; MAS and maize H3 histone. In some embodiments, the constitutive promoter is the ALS promoter, XbaI/NcoI fragment 5' to the *Brassica napus* ALS3 structural gene (or a nucleotide sequence similarity to said XbaI/NcoI fragment).

In some embodiments, the promoter is a plant tissue-specific or tissue-preferential promoter. In some embodiments, the promoter is isolated or derived from a soybean gene. Illustrative soybean tissue-specific promoters include AR-Pro1, AR-Pro2, AR-Pro3, AR-Pro4, AR-Pro5, AR-Pro6, AR-Pro7, AR-Pro8, and AR-Pro9.

In some embodiments, the plant is a seed-specific promoter. In some embodiments, the seed-specific promoter is selected from the group consisting of PvPhas, BnNap, AtOle1, GmSeed2, GmSeed3, GmSeed5, GmSeed6, GmSeed7, GmSeed8, GmSeed10, GmSeed11, GmSeed12, pBCON, GmCEP1-L, GmTHIC, GmBg7S1, GmGRD, GmOLEA, GmOLER, Gm2S-1, and GmBBld-II. In some embodiments, the seed-specific promoter is PvPhas and comprises the sequence of SEQ ID NO: 18, or a sequence at least 90%, at least 95%, at least 96%, at least 97%, at least 98%, or at least 99% identical thereto. In some embodiments, the seed-specific promoter is GmSeed2 and comprises the sequence of SEQ ID NO: 19, or a sequence at least 90%, at least 95%, at least 96%, at least 97%, at least 98%, or at least 99% identical thereto. In some embodiments, the promoter is a Cauliflower Mosaic Virus (CaMV) 35S promoter.

In some embodiments, the promoter is a soybean polyubiquitin (Gmubi) promoter, a soybean heat shock protein 90-like (GmHSP90L) promoter, a soybean Ethylene Response Factor (GmERF) promoter. In some embodiments, the promoter is a constitutive soybean promoter derived from GmScreamM1, GmScreamM4, GmScreamM8 genes or GmubiXL genes.

In some embodiments, the 5' UTR is selected from the group consisting of Arc5'UTR and glnB1UTR. In some embodiments, the 5' untranslated region is Arc5'UTR and comprises the sequence of SEQ ID NO: 20, or a sequence at least 90%, at least 95%, at least 96%, at least 97%, at least 98%, or at least 99% identical thereto.

In some embodiments, the terminator sequence is isolated or derived from a gene encoding Nopaline synthase, Arc5-1, an Extensin, Rb7 matrix attachment region, a Heat shock protein, Ubiquitin 10, Ubiquitin 3, and M6 matrix attachment region. In some embodiments, the terminator sequence is isolated or derived from a Nopaline synthase gene and comprises the sequence of SEQ ID NO: 22, or a sequence at least 90%, at least 95%, at least 96%, at least 97%, at least 98%, or at least 99% identical thereto.

In some embodiments, the nucleic acid comprises a first terminator sequence and a second terminator sequence (i.e., a dual terminator). In some embodiments, the dual terminator is EU:Rb7. In some embodiments, the dual terminator is AtHSP:AtUbi10. In some embodiments, the dual terminator is EU:StUbi3. In some embodiments, the dual terminator is EU:TM6.

In some embodiments, the dual terminator is EU:Rb7 and comprises the sequence of SEQ ID NO: 138, or a sequence at least 90% at least 95%, at least 96%, at least 97%, at least 98%, or at least 99% identical thereto.

In some embodiments, the dual terminator is AtHSP:AtUbi10 and comprises the sequence of SEQ ID NO: 141, or a sequence at least 90% at least 95%, at least 96%, at least 97%, at least 98%, or at least 99% identical thereto.

In some embodiments, the dual terminator is EU:StUbi3 and comprises the sequence of SEQ ID NO: 144, or a sequence at least 90%, at least 95%, at least 96%, at least 97%, at least 98%, or at least 99% identical thereto.

In some embodiments, the dual terminator is EU:TM6 and comprises the sequence of SEQ ID NO: 146, or a sequence at least 90% at least 95%, at least 96%, at least 97%, at least 98%, or at least 99% identical thereto.

In some embodiments, the nucleic acid comprises a 3' UTR. For example, the 3' untranslated region may be Arc5-1 and comprise SEQ ID NO: 21, or a sequence at least 90%, at least 95%, at least 96%, at least 97%, at least 98%, or at least 99% identical thereto.

In some embodiments the nucleic acid comprises a gene encoding a selectable marker. One illustrative selectable marker gene for plant transformation is the neomycin phosphotransferase II (nptll) gene, isolated from transposon Tn5, which, when placed under the control of plant regulatory signals, confers resistance to kanamycin. Another exemplary marker gene is the hygromycin phosphotransferase gene which confers resistance to the antibiotic hygromycin. In some embodiments, the selectable marker is of bacterial origin and confers resistance to antibiotics such as gentamycin acetyl transferase, streptomycin phosphotransferase, and aminoglycoside-3'-adenyl transferase, the bleomycin resistance determinant. In some embodiments, the selectable marker genes confer resistance to herbicides such as glyphosate, glufosinate or bromoxynil. In some embodiments, the selectable marker is mouse dihydrofolate reductase, plant 5-enolpyruvylshikimate-3-phosphate synthase and plant acetolactate synthase. In some embodiments, the selectable marker is acetolactate synthase (e.g., AtCsr1.2).

In some embodiments, a nucleic acid comprises an endoplasmic reticulum retention signal. For example, in some embodiments, a nucleic acid comprises a KDEL sequence (SEQ ID NO: 23). In some embodiments, the nucleic acid may comprise an endoplasmic reticulum retention signal selected from any one of SEQ ID NO: 23-70.

Shown in Table 9 are exemplary promoters, 5' UTRs, signal peptides, and terminators that may be used in the nucleic acids of the disclosure.

TABLE 9

Promoters, 5' UTRs, signal peptides and terminators

| Type | Name | Description | Native Species | Illustrative Accession No. (Glyma, GenBank) |
|---|---|---|---|---|
| Promoter | PvPhas | Phaseolin-1 (aka β-phaseolin) | Common bean (*Phaseolus vulgaris*) | J01263.1 |
|  | BnNap | Napin-1 | Rapeseed (*Brassica napus*) | J02798.1 |
|  | AtOle1 | Oleosin-1 (Ole1) | Arabidopsis (*Arabidopsis thaliana*) | X62353.1, AT4G25140 |
|  | GmSeed2 | Gy1 (Glycinin 1) | Soybean (*Glycine max*) | Glyma.03G163500 |
|  | GmSeed3 | cysteine protease | Soybean (*Glycine max*) | Glyma.08G116300 |
|  | GmSeed5 | Gy5 (Glycinin 5) | Soybean (*Glycine max*) | Glyma.13G123500 |
|  | GmSeed6 | Gy4 (Glycinin 4) | Soybean (*Glycine max*) | Glyma.10G037100 |
|  | GmSeed7 | Kunitz trypsin protease inhibitor | Soybean (*Glycine max*) | Glyma.01G095000 |
|  | GmSeed8 | Kunitz trypsin protease inhibitor | Soybean (*Glycine max*) | Glyma.08G341500 |
|  | GmSeed10 | Legume Lectin Domain | Soybean (*Glycine max*) | Glyma.02G012600 |
|  | GmSeed11 | β-conglycinin a subunit | Soybean (*Glycine max*) | Glyma.20G148400 |
|  | GmSeed12 | β-conglycinin a' subunit | Soybean (*Glycine max*) | Glyma.10G246300 |
|  | pBCON | β-conglycinin β subunit | Soybean (*Glycine max*) | Glyma.20G148200 |

TABLE 9-continued

Promoters, 5' UTRs, signal peptides and terminators

| Type | Name | Description | Native Species | Illustrative Accession No. (Glyma, GenBank) |
|---|---|---|---|---|
| | GmCEP1-L | KDEL-tailed cysteine endopeptidase CEP1-like | Soybean (*Glycine max*) | Glyma06g42780 |
| | GmTHIC | phosphomethylpyrimidine synthase | Soybean (*Glycine max*) | Glyma11g26470 |
| | GmBg7S1 | Basic 7S globulin precursor | Soybean (*Glycine max*) | Glyma03g39940 |
| | GmGRD | glucose and ribitol dehydrogenase-like | Soybean (*Glycine max*) | Glyma07g38790 |
| | GmOLEA | Oleosin isoform A | Soybean (*Glycine max*) | Glyma.19g063400 |
| | GmOLEB | Oleosin isoform B | Soybean (*Glycine max*) | Glyma.16g071800 |
| | Gm2S-1 | 2S albumin | Soybean (*Glycine max*) | Glyma13g36400 |
| | GmBBId-II | Bowman-Birk protease inhibitor | Soybean (*Glycine max*) | Glyma16g33400 |
| 5'UTR | Arc5'UTR | arc5-1 gene | *Phaseolus vulgaris* | J01263.1 |
| | glnB1UTR | 65 bp of native glutamine synthase | Soybean (*Glycine max*) | AF301590.1 |
| Signal peptide | GmSCB1 | Seed coat BURP domain protein | Soybean (*Glycine max*) | Glyma07g28940.1 |
| | StPat21 | Patatin | Tomato (*Solanum lycopersicum*) | CAA27588 |
| | 2Sss | 2S albumin | Soybean (*Glycine max*) | Glyma13g36400 |
| | Sig2 | Glycinin G1 N-terminal peptide | Soybean (*Glycine max*) | Glyma.03G163500 |
| | Sig12 | Beta-conglycinin alpha prime subunit N-terminal peptide | Soybean (*Glycine max*) | Glyma.10G246300 |
| | Sig8 | Kunitz trypsin inhibitor N-terminal peptide | Soybean (*Glycine max*) | Glyma.08G341500 |
| | Sig10 | Lectin N-terminal peptide from Glycine max | Soybean (*Glycine max*) | Glyma.02G012600 |
| | Sig11 | Beta-conglycinin alpha subunit N-terminal peptide | Soybean (*Glycine max*) | Glyma.20G148400 |
| | Coixss | Alpha-coixin N-terminal peptide from Coix lacryma-job | Coix lacryma-job | |
| | KDEL | C-terminal amino acids of sulfhydryl endopeptidase | *Phaseolus vulgaris* | |
| Terminator | NOS | Nopaline synthase gene termination sequence | *Agrobacterium tumefaciens* | |
| | ARC | arc5-1 gene termination sequence | *Phaseolus vulgaris* | J01263.1 |
| | EU | Extensin termination sequence | *Nicotiana tabacum* | |
| | Rb7 | Rb7 matrix attachment region termination sequence | *Nicotiana tabacum* | |
| | HSP or AtHSP | Heat shock termination sequence | *Arabidopsis thaliana* | |
| | AtUbi10 | Ubiquitin 10 termination sequence | *Arabidopsis thaliana* | |
| | Stubi3 | Ubiquitin 3 termination | *Solanum tuberosum* | |
| | TM6 | M6 matrix attachment region termination sequence | *Nicotiana tabacum* | |
| Dual terminators | EU:Rb7 | Extensin termination sequence:Rb7 matrix attachment region termination sequence | *Nicotiana tabacum* | |
| | AtHSP:AtUbi10 | Heat shock termination sequence:Ubiquitin 10 termination sequence | *Arabidopsis thaliana* | |
| | EU:StUbi3 | Rb7 matrix attachment region termination sequence:Ubiquitin 3 termination | *Nicotiana tabacum, Solanum tuberosum* | |
| | EU:TM6 | Rb7 matrix attachment region termination sequence:M6 matrix | *Nicotiana tabacum* | |

TABLE 9-continued

Promoters, 5' UTRs, signal peptides and terminators

| Type | Name | Description | Native Species | Illustrative Accession No. (Glyma, GenBank) |
|---|---|---|---|---|
| | | attachment region termination sequence | | |

Illustrative nucleic acids of the disclosure are provided in FIG. 1A-FIG. 1P and FIG. 2A-FIG. 2P. In some embodiments a nucleic acid comprises, from 5' to 3', a promoter, a 5'UTR, a sequence encoding an unstructured milk protein, a sequence encoding a structured mammalian protein, an endoplasmic reticulum retention signal, and a terminator (See, e.g., FIG. 1A). In some embodiments a nucleic acid comprises, from 5' to 3', a promoter, a 5'UTR, a sequence encoding an unstructured milk protein, a sequence encoding a linker, a sequence encoding a structured mammalian protein, an endoplasmic reticulum retention signal, and a terminator (See, e.g., FIG. 1B). In some embodiments a nucleic acid comprises, from 5' to 3', a promoter, a 5'UTR, a sequence encoding an unstructured milk protein, a sequence encoding a linker, a sequence encoding a structured mammalian protein, and a terminator (See, e.g., FIG. 1C). In some embodiments a nucleic acid comprises, from 5' to 3', a promoter, a 5'UTR, a sequence encoding an unstructured milk protein, a sequence encoding a structured mammalian protein, and a terminator (See, e.g., FIG. 1D). In some embodiments a nucleic acid comprises, from 5' to 3', a promoter, a 5'UTR, a sequence encoding a structured mammalian protein, a sequence encoding an unstructured milk protein, an endoplasmic reticulum retention signal, and a terminator (See, e.g., FIG. 1E). In some embodiments a nucleic acid comprises, from 5' to 3', a promoter, a 5'UTR, a sequence encoding a structured mammalian protein, a sequence encoding a linker, a sequence encoding an unstructured milk protein, an endoplasmic reticulum retention signal, and a terminator (See, e.g., FIG. 1F). In some embodiments a nucleic acid comprises, from 5' to 3', a promoter, a 5'UTR, a sequence encoding a structured mammalian protein, a sequence encoding a linker, a sequence encoding an unstructured milk protein, and a terminator (See, e.g., FIG. 1G). In some embodiments a nucleic acid comprises, from 5' to 3', a promoter, a 5'UTR, a sequence encoding a structured mammalian protein, a sequence encoding an unstructured milk protein, and a terminator (See, e.g., FIG. 1H). In some embodiments a nucleic acid comprises, from 5' to 3', a promoter, a 5'UTR, a sequence encoding a signal peptide, a sequence encoding an unstructured milk protein, a sequence encoding a structured mammalian protein, an endoplasmic reticulum retention signal, and a terminator (See, e.g., FIG. 1I). In some embodiments a nucleic acid comprises, from 5' to 3', a promoter, a 5'UTR, a sequence encoding a signal peptide, a sequence encoding an unstructured milk protein, a sequence encoding a linker, a sequence encoding a structured mammalian protein, an endoplasmic reticulum retention signal, and a terminator (See, e.g., FIG. 1J). In some embodiments a nucleic acid comprises, from 5' to 3', a promoter, a 5'UTR, a sequence encoding a signal peptide, a sequence encoding an unstructured milk protein, a sequence encoding a linker, a sequence encoding a structured mammalian protein, and a terminator (See, e.g., FIG. 1K). In some embodiments a nucleic acid comprises, from 5' to 3', a promoter, a 5'UTR, a sequence encoding a signal peptide, a sequence encoding an unstructured milk protein, a sequence encoding a structured mammalian protein, and a terminator (See, e.g., FIG. 1L). In some embodiments a nucleic acid comprises, from 5' to 3', a promoter, a 5'UTR, a sequence encoding a signal peptide, a sequence encoding a structured mammalian protein, a sequence encoding an unstructured milk protein, an endoplasmic reticulum retention signal, and a terminator (See, e.g., FIG. 1M). In some embodiments a nucleic acid comprises, from 5' to 3', a promoter, a 5'UTR, a sequence encoding a signal peptide, a sequence encoding a structured mammalian protein, a sequence encoding a linker, a sequence encoding an unstructured milk protein, an endoplasmic reticulum retention signal, and a terminator (See, e.g., FIG. 1N). In some embodiments a nucleic acid comprises, from 5' to 3', a promoter, a 5'UTR, a sequence encoding a signal peptide, a sequence encoding a structured mammalian protein, a sequence encoding a linker, a sequence encoding an unstructured milk protein, and a terminator (See, e.g., FIG. 1O). In some embodiments a nucleic acid comprises, from 5' to 3', a promoter, a 5'UTR, a sequence encoding a signal peptide, a sequence encoding a structured mammalian protein, a sequence encoding an unstructured milk protein, and a terminator (See, e.g., FIG. 1P).

Figures 2A, 2P:
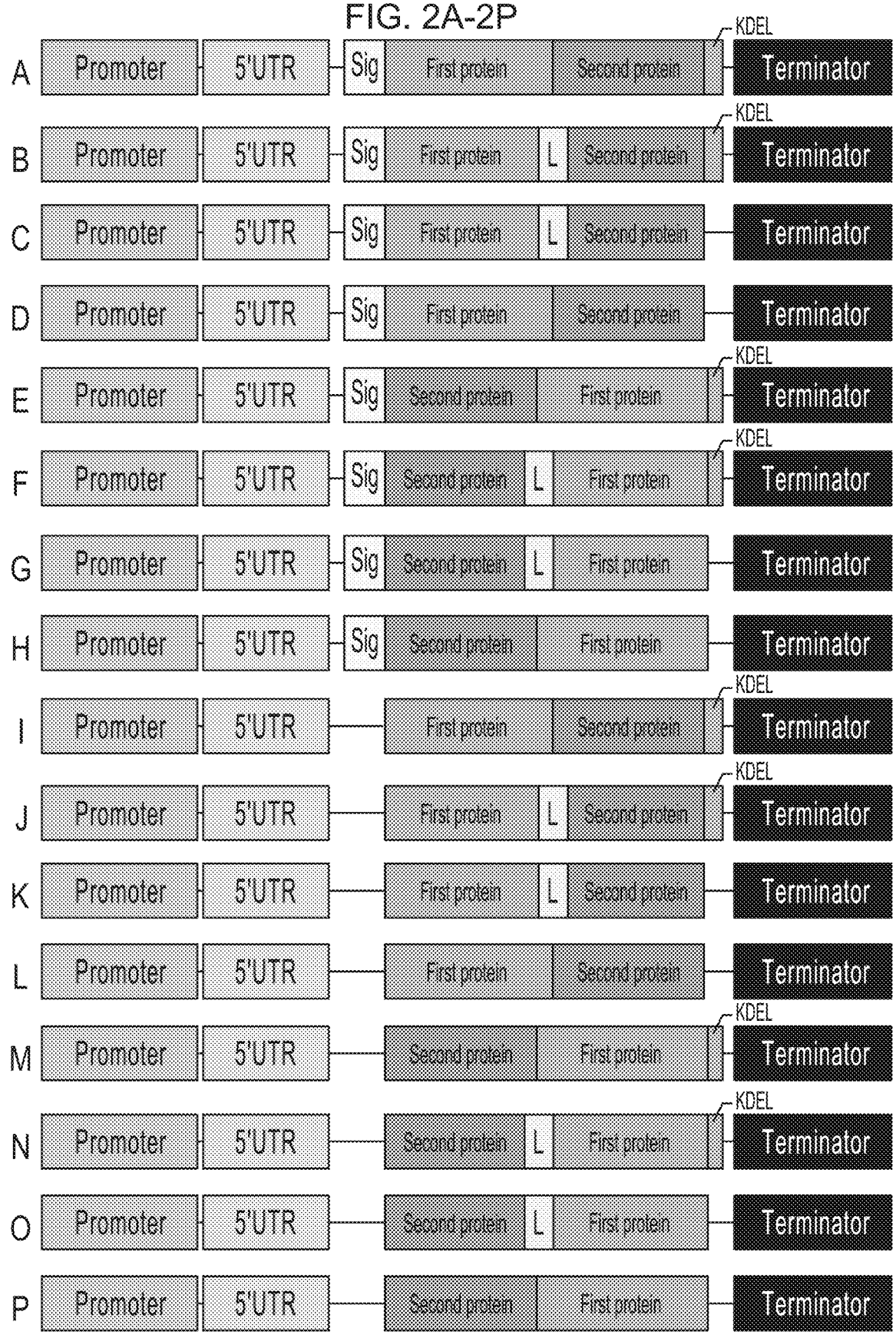

In some embodiments a nucleic acid comprises, from 5' to 3', a promoter, a 5'UTR, a sequence encoding a signal peptide, a sequence encoding first protein, a sequence encoding a second protein, an endoplasmic reticulum retention signal, and a terminator (See, e.g., FIG. 2A). In some embodiments a nucleic acid comprises, from 5' to 3', a promoter, a 5'UTR, a sequence encoding a signal peptide, a sequence encoding first protein, a sequence encoding a linker, a sequence encoding a second protein, an endoplasmic reticulum retention signal, and a terminator (See, e.g., FIG. 2B). In some embodiments a nucleic acid comprises, from 5' to 3', a promoter, a 5'UTR, a sequence encoding a signal peptide, a sequence encoding a first protein, a sequence encoding a linker, a sequence encoding a second protein, and a terminator (See, e.g., FIG. 2C). In some embodiments a nucleic acid comprises, from 5' to 3', a promoter, a 5'UTR, a sequence encoding a signal peptide, a sequence encoding a first protein, a sequence encoding a second protein, and a terminator (See, e.g., FIG. 2D). In some embodiments a nucleic acid comprises, from 5' to 3', a promoter, a 5'UTR, a sequence encoding a signal peptide, a sequence encoding a second protein, a sequence encoding a first protein, an endoplasmic reticulum retention signal, and a terminator (See, e.g., FIG. 2E). In some embodiments a nucleic acid comprises, from 5' to 3', a promoter, a 5'UTR, a sequence encoding a signal peptide, a sequence encoding a second protein, a sequence encoding a linker, a sequence encoding a first protein, an endoplasmic reticulum retention signal, and a terminator (See, e.g., FIG. 2F). In some embodiments a nucleic acid comprises, from 5' to 3', a promoter, a 5'UTR, a sequence encoding a signal peptide, a sequence encoding a second protein, a sequence encoding a linker, a sequence encoding a first protein, and a terminator (See, e.g., FIG. 2G). In some embodiments a nucleic acid comprises, from 5' to 3', a promoter, a 5'UTR, a sequence encoding a signal peptide, a sequence encoding a second protein, a sequence encoding first protein, and a terminator (See, e.g., FIG. 2H).

In some embodiments a nucleic acid comprises, from 5' to 3', a promoter, a 5'UTR, a sequence encoding a first protein, a sequence encoding a second protein, an endoplasmic reticulum retention signal, and a terminator (See, e.g., FIG. 2I). In some embodiments a nucleic acid comprises, from 5' to 3', a promoter, a 5'UTR, a sequence encoding a first protein, a sequence encoding a linker, a sequence encoding a second protein, an endoplasmic reticulum retention signal, and a terminator (See, e.g., FIG. 2J). In some embodiments a nucleic acid comprises, from 5' to 3', a promoter, a 5'UTR, a sequence encoding a first protein, a sequence encoding a linker, a sequence encoding a second protein, and a terminator (See, e.g., FIG. 2K). In some embodiments a nucleic acid comprises, from 5' to 3', a promoter, a 5'UTR, a sequence encoding a first protein, a sequence encoding a second protein, and a terminator (See, e.g., FIG. 2L). In some embodiments a nucleic acid comprises, from 5' to 3', a promoter, a 5'UTR, a sequence encoding a second protein, a sequence encoding a first protein, an endoplasmic reticulum retention signal, and a terminator (See, e.g., FIG. 2M). In some embodiments a nucleic acid comprises, from 5' to 3', a promoter, a 5'UTR, a sequence encoding a second protein, a sequence encoding a linker, a sequence encoding a first protein, an endoplasmic reticulum retention signal, and a terminator (See, e.g., FIG. 2N). In some embodiments a nucleic acid comprises, from 5' to 3', a promoter, a 5'UTR, a sequence encoding a second protein, a sequence encoding a linker, a sequence encoding a first protein, and a terminator (See, e.g., FIG. 2O). In some embodiments a nucleic acid comprises, from 5' to 3', a promoter, a 5'UTR, a sequence encoding a second protein, a sequence encoding a first protein, and a terminator (See, e.g., FIG. 2P).

Figure 4:
FIG. 4 shows an example expression cassette comprising a OKC1-T:OLG1 fusion (Optimized Kappa Casein version 1: beta-lactoglobulin version 1, SEQ ID NOs: 71-72), expression of which is driven by PvPhas promoter fused with arc5'UTR:sig10, followed by the ER retention signal (KDEL, SEQ ID NO: 23) and the 3'UTR of the arc5-1 gene, "arc-terminator". "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale).

In some embodiments, the nucleic acid comprises an expression cassette comprising a OKC1-T:OLG1 (Optimized Kappa Casein version 1: beta-lactoglobulin version 1) fusion driven by PvPhas promoter fused with arc5'UTR: sig10, followed by the ER retention signal (KDEL, SEQ ID NO: 23) and the 3'UTR of the arc5-1 gene, "arc-terminator" (See, e.g., FIG. 4). In some embodiments, the nucleic acid comprises SEQ ID NO: 72.

Figure 5:
FIG. 5 shows an example expression cassette comprising a OBC-T2:FM:OLG1 fusion (Optimized Beta Casein Truncated version 2:Chymosin cleavage site:beta-lactoglobulin version 1, SEQ ID NOs: 73-74), expression of which driven by PvPhas promoter fused with arc5'UTR:sig10, followed by the 3'UTR of the arc5-1 gene, "arc-terminator". "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale). The Beta Casein is "truncated" in that the bovine secretion signal is removed and replaced with a plant targeting signal.

In some embodiments, the nucleic acid comprises an expression cassette comprising a OBC-T2:FM:OLG1 (Optimized Beta Casein Truncated version 2:Chymosin cleavage site:beta-lactoglobulin version 1) fusion driven by PvPhas promoter fused with arc5'UTR:sig10, followed by the 3'UTR of the arc5-1 gene, "arc-terminator" (See, e.g., FIG. 5). In some embodiments, the nucleic acid comprises SEQ ID NO: 74. The Beta Casein is "truncated" in that the bovine secretion signal is removed and replaced with a plant targeting signal.

Figure 6:
FIG. 6 shows an example expression cassette comprising a OaS1-T:FM:OLG1 fusion (Optimized Alpha S1 Casein Truncated version 1:Chymosin cleavage site:beta-lactoglobulin version 1, SEQ ID NOs: 75-76), expression of which is driven by PvPhas promoter fused with arc5'UTR: sig10, followed by the 3'UTR of the arc5-1 gene, "arc-terminator". "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale). The Alpha S1 Casein is "truncated" in that the bovine secretion signal is removed and replaced with a plant targeting signal.

In some embodiments, the nucleic acid comprises an expression cassette comprising a OaS1-T:FM:OLG1 (Optimized Alpha S1 Casein Truncated version 1:Chymosin cleavage site:beta-lactoglobulin version 1) fusion driven by PvPhas promoter fused with arc5'UTR:sig10, followed by the 3'UTR of the arc5-1 gene, "arc-terminator" (See, e.g., FIG. 6). In some embodiments, the nucleic acid comprises SEQ ID NO: 76. The Alpha S1 is "truncated" in that the bovine secretion signal is removed and replaced with a plant targeting signal.

Figure 7:
FIG. 7 shows an example expression cassette comprising a para-OKC1-T:FM:OLG1:KDEL fusion (Optimized paraKappa Casein version 1:Chymosin cleavage site:beta-lactoglobulin version 1, SEQ ID NOs: 77-78), expression of which is driven by PvPhas promoter fused with arc5'UTR: sig 10, followed by the ER retention signal (KDEL, SEQ ID NO: 23) and the 3'UTR of the arc5-1 gene, "arc-terminator". "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale).

In some embodiments, the nucleic acid comprises an expression cassette comprising a para-OKC1-T:FM:OLG1:KDEL (Optimized paraKappa Casein version 1:Chymosin cleavage site:beta-lactoglobulin version 1) fusion driven by PvPhas promoter fused with arc5'UTR: sig 10, followed by the ER retention signal (KDEL, SEQ ID NO: 23) and the 3'UTR of the arc5-1 gene, "arc-terminator" (See, e.g., FIG. 7). In some embodiments, the nucleic acid comprises SEQ ID NO: 78.

Figure 8:
FIG. 8 shows an example expression cassette comprising a para-OKC1-T:FM:OLG1 fusion (Optimized paraKappa Casein version 1:Chymosin cleavage site:beta-lactoglobulin version 1, SEQ ID NOs: 79-80), expression of which is driven by PvPhas promoter fused with arc5'UTR: sig 10, followed by the 3'UTR of the arc5-1 gene, "arc-terminator." "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale).

In some embodiments, the nucleic acid comprises an expression cassette comprising a para-OKC1-T:FM:OLG1 (Optimized paraKappa Casein version 1:Chymosin cleavage site:beta-lactoglobulin version 1) fusion driven by PvPhas promoter fused with arc5'UTR: sig 10, followed by the 3'UTR of the arc5-1 gene, "arc-terminator" (See, e.g., FIG. 8). In some embodiments, the nucleic acid comprises SEQ ID NO: 80.

Figure 9:
FIG. 9 shows an example expression cassette comprising a OKC1-T:OLG1 fusion (Optimized Kappa Casein version 1: beta-lactoglobulin version 1, SEQ ID NOs: 81-82), expression of which is driven by the promoter and signal peptide of glycinin 1 (GmSeed2:sig2) followed by the ER retention signal (KDEL, SEQ ID NO: 23) and the nopaline synthase gene termination sequence (nos term). Coding regions and regulatory sequences are indicated as blocks (not to scale).

In some embodiments, the nucleic acid comprises an expression cassette comprising a OKC1-T-OLG1 (Optimized Kappa Casein version 1: beta-lactoglobulin version 1) fusion that is driven by the promoter and signal peptide of glycinin 1 (GmSeed2:sig2) followed by the ER retention signal (KDEL, SEQ ID NO: 23) and the nopaline synthase gene termination sequence (nos term) (See, e.g., FIG. 9). In some embodiments, the nucleic acid comprises SEQ ID NO: 82.

In some embodiments, a nucleic acid encoding a fusion protein comprises the sequence of any one of SEQ ID NO: 72, 74, 76, 78, 80, 82, 134, or 136. In some embodiments, a nucleic acid encoding a fusion protein comprises the sequence of any one of SEQ ID NO: 615, 617, 619, 621, 623, 625, 627, 629, 631, 633, 635, 637, 639, 641, 643, 645, 647, 649, 651, 653, 655, 657, 659, 661, 663, 792, 794, 796, or 798.

In some embodiments, the nucleic acids are codon optimized for expression in a host cell. Codon optimization is a process used to improve gene expression and increase the translational efficiency of a gene of interest by accommodating codon bias of the host organism (i.e., the organism in which the gene is expressed). Codon-optimized mRNA sequences that are produced using different programs or approaches can vary because different codon optimization strategies differ in how they quantify codon usage and implement codon changes. Some approaches use the most optimal (frequently used) codon for all instances of an amino acid, or a variation of this approach. Other approaches adjust codon usage so that it is proportional to the natural distribution of the host organism. These approaches include codon harmonization, which endeavors to identify and maintain regions of slow translation thought to be important for protein folding. Alternative approaches involve using codons thought to correspond to abundant tRNAs, using codons according to their cognate tRNA concentrations, selectively replacing rare codons, or avoiding occurrences of codon-pairs that are known to translate slowly. In addition to approaches that vary in the extent to which codon usage is considered as a parameter, there are hypothesis-free approaches that do not consider this parameter. Algorithms for performing codon optimization are known to those of skill in the art and are widely available on the Internet.

In some embodiments the nucleic acids are codon optimized for expression in a plant species. The plant species may be, for example, a monocot or a dicot. In some embodiments, the plant species is a dicot species selected from soybean, lima bean, *Arabidopsis*, tobacco, rice, maize, barley, sorghum, wheat and/or oat. In some embodiments, the plant species is soybean.

In some embodiments, the nucleic acids are codon optimized for expression in a eukaryotic microorganism. The species may be, for example, *Saccharomyces* spp., *Kluyveromyces* spp., *Pichia* spp., *Aspergillus* spp., *Tetrahymena* spp., *Yarrowla* spp., *Hansemila* spp., *Blastobotrys* spp., *Candida* spp., *Zygosaccharomyces* spp., *Debrayomyces* spp., *Fusarium* spp., and *Trichoderma* spp.

In some embodiments, the nucleic acids are codon optimized for expression in a bacterial cell. The bacterial species may be, for example, *Escherichia coli, Caulobacter crescentus, Rodhobacter sphaeroides, Pseudoalteromonas haloplanktis, Shewanella* sp., *Pseudomonas putida, P. aeruginosa, P. fluorescens, Halomonas elongate, Chromohalobacter salexigens, Streptomyces lividans, S. griseus, Nocardia lactamdurans, Mycobacterium smegmatis, Corynebacterium glutamicum, C. ammoniagenes, Brevibacterium lactofermentum, Bacillus subtilis, B. brevis, B. megaterium, B. licheniformis, B. amyloliquefaciens, Lactococcus lactis, L. plantarum, L. casei, L. reuteri, L. gasseri*.

In some embodiments, a nucleic acid may encode more than one fusion protein. For example, in some embodiments, a nucleic acid may encode two, three, four, five, six, seven, eight, nine, or ten fusion proteins, or more. Expression of each fusion protein from the nucleic acid may be driven by a separate promoter. For example, in some embodiments, a nucleic acid comprises a first promoter configured to drive expression of a sequence encoding a first fusion protein, and a second promoter configured to drive expression of a sequence encoding a second fusion protein. In some embodiments, a nucleic acid comprises a first promoter operably linked to a sequence encoding a first fusion protein, and a second promoter operably linked to a sequence encoding a second fusion protein.

The nucleic acids of the disclosure may be contained within a vector. The vector may be, for example, a viral vector or a non-viral vector. In some embodiments, the non-viral vector is a plasmid, such as an *Agrobacterium* Ti plasmid. In some embodiments, the non-viral vector is a lipid nanoparticle.

In some embodiments, the vector comprises a nucleic acid encoding multiple fusion proteins. For example, in some embodiments, a vector comprises a nucleic acid comprising a sequence encoding a first fusion protein and a sequence encoding a second fusion protein. A first promoter may drive expression of the first fusion protein, and a second promoter may drive expression of the second fusion protein. In some embodiments, the first promoter and the second promoter are the same. In some embodiments, the first promoter and the second promoter are different.

In some embodiments, a vector comprises a nucleic acid comprising a sequence encoding a first fusion protein, a sequence encoding a second fusion protein, and a sequence encoding a third fusion protein. A first promoter may drive expression of the first fusion protein, a second promoter may drive expression of the second fusion protein, and a third promoter may drive expression of the third fusion protein. In some embodiments, each of the first, second, and third promoter are different. In some embodiments, at least two of the first, second, and third promoter are different. In some embodiments, the first, second, and third promoter are the same.

In some embodiments, a vector comprises a nucleic acid encoding a recombinant fusion protein, wherein the recombinant fusion protein comprises: (i) an unstructured milk protein, and (ii) a structured animal (e.g., mammalian or avian) protein. In some embodiments, the vector is an *Agrobacterium* Ti plasmid. In some embodiments, a vector comprises a nucleic acid encoding a recombinant fusion protein, wherein the recombinant fusion protein comprises: (1) a milk protein, and (2) a second protein. In some embodiments, the second protein is also a milk protein. In some embodiments, the second protein is beta-lactoglobulin. In some embodiments, the second protein is a mammalian or avian protein. In some embodiments, the vector is an *Agrobacterium* Ti plasmid. In some embodiments, the vector is a vector for use with an *Agrobacterium* binary vector transformation system. In some embodiments, the fusion protein is cleaved to liberate the milk protein and the second protein before either one is used to prepare a composition as described herein (See, e.g., FIG. 13). The fusion protein may be cleaved, for example, with one or more proteases.

In some embodiments, a method for expressing a casein protein (including fusion proteins comprising a casein protein) in a plant comprises contacting the plant with a vector of the disclosure. In some embodiments, a method for expression of a casein protein in a plant comprises contacting the plant with an *Agrobacterium* cell comprising a vector of the disclosure. In some embodiments, the method comprises maintaining the plant or part thereof under conditions in which the fusion protein is expressed.

In some embodiments, a method for expressing a fusion protein in a plant comprises contacting the plant with a vector of the disclosure. In some embodiments, the method comprises maintaining the plant or part thereof under conditions in which the fusion protein is expressed.

Plants Expressing Fusion Proteins

Also provided herein are transgenic plants expressing one or more fusion proteins of the disclosure. In some embodiments, the transgenic plants stably express the fusion protein. In some embodiments, the transgenic plants transiently express the fusion protein. In some embodiments, the transgenic plants stably express the fusion protein in the plant in an amount of at least 1% per the total protein weight of the soluble protein extractable from the plant. For example, the transgenic plants may stably express the fusion protein in an amount of at least 1%, at least 1.5%, at least 2%, at least 2.5%, at least 3%, at least 3.5%, at least 4%, at least 4.5%, at least 5%, at least 5.5%, at least 6%, at least 6.5%, at least 7%, at least 7.5%, at least 8%, at least 8.5%, at least 9%, at least 9.5%, at least 10%, at least 10.5%, at least 11%, at least 11.5%, at least 12%, at least 12.5%, at least 13%, at least 13.5%, at least 14%, at least 14.5%, at least 15%, at least 15.5%, at least 16%, at least 16.5%, at least 17%, at least 17.5%, at least 18%, at least 18.5%, at least 19%, at least 19.5%, at least 20%, or more of total protein weight of soluble protein extractable from the plant.

In some embodiments, the transgenic plants stably express the fusion protein in an amount of less than about 1% of the total protein weight of soluble protein extractable from the plant. In some embodiments, the transgenic plants stably express the fusion protein in the range of about 1% to about 2%, about 3% to about 4%, about 4% to about 5%, about 5% to about 6%, about 6% to about 7%, about 7% to about 8%, about 8% to about 9%, about 9% to about 10%, about 10% to about 11%, about 11% to about 12%, about 12% to about 13%, about 13% to about 14%, about 14% to about 15%, about 15% to about 16%, about 16% to about 17%, about 17%, to about 18%, about 18% to about 19%, about 19% to about 20%, or more than about 20% of the total protein weight of soluble protein extractable from the plant.

In some embodiments, the transgenic plant stably expresses the fusion protein in an amount in the range of about 0.5% to about 3%, about 1% to about 4%, about 1% to about 5%, about 2% to about 5%, about 1% to about 10%, about 2% to about 10%, about 3% to about 10%, about 5 to about 12%, about 4% to about 10%, or about 5% to about 10%, about 4% to about 8%, about 5% to about 15%, about 5% to about 18%, about 10% to about 20%, or about 1% to about 20% of the total protein weight of soluble protein extractable from the plant.

In some embodiments, the fusion protein is expressed at a level at least 2-fold higher than a milk protein expressed individually (i.e., expressed alone, not as part of a fusion protein) in a plant. For example, in some embodiments, the fusion protein is expressed at a level at least 2-fold, at least 2.5-fold, at least 3-fold, at least 3.5-fold, at least 4-fold, at least 4.5-fold, at least 5-fold, at least 5.5-fold, at least 6-fold, at least 7-fold, at least 7.5-fold, at least 8-fold, at least 8.5-fold, at least 9-fold, at least 9.5-fold, at least 10-fold, at least 25-fold, at least 50-fold, or at least 100-fold higher than a milk protein expressed individually in a plant.

In some embodiments, the fusion protein allows for accumulation of a casein protein in the plant at least 2-fold higher than a casein protein expressed individually (i.e., expressed alone, not as a part of a fusion protein) in a plant. For example, in some embodiments, the casein protein expressed in a fusion protein accumulates in the plant at least 2-fold, at least 2.5-fold, at least 3-fold, at least 3.5-fold, at least 4-fold, at least 4.5-fold, at least 5-fold, at least 5.5-fold, at least 6-fold, at least 7-fold, at least 7.5-fold, at least 8-fold, at least 8.5-fold, at least 9-fold, at least 9.5-fold, at least 10-fold, at least 25-fold, at least 50-fold, or at least 100-fold higher than a casein protein expressed individually.

In some embodiments, the fusion protein is stably expressed in the plant in an amount of 1% or higher per the total protein weight of the soluble protein extractable from the plant. In some embodiments, the fusion protein is stably expressed in the plant in an amount of 2% or higher per the total protein weight of the soluble protein extractable from the plant. In some embodiments, the fusion protein is stably expressed in the plant in an amount of 3% or higher per the total protein weight of the soluble protein extractable from the plant. In some embodiments, the fusion protein is stably expressed in the plant in an amount of 4% or higher per the total protein weight of the soluble protein extractable from the plant. In some embodiments, the fusion protein is stably expressed in the plant in an amount of 5% or higher per the total protein weight of the soluble protein extractable from the plant. In some embodiments, the fusion protein is stably expressed in the plant in an amount of 6% or higher per the total protein weight of the soluble protein extractable from the plant. In some embodiments, the fusion protein is stably expressed in the plant in an amount of 7% or higher per the total protein weight of the soluble protein extractable from the plant. In some embodiments, the fusion protein is stably expressed in the plant in an amount of 8% or higher per the total protein weight of the soluble protein extractable from the plant. In some embodiments, the fusion protein is stably expressed in the plant in an amount of 9% or higher per the total protein weight of the soluble protein extractable from the plant. In some embodiments, the fusion protein is stably expressed in the plant in an amount of 10% or higher per the total protein weight of the soluble protein extractable from the plant. In some embodiments, the fusion protein is stably expressed in the plant in an amount of 11% or higher per the total protein weight of the soluble protein extractable from the plant. In some embodiments, the fusion protein is stably expressed in the plant in an amount of 12% or higher per the total protein weight of the soluble protein extractable from the plant. In some embodiments, the fusion protein is stably expressed in the plant in an amount of 13% or higher per the total protein weight of the soluble protein extractable from the plant. In some embodiments, the fusion protein is stably expressed in the plant in an amount of 14% or higher per the total protein weight of the soluble protein extractable from the plant. In some embodiments, the fusion protein is stably expressed in the plant in an amount of 15% or higher per the total protein weight of the soluble protein extractable from the plant. In some embodiments, the fusion protein is stably expressed in the plant in an amount of 16% or higher per the total protein weight of the soluble protein extractable from the plant. In some embodiments, the fusion protein is stably expressed in the plant in an amount of 17% or higher per the total protein weight of the soluble protein extractable from the plant. In some embodiments, the fusion protein is stably expressed in the plant in an amount of 18% or higher per the total protein weight of the soluble protein extractable from the plant. In some embodiments, the fusion protein is stably expressed in the plant in an amount of 19% or higher per the total protein weight of the soluble protein extractable from the plant. In some embodiments, the fusion protein is stably expressed in the plant in an amount of 20% or higher per the total protein weight of the soluble protein extractable from the plant.

In some embodiments, a transformed plant comprises in its genome: a recombinant DNA construct encoding a first protein and a second protein, wherein the first protein and/or the second protein is a milk protein. In some embodiments, a transformed plant comprises in its genome: a recombinant DNA construct encoding a first protein and a second protein, wherein the first protein is a milk protein and the second protein is a non-milk protein. In some embodiments, a transformed plant comprises in its genome a recombinant DNA construct encoding a fusion protein, wherein the fusion protein comprises a first protein and a second protein, wherein the first protein and the second protein are milk proteins. In some embodiments, a transformed plant comprises in its genome a recombinant DNA construct encoding a fusion protein, wherein the fusion protein comprises from N-terminus to C-terminus, the first protein and the second protein. In some embodiments, the fusion protein comprises, from N-terminus to C-terminus, the second protein and the first protein.

In some embodiments, a transformed plant comprises in its genome: a recombinant DNA construct encoding a fusion protein, wherein the fusion protein comprises (i) a milk protein, and (ii) an animal (e.g., mammalian or avian) protein. In some embodiments, a transformed plant comprises in its genome a recombinant DNA construct encoding a fusion protein, wherein the fusion protein comprises from N-terminus to C-terminus, the milk protein and the animal (e.g., mammalian or avian) protein. In some embodiments, the fusion protein comprises, from N-terminus to C-terminus, the animal (e.g., mammalian or avian) protein and the milk protein.

In some embodiments, a transformed plant comprises in its genome: a recombinant DNA construct encoding a fusion protein, wherein the fusion protein comprises a milk protein such as a casein protein. In some embodiments, a transformed plant comprises in its genome: a recombinant DNA construct encoding a fusion protein, wherein the fusion protein comprises a milk protein selected from α-S1 casein, α-S2 casein, β-casein, and κ-casein. In some embodiments, the milk protein is α-S1 casein. In some embodiments, the milk protein is α-S1 casein and comprises the sequence SEQ ID NO: 8, or a sequence at least 90% identical thereto. In some embodiments, the milk protein is α-S2 casein. In some embodiments, the milk protein is α-S2 casein and comprises the sequence SEQ ID NO: 84, or a sequence at least 90% identical thereto. In some embodiments, the milk protein is β-casein. In some embodiments, the milk protein is β-casein and comprises the sequence of SEQ ID NO: 6, or a sequence at least 90% identical thereto. In some embodiments, the milk protein is κ-casein. In some embodiments, the milk protein is κ-casein and comprises the sequence of SEQ ID NO: 4, or a sequence at least 90% identical thereto. In some embodiments, the milk protein is para-κ-casein. In some embodiments, the milk protein is para-κ-casein and comprises the sequence of SEQ ID NO: 2, or a sequence at least 90% identical thereto. In some embodiments, the milk protein is β-lactoglobulin. In some embodiments, the milk protein is β-lactoglobulin and comprises the sequence of SEQ ID NO: 10, or a sequence at least 90% identical thereto. In some embodiments, the milk protein is α-lactalbumin, lysozyme, lactoferrin, lactoperoxidase, or an immunoglobulin (e.g., IgA, IgG, IgM, or IgE).

In some embodiments, a transformed plant comprises in its genome: a recombinant DNA construct encoding a fusion protein, wherein the fusion protein comprises a mammalian protein selected from hemoglobin, or collagen, IgM, or IgE. In some embodiments, a transformed plant comprises in its genome: a recombinant DNA construct encoding a fusion protein, wherein the fusion protein comprises an avian protein selected from lysozyme, ovalbumin, ovotransferrin, and ovoglobulin.

In some embodiments, a transformed plant comprises in its genome: a recombinant DNA construct encoding a fusion protein, wherein the fusion protein comprises a casein protein and β-lactoglobulin. In some embodiments, a transformed plant comprises in its genome: a recombinant DNA construct encoding a fusion protein, wherein the fusion protein comprises κ-casein and β-lactoglobulin. In some embodiments, the fusion protein comprises para-κ-casein and β-lactoglobulin. In some embodiments, the fusion protein comprises β-casein and β-lactoglobulin. In some embodiments, the fusion protein comprises α-S1 casein and β-lactoglobulin. In some embodiments, the fusion protein comprises two, three, four, five, or six β-caseins.

In some embodiments, a transformed plant comprises in its genome: a recombinant DNA construct encoding a fusion protein; wherein the fusion protein comprises (1) κ-casein, and (ii) β-lactoglobulin. In some embodiments the fusion protein is expressed in the plant in an amount of 1% or higher per the total protein weight of the soluble protein extractable from the plant.

In some embodiments, a transformed plant comprises in its genome: a recombinant DNA construct encoding a fusion protein, wherein the fusion protein comprises a first protein and a second protein, wherein the first protein and the second protein are each casein proteins. In some embodiments, the recombinant fusion protein comprises-casein and para-κ-casein. In some embodiments, the recombinant fusion protein comprises κ-casein and β-casein. In some embodiments, the recombinant fusion protein comprises κ-casein and α-S1-casein. In some embodiments, the recombinant fusion protein comprises κ-casein and α-S2-casein. In some embodiments, the recombinant fusion protein comprises para-κ-casein and β-casein. In some embodiments, the recombinant fusion protein comprises para-κ-casein and α-S1-casein. In some embodiments, the recombinant fusion protein comprises para-κ-casein and α-S2-casein. In some embodiments, the recombinant fusion protein comprises β-casein and α-S1-casein. In some embodiments, the recombinant fusion protein comprises β-casein and α-S2-casein. In some embodiments, the recombinant fusion protein comprises α-S1-casein and α-S2-casein.

In some embodiments, the recombinant fusion protein comprises two or more of the same casein proteins. In some embodiments, the recombinant fusion protein comprises κ-casein and κ-casein. In some embodiments, the recombinant fusion protein comprises β-casein and β-casein. In some embodiments, the recombinant fusion protein comprises para-κ-casein and para-κ-casein. In some embodiments, the recombinant fusion protein comprises α-S1-casein and α-S1-casein. In some embodiments, the recombinant fusion protein comprises α-S2-casein and α-S2-casein.

In some embodiments, the transformed plant is a monocot. For example, in some embodiments, the plant may be a monocot selected from turf grass, maize (corn), rice, oat, wheat, barley, sorghum, orchid, iris, lily, onion, palm, and duckweed.

In some embodiments, the transformed plant is a dicot. For example, in some embodiments, the plant may be a dicot selected from *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus. In some embodiments, the plant is a soybean (*Glycine max*).

In some embodiments, the plant is a non-vascular plant selected from moss, liverwort, hornwort or algae. In some embodiments, the plant is a vascular plant reproducing from spores (e.g., a fern).

In some embodiments, the recombinant DNA construct is codon-optimized for expression in the plant. For example, in some embodiments, the recombinant DNA construct is codon-optimized for expression in a soybean plant.

The transgenic plants described herein may be generated by various methods known in the art. For example, a nucleic acid encoding a fusion protein may be contacted with a plant, or a part thereof, and the plant may then be maintained under conditions wherein the fusion protein is expressed. In some embodiments, the nucleic acid is introduced into the plant, or part thereof, using one or more methods for plant transformation known in the art, such as *Agrobacterium*-mediated transformation, particle bombardment-medicated transformation, electroporation, and microinjection.

In some embodiments, a method for stably expressing a recombinant fusion protein in a plant comprises (i) transforming a plant with a plant transformation vector comprising an expression cassette comprising: a sequence encoding a fusion protein, wherein the fusion protein comprises a milk protein, and an animal (e.g., mammalian or avian) protein; and (ii) growing the transformed plant under conditions wherein the recombinant fusion protein is expressed. In some embodiments, the milk protein is κ-casein. In some embodiments, the animal protein is β-lactoglobulin. In some embodiments, the milk protein is κ-casein and the animal protein is β-lactoglobulin. In some embodiments, the recombinant fusion protein is expressed in an amount of 1% or higher per the total protein weight of the soluble protein extractable from the plant.

Casein Accumulation in Plants

As described herein, fusion proteins comprising one or more milk proteins (e.g., casein proteins) accumulate to a greater extent in plant cells than the milk proteins expressed individually (not as fusion proteins). Caseins aggregate and bind to calcium-phosphate to form micelles. Without being bound by any theory, it is believed that native plant proteases are capable of degrading caseins by cleavage at various protease recognition sites (FIG. 11A). Thus, when caseins are expressed alone (i.e., not as a fusion protein), they are degraded quickly and do not accumulate in the cells. When caseins are fused to a second protein (FIG. 11B, FIG. 11C), the second protein may partially or fully limit protease access to the cleavage site on the caseins and may reduce degradation thereof. The extent of protection may vary depending on the properties of the second protein. For example, fusion proteins comprising two caseins (e.g., homodimers or heterodimers, FIG. 11C) may be able adopt a conformation that partially or fully prevents access to one or more protease cleavage sites. Some non-casein proteins, such as beta-lactoglobulin, GFP, or lysozyme, may also partially or fully block protease access, allowing casein accumulation at high levels in the cell (FIG. 11B). Without being bound by any theory, it is believed that fusion of a casein to a second protein comprising one, two or all three of the following characteristics is able to prevent access to one or more protease cleavage sites on the casein: (i) a molecular weight of 15 kDa or higher; (ii) at least 30% hydrophobic amino acids; and/or (iii) less than about 2.5 disulfide bonds per 10 kDa molecular weight.

Protease access to cleavage sites on a casein protein may also be blocked, for example, by the addition of one or more post-translational modifications to the casein, such as phosphorylation, glycosylation (FIG. 11D) or lipidation (FIG. 11E). Thus, in some embodiments, a recombinant casein protein described herein comprises one or more post-translational modifications. The post-translational modifications may, in some embodiments, prevent proteolysis by endogenous plant proteases. For example, the presence of one or more post-translational modifications on a recombinant casein may reduce proteolysis of the casein in a plant cell by at least 10%, at least 20%, at least 30%, at least 40%, at least 50%, at least 60%, at least 70%, at least 80%, at least 90%, at least 100%, at least 200% or more, relative to the proteolysis of a casein that does not have the one or more post-translational modifications. In some embodiments, the presence of one or more post-translational modifications on a recombinant casein may lead to an increase in expression of at least 2-fold, at least 3-fold, at least 4-fold, at least 5-fold, at least 10-fold, at least 20-fold, at least 30-fold, at least 40-fold, at least 50-fold or more, relative to the expression of a casein that does not have the one or more post-translational modifications. The recombinant casein proteins comprising post-translational modifications described herein may be expressed alone or may be expressed in a fusion protein (e.g., a casein protein homo- or hetero-multimer).

In some embodiments, the post-translational modifications may be non-mammalian post-translational modifications. For example, the post-translational modifications may be plant post-translational modifications. In some embodiments, the post-translational modifications may not typically occur in a casein protein when expressed in a plant or an animal cell. A non-limiting list of post-translational modifications that may be used to prevent proteolysis by endogenous plant proteases includes glycosylation (e.g., O-glycans, N-glycans, or glycosaminoglycans such as heparin, heparan sulfate, chondroitin sulfate, keratan sulfate or dermatan sulfate), phosphorylation, lipidation, ubiquitylation, nitrosylation, methylation, acetylation, amidation, prenylation, alkylation, gamma-carboxylation, biotinylation, oxidation, or sulfation. In some embodiments, the post-translational modification is phosphorylation.

In some embodiments, a recombinant milk protein (e.g., a casein protein) comprises a site for post-translational modification that is not present in the native form of the protein. In some embodiments, a recombinant milk protein (e.g., a casein protein) comprises at least one, at least two, at least three, at least four, at least five, at least six, at least seven, at least eight, at least nine, or more sites for post-translational modifications that are not present in the native form of the protein. In some embodiments, a recombinant milk protein (e.g., a casein protein) comprises at least one, at least two, at least three, at least four, at least five, at least six, at least seven, at least eight, at least nine, or more post-translational modifications at sites that are not present in the native form of the protein.

In some embodiments, a recombinant milk protein (e.g., a casein protein) comprises an amino acid sequence that is modified to promote addition of one or more post-translational modifications in a plant cell. In some embodiments, the one or more post-translational modifications are selected from glycosylation, phosphorylation, lipidation, ubiquitylation, nitrosylation, methylation, acetylation, amidation, prenylation, alkylation, gamma-carboxylation, biotinylation, oxidation, and sulfation. In some embodiments, the amino acid sequence of a recombinant casein protein may be modified to introduce one or more glycosylation or phosphorylation sites.

In some embodiments, a milk protein is expressed in a plant, wherein the milk protein comprises an amino acid sequence that is modified to promote addition of one or more post-translational modifications, and wherein the milk protein comprises one or more post-translational modifications that are not present in a non-modified milk protein expressed in the same type of plant. In some embodiments, the milk protein is expressed in a plant in an amount of 1% or higher per total protein weight of soluble protein extractable from the plant. In some embodiments, the milk protein is a casein protein selected from α-S1 casein, α-S2 casein, β-casein, κ-casein, and para-κ-casein.

In some embodiments, a fusion protein comprises (i) a recombinant milk protein that comprises an amino acid sequence that is modified to promote addition of one or more post-translational modifications in a plant cell, and (ii) at least one additional protein. In some embodiments, the at least one additional protein is a milk protein. In some embodiments, the at least one additional protein is a casein protein selected from α-S1 casein, α-S2 casein, β-casein, κ-casein, and para-κ-casein. In some embodiments, the at least one additional protein is β-lactoglobulin. In some embodiments, the recombinant milk protein is κ-casein or para-κ-casein and the at least one additional protein is β-lactoglobulin. In some embodiments, the recombinant milk protein is β-casein and the at least one additional protein is β-lactoglobulin. In some embodiments, the recombinant milk protein is α-S1 casein or α-S2 casein and the at least one additional protein is β-lactoglobulin. In some embodiments, the fusion protein is expressed in a plant in an amount of 1% or higher per total protein weight of soluble protein extractable from the plant. In some embodiments, the plant is soybean.

In some embodiments, a transgenic plant expresses a milk protein comprising an amino acid sequence that is modified to promote addition of one or more post-translational modifications, or a fusion protein comprising the same.

Proteolysis of recombinant caseins in plant cells may also be prevented by modifying the plant cell itself. Without being bound by any theory, it is believed that in wildtype seeds, proteases present in one or more cellular compartments may bind to and cleave casein expressed therein. Thus, casein does not accumulate at high levels in the seeds (See FIG. 18, top panel). In contrast, when expression of one or more proteases is knocked-down or knocked-out in the seed (indicated by "X" in the bottom panel of FIG. 18), degradation of the casein is substantially prevented. Accordingly, the casein can accumulate in the seed. This strategy may be used to increase expression in the seed of casein monomers (i.e., caseins expressed alone, not as a fusion protein), or fusion proteins comprising one or more caseins.

In some embodiments, expression of one or more endogenous plant proteases may be knocked down or knocked out in a plant cell (e.g., a seed). The one or more proteases may be, for example, one or more proteases endogenously expressed in a plant (e.g., a soybean), such as cysteine proteases, serine proteases, threonine proteases, or aspartic proteases, glutamic proteases, metalloproteases, or asparagine peptide lyases. A non-limiting list of genes encoding proteases that may be knocked down or knocked out in a plant cell is provided below in Table 10. Additional proteases that may be knocked down or knocked out in a soybean cell are described in Shamimuzzaman M., Vodkin L (2018) Ribosome profiling reveals changes in translational status of soybean transcripts during immature cotyledon development. *PLOS ONE* 13 (3): e0194596.

In some embodiments, expression of at least one, at least two, at least three, at least four, at least five, at least six, at least seven, at least eight, at least nine, at least ten or more proteases may be knocked down or knocked out in a plant cell.

TABLE 10

Genes encoding proteases that are transcriptionally active in soybeans
Soybean Gene ID Glyma.02g213000
Glyma.03g125400
Glyma.03g239700
Glyma.04g022500
Glyma.04g027600
Glyma.04g091800
Glyma.06g022600
Glyma.06g027700
Glyma.06G272700
Glyma.06g275300
Glyma.08g116300
Glyma.08G116400
Glyma.09g187200
Glyma.09g226700
Glyma.09g249500
Glyma.10g207100
Glyma.12G010100
Glyma.13g027600
Glyma.13g196200
Glyma.13g208200
Glyma.13g255900
Glyma.13g321700
Glyma.14g048000
Glyma.14g064600
Glyma.14g085800
Glyma.14g216300
Glyma.15g177800
Glyma.15g234300
Glyma.16G018900
Glyma.17g164100
Glyma.17g239000
Glyma.17g254900
Glyma.18G242900
Glyma.18g250100
Glyma.19G236600

TABLE 11

Proteases that may be knocked down or knocked out in a plant cell

| Protein Name | Accession No. (Uniprot) | DNA Sequence | Protein Sequence |
|---|---|---|---|
| Peptidase A1 domain-containing protein | Glyma.04g091800 | 851 | 852 |
| Cysteine proteinase | Glyma.10g207100 | 853 | 854 |
| 34 kDa maturing seed protein | Glyma.08g116300 | 855 | 856 |
| Uncharacterized protein (cysteine protease family C1-related) | Glyma.06g275300 | 857 | 858 |
| Uncharacterized protein (Subsilin-like serine peptidase) | Glyma.17g164100 | 859 | 560 |

In some embodiments, a plant cell for expressing recombinant milk proteins is provided, wherein expression of one or more proteases is reduced (e.g., knocked down or knocked out) in the cell. The expression of the one or more proteases may be reduced (e.g., knocked down or knocked out), for example, using a gene editing technology (e.g., CRISPR, TALENs, Zn Finger Nuclease, etc.) or base editing technology (e.g., using a cytidine deaminase or an adenosine deaminase). In some embodiments, expression of the one or more proteases may be reduced using RNA interference (e.g., microRNAs or siRNAs). In some embodiments the one or more proteases that is knocked down or knocked out is a cysteine protease, a serine protease, or an aspartyl protease. In some embodiments, the one or more proteases that is knocked down or knocked out is any one of the proteases listed in Table 10 or Table 11. In some embodiments, the one or more proteases that is knocked down or knocked out comprises the sequence of any one of SEQ ID NO: 852, 584, 856, 858, or 860. In some embodiments, the one or more proteases that is knocked down or knocked out comprises a sequence with at least 85%, at least 90%, at least 91%, at least 92%, at least 93%, at least 94%, at least 95%, at least 96%, at least 97%, at least 98%, or at least 99% sequence identity with any one of SEQ ID NO: 852, 584, 856, 858, or 860. In some embodiments, the one or more proteases that is knocked down or knocked out comprises a sequence of any one of SEQ ID NO: 852, 584, 856, 858, or 860 plus at least 1, at least 2, at least 3, at least 4, at least 5, at least 6, at least 7, at least 8, at least 9, at least 10, at least 11, at least 12, at least 13, at least 14, at least 15, or more amino acid substitutions. The expression or activity of endogenous plant proteases may also be reduced using small molecule inhibitors thereof (i.e., protease inhibitors).

Also provided is a transgenic plant comprising a plant cell for expressing recombinant milk proteins, wherein expression of one or more proteases is reduced (e.g., knocked down or knocked out) in the plant.

In some embodiments, a method for stably expressing a recombinant milk protein in a plant comprises: (i) reducing expression of one or more proteases in the plant, (ii) transforming the plant with a plant transformation vector comprising an expression cassette encoding a recombinant milk protein or a fusion protein comprising the same, (iii) growing the transformed plant under conditions wherein the recombinant milk protein is expressed in an amount of 1% or higher per total weight of soluble protein extractable from the plant.

In some embodiments, a recombinant casein protein that comprises one or more post-translational modifications is produced in a plant cell by expressing or over-expressing one or more enzymes in the plant cell, such as an enzyme known to perform post-translational modifications (e.g., a kinase, a phosphatase, or glycosyltransferase). In some embodiments, a recombinant casein protein that comprises one or more post-translational modifications is produced in a plant cell by knocking out or knocking down one or more enzymes the plant cell known to remove or prevent addition of post-translational modifications (e.g., a phosphatase or an endoglycosidase). In some embodiments, a recombinant casein protein that comprises one or more post-translational modifications is produced in a plant cell by contacting the cell with one or more precursors of the post-translational modification (e.g., a nucleotide sugar precursor).

In some embodiments, a recombinant casein protein comprises one or more glycoprotein tags. For example, in some embodiments, a recombinant casein protein may comprise a glycoprotein tag derived from a hydroxyproline (Hyp)-rich glycoprotein (GRGP). In some embodiments, the glycoprotein tag comprises SP repeats. For example, the glycoprotein tag may be derived from a glycoprotein comprising 11 tandem SP repeats (See Glyma.02 g204500, annotated as early nodulin-like protein 10 in soy). In some embodiments, the fusion protein comprises the M domain of CD45 (receptor-type tyrosine-protein phosphatase C), or a fragment or derivative thereof. For example, in some embodiments, the fusion protein comprises amino acids Ala231 to Asp 290 of Uniprot Accession No. P08575. In some embodiments, the glycoprotein tag comprises the sequence of SEQ ID NO: 824. In some embodiments, the glycoprotein tag is encoded by the sequence SEQ ID NO: 825. In some embodiments, the glycoprotein tag comprises the sequence of SEQ ID NO: 827. In some embodiments, the glycoprotein tag is encoded by the sequence of SEQ ID NO: 826. The glycoprotein tag may be fused, in some embodiments, to the N-terminus or the C-terminus of the casein protein.

Illustrative expression cassettes for expressing a gene of interest (GOI; e.g., a casein) fused to a glycoprotein tag are provided in FIG. 25A-25F. In some embodiments, an expression cassette comprises a promoter, a signal peptide, a glycoprotein tag, a GOI (e.g., a casein) and a terminator (See FIG. 25A). In some embodiments, an expression cassette comprises a promoter, a signal peptide, a GOI, a glycoprotein tag, and a terminator. (See FIG. 25B). In some embodiments, an expression cassette comprises the GmSeed 2 promoter (SEQ ID NO: 813), the pat21ss signal peptide (SEQ ID NO: 823), a (SP) 11 glycoprotein tag (SEQ ID NO: 825), a GOI (e.g., a casein) and the AtHSP/AtUBi10 Terminator (SEQ ID NO: 815, 816) (See FIG. 25C). In some embodiments, an expression cassette comprises the GmSeed 2 promoter (SEQ ID NO: 813), the pat21ss signal peptide (SEQ ID NO: 823), a GOI (e.g., a casein), a (SP) 11 glycoprotein tag (SEQ ID NO: 825), and the AtHSP/AtUBi10 Terminator (SEQ ID NO: 815,816) (See FIG. 25D). In some embodiments, an expression cassette comprises the GmSeed 2 promoter (SEQ ID NO: 813), the sig2 signal peptide (SEQ ID NO: 814), a CD45 tag (SEQ ID NO: 827), a GOI (e.g., a casein), a KDEL sequence (SEQ ID NO: 23), and the AtHSP/AtUBi10 Terminator (SEQ ID NO: 815, 816) (See FIG. 25E). In some embodiments, an expression cassette comprises the GmSeed 2 promoter (SEQ ID NO: 813), the sig2 signal peptide (SEQ ID NO: 814), a GOI (e.g., a casein), a CD45 tag (SEQ ID NO: 827), a KDEL sequence (SEQ ID NO: 23), and the AtHSP/AtUBi10 Terminator (SEQ ID NO: 815, 816) (See FIG. 25F).

Following protein synthesis, many eukaryotic proteins undergo post-translational modification (PTM). These modifications may be for example, the covalent addition of a function group, and contributes to protein diversity and function. Examples of PTMs include, but are not limited to, phosphorylation, glycosylation, ubiquitination, nitrosylation, methylation, acetylation, and lipidation. The proteins within milk also undergo PTM (Greenberg et al., "Human beta-casein. Amino acid sequence and identification of phosphorylation sites," *J. Biol. Chem.*, 1984, 259 (8): 5132-5138, Imafidon et al., "Isolation, purification, and alteration of some functional groups of major milk proteins: a review," *Crit. Rev. Food. Sci. Nutr.* 37 (7): 663-689, 1997). For example, alpha and beta caseins are phosphorylated, and kappa casein is glycosylated. It has been reported that caseins assemble in a colloidal complex with calcium phosphate and other minerals.

In some embodiments, a casein protein expressed in a plant cell comprises different post-translational modifications relative to the same casein protein expressed by a mammalian cell. In some embodiments, a casein protein expressed in a plant cell does not comprise any post-translational modifications. In some embodiments, a casein protein expressed in a plant cell has reduced phosphorylation compared to the same casein protein expressed in a mammalian cell. In some embodiments, a casein protein expressed in a plant cell has increased phosphorylation compared to the same casein protein expressed in a mammalian cell.

In some embodiments, the compositions and methods described herein can be used to produce a casein protein that does not comprise any post-translational modifications. In some embodiments, the compositions and methods described herein can be used to produce a casein protein that is substantially free of phosphorylation. In some embodiments, the compositions and methods described herein can be used to produce a casein protein in a plant cell that comprises substantially the same level of post-translational modifications relative to the same casein protein expressed in a mammalian cell. In some embodiments, the compositions and methods described herein can be used to produce a casein protein that comprises substantially the same level of phosphorylation relative to the same casein protein expressed in a mammalian cell. For example, in some embodiments, a casein protein expressed in a plant cell may comprise at least 50%, at least 60%, at least 70%, at least 80%, at least 90%, or at least 95% of the number of phosphates relative to the same casein protein expressed in a mammalian cell.

Methods for Producing Recombinant Milk Proteins, Including Casein Proteins

The recombinant milk proteins (e.g., casein proteins) described herein may be produced in a number of non-mammalian species, including for example, plants and microorganisms such as yeast and bacteria.

The recombinant casein proteins may be expressed in one or more non-mammalian cells using genetic sequences (e.g., DNA or RNA sequences) isolated or derived from cow (*Bos taurus*), goat (*Capra hircus*), sheep (*Ovis aries*), water buffalo (*Bubalus bubalis*), dromedary camel (*camelus dromedaries*), bactrian camel (*Camelus bactrianus*), wild yak (*Bos mutus*), horse (*Equus caballus*), donkey (*Equus asinus*), reindeer (*Rangifer tarandus*), Eurasian elk (*Alces alces*), alpaca (*vicugna pacos*), zebu (*Bos indicus*), llama (*Lama glama*), or human (*Homo sapiens*). In some embodiments, a genetic sequence used to encode the recombinant casein has at least 80%, at least 85%, at least 90%, at least 95%, at least 96%, at least 97%, at least 98%, or at least 99% identity with the genetic sequence sued to encode a casein protein in one or more of cow (*Bos taurus*), goat (*Capra hircus*), sheep (*Ovis aries*), water buffalo (*Bubalus bubalis*), dromedary camel (*camelus dromedaries*), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*Vicugna pacos*), zebu (*bos indicus*), llama (*Lama glama*), or human (*Homo sapiens*). In some embodiments, the recombinant casein protein expressed in a non-mammalian cell has at least 80%, at least 85%, at least 90%, at least 95%, at least 96%, at least 97%, at least 98%, or at least 99% identity with a casein protein from one or more of cow (*Bos taurus*), goat (*Capra hircus*), sheep (*Ovis aries*), water buffalo (*Bubalus bubalis*), dromedary camel (*camelus* dromedaries), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*Vicugna pacos*), zebu (*Bos indicus*), llama (*Lama glama*), or human (*Homo sapiens*).

When expressed in a plant, the recombinant casein proteins may be extracted using standard methods known in the art. For example, the casein proteins may be extracted using solvent or aqueous extraction or using phenol extraction. Once extracted, the casein proteins may be maintained in a buffered environment (e.g., Tris, MOPS, HEPES), in order to avoid sudden changes in the pH. The casein proteins may also be maintained at a particular temperature, such as 4° C. One or more additives may be used to aid the extraction process (e.g., salts, protease/peptidase inhibitors, osmolytes, reducing agents, etc.)

Protein Co-Expression in Plants

Another way to increase accumulation of one or more recombinant proteins, such as milk proteins, in a plant cell is to co-express the protein with a second protein, such as a protein capable of forming a protein body (e.g., a prolamin). Without being bound by any theory, it is believed that co-expressing a milk protein and a prolamin protein in a plant cell will cause protein body formation in the plant cell, wherein the milk protein gets sequestered into and/or associated with the protein body. This protects the milk protein from degradation by one or more proteases and increases accumulation thereof in the plant cell.

In some embodiments, two or more recombinant proteins may be co-expressed in a plant cell. In some embodiments, one of the two or more recombinant proteins is a milk protein (e.g., casein protein). In some embodiments, the milk protein is selected from the group consisting of: α-S1 casein, α-S2 casein, β-casein, κ-casein, para-κ-casein, β-lactoglobulin, α-lactalbumin, lysozyme, lactoferrin, lactoperoxidase, and an immunoglobulin. In some embodiments, the milk protein is β-casein or β-lactoglobulin.

In some embodiments, one of the two or more proteins is a protein capable of forming a protein body. For example, in some embodiments, one of the two or more proteins is a prolamin (e.g., zein and/or canein). In some embodiments, the prolamin is selected from the group consisting of: gliadin, a hordein, a secalin, a zein, a kafirin, and an avenin. In some embodiments, the protein capable of forming a protein body is a hydrophobin or an elastin-like protein. In some embodiments, at least two proteins are co-expressed in a plant cell (e.g., a casein protein and a prolamin). In some embodiments, the at least two proteins are casein and zein (e.g., gamma-zein). In some embodiments, the at least two proteins are casein and canein.

In some embodiments, a method for expressing a first recombinant protein in a cell comprises: (i) contacting the cell with a vector encoding a first recombinant protein, and (ii) contacting the cell with a vector encoding a second recombinant protein, wherein the second recombinant protein is capable of forming a protein body (e.g., a prolamin.)

In some embodiments, the first recombinant protein is a casein protein, such as a milk protein.

A milk protein (e.g., a casein protein) may, in some embodiments, be co-expressed with a protein capable of forming a protein body (e.g., a prolamin) in a transgenic plant. In some embodiments, co-expressing a milk protein (e.g., a casein protein) with a protein capable of forming a protein body (e.g., a prolamin) in a transgenic plant leads to accumulation of the milk protein in an amount of at least 1%, at least 1.5%, at least 2%, at least 2.5%, at least 3%, at least 3.5%, at least 4%, at least 4.5%, at least 5%, at least 5.5%, at least 6%, at least 6.5%, at least 7%, at least 7.5%, at least 8%, at least 8.5%, at least 9%, at least 9.5%, at least 10%, at least 10.5%, at least 11%, at least 11.5%, at least 12%, at least 12.5%, at least 13%, at least 13.5%, at least 14%, at least 14.5%, at least 15%, at least 15.5%, at least 16%, at least 16.5%, at least 17%, at least 17.5%, at least 18%, at least 18.5%, at least 19%, at least 19.5%, at least 20%, or more of total protein weight of soluble protein extractable from the plant.

Figure 27:
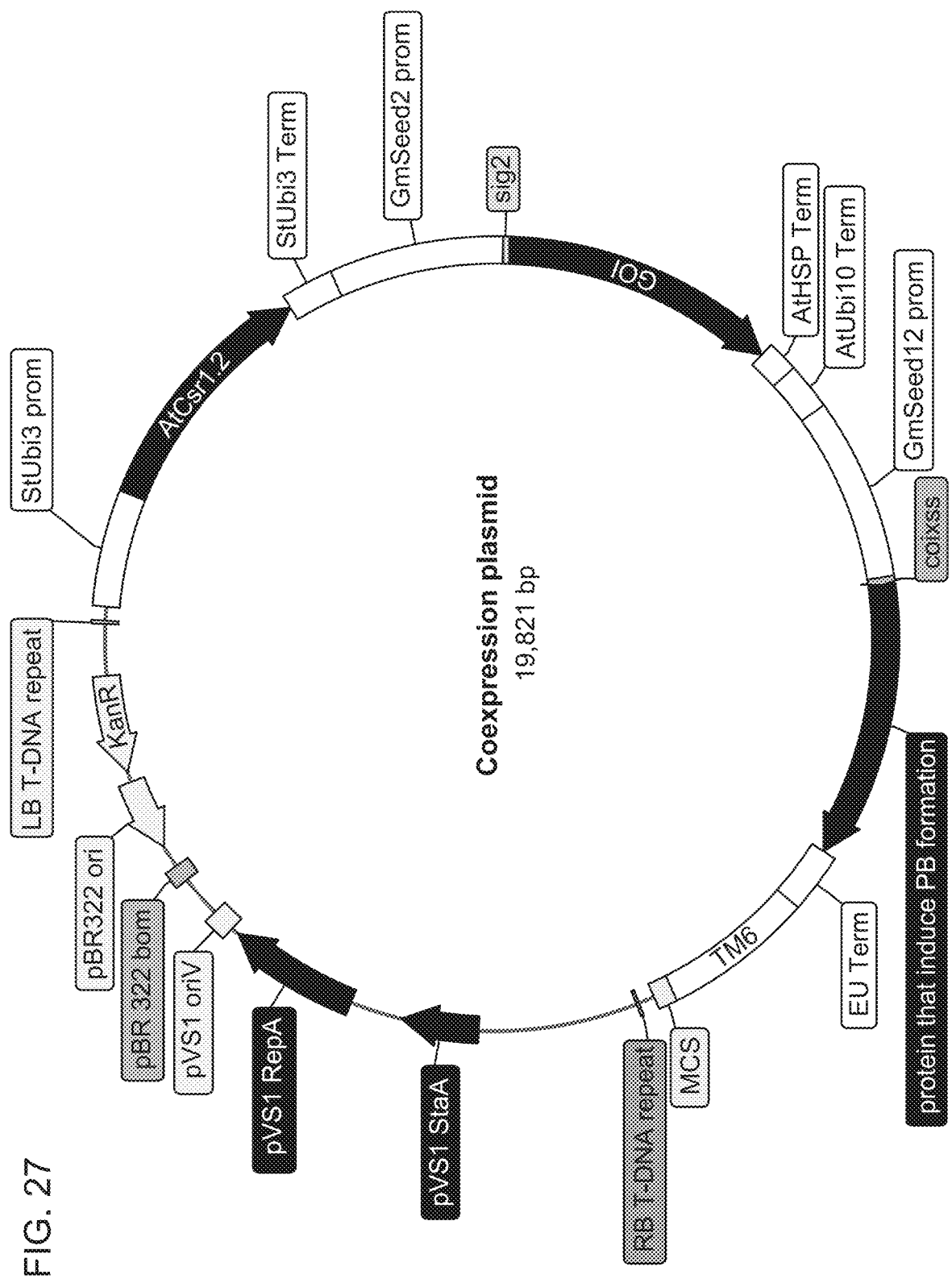
FIG. 27 shows a binary *Agrobacterium* vector used to co-express a Gene of Interest (GOI, e.g., a casein protein) and a protein capable of inducing a protein body in a plant cell.

Illustrative constructs for co-expressing a milk protein (e.g., a casein protein) and a protein capable of inducing formation of a protein body in a plant cell are provided in FIG. 26A-26G. In some embodiments, a construct comprises (i) a first expression cassette comprising a promoter, a signal peptide, a Gene of Interest (e.g., a casein protein) and a terminator, and (ii) a second expression cassette comprising a promoter, a signal peptide, a protein that induces protein body formation, and a terminator (See FIG. 26A). In some embodiments, a construct comprises (i) a first expression cassette comprising a promoter, a signal peptide, a Gene of Interest (e.g., a casein protein) and a terminator, and (ii) a second expression cassette comprising a promoter, a signal peptide, a prolamin, and a terminator (See FIG. 26B). In some embodiments, a construct comprises (i) a first expression cassette comprising a promoter, a signal peptide, a Gene of Interest (e.g., a casein protein) and a terminator, and (ii) a second expression cassette comprising a promoter, a signal peptide, a zein, and a terminator (See FIG. 26C). In some embodiments, a construct comprises (i) a first expression cassette comprising a promoter, a signal peptide, a Gene of Interest (e.g., a casein protein) and a terminator, and (ii) a second expression cassette comprising a promoter, a signal peptide, a canein, and a terminator (See FIG. 26D). In some embodiments, a construct comprises (i) a first expression cassette comprising a promoter, a signal peptide, a Gene of Interest (e.g., a casein protein) and a terminator, and (ii) a second expression cassette comprising a promoter, a signal peptide, a hydrophobin, and a terminator (See FIG. 26E). In some embodiments, a construct comprises (i) a first expression cassette comprising a promoter, a signal peptide, a Gene of Interest (e.g., a casein protein) and a terminator, and (ii) a second expression cassette comprising a promoter, a signal peptide, an elastin-like protein, and a terminator (See FIG. 26F). In some embodiments, a construct comprises (i) a first expression cassette comprising a GmSeed2 promoter, a Sig2 signal peptide, a Gene of Interest (e.g., a casein protein) and a AtHSP/AtUbi10 terminator, and (ii) a second expression cassette comprising a GmSeed 12 promoter, a Coixss signal peptide, a protein that induces protein body formation, and a EU Term/Tm6 terminator (See FIG. 26G). An illustrative binary vector for use in coexpressing a casein and a protein that can induce protein body formation is provided in FIG. 27.

In some embodiments, a milk protein (e.g., a casein protein) can be co-expressed with one or more proteins capable of adding or removing a post-translational modification to/from a milk protein. For example, in some embodiments, the milk protein may be co-expressed with one or more of a kinase, a phosphatase, or a glycosyltransferase. In some embodiments, the milk protein is co-expressed with a kinase. The kinase may be for example, a kinase that phosphorylates Ser-X-Glu/pSer motifs. In some embodiments, the kinase may be a kinase in the family 20C, such as the Fam20C kinase. In some embodiments, the kinase may be a fragment or derivative of the Fam20C kinase, such as a truncated Fam20C comprising amino acids 94-586 of the native protein. In some embodiments, the kinase comprises amino acids 94-586 of SEQ ID NO: 821, or a sequence at least 90%, at least 95%, at least 96%, at least 97%, at least 98%, or at least 99% identical thereto. In some embodiments, the kinase is encoded by the sequence of SEQ ID NO: 820, or a sequence at least 90%, at least 95%, at least 96%, at least 97%, at least 98%, or at least 99% identical thereto.

Illustrative expression cassettes that may be used to co-express a milk protein (e.g., a casein protein) with a kinase (or other enzyme capable of adding/removing a PTM) are shown in FIG. 24A-24E. In some embodiments, a construct for co-expression of a milk protein in a cell comprises: (i) a first expression cassette comprising a promoter, a signal peptide, a Gene of Interest (GOI, e.g., a casein protein) and a terminator, and (ii) a second expression cassette comprising a promoter, a 5'UTR, a signal peptide, a Gene of Interest (GOI, e.g., a kinase), and a terminator (See FIG. 24B). In some embodiments, a construct for co-expression of a milk protein in a cell comprises: (i) a first expression cassette comprising a promoter, a signal peptide, a Gene of Interest (GOI, e.g., a casein protein) and a terminator, and (ii) a second expression cassette comprising a promoter, a 5'UTR, a signal peptide, a Gene of Interest (GOI, e.g., a kinase in the 20C family), and a terminator (See FIG. 24A). In some embodiments, a construct for co-expression of a milk protein in a cell comprises: (i) a first expression cassette comprising a promoter, a signal peptide, a Gene of Interest (GOI, e.g., a casein protein) and a terminator, and (ii) a second expression cassette comprising a promoter, a 5'UTR, a signal peptide, a Gene of Interest (GOI, e.g., a Fam20C kinase), and a terminator (See FIG. 24C). In some embodiments, a construct for co-expression of a milk protein in a cell comprises: (i) a first expression cassette comprising a promoter, a signal peptide, a Gene of Interest (GOI, e.g., a casein protein) and a terminator, and (ii) a second expression cassette comprising a promoter, a 5'UTR, a signal peptide, a Gene of Interest (GOI, e.g., a truncated Fam20C kinase), and a terminator (See FIG. 24D). In some embodiments, the promoter may be the GmSeed2 promoter (SEQ ID NO: 813) or the PvPhas promoter (SEQ ID NO: 817). In some embodiments, the promoter may be the Sig2 signal peptide (SEQ ID NO: 814) or the sig10 signal peptide (SEQ ID NO: 819). In some embodiments, the terminator may be the AtHSP/AtUbi10 Terminator (SEQ ID NO: 815, 816) or the 3arc Terminator (SEQ ID NO: 822). In some embodiments, the 5'UTR may be the Arc 5'UTR (SEQ ID NO: 818). In some embodiments, the construct for co-expression of a milk protein in a cell comprises the construct of FIG. 24E. An illustrative binary vector is provided in FIG. 23.

In some embodiments, a milk protein (e.g., a casein protein) can be co-expressed with one or more proteins capable of inhibiting a protease. Illustrative plant proteins that may be used to inhibit one or more proteases are shown above in Table 4. In some embodiments, a milk protein may be co-expressed with any one of the proteins shown in Table 4. In some embodiments, a milk protein is co-expressed with a protein that comprises the sequence of any one of SEQ ID NO: 840, 842, 844, 846, 848 or 850. In some embodiments, a milk protein may be co-expressed with a protein having a sequence with at least 85%, at least 90%, at least 91%, at least 92%, at least 93%, at least 94%, at least 95%, at least 96%, at least 97%, at least 98%, or at least 99% identity to any one of SEQ ID NO: 840, 842, 844, 846, 848 or 850. In some embodiments, the milk protein may be co-expressed with a protein having the sequence of any one of SEQ ID NO: 840, 842, 844, 846, 848 or 850 plus at least 1, at least 2, at least 3, at least 4, at least 5, at least 6, at least 7, at least 8, at least 9, at least 10, at least 11, at least 12, at least 13, at least 14, at least 15, or more amino acid substitutions.

In some embodiments, protein co-expression can be utilized to reduce or prevent degradation of the one or more proteins in the plant cell, such as protease-mediated degradation in the plant cell. In some embodiments, the protein-co-expression is useful to reduce or prevent degradation of one or more milk proteins by proteases in a plant cell. In some embodiments co-expressing one or more milk proteins (e.g., casein protein) and a prolamin (e.g., a canein or a zein) may lead to the formation of a protein body in a seed of a plant. In some embodiments, the one or more milk proteins can be sequestered in and/or associated with the protein body, which in turn partially or fully shields the one or more milk proteins from degradation by plant cell proteases thereby allowing for accumulation of the one or more milk proteins. In some embodiments, the one or more milk proteins can be sequestered in the protein body, which in turn may protect a plant cell from potential toxic effects of recombinant proteins, such as any toxic effects of the one or more proteins.

In some embodiments, protein co-expression is effective in increasing at least one of concentration, stability, or expression of one or more proteins in a plant cell. In some embodiments, protein co-expression is effective in increasing concentration of one or more proteins in a plant cell as determined by detecting the amount of the one or more protein in the plant cell. In some embodiments, protein co-expression is effective in increasing stability of one or more proteins in a plant cell. Increased stability can be determined by detecting persistence of the one or more proteins in the plant cell over time or detecting a level of degradation. In some embodiments, protein co-expression is effective in increasing expression of one or more proteins in a plant cell. Increased expression can be determined by measuring protein level and/or accumulation in the plant cell. In some embodiments, protein co-expression is effective in increasing at least one of: concentration, stability, or expression of one or more proteins by at least about 1-fold, 10-fold, 19-fold, 28-fold, 37-fold, 46-fold, 55-fold, 64-fold, 73-fold, 82-fold, 91-fold, 100-fold, 109-fold, 118-fold, 127-fold, 136-fold, 145-fold, 154-fold, 163-fold, 172-fold, 181-fold, 190-fold, 199-fold, 208-fold, 217-fold, 226-fold, 235-fold, 244-fold, 253-fold, 262-fold, 271-fold, 280-fold, 289-fold, 298-fold, or up to about 300-fold as compared to an otherwise comparable method lacking the protein co-expression. In some embodiments, protein co-expression is effective in increasing at least one of concentration, stability, or expression of one or more proteins in a plant cell by at least about 1-fold to 10-fold, 5-fold to 30-fold, 20-fold to 50-fold, 40-fold to 100-fold, or 100-fold to 200-fold as compared to an otherwise comparable method lacking the protein co-expression.

In some embodiments, protein co-expression is effective in reducing toxicity of recombinant expression of the one or more proteins in a plant cell. In some embodiments, protein co-expression is effective in reducing toxicity of recombinant expression of one or more proteins in a plant cell by at least about 1-fold, 10-fold, 19-fold, 28-fold, 37-fold, 46-fold, 55-fold, 64-fold, 73-fold, 82-fold, 91-fold, 100-fold, 109-fold, 118-fold, 127-fold, 136-fold, 145-fold, 154-fold, 163-fold, 172-fold, 181-fold, 190-fold, 199-fold, 208-fold, 217-fold, 226-fold, 235-fold, 244-fold, 253-fold, 262-fold, 271-fold, 280-fold, 289-fold, 298-fold, or up to about 300-fold as compared to an otherwise comparable method lacking the protein co-expression. In some embodiments, protein co-expression is effective in reducing toxicity associated with recombinant expression of one or more proteins in a plant cell by at least about 1-fold to 10-fold, 5-fold to 30-fold, 20-fold to 50-fold, 40-fold to 100-fold, or 100-fold to 200-fold as compared to an otherwise comparable method lacking the protein co-expression.

In some embodiments, protein co-expression may be achieved via transformation of a composition comprising one or more vectors encoding the one or more proteins into a plant cell. In some embodiments, one or more vectors are binary *agrobacterium* vectors. In some embodiments, one or more vectors encodes for one or more protein sequences. In some embodiments, a single vector encodes for two or more protein sequences. In some embodiments, two or more vectors are used to introduced two or more sequences into a plant cell. In some embodiments, a vector encodes for a milk protein (e.g., casein protein) and a prolamin (e.g., a canein or a zein). In some embodiments, a vector encodes for a milk protein and a protein capable of forming a protein body. In some embodiments a first vector encodes for a milk protein and a second vector encodes for a prolamin. In some embodiments, a first vector encodes for a milk protein and a second vector encodes for a prolamin. Also provided are compositions that comprise one or more vectors described herein.

Food Compositions Comprising a Fusion Protein or a Protein Derived Therefrom

The fusion proteins, recombinant proteins, and transgenic plants described herein may be used to prepare food compositions. The fusion protein may be used directly to prepare the food composition (i.e., used in the form of a fusion protein), or the fusion protein may first be separated into its constituent proteins. For example, in some embodiments, a food composition may comprise (i) a fusion protein, (ii) a milk protein (structured or unstructured) or (iii) a non-milk protein, such as a structured mammalian, avian, or plant protein.

More specifically, the present disclosure provides alternative dairy compositions, solid phase protein-stabilized emulsions (including cheese compositions), and colloidal suspensions, each comprising one or more casein proteins. The casein proteins may be isolated or recombinant and may be selected from the group consisting of kappa-casein, para-kappa-casein, beta-casein, alpha-S1-casein and alpha-S2-casein. The compositions, emulsions, or suspensions described herein may be used to produce food compositions (e.g., cheese, yogurt, ice cream, etc.) that have organoleptic properties similar to traditional animal-derived dairy compositions. For example, the food compositions described herein may have one or more characteristics of a traditional animal-derived dairy composition, such as taste, aroma, appearance, handling, mouthfeel, density, structure, texture, elasticity, springiness, coagulation, binding, leavening, aeration, foaming, creaminess and emulsification. The food compositions described herein offer a sustainable, environmentally-friendly, cruelty-free alternative to traditional animal-derived dairy compositions.

In some embodiments, the alternative dairy compositions, solid phase, protein-stabilized emulsions, and colloidal suspensions comprising recombinant casein proteins have non-mammalian PTMs. In some embodiments, the recombinant casein proteins are not phosphorylated or glycosylated. In some embodiments, the recombinant casein proteins have an alternative PTM pattern, as compared to naturally occurring casein proteins.

PTMs have been reported to be important for the casein micelle structure, which determines the physical properties of milk. Unexpectedly, the recombinant proteins described herein are still able to confer to the compositions described herein one or more organoleptic properties similar to animal-derived dairy compositions, such as taste, appearance, mouthfeel, structure, texture, density, elasticity, springiness, coagulation, binding, leavening, aeration, foaming, creaminess, and emulsification.

Food compositions, including alternative dairy compositions, solid phase protein-stabilized emulsions, and colloidal suspensions, are described in more detail below.

Solid Phase Protein-Stabilized Emulsions

Provided herein are solid phase, protein-stabilized emulsions comprising at least one milk protein. For example, in some embodiments, a solid phase, protein-stabilized emulsion comprises at least one casein protein. In some embodiments, a protein-stabilized emulsion comprises at least one recombinant casein protein. In some embodiments, a protein-stabilized emulsion comprises at least one plant-expressed casein protein. In some embodiments, a protein-stabilized emulsion comprises at least one casein protein isolated from milk (e.g., bovine milk). In some embodiments, the protein-stabilized emulsion is a cheese composition.

In some embodiments, a solid-phase protein stabilized protein emulsion comprises only one casein protein. In some embodiments, the one casein protein is recombinant beta-casein protein.

In some embodiments, a solid-phase protein stabilized protein emulsion comprises only two casein proteins. In some embodiments, the two casein proteins are recombinant beta-casein protein and kappa-casein protein. In some embodiments, the two casein proteins are recombinant beta-casein protein and para-kappa-casein protein. In some embodiments, the two casein proteins are recombinant beta-casein protein and alpha-S1-casein protein. In some embodiments, the two casein proteins are recombinant beta-casein protein and alpha-S2-casein protein.

In some embodiments, a solid-phase, protein stabilized emulsion comprises only three casein proteins. In some embodiments, the three casein proteins are recombinant beta-casein, kappa-casein, and para-kappa-casein. In some embodiments, the three casein proteins are recombinant beta-casein, kappa-casein, and alpha-S1-casein. In some embodiments, the three casein proteins are recombinant beta-casein, kappa-casein, and alpha-S2-casein. In some embodiments, the three casein proteins are recombinant beta-casein, para-kappa-casein, and alpha-S1-casein. In some embodiments, the three casein proteins are recombinant beta-casein, para-kappa-casein, and alpha-S2-casein.

In some embodiments, a solid-phase, protein stabilized emulsion comprises only four casein proteins. In some embodiments, one of the four casein proteins is recombinant beta-casein.

The casein proteins used in the solid-phase, protein-stabilized emulsions described herein may be selected from kappa-casein, para-kappa-casein, beta-casein, alpha-S1-casein and alpha-S2-casein. In some embodiments, the solid-phase protein stabilized emulsions may comprise, in addition to the casein protein(s), one or more additional milk proteins. In some embodiments, the solid-phase protein stabilized emulsions may comprise, in addition to the casein protein(s), one or more plant proteins.

In some embodiments, the emulsion has a firmness of at least 150 grams. In some embodiments, the emulsion has a melting point of about 35° C. to about 100° C. In some embodiments, the emulsion has an ability to stretch to at least 3 cm in length without breaking. In some embodiments, the emulsion has a firmness of at least 150 grams and a melting point of about 35° C. to about 100° C. In some embodiments, the emulsion has a firmness of at least 150 grams and an ability to stretch to at least 3 cm in length without breaking. In some embodiments, the emulsion has a melting point of about 35° C. to about 100° C. and an ability to stretch to at least 3 cm in length without breaking. In some embodiments, the emulsion has a firmness of at least 150 grams, a melting point of about 35° C. to about 100° C., and an ability to stretch to at least 3 cm in length without breaking.

Firmness, also referred to herein as hardness, may be measured by a number of methods known in the art, such as by compression, or using an instrument such as the Instron Testing Machine (A. H. Chen et al., Textural analysis of cheese, 1979, *J. Dariy Sci.* 62:901-907). For example, a cylindrical-shaped sample of a solid-phase, protein stabilized emulsion may be compressed from 50% to 100% relative to its original height and/or width. The cylindrical shaped-sample may have a height in the range of about 1 to about 10 cm, or more, and a diameter in the range of about 1 to about 10 cm, or more. The compression may occur at a predetermined temperature, such as a temperature in the range of about 0° C. to about 5° C., about 5° C. to about 10° C., about 10° C. to about 20° C., about 15° C. to about 25° C., about 20° C. to about 25° C., about 25° C. to about 25° C. In some embodiments, firmness may be determined by compressing a cylindrical-shaped sample having a height of about 3 cm, and a diameter of about 3 cm may be compressed to a height of 1.5 cm at 5° C. The compositions described herein may have a firmness in the range of about 50 to 100 grams, about 100 to about 150 grams, about 150 grams to about 200 grams, about 200 to about 300 grams, about 300 grams to about 400 grams, about 400 grams to about 500 grams, about 500 grams to about 600 grams, about 600 grams to about 700 grams, about 700 grams to about 800 grams, about 800 grams to about 900 grams, about 900 grams to 1 kilogram, or more.

Stretch ability may be analyzed by standard assays known in the art. For example, stretch ability may be determined by heating a 100 gram mass of an emulsion at a temperature of 225° C. for 4 minutes, cooling to about 90° C., and then pulling with a fork placed beneath the mass. Other methods to test stretch ability are well known in the art. See for example, Fife R. L et al, Test for measuring the stretch ability of melted cheese, 2002, *J. Dairy Sci.* 85 (12): 3539-3545.

In some embodiments, the recombinant casein protein may be expressed by a plant (i.e., it is a "plant-expressed" protein). In some embodiments, the recombinant protein may be expressed in a monocot, such as turf grass, maize (corn), rice, oat, wheat, barley, sorghum, orchid, iris, lily, onion, palm, or duckweed. In some embodiments, the recombinant casein protein may be expressed in a dicot, such as *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus. In some embodiments, the recombinant casein protein may be expressed in a non-vascular plant selected from moss, liverwort, hornwort or algae. In some embodiments, the recombinant casein protein may be expressed in a vascular plant reproducing from spores (e.g., a fern). In some embodiments, the recombinant casein protein is expressed in a soybean plant.

In some embodiments, the recombinant casein protein is expressed in a microorganism. Microorganisms used for recombinant protein production are well known in the art (see for example, Ferrer-Miralles et al., Bacterial cell factories for recombinant protein production; expanding the catalogue, 2013, *Microb Cell Fact.* 2013; 12:113). In some embodiments, the recombinant casein protein is expressed in a yeast or a bacterium (i.e., it is "yeast-expressed" or "bacterial-expressed"). For example, the recombinant casein protein may be expressed in bacteria such as *Escherichia coli, Caulobacter crescentus, Rodhobacter sphaeroides, Pseudoalteromonas haloplanktis, Shewanella* sp., *Pseudomonas putida, P. aeruginosa, P. fluorescens, Halomonas* elongate, *Chromohalobacter salexigens, Streptomyces lividans, S. griseus, Nocardia lactamdurans, Mycobacterium smegmatis, Corynebacterium glutamicum, C. ammoniagenes, Brevibacterium lactofermentum, Bacillus subtilis, B. brevis, B. megaterium, B. licheniformis, B. amyloliquefaciens, Lactococcus lactis, L. plantarum, L. casei, L. reuteri,* or *L. gasseri.*

In some embodiments, the recombinant casein protein is expressed in a eukaryotic microorganism, such as *Saccharomyces* spp., *Kluyveromyces* spp., *Pichia* spp., *Aspergillus* spp., *Tetrahymena* spp., *Yarrowla* spp., *Hansemila* spp., *Blastobotrys* spp., *Candida* spp., *Zygosaccharomyces* spp., *Debrayomyces* spp., *Fusarium* spp., and *Trichoderma* spp.

In some embodiments, the solid-phase, protein stabilized emulsions comprise ash. In some embodiments, the solid-phase, protein stabilized emulsions comprise at least one lipid and at least one salt. "Lipid" means any of a class of molecules that are soluble in nonpolar solvents (such as ether and hexane) and relatively or completely insoluble in water. Lipid molecules are typically composed of long hydrocarbon tails that are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); and nonglycerides (sphingolipids, tocopherols, tocotrienols, sterol lipids including cholesterol and steroid hormones, prenol lipids including terpenoids, fatty alcohols, waxes, and polyketides).

Examples of lipids that may be included in the solid-phase, protein stabilized emulsion include, for example, dairy fats or vegetable oils such as palm oil or palm kernel oil, butter oil, anhydrous milkfat, soybean oil, corn oil, rapeseed oil, canola oil, sunflower oil, safflower oil, coconut oil, rice bran oil, olive oil, sesame oil, flaxseed oil, hemp oil, cottonseed oil, peanut oil, almond oil, beech nut oil, brazil nut oil, cashew oil, hazelnut oil, macadamia oil, mongongo nut oil, pecan oil, pine nut oil, pistachio oil, walnut oil, pumpkin seed oil, grapefruit seed oil, lemon oil, apricot oil, apple seed oil, argan oil, avocado oil, or orange oil. In some embodiments, the solid-phase, protein stabilized emulsion comprises butter or margarine.

Examples of salts that may be included in the emulsion include, but are not limited to, magnesium chloride, sodium chloride, calcium chloride, sodium phosphates and trisodium citrate.

In some embodiments, the emulsion comprises at least two plant-expressed casein proteins each selected from kappa-casein, para-kappa-casein, beta-casein, alpha-S1-casein and alpha-S2-casein. In some embodiments, the emulsion comprises at least three plant-expressed casein proteins each selected from kappa-casein, para-kappa-casein, beta-casein, alpha-S1-casein and alpha-S2-casein. In some embodiments, the emulsion comprises at least four plant-expressed casein proteins each selected from kappa-casein, para-kappa-casein, beta-casein, alpha-S1-casein and alpha-S2-casein. In some embodiments, the emulsion comprises at least one additional mammalian or plant protein that is not a casein protein.

Examples of combinations of casein, mammalian, and/or plant proteins that may be used in the solid phase, protein stabilized emulsions are shown below in Table 12. The casein or casein protein combination shown in Column 1 may be combined with one or more of the mammalian proteins listed in Column 2, and/or one or more of the plant proteins listed in Column three. In some embodiments, the solid-phase protein stabilized emulsions described herein comprise proteins from Column 1, and do not include any proteins from Column 2 or Column 3.

pinto beans, green peas, and lentils. In some embodiments, the emulsion comprises protein from a grain, such as, for example, wheat, millet, barley, oats, rice, spelt, teff, amaranth, and *quinoa*. In some embodiments, the emulsion comprises protein from nuts, hempseed, chia seed, nutritional yeast, or *spirulina*. In some embodiment, the emulsion further comprises protein from potato. In some embodiments, the emulsion further comprises protein from a plant of the family Fabaceae.

In some embodiments, the emulsion has a pH of about 5.0 to about 6.7. In some embodiments, the emulsion has a pH of about 5.2 to about 5.9. In some embodiments, the emulsion has a pH of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, or about 6.9.

In some embodiments, the emulsion may further comprise one or more additional agents, such as an edible gum, starch, and/or gelling agent. Examples of edible gums include, but are not limited to, curdian, locust bean gum, carrageenan, gellan gum, xanthan gum, guar gum, agar agar, gelatin, sodium alginate, or combinations thereof. Examples of starch include, but are not limited to, potato starch, corn starch, rice flour, pea flour, modified starch, and combinations thereof. Examples of gelling agents include, but are not limited to, pectin, alginate, vegetable gums, gelatin, agar, methyl cellulose, enzymes (transglutaminase) and hydor-

TABLE 12

Example combinations of casein, mammalian, and/or plant proteins

| Casein proteins (Column 1) | Mammalian proteins (Column 2) | Plant proteins (Column 3) |
| --- | --- | --- |
| κ-casein | Alpha-lactalbumin | Oleosins |
| Para-κ-casein | Beta-lactoglobulin | Leghemoglobin |
| β-casein | Albumin | Extensin-like protein family |
| α-S1-casein | Lysozyme | |
| α-S2-casein | Collagen family | Prolamine |
| κ-casein & para-κ-casein | Hemoglobin | Glutenin |
| κ-casein & β-casein | | Gamma-kafirin preprotein |
| κ-casein & α-S1-casein | | |
| κ-casein & α-S2-casein | | Alpha globulin |
| Para-κ-casein & β-casein | | Basic 7S globulin precursor |
| Para-κ-casein & α-S1-casein | | |
| Para-κ-casein & α-S2-casein | | 2S albumin |
| β-casein & α-S1-casein | | Beta-conglycinins |
| β-casein & α-S2-casein | | Glycinins |
| α-S1-casein & α-S2-casein | | Canein |
| κ-casein, para-κ-casein, & β-casein | | Zein |
| κ-casein, para-κ-casein, & α-S1-casein | | Patatin |
| κ-casein, para-κ-casein, & α-S2-casein | | Kunitz-Trypsin inhibitor |
| Para-κ-casein, β-casein, & α-S1-casein | | |
| Para-κ-casein, β-casein, & α-S2-casein | | Bowman-Birk inhibitor |
| β-casein, α-S1-casein, & α-S2-casein | | |
| κ-casein, β-casein, & α-S1-casein | | Cystatine |
| κ-casein, β-casein, & α-S2-casein | | |
| κ-casein, α-S1-casein & α-S2-casein | | |
| para-κ-casein, α-S1-casein & α-S2-casein | | |
| κ-casein, para-κ-casein, β-casein, α-S1-casein | | |
| κ-casein, para-κ-casein, β-casein, & α-S2-casein | | |
| Para-κ-casein, β-casein, α-S1-casein, & α-S2-casein | | |
| κ-casein, β-casein, α-S1-casein, & α-S2-casein | | |
| κ-casein, para-κ-casein, α-S1-casein & α-S2-casein | | |

In some embodiments, the emulsion further comprises plant protein. For example, in some embodiments, the emulsion comprises protein from a legume, such as, for example, soybeans, chickpeas, kidney beans, black beans, oxypropylmethyl cellulose. In some embodiments, the emulsion may further comprise an acid or a base, such as lemon juice, lactic acid, acetic acid, citric acid, sodium citrate, sodium orthophosphates, sodium pyrophosphates, sodium polyphosphates, potassium citrate, potassium orthophosphates, potassium pyrophosphates, sorbic acid, potassium sorbate, tartaric acid, and sodium aluminum phosphate.

In some embodiments, the emulsion does not contain an organoleptically functional amount of beta-lactoglobulin. In some embodiments, the emulsion may comprise beta-lactoglobulin in the amount of about 0.01% (w/v) to about 0.1% (w/v), about 0.1% (w/v) to about 0.5% (w/v), about 0.5% (w/v) to about 1.0% (w/v), about 1.0% (w/v) to about 2% (w/v), about 2% (w/v) to about 3% (w/v), about 3% (w/v) to about 5% (w/v), about 5% (w/v) to about 10% (w/v), about 10% (w/v) to about 20% (w/v), about 20% (w/v) to about 40% (w/v), or more, of the emulsion.

As used herein, an "organoleptically functional amount of beta-lactoglobulin" refers to an amount of beta-lactoglobulin that significantly impacts one or more organoleptic properties of the composition. An organoleptic property is "significantly impacted" if it represents a change that can be detected by a human, using one or more of the senses taste, sight, smell, and/or touch. In some embodiments, a solid-phase, protein stabilized emulsion that does not comprise an organoleptically functional amount of beta-lactoglobulin may comprise only trace amounts of beta-lactoglobulin. In some embodiments, the emulsion may comprise beta-lactoglobulin in the range of about 0.01% (w/v) to about 0.1% (w/v), about 0.1% (w/v) to about 0.5% (w/v), about 0.5% (w/v) to about 1.0% (w/v), about 1.0% (w/v) to about 2% (w/v), about 2% (w/v) to about 3% (w/v), about 3% (w/v) to about 5% (w/v), about 5% (w/v) to about 10% (w/v), about 10% (w/v) to about 20% (w/v), about 20% (w/v) to about 40% (w/v), or more, of the emulsion.

In some embodiments, a solid phase, protein-stabilized emulsion comprises one plant-expressed casein protein selected from kappa-casein, para-kappa-casein, beta-casein, alpha-S1-casein, and alpha-S2-casein; wherein the emulsion does not contain any additional casein proteins; and wherein the emulsion has at least one of the following characteristics: i) a firmness of at least 150 grams; ii) a melting point of about 35° C. to about 100° C.; or iii) ability to stretch to at least 3 cm in length without breaking. In some embodiments, the emulsion further comprises at least one lipid and at least one salt. In some embodiments, the plant-expressed casein protein is expressed in a soybean plant. In some embodiments, the emulsion has a pH of about 5.2 to about 5.9. In some embodiments, the emulsion does not contain an organoleptically functional amount of beta-lactoglobulin. In some embodiments, the emulsion may comprise beta-lactoglobulin in the amount of about 0.01% (w/v) to about 0.1% (w/v), about 0.1% (w/v) to about 0.5% (w/v), about 0.5% (w/v) to about 1.0% (w/v), about 1.0% (w/v) to about 2% (w/v), about 2% (w/v) to about 3% (w/v), about 3% (w/v) to about 5% (w/v), about 5% (w/v) to about 10% (w/v), about 10% (w/v) to about 20% (w/v), about 20% (w/v) to about 40% (w/v), or more.

In some embodiments, a solid phase, protein-stabilized emulsion comprises: a plant-expressed casein protein selected from kappa-casein, para-kappa-casein, beta-casein, alpha-S1-casein, and alpha-S2-casein; and further comprises plant-expressed beta-lactoglobulin; wherein the ratio of the casein protein to the beta-lactoglobulin is about 8:1 to about 1:2. In some embodiments, the emulsion has at least one of the following characteristics: i) a firmness of at least 150 grams; ii) a melting point of about 35° C. to about 100° C.; or iii) ability to stretch to at least 3 cm in length without breaking. In some embodiments, the emulsion comprises at least at least one additional mammalian or plant protein that is not a casein protein. In some embodiments, the ratio of the casein protein to the beta-lactoglobulin is 1:2. In some embodiments, the ratio of the casein protein to the beta-lactoglobulin is about 2:1. In some embodiments, the emulsion has a pH of about 5.2 to about 5.9.

In some embodiments, a solid-phase protein-stabilized emulsion comprises about 8% (w/v) to about 25% (w/v) total protein, such as about 8% to about 10%, about 10% to about 15%, about 15% to about 20%, or about 20 to about 25% total protein. In some embodiments, a solid-phase protein stabilized emulsion comprises about 1% to about 10% (w/v) total protein. In some embodiments, a solid-phase protein stabilized emulsion comprises about 25% to about 35%, about 35% to about 45%, about 45% to about 55%, about 55% to about 65%, about 65% to about 75% (w/v), or more total protein.

In some embodiments, about 1% to about 5% of the total protein in the solid-phase protein stabilized emulsion is casein protein. In some embodiments, about 5% to about 10% of the total protein in the solid-phase protein stabilized emulsion is casein protein. In some embodiments, about 10% to about 20% of the total protein in the solid-phase protein stabilized emulsion is casein protein. In some embodiments, about 20% to about 30% of the total protein in the solid-phase protein stabilized emulsion is casein protein. In some embodiments, about 30% to about 40% of the total protein in the solid-phase protein stabilized emulsion is casein protein. In some embodiments, about 40% to about 50% of the total protein in the solid-phase protein stabilized emulsion is casein protein. In some embodiments, about 50% to about 60% of the total protein in the solid-phase protein stabilized emulsion is casein protein. In some embodiments, about 60% to about 70% of the total protein in the solid-phase protein stabilized emulsion is casein protein. In some embodiments, about 70% to about 80% of the total protein in the solid-phase protein stabilized emulsion is casein protein. In some embodiments, about 80% to about 90% of the total protein in the solid-phase protein stabilized emulsion is casein protein. In some embodiments, about 90% to about 100% of the total protein in the solid-phase protein stabilized emulsion is casein protein.

In some embodiments, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or more of the total protein in the solid-phase protein stabilized emulsion is casein protein.

In some embodiments, about 20% to about 100% of the casein protein in the solid-phase protein-stabilized emulsion is kappa casein. For example, the emulsion may comprise about 20% to about 30%, about 30% to about 40%, about 40% to about 50%, about 50% to about 60%, about 60% to about 70%, about 70% to about 80%, about 80% to about 90%, or about 90% to about 100% kappa casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the solid-phase protein-stabilized emulsion is kappa casein.

In some embodiments, about 20% to about 100% of the casein protein in the solid-phase protein-stabilized emulsion is para-kappa casein. For example, the emulsion may comprise about 20% to about 30%, about 30% to about 40%, about 40% to about 50%, about 50% to about 60%, about 60% to about 70%, about 70% to about 80%, about 80% to about 90%, or about 90% to about 100% para-kappa casein.

In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the solid-phase protein-stabilized emulsion is para-kappa casein.

In some embodiments, about 20% to about 100% of the casein protein in the solid-phase protein-stabilized emulsion is beta casein. In some embodiments, about 50% to about 100% of the casein protein in the solid-phase protein-stabilized emulsion is beta casein. For example, the emulsion may comprise about 20% to about 30%, about 30% to about 40%, about 40% to about 50%, about 50% to about 60%, about 60% to about 70%, about 70% to about 80%, about 80% to about 90%, or about 90% to about 100% beta casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the solid-phase protein-stabilized emulsion is beta casein.

In some embodiments, about 20% to about 100% of the casein protein in the solid-phase protein-stabilized emulsion is alpha-S1-casein. In some embodiments, about 50% to about 100% of the casein protein in the solid-phase protein-stabilized emulsion is alpha-S1-casein. For example, the emulsion may comprise about 20% to about 30%, about 30% to about 40%, about 40% to about 50%, about 50% to about 60%, about 60% to about 70%, about 70% to about 80%, about 80% to about 90%, or about 90% to about 100% alpha-S1-casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the solid-phase protein-stabilized emulsion is alpha-S1-casein.

In some embodiments, about 20% to about 100% of the casein protein in the solid-phase protein-stabilized emulsion is alpha-S2-casein. In some embodiments, about 50% to about 100% of the casein protein in the solid-phase protein-stabilized emulsion is alpha-S2-casein. For example, the emulsion may comprise about 20% to about 30%, about 30% to about 40%, about 40% to about 50%, about 50% to about 60%, about 60% to about 70%, about 70% to about 80%, about 80% to about 90%, or about 90% to about 100% alpha-S2-casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the solid-phase protein-stabilized emulsion is alpha-S2-casein.

In some embodiments, a solid-phase protein-stabilized emulsion comprises about 8% (w/v) to about 25% (w/v) total protein, one or more lipids, and one or more salts; wherein at least 4% of the total protein comprises casein proteins selected from kappa-casein, para-kappa-casein, beta-casein, alpha-S1-casein, and alpha-S2-casein; wherein the emulsion has at least one of the following characteristics: i) a firmness of at least 150 grams; ii) a melting point of about 35° C. to about 100° C.; or iii) ability to stretch to at least 3 cm in length without breaking. In some embodiments, at least 20% to 100% of the casein protein is kappa casein. In some embodiments, at least 20% to 100% of the casein protein is para-kappa casein. In some embodiments, at least 50% to 100% of the casein protein is beta-casein. In some embodiments, at least 50% to 100% of the casein protein is alpha-S1-casein. In some embodiments, at least 20% to 100% of the casein protein is alpha-S2-casein. In some embodiments, casein protein is expressed in a plant. In some embodiments, the emulsion has a pH of about 5.2 to about 5.9. In some embodiments, the composition comprises only one, only two, only three, or only four casein proteins selected from kappa-casein, para-kappa-casein, beta-casein, alpha-S1-casein, and alpha-S2-casein. In some embodiments, the emulsion does not contain an organoleptically functional amount of beta-lactoglobulin. In some embodiments, the emulsion may comprise beta-lactoglobulin in the amount of about 0.01% (w/v) to about 0.1% (w/v), about 0.1% (w/v) to about 0.5% (w/v), about 0.5% (w/v) to about 1.0% (w/v), about 1.0% (w/v) to about 2% (w/v), about 2% (w/v) to about 3% (w/v), about 3% (w/v) to about 5% (w/v), about 5% (w/v) to about 10% (w/v), about 10% (w/v) to about 20% (w/v), about 20% (w/v) to about 40% (w/v), or more.

Alternative Dairy Compositions Comprising One or More Isolated or Recombinant Casein Proteins The milk or casein proteins described herein may also be used to prepare alternative dairy compositions. For example, in some embodiments, an alternative dairy composition comprises one or more casein proteins, such as recombinant casein proteins. In some embodiments, the casein proteins are selected from kappa-casein, para-kappa-casein, beta-casein, alpha-S1-casein and alpha-S2-casein. In some embodiments, the alternative dairy composition comprises only one casein protein. In some embodiments, the alterative diary composition comprises two, three, or four casein proteins.

In some embodiments, the disclosure relates to an alternative dairy composition comprising a casein protein selected from kappa-casein, para-kappa-casein, beta-casein, alpha-S1-casein, and alpha-S2-casein; and a beta-lactoglobulin. In some embodiments the casein protein is recombinant. In some embodiments, the beta-lactoglobulin is recombinant. In some embodiments, both the casein protein and the beta-lactoglobulin are recombinant. In some embodiments, the ratio of the casein protein to the beta-lactoglobulin is about 8:1 to about 1:2. In some embodiments, the ratio of the casein protein to the beta-lactoglobulin is about 8:1 to about 2:1.

In some embodiments, an alternative dairy composition comprises about 8% (w/v) to about 25% (w/v) total protein, such as about 8% to about 10%, about 10% to about 15%, about 15% to about 20%, or about 20 to about 25% total protein. In some embodiments, an alternative dairy composition comprises about 1% to about 10% (w/v) total protein. In some embodiments, an alternative dairy composition comprises about 25% to about 35%, about 35% to about 45%, about 45% to about 55%, about 55% to about 65%, about 65% to about 75% (w/v), or more total protein.

In some embodiments, about 1% to about 5% of the total protein in the alternative dairy composition is casein protein. In some embodiments, about 5% to about 10% of the total protein in the alternative dairy composition is casein protein. In some embodiments, about 10% to about 20% of the total protein in the alternative dairy composition is casein protein. In some embodiments, about 20% to about 30% of the total protein in the alternative dairy composition is casein protein. In some embodiments, about 30% to about 40% of the total protein in the alternative dairy composition is casein protein. In some embodiments, about 40% to about 50% of the total protein in the alternative dairy composition is casein protein. In some embodiments, about 50% to about 60% of the total protein in the alternative dairy composition is casein protein. In some embodiments, about 60% to about 70% of the total protein in the alternative dairy composition is casein protein. In some embodiments, about 70% to about 80% of the total protein in the alternative dairy composition is casein protein. In some embodiments, about 80% to about 90% of the total protein in the alternative dairy composition is casein protein. In some embodiments, about 90% to about 100% of the total protein in the alternative dairy composition is casein protein.

In some embodiments, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or more of the total protein in the alternative dairy composition is casein protein.

In some embodiments, about 20% to about 100% of the casein protein in the alternative dairy composition is kappa casein. For example, the alternative dairy composition may comprise about 20% to about 30%, about 30% to about 40%, about 40% to about 50%, about 50% to about 60%, about 60% to about 70%, about 70% to about 80%, about 80% to about 90%, or about 90% to about 100% kappa casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the alternative dairy composition is kappa casein.

In some embodiments, about 20% to about 100% of the casein protein in the alternative dairy composition is para-kappa casein. For example, the alternative dairy composition may comprise about 20% to about 30%, about 30% to about 40%, about 40% to about 50%, about 50% to about 60%, about 60% to about 70%, about 70% to about 80%, about 80% to about 90%, or about 90% to about 100% para-kappa casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the alternative dairy composition is para-kappa casein.

In some embodiments, about 20% to about 100% of the casein protein in the alternative dairy composition is beta casein. In some embodiments, about 50% to about 100% of the casein protein in the alternative dairy composition is beta casein. For example, the alternative dairy composition may comprise about 20% to about 30%, about 30% to about 40%, about 40% to about 50%, about 50% to about 60%, about 60% to about 70%, about 70% to about 80%, about 80% to about 90%, or about 90% to about 100% beta casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the alternative dairy composition is beta casein.

In some embodiments, about 20% to about 100% of the casein protein in the alternative dairy composition is alpha-S1-casein. In some embodiments, about 50% to about 100% of the casein protein in the alternative dairy composition is alpha-S1-casein. For example, the alternative dairy composition may comprise about 20% to about 30%, about 30% to about 40%, about 40% to about 50%, about 50% to about 60%, about 60% to about 70%, about 70% to about 80%, about 80% to about 90%, or about 90% to about 100% alpha-S1-casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the alternative dairy composition is alpha-S1-casein.

In some embodiments, about 20% to about 100% of the casein protein in the alternative dairy composition is alpha-S2-casein. In some embodiments, about 50% to about 100% of the casein protein in the alternative dairy composition is alpha-S2-casein. For example, the alternative dairy composition may comprise about 20% to about 30%, about 30% to about 40%, about 40% to about 50%, about 50% to about 60%, about 60% to about 70%, about 70% to about 80%, about 80% to about 90%, or about 90% to about 100% alpha-S2-casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the alternative dairy composition is alpha-S2-casein.

In some embodiments, an alternative dairy composition comprises kappa casein and essentially no para-kappa casein. For example, in some embodiments, the alternative dairy composition comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1%, para-kappa casein. In some embodiments, the alternative dairy composition comprises about 0.01% to about 1%, about 0.01% to about 0.9%, about 0.01% to about 0.8%, about 0.01% to about 0.7%, about 0.01% to about 0.6%, about 0.1% to about 0.5%, about 0.1% to about 0.4%, about 0.1% to about 0.3%, about 0.1% to about 0.2%, or about 0.01% to about 0.1% para-kappa casein. In some embodiments, the kappa casein is recombinant. In some embodiments, the kappa casein is expressed in a plant. In some embodiments, the kappa casein is expressed in a soybean plant.

In some embodiments, an alternative dairy composition comprises one to four recombinant milk proteins, each selected from kappa-casein, para-kappa-casein, beta-casein, alpha-S1-casein, and alpha-S2-casein. In some embodiments, an alternative dairy composition comprises 1, 2, 3, or 4 casein proteins. In some embodiments, an alternative dairy composition comprises only one casein protein.

In some embodiments, an alternative dairy composition comprises recombinant beta-casein and at least one lipid and does not comprise an organoleptically functional amount of beta-lactoglobulin. In some embodiments, the composition does not comprise any additional casein proteins. In some embodiments, the composition comprises at least one additional casein protein. In some embodiments, the at least one additional casein protein is selected from kappa-casein, para-kappa-casein, alpha-S1-casein and alpha-S2-casein. In some embodiments, the at least one additional casein is kappa-casein or para-kappa-casein. In some embodiments, at least 50%, at least 75%, or at least 90% by weight of the total casein protein in an alternative dairy composition is beta-casein. In some embodiments, the beta-casein is expressed in a plant. In some embodiments, the beta-casein is expressed in a soybean plant. In some embodiments, all caseins in the composition are plant expressed. In some embodiments, the composition comprises a fusion protein comprising recombinant beta-casein.

In some embodiments, the alternative dairy composition comprises two of the milk proteins selected from kappa-casein, para-kappa-casein, beta-casein, alpha-S1-casein, and alpha-S2-casein. In some embodiments, the alternative dairy composition comprises three of the milk proteins selected from kappa-casein, para-kappa-casein, beta-casein, alpha-S1-casein, and alpha-S2-casein. In some embodiments, the alternative dairy composition comprises four of the milk proteins selected from kappa-casein, para-kappa-casein, beta-casein, alpha-S1-casein, and alpha-S2-casein. In some embodiments, the one or more milk protein(s) is (are) plant-expressed. In some embodiments, the milk protein(s) is (are) expressed in a soybean plant. In some embodiments, the milk protein(s) is (are) yeast- or bacterial-expressed. Exemplary combinations of 1, 2, 3, or 4 casein proteins that may be used in the alternative dairy compositions described herein are shown above in Table 12.

In some embodiments, the disclosure relates to an alternative dairy composition comprising one to four plant-expressed recombinant milk proteins (i.e., 2, 3, or 4 plant-expressed recombinant milk proteins), wherein the recombinant milk proteins confer one, two, three or more organoleptic properties similar to a dairy composition (i.e., a dairy composition comprising mammalian milk such as bovine milk) selected from the group consisting of taste, appearance, mouthfeel, structure, texture, density, elasticity, springiness, coagulation, binding, leavening, aeration, foaming, creaminess, and emulsification. In some embodiments, the plant-expressed milk proteins are selected from beta lactoglobulin, kappa-casein, para-kappa-casein, beta-casein, alpha-S1-casein, and alpha-S2-casein. In some embodiments, the recombinant beta-casein protein confers on the alternative dairy composition one, two, or more characteristics of a dairy food product selected from the group consisting of: taste, aroma, appearance, handling, mouthfeel, density, structure, texture, elasticity, springiness, coagulation, binding, leavening, aeration, foaming, creaminess and emulsification.

In some embodiments, the alternative dairy compositions described above comprise at least one additional mammalian or plant protein that is not a casein protein. Examples of combinations of casein, mammalian, and/or plant proteins are shown above in Table 12.

In some embodiments, the alternative dairy compositions described herein may comprise plant protein. For example, in some embodiments, the alternative dairy compositions comprise protein from a legume, such as, for example, soybeans, chickpeas, kidney beans, black beans, pinot beans, green peas, and lentils. In some embodiments, the alternative dairy compositions comprise protein from a grain, such as, for example, wheat, millet, barley, oats, rice, spelt, teff, amaranth, and *quinoa*. In some embodiments, the alternative dairy compositions comprise protein from nuts, hempseed, chia seed, nutritional yeast, or *spirulina*. In some embodiments, the alternative diary composition comprises protein from potato. In some embodiments, the alternative diary composition comprises protein from a plant of the family Fabaceae.

In some embodiments, the alternative dairy compositions described above have at least one of the following characteristics: i) a firmness of at least 150 grams; ii) a melting point of about 35° C. to about 100° C.; or iii) ability to stretch to at least 3 cm in length without breaking. In some embodiments, the alternative diary compositions described above have the ability to stretch to at least 4 cm, at least 5 cm, at least 6 cm, at least 7 cm, at least 8 cm, at least 9 cm, at least 10 cm, at least 11 cm, at least 12 cm, at least 13 cm, at least 14 cm, at least 15 cm, at least 16 cm, at least 17 cm, at least 18 cm, at least 19 cm, or at least 10 cm in length without breaking. In some embodiments, the alternative dairy compositions described above have the ability to stretch to at least 5 cm in length without breaking. Testing methods and ranges firmness, melting point, and stretch are disclosed above.

In some embodiments, the alternative diary compositions comprise ash. In some embodiments, the alternative dairy compositions comprise at least one lipid and/or at least one salt. Examples of lipids include fatty acids (saturated and unsaturated); glycerides or glycerolipids (such as monoglycerides, diglycerides, triglycerides or neutral fats, and phosphoglycerides or glycerophospholipids); and nonglycerides (sphingolipids, tocopherols, tocotrienols, sterol lipids including cholesterol and steroid hormones, prenol lipids including terpenoids, fatty alcohols, waxes, and polyketides).

Examples of lipids that may be included in the alternative dairy compositions include, for example, dairy fats or vegetable oils such as palm oil or palm kernel oil, soybean oil, corn oil, rapeseed oil, canola oil, sunflower oil, safflower oil, coconut oil, rice bran oil, olive oil, sesame oil, flaxseed oil, hemp oil, cottonseed oil, peanut oil, almond oil, beech nut oil, brazil nut oil, cashew oil, hazelnut oil, macadamia oil, mongongo nut oil, pecan oil, pine nut oil, pistachio oil, walnut oil, pumpkin seed oil, grapefruit seed oil, lemon oil, apricot oil, apple seed oil, argan oil, avocado oil, or orange oil. In some embodiments, the solid-phase, protein stabilized emulsion comprises butter or margarine.

Examples of salts that may be included in the alternative dairy composition include, but are not limited to, magnesium chloride, sodium chloride, calcium chloride, sodium phosphate and trisodium citrate.

In some embodiments, the alternative dairy compositions do not contain an organoleptically functional amount of beta-lactoglobulin. In some embodiments, the alternative dairy composition may comprise beta-lactoglobulin in the amount of about 0.01% (w/v) to about 0.1% (w/v), about 0.1% (w/v) to about 0.5% (w/v), about 0.5% (w/v) to about 1.0% (w/v), about 1.0% (w/v) to about 2% (w/v), about 2% (w/v) to about 3% (w/v), about 3% (w/v) to about 5% (w/v), about 5% (w/v) to about 10% (w/v), about 10% (w/v) to about 20% (w/v), about 30% (w/v) to about 40% (w/v), or more, of the composition.

In some embodiments, the alternative dairy compositions comprise one or more recombinant casein proteins that are expressed in a microorganism. In some embodiments, the recombinant casein protein is yeast-expressed or bacterial-expressed. In some embodiments, the recombinant casein protein is expressed in a bacterium. Microorganisms used for recombinant protein production are well known in the art (see for example, Ferrer-Miralles et al., Bacterial cell factories for recombinant protein production; expanding the catalogue, 2013, *Microb Cell Fact.* 2013; 12:113). For example, the recombinant casein protein may be expressed in a bacteria such as *Escherichia coli, Caulobacter crescentus, Rodhobacter sphaeroides, Pseudoalteromonas haloplanktis, Shewanella* sp., *Pseudomonas putida, P. aeruginosa, P. fluorescens, Halomonas elongate, Chromohalobacter salexigens, Streptomyces lividans, S. griseus, Nocardia lactamdurans, Mycobacterium smegmatis, Corynebacterium glutamicum, C. ammoniagenes, Brevibacterium lactofermentum, Bacillus subtilis, B. brevis, B. megaterium, B. licheniformis, B. amyloliquefaciens, Lactococcus lactis, L. plantarum, L. casei, L. reuteri*, or *L. gasseri*.

In some embodiments, the recombinant casein proteins are expressed in a microorganism that is a eukaryotic cell, such as *Saccharomyces* spp., *Kluyveromyces* spp., *Pichia* spp., *Aspergillus* spp., *Tetrahymena* spp., *Yarrowla* spp.,

*Hansemila* spp., *Blastobotrys* spp., *Candida* spp., *Zygosaccharomyces* spp., *Debrayomyces* spp., *Fusarium* spp., and *Trichoderma* spp.

In some embodiments, the one or more recombinant casein proteins are expressed in a plant. In some embodiments, the plant may be a monocot selected from turf grass, maize (corn), rice, oat, wheat, barley, sorghum, orchid, iris, lily, onion, palm, and duckweed. In some embodiments, the plant is a dicot selected from *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus. In some embodiments, the plant is a non-vascular plant selected from moss, liverwort, hornwort or algae. In some embodiments, the plant is a vascular plant reproducing from spores (e.g., a fern). In some embodiments, the recombinant casein protein is expressed in a soybean plant.

In some embodiments, the alternative dairy compositions described above have a pH of about 2 to about 8. In some embodiments, the alternative dairy compositions described above have a pH of about 4 to about 8. Table 13 below shows exemplary ranges of pH for common mammalian derived dairy products.

TABLE 13 pH ranges of common dairy products

| Dairy product | pH range |
|---|---|
| Milk | 6.7-6.9 |
| Butter | 6.1-6.4 |
| Yogurt | 2.0-4.5 |
| Brie | 6.0-6.5 |
| Cheddar | 5.1-5.3 |
| Cream cheese | 4.6-5.1 |
| Feta | 4.1-4.5 |
| Parmesan | 5.2-5.3 |
| Ricotta | 6.0 |

Examples of alternative dairy compositions that may be produced as described herein include, but are not limited to, alternative versions of milk, cream, butter, and cheese. Other example alternative dairy compositions include ice cream, frozen desserts, frozen yogurt or custard, yogurt, cottage cheese, cream cheese, curds, crème fraiche, toppings, icings, fillings, low-fat spreads, dairy-based dry mixes, geriatric nutrition compositions, coffee creamers, analog dairy products, follow-up formula, baby formula, infant formula, milk, dairy beverages, acid dairy drinks, smoothies, milk tea, margarine, butter alternatives, growing up milks, low-lactose products, buttermilk, sour cream, skyr, leben, lassi, kefir, and beverages. In some embodiments, the alternative diary compositions may be cultured milks, such as drinkable yogurts. The alternative dairy compositions may also be powders containing a milk protein, or a low-lactose product. An illustrative method for preparing an alternative dairy composition is provided in FIG. 13.

An alternative milk composition may be produced, for example, by mixing a liquid comprising at least one isolated or recombinant milk or casein protein, with ash, lipids, and/or a sweetener, and optionally one or more flavor compounds and/or color agents. In some embodiments, one or more vitamins are added to the alternative milk composition, such as retinal, carotene, vitamins, vitamin D, vitamin E, vitamin B12, thiamin, or riboflavin. This milk alternative may then be used to produce, for example, butter, ice cream, frozen desserts, frozen yogurt or custard, yogurt, cottage cheese, cream cheese, curds, and crème fraiche.

In some embodiments, the alternative dairy composition comprises one or more sweeteners. Examples of sweeteners include, but are not limited to, saccharides, such as glucose, mamiose, maltose, fructose, galactose, lactose, sucrose, monatin, and tagatose. In some embodiments the sweetener is selected from *stevia*, aspartame, cyclamate, saccharin, sucralose, mogrosides, brazzein, curculin, erythritol, glycyrrhizin, inulin, isomalt, lacititol, mabinlin, malititol, mamiitol, miraculin, monatin, monelin, osladin, pentadin, sorbitol, thaumatin, xylitol, acesulfame, potassium, advantame, alitame, aspartame-acesulfame, sodium cyclamate, dulcin, glucin, neohesperidin, dihyrdochalcone, neotame, and P-4000.

In some embodiments, an alternative dairy food composition comprises calcium. In some embodiments, the composition comprises calcium at a concentration of about 0% to about 2% by weight. In some embodiments, the composition comprises calcium at a concentration of about 0.001% to about 2% by weight. In some embodiments, the composition comprises calcium at a concentration of about 0.01% to about 2% by weight. In some embodiments, the composition comprises calcium at a concentration of about 0.1% to about 2% by weight. In some embodiments, the composition comprises calcium at a concentration of about 1% to about 2% by weight. In some embodiments, the composition comprises calcium at a concentration of about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0% by weight.

Thus, in some embodiments, the alternative dairy composition is a milk composition. In some embodiments, the alternative dairy composition is a cheese composition. In some embodiments, the alternative dairy composition is cream composition. In some embodiments, the alternative dairy composition is a yogurt composition (e.g., a frozen yogurt composition, a sugar-free yogurt composition, a low-fat yogurt composition, a Greek yogurt composition, a drinkable yogurt composition, etc.). In some embodiments, the alternative dairy composition is ice cream. In some embodiments, alternative dairy composition is a frozen custard composition. In some embodiments, the alternative dairy composition is a frozen dessert. In some embodiments, the alternative dairy composition is a crème fraiche composition. In some embodiments, the alternative dairy composition is curd composition. In some embodiments, the alternative dairy composition is a cottage cheese composition. In some embodiments, the alternative dairy composition is cream composition. In some embodiments, the alternative dairy composition is a sour cream composition.

Cheese Compositions

Traditionally, cheese is made with milk, which comprises a number of proteins including various casein proteins (see Table 14 below for exemplary compositions of human and cow milk). Coagulation of the milk proteins occurs by way of an acid and/or rennet addition, which causes the milk to curdle. Rennet is a bacterial enzyme that cleaves kappa-casein, generating para-kappa-casein, which then links up with the calcium and phosphate present in milk to join casein micelles together. These solids curds are collected and/or separated from the liquid (whey) and various procedures of pressing, forming, and aging yield different cheese products.

TABLE 14

Illustrative Milk Protein Compositions

| Protein | Human milk (mg/mL) | Bovine (cow) milk (mg/mL) |
|---|---|---|
| α-lactalbumin | 2.2 | 1.2 |
| α-s1-casein | 0 | 11.6 |
| α-s2-casein | 0 | 3.0 |
| β-casein | 2.2 | 9.6 |
| κ-casein | 0.4 | 3.6 |
| γ-casein | 0 | 1.6 |
| Immunoglobulins | 0.8 | 0.6 |
| Lactoferrin | 1.4 | 0.3 |
| β-lactoglobulin | 0 | 3.0 |
| Lysozyme | 0.5 | Traces |
| Serum albumin | 0.4 | 0.4 |
| Other | 0.8 | 0.6 |

Described herein are cheese compositions comprising a different protein composition compared to that of any mammalian milk (i.e., a non-naturally occurring protein composition). For example, in some embodiments, a cheese composition can be prepared using only one milk protein. In some embodiments, a cheese composition can be prepared using only two milk proteins. In some embodiments, a cheese composition may be prepared using only three milk proteins. In some embodiments, a cheese composition may be prepared using only four milk proteins. In some embodiments, a cheese composition comprises one or more milk proteins at a ratio that is not found in any mammalian milk (e.g., a non-naturally occurring ratio).

In some embodiments, a cheese composition comprises one milk protein, which may be derived from animal-produced milk, or recombinantly expressed. In some embodiments, a cheese composition comprises two, three, our four milk proteins, wherein each milk protein is derived from animal-produced milk or is recombinantly expressed. In some embodiments, the milk protein is a casein protein.

In some embodiments, a cheese composition may comprise beta-casein as the only casein protein (i.e., 100% beta-casein). In some embodiments, a cheese composition comprises beta-casein and at least one additional casein protein. In some embodiments, the at least one additional casein protein is selected from kappa-casein, para-kappa-casein, beta-casein, alpha-S1-casein and alpha-S2-casein. In some embodiments, the at least one additional casein protein is kappa-casein. In some embodiments, the at least one additional casein protein is para-kappa-casein.

In some embodiments, a cheese composition comprises two or more casein proteins, wherein about 95% by weight of the casein protein in the composition is beta-casein. In some embodiments, a cheese composition comprises two or more casein proteins, wherein about 90% by weight of the casein protein in the composition is beta-casein. In some embodiments, a cheese composition comprises two or more casein proteins, wherein about 85% by weight of the casein protein in the composition is beta-casein. In some embodiments, a cheese composition comprises two or more casein proteins, wherein about 80% by weight of the casein protein in the composition is beta-casein. In some embodiments, a cheese composition comprises two or more casein proteins, wherein about 75% by weight of the casein protein in the composition is beta-casein. In some embodiments, a cheese composition comprises two or more casein proteins, wherein about 70% by weight of the casein protein in the composition is beta-casein. In some embodiments, a cheese composition comprises two or more casein proteins, wherein about 65% by weight of the casein protein in the composition is beta-casein. In some embodiments, a cheese composition comprises two or more casein proteins, wherein about 60% by weight of the casein protein in the composition is beta-casein. In some embodiments, a cheese composition comprises two or more casein proteins, wherein about 55% by weight of the casein protein in the composition is beta-casein. In some embodiments, a cheese composition comprises two or more casein proteins, wherein about 50% by weight of the casein protein in the composition is beta-casein.

In some embodiments, a cheese composition may comprise 95%, beta-casein and 5% of one or more additional casein proteins. In some embodiments, it may comprise 90%, beta-casein and 10% of one or more additional casein proteins. In some embodiments, it may comprise 85%, beta-casein and 15% of one or more additional casein proteins. In some embodiments, it may comprise 80%, beta-casein and 20% of one or more additional casein proteins. In some embodiments, it may comprise 75%, beta-casein and 25% of one or more additional casein proteins. In some embodiments, it may comprise 70%, beta-casein and 30% of one or more additional casein proteins. The other casein proteins may be kappa-casein, para-kappa-casein, alpha-S1-casein, and/or alpha-S2-casein.

In some embodiments, the cheese composition comprises 75% beta-casein and 25% alpha caseins (i.e., a mixture of alpha-S1-casein and alpha-S2-casein). In some embodiments, the cheese composition comprises 75% beta-casein and 25% kappa-casein. In some embodiments, the cheese composition comprises 50% beta-casein and 50% kappa-casein. In some embodiments, the cheese composition comprises 50% beta-casein and 50% alpha caseins.

In some embodiments the beta-casein is recombinant beta-casein. In some embodiments, the recombinant beta-casein protein is plant-expressed. In some embodiments, the recombinant beta-casein is expressed in a soybean. In some embodiments, all the caseins in the cheese composition are plant-expressed. In some embodiments, the recombinant casein protein is derived from a fusion protein. In some embodiments, the cheese composition does not contain an organoleptically functional amount of beta-lactoglobulin.

In some embodiments, a cheese composition comprises para-kappa-casein produced without the use of any enzyme that cleaves kappa-casein to para-kappa-casein. In some embodiments, a cheese composition comprises para-kappa-casein produced without the use of any acid that cleaves kappa-casein to para-kappa-casein. In some embodiments, a cheese composition comprises para-kappa-casein produced without the use of any enzyme or acid that cleaves kappa-casein to para-kappa-casein. In some embodiments, a cheese composition comprises a recombinantly expressed para-kappa-casein. In some embodiments, a cheese composition comprises substantially no casein, such as 0.01% (w/v) to 0.1% (w/v) or 0.1% (w/v) to 0.1% (w/v) casein.

In some embodiments, a cheese composition comprises about 8% (w/v) to about 25% (w/v) total protein, such as about 8% to about 10%, about 10% to about 15%, about 15% to about 20%, or about 20 to about 25% total protein. In some embodiments, a cheese composition comprises about 1% to about 10% (w/v) total protein. In some embodiments, a cheese composition comprises about 25% to about 35%, about 35% to about 45%, about 45% to about 55%, about 55% to about 65%, about 65% to about 75% (w/v), or more total protein.

In some embodiments, about 1% to about 5% of the total protein in the cheese composition is casein protein. In some embodiments, about 5% to about 10% of the total protein in the cheese composition is casein protein. In some embodiments, about 10% to about 20% of the total protein in the cheese composition is casein protein. In some embodiments, about 20% to about 30% of the total protein in the cheese composition is casein protein. In some embodiments, about 30% to about 40% of the total protein in the cheese composition is casein protein. In some embodiments, about 40% to about 50% of the total protein in the cheese composition is casein protein. In some embodiments, about 50% to about 60% of the total protein in the cheese composition is casein protein. In some embodiments, about 60% to about 70% of the total protein in the cheese composition is casein protein. In some embodiments, about 70% to about 80% of the total protein in the cheese composition is casein protein. In some embodiments, about 80% to about 90% of the total protein in the cheese composition is casein protein. In some embodiments, about 90% to about 100% of the total protein in the cheese composition is casein protein.

In some embodiments, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or more of the total protein in the cheese composition is casein protein.

In some embodiments, about 20% to about 100% of the casein protein in the cheese composition is kappa casein. For example, the cheese composition may comprise about 20% to about 30%, about 30% to about 40%, about 40% to about 50%, about 50% to about 60%, about 60% to about 70%, about 70% to about 80%, about 80% to about 90%, or about 90% to about 100% kappa casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the cheese composition is kappa casein.

In some embodiments, about 20% to about 100% of the casein protein in the cheese composition is para-kappa casein. For example, the cheese composition may comprise about 20% to about 30%, about 30% to about 40%, about 40% to about 50%, about 50% to about 60%, about 60% to about 70%, about 70% to about 80%, about 80% to about 90%, or about 90% to about 100% para-kappa casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the cheese composition is para-kappa casein.

In some embodiments, about 20% to about 100% of the casein protein in the cheese composition is beta casein. In some embodiments, about 50% to about 100% of the casein protein in the cheese composition is beta casein. For example, the cheese composition may comprise about 20% to about 30%, about 30% to about 40%, about 40% to about 50%, about 50% to about 60%, about 60% to about 70%, about 70% to about 80%, about 80% to about 90%, or about 90% to about 100% beta casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the cheese composition is beta casein.

In some embodiments, about 20% to about 100% of the casein protein in the cheese composition is alpha-S1-casein. In some embodiments, about 50% to about 100% of the casein protein in the cheese composition is alpha-S1-casein. For example, the cheese composition may comprise about 20% to about 30%, about 30% to about 40%, about 40% to about 50%, about 50% to about 60%, about 60% to about 70%, about 70% to about 80%, about 80% to about 90%, or about 90% to about 100% alpha-S1-casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the cheese composition is alpha-S1-casein.

In some embodiments, about 20% to about 100% of the casein protein in the cheese composition is alpha-S2-casein. In some embodiments, about 50% to about 100% of the casein protein in the cheese composition is alpha-S2-casein. For example, the cheese composition may comprise about 20% to about 30%, about 30% to about 40%, about 40% to about 50%, about 50% to about 60%, about 60% to about 70%, about 70% to about 80%, about 80% to about 90%, or about 90% to about 100% alpha-S2-casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the cheese composition is alpha-S2-casein.

In some embodiments, a cheese composition comprises a stable, protein-stabilized emulsion described herein. In some embodiments, a cheese composition comprises more than one of the stable, protein-stabilized emulsions described herein. In some embodiments, a cheese composition is made using at least one stable, protein-stabilized emulsion described herein.

In some embodiments, a cheese composition comprises a colloidal suspension described herein. In some embodiments, a cheese composition comprises more than one colloidal suspension described herein. In some embodiments, a cheese composition is made using at least one of the colloidal suspensions described herein.

In some embodiments, a cheese composition described herein may comprise plant protein. For example, in some embodiments, the cheese composition comprises protein from a legume, such as, for example, soybeans, chickpeas, kidney beans, black beans, pinto beans, green peas, and lentils. In some embodiments, the cheese composition comprises protein from a grain, such as, for example, wheat, millet, barley, oats, rice, spelt, teff, amaranth, and *quinoa*. In some embodiments, the cheese composition comprises protein from nuts, hempseed, chia seed, nutritional yeast, or *spirulina*. In some embodiments, the cheese composition comprises protein from potato. In some embodiments, the cheese composition comprises protein from a plant of the family Fabaceae.

In some embodiments, the cheese compositions described herein may be substantially transparent. As used herein, "substantially transparent" means having an opacity of about 50%, about 40%, about 30%, about 20%, about 10% or less. In some embodiments, the cheese composition has about 0% opacity. In some embodiments, the cheese compositions described herein are substantially transparent when in solid form. In some embodiments, the cheese compositions described herein are substantially transparent when melted.

In some embodiments, the cheese compositions described herein may have at least one, at least two, or at least three desirable organoleptic properties. In some embodiments, the cheese compositions described herein may have at least one, at least two, or at least three organoleptic properties that is similar to that of cheese (i.e., cheese produced using mammalian milk, such as bovine milk or goat milk). For example, in some embodiments, the cheese compositions may have at least one, at least two, or at least three organoleptic properties found in the cheeses of Table 15 or Table 16.

In some embodiments, the cheese compositions described herein may be used in a similar manner (e.g., for cooking, etc.) as one or more of the cheeses listed in Table 15 or Table 16. In some embodiments, the cheese compositions described herein may be used as a substitute for one or more of the cheeses listed in Table 15 or Table 16.

TABLE 15

Illustrative types of cheese

| Category | Examples |
| --- | --- |
| Soft Fresh Cheeses | Cottage Cheese |
| | Cream Cheese |
| | Feta |
| | Mascarpone |
| | Neufchâtel |
| | Queso Blanco |
| | Ricotta |
| Soft-Ripened Cheeses | Brie (single, double and triple cream and flavored) |
| | Camembert |
| Semi-Soft Chesses | Brick, dry- and washed-rind |
| | Fontina |
| | Havarti |
| | Limburger |
| | Monterey Jack |
| | Muenster |
| | Pepper Jack |
| Blue-Veined Cheeses | Blue Cheese |
| | Gorgonzola, creamy style |
| | Gorgonzola, crumbly style |
| Gouda & Edam | Gouda |
| | Smoked Gouda |
| | Edam |
| Pasta Filata and Related Cheeses | Fresh Mozzarella |
| | Low-Moisture, Part-Skim Mozzarella |
| | Low-Moisture, Whole Milk Mozzarella |
| | Part-Skim Mozzarella |
| | Whole Milk Mozzarella |
| | Provolone, mild, aged and smoked |
| | String Cheese |
| | Pizza Cheese |
| | Individually Quick Frozen mozzarella (IQF) |
| Cheddar & Colby | Cheddar |
| | Smoked Cheddar |
| | Colby |
| Swiss Cheeses | Baby Swiss |
| | Swiss |
| | Gruyère |
| Hard Cheeses | Asiago |
| | Parmesan |
| | Romano |
| | Pepato |
| Process Cheeses | Pasteurized Process Cheese |
| | Pasteurized Process Cheese Food |
| | Pasteurized Process Cheese Spread |
| | Pasteurized Process Cheese Product |
| | Cold-Pack |
| | High-Melt Cheeses |
| Powder & Enzyme-modified Cheeses | Cheese Powders |
| | Enzyme Modified Cheeses (EMCs) |
| Custom & Convenience Cheese Products | Pre-blends |
| | Pre-cut Cheese |
| | Shredded Cheese |
| | Grated Cheese |
| | Cheese Sauce |
| | Portion Packaged Cheese |
| Cheeses for Special Needs | Low-fat Cheeses |
| | No-fat Cheeses |
| | Low-sodium Cheeses |
| | Kosher Cheeses |

TABLE 15-continued

Illustrative types of cheese

| Category | Examples |
| --- | --- |
| | Halal Cheeses |
| | Organic Cheeses |

Cheese may also be categorized based on moisture content. Shown below in Table 16 are example categories of cheeses and their respective moisture content (from Jana A H et al., *J. Food Sci Technol* (2017) 54 (12): 3776-3778).

TABLE 16

Moisture content of cheeses

| Cheese type | Moisture content (%) | Examples |
| --- | --- | --- |
| Soft cheese | 50-80 | Cottage, Quark, Baker's, Mozzarella, Camembert, Feta |
| Semi-soft cheese | 39-50 | Blue, Limburger, Provolone, Tilsiter |
| Hard cheese | Max. 39 | Cheddar, Colby, Edam, Swiss, Gouda |
| Very hard cheese | Max. 34 | Parmesan, Romano, Sardo, Grana |

In some embodiments, a cheese composition described herein has a moisture content of between about 30% and about 80%. In some embodiments, a cheese composition described herein has between about 45% to 60% moisture content.

Cheese and cheese compositions have functional properties such as moisture content, firmness, stretchability, melting, viscosity/flow, oiling off, browning/blistering, whitening/decolorization, spreadability, grating, slicing, dicing, shredding/mincing, mouthfeel, flavor, aroma, freezing ability, and overall appearance. These properties can be determined by any number of means well known in the art.

Firmness and stretch may be analyzed as described above. Moisture content may be measured for example, as described in Bradley, R. L., Jr., and M. A. Vanderwarn. 2001, Determination of moisture in cheese and cheese products, *J. AOAC* 84:570-592. Texture may be analyzed as described in Kapoor et al., 2005, Small-scale manufacture of process cheese using a rapid visco analyzer, *J. Dairy Sci.* 88:3382-3391, using a TA.XT2 Texture Analyzer (see also Drake et al., 1999 Relationship between instrumental and sensory measurements of cheese texture, *J. Texture Stud.* 30:451-476) or for example by Breene 1975, Application of texture profile analysis to instrumental food texture evaluation, *J. Texture Stud.* 6:53-82.

In some embodiments, a cheese composition has the ability to stretch to at least 3 cm in length without breaking, as determined by heating a 100 gram mass of the composition at a temperature of 225° C. for 4 minutes and cooling to about 90° C. and pulling with a fork placed beneath the mass. In some embodiments, a cheese composition has the ability to stretch to at least 4 cm in length without breaking, as determined by heating a 100 gram mass of the composition at a temperature of 225° C. for 4 minutes and cooling to about 90° C. and pulling with a fork placed beneath the mass. In some embodiments, a cheese composition has the ability to stretch to at least 5 cm in length without breaking, as determined by heating a 100 gram mass of the composition at a temperature of 225° C. for 4 minutes and cooling to about 90° C. and pulling with a fork placed beneath the mass. In some embodiments, a cheese composition has the ability to stretch to at least 6 cm in length without breaking, as determined by heating a 100 gram mass of the composition at a temperature of 225° C. for 4 minutes and cooling to about 90° C. and pulling with a fork placed beneath the mass. In some embodiments, a cheese composition has the ability to stretch to at least 9 cm in length without breaking, as determined by heating a 100 gram mass of the composition at a temperature of 225° C. for 4 minutes and cooling to about 90° C. and pulling with a fork placed beneath the mass. In some embodiments, a cheese composition has the ability to stretch to at least 12 cm in length without breaking, as determined by heating a 100 gram mass of the composition at a temperature of 225° C. for 4 minutes and cooling to about 90° C. and pulling with a fork placed beneath the mass. In some embodiments, a cheese composition has the ability to stretch to at least 15 cm in length without breaking, as determined by heating a 100 gram mass of the composition at a temperature of 225° C. for 4 minutes and cooling to about 90° C. and pulling with a fork placed beneath the mass. In some embodiments, a cheese composition has the ability to stretch to at least 18 cm in length without breaking, as determined by heating a 100 gram mass of the composition at a temperature of 225° C. for 4 minutes and cooling to about 90° C. and pulling with a fork placed beneath the mass.

In some embodiments, a cheese composition described herein has a firmness of at least 150 grams, as determined by compressing a cylindrical-shaped sample of the cheese composition having a height of 3 cm and a diameter of 3 cm to a height of 1.5 cm at 5° C. In some embodiments, a cheese composition described herein has a firmness of at least 300 grams, as determined by compressing a cylindrical-shaped sample of the cheese composition having a height of 3 cm and a diameter of 3 cm to a height of 1.5 cm at 5° C. In some embodiments, a cheese composition described herein has a firmness of at least 600 grams, as determined by compressing a cylindrical-shaped sample of the cheese composition having a height of 3 cm and a diameter of 3 cm to a height of 1.5 cm at 5° C. In some embodiments, a cheese composition described herein has a firmness of at least 1000 grams, as determined by compressing a cylindrical-shaped sample of the cheese composition having a height of 3 cm and a diameter of 3 cm to a height of 1.5 cm at 5° C. In some embodiments, a cheese composition described herein has a firmness of at least 2000 grams, as determined by compressing a cylindrical-shaped sample of the cheese composition having a height of 3 cm and a diameter of 3 cm to a height of 1.5 cm at 5° C. In some embodiments, a cheese composition described herein has a firmness in the range of about 600 to about 3000 grams, for example about 650 to about 1000 grams, about 1000 grams to about 1500 grams, about 1500 grams to about 2000 grams, about 2500 grams to about 3000 grams, as determined by compressing a cylindrical-shaped sample of the cheese composition having a height of 3 cm and a diameter of 3 cm to a height of 1.5 cm at 5° C.

As will be understood by those of skill in the art, melting properties can be influenced by a number of factors, including water content, fat content, protein content, and other the presence of other ingredients such as salt, acid, and stabilizers. Meltability may be measured with a rapid visco analyzer (RVA) (Metzger et al., 2002, RVA: Process cheese manufacture, *Aust. J. Dairy Technol.* 57:136; Kapoor et al., 2004, Comparison of pilot scale and rapid visco analyzer process cheese manufacture, *J. Dairy Sci.* 87:2813-2821; Prow et al., 2005, Melt analysis of process cheese spread or product using a rapid visco analyzer, *J. Dairy Sci.* 88:1277-1287). Meltability may also be measured by the Schreiber melt test (1977), wherein a 0.5 cm high plug of cheese is placed in a glass petri dish and heated in an oven at 450° F. for 5 minutes. Other melting tests include the Arnott test (1957), the tube test (1958), the melt analysis/UW melt meter (1997), and the Dynamic Stress Rheometry (DSR) (1998). Shown in Table 17 are some examples of cheeses and their melting temperatures. In some embodiments, the cheese compositions described herein have a melting temperature similar to one or more of the cheeses in Table 17. In some embodiments, the cheese compositions described herein have a melting temperature in the range of 100° F. to 200° F., such as about 120° F., 130° F., 150° F., or 180° F.

TABLE 17

Melting ranges for cheese

| Cheese type | Melt temperature | Examples |
| --- | --- | --- |
| Process cheese | 120° F./49° C. | Pasteurized Process Cheese |
| Soft or semi-soft cheese | 130° F./54° C. | Mozzarella |
| Hard cheese | 150° F./66° C. | Cheddar, Colby, Edam, Swiss, Gouda |
| Very hard cheese | 180° F./82° C. | Parmesan, Romano, Sardo, Grana |

In some embodiments, the cheese composition has a melting point of about 35° C. to about 100° C. In some embodiments, the cheese composition has a melting point of about 40° C. to about 50° C. In some embodiments, the cheese composition has a melting point of about 50° C. to about 60° C. In some embodiments, the cheese composition has a melting point of about 60° C. to about 70° C. In some embodiments, the cheese composition has a melting point of about 70° C. to about 90° C.

As mentioned above, the properties of cheese can be influenced by a number of factors, such as lipids, salts, and/or calcium. Lipids that may be added to the cheese compositions disclosed herein include, for example, dairy fats or vegetable oils such as palm oil or palm kernel oil, butter oil, anhydrous milkfat, soybean oil, corn oil, rapeseed oil, canola oil, sunflower oil, safflower oil, coconut oil, rice bran oil, olive oil, sesame oil, flaxseed oil, hemp oil, cottonseed oil, peanut oil, almond oil, beech nut oil, brazil nut oil, cashew oil, hazelnut oil, macadamia oil, mongongo nut oil, pecan oil, pine nut oil, pistachio oil, walnut oil, pumpkin seed oil, grapefruit seed oil, lemon oil, apricot oil, apple seed oil, argan oil, avocado oil, or orange oil.

Examples of salts that may be included in in a cheese composition clude, but are not limited to, magnesium chloride, sodium chloride, calcium chloride, sodium phosphates and trisodium citrate. In some embodiments, a cheese composition comprises at least one lipid and at least one salt. In some embodiments, a cheese composition comprises calcium. In some embodiments, a cheese composition comprises calcium at a concentration of about 0 to about 2% by weight. In some embodiments, a cheese composition comprises calcium at a concentration of about 0.001 to about 2% by weight. In some embodiments, a cheese composition comprises calcium at a concentration of about 0.01 to about 2% by weight. In some embodiments, a cheese composition comprises calcium at a concentration of about 0.1 to about 2% by weight. In some embodiments, a cheese composition comprises calcium at a concentration of about 1 to about 2% by weight. In some embodiments, a cheese composition has a pH of about 5.2 to about 5.9. In some embodiments, a cheese composition comprises at least one organoleptic property similar to cheese (i.e., cheese produced using mammalian milk, such as bovine milk or goat milk) selected from the group consisting of taste, appearance, mouthfeel, structure, texture, density, elasticity, springiness, coagulation, binding, leavening, aeration, foaming, creaminess, and emulsification. In some embodiments, the cheese composition comprises at least two organoleptic properties similar to cheese (i.e., cheese produced using mammalian milk, such as bovine milk or goat milk) selected from the group consisting of taste, appearance, mouthfeel, structure, texture, density, elasticity, springiness, coagulation, binding, leavening, aeration, foaming, creaminess, and emulsification. In some embodiments, the cheese composition comprises at least three organoleptic properties similar to cheese (i.e., cheese produced using mammalian milk, such as bovine milk or goat milk) selected from the group consisting of taste, appearance, mouthfeel, structure, texture, density, elasticity, springiness, coagulation, binding, leavening, aeration, foaming, creaminess, and emulsification.

In some embodiments, a cheese composition comprises one or more vitamins, such as retinal, carotene, vitamins, vitamin D, vitamin E, vitamin B12, thiamin, or riboflavin.

Colloidal Suspensions Comprising One or More Isolated or Recombinant Casein Proteins A colloidal suspension is a mixture having particles suspended in a continuous phase with another component. The particles may be, for example, proteins. The other component may be, for example water. Many different kinds of foods may be colloidal suspensions, including beverages and other foods such as jam, ice cream, mayonnaise, etc. One example of a colloidal suspension is milk.

The colloidal suspensions described herein may be a Newtonian fluid or a non-Newtonian fluid. Newtonian fluids are characterized by a viscosity that is independent of shear rate; they follow Newton's law of viscosity. Apparent viscosity is the shear stress applied to a fluid divided by the shear rate (expressed in Pascal-second or centipoise units). For a Newtonian fluid, the apparent viscosity is constant. Water is an example of a Newtonian fluid. Non-Newtonian fluids do not follow Newton's law of viscosity; their viscosity can change (for example, become more liquid or more solid) when under force. Ketchup is an example of a non-Newtonian fluid.

In some embodiments, a colloidal suspension comprises: 1-4 milk proteins (i.e., 1, 2, 3, or 4 recombinant milk proteins). The milk proteins may be recombinant or may be isolated from a mammalian milk. In some embodiments, the milk proteins may be plant-expressed.

In some embodiments, a colloidal suspension comprises recombinant beta-casein and at least one lipid and does not contain an organoleptically functional amount of beta-lactoglobulin. In some embodiments, the colloidal suspension does not comprise any additional casein proteins. In some embodiments, the colloidal suspension comprises at least one additional casein protein. In some embodiments, the at least one additional casein protein is selected from kappa-casein, para-kappa-casein, beta-casein, alpha-S1-casein and alpha-S2-casein. In some embodiments, the at least one additional casein protein is kappa-casein or para-kappa-casein. In some embodiments, the colloidal suspension is a non-Newtonian fluid.

In some embodiments, at least 80%, at least 90%, or at least 95% by weight of the total casein protein in a colloidal suspension is beta-casein. In some embodiments, the beta-casein is expressed in a plant. In some embodiments, the beta-casein is expressed in a soybean plant. In some embodiments, all caseins in the composition are plant expressed. In some embodiments, the composition comprises a fusion protein comprising recombinant beta-casein.

In some embodiments, a colloidal suspension is a non-Newtonian fluid. In some embodiments, a colloidal suspension is characterized as a shear thinning fluid with an apparent viscosity greater than 10 centipoise, at a shear rate of 1 sec$^{-1}$. In some embodiments, the suspension is an aqueous suspension.

In some embodiments, the milk proteins comprise between 0.5% (w/v) to 15% (w/v) of the composition, such as about 0.5% (w/v); about 1.0% (w/v), about 1.5% (w/v), about 2.0% (w/v), about 2.5% (w/v), about 3.0% (w/v), about 3.5% (w/v), about 4.0% (w/v), about 4.5% (w/v), about 5.0% (w/v), about 5.5% (w/v), about 6.0% (w/v), about 6.5% (w/v), about 7.0% (w/v), about 7.5% (w/v), about 8.0% (w/v), about 8.5% (w/v), about 9.0% (w/v), about 9.5% (w/v), about 10.1% (w/v), about 10.5% (w/v), about 11.0% (w/v), about 11.5% (w/v), about 12.0% (w/v), about 12.5% (w/v), about 13.0% (w/v), about 13.5% (w/v), about 14.0% (w/v), about 14.5% (w/v), or about 15.0% (w/v). In some embodiments, the colloidal suspension may comprise one or more additional components, such as ash. In some embodiments, the colloidal suspension may comprise one or more vitamins such as retinal, carotene, vitamins, vitamin D, vitamin E, vitamin B12, thiamin, or riboflavin.

In some embodiments, a colloidal suspension comprises about 8% (w/v) to about 25% (w/v) total protein, such as about 8% to about 10%, about 10% to about 15%, about 15% to about 20%, or about 20 to about 25% total protein. In some embodiments, a colloidal suspension comprises about 1% to about 10% (w/v) total protein. In some embodiments, a colloidal suspension comprises about 25% to about 35%, about 35% to about 45%, about 45% to about 55%, about 55% to about 65%, about 65% to about 75% (w/v), or more total protein.

In some embodiments, about 1% to about 5% of the total protein in the colloidal suspension is casein protein. In some embodiments, about 5% to about 10% of the total protein in the colloidal suspension is casein protein. In some embodiments, about 10% to about 20% of the total protein in the colloidal suspension is casein protein. In some embodiments, about 20% to about 30% of the total protein in the colloidal suspension is casein protein. In some embodiments, about 30% to about 40% of the total protein in the colloidal suspension is casein protein. In some embodiments, about 40% to about 50% of the total protein in the colloidal suspension is casein protein. In some embodiments, about 50% to about 60% of the total protein in the colloidal suspension is casein protein. In some embodiments, about 60% to about 70% of the total protein in the colloidal suspension is casein protein. In some embodiments, about 70% to about 80% of the total protein in the colloidal suspension is casein protein. In some embodiments, about 80% to about 90% of the total protein in the colloidal suspension is casein protein. In some embodiments, about 90% to about 100% of the total protein in the colloidal suspension is casein protein.

In some embodiments, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or more of the total protein in the colloidal suspension is casein protein.

In some embodiments, about 20% to about 100% of the casein protein in the colloidal suspension is kappa casein. For example, the colloidal suspension may comprise about 20% to about 30%, about 30% to about 40%, about 40% to about 50%, about 50% to about 60%, about 60% to about 70%, about 70% to about 80%, about 80% to about 90%, or about 90% to about 100% kappa casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the colloidal suspension is kappa casein.

In some embodiments, about 20% to about 100% of the casein protein in the colloidal suspension is para-kappa casein. For example, the colloidal suspension may comprise about 20% to about 30%, about 30% to about 40%, about 40% to about 50%, about 50% to about 60%, about 60% to about 70%, about 70% to about 80%, about 80% to about 90%, or about 90% to about 100% para-kappa casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the colloidal suspension is para-kappa casein.

In some embodiments, about 20% to about 100% of the casein protein in the colloidal suspension is beta casein. In some embodiments, about 50% to about 100% of the casein protein in the colloidal suspension is beta casein. For example, the colloidal suspension may comprise about 20% to about 30%, about 30% to about 40%, about 40% to about 50%, about 50% to about 60%, about 60% to about 70%, about 70% to about 80%, about 80% to about 90%, or about 90% to about 100% beta casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the colloidal suspension is beta casein.

In some embodiments, about 20% to about 100% of the casein protein in the colloidal suspension is alpha-S1-casein. In some embodiments, about 50% to about 100% of the casein protein in the colloidal suspension is alpha-S1-casein. For example, the colloidal suspension may comprise about 20% to about 30%, about 30% to about 40%, about 40% to about 50%, about 50% to about 60%, about 60% to about 70%, about 70% to about 80%, about 80% to about 90%, or about 90% to about 100% alpha-S1-casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the colloidal suspension is alpha-S1-casein.

In some embodiments, about 20% to about 100% of the casein protein in the colloidal suspension is alpha-S2-casein. In some embodiments, about 50% to about 100% of the casein protein in the colloidal suspension is alpha-S2-casein. For example, the colloidal suspension may comprise about 20% to about 30%, about 30% to about 40%, about 40% to about 50%, about 50% to about 60%, about 60% to about 70%, about 70% to about 80%, about 80% to about 90%, or about 90% to about 100% alpha-S2-casein. In some embodiments, about 20% to about 30%, about 30% to about 40%, about 40% to about 50%, about 50% to about 60%, about 60% to about 70%, about 70% to about 80%, about 80% to about 90%, or about 90% to about 100% of the casein protein in the colloidal suspension is alpha-S2-casein.

In some embodiments, colloidal suspension has at least one organoleptic property that is substantially similar to bovine milk. In some embodiments, the organoleptic property is selected from the group consisting of taste, appearance, mouthfeel, structure, texture, density, elasticity, springiness, coagulation, binding, leavening, aeration, foaming, creaminess, and emulsification. In some embodiments, colloidal suspension has at least two, at least three, at least four, at least five, or more organoleptic properties that are substantially similar to bovine milk. In some embodiments, the plant-expressed milk proteins are recombinant, and are selected from beta lactoglobulin, kappa-casein, para-kappa-casein, beta-casein, alpha-S1-casein, and alpha-S2-casein.

In some embodiments, the colloidal suspensions described herein may be used to produce one or more food compositions such as butter, ice cream, frozen yogurt or custard, yogurt, frozen desserts, cottage cheese, cream cheese, curds, and crème fraiche.

Methods for Making the Food Compositions Described Herein

Also provided herein are methods for making solid phase, protein-stabilized emulsions, colloidal suspensions, dairy alternatives and food compositions described herein (collectively referred to in this section as "compositions"). In some embodiments, a method for making a composition comprises isolating one or more casein proteins from a mammalian milk. In some embodiments, a method for making a composition comprises expressing a casein protein in a cell (e.g., in a plant, or microorganism), extracting the recombinant protein, and preparing a composition comprising recombinant casein protein (See, e.g., FIG. 13).

Figure 13:
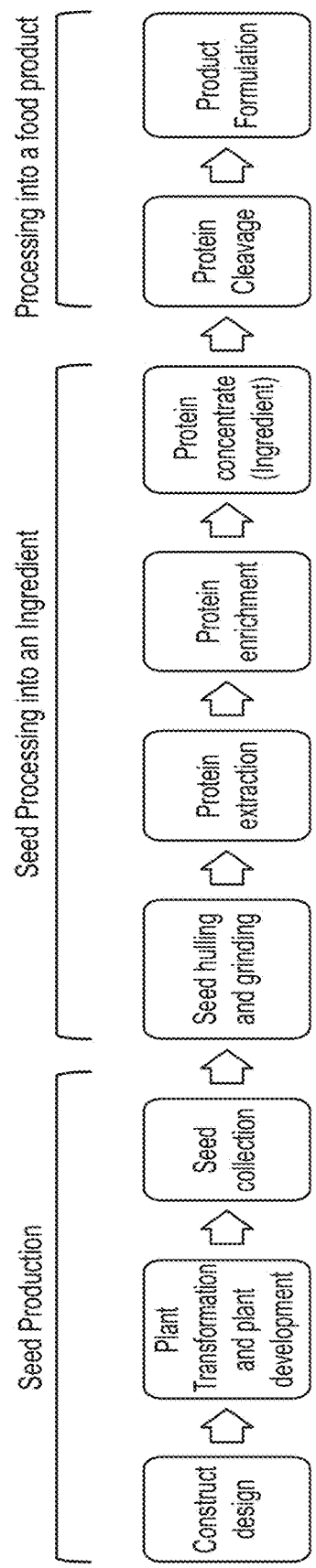
FIG. 13 is a flow-chart showing an illustrative process for producing a food composition comprising an unstructured milk protein, as described herein. Initially, an expression construct for expression of a fusion protein in a plant cell is designed. The construct is transformed into a plant, and the plant is regenerated. Seeds are collected from the plant, and processed (e.g., by seed hulling and grinding) to produce a seed processing composition. Protein is extracted, and optionally enriched and/or concentrated (i.e., to produce a protein concentrate composition). The extracted fusion protein may optionally be cleaved or used directly to produce a food composition.

Initially, all ingredients for the composition are provided. For example, in some embodiments, the one or more milk proteins are provided. The milk proteins may be isolated from a mammalian milk, or may be produced recombinantly (e.g., by expression in a plant). An illustrative process for preparing a recombinant protein for use in making a composition as described herein is illustrated in FIG. 13 and is also described below. In some embodiments, one or more lipids, salts, acids, etc. are also provided. In some embodiments, ash is provided. In some embodiments, one or more vitamins is provided, such as retinal, carotene, vitamins, vitamin D, vitamin E, vitamin B12, thiamin, or riboflavin.

The ingredients are then combined and mixed. In some embodiments, the mixing is performed at a pre-determined temperature, for example a temperature in the range of about 0° C. to about 10° C., about 10° C. to about 20° C., about 20° C. to about 40° C., about 40° C. to about 50° C., about 50° C. to about 60° C., about 60° C. to about 70° C., about 70° C. to about 80° C., about 80° C. to about 90° C., about 90° C. to about 100° C. or higher. In some embodiments, the mixing is performed at a temperature of about 40° C. In some embodiments, the mixing is performed at a temperature of about 85° C. In some embodiments, the mixing is performed at a temperature of about 90° C. In some embodiments, the mixing is performed at a temperature of about 95° C. In some embodiments, the mixing is performed at a speed that will not negatively affect the properties of the composition, such as a speed of about 100 RPM, 200 RPM, 300 RPM, 400 RPM, 500 RPM, 600 RPM, 700 RPM, 800 RPM, 900 RPM, 1000 RPM, or more. In some embodiments the mixing lasts for about 1 minute, about 2 minutes, about 3 minutes, about 4 minutes, about 5 minutes, about 6 minutes, about 7 minutes, about 8 minutes, about 9 minutes, about 10 minutes, or more.

In some embodiments, the composition is mixed only once. In some embodiments, the composition is mixed more than once, such as twice, three times, four times, five times, or more. In some embodiments, the temperature is changed between each mix. For example, in some embodiments, the composition is mixed a first time at a first temperature, and a second time at a second temperature. In some embodiments, the composition is mixed a first time at a first temperature, a second time at a second temperature, and a third time at a third temperature. In some embodiments, the composition is mixed a first time at a first temperature, a second time at a second temperature, a third time at a third temperature, and a fourth time at a fourth temperature. In some embodiments, the composition is mixed a first time at 40° C., a second time at 95° C., a third time at 90° C., and a fourth time at 85° C. After mixing and/or between different mixings the composition my be allowed to rest.

The compositions are then poured into molds. The molds may be of any shape, such as cube-shaped, cylindrical-shaped, triangular prism-shaped, spherical-shaped, cone-shaped, or rectangular prism-shaped. The compositions may then be covered, cooled and stored. In some embodiments, the compositions may be stored for at least 1 day, at least 3 days, at least 5 days, at least 7 days, at least 30 days, at least 180 days, or at least 360 days.

The pH of the composition may be monitored during production thereof. In some embodiments, the pH may be adjusted to a target pH, such as a pH in the range of about 5.5 to about 5.7. As will be understood by those of ordinary skill in the art, the pH may be adjusted up or down using acids or bases. Exemplary acids that may be used to adjust the pH include lactic acid, citric acid, or sodium citrate.

An illustrative method for preparing a food composition of the disclosure is provided in FIG. 13. The first step in this method is production of a seed expressing a fusion protein. In this process, an expression construct is designed. The construct is then transformed into a plant. The plant is grown under conditions that allow for expression of the fusion protein. Subsequently, seeds may be collected from the plant for further processing.

The next step in the method for preparing a food composition illustrated in FIG. 13 is seed processing, to prepare one or more ingredients for use in a food composition. First, the seeds are hulled and ground. Protein (including the fusion protein and other seed proteins) is extracted from the seed. The protein fraction may then be enriched. Specifically, the protein fraction may be enriched for fusion protein. Optionally, the fusion protein may then be concentrated.

The plant protein, including fusion proteins, may be extracted from a plant using standard methods known in the art. For example, the proteins may be extracted using solvent or aqueous extraction. In some embodiments, the oil may be separated from the proteins using hexane or ethanol extraction to produce a white flake. The proteins may be extracted from the white flake using controlled temperature in an aqueous buffered environment (e.g., carbonate, citrate), in order to control the pH. The fusion proteins can be separated from the plant proteins using selective precipitation of one or more of the proteins with centrifugation or filtration methods. In some embodiments, one or more additives may be used to aid the extraction processes (e.g., salts, protease/peptidase inhibitors, osmolytes, solvents, reducing agents, etc.) The following step is processing the fusion protein into a food product. In some embodiments, constituent proteins of the fusion protein may be separated from one another before they are used to formulate a product. In some embodiments, only one of the constituent proteins of the fusion protein is used in the product. In some embodiments, more than one of the constituent proteins of the fusion protein is used in the product. In some embodiments, all of the constituent proteins of the fusion protein may be used in the product. In some embodiments, the fusion protein may be used itself in the food product. The product is then formulated as desired.

Figure 17:
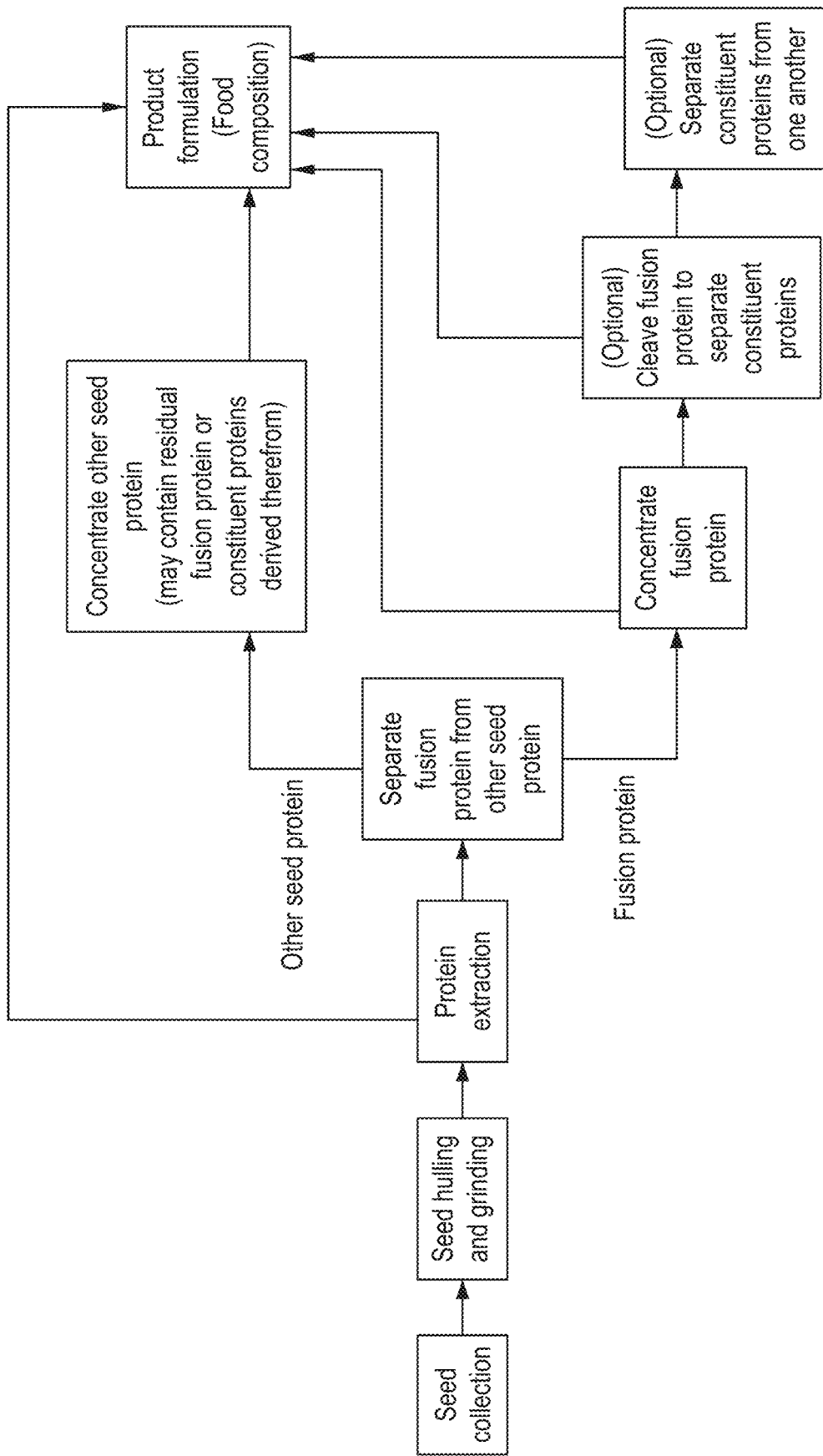
FIG. 17 is a schematic showing an illustrative process for producing a food composition. The food composition produced according to this method may comprise one or more of: (i) one or more constituent proteins derived from a fusion protein, (ii) the fusion protein itself, or (ii) other protein extracted from the seed that was used to produce the fusion protein.

FIG. 17 also illustrates a method for preparing a food composition. In this method, after seeds are collected, hulled and ground, and protein has been extracted, the fusion protein is separated from other seed protein. In some embodiments, this separation is not 100% efficient, meaning that the "other seed protein" fraction may still contain some residual fusion protein. For example, in some embodiments, the other seed protein fraction may comprise about 0.1%, about 0.3%, about 0.5%, about 0.7%, about 1%, about 2%, about 3%, about 4%, about 5%, about 6%, about 7%, about 8%, about 9%, about 10%, about 20%, about 30%, or about 50% fusion protein by weight. The other seed protein fraction may then be used directly in a food composition. Alternatively, the other seed protein fraction may be combined with concentrated fusion protein. In some embodiments, the other seed protein fraction is combined with one or more of the constituent proteins from the fusion protein. In some embodiments, the other seed protein fraction is combined with all of the constituent proteins from the fusion protein.

It may be advantageous to use a seed processing composition comprising plant protein and a fusion protein (e.g., about 0.1%, about 0.3%, about 0.5%, about 0.7%, about 1%, about 2%, about 3%, about 4%, about 5%, about 6%, about 7%, about 8%, about 9%, about 10%, about 20%, about 30%, or about 50% fusion protein by weight) as an ingredient in a food composition. Using both (i) a fusion protein produced by a seed and (ii) other protein extracted from the seed allows for efficient use of resources and reduces waste. Such processes may simplify food manufacturing processes, and reduce the unit cost to manufacture each product. Thus, provided herein is a method of making a food composition, the method comprising: (i) expressing a fusion protein in a transformed plant; and (ii) preparing a food composition comprising the fusion protein and plant protein from the same transformed plant in which the fusion protein was produced. In some embodiments, the transformed plant is a soybean. In some embodiments, the transformed plant is pea.

Figure 19:
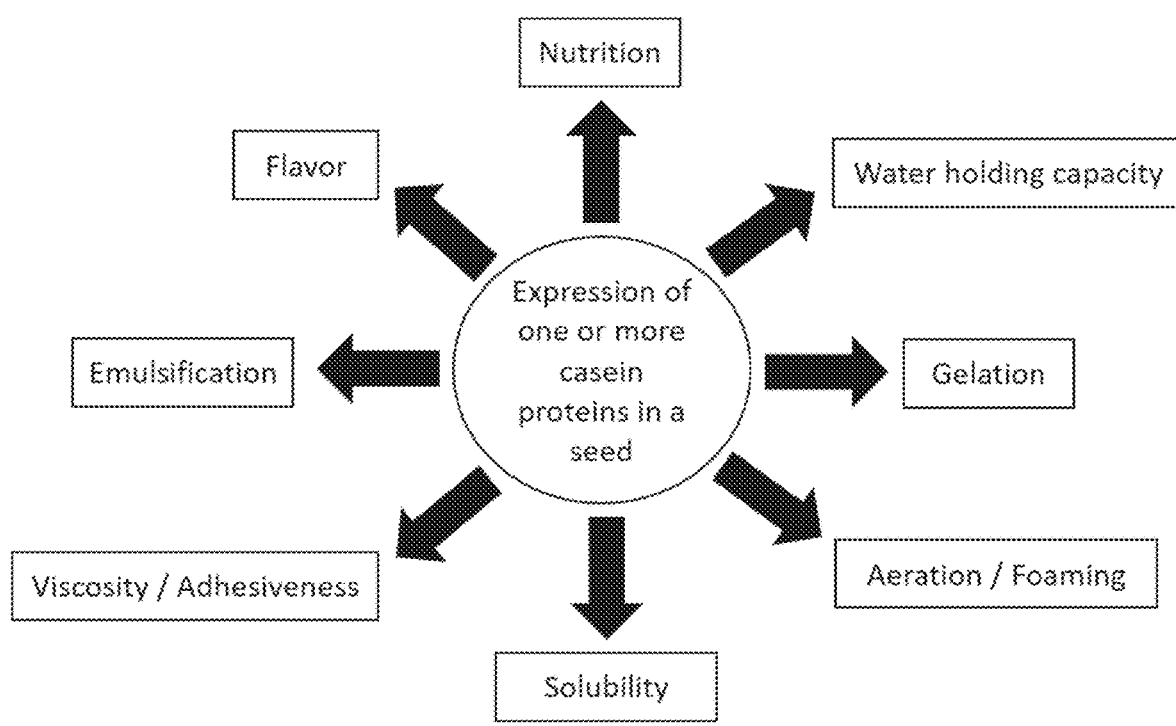
FIG. 19 is a schematic demonstrating how the properties of a seed processing composition, or a food composition comprising the same, may be improved if the composition comprises one or more casein proteins. These properties may be improved if the composition comprises a casein protein monomer (i.e., a casein protein that is not part of a fusion protein), or a fusion protein comprising one or more caseins.

Without being bound by any theory, it is believed that having a casein protein (i.e., as a monomer or as part of a fusion protein) in a plant protein composition may improve the properties of the plant protein composition. FIG. 19 illustrates various properties that may be improved due to the presence of one or more caseins in a plant protein composition, including. In some embodiments, a plant protein composition comprising one or more casein proteins has improved nutritional properties compared to a plant protein composition that does not contain a casein protein. In some embodiments, a plant protein composition comprising one or more casein proteins has improved organoleptic properties, such as taste, compared to a plant protein composition that does not contain a casein protein. In some embodiments, a plant protein composition comprising one or more casein proteins has improved water holding capacity compared to a plant protein composition that does not contain a casein protein. In some embodiments, a plant protein composition comprising one or more casein proteins has improved emulsification compared to a plant protein composition that does not contain a casein protein. In some embodiments, a plant protein composition comprising one or more casein proteins has improved gelation compared to a plant protein composition that does not contain a casein protein. In some embodiments, a plant protein composition comprising one or more casein proteins has improved viscosity and/or adhesiveness compared to a plant protein composition that does not contain a casein protein. In some embodiments, a plant protein composition comprising one or more casein proteins has improved aeration and/or foaming compared to a plant protein composition that does not contain a casein protein. In some embodiments, a plant protein composition comprising one or more casein proteins has improved solubility compared to a plant protein composition that does not contain a casein protein. Illustrative improvements in each one of these properties are described in further detail below.

Nutrition: The presence of a casein protein (alone, or expressed as a fusion protein) in the plant protein composition may enhance the nutritional properties of the plant protein composition and/or any food compositions comprising the plant protein composition. For example, the presence of the casein protein may, in some embodiments, improve the balance of essential amino acids. Pea protein has a PDCAAS (protein digestibility corrected amino acid score) of about 0.82. Nutritionally complete proteins have a score of about 1.0. By expressing a casein protein (fused to, for example, ovalbumin and/or beta-lactoglobulin) at sufficient levels in a pea plant, the PDCAAS of the protein extracted from the pea plant may reach 1.0, provided that the limiting amino acids (e.g., methionine) are raised. In some embodiments, a plant protein composition comprising a casein protein comprises a PDCAAS of about 0.90, about 0.95, about 1.0, or about 1.05.

Gelation: In some embodiments, the casein protein present in the plant protein composition may enhance gelation of the plant protein composition and/or any food compositions comprising the plant protein composition. Many of the proteins used as fusion partners in the fusion proteins described herein, including whey proteins (e.g., beta-lactoglobulin) and egg proteins are often added to a number of food products such as meats and bakery products, because the proteins gel after heating and cooling. Seed proteins are generally insoluble under the processing conditions used to prepare many foods, such as meats and bakery products. Methylcellulose is often added to plant-based meats to impart gelling, and egg white has historically been used in some vegetarian products. However, eggs are not considered vegan and do not meet the standard of "plant-based" for many individuals. Thus, by using a plant composition comprising one or more casein proteins (fused to, for example, an egg protein and/or a whey protein), enhanced gelation may be achieved without using animal products.

Solubility: In some embodiments, the casein protein present in the plant protein composition may enhance solubility of the plant protein composition and/or any food compositions comprising the plant protein composition. Seed proteins typically have poor solubility at acidic and neutral pH. Beverage formulations are suspensions utilizing hydrocolloids such as gellan gum to keep the proteins from settling out. Conversely, casein proteins are soluble at neutral pH, and whey proteins are soluble at acidic pH. Both caseins and whey are soluble at neutral pH. In some embodiments, beverages made with seed protein enhanced by the expression of casein proteins (expressed alone or fused to, for example, a whey protein) exhibit a smoother and/or less chalky mouthfeel.

Emulsification: In some embodiments, the casein protein present in the plant protein composition may enhance emulsification of the plant protein composition and/or any food compositions comprising the plant protein composition. Caseinates are effective at emulsifying lipids with a low viscosity, and this property is used in spray drying to produce powdered coffee creamers and powdered sauces with lipids used in convenience foods. Seed proteins do not have these attributes, and additives such as starches chemically modified with octenyl succinic anhydride are often used as additives in plant protein compositions. Food compositions made with plant protein compositions comprising casein proteins will have improved emulsification properties for a number of different applications.

Water holding capacity: In some embodiments, the casein protein may enhance the water holding capacity of the plant protein. During the processing of the plant protein, pH and heat conditions can be modified to denature the casein protein to enhance this property.

Aeration/Foaming: Aeration and foaming properties of the plant protein can be improved by the addition of the casein proteins. Caseins have excellent foaming properties, as evidenced by their incorporation in frozen whipped toppings. Egg proteins and beta-lactoglobulin also demonstrate good foaming properties. The surface-active properties of these proteins are beneficial in food compositions.

Viscosity/Adhesiveness: Unstructured casein proteins can unfold to interact with other components of a food composition to impart viscosity and adhesiveness. Granola bars can utilize casein proteins at specific concentrations to form a viscous solution that holds the particulates together.

Flavor: The casein proteins can also improve the flavor of plant proteins. In addition to acting as binders for off flavors, casein proteins can impart desirable flavors to food compositions. Hydrolyzed protein caseins impart a savory umami flavor similar to those from autolyzed yeast extract. Some of the expressed casein are hydrolyzed by plant enzymes in the seed, and the resultant peptides can provide savory flavors.

In some embodiments, a plant protein composition comprising a fusion protein is used to produce a food composition. The food composition may be, for example, a meat analog, a nutritional bar, a bakery product, a beverage, mashed potatoes, or candy. In some embodiments, the food composition is for a human. For example, the food composition may be infant formula. In some embodiments, the food composition is for a companion animal (e.g., a dog, cat, rabbit, hamster, guinea pig, horse, etc.) For example, the food composition may be pet food.

Also provided herein are various compositions prepared during a method of making a food composition. For example, in some embodiments, a seed processing composition is provided. In some embodiments, a seed processing composition comprises (a) a fusion protein comprising i) a full-length κ-casein or para-κ-casein component; and ii) a β-lactoglobulin component; and (b) plant seed tissue. In some embodiments, a seed processing composition comprises (a) a fusion protein comprising i) a beta-casein component; and ii) α-lactoglobulin component; and (b) plant seed tissue. In some embodiments, a seed processing composition comprises (a) a fusion protein comprising i) a milk protein (e.g., a casein protein); and ii) a second protein (i.e., a fusion partner); and (b) plant seed tissue. In some embodiments, the plant seed tissue is ground. In some embodiments, the plant seed tissue is from soybean. In some embodiments, the seed processing composition comprises at least one member selected from the group consisting of: enzyme (e.g., chymosin), protease, extractant, solvent (e.g., ethanol, or hexane), buffer, additive, salt, protease inhibitor, peptidase inhibitor, osmolyte, and reducing agent.

In some embodiments, a protein concentrate composition is provided. In some embodiments, the protein concentrate composition comprises: a fusion protein, comprising i) a full-length κ-casein or para-κ-casein component; and ii) a β-lactoglobulin component. In some embodiments, the protein concentrate composition comprises: a fusion protein, comprising i) a beta-casein component; and ii) a β-lactoglobulin component. In some embodiments, the protein concentrate composition comprises: a fusion protein, comprising i) a milk protein (e.g., a casein protein); and ii) a second protein (i.e., a fusion partner). In some embodiments, the fusion protein is present in an enriched amount, relative to other components present in the composition. In some embodiments, there is substantially no plant seed tissue present in the protein concentrate composition. In some embodiments, the protein concentrate composition further comprises at least one member selected from the group consisting of: enzyme (e.g., chymosin), protease, extractant, solvent (e.g., ethanol, or hexane), buffer, additive, salt, protease inhibitor, peptidase inhibitor, osmolyte, and reducing agent.

In some embodiments, a food composition comprises a fusion protein comprising a first protein and a second protein. In some embodiments, a food composition comprises a first protein, wherein the first protein is derived from (i.e., separated from) a fusion protein comprising at least the first protein and a second protein. In some embodiments, a food composition comprises (i) a fusion protein comprising a first protein and a second protein and (ii) at least one of the first protein and the second protein, wherein the first protein and/or the second protein has been separated from the fusion protein. The first protein and/or second protein which have been separated from the fusion protein may comprise, in some embodiments, at least at least one non-native amino acid from an introduced protease cleavage site (e.g., a chymosin cleavage site).

In some embodiments, the food composition is a solid. In some embodiments, the food composition is a liquid. In some embodiments, the food composition is a powder.

In some embodiments, the food composition is a solid phase, protein-stabilized emulsion. In some embodiments, the food composition is a colloidal suspension.

In some embodiments, the fusion proteins and transgenic plants described herein may be used to prepare a food composition such as cheese or processed cheese products. In some embodiments, the food composition is an alternative dairy composition selected such as milk, cream, or butter. The alternative milk composition may be used to prepare alternative dairy compositions such as yogurt and fermented dairy products, directly acidified counterparts of fermented dairy products, cottage cheese, dressing, curds, crème fraiche, toppings, icings, fillings, low-fat spreads, dairy-based dry mixes, frozen dairy products, frozen desserts, desserts, baked goods, soups, sauces, salad dressing, geriatric nutrition, creams and creamers, analog dairy products, follow-up formula, baby formula, infant formula, milk, dairy beverages, acid dairy drinks, smoothies, milk tea, butter, margarine, butter alternatives, growing up milks, low-lactose products and beverages, medical and clinical nutrition products, protein/nutrition bar applications, sports beverages, confections, meat products, analog meat products, meal replacement beverages, and weight management food and beverages.

In some embodiments the fusion proteins and transgenic plants described herein may be used to prepare a dairy product. In some embodiments, the dairy product is a fermented dairy product. An illustrative list of fermented dairy products includes cultured buttermilk, sour cream, yogurt, skyr, leben, lassi, or kefir. In some embodiments the fusion proteins and transgenic plants described herein may be used to prepare cheese products.

In some embodiments the fusion proteins and transgenic plants described herein may be used to prepare a powder containing a milk protein. In some embodiments, the fusion proteins and transgenic plants described herein may be used to prepare a low-lactose product.

In some embodiments, a method for making a food composition comprises, expressing a recombinant fusion protein of the disclosure in a plant, extracting the recombinant fusion protein from the plant, optionally separating the milk protein from the mammalian or plant protein, and creating a food composition using the fusion protein and/or the milk protein.

In some embodiments, a method of expressing, extracting, and making a food composition from a fusion protein, comprises: expressing a fusion protein in a host cell, the fusion protein comprising a first protein and a second protein; extracting the fusion protein from the host cell; and processing the fusion protein into a food composition. The food composition may be, for example, cheese, processed cheese product, yogurt, fermented dairy product, directly acidified counterpart of fermented dairy product, cottage cheese dressing, frozen dairy product, frozen dessert, dessert, baked good, topping, icing, filling, low-fat spread, dairy-based dry mix, soup, sauce, salad dressing, geriatric nutrition, cream, creamer, analog dairy product, follow-up formula, baby formula, infant formula, milk, dairy beverage, acid dairy drink, smoothie, milk tea, butter, margarine, butter alternative, growing up milk, low-lactose product, low-lactose beverage, medical and clinical nutrition product, protein bar, nutrition bar, sport beverage, confection, meat product, analog meat product, meal replacement beverage, weight management food and beverage, dairy product, cultured buttermilk, sour cream, yogurt, skyr, leben, lassi, kefir, powder containing a milk protein, and low-lactose product. In some embodiments, the food composition is a dairy product. In some embodiments, the food composition is a cheese.

In some embodiments, a method for making a food composition comprises, expressing a recombinant fusion protein of the disclosure in a plant, extracting one or both of the proteins, and creating a food composition using the milk protein. In some embodiments, the first protein and the second protein are separated from one another in the plant cell, prior to extraction. In some embodiments, the first protein is separated from the second protein after extraction, for example by contacting the fusion protein with an enzyme that cleaves the fusion protein. The enzyme may be, for example, chymosin. In some embodiments, the fusion protein is cleaved using rennet.

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world, or that they disclose essential matter.

EXAMPLES

The following experiments demonstrate different recombinant fusion constructs comprising a milk protein (e.g., a casein) and at least one other protein, as well as methods of producing and testing the fusion proteins. While the examples below describe expression in soybean, it will be understood by those skilled in the art that the constructs and methods disclosed herein may be tailored for expression in any organism.

The following examples also demonstrate the production of various cheese compositions and characterization of their properties. Traditionally cheese is made from milk, which comprises a mixture of casein proteins. To test whether a cheese composition having acceptable organoleptic and physical properties could be made using only one casein protein, or different combinations/ratios of casein proteins as compared to that found in any mammalian milk, various experiments described below were performed. While the examples below utilize isolated caseins isolated from bovine milk, it will be understood by those skilled in the art that the recipes and methods disclosed herein may be tailored for use with other isolated caseins and recombinant caseins, including caseins expressed in a plant.

Example 1: Construction of Expression Vectors for Plant Transformation for Stable Expression of Recombinant Fusion Proteins Binary Vector Design While a number of vectors may be utilized for expression of the fusion proteins disclosed herein, the example constructs described below were built in the binary pCAMBIA3300 (Creative Biogene, VET1372) vector, which was customized for soybean transformation and selection. In order to modify the vector, pCAMBIA3300 was digested with HindIII and AseI allowing the release of the vector backbone (LB T-DNA repeat_KanR_pBR322 ori_pBR322 bom_pVS1 oriV_pVs1 repA_pVS1 StaA_RB T-DNA repeat). The 6598 bp vector backbone was gel extracted and a synthesized multiple cloning site (MCS) was ligated via In-Fusion cloning (In-Fusion® HD Cloning System CE, available on the world wide web at clontech.com) to allow modular vector modifications. A cassette containing the *Arabidopsis thaliana* Csr1.2 gene for acetolactate synthase was added to the vector backbone to be used as a marker for herbicide selection of transgenic plants. In order to build this cassette, the regulatory sequences from *Solanum tuberosum* ubiquitin/ribosomal fusion protein promoter (StUbi3 prom; −1 to −922 bp) and terminator (StUbi3 term; 414 bp) (GenBank accession no. L22576.1) were fused to the mutant (S653N) acetolactate synthase gene (Csr1.2; GenBank accession no. X51514.1) (Sathasivan et al, 1990; Ding et al, 2006) to generate imazapyr-resistant traits in soybean plants. The selectable marker cassette was introduced into the digested (EcoRI) modified vector backbone via In-Fusion cloning to form vector pAR15-00 (FIG. 2).

Recombinant DNA constructs were designed to express milk proteins in transgenic plants. The coding regions of the expression cassettes outlined below contain a fusion of codon-optimized nucleic acid sequences encoding bovine milk proteins, or a functional fragment thereof. To enhance protein expression in soybean, the nucleic acid sequences encoding β-lactoglobulin (GenBank accession no. X14712.1), κ-casein (GenBank accession no. CAA25231), β-casein (GenBank accession no. M15132.1), and αS1-casein (GenBank accession no. X59836.1) were codon optimized using *Glycine max* codon bias and synthesized (available on the world wide web at idtdna.com/CodonOpt). The signal sequences were removed (i.e., making the constructs "truncated") and the new versions of the genes were renamed as OLG1 (β-lactoglobulin version 1, SEQ ID NO: 9), OLG2 (β-lactoglobulin version 2, SEQ ID NO: 11), OLG3 (β-lactoglobulin version 3, SEQ ID NO: 12), OLG4 (β-lactoglobulin version 4, SEQ ID NO: 13), OKC1-T (Optimized κ-casein Truncated version 1, SEQ ID NO: 3), paraOKC1-T (only the para-K portion of OKC1-T, SEQ ID NO: 1), OBC-T2 (Optimized β-casein Truncated version 2, SEQ ID NO: 5), and OaS1-T (Optimized αS1-casein Truncated version 1, SEQ ID NO: 7). As will be understood by those skilled in the art, codon optimized nucleic acid sequences can present from about 60% to about 100% identity to the native version of the nucleic acid sequence.

Figure 3:
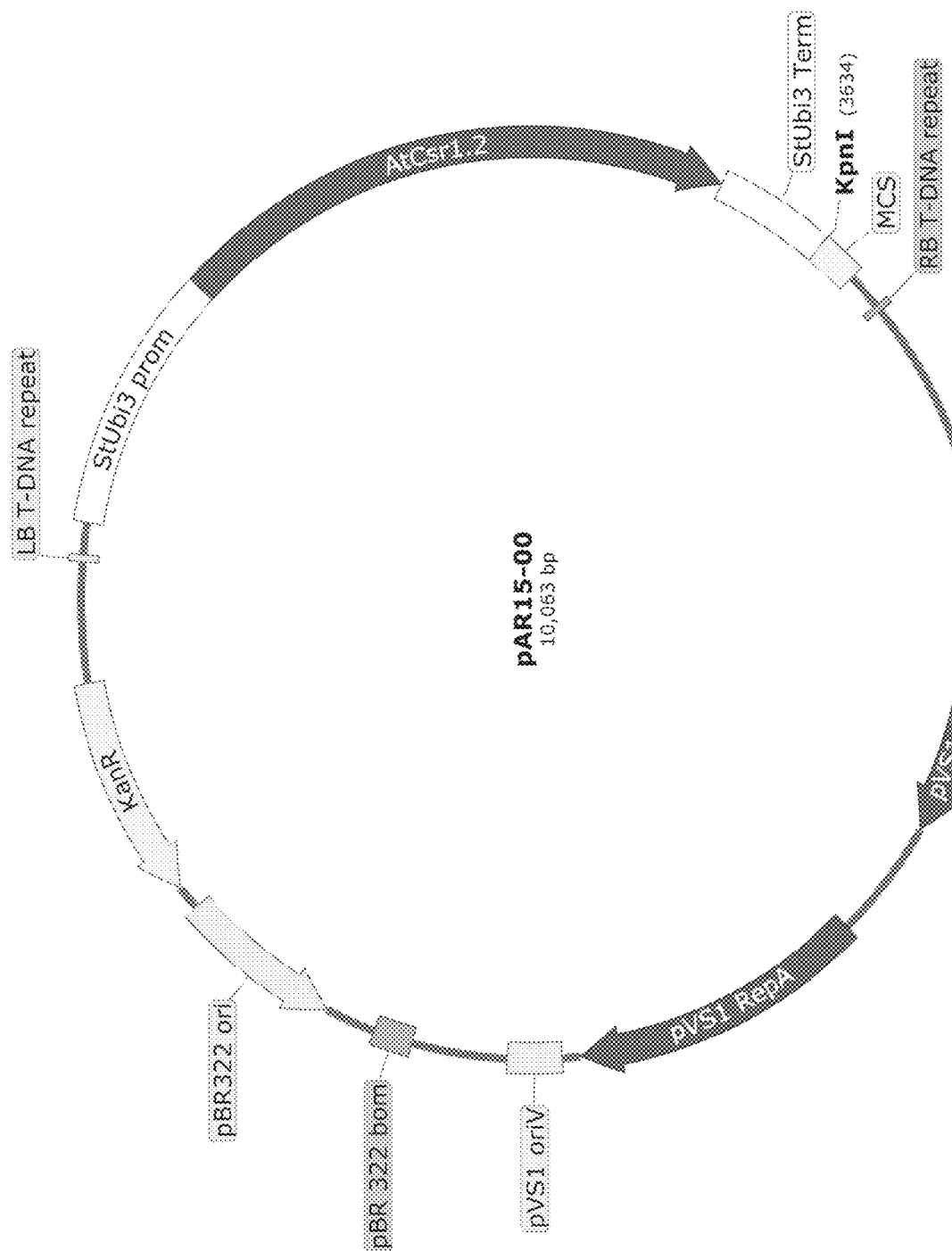
FIG. 3 shows the modified pAR 15-00 binary vector containing a selectable marker cassette conferring herbicide resistance. Coding regions and regulatory sequences are indicated as blocks (not to scale).

All the expression cassettes described below and shown in FIG. 4-FIG. 9 contained codon-optimized nucleic acid sequences encoding bovine milk proteins, or a functional fragment thereof, a seed specific promoter, a 5'UTR, a signal sequence (Sig) that directs foreign proteins to the protein storage vacuoles, and a termination sequence. In some versions of the constructs a linker such as a linker comprising a chymosin cleavage site (FM), was placed between the two proteins and/or a C-terminal KDEL sequence (SEQ ID NO: 23) for ER retention was included. Expression cassettes were inserted in the pAR15-00 vector described above utilizing a KpnI restriction site with the MCS (FIG. 3). Coding regions and regulatory sequences are indicated as blocks (not to scale) in FIG. 4-FIG. 9.

κ-Casein-β-Lactoglobulin Fusion with KDEL

Shown in FIG. 4 is an example expression cassette comprising κ-casein (OKC1-T, SEQ ID NO: 3) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; GenBank accession no. Glyma.02G012600, SEQ ID NO: 14) (Darnowski et al, 20020); and, the 3'UTR of the arc5-1 gene, (arc term 1197 bp; GenBank accession no. Z50202.1, SEQ ID NO: 21) (De Jaeger et al, 2002). A C-terminal KDEL (SEQ ID NO: 23) was also included for ER retention.

β-Case In-β-Lactoglobulin Fusion with Linker

Shown in FIG. 5 is an example expression cassette comprising β-casein (OBC-T2, SEQ ID NO: 5) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; accession no. Glyma.02G012600, SEQ ID NO: 14) (Darnowski et al, 2002); and, the 3'UTR of the arc5-1 gene, (arc term 1197 bp; accession no. Z50202.1, SEQ ID NO: 21) (De Jaeger, et al 2002). A linker comprising a chymosin cleavage site (FM) was inserted between the two proteins.

αS1-Casein-β-Lactoglobulin Fusion with Linker

Shown in FIG. 6 is an example expression cassette comprising αS1-casein (OaS1-T, SEQ ID NO: 7) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; accession no. Glyma.02G012600, SEQ ID NO: 14) (Darnowski et al, 2002); and, the 3'UTR of the arc5-1 gene, (arc term 1197 bp; GenBank accession no. Z50202.1, SEQ ID NO: 21) (De Jaeger et al, 2002). A linker comprising a chymosin cleavage site (FM) was inserted between the two proteins.

Para-κ-Casein-β-Lactoglobulin Fusion with Linker and KDEL

Shown in FIG. 7 is an example expression cassette comprising para-κ-casein (paraOKC1-T, SEQ ID NO: 1) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; GenBank accession no. Glyma.02G012600, SEQ ID NO: 14) (Darnowski et al, 2002); and, the 3'UTR of the arc5-1 gene, (arc term 1197 bp; GenBank accession no. Z50202.1, SEQ ID NO: 21) (De Jaeger et al 2002). A linker comprising a chymosin cleavage site (FM) was inserted between the two proteins and a C-terminal KDEL (SEQ ID NO: 23) was also included for ER retention.

Para-κ-Casein-β-Lactoglobulin Fusion with Linker

Shown in FIG. 8 is an example expression cassette comprising para-κ-casein (paraOKC1-T, SEQ ID NO: 1) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; GenBank accession no. Glyma.02G012600, SEQ ID NO: 14) (Darnowski et al, 2002); and, the 3'UTR of the arc5-1 gene, (arc term 1197 bp; GenBank accession no. Z50202.1, SEQ ID NO: 21) (De Jaeger et al 2002). A linker comprising a chymosin cleavage site (FM) was inserted between the two proteins.

Fusion Protein with Seed2 Promoter, Sig2 and Nopaline Synthase Terminator

Shown in FIG. 9 is an example expression cassette comprising κ-casein (OKC1-T, SEQ ID NO: 3) and β-lactoglobulin (OLG1, SEQ ID NO: 9). The regulatory sequences that were used in order to produce the heterologous milk proteins in soybean seeds include the promoter and signal peptide of glycinin 1 (GmSeed2 (SEQ ID NO: 19):sig2 (SEQ ID NO: 16)) followed by the ER retention signal (KDEL, SEQ ID NO: 23) and the Nopaline synthase termination sequence (nos term, SEQ ID NO: 22).

Exemplary Protein Co-Expression Vector

Binary pCAMBIA3300 vectors individually encoding for: (1) a prolamin (e.g., Canein or Zein); (2) a milk protein (e.g., Casein); or (3) both a prolamin and a milk protein are generated to co-express a milk protein and prolamin in plant cells (See FIG. 26A-26G, FIG. 27). Co-expression of a milk protein and prolamin will result in generation of a protein body in the plant cell capable of shielding the milk protein from degradation or capable of reducing toxicity, if any, associated with recombinant expression of the milk protein in the plant cell.

Example 2: Identification of Transgenic Events, Recombinant Protein Extraction and Detection To quantify recombinant protein expression levels, DNA constructs such as those shown in FIG. 4-FIG. 9 were transformed into soybean using transformation protocols well known in the art, for example, by bombardment or *agrobacterium*. Total soybean genomic DNA was isolated from the first trifoliate leaves of transgenic events using the PureGene tissue DNA isolation kit (product #158667: QIAGEN, Valencia, CA, USA). Trifoliates were frozen in liquid nitrogen and pulverized. Cells were lysed using the PureGene Cell Lysis Buffer, proteins were precipitated using the PureGene Protein Precipitation Buffer, and DNA was precipitated from the resulting supernatant using ethanol. The DNA pellets were washed with 70% ethanol and resuspended in water.

Genomic DNA was quantified by the Quant-iT PicoGreen (product #P7589: ThermoFisher Scientific, Waltham, MA, USA) assay as described by manufacturer, and 150 ng of DNA was digested overnight with EcoRI, HindIII, NcoI, and/or KpnI, 30 ng of which was used for a BioRad ddPCR reaction, including labelled FAM or HEX probes for the transgene and Lectin1 endogenous gene respectively. Transgene copy number (CNV) was calculated by comparing the measured transgene concentration to the reference gene concentration. A CNV of greater than or equal to one was deemed acceptable.

Preparation of Total Soluble Protein Samples

Total soluble soybean protein fractions were prepared from the seeds of transgenic events by bead beating seeds (seeds collected about 90 days after germination) at 15000 rpm for 1 min. The resulting powder was resuspended in 50 mM Carbonate-Bicarbonate pH 10.8, 1 mM DTT, 1×HALT Protease Inhibitor Cocktail (Product #78438 ThermoFisher Scientific). The resuspended powder was incubated at 4° C. for 15 minutes and then the supernatant collected after centrifuging twice at 4000 g, 20 min, 4° C. Protein concentration was measured using a modified Bradford assay (Thermo Scientific Pierce 660 nm assay; Product #22660 ThermoFisher Scientific) using a bovine serum albumin (BSA) standard curve.

Recombinant Protein Quantification Via Western Blot Densitometry

SDS-PAGE was performed according to manufacturer's instructions (Product #5678105BioRad, Hercules, CA, USA) under denaturing and reducing conditions. 5 µg of total protein extracts were loaded per lane. For immunoblotting proteins separated by SDS-PAGE were transferred to a PVDF membrane using Trans-Blot® Turbo™ Midi PVDF Transfer Packs (Product #1704157 BioRad) according to manufacturer's guidelines. Membranes were blocked with 3% BSA in phosphate buffered saline with 0.5% Tween-20, reacted with antigen specific antibody and subsequently reacted with fluorescent goat anti rabbit IgG (Product #60871 BioRad, CA). Membranes were scanned according to manufacturer's instructions using the ChemiDoc MP Imaging System (BioRad, CA) and analyzed using ImageLab Version 6.0.1 Standard Edition (Bio-Rad Laboratories, Inc.) Recombinant protein from the seeds of transgenic events was quantified by densitometry from commercial reference protein spike-in standards.

Figures 10A, 10B, 10C, 10D:
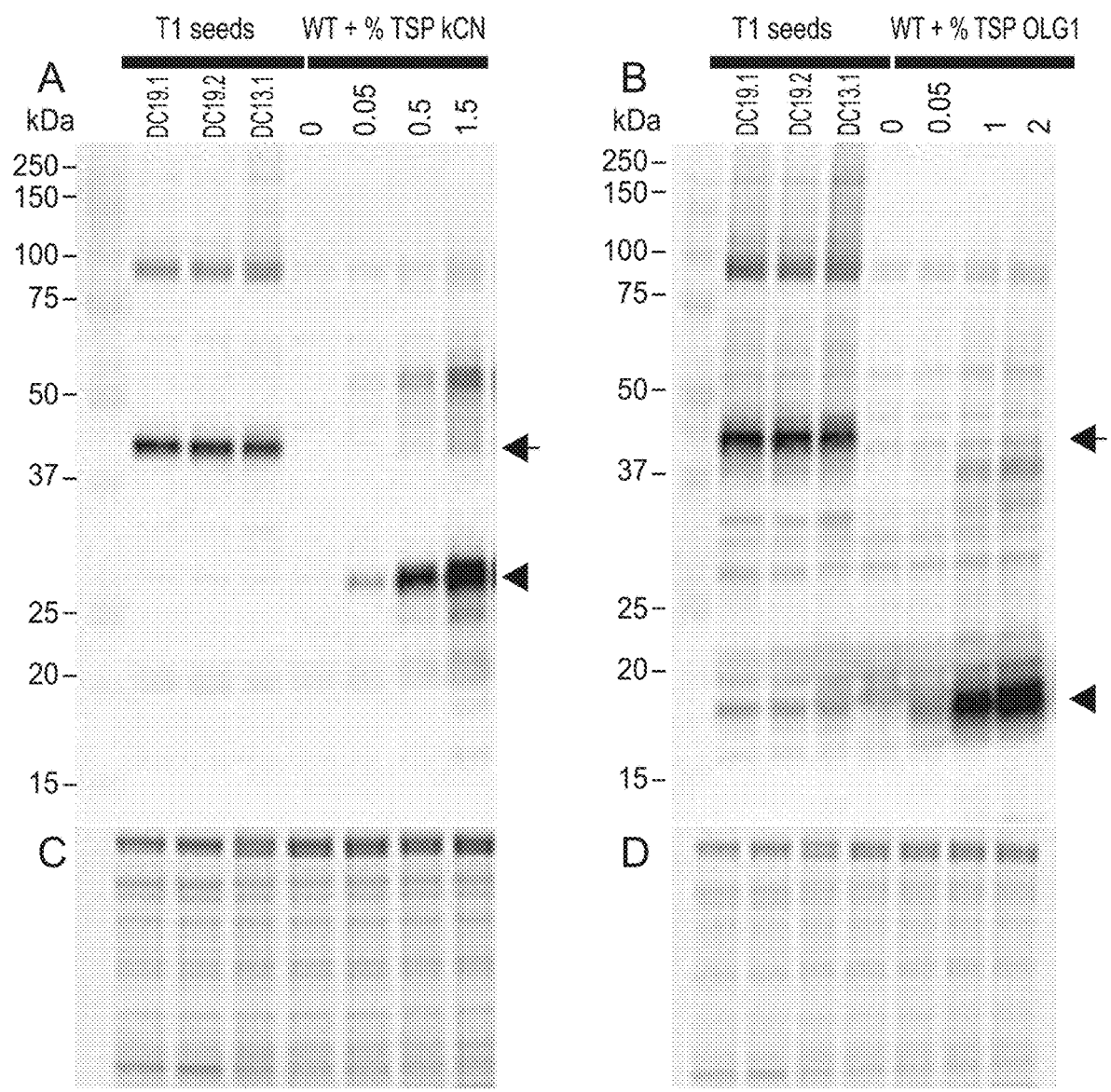
FIGS. 10A, 10B, 10C, and 10D show protein detection by western blotting.

Shown in FIG. 10A, FIG. 10B, FIG. 10C, and FIG. 10D are Western Blots of protein extracted from transgenic soybeans expressing the κ-casein-β-lactoglobulin expression cassette shown in FIG. 4. FIG. 10A shows the fusion protein detected using a primary antibody raised against κ-casein. The first lane is a molecular weight marker. Lanes two (DCI 9.1) and three (DCI 9.2) represent individual seeds from a single transgenic line. Lane four (DCI 3.1) represents a seed from a separate transgenic line. Lane five is protein extracted from wild-type soybean plants, and lanes six-eight are protein extracted from wild-type soybean plants spiked with 0.05% commercial κ-casein (lane 6), 0.5% commercial κ-casein (lane 7), and 1.5% commercial κ-casein (lane 8). The κ-casein commercial protein is detected at an apparent molecular weight (MW) of ~26 kDa (theoretical: 19 kDa—arrow). The fusion protein is detected at an apparent MW of ~40 kDa (theoretical: 38 kDa—arrowhead).

FIG. 10B shows the fusion protein detected using a primary antibody raised against β-lactoglobulin. The first lane is a molecular weight marker. Lanes two (DCI 9.1) and three (DCI 9.2) represent individual seeds from a single transgenic line. Lane four (DCI 3.1) represents a seed from a separate transgenic line. Lane five is protein extracted from wild-type soybean plants, and lanes six-eight are protein extracted from wild-type soybean plants spiked with 0.05% commercial β-lactoglobulin (lane 6), 1% commercial β-lactoglobulin (lane 7), and 2% commercial β-lactoglobulin (lane 8). The β-lactoglobulin commercial protein is detected at an apparent MW of ~18 kDa (theoretical: 18 kDa—arrow). The fusion protein is detected at an apparent MW of ~40 kDa (theoretical: 38 kDa—arrowhead). FIG. 10C and FIG. 10D show the protein gels as control for equal lane loading (image is taken at the end of the SDS run) for FIG. 10A and FIG. 10B, respectively.

Shown in FIG. 15A and FIG. 15B are Western Blots of protein extracted from transgenic soybeans expressing a β-casein-β-lactoglobulin fusion protein. FIG. 15A shows the fusion protein detected using a primary antibody raised against β-casein. The first lane is a molecular weight marker. Lane two (IX2) represents individual seeds from a single transgenic line. Lanes three through seven are samples comprising protein extracted from wild-type soybean plants spiked with 3% commercial β-casein (lane 3), 1.5% commercial β-casein (lane 4), 0.75% commercial β-casein (lane 5), 0.37% commercial β-casein (lane 6), and 0% commercial β-casein (lane 7). The fusion protein was detected at an apparent MW of ~40 kDa (arrow; theoretical: 42 kDa).

Other combinations of proteins were tested and evaluated for the percentage of recombinant protein. Cassettes having the same promoter (Seed2-sig), signal peptide (EUT:Rb7T), and in some instances a different terminator, were built with either α-S1-casein, β-casein, κ-casein, or the fusion of β-lactoglobulin (LG) with κ-casein (kCN) (See FIG. 3 and FIG. 8). As shown below in Table 18, none of the cassettes encoding α-S1-casein, β-casein, or κ-casein alone were able to produce expression of the protein at a level that exceeded 1% total soluble protein. However, when κ-casein was fused with β-lactoglobulin, κ-casein was expressed at a level that was greater than 1% total soluble protein. Similarly, when β-casein or alpha-S1-casein were fused with β-lactoglobulin, the β-casein and the alpha-S1-casein were expressed at a level that was greater than 1% total soluble protein.

TABLE 18

Expression levels of milk proteins expressed alone or in a fusion protein

| | | Total events[1] analyzed | Number of events[1] accumulating the recombinant protein at the concentration: | |
|---|---|---|---|---|
| | | | 0-1% TSP | Above 1% TSP |
| Single Proteins | κ-Casein | 89 | 89 | 0 |
| | β-Casein | 12 | 12 | 0 |
| | αS1-Casein | 6 | 6 | 0 |
| Fusion | κ-Casein-LG | 23 | 12 | 11 |
| | β-Casein-LG | 25 | 5 | 20 |
| | αS1-Casein-LG | 10 | 4 | 6 |

[1]As used in Table 18, the each "event" refers to an independent transgenic line.

As will be readily understood by those of skill in the art, T-DNA insertion into the plant genome is a random process and each T-DNA lands at an unpredictable genomic position. Thus, for example, each of the 23 events generated in Table 18 for the κ-Casein-LG fusion protein have different genomic insertion loci. The genomic context greatly influences the expression levels of a gene, and each locus will be either favorable or unfavorable for the expression of the recombinant genes. The variability observed at the protein level is a reflection of that random insertion process, and explains why 12 out of 23 events present expression levels below 1%.

Example 3: Expression of Casein Multimers

A casein multimer is a fusion protein comprising at least a first casein protein and a second casein protein, wherein the first and second casein proteins are the same (homo-multimer) or different (hetero-multimer). Expression vectors for producing casein multimers were created, using the methods described in Example 1. Specifically, expression vectors were created to express casein multimers comprising: (i) kappa-casein fused to kappa-casein, (ii) kappa-casein fused to beta-casein, and (iii) kappa-casein fused to alpha-S1-casein. Expression vectors were also created to express: (iv) kappa-casein fused to GFP, and (v) kappa-casein fused to beta-lactoglobulin.

Illustrative casein multimers prepared during this study are shown below in Table 19. Colons (:) are used to indicate junctions between various elements of the fusion protein. KDEL indicates the use of a KDEL sequence (i.e., an endoplasmic reticulum retention signal; SEQ ID NO: 23) and FM indicates the use of a linker comprising a chymosin cleavage site.

TABLE 19

Illustrative Casein Multimers

| Description | Abbreviated Description | DNA Sequence (SEQ ID NO) | Amino Acid Sequence (SEQ ID NO) |
|---|---|---|---|
| Optimized para kappa-casein truncated version 1 (paraOKC1-T):FM:Optimized beta-lactoglobulin version 1 (OLG1) | paraOKC1-T:FM:OLG1 | 615 | 616 |
| Optimized para kappa-casein truncated version 1 (paraOKC1-T):FM:Optimized beta-lactoglobulin version 1 (OLG1):KDEL | paraOKC1-T:FM:OLG1:KDEL | 617 | 618 |

TABLE 19-continued

Illustrative Casein Multimers

| Description | Abbreviated Description | DNA Sequence (SEQ ID NO) | Amino Acid Sequence (SEQ ID NO) |
|---|---|---|---|
| Optimized para kappa-casein truncated version 1 (paraOKC1-T):Optimized beta-lactoglobulin version 1 (OLG1) | paraOKC1-T:OLGI | 619 | 620 |
| Optimized para kappa-casein truncated version 1 (paraOKC1-T):Optimized beta-lactoglobulin version 1 (OLG1):KDEL | paraOKC1-T:OLG1:KDEL | 621 | 622 |
| Optimized beta-lactoglobulin version 1 (OLG1):FM: Optimized para kappa-casein truncated version 1 (paraOKC1-T) | OLG:FM:paraOKC1-T | 623 | 624 |
| Optimized beta-lactoglobulin version 1 (OLG1):FM: Optimized para kappa-casein truncated version 1 (paraOKC1-T):KDEL | OLG:FM:paraOKC1-T:KDEL | 625 | 626 |
| Optimized beta-lactoglobulin version 1 (OLG1):Optimized para kappa-casein truncated version 1 (paraOKC1-T) | OLG:paraOKC1-T | 627 | 628 |
| Optimized beta-lactoglobulin version 1 (OLG1):Optimized para kappa-casein truncated version 1 (paraOKC1-T):KDEL | OLG:paraOKC1-T:KDEL | 629 | 630 |
| Optimized alpha S1-casein truncated version 1 (OaS1-T):FM:Optimized beta-lactoglobulin version 1 (OLG1) | OaS1-T:FM:OLG1 | 631 | 632 |
| Optimized alpha S1-casein truncated version 1 (OaS1-T):FM:Optimized beta-lactoglobulin version 1 (OLG1):KDEL | OaS1-T:FM:OLG1:KDEL | 633 | 634 |
| Optimized alpha S1-casein truncated version 1 (OaS1-T):Optimizedbeta-lactoglobulinversion 1 (OLG1) | OaS1-T:OLG1 | 635 | 636 |
| Optimized alpha S1-casein truncated version 1 (OaS1-T):Optimizedbeta-lactoglobulin version 1 (OLG1):KDEL | OaS1-T:OLG1:KDEL | 637 | 638 |
| Optimized beta-lactoglobulin version 1 (OLG1):FM: Optimized alpha S1-casein truncated version 1 (OaS1-T) | OLG1:FM:OaS1-T | 639 | 640 |
| Optimized beta-lactoglobulin version 1 (OLG1):FM: Optimized alpha S1-casein truncated version 1 (OaS1-T):KDEL | OLG1:FM:OaS1-T:KDEL | 641 | 642 |
| Optimized beta-lactoglobulin version 1 (OLG1): Optimized alpha S1-casein truncated version 1 (OaS1-T) | OLG1:OaS1-T | 643 | 644 |
| Optimized beta-lactoglobulin version 1 (OLG1): Optimized alpha S1-casein truncated version 1 (OaS1-T):KDEL | OLG1:OaS1-T:KDEL | 645 | 646 |
| Optimized beta-lactoglobulin version 1 (OLG1): FM:Optimized beta-casein (A2 variant) truncated version 2 | OLG1:FM:OBC-T2 | 647 | 648 |
| Optimized beta-casein (A2 variant) truncated version 2:Optimized kappa-casein truncated version 1 (OKC1-T):Optimized beta-lactoglobulin version 1 (OLG1) | OBC-T2:OKC1-T:OLG1 | 649 | 650 |
| Optimized beta-casein (A2 variant) truncated version 3:Optimized beta-casein (A2 variant) truncated version 2:Optimized kappa-casein truncated version 1 (OKC1-T):Optimized beta-lactoglobulin version 1 (OLG1) | OBC-T3:OBC-T2:OKC1-T:OLG1 | 651 | 652 |
| Optimized beta-casein (A2 variant) truncated version 4:Optimized beta-casein (A2 variant) truncated version 3:Optimized beta-casein (A2 variant) truncated version 2:Optimized kappa-casein truncated version 1 (OKC1-T):Optimized beta-lactoglobulin version 1 (OLG1) | OBC-T4:OBC-T3:OBC-T2:OKC1-T:OLG1 | 653 | 654 |
| Optimized beta-casein (A2 variant) truncated version 5:Optimized beta-casein (A2 variant) truncated version 5:Optimized beta-casein (A2 variant) truncated version 4:Optimized beta-casein (A2 variant) truncated version 3:Optimized beta-casein (A2 variant) truncated version 2:Optimized para kappa-casein truncated version 1 (paraOKC1-T):Optimized beta-lactoglobulin version 1 (OLG1) | OBC-T5:OBC-T4:OBC-T3:OBC-T2:OKC1-T:OLG1 | 655 | 656 |
| Optimized beta-casein (A2 variant) truncated version 5:Optimized beta-casein (A2 variant) truncated version 5:Optimized beta-casein (A2 variant) truncated version 4:Optimized beta-casein (A2 variant) truncated version 3:Optimized beta-casein (A2 variant) truncated version 2:Optimized beta-lactoglobulin version 1 (OLG1) | OBC-T5:OBC-T4:OBC-T3:OBC-T2:OLG1 | 657 | 658 |

TABLE 19-continued

Illustrative Casein Multimers

| Description | Abbreviated Description | DNA Sequence (SEQ ID NO) | Amino Acid Sequence (SEQ ID NO) |
|---|---|---|---|
| Optimized beta-casein (A2 variant) truncated version 5:Optimized beta-casein (A2 variant) truncated version 4:Optimized beta-casein (A2 variant) truncated version 3:Optimized beta-casein (A2 variant) truncated version 2 | OBC-T5:OBC-T4:OBC-T3:OBC-T2 | 659 | 660 |
| Optimized beta-casein (A2 variant) truncated version 5:FM:Optimized beta-casein (A2 variant) truncated version 4:FM:Optimized beta-casein (A2 variant) truncated version 3:FM:Optimized beta-casein (A2 variant) truncated version 2:FM:Optimized beta-lactoglobulin version 1 (OLG1) | OBC-T5:FM:OBC-T4:FM:OBC-T3:FM:OBC-T2:FM:OLG1 | 661 | 662 |
| Optimized beta-casein (A2 variant) truncated version 5:FM:Optimized beta-casein (A2 variant) truncated version 4:FM:Optimized beta-casein (A2 variant) truncated version 3:FM:Optimized beta-casein (A2 variant) truncated version 2 | OBC-T5:FM:OBC-T4:FM:OBC-T3:FM:OBC-T2 | 663 | 664 |
| Optimized beta-casein (A2 variant) truncated version 4:FM:Optimized beta-casein (A2 variant) truncated version 3:FM:Optimized beta-casein (A2 variant) truncated version 2 | OBC-T4:FM:OBC-T3:FM:OBC-T2 | 792 | 793 |
| Optimized beta-casein (A2 variant) truncated version 4:FM:Optimized beta-casein (A2 variant) truncated version 3:FM:Optimized beta-casein (A2 variant) truncated version 2:FM:Optimized beta-lactoglobulin version 1 (OLG1) | OBC-T4:FM:OBC-T3:FM:OBC-T2:FM:OLG1 | 794 | 795 |
| Optimized beta-casein (A2 variant) truncated version 4:Optimized beta-casein (A2 variant) truncated version 3:Optimized beta-casein (A2 variant) truncated version 2 | OBC-T4:OBC-T3:OBC-T2 | 796 | 797 |
| Optimized beta-casein (A2 variant) truncated version 4:Optimized beta-casein (A2 variant) truncated version 3:Optimized beta-casein (A2 variant) truncated version 2:Optimized beta-lactoglobulin version 1 (OLG1) | OBC-T4:OBC-T3:OBC-T2:OLG1 | 798 | 799 |

The expression constructs were transformed into soybean, as described in Example 2. Quantification of casein multimer expression was performed using Western Blot Densitometry. Table 20 shows expression levels of the casein proteins when expressed in the indicated multimer constructs, relative to the caseins expressed alone (i.e., not as part of a fusion protein).

TABLE 20

Expression levels of casein multimers relative to caseins expressed alone

| Casein Multimer Fusion Protein | Fold increase in expression relative to κ-Casein alone | Fold increase in expression relative to β-Casein alone | Fold increase in expression relative to αS1-Casein alone |
|---|---|---|---|
| κ-Casein: κ-Casein | 3.4 | — | — |
| κ-Casein: β-Casein | 17 | 2.5 | — |
| κ-Casein: αS1-Casein | 5 | — | 32 |
| κ-Casein: GFP | 16 | — | — |
| αS1-Casein: GFP | — | — | 77 |
| κ-Casein: β-Lactoglobulin | 68 | — | — |
| β-Casein: β-Lactoglobulin | — | 27 | — |
| αS1-Casein-β: Lactoglobulin | — | — | 522 |
| κ-Casein: α-Lactalbumin | 10 | — | — |
| β-casein: α-Lactalbumin | — | 2.8 | — |
| αS1-Casein: α-Lactalbumin | — | — | 150 |

TABLE 20-continued

Expression levels of casein multimers relative to caseins expressed alone

| Casein Multimer Fusion Protein | Fold increase in expression relative to κ-Casein alone | Fold increase in expression relative to β-Casein alone | Fold increase in expression relative to αS1-Casein alone |
|---|---|---|---|
| β-Casein: β-Casein: β-Casein | — | 10.7 | — |
| β-Casein: β-Casein: β-Casein: β-Casein | — | 14.5 | — |

As shown in Table 20, expression of the casein proteins as multimers led to significant increases in expression relative to the caseins expressed alone. Specifically, expression of kappa-casein as a casein homo-multimer led to a 3.4-fold increase in expression relative to expression of casein alone. Expression of kappa-casein as a multimer with beta-casein led to 17-fold and 2.5-fold increases in expression, respectively, relative to either protein expressed alone. Expression of kappa-casein as a multimer with alpha-S1-casein led to 5-fold and 32-fold increases in expression, respectively, relative to either protein expressed alone. Expression of kappa-casein fused to GFP led to a 16-fold increase in expression. Expression of kappa-casein fused to beta-lactoglobulin led to a 68-fold increase in expression, and expression of beta-casein fused to beta-lactoglobulin led to an 11.5-fold increase in expression. Expression of beta-casein or alpha-S-casein was also increased by fusion to alpha-lactalbumin (2.8-fold and 150-fold respectively).

Expression of β-casein as a trimer or tetramer also led to significant increases in expression relative to β-casein expressed alone (18-fold and 18.5-fold, respectively).

Without being bound by any theory, it is believed that fusing a first casein protein to a second protein partially or fully shields each of the proteins from degradation by host cell proteases and allows for accumulation of the casein in the cell.

Example 4: Kappa-Casein is Sensitive to Soybean Endogenous Proteolysis Activity To determine whether endogenous host cell proteases are responsible for degradation of casein proteins expressed alone, soybean total protein extracts were spiked with 100 ng of commercial kappa-casein, in the presence or absence of Halt® Protease Inhibitor Cocktail (Thermo Fisher Scientific®). All samples were incubated at 37° C. for two hours. The samples were then subjected to analysis using a Western blot. The protein was detected using a primary antibody against kappa-casein.

Figure 14A:
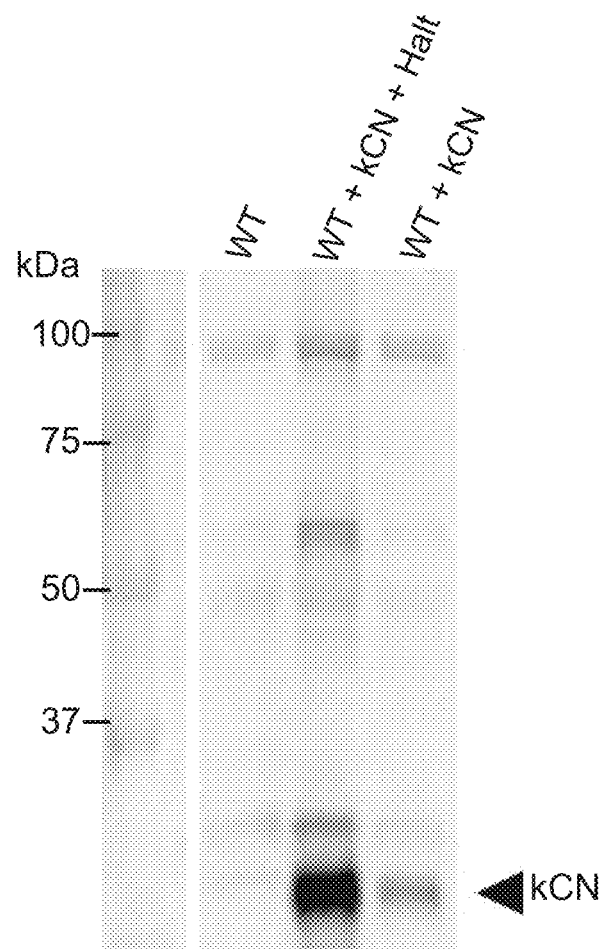
FIGS. 14A and 14B are images of a western blot used to detect kappa-casein protein (kCN) in samples comprising soybean total protein extracts (WT) and soybean total protein extracts spiked with 100 ng of KCN in the presence (WT+kCN+Halt) or absence (WT+kCN) of protease inhibitors. 5 μg of total protein was loaded in each lane.
Figure 14B:
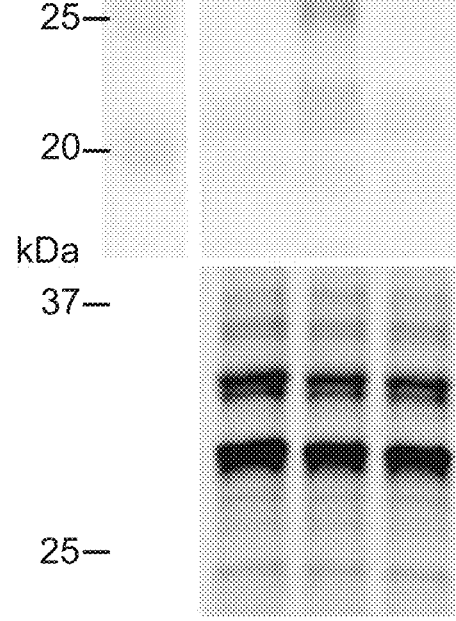

As shown in FIG. 14A and FIG. 14B, most of the kappa-casein added to the cellular extracts was degraded, and this degradation was prevented by the addition of protease inhibitors. This data confirms that kappa-casein is sensitive to soybean endogenous proteolysis activity. Inhibition of endogenous proteolysis activity may lead to increased casein accumulation in transformed cells.

Example 5: Food Compositions

The transgenic plants expressing the recombinant fusion proteins described herein can produce milk proteins for the purpose of food industrial, non-food industrial, pharmaceutical, and commercial uses described in this disclosure. Illustrative methods for making a food composition are provided in FIG. 13 and FIG. 17.

A fusion protein comprising an unstructured milk protein (e.g. a casein such as para-κ-casein, κ-casein, β-casein, αS1-casein, or αS2-casein), and a structured mammalian protein (e.g. β-lactoglobulin) is expressed in a transgenic plant (e.g. a soybean plant). The fusion protein comprises a chymosin cleavage site between the milk protein (e.g. a casein such as para-κ-casein, κ-casein, β-casein, αS1-casein, or αS2-casein) and the β-lactoglobulin.

The fusion protein is extracted from the plant. The fusion protein is then treated with chymosin, to separate the milk protein (e.g. a casein) from the β-lactoglobulin. The casein is isolated and/or purified and used to make a food composition (e.g., cheese).

Example 6: Determination of Physicochemical Parameters that Contribute to Casein Accumulation in Plants The purpose of the experiments described in this example was to determine the physicochemical parameters of proteins (i.e., fusion partners) that, when fused to a casein protein, are capable of enhancing accumulation thereof.

Various proteins having distinct physicochemical properties were fused to kappa-casein. The physicochemical properties thereof are listed in Table 21. The fusion proteins were then expressed in soybean plants as described above. Protein expression levels of the fusion protein and relative increases thereof relative to casein alone (not expressed as a fusion) were measured.

Results are summarized in Table 21. The term "KCN-fusion % TSP" refers to protein expression levels of the fusion protein, as a percent of total soluble protein. The term "% KCN only" refers to increases in kappa-casein expression relative to kappa casein expressed alone (not as a fusion). The % KCN only value was calculated by division the KCN-fusion % TSP value by 0.059 (i.e., the percent accumulation of kappa-casein by itself).

TABLE 21

Proteins fused to kappa casein and physicochemical parameters thereof

| Full name | Uniprot Accession No. | MW in kDa | Percentage hydrophobic AA/Total AA (%) | Number of disulfide bonds/ per 10 kDa | KCN-fusion % TSP | % KCN only |
|---|---|---|---|---|---|---|
| Kappa Casein | P02668 | 18.9 | 48.04 | 0.53 | 0.2 | 339 |
| Beta Casein | P02668 | 23.5 | 53.11 | 0 | 1 | 1695 |
| Alpha Casein | P18626 | 22.9 | 45.23 | 0 | 0.29 | 492 |
| Beta Lactoglobulin | P02754 | 18.2 | 48.15 | 1.1 | 4 | 6780 |
| Alpha Lactalbumin | P00711 | 14.1 | 36.59 | 2.2 | 0.34 | 1017 |
| Green Fluorescent Protein | P42212 | 26.8 | 40.76 | 0 | 0.94 | 1593 |
| Lysozyme | Q6B411 | 14.9 | 39.23 | 2.68 | 0.05 | 85 |
| 2S globulin | P19594 | 16.1 | 24.82 | 2.48 | 0.1 | 169 |
| Oleosin A | P29530 | 23.5 | 51.11 | 0 | 0.1 | 169 |
| Oleosin B | P29531 | 23.4 | 50.67 | 0 | 0.1 | 169 |
| Kunitz-Trypsin inhibitor | Q39898 | 21 | 41.67 | 0.95 | 0.001 | 16.9 |
| Bowman-Birk inhibitor | I1MQD2 | 9 | 25 | 3.33 | 0.05 | 85 |
| Hydrophobin II | P79073 | 7.19 | 49.3 | 5.56 | 0.025 | 42 |

Figure 16A:
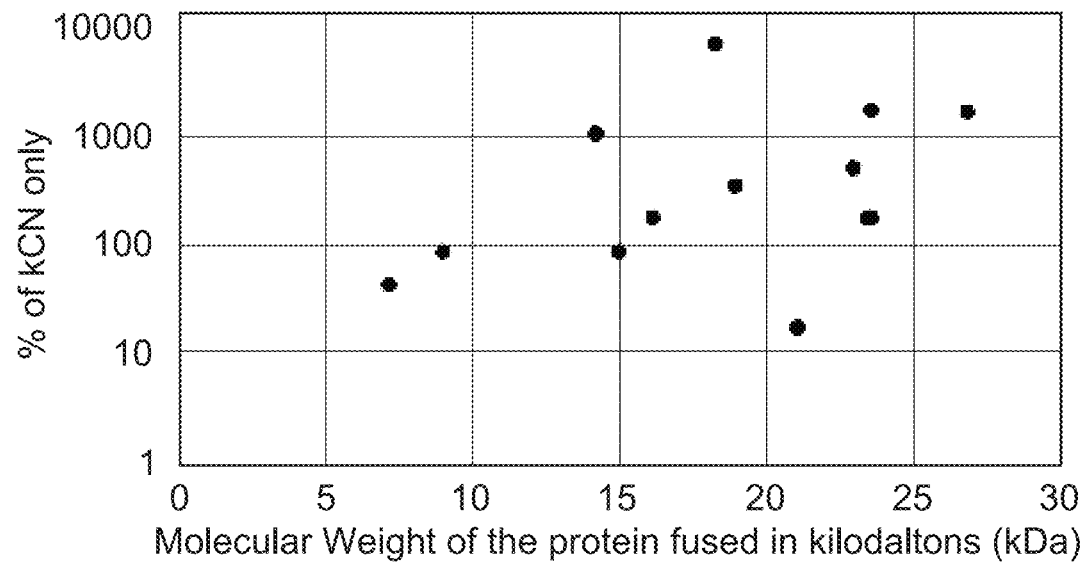
FIG. 16A shows molecular weight of various proteins, and levels of kappa-casein expression observed in transformed soybeans when those proteins are fused to the kappa-casein.
Figure 16B:
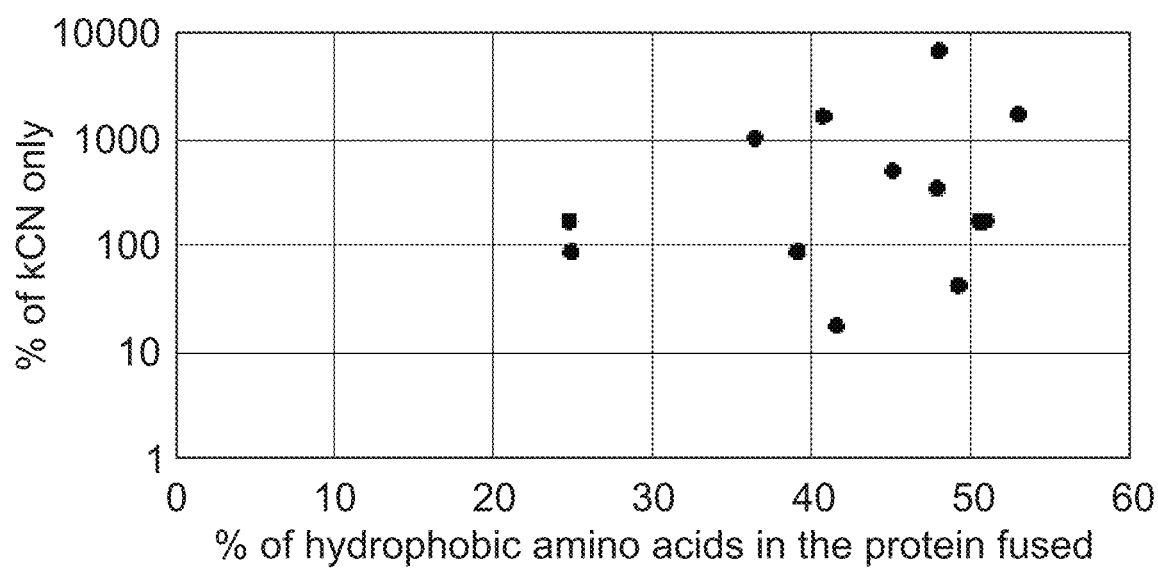
FIG. 16B shows hydrophobicity of various proteins, and levels of kappa-casein expression observed in transformed soybeans when those proteins are fused to the kappa-casein.
Figure 16C:
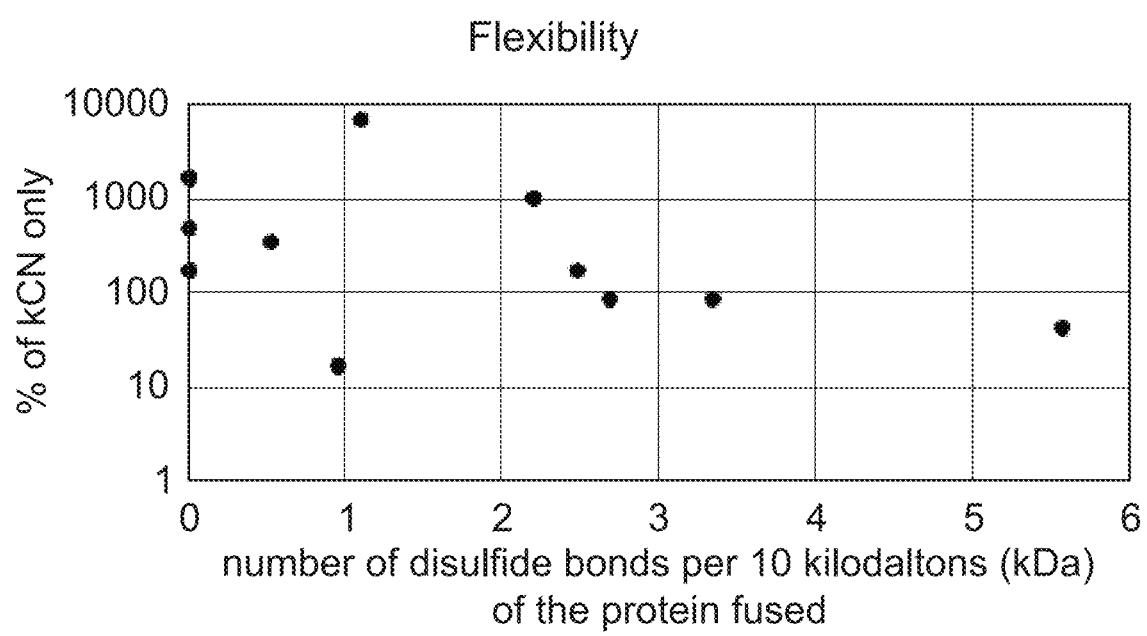
FIG. 16C shows flexibility of various proteins (i.e., number of disulfide bonds), and levels of kappa-casein expression observed in transformed soybeans when those proteins are fused to the kappa-casein. Expression levels shown in FIG. 16A-16C are relative to kappa casein expressed alone (i.e., not as a fusion, KCN only). The values for % KCN only are presented as a $\log_{10}$ scale. Values above 100% indicate that kappa-casein was stabilized by the fusion.

An analysis of the data shown in Table 21 is provided in FIG. 16A, FIG. 16B, and FIG. 16C. This analysis suggests that there are several physicochemical properties of proteins that when fused to kappa-casein, may contribute to accumulation of the kappa-casein. The first is molecular weight. In general, a protein (fusion partner) with molecular weight of 15 kDa or higher tended to increase accumulation (FIG. 16A). The second is hydrophobicity. A protein (fusion partner) having greater than about 30% hydrophobic amino acids also tended to increase accumulation (FIG. 16B). The third is flexibility. A protein (fusion partner) with less than about 2.5 disulfide bonds per 10 kDa molecular weight also tended to increase accumulation (FIG. 16B). The disulfide bonds were predicted using a computer program. Notably, the number of cysteines in the protein, on its own, was not predictive of the protein's ability to contribute to accumulation of the kappa-casein.

Notably, as evidenced by the data in Table 21 and FIG. 16A-16C, the fusion partner did not need to have all three of these characteristics in order to increase accumulation of kappa-casein. For example, increases in accumulation were observed in some cases where the fusion partner had only one, only two or all three of these characteristics.

Example 7: Fusion Proteins Comprising Milk Proteins and Prolamin Proteins

To determine the impact of including a prolamin in a fusion protein on accumulation thereof in a seed, expression vectors for producing fusion proteins comprising a milk protein and a prolamin protein were created using the methods described in Example 1. Specifically, expression vectors were created to express fusion proteins comprising: (i) canein (gCan27) fused to β-casein, (ii) zein (γ-zein) fused to β-casein, and (iii) canein (gCan27) fused to κ-casein.

Illustrative fusion proteins used during this study are shown below in Table 22. Colons (:) are used to indicate junctions between various elements of the fusion protein. FM indicates the use of a linker comprising a chymosin cleavage site.

TABLE 22

Fusion Proteins Comprising a Prolamin

| Description | Abbreviated Description | DNA Sequence (SEQ ID NO) | Amino Acid Sequence (SEQ ID NO) |
|---|---|---|---|
| 27 kD gamma canein (gcan27):FM:Optimized beta casein truncated version 2 (OBC-T2):FM | gCan27:FM:OBC-T2 | 802 | 803 |
| Gamma zein (yZein):Optimized beta-casein truncated version 2 (OBC-T2) | yZein:OBC-T2 | 806 | 807 |

Figure 21:
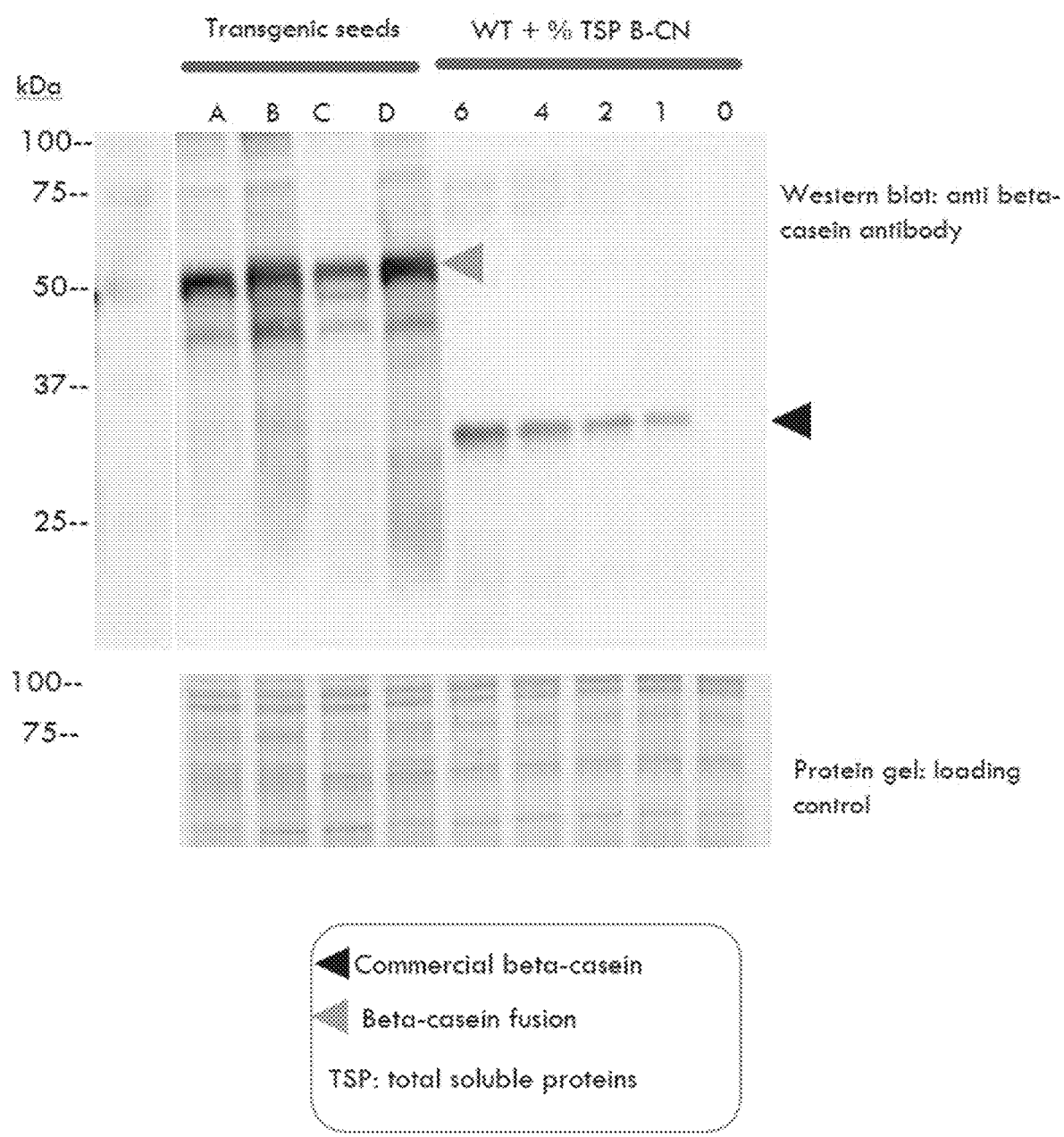
FIG. 21 shows protein detection by western blotting. The top panel shows detection of a fusion protein comprising β-casein and casein using a primary antibody raised against β-casein (B-CN). Commercial protein was detected at an apparent MW of ~30 kDa (arrowhead; theoretical: 23.5 kDa). The fusion protein was detected at an apparent MW of ~50 kDa (arrow; theoretical: 44.3 kDa). The first lane shows molecular weight markers. The second lane shows protein from T1 seed from recombinant plant line KV7. Lane 3-7 shows soybean wildtype seed extracts spiked with 0%, 1%, 2%, 4%, or 6% TSP commercially available β-casein. The bottom panel shows a protein gel as a control for equal lane loading, visualized using stain-free detection by Bio Rad® (image is taken at the end of the SDS run). 2.5 μg of total protein extracts were loaded per lane.
Figure 22:
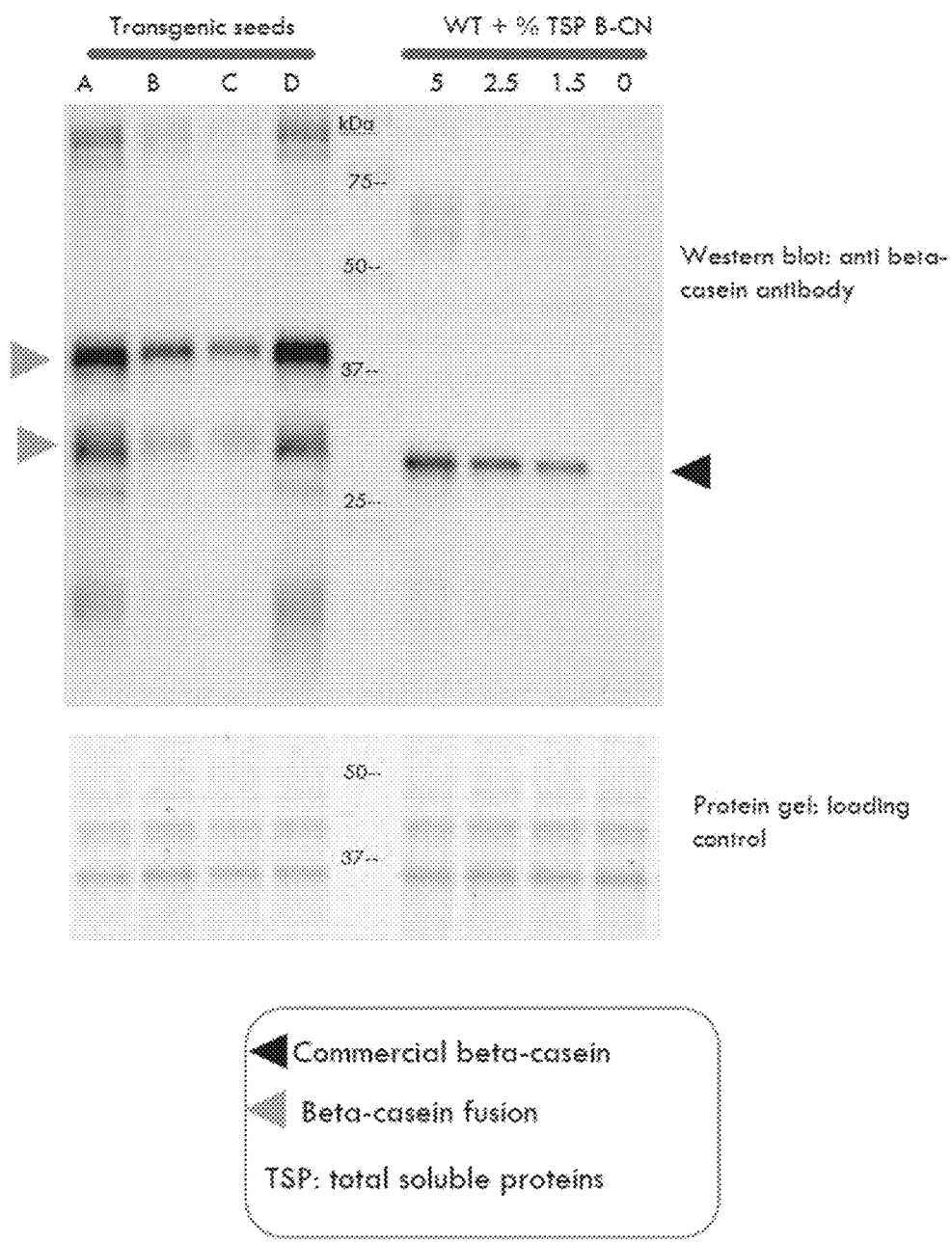
FIG. 22 shows protein detection by western blotting. The top panel shows detection of a fusion protein comprising-casein and a partial zein (amino acids 17-112) using a primary antibody raised against β-casein (B-CN). Commercial protein was detected at an apparent MW of ~30 kDa (arrowhead; theoretical: 23.5 kDa). The fusion protein was detected at an apparent MW of ~30 kDa (arrow; theoretical: 23.5 kDa). The first four lanes show protein from T1 seed from a recombinant plant. The fifth lane shows molecular weight markers. Lanes 6-9 shows soybean wildtype seed extracts spiked with 0%, 1.5%, 2.5%, or 5% TSP commercially available β-casein. The bottom panel shows a protein gel as a control for equal lane loading, visualized using stain-free detection by Bio Rad® (image is taken at the end of the SDS run). 2.5 μg of total protein extracts were loaded per lane.

The expression constructs were transformed into soybean, as described in Example 2. Western blots showing detection of beta-casein in transgenic seed extracts are provided in FIG. 21 and FIG. 22. Quantification of casein multimer expression was performed using Western Blot Densitometry. Table 23 shows expression levels of the beta-casein protein when expressed in the indicated fusion constructs, relative to the beta-casein expressed alone (i.e., not as part of a fusion protein).

TABLE 23

Expression levels of beta-casein when fused to a prolamin relative to caseins expressed alone

| Casein Multimer Fusion Protein | Fold increase in expression relative to κ-Casein alone | Fold increase in expression relative to B-Casein alone |
|---|---|---|
| gCan27: κ-Casein | 16 | — |
| gCan27: β-Casein | — | 40 |
| Zein: β-Casein | — | 55 |

As shown in Table 23, fusion of caseins to either canein or zein led to significant increases in expression relative to the caseins expressed alone. Specifically, expression of kappa-casein fused to gCan27 led to a 16-fold increase in expression relative to expression of kappa-casein alone. Expression of beta-casein fused to gCan27 led to a 40-fold increase in expression, relative to beta-casein expressed alone. Fusion of beta-casein to zein led to a 55-fold increase in expression, relative to beta-casein expressed alone. In each of these experiments, the casein protein accumulated in the seeds at a level well above 1% TSP.

Figure 20:
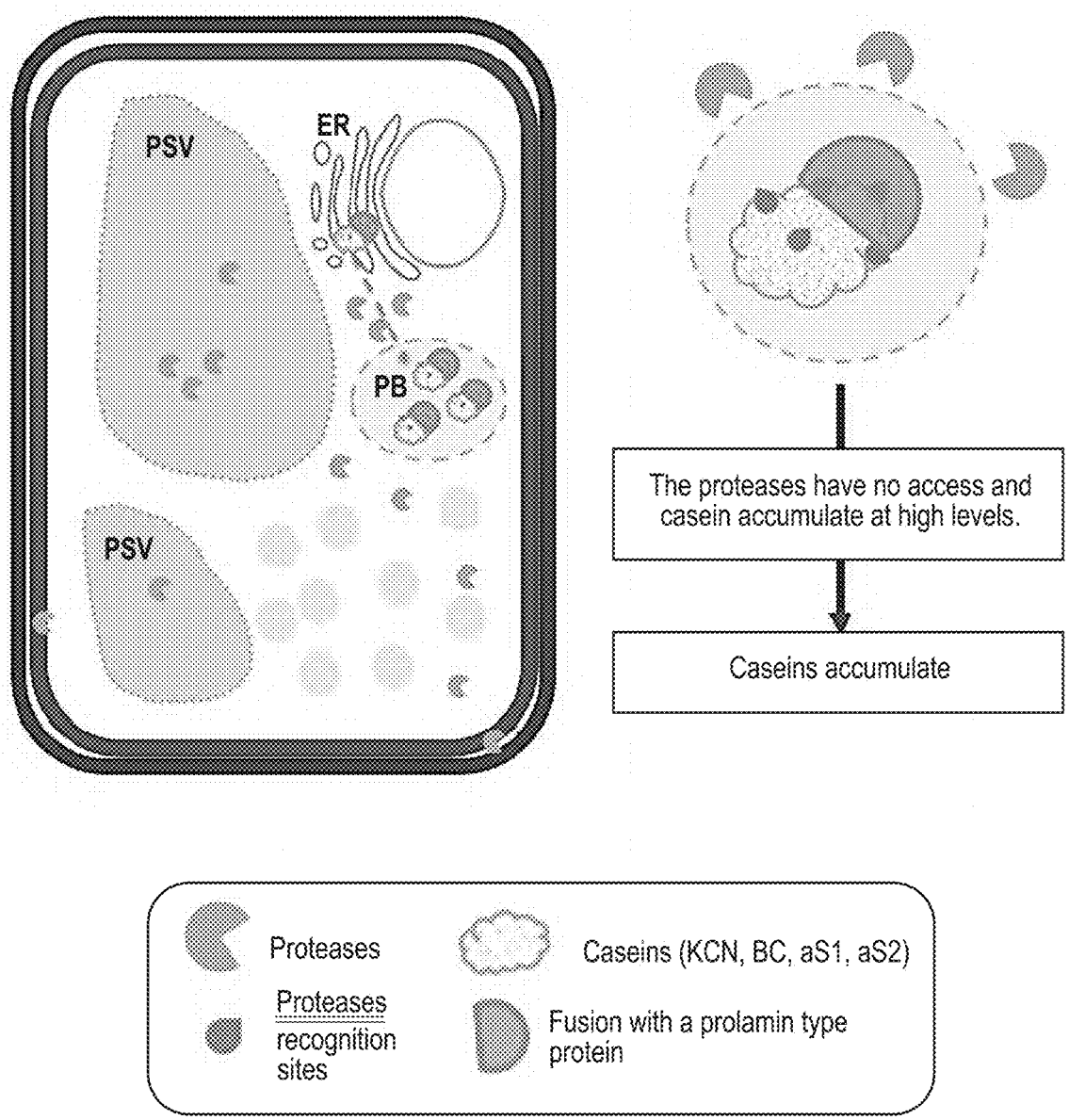
FIG. 20 is a schematic demonstrating an illustrative mechanism that may be used to protect one or more proteins (e.g., casein proteins) from degradation in a host cell, leading to accumulation thereof. The protein (e.g., a casein protein) is fused to one or more proteins that is capable of forming a protein body (e.g., a prolamin). After the fusion protein is synthesized and retained in the endoplasmic reticulum (ER), a protein body is formed (PB). The fusion protein (including, for example, the casein protein) is contained within the PB. Proteases that would degrade the caseins, do not have access to the fusion protein inside the PB. In this figure, the term "PSV" refers to protein storage vacuole.

Without being bound by any theory, it is believed that fusing a casein protein to a prolamin (e.g., a canein or a zein) leads to the formation of a protein body in the seed. The casein is then sequestered in the protein body, which partially or fully shields the casein from degradation by host cell proteases, and allows for accumulation of the casein in the cell. An illustrative mechanism for protein body formation is found in FIG. 20.

Example 8: Phosphorylation Prevents Degradation of Caseins in a Plant Cell

It was hypothesized that various post-translational modifications, such as phosphorylation, may have a "shielding" effect which prevents degradation of milk proteins, especially casein proteins, in a plant cell. Specifically, it was hypothesized that by adding one or more phosphates to a casein protein expressed in a plant cell, it may be possible to block and/or reduce the access of plant proteases to various cleavage sites on the protein. By reducing the ability of the plant proteases to degrade the milk protein, higher levels of protein accumulation may be possible.

To test this hypothesis, the enzyme Fam20C was co-expressed with one or more caseins in a plant cell. Fam20C is a serine kinase and is responsible for the phosphorylation of caseins (Bauman, D. E., et al. "Major advances associated with the biosynthesis of milk." Journal of dairy science 89, no. 4 (2006): 1235-1243.)

Figure 23:
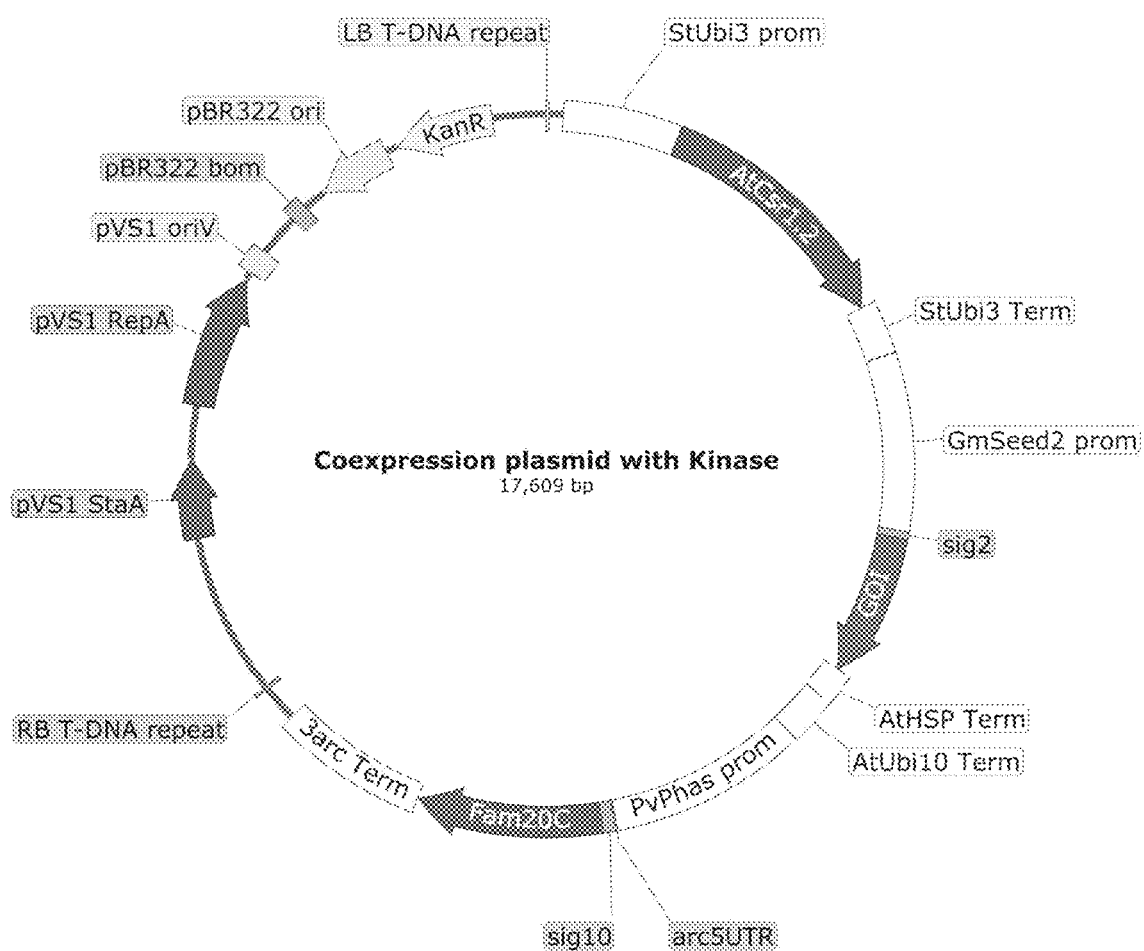
FIG. 23 shows a binary *Agrobacterium* vector used to co-express a Gene of Interest (GOI, e.g., a casein protein) and a kinase (e.g., a Fam20C kinase) in a plant cell.
Figures 24A, 24B, 24C, 24D, 24E:
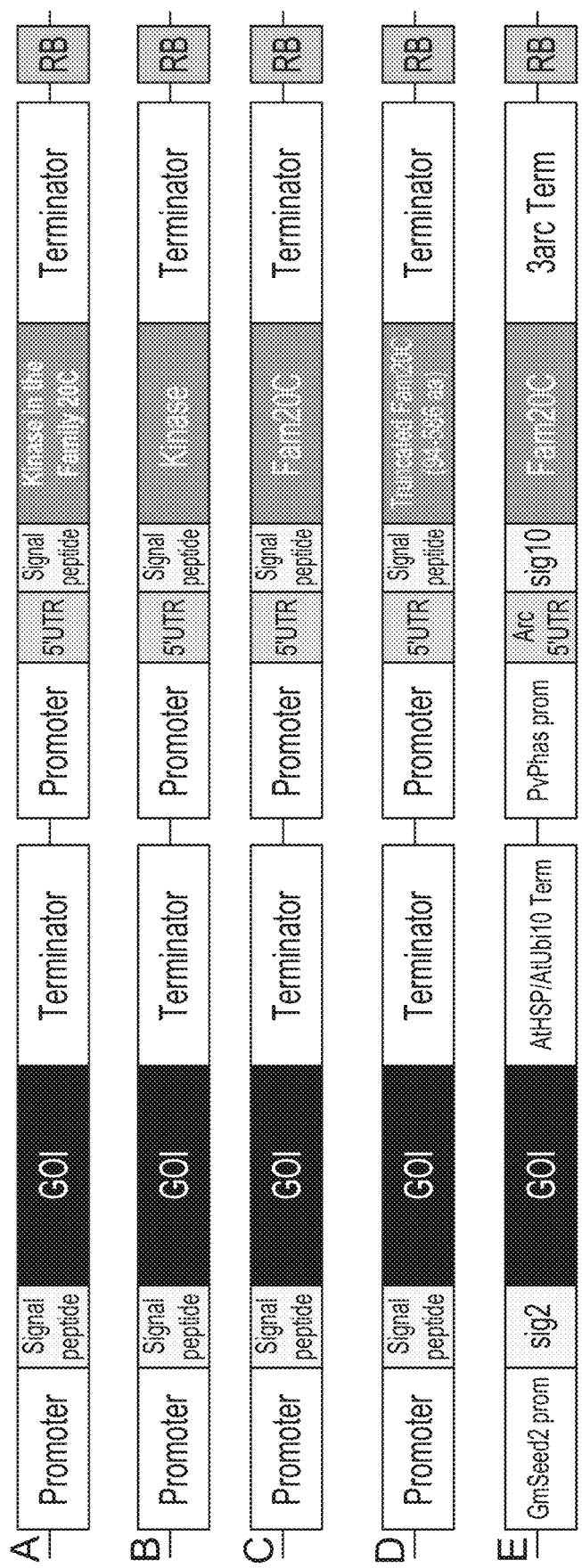
FIG. 24A-24E shows expression constructs used to co-express a Gene of Interest (GOI, e.g., a casein protein) and a kinase (e.g., a Fam20C kinase) in a plant cell.
Figures 25A, 25B, 25C, 25D, 25E, 25F:
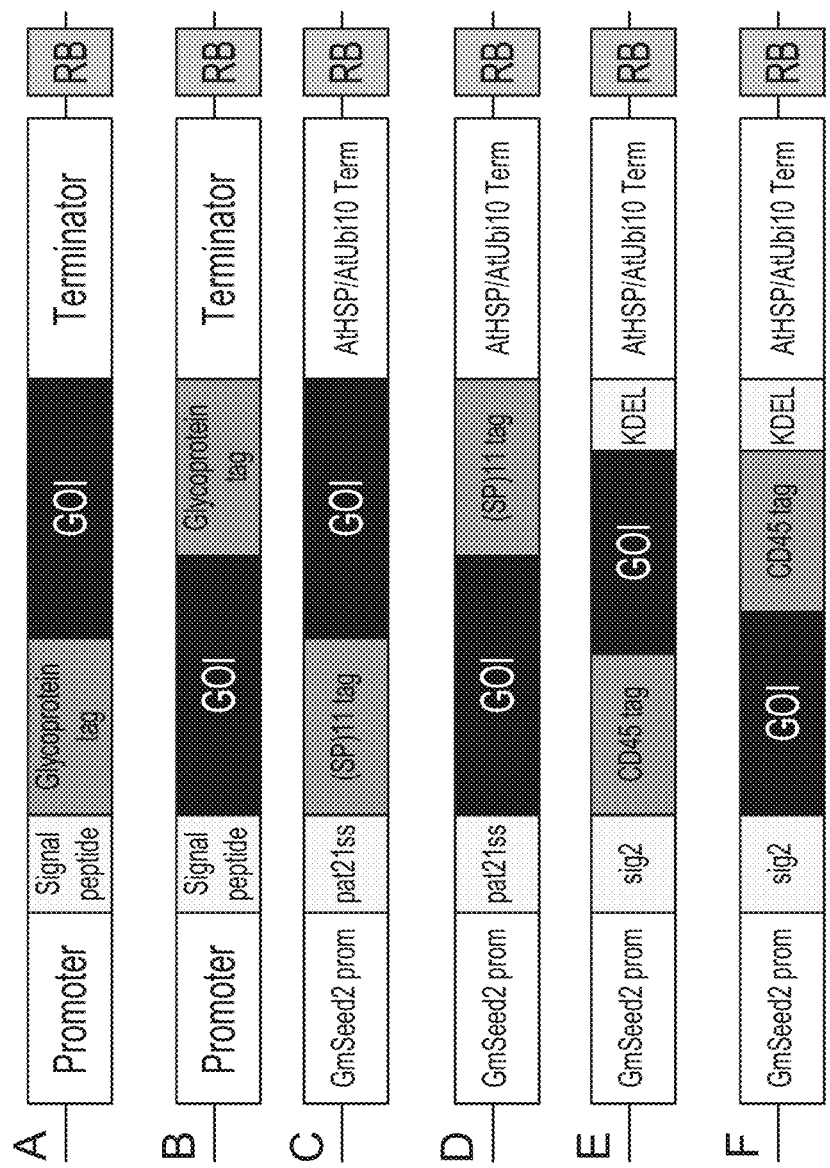
FIG. 25A-25F show expression constructs used to express a Gene of Interest (GOI, e.g., a casein protein) in a plant cell, wherein the GOI is fused to a glycoprotein tag, such as a (SP) 11 tag.
Figures 26A, 26B, 26C, 26D, 26E, 26F, 26G:
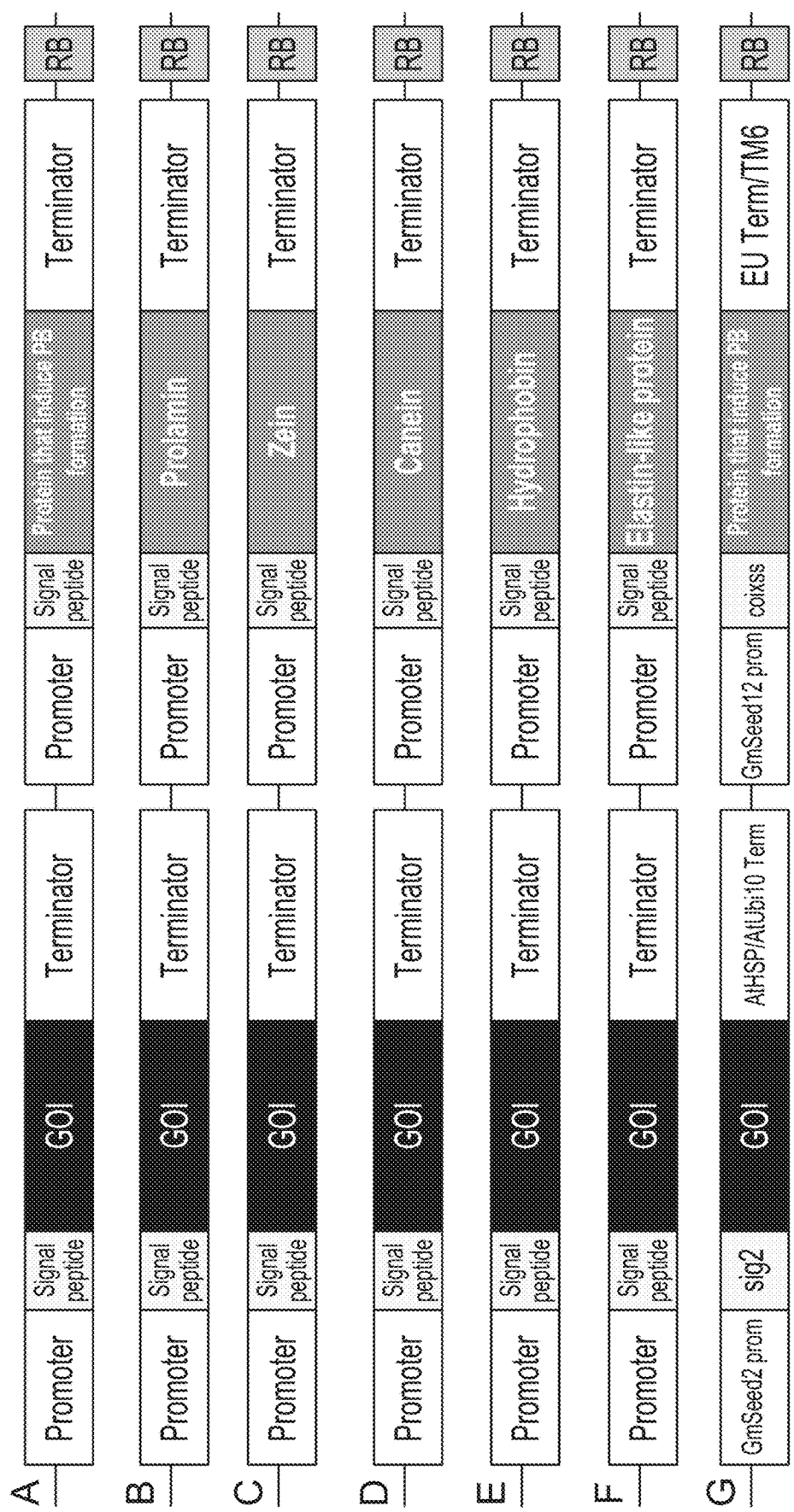
FIG. 26A-26G shows expression constructs used to co-express a Gene of Interest (GOI, e.g., a casein protein) and a protein capable of inducing a protein body (e.g., a prolamin, zein, canein, hydrophobin, or elastin-like protein) in a plant cell.

The expression construct used in this study is shown in FIG. 24E. The construct comprised (i) a first expression cassette comprising the GmSeed2 promoter (SEQ ID NO: 813), a sig2 signal peptide (SEQ ID NO: 814), a sequence encoding a fusion protein (GOI, see table below), and an AtHSP/AtUbi10 Terminator (SEQ ID NO: 815, 816), and (ii) a second expression cassette comprising the pvPhas promoter (SEQ ID NO: 817), an Arc5'UTR (SEQ ID NO: 818), a sig10 signal peptide (SEQ ID NO: 819), a sequence encoding the Fam20c kinase (SEQ ID NO: 821), and a 3 arc terminator (SEQ ID NO: 822). This expression construct was cloned into a binary *Agrobacterium* vector, as illustrated in FIG. 23. The vector was then transformed into soybean plants, and protein expression was measured in the seeds using a Western Blot. An anti-beta-casein antibody was used to detect fusion protein expression. Results are shown in Table 24.

TABLE 24

Expression levels of caseins when co-expressed with a kinase compared to caseins expressed alone

| | | Increased fold vs KCN | Increased fold vs BCN | Increased fold vs aS1 |
|---|---|---|---|---|
| No Kinase | κ-Casein-B-Casein | 17 | 2.5 | na |
| Kinase | κ-Casein-B-Casein/Fam20C | 254 | 38 | na |
| | κ-Casein-B-Casein-aS1-Casein/Fam20C | 185 | 25 | 1000 |

Table 24 compares expression levels of the casein when expressed alone vs. as a fusion protein, with or without Fam20c co-expression. When expressed without the kinase, the kappa-casein: beta-casein fusion protein produced a 17-fold increase in kappa-casein expression relative to kappa-casein expressed alone, and a 2.5-fold increase in beta-casein expression relative to beta-casein expressed alone. When this fusion protein was co-expressed with Fam20C, the expression of kappa-casein was 254-fold greater than kappa-casein expressed alone, and 38-fold greater than beta-casein expressed alone. Notably, expression of a kappa-casein: beta-casein: alpha-S1-casein fusion with a kinase resulted in a 185-fold increase in kappa-casein relative to kappa-casein alone, 25-fold increase in expression of beta-casein relative to beta-casein alone, and 1000-fold increase in alpha-S1-casein relative to alpha-S1-casenin alone.

Taken together, these data indicate that co-expression of a kinase with a fusion protein comprising one or more casein proteins in a plant cell leads to an increase in accumulation of the casein protein in the cell. Without being bound by any theory, it is believed that the addition of one or more phosphates to the casein protein protects it from degradation by one or more plant proteases.

Example 9: Fusion to a Highly Glycosylated Peptide to Increase Accumulation of Caseins in a Plant Cell Certain genetic elements increase the secretion and stability of proteins in plant cells (Jia Li et al., Secretion of Active Recombinant Phytase from Soybean Cell-Suspension Cultures, 1997; Jianfeng Xu et al., High-Yields and Extended Serum Half-Life of Human Interferon a2b Expressed in Tobacco Cells as Arabinogalactan-Protein Fusions, 2007). Many aspects of plant growth involve hydroxyproline (Hyp)-rich glycoproteins (GRGPs). Accordingly, it was hypothesized that fusion of a casein to a glycoprotein tag could be used to increase accumulation of the casein in a plant cell.

In this experiment, a glycoprotein comprising 11 tandem SP repeats was identified from a native soybean protein (Glyma.02 g204500), annotated as early nodulin-like protein 10. This tag, dubbed the (SP) 11 tag, was codon optimized in IDT and fused to the N- or C-terminus of kappa-casein (See FIG. 25A-25C). The (SP) 11-kappa-casein was then cloned into a binary *Agrobacterium* vector, and transformed into soy.

Notably, the expression of (SP) 11-kappa-casein in the seeds was increased 13-fold over expression of kappa-casein alone (i.e., not fused with a glycoprotein tag). This data indicates that fusion with a glycoprotein tag may be used to increase accumulation of caseins in a plant cell.

In a similar experiment, the M domain of CD45 (receptor-type tyrosine-protein phosphatase C) will be fused to kappa-casein. The M domain is known to function as an ER-retention signal. Briefly, the M-domain from CD45 (Uniprot Accession No. P08575, amino acids Ala231 to Asp 290) will be codon optimized using the *Glycine max* codon usage bias, and fused to the N- or C-terminus of kappa-casein. In some constructs, a KDEL sequence (SEQ ID NO: 23) may be added to the C-terminus of the M-domain or the GOI (see FIG. 25E-25F). It is expected that fusion of the M domain to the C-terminus will cause ER retention of the fusion protein, leading to increased accumulation thereof in the cell.

Example 10: Cheese Composition Made with Beta-Casein Protein

To test whether a cheese composition having acceptable organoleptic and physical properties could be made using only beta-casein protein (i.e., without any other caseins), isolated beta casein from bovine milk was the sole casein protein used in the recipe below. The beta casein was provided in the form of a powder, comprising 84% protein with >98% purity of beta casein.

| 100% Beta casein cheese composition | |
|---|---|
| Water | 42.07% |
| Butter | 31.25% |
| Beta casein powder (84% protein) | 13.10% |
| Modified potato starch | 11.00% |
| Salt | 1.70% |
| Sodium citrate | 0.80% |
| Calcium chloride | 0.08% |

To make the cheese composition, all ingredients were added to a rapid visco analyzer (RVA) tube. The mixture was heated to 40° C. and mixed at 200 RPM for 2 minutes. The speed was increased to 500 RPM and mixed for an additional 3 minutes. The mixture was then allowed to rest for a minimum of 5 minutes before heating to 95° C. and mixing at 960 RPM for 1 minute. Then, the speed and temperature were reduced to 500 RPM and 90° C. for 1 minute. The temperature was reduced further to 85° C. and the composition was mixed for one more minute at 500 RPM. The hot cheese composition was poured into cylindrical molds (¾" diameter pipe, 1" in length with cap on bottom), covered with plastic wrap, and refrigerated for a minimum of 5 days. The target pH was 5.5 to 5.7, and was adjusted with lactic acid, citric acid, or sodium citrate. Meltability was analyzed as described below (see also the cheese labeled "D" in FIG. 28)

A cheese composition was also made with 50% beta casein protein and reduced amounts of other casein proteins using the following recipe:

| 50% Beta casein cheese composition | |
|---|---|
| Water | 43.7% |
| Butter | 31.3% |
| Acid casein (95% protein dry basis) | 10.4% |
| Modified potato starch | 6.00% |
| Beta casein powder (84% protein) | 2.80% |
| Trisodium citrate | 1.70% |
| Salt | 1.70% |
| Sodium aluminum phosphate, basic | 1.70% |
| Citric acid | 0.70% |

To make the cheese composition, 60% of the water and all other ingredients were added to a RVA tube and heated to 50° C. and mixed at 500 RPM for 5 minutes. The remaining water was added to the RVA tube and the mixture was heated to 95° C. and mixed at 960 RPM for 1 minute, then reduced to 500 RPM and 90° C. for 1 minute. The temperature was reduced to 85° C., and the composition was mixed at 500 RPM for one more minute. The hot cheese composition was poured into cylindrical molds (¾" diameter pipe, 1" in length with cap on bottom), covered with plastic wrap, and refrigerated for 5 days. The target pH was 5.5 to 5.7, and was adjusted with lactic acid, citric acid, or sodium citrate. For cheese analysis, see samples 3 and 4 of Table 25.

Example 11: Cheese Composition Made with Kappa Casein Protein

To test whether a cheese composition having acceptable organoleptic and physical properties could be made using only kappa-casein protein (i.e., without any other casein proteins), isolated kappa casein from bovine was the sole casein protein used in the recipe below. The kappa-casein was provided in the form of a powder, which comprised 85% protein and greater than 70% purity of kappa casein.

| 100% Kappa casein cheese composition | |
| --- | --- |
| Water | 45.0% |
| Butter | 31.3% |
| Kappa casein powder | 13.8% |
| Modified potato starch | 6.0% |
| Salt | 1.7% |
| Sodium citrate | 0.6% |
| Citric acid | 0.6% |
| Sodium aluminum phosphate (basic) | 0.9% |
| Calcium chloride | 0.1% |

All ingredients were added to a rapid visco analyzer (RVA) tube. The mixture was heated to 40° C. and mixed at 200 RPM for 2 minutes. The speed was increased to 500 RPM, and the composition was mixed for an additional 3 minutes. The mixture was then allowed to rest for a minimum of 5 minutes before heating to 95° C., and mixing at 960 RPM for 1 minute. Then, the speed and temperature were reduced to 500 RPM and 90° C. for 1 minute. The temperature was reduced further to 85° C., and the composition was mixed for one more minute at 500 RPM. The hot cheese composition was poured into cylindrical molds (¾" diameter pipe, 1" in length with cap on bottom), covered with plastic wrap, and refrigerated for 5 days. The target pH was 5.5 to 5.7 and was adjusted with lactic acid, citric acid, or sodium citrate. Meltability was analyzed as described below (see also the cheese labeled "B" in FIG. 28).

Example 12: Cheese Composition Made with Alpha-Casein Protein

To test whether a cheese composition having acceptable organoleptic and physical properties could be made using only alpha-casein proteins, isolated alpha casein (a mixture of alpha-S1 and alpha-S2 caseins) from bovine was the sole casein protein used in the recipe below. The alpha-casein was provided in the form of a powder, which comprised approximately 87% protein and greater than 90% purity of alpha casein.

| 100% alpha casein cheese composition | |
| --- | --- |
| Water | 41.8% |
| Butter | 31.3% |
| Alpha casein powder | 12.6% |
| Modified potato starch | 11.0% |
| Salt | 1.7% |
| Sodium citrate | 0.8% |
| Citric acid | 0.2% |
| Sodium aluminum phosphate (basic) | 0.5% |
| Calcium chloride | 0.08% |

All ingredients were added to a rapid visco analyzer (RVA) tube. The mixture was heated to 40° C. and mixed at 200 RPM for 2 minutes. The speed was increased to 500 RPM, and the composition was mixed for an additional 3 minutes. The mixture was then allowed to rest for a minimum of 5 minutes before heating to 95° C., and mixing at 960 RPM for 1 minute. Then, the speed and temperature were reduced to 500 RPM and 90° C. for 1 minute. The temperature was reduced further to 85° C., and the composition was mixed for one more minute at 500 RPM. The hot cheese composition was poured into cylindrical molds (¾" diameter pipe, 1" in length with cap on bottom), covered with plastic wrap, and refrigerated for 5 days. The target pH was 5.5 to 5.7 and was adjusted with lactic acid, citric acid, or sodium citrate. Meltability was analyzed as described below.

Example 13: Cheese Composition Made with Alpha- and Beta-Casein Proteins

To test whether a cheese composition having acceptable organoleptic and physical properties could be made using alpha- and beta-casein, alpha-casein and beta-casein powder obtained from bovine were used to create cheese compositions comprising 50% alpha-casein and 50% beta-casein, 25% alpha-casein and 75% beta-casein, and 75% alpha-casein and 25% beta-casein, as shown in the recipes below.

| | 50% alpha-casein and 50% beta-casein | 25% alpha-casein and 75% beta-casein | 75% alpha-casein and 25% beta-casein |
| --- | --- | --- | --- |
| Water | 42.0% | 41.8% | 42.0% |
| Butter | 31.3% | 31.3% | 31.3% |
| Modified potato starch | 10.5% | 10.5% | 10.5% |
| Alpha casein powder | 6.3% | 3.2% | 9.5% |
| Beta casein powder (84% protein) | 6.5% | 9.8% | 3.3% |
| Trisodium citrate | 0.9% | 0.9% | 0.9% |
| Salt | 1.7% | 1.7% | 1.7% |
| Sodium aluminum phosphate, basic | 0.5% | 0.5% | 0.5% |
| Citric acid | 0.2% | 0.2% | 0.2% |
| Calcium chloride | 0.08% | 0.08% | 0.08% |

To make the cheese composition, 60% of the water and all other ingredients were added to a RVA tube and heated to 50° C. The composition was then mixed at 500 RPM for 5 minutes. The remaining water was added, and the mixture was heated to 95° C. and mixed at 960 RPM for 1 minute. Then, the composition was mixed at 500 RPM at 90° C. for 1 minute. The temperature was reduced to 85° C., and the composition was mixed at 500 RPM for one more minute. The hot cheese composition was poured into cylindrical molds (¾" diameter pipe, 1" in length with cap on bottom), covered with plastic wrap, and refrigerated for 5 days. The target pH was 5.5 to 5.7, and was adjusted with lactic acid, citric acid, or sodium citrate. Meltability was analyzed as described below.

Example 14: Cheese Composition Made with Beta- and Kappa-Casein Proteins

To test whether a cheese composition having acceptable organoleptic and physical properties could be made using beta- and kappa-casein, bovine kappa-casein and beta-casein powder were used to create two cheese compositions, one comprising 75% kappa casein and 25% beta casein, and another comprising 50% kappa casein and 50% beta casein, as shown in the recipes below.

| | 75% kappa casein and 25% beta casein | 50% kappa casein and 50% beta casein |
| --- | --- | --- |
| Water | 41.9% | 41.7% |
| Butter | 31.3% | 31.3% |
| Modified potato starch | 10.5% | 10.5% |
| Kappa casein powder | 9.7% | 6.5% |
| Beta casein powder (84% protein) | 3.3% | 6.6% |
| Trisodium citrate | 0.8% | 0.8% |
| Salt | 1.7% | 1.7% |
| Sodium aluminum phosphate, basic | 0.5% | 0.5% |
| Citric acid | 0.3% | 0.3% |
| Calcium chloride | 0.04% | 0.08 |

To make the cheese composition, 60% of the water and all other ingredients were added to a RVA tube and heated to 50° C. The composition was then mixed at 500 RPM for 5 minutes. The remaining water was added, and the mixture was heated to 95° C. and mixed at 960 RPM for 1 minute. Then, the composition was mixed at 500 RPM at 90° C. for 1 minute. The temperature was reduced to 85° C., and the composition was mixed at 500 RPM for one more minute. The hot cheese composition was poured into cylindrical molds (¾" diameter pipe, 1" in length with cap on bottom), covered with plastic wrap, and refrigerated for 5 days. The target pH was 5.5 to 5.7, and was adjusted with lactic acid, citric acid, or sodium citrate. Meltability was analyzed as described below (see also the cheeses labeled "A" and "C" in FIG. 28).

Figure 28:
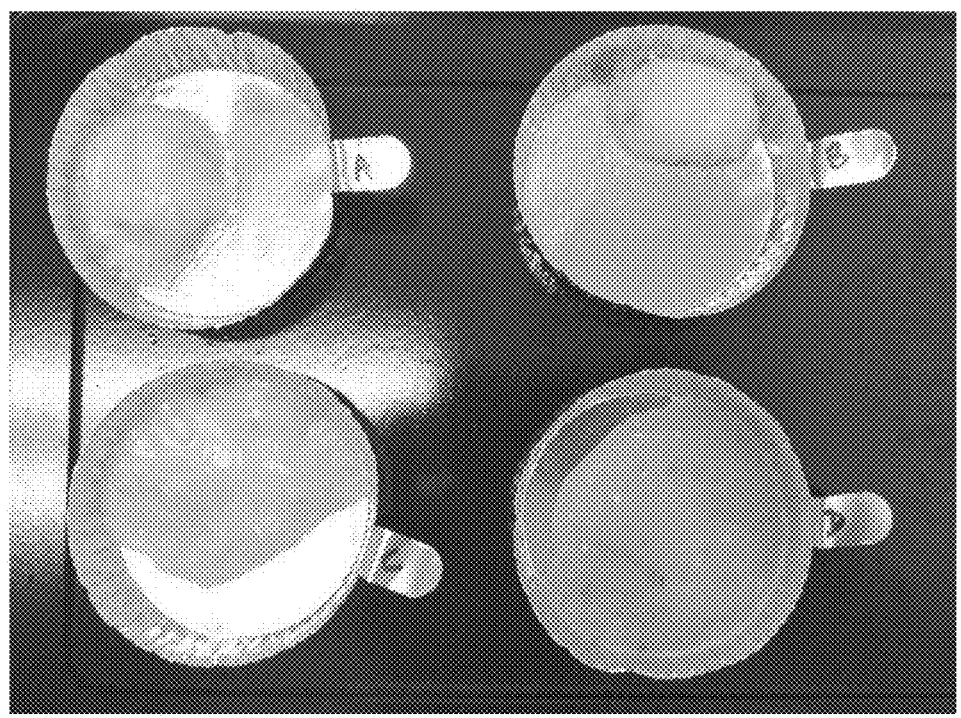
FIG. 28 is a photograph which depicts the melting properties of various cheese compositions made with isolated kappa and beta-caseins. Top left: composition A (75% kappa-casein, 25% beta-casein); top right: composition B (100% kappa-casein); bottom left: composition C (50% kappa-casein, 50% beta-casein), bottom right: composition A (100% beta-casein).

Example 15: Functional Properties of Cheese Compositions Made with Beta- and Kappa-Caseins To test the organoleptic and physical properties, the cheese compositions were analyzed for various properties, including melt, stretch, firmness, and transparency. For the melting test, the cheeses were placed in a 450° F. oven for 5 minutes. A score of 0=no change from the initial appearance; 1=up to 25% coverage of pan; 2=25% to 50% pan coverage; 3=50% to 75% pan coverage; and 4=greater than 75% pan coverage. Shown in FIG. 28 are the results of the test with cheese compositions comprising (A) 75% kappa casein, 25% beta casein; (B) 100% kappa casein; (C) 50% kappa casein, 50% beta casein; and (D) 100% beta casein. Composition A had a melt score of 2; composition B was unchanged and therefore had a melt score of 0; composition C had a melt score of 3; and composition D exhibited the greatest meltability with a score of 4.

Additional cheese composition samples comprising different ratios of caseins and total protein were analyzed for stretchability and meltability after aging for a minimum of 5 days (Tables 25-27). Cheese composition stretch was measured by an assay testing the ability to stretch (cm in length) without breaking, after heating a 100 gram mass of the emulsion to a temperature of about 225° C. for 4 minutes and cooling to about 90° C. and pulling with a fork placed beneath the mass. Firmness and transparency were also observed by sensory evaluation (data not shown).

Shown in Table 5, below, are data collected from cheese compositions comprising between 11-11.5% protein, and in Table 26, data collected from cheese comprising between 13-13.5% protein. Compositions 1 and 2 comprise caseins at a ratio that is similar to the approximate percentages of caseins in bovine milk. Compositions 3, 4, 7, and 8 have levels of beta-casein higher than that found in milk, and compositions 5, 6, 8, 9, and 10 have levels of kappa-casein higher than that found in bovine milk.

TABLE 25

Stretch and melt of cheese compositions comprising between 11-11.5% protein

| | Protein contribution (%) | | | | Stretch | CaCl₂ |
| | Alpha-S1 + Alpha-S2 | Beta | Kappa | Melt | (cm) | (% w/w) |
| --- | --- | --- | --- | --- | --- | --- |
| 1 | 50 | 37.5 | 12.5 | 4 | 5 | 0 |
| 2 | 50 | 37.5 | 12.5 | 4 | 8.5 | 0.25 |
| 3 | 40 | 50 | 10 | 3 | 5 | 0 |
| 4 | 40 | 50 | 10 | 3 | 8.5 | 0.25 |

TABLE 25-continued

Stretch and melt of cheese compositions comprising between 11-11.5% protein

| | Protein contribution (%) | | | | Stretch | CaCl₂ |
| | Alpha-S1 + Alpha-S2 | Beta | Kappa | Melt | (cm) | (% w/w) |
| --- | --- | --- | --- | --- | --- | --- |
| 5 | 43 | 32 | 25 | 4 | 6.5 | 0 |
| 6 | 43 | 32 | 25 | 3 | 3 | 0.25 |
| 7 | 0 | 100 | 0 | 4 | 20 | 0.4 |
| 8 | 0 | 50 | 50 | 3 | 17.5 | 0.08 |
| 9 | 0 | 25 | 75 | 2 | 0 | 0.04 |
| 10 | 0 | 0 | 100 | 0 | 0 | 0.12 |

TABLE 26

Stretch and melt of cheese compositions comprising between 13-13.5% protein

| | Protein contribution (%) | | | | Stretch | CaCl₂ |
| | Alpha-S1 + Alpha-S2 | Beta | Kappa | Melt | (cm) | (% w/w) |
| --- | --- | --- | --- | --- | --- | --- |
| 1 | 50 | 37.5 | 12.5 | 3 | 5 | 0 |
| 2 | 50 | 37.5 | 12.5 | 2 | 5.5 | 0.25 |
| 3 | 34 | 57 | 9 | 2.5 | 5 | 0 |
| 4 | 34 | 57 | 9 | 3 | 5 | 0.25 |
| 5 | 39 | 32 | 29 | 3 | 4.5 | 0 |
| 6 | 39 | 32 | 29 | 2 | 4 | 0.25 |

As evidenced by the data above, cheese compositions made with beta-casein exhibited good melting and stretch after aging for at least five days. Use of the tested amounts of beta-casein also softened the cheese composition compared to standard casein ratios. The beta-casein cheese composition was affected by calcium level similar to that of the control cheese composition, and it was also found to be highly soluble. The cheese composition was substantially transparent when melted.

Kappa-casein imparted firmness to the cheese composition relative to standard casein ratios, but was more reactive to calcium than beta casein and control cheese compositions 1 and 2. Levels of less than 25% kappa casein did not impact stretch and stretch may improve slightly, whereas increasing levels of kappa casein restricted melt and reduced stretch after refrigeration for five days. Immediately after cooking, the 100% kappa casein cheese compositions can stretch to greater than 25 cm.

The alpha-caseins, alpha-S1-casein and alpha-S2-casein, are assumed to provide cheese firmness, as cheeses with depleted levels of alpha-S1-casein and alpha-S2-casein are softer than the control cheeses.

Figure 29:
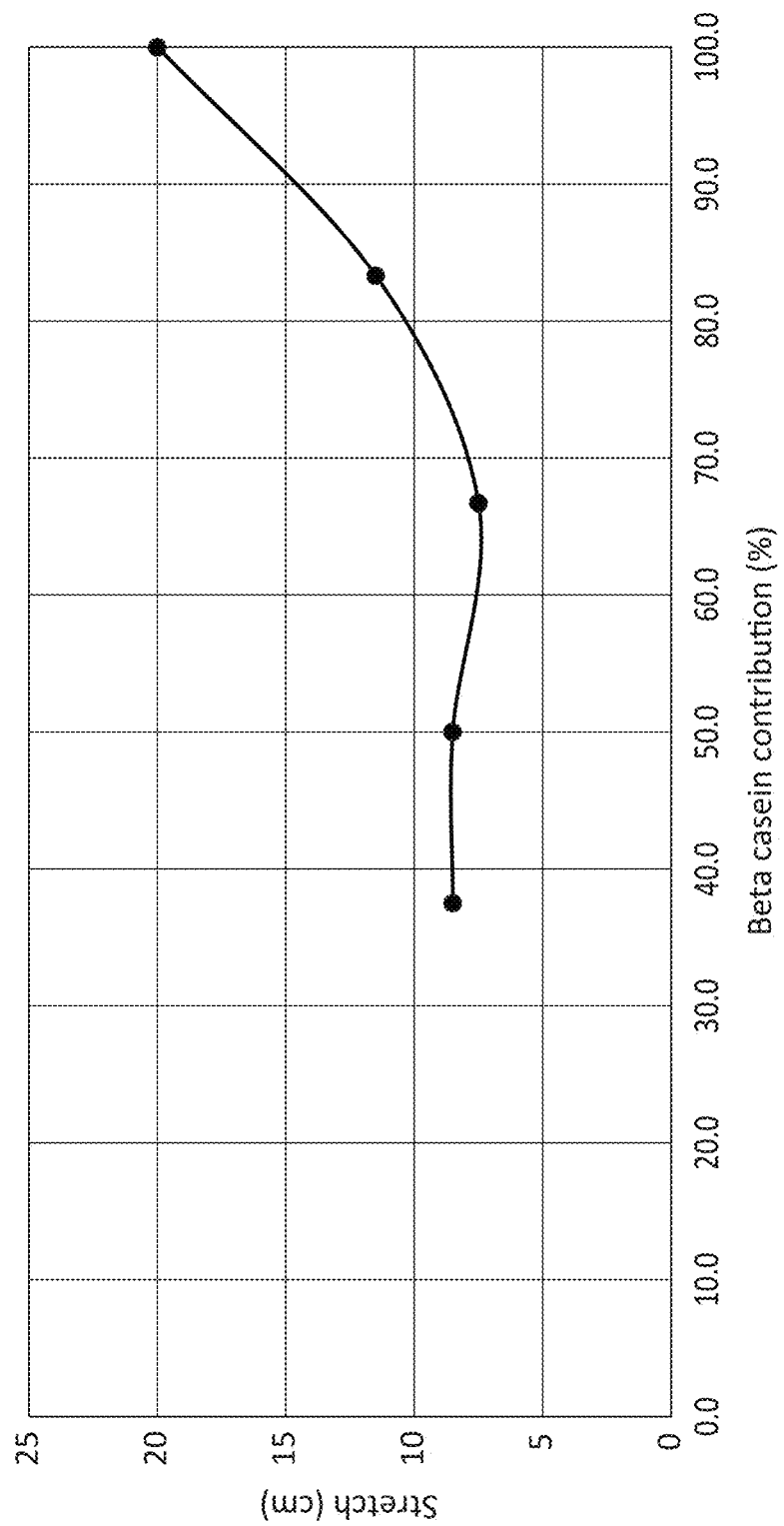
FIG. 29 is a line graph showing cheese stretch with increasing contribution of protein from beta-casein (see also Tables 23-28).

Cheese stretch was impacted by percent contribution of beta-casein. Specifically, increasing the amount of beta-casein correlated with an increase in stretch. As shown in Table 27 below, and FIG. 29, cheese compositions comprising, for example, 50% beta-casein had a stretch of 8.5 cm, whereas cheese comprising 100% beta-casein had a stretch of 20 cm. All cheese compositions comprised 11.5% total protein and CaCl₂).

TABLE 27

Cheese stretch with increasing contribution of protein from beta-casein

| % beta-casein | Stretch (cm) |
| --- | --- |
| 37.5 | 8.5 |
| 50.0 | 8.5 |

TABLE 27-continued

Cheese stretch with increasing contribution of protein from beta-casein

| % beta-casein | Stretch (cm) |
|---|---|
| 66.7 | 7.5 |
| 83.3 | 11.5 |
| 100.0 | 20 |

Example 16: Functional Properties of Additional Cheese Compositions

The analysis performed in Example 15 was repeated with additional compositions, as shown in Tables 28-30. The compositions comprised 100% beta-casein, 100% kappa-casein, or 100% alpha-caseins, or mixtures thereof. The actual percent of protein by weight of the compositions varied between 10-11.75%, and the $CaCl_2$ concentration ranged from 0% to 0.16% (by weight). Melt, stretch, and firmness were determined as described above.

TABLE 28

Functional properties of additional cheese compositions comprising only one casein

| % protein | % CaCl$_2$ | melt | stretch | firmness | pH |
|---|---|---|---|---|---|
| 100% Beta-casein ||||||
| 11.75 | 0 | 2 | 1.5 | very firm | 5.23 |
| 10 | 0 | 3 | 15 | soft | 5.28 |
| 10 | 0 | 3 | 0 | very soft | 5.6 |
| 11 | 0.04 | 4 | 6.5 | firm | 5.63 |
| 11 | 0.08 | 4 | 20 | firm | 5.55 |
| 11 | 0.08 | 3 | 6.5 | soft | 5.59 |
| 100% Kappa-casein ||||||
| 11.75 | 0.2 | 2 | 0 | firm | 5.65 |
| 11.75 | 0.12 | 3 | 0 | firm | 5.44 |
| 11.75 | 0.06 | 2 | 1.5 | firm | 5.67 |
| 11 | 0.04 | 2 | 0 | firm | 5.67 |
| 11.75 | 0.12 | 1 | 0 | firm | 5.06 |
| 100% Alpha-casein ||||||
| 11* | 0 | 3 | 0 | brittle | 6.01 |
| 11* | 0.08 | 3 | 0 | slightly soft | 5.8 |
| 11* | 0 | 3 | 0 | firm | 5.91 |
| 11* | 0.08 | 3 | 0 | firm | 5.9 |
| 11 | 0 | 2 | 0 | very firm | 6.26 |

*indicates that the compositions were undercooked

TABLE 29

Functional properties of additional cheese compositions comprising mixtures of caseins Beta-casein and Kappa-casein

| Sample No. | % beta | % kappa | % CaCl$_2$ | melt | stretch | firmness | pH |
|---|---|---|---|---|---|---|---|
| 1 | 5.5 | 5.5 | 0.04 | 4 | 7 | firm | 5.5 |
| 2 | 2.75 | 8.25 | 0.04 | 2 | 0 | very firm | 5.64 |
| 3 | 5.5 | 5.5 | 0.08 | 4 | 17.5 | firm | 5.36 |

Alpha-caseins and beta-casein

| | % alpha | % beta | % CaCl$_2$ | melt | stretch | firmness | pH |
|---|---|---|---|---|---|---|---|
| 1 | 5.5 | 5.5 | 0.16 | 4 | 0 | firm | 5.87 |
| 2 | 5.5 | 5.5 | 0.08 | 3 | 1.5 | firm | 6.01 |
| 3 | 5.5 | 5.5 | 0 | 3 | 1.5 | firm | 5.98 |
| 4 | 2.75 | 8.25 | 0.16 | 4 | 5 | firm | 5.94 |
| 5 | 2.75 | 8.25 | 0.08 | 3 | 1.5 | firm | 5.72 |
| 6 | 2.75 | 8.25 | 0 | 4 | 5.5 | firm | 5.68 |
| 7 | 8.25 | 2.75 | 0.16 | 3 | 0 | firm | 5.91 |
| 8 | 8.25 | 2.75 | 0.08 | 2 | 0 | firm | 5.92 |
| 9 | 8.25 | 2.75 | 0 | 2 | 0 | firm | 5.91 |

TABLE 30

Cheese melt and stretch with increasing contribution of protein from beta-casein

| % Beta-casein | % Alpha-caseins | % Kappa-casein | Melt | Stretch (cm) |
|---|---|---|---|---|
| 0 | 100 | 0 | 3 | 0 |
| 0 | 0 | 100 | 0 | 0 |
| 25 | 75 | 0 | 2 | 0 |
| 25 | 0 | 75 | 2 | 0 |
| 50 | 50 | 0 | 3 | 1.5 |
| 50 | 0 | 50 | 3 | 10.5 |
| 75 | 25 | 0 | 3 | 1.5 |
| 75 | 0 | 25 | 3 | 14.5 |
| 100 | 0 | 0 | 3 | 8.5 |

Figure 30:
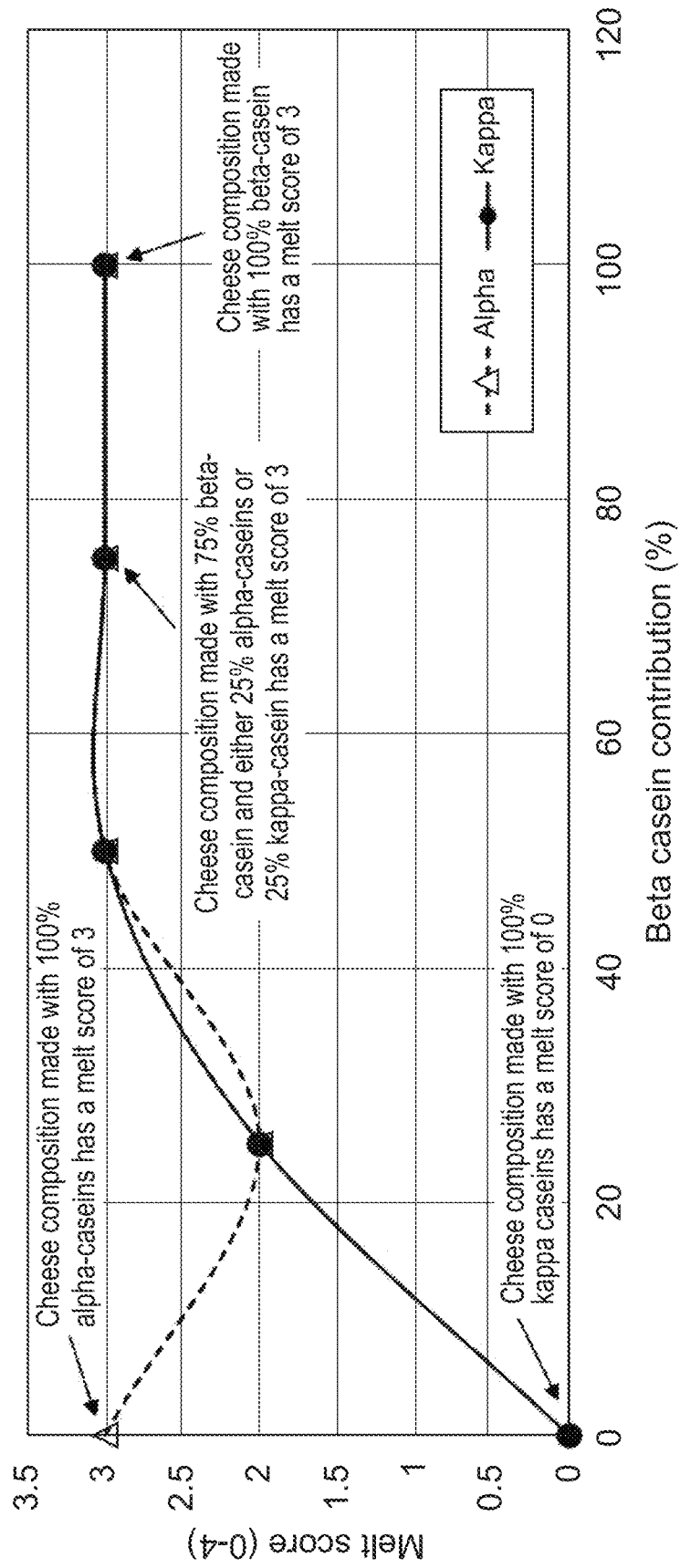
FIG. 30 is a line graph showing melt scores of cheese compositions comprising one or more of beta-casein, kappa-casein and alpha casein (see also Tables 23-28).
Figure 31:
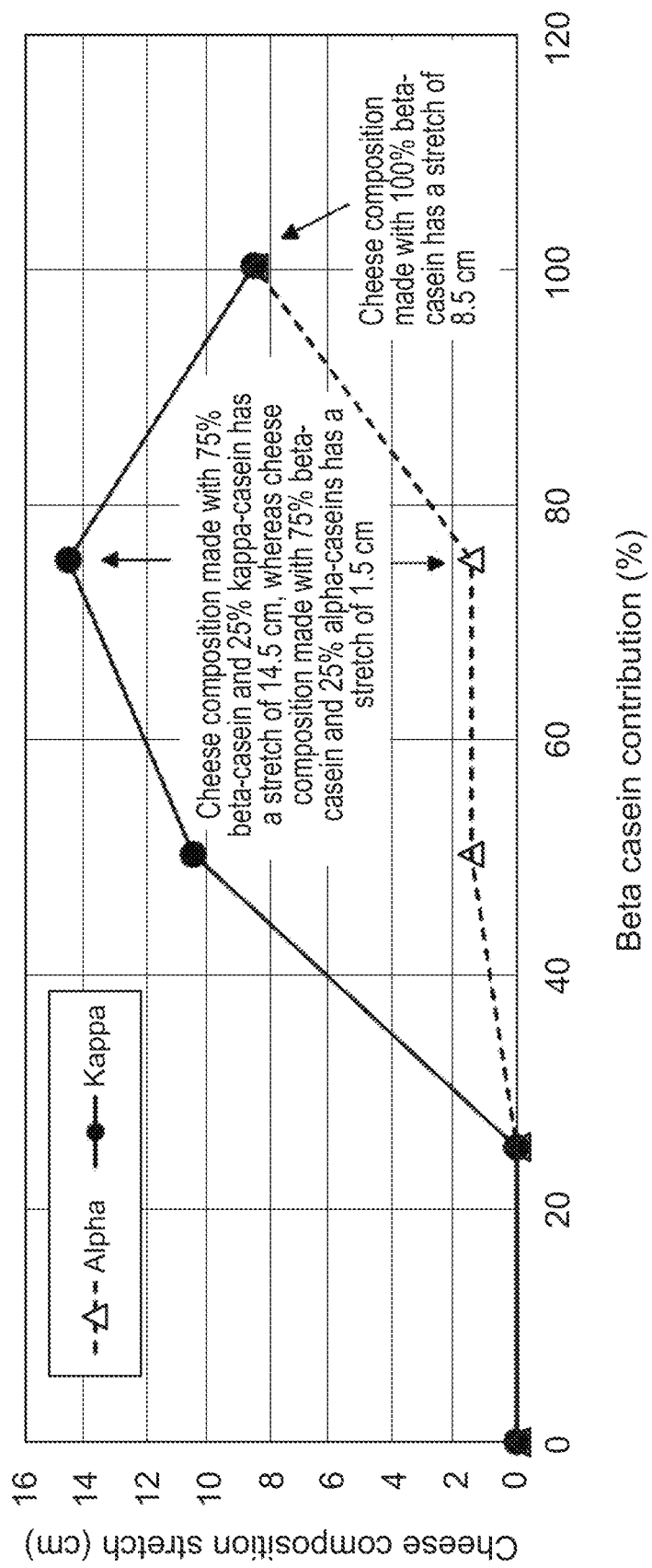
FIG. 31 is a line graph showing stretch of cheese compositions comprising one or more of beta-casein, kappa-casein and alpha casein (see also Tables 23-28).

As shown by the data in Table 28-30 above and FIGS. 30-31, beta-casein is the only casein that imparts both melt and stretch in a cheese composition under these conditions. Alpha caseins do not appear to impart stretch and do not significantly restrict melt. Alpha-caseins contribute to cheese firmness (data not shown). Kappa-casein also imparts firmness but negatively impacts melt. Like beta-casein it can contribute to stretch but only when combined with another protein.

Example 17: Cheese Compositions with Beta-Lactoglobulin

To determine the effect of adding beta-lactoglobulin on the functional and organoleptic properties of the compositions, various cheese compositions were generated with different amounts of beta-lactoglobulin.

TABLE 31

Stretch and melt of cheese composition with the addition of beta-lactoglobulin

| Protein contribution (%) | | | | | | | |
|---|---|---|---|---|---|---|---|
| Alpha-S1 + Alpha-S2 | Beta | Kappa | Beta Lacto-globulin | Soy | % Protein | Melt | Stretch (cm) |
| 50 | 37.5 | 12.5 | 0 | 0 | 11.5 | 4 | 5 |
| 39.8 | 29.8 | 9.9 | 20.5 | 0 | 11.5 | 3 | 0 |
| 31.6 | 23.7 | 7.9 | 0 | 20.5 | 11.5 | 4 | 4.5 |
| 50 | 37.5 | 12.5 | 0 | 0 | 13.2 | 3 | 8.5 |
| 34.6 | 26 | 8.7 | 30.8 | 0 | 13.2 | 2 | 0 |
| 24.0 | 18 | 6 | 0 | 30.8 | 13.2 | 3 | 0 |

As shown in Table 31 above, at 20% and 30% casein replacement levels, stretch was eliminated. Cheese composition melt, stretch, firmness were closer to the control with soy protein isolate compared to beta-lactoglobulin at both replacement levels tested.

Similar results were achieved with compositions comprising kappa-casein and beta-lactoglobulin (Table 32), beta-casein and beta-lactoglobulin (Table 33). The addition of beta-lactoglobulin to the cheese compositions softened them, restricted melt, and imparted an opacity due to protein aggregation.

TABLE 32

Stretch and melt of kappa-casein cheese composition with the addition of beta-lactoglobulin
Kappa-casein + Beta-lactoglobulin

| % protein | % CaCl$_2$ | melt | stretch | firmness | pH | % BLG |
|---|---|---|---|---|---|---|
| 10 | 0.06 | 2 | 0 | firm | 5.95 | 2.5 |

TABLE 33

Stretch and melt of beta-casein cheese composition with the addition of beta-lactoglobulin
Beta-casein + beta-lactogloublin

| % protein | % CaCl$_2$ | melt | stretch | firmness | pH | % BLG |
|---|---|---|---|---|---|---|
| 10 | 0 | 3 | 0 | slightly soft (between soft and firm) | 5.43 | 2.5 |

Example 18: Estimation of Apparent Viscosity

An exemplary milk composition comprising beta-casein as the only casein (BC milk), a yogurt composition comprising beta-casein as the only casein (BC yogurt), and an ice cream mix composition comprising beta-casein as the only casein (BC IC mix) are described in Table 34, below.

TABLE 34

Food compositions for viscosity analysis

| Ingredient | % |
|---|---|
| Beta casein milk | |
| Beta casein powder | 3.0 |
| Sodium citrate | 0.2 |
| Lactic acid (88%) | 0.1 |
| Sodium chloride | 0.2 |
| Calcium chloride | 0.2 |
| Palm oil | 3.3 |
| Soy lecithin | 0.2 |
| Glucose | 4.0 |
| Water | 88.9 |
| Beta casein yogurt (plain) | |
| Beta casein powder | 4.0 |
| Sodium citrate | 0.2 |
| Sodium chloride | 0.2 |
| Calcium chloride | 0.2 |
| Coconut oil | 4.0 |
| Soy lecithin | 0.3 |
| Modified tapioca starch | 3.5 |
| Glucose | 4.0 |
| Water | 83.6 |
| Beta casein ice cream mix | |
| Beta casein powder | 4.5 |
| Sodium citrate | 0.2 |
| Lactic acid (88%) | 0.1 |
| Sodium chloride | 0.2 |
| Tetrasodium pyrophosphate | 0.2 |
| Cocoa butter | 12.0 |
| Calcium sulfate | 0.2 |

TABLE 34-continued

Food compositions for viscosity analysis

| Ingredient | % |
|---|---|
| Mono & diglycerides | 0.5 |
| Cellulose gum | 0.2 |
| Sucrose | 20.0 |
| Vanilla extract | 0.5 |
| Water | 61.5 |

To make a BC milk composition, water is heated to 100-120° F., and lecithin and melted palm oil are added. Subsequently, the remaining ingredients (except lactic acid) are added with agitation and minimal air incorporation. The pH is adjusted to the range of 6.5-7.0 with lactic acid. The composition is then heated to 140° F. and homogenized (two stage, 2000 psi total). Then, the composition is heated to 175° F. and held at that temperature for 20 seconds before cooling to 40° F.

To make a BC yogurt composition, water is heated to 100-120° F., and lecithin and melted coconut oil are added. Subsequently, the remaining ingredients (except lactic acid) are added with agitation and minimal air incorporation. The pH is adjusted to the range of 6.5-7.0 with lactic acid. The composition is then heated to 140° F. and homogenized (two stage, 2000 psi total). Then, the composition is heated to 185° F. and held at that temperature for 5 minutes. The composition is then cooled to 110° F. and yogurt cultures are added. The composition is fermented at 108° F. until the pH is 4.6. The composition is then stirred and cooled to 40° F.

To make a BC IC composition, water is heated to 100-120° F., and lecithin and melted cocoa butter are added. Subsequently, the remaining ingredients (except lactic acid) are added with agitation and minimal air incorporation. The pH is adjusted to the range of 6.5-7.0 with lactic acid. The composition is then heated to 140° F. and homogenized (two stage, 2000 psi total). Then, the composition is heated to 175° F. and held at that temperature for 20 seconds before cooling to 40° F.

Theoretical approximations of the apparent viscosity for these BC milk, BC yogurt, and BC IC mix may be determined. Specifically, these approximations may be based on the rheological analysis of formulations made with bovine milk and adjustments made from observations made during the work with various cheese compositions described herein.

Figure 32:
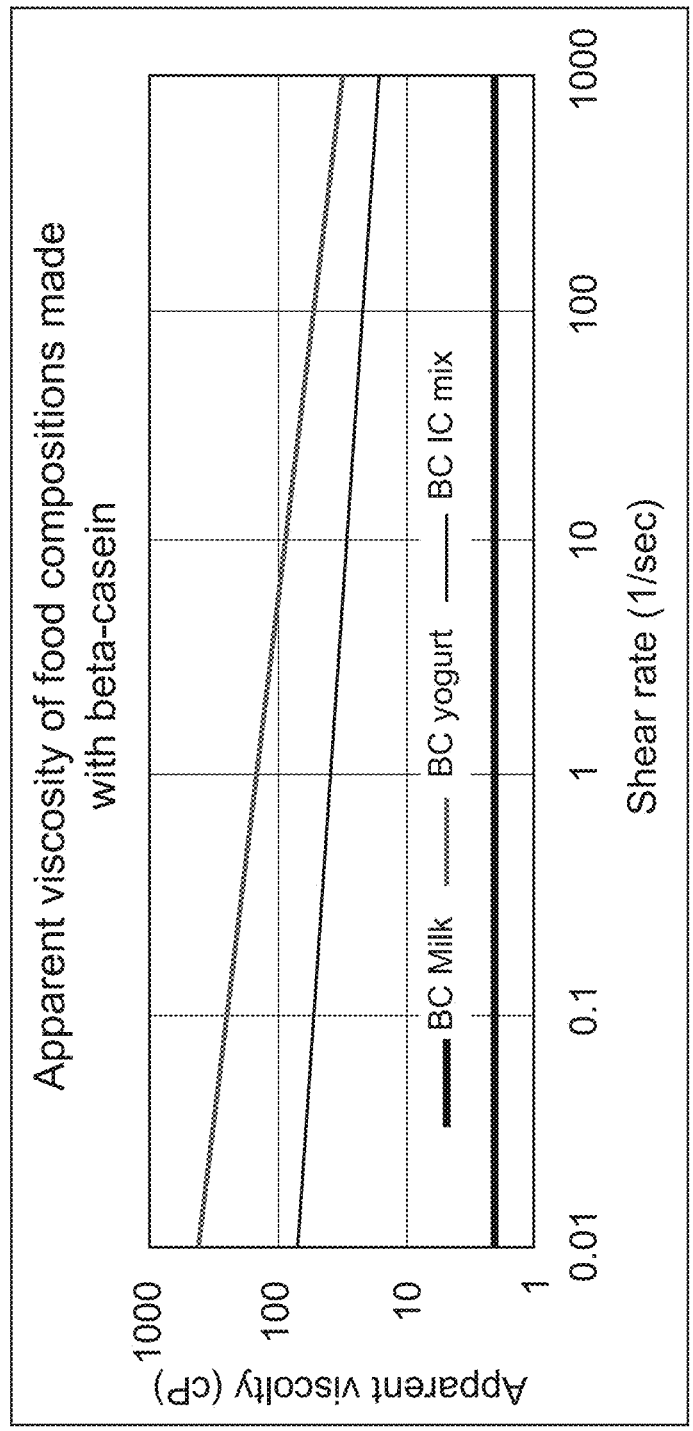
FIG. 32 is a graph showing estimated apparent viscosity (in centipoise (cP)) at shear rates in the range of 0.01 to 1000 $sec^{-1}$ for a milk composition comprising beta-casein as the only casein (BC milk), a yogurt composition comprising beta-casein as the only casein (BC yogurt), and an ice cream mix composition comprising beta-casein as the only casein (BC IC mix).

Approximations are shown in FIG. 32. The BC milk compositions are estimated to have an apparent viscosity of about 2 cP over all shear rates analyzed. In contrast, the BC yogurt and the BC IC mix compositions are estimated to have a higher apparent viscosity, which is expected to decrease at higher shear rates, characteristic of non-Newtonian compositions.

Taken together, this data indicates that the BC yogurt and BC IC mix compositions are expected to be non-Newtonian compositions.

Example 19: Expression of a Fusion Protein Comprising Beta-Casein in *E. Coli*

To determine whether the fusion proteins of the disclosure may be detectably expressed in a bacterial system, a beta-casein tetramer (i.e., a fusion protein comprising four beta-caseins) was expressed in *E. Coli*. Specifically, the pET system (Novagen) was used for the cloning and expression of the proteins of interest in *E. coli*. A DNA sequence encoding the beta-casein tetramer was PCR amplified and cloned into the NcoI and BlpI sites of pET-28a (+) expression vector via In-Fusion (Takara) cloning. The ligated vector was transformed into Stellar™ competent cells. Subsequently, the DNA of positive clones was used to transform BL21-CodonPlus strain (Agilent Technologies) which encodes a T7 RNA polymerase under control of the lacUV5 promoter for easy expression.

To induce protein expression, an overnight culture grown to stationary phase was diluted (1/100) and then grown to mid-log phase (OD600~0.4-0.6). The mid-log phase culture was pelleted, and the supernatant was removed. Protein expression was induced by the addition of IPTG (0.5 mM final concentration) to the pellet, and the cells were incubated for 3 hours at 37° C. with 160 rpm shaking. To extract the proteins of interest, the BugBuster® (Novagen) master mix was utilized following the manufacturer's instructions with the addition HALT protease inhibitor. The proteins were separated using SDS-PAGE and transferred to nitrocellulose membrane. The fusion protein was detected using a primary antibody raised against beta-casein.

Figure 33:
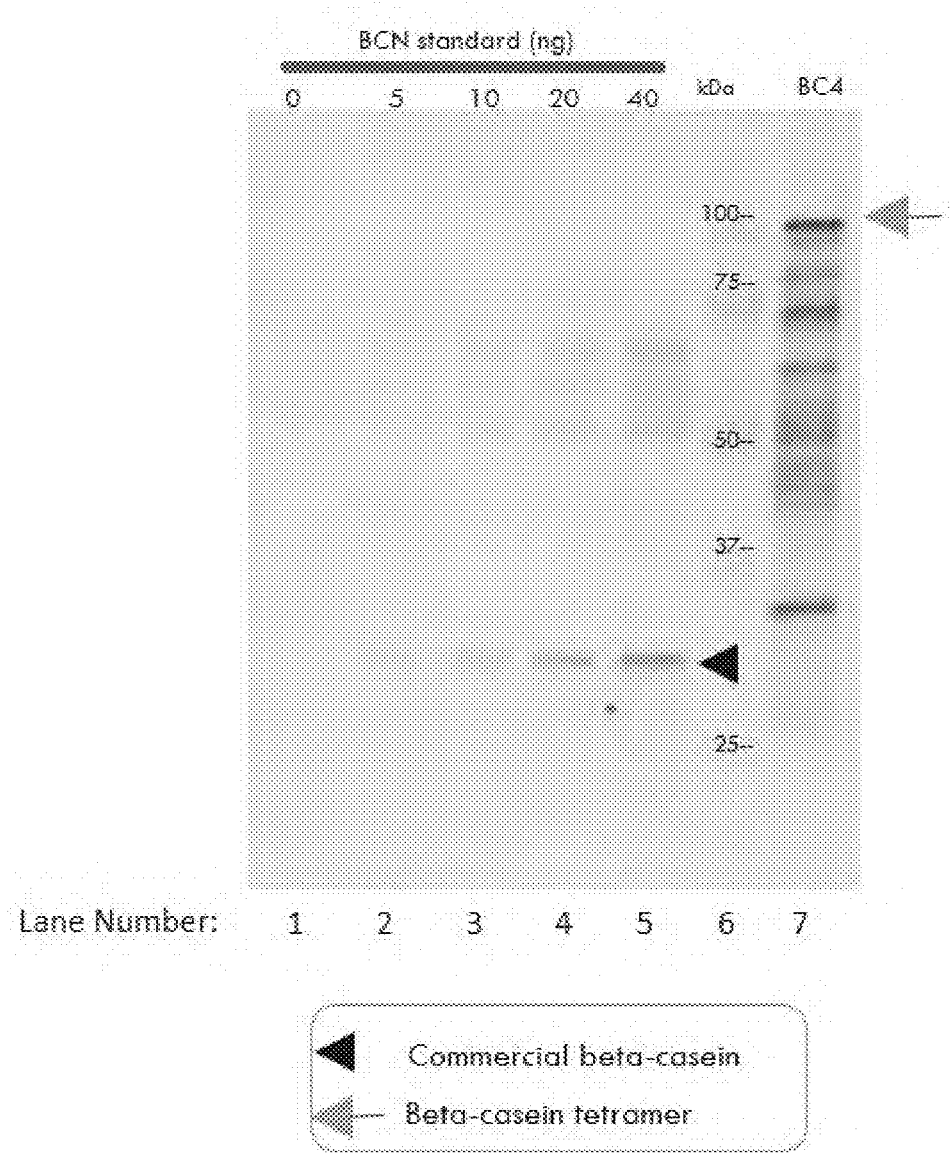
FIG. 33 is a western blot showing expression of a beta-casein tetramer (BC4) in *E. Coli*. Commercial beta-casein, in monomeric form, was detected at an apparent molecular weight of ~30 kDA (theoretical: 23.5 kDa—arrowhead). The BC4 fusion protein was detected at an apparent MW of ~100 kDa (theoretical: 94 kDa—arrow).

As shown in FIG. 33, the beta-casein tetramer (BC4) accumulated to detectable levels in *E. Coli*. Lanes 1-5 of FIG. 33 show wildtype *E. coli* extracts with commercial beta-casein protein spiked in at 0, 5, 10, 20 and 40 ng per lane, as a standard. Lane 6 shows molecular weight markers. Lane 7 shows Beta-casein tetramer expressed in *E. Coli* after 3 h of induction with IPTG.

Example 20: Expression of a Fusion Protein Comprising Beta-Casein in Tobacco Leaves To determine whether the fusion proteins of the disclosure may be detectably expressed in a tobacco system, a fusion protein comprising beta-casein fused to beta-lactoglobulin was expressed in tobacco leaves.

A DNA sequence encoding a fusion protein comprising, from N-terminus to C-terminus, beta-lactoglobulin and beta-casein, was inserted into the AR17 vector backbone in between a double 35S promoter and EUT:Rb7T double terminator. The plasmid was transformed into *agrobacterium* strain AGL1 and the positive *agrobacterium* colonies were cultured overnight in selective media. To prepare the infiltration solution, the *agrobacterium* culture was precipitated by centrifugation at 1,000 g for 10 mins and resuspended in equal volume of the infiltration medium (50 mM MES, 2 mM $Na_3PO_4$, 5 mg/mL D-glucose and 0.1 mM acetosyringone). This washing step was repeated a second time.

The fusion protein expressing strain was co-infiltrated in tobacco leaves with the post-translational gene silencing inhibitor p19 strain and the protease inhibitor NbPR4 strain to enhance the fusion protein expression. Concentration of the fusion protein expressing-strain, and strains p19 and NbPR4, was adjusted to an optical density (OD) of 1, 0.5 and 0.5 respectively, immediately before co-infiltration into the leaves. Six to eight-week-old Nicothiana *benthamiana* plants were used for infiltrations. Four different fully expanded leaves were infiltrated as biological replicates.

Protein samples were harvested three days after infiltration. Total soluble proteins were extracted with equal volume of extraction buffer (1×PBS PH7.4, 5 mM DTT, 0.1% Tween20 and 1×HALT protease inhibitors). Total protein concentrations were measured using Pierce 660 reagent. To visualize the target protein expression, 1 μg of total soluble protein were separated on SDS-PAGE, transferred to nitrocellulose membrane, and probed with a beta-casein primary antibody.

Results are shown in FIG. 34. Lanes 1-5 show wild type tobacco protein extracts spiked with 0, 0.5, 1, 2, or 4 nanograms of commercially available beta-casein. Lane 6 shows molecular weight markers. Lanes 7-8 shows infiltration of tobacco leaves with the fusion protein. This data shows that the fusion protein accumulated in tobacco leaves at a level above 4% total soluble protein.

Milk Protein Sequences

The following Table 35 describes various representative species of milk proteins exemplified in the disclosure.

TABLE 35

Milk Protein Sequences of the Disclosure

| SEQ ID NO | Description | Genus/species | Accession Number |
|---|---|---|---|
| Kappa casein sequences ||||
| 3 | Optimized kappa-casein truncated version 1 (OKC1-T) | Artificial (codon optimized *Bos taurus*) | |
| 4 | Optimized kappa-casein truncated version 1 (OKC1-T) | *Bos taurus* | |
| 85 | Kappa casein | *Capra hircus* | |
| 86 | Kappa casein | *Ovis aries* | |
| 87 | Kappa casein | *Bubalus bubalis* | |
| 88 | Kappa casein | *Camelus dromedaries* | |
| 89 | Kappa casein | *Camelus bactrianus* | |
| 90 | Kappa casein | *Bos mutus* | |
| 91 | Kappa casein | *Equus caballus* | |
| 92 | Kappa casein | *Equus asinus* | |
| 93 | Kappa casein | *Rangifer tarandus* | |
| 94 | Kappa casein | *Alces alces* | |
| 95 | Kappa casein | *Vicugna pacos* | |
| 96 | Kappa casein | *Bos indicus* | |
| 97 | Kappa casein | *Lama glama* | |
| 98 | Kappa casein | *Homo sapiens* | |

TABLE 35-continued

Milk Protein Sequences of the Disclosure

| SEQ ID NO | Description | Genus/species | Accession Number |
|---|---|---|---|
| 148 | Kappa casein | Bos taurus | NP_776719.1 |
| 149 | | | AAI02121.1 |
| 150 | | | AAA30433.1 |
| 151 | | | AAB26704.1 |
| 152 | | | 1406275A |
| 153 | | | AAF72097.1 |
| 154 | | | AAD32139.1 |
| 155 | | | XP_024848756.1 |
| 156 | | | CAF03625.1 |
| 157 | | | ABN42697.1 |
| 158 | | | AAD32140.1 |
| 159 | | | ALC76014.1 |
| 160 | | | DAA28589.1 |
| 161 | | | ADT82665.1 |
| 162 | | | ADT82666.1 |
| 163 | | | CAH56573.1 |
| 164 | | | ADT82669.1 |
| 165 | Kappa casein | Capra hircus | QIZ03342.1 |
| 166 | | | AYN74373.1 |
| 167 | | | AAM12026.1 |
| 168 | | | AFZ92921.1 |
| 169 | | | NP_001272516.1 |
| 170 | | | AAM12027.1 |
| 171 | | | AAR06605.1 |
| 172 | | | AAL90873.1 |
| 173 | | | AFZ92919.1 |
| 174 | | | QIZ03345.1 |
| 175 | | | AAR91623.1 |
| 176 | | | AAK17010.1 |
| 177 | | | AAL93193.1 |
| 178 | | | AFZ92918.1 |
| 179 | | | AAL90872.1 |
| 180 | | | AFZ92917.1 |
| 181 | | | AAO39432.1 |
| 182 | | | AAL90871.1 |
| 183 | | | AAO39431.1 |
| 184 | Kappa casein | Ovis aries | NP_001009378.1 |
| 185 | | | AAP69943.1 |
| 186 | Kappa casein | Bubalus bubalis | NP_001277901.1 |
| 187 | | | AXE74388.1 |
| 188 | | | APQ30586.1 |
| 189 | | | AXE74385.1 |
| 190 | | | XP_006071184.1 |
| 191 | | | AXE74386.1 |
| 192 | Kappa casein | Bos mutus | XP_005897104.1 |
| 193 | | | XP_014334109.1 |
| 194 | | | MXQ92034.1 |
| 195 | Kappa casein | Bos indicus | XP_019818432.1 |
| 196 | | | ACF15188.1 |
| 197 | | | ACF15186.1 |
| 198 | | | ACF15190.1 |
| 199 | | | ABY81250.1 |
| 200 | | | ABY81251.1 |
| 201 | | | ADT82668.1 |
| 202 | | | ADT82663.1 |
| 203 | | | ADT82671.1 |
| 204 | | | ADT82670.1 |
| 205 | | | AAQ73171.1 |
| 206 | Kappa casein | Jeotgalicoccus coquinae | WP_188357548.1 |
| 207 | (Hypothetical Protein) | | WP_188357549.1 |
| 208 | Kappa casein isoform X1 | Bison bison bison | XP_010837415.1 |
| 209 | | | XP_010837416.1 |
| 210 | Kappa casein | Bos grunniens | AFM93768.1 |
| 211 | | | AXE74296.1 |
| 212 | | | AAM25910.1 |
| 213 | | | ABU53615.1 |
| 214 | | | AAM25909.1 |
| 215 | | | AAF63191.1 |
| 216 | Kappa casein | Bos indicus x Bos taurus | AAF72096.1 |
| 217 | | | AAF72098.1 |
| 218 | Kappa casein (precursor) | Oreamnos americanus | P50423.1 |
| 219 | Kappa casein (precursor) | Naemorhedus goral | P50422.1 |
| 220 | Kappa casein | Odocoileus virginianus texanus | XP_020729185.1 |
| 221 | Kappa casein (precursor) | Capricornis sumatraensis | P50420.1 |

TABLE 35-continued

Milk Protein Sequences of the Disclosure

| SEQ ID NO | Description | Genus/species | Accession Number |
|---|---|---|---|
| 222 | Kappa casein (precursor) | *Capricornis crispus* | BAA03287.1 |
| 223 | | | P42156.1 |
| 224 | Kappa casein (precursor) | *Capricornis swinhoei* | P50421.1 |
| 225 | Kappa casein (precursor) | *Saiga tatarica* | P50425.1 |
| 226 | Kappa casein (precursor) | *Rupicapra rupicapra* | P50424.1 |
| 227 | Kappa casein (precursor) | *Cervus nippon* | P42157.1 |
| 228 | Kappa casein | *Bos frontalis* | ADF58295.1 |
| 229 | Kappa casein (hypothetical protein FD755_023011) | *Muntiacus reevesi* | KAB0354473.1 |
| 230 | Kappa casein (hypothetical protein FD754_018150) | *Muntiacus muntjak* | KAB0341224.1 |
| 231 | Kappa casein | *Madoqua saltiana* | AFY03578.1 |
| 232 | Kappa casein | *Gazella dorcas* | AFY03574.1 |
| 233 | Kappa casein | *Gazella arabica* | AFY03576.1 |
| 234 | Kappa casein | *Capra ibex ibex* | AAP80529.1 |
| 235 | Kappa casein | *Ovis ammon severtzovi* | ADB66396.1 |
| 236 | Kappa casein | *Ovis orientalis gmelini* | ADB66423.1 |
| 237 | | | ADB66420.1 |
| 238 | Kappa casein (hypothetical protein G4228_004474) | *Cervus hanglu yarkandensis* | KAF4013038.1 |
| 239 | Kappa casein | *Procapra gutturosa* | AFY03581.1 |
| 240 | | | AFY03580.1 |
| 1 | Optimized para-kappa-casein truncated version 1 (paraOKC1-T) | Artificial (codon optimized *Bos taurus*) | |
| 2 | Optimized para-kappa-casein truncated version 1 (paraOKC1-T) | *Bos taurus* | |
| 241 | Kappa casein isoform X1 | *Bos taurus* | AAA30433.1 |
| 242 | | | 1406275A |
| 243 | | | AAI02121.1 |
| 244 | | | NP_776719.1 |
| 245 | | | DAA28589.1 |
| 246 | | | AAB26704.1 |
| 247 | | | XP_024848756.1 |
| 248 | | | ABN42697.1 |
| 249 | | | AAF72097.1 |
| 250 | | | 721588A |
| 251 | | | AAD32139.1 |
| 252 | | | AAD32140.1 |
| 253 | | | CAF03625.1 |
| 254 | Kappa casein | *Jeotgalicoccus coquinae* | WP_188357548.1 |
| 255 | (hypothetical protein) | | WP_188357549.1 |
| 256 | Kappa casein isoform X1 | *Bos mutus* | XP_005897104.1 |
| 257 | | | XP_014334109.1 |
| 258 | | | MXQ92034.1 |
| 259 | Kappa casein | *Bos indicus* | XP_019818432.1 |
| 260 | | | ACF15188.1 |
| 261 | | | ABY81250.1 |
| 262 | | | ABY81251.1 |
| 263 | | | ACF15186.1 |
| 264 | | | ACF15190.1 |
| 265 | | | ADT82668.1 |
| 266 | Kappa casein | *Bos grunniens* | AXE74296.1 |
| 267 | | | AFM93768.1 |
| 268 | | | AAM25910.1 |
| 269 | | | AAM25909.1 |
| 270 | | | ABU53615.1 |
| 271 | Kappa casein isoform X1 | *Bison bison bison* | XP_010837415.1 |
| 272 | | | XP_010837416.1 |
| 273 | Kappa casein (precursor) | *Bubalus bubalis* | NP_001277901.1 |
| 274 | | | XP_006071184.1 |
| 275 | | | AXE74388.1 |
| 276 | | | AXE74385.1 |
| 277 | | | APQ30586.1 |
| 278 | | | AXE74386.1 |
| 279 | Kappa casein (precursor) | *Oreamnos americanus* | P50423.1 |
| 280 | Kappa casein (precursor) | *Capricornis swinhoei* | P50421.1 |
| 281 | Kappa casein (precursor) | *Naemorhedus goral* | P50422.1 |
| 282 | Kappa casein (precursor) | *Capricornis sumatraensis* | P50420.1 |
| 283 | Kappa casein (precursor) | *Capricornis crispus* | BAO03287.1 |

TABLE 35-continued

Milk Protein Sequences of the Disclosure

| SEQ ID NO | Description | Genus/species | Accession Number |
|---|---|---|---|
| 284 | | | P42156.1 |
| 285 | Kappa casein (precursor) | *Saiga tatarica* | P50425.1 |
| 286 | Kappa casein | *Bos indicus x Bos taurus* | AAF72096.1 |
| 287 | | | AAF72098.1 |
| 288 | Kappa casein (precursor) | *Capra hircus* | NP_001272516.1 |
| 289 | | | AYN74373.1 |
| 290 | | | QIZ03345.1 |
| 291 | | | QIZ03342.1 |
| 292 | | | AFZ92921.1 |
| 293 | | | AAR06605.1 |
| 294 | | | AAM12026.1 |
| 295 | | | AAL93193.1 |
| 296 | | | AAR91623.1 |
| 297 | | | AFZ92917.1 |
| 298 | | | AAM12027.1 |
| 299 | | | AAL90873.1 |
| 300 | | | AFZ92918.1 |
| 301 | | | AAL90871.1 |
| 302 | | | AAL90872.1 |
| 303 | | | AAL31535.1 |
| 304 | | | AAL31534.1 |
| 305 | | | ABK59545.1 |
| 306 | | | AAO39432.1 |
| 307 | | | AFZ92919.1 |
| 308 | | | AAK17010.1 |
| 309 | | | AAO39431.1 |
| 310 | | | AAP80475.1 |
| 311 | Kappa casein | *Odocoileus virginianus texanus* | XP_020729185.1 |
| 312 | Kappa casein (precursor) | *Rupicapra rupicapra* | P50424.1 |
| 313 | Kappa casein (precursor) | *Ovis aries* | NP_001009378.1 |
| 314 | | | AAP69943.1 |
| 315 | Kappa casein (precursor) | *Cervus nippon* | P42157.1 |
| 316 | Kappa casein | *Gazella arabica* | AFY03576.1 |
| 317 | Kappa casein (hypothetical protein FD754_018150) | *Muntiacus muntjak* | KAB0341224.1 |
| 318 | Kappa casein (hypothetical protein FD755_023011) | *Muntiacus reevesi* | KAB0354473.1 |
| 319 | Kappa casein | *Gazella dorcas* | AFY03575.1 |
| 320 | Kappa casein | *Procapra gutturosa* | AFY03581.1 |
| 321 | | | AFY03580.1 |
| 322 | Kappa casein | *Madoqua saltiana* | AFY03578.1 |
| 323 | Kappa casein | *Ammotragus lervia* | QIN85723.1 |
| 324 | | | QIN85720.1 |
| 325 | | | QIN85721.1 |
| 326 | Kappa casein | *Capra sibirica* | AAP80568.1 |
| 327 | Kappa casein | *Ovis canadensis canadensis* | ADB66397.1 |
| 328 | | | ADB66402.1 |
| 329 | Kappa casein | *Gazella subgutturosa marica* | AFY03577.1 |
| 330 | Kappa casein | *Antilope cervicapra* | AFY03573.1 |
| 331 | Kappa casein | *Capra ibex ibex* | AAP80529.1 |
| 332 | Kappa casein | *Ovis vignei arkal* | ADB66436.1 |
| 333 | | | ADB66442.1 |
| 334 | Kappa casein | *Ovis ammon collium* | ADB66395.1 |
| 335 | Kappa casein | *Ovis vignei blanfordi* | ADB66445.1 |
| 336 | Kappa casein | *Ovis orientalis gmelini* | ADB66423.1 |
| 337 | | | ADB66420.1 |
| 338 | Kappa casein | *Ovis orientalis x vignei* | ADB66465.1 |
| 339 | Kappa casein | *Ovis vignei vignei* | ADB66456.1 |
| 340 | Kappa casein | *Ovis ammon severtzovi* | ADB66396.1 |
| Alpha S1 casein sequences | | | |
| 7 | Optimized alpha S1-casein truncated version 1(OaS1-T) | Artificial (codon optimized *Bos taurus*) | |
| 8 | Optimized alpha S1-casein truncated version 1(OaS1-T) | *Bos taurus* | |
| 99 | Alpha S1 casein | *Capra hircus* | |
| 100 | Alpha S1 casein | *Ovis aries* | |
| 101 | Alpha S1 casein | *Bubalus bubalis* | |
| 102 | Alpha S1 casein | *Camelus dromedaries* | |

TABLE 35-continued

Milk Protein Sequences of the Disclosure

| SEQ ID NO | Description | Genus/species | Accession Number |
|---|---|---|---|
| 103 | Alpha S1 casein | *Camelus bactrianus* | |
| 104 | Alpha S1 casein | *Bos mutus* | |
| 105 | Alpha S1 casein | *Equus caballus* | |
| 106 | Alpha S1 casein | *Equus asinus* | |
| 107 | Alpha S1 casein | *Bos indicus* | |
| 108 | Alpha S1 casein | *Lama glama* | |
| 109 | Alpha S1 casein | *Homo sapiens* | |
| 341 | Alpha S1 casein | *Bos taurus* | ABW98943.1 |
| 342 | | | XP_024848771.1 |
| 343 | | | ABW98940.1 |
| 344 | | | ACG63494.1 |
| 345 | | | XP_015327132.1 |
| 346 | | | XP_024848772.1 |
| 347 | | | 1308122A |
| 348 | | | ABW98949.1 |
| 349 | | | AAA30429.1 |
| 350 | | | XP_015327135.1 |
| 351 | | | XP_015327134.1 |
| 352 | | | XP_024848773.1 |
| 353 | | | XP_015327133.1 |
| 354 | | | XP_024848774.1 |
| 355 | | | XP_015327136.1 |
| 356 | | | XP_024848775.1 |
| 357 | | | XP_005208084.1 |
| 358 | | | XP_024848776.1 |
| 359 | | | XP_015327137.1 |
| 360 | | | XP_015327138.1 |
| 361 | | | XP_024848777.1 |
| 362 | | | XP_024848778.1 |
| 363 | | | XP_015327139.1 |
| 364 | | | ABW98944.1 |
| 365 | | | XP_015327140.1 |
| 366 | | | XP_024848779.1 |
| 367 | | | XP_015327141.1 |
| 368 | | | XP_024848780.1 |
| 369 | | | XP_015327142.1 |
| 370 | | | ABW98945.1 |
| 371 | | | XP_024848782.1 |
| 372 | | | ABW98951.1 |
| 373 | | | XP_024848784.1 |
| 374 | | | XP_024848783.1 |
| 375 | | | ABW98950.1 |
| 376 | | | ABW98941.1 |
| 377 | | | XP_005208086.1 |
| 378 | | | ABW98942.1 |
| 379 | | | ABW98937.1 |
| 380 | | | ABW98952.1 |
| 381 | | | ABW98954.1 |
| 382 | | | ABW98953.1 |
| 383 | | | ABW98955.1 |
| 384 | | | ABW98957.1 |
| 385 | Alpha S1 casein | *Capra hircus* | XP_017904616.1 |
| 386 | | | QIZ03312.1 |
| 387 | | | ALJ30147.1 |
| 388 | | | P18626.2 |
| 389 | | | XP_017904617.1 |
| 390 | | | AFN44013.1 |
| 391 | | | QIZ03319.1 |
| 392 | | | CAA51022.1 |
| 393 | | | NP_001272624.1 |
| 394 | | | ALJ30148.1 |
| 395 | | | QIZ03317.1 |
| 396 | | | QIZ03310.1 |
| 397 | | | QIZ03318.1 |
| 398 | | | XP_017904618.1 |
| 399 | | | XP_017904620.1 |
| 400 | | | XP_017904619.1 |
| 401 | | | XP_017904621.1 |
| 402 | | | XP_017904622.1 |
| 403 | Alpha S1 casein | *Ovis aries* | XP_012034747.1 |
| 404 | | | P04653.3 |
| 405 | | | AAB34797.1 |
| 406 | | | ACJ46472.1 |
| 407 | | | XP_027826521.1 |

TABLE 35-continued

Milk Protein Sequences of the Disclosure

| SEQ ID NO | Description | Genus/species | Accession Number |
|---|---|---|---|
| 408 | | | XP_027826520.1 |
| 409 | | | ACR58469.1 |
| 410 | | | ACJ46473.1 |
| 411 | | | AAB34798.1 |
| 412 | | | NP_001009795.1 |
| 413 | Alpha S1 casein | Bubalus bubalis | AAZ14098.1 |
| 414 | | | APQ30583.1 |
| 415 | | | O62823.2 |
| 416 | | | XP_006071187.1 |
| 417 | | | QCP57314.1 |
| 418 | | | XP_025145744.1 |
| 419 | | | QPO15022.1 |
| 420 | | | XP_025145745.1 |
| 421 | | | ACJ14317.1 |
| 422 | | | XP_006071188.1 |
| 423 | | | XP_025145747.1 |
| 424 | | | XP_025145746.1 |
| 425 | | | XP_025145748.1 |
| 426 | | | XP_025145749.1 |
| 427 | | | XP_025145750.1 |
| 428 | | | XP_025145751.1 |
| 429 | | | XP_025145752.1 |
| 430 | | | XP_025145753.1 |
| 431 | Alpha S1 casein | Bos mutus | XP_005902100.1 |
| 432 | Alpha S1 casein | Bos indicus | XP_019818428.1 |
| 433 | Alpha S1 casein | Jeotgalicoccus coquinae | WP_188357546.1 |
| 434 | (hypothetical protein) | | GGE26809.1 |
| 435 | Alpha S1 casein | Bison bison bison | XP_010850445.1 |
| 436 | Alpha S1 casein | Bos grunniens | AXE74293.1 |
| 437 | Alpha S1 casein | Jeotgalicoccus aerolatus | WP_188349304.1 |
| 438 | (hypothetical protein) | | WP_188352531.1 |
| 439 | Alpha S1 casein (hypothetical protein FD754_018154) | Muntiacus muntjak | KAB0341228.1 |
| 440 | Alpha S1 casein (hypothetical protein FD755_023008) | Muntiacus reevesi | KAB0354470.1 |
| Alpha S2 casein sequences | | | |
| 83 | Optimized alpha S2-casein truncated version 1(OaS2-T) | Artificial (codon optimized Bos taurus) | |
| 84 | Optimized alpha S2-casein truncated version 1(OaS2-T) | Bos taurus | |
| 110 | Alpha S2 casein | Capra hircus | |
| 111 | Alpha S2 casein | Ovis aries | |
| 112 | Alpha S2 casein | Bubalus bubalis | |
| 113 | Alpha S2 casein | Camelus dromedaries | |
| 114 | Alpha S2 casein | Camelus bactrianus | |
| 115 | Alpha S2 casein | Bos mutus | |
| 116 | Alpha S2 casein | Equus caballus | |
| 117 | Alpha S2 casein | Equus asinus | |
| 118 | Alpha S2 casein | Vicugna pacos | |
| 119 | Alpha S2 casein | Bos indicus | |
| 120 | Alpha S2 casein | Lama glama | |
| 441 | Alpha S2 casein | Bos taurus | AAI14774.1 |
| 442 | | | XP_024848786.1 |
| 443 | | | XP_015327143.1 |
| 444 | Alpha S2 casein | Capra hircus | QIS93310.1 |
| 445 | | | NP_001272514.1 |
| 446 | | | CAB94236.1 |
| 447 | | | QIS93322.1 |
| 448 | | | AAB32166.1 |
| 449 | | | QIS93306.1 |
| 450 | | | XP_013820127.2 |
| 451 | | | QIS93323.1 |
| 452 | | | QIZ03322.1 |
| 453 | | | QIS93316.1 |
| 454 | | | CAB59920.1 |
| 455 | | | CAC21704.2 |
| 456 | | | QIS93307.1 |
| 457 | | | XP_013820130.2 |
| 458 | | | QIS93319.1 |

TABLE 35-continued

Milk Protein Sequences of the Disclosure

| SEQ ID NO | Description | Genus/species | Accession Number |
|---|---|---|---|
| 459 | | | QIS93321.1 |
| 460 | | | XP_013820128.2 |
| 461 | | | QIS93304.1 |
| 462 | | | XP_013820129.2 |
| 463 | | | QIS93305.1 |
| 464 | | | QIS93314.1 |
| 465 | | | QIS93317.1 |
| 466 | | | XP_013820132.2 |
| 467 | | | XP_013820131.2 |
| 468 | Alpha S2 casein | *Ovis aries* | ADB65931.1 |
| 469 | | | NP_001009363.1 |
| 470 | | | ADB65933.1 |
| 471 | | | ADB65935.1 |
| 472 | | | ADB65934.1 |
| 473 | | | ADB65932.1 |
| 474 | Alpha S2 casein | *Bubalus bubalis* | NP_001277794.1 |
| 475 | | | AAZ80050.1 |
| 476 | | | CAA06534.2 |
| 477 | | | AFB69498.1 |
| 478 | | | XP_006071185.2 |
| 479 | | | AAZ57423.1 |
| 480 | | | APQ30584.1 |
| 481 | | | XP_025145302.1 |
| 482 | | | XP_025145301.1 |
| 483 | Alpha S2 casein | *Bos mutus* | XP_014335716.1 |
| 484 | | | ELR51813.1 |
| 485 | Alpha S2 casein (hypothetical protein) | *Jeotgalicoccus aerolatus* | WP_188352530.1 |
| 486 | | | GGE08804.1 |
| 487 | Alpha S2 casein (hypothetical protein) | *Jeotgalicoccus coquinae* | WP_188357545.1 |
| 488 | Alpha S2 casein | *Bos grunniens* | AXE74294.1 |
| 489 | Alpha S2 casein | *Bison bison bison* | XP_010850447.1 |
| 490 | Alpha S2 casein | *Bos indicus x Bos taurus* | XP_027401112.1 |
| 491 | Alpha S2 casein | *Odocoileus virginianus texanus* | XP_020729187.1 |
| 492 | Alpha S2 casein (hypothetical protein FD754_018155) | *Muntiacus muntjak* | KAB0341229.1 |
| 493 | Alpha S2 casein (hypothetical protein FD755_022792) | *Muntiacus reevesi* | KAB0354254.1 |
| 494 | Alpha S2 casein (CSN1S2) | *Cervus elaphus hippelaphus* | OWK13818.1 |
| | | Beta-casein sequences | |
| 5 | Optimized beta-casein truncated version 2 (OBC-T2) | Artificial (codon optimized *Bos taurus*) | |
| 6 | Optimized beta-casein truncated version 2 (OBC-T2) | *Bos taurus* | |
| 121 | Beta casein | *Capra hircus* | |
| 122 | Beta casein | *Ovis aries* | |
| 123 | Beta casein | *Bubalus bubalis* | |
| 124 | Beta casein | *Camelus dromedaries* | |
| 125 | Beta casein | *Camelus bactrianus* | |
| 126 | Beta casein | *Bos mutus* | |
| 127 | Beta casein | *Equus caballus* | |
| 128 | Beta casein | *Equus asinus* | |
| 129 | Beta casein | *Alces alces* | |
| 130 | Beta casein | *Vicugna pacos* | |
| 131 | Beta casein | *Bos indicus* | |
| 132 | Beta casein | *Lama glama* | |
| 133 | Beta casein | *Homo sapiens* | |
| 495 | Beta casein | *Bos taurus* | AAB29137.1 |
| 496 | | | AAA30431.1 |
| 497 | | | 1314242A |
| 498 | | | AGT56763.1 |
| 499 | | | AAI11173.1 |
| 500 | | | XP_010804480.2 |
| 501 | | | AAA30430.1 |
| 502 | | | XP_015327157.2 |
| 503 | | | ABR10906.1 |
| 504 | | | ABL74247.1 |
| 505 | | | QCI03091.1 |

TABLE 35-continued

Milk Protein Sequences of the Disclosure

| SEQ ID NO | Description | Genus/species | Accession Number |
|---|---|---|---|
| 506 | | | QCI03090.1 |
| 507 | | | CAC37028.1 |
| 508 | Beta casein | Capra hircus | P33048.1 |
| 509 | | | QIZ03333.1 |
| 510 | | | CAB39200.1 |
| 511 | | | AAK97639.1 |
| 512 | | | XP_005681778.2 |
| 513 | | | QLI42602.1 |
| 514 | | | XP_013820153.1 |
| 515 | | | QLI42606.1 |
| 516 | | | QHN12643.1 |
| 517 | | | ABQ52487.1 |
| 518 | | | QHN12642.1 |
| 519 | | | CAB39313.1 |
| 520 | | | QHN12644.1 |
| 521 | | | AWN06750.1 |
| 522 | Beta casein | Ovis aries | P11839.3 |
| 523 | | | NP_001009373.1 |
| 524 | Beta casein | Bubalus bubalis | QHB80269.1 |
| 525 | | | APQ30585.1 |
| 526 | | | QHB80272.1 |
| 527 | | | QHB80273.1 |
| 528 | | | NP_001277808.1 |
| 529 | | | Q9TSI0.1 |
| 530 | | | XP_006071186.1 |
| 531 | | | CAA06535.1 |
| 532 | | | 1004269A |
| 533 | | | ADD31643.1 |
| 534 | | | ADD31644.1 |
| 535 | | | AAT09469.1 |
| 536 | | | ABL10285.1 |
| 537 | | | ABA41625.1 |
| 538 | | | ABA41623.1 |
| 539 | Beta casein | Bos mutus | MXQ92033.1 |
| 540 | | | XP_014335713.1 |
| 541 | | | XP_005902099.2 |
| 542 | | | XP_014335715.1 |
| 543 | | | XP_014335714.1 |
| 544 | Beta casein | Bos indicus | AQY78354.1 |
| 545 | | | AQY78355.1 |
| 546 | | | ABL75279.1 |
| 547 | | | ABY27644.1 |
| 548 | | | AWN06759.1 |
| 549 | | | AGZ84117.1 |
| 550 | Beta casein | Bison bison bison | XP_010850446.1 |
| 551 | Beta casein (hypothetical protein) | Jeotgalicoccus aerolatus | WP_188352529.1 |
| 552 | Beta casein (hypothetical protein) | Jeotgalicoccus coquinae | WP_188357544.1 |
| 553 | Beta casein (precursor) | Bos indicus x Bos taurus | ARU83745.1 |
| 554 | | | AWN06757.1 |
| 555 | | | AWN06758.1 |
| 556 | Beta casein | Bos grunniens | AXE74295.1 |
| 557 | | | AEY63644.1 |
| 558 | | | AEY63645.1 |
| 559 | | | AEC13563.1 |
| 560 | Beta casein | Neophocaena asiaeorientalis asiaeorientalis | XP_024597374.1 |
| 561 | Beta casein | Odocoileus virginianus texanus | XP_020729180.1 |
| 562 | Beta casein (hypothetical protein FD755_022863) | Muntiacus reevesi | KAB0354325.1 |
| 563 | Beta casein (hypothetical protein FD754_022431) | Muntiacus muntjak | KAB0345505.1 |
| | Beta-Lactoglobulin sequences | | |
| 9 | Optimized Beta Lactoglobulin 1 (OLG1) | Artificial (codon optimized Bos taurus) | |
| 10 | Optimized Beta Lactoglobulin 1 (OLG1) | Bos taurus | |
| 11 | Optimized Beta Lactoglobulin 2 (OLG2) | Artificial (codon optimized Bos taurus) | |

TABLE 35-continued

Milk Protein Sequences of the Disclosure

| SEQ ID NO | Description | Genus/species | Accession Number |
|---|---|---|---|
| 12 | Optimized Beta Lactoglobulin 3 (OLG3) | Artificial (codon optimized Bos taurus) | |
| 13 | Optimized Beta Lactoglobulin 4 (OLG4) | Artificial (codon optimized Bos taurus) | |
| 564 | Beta Lactoglobulin | Bos taurus | 5K06_A |
| 565 | | | IB0O_A |
| 566 | | | NP_776354.2 |
| 567 | | | 3PH5_A |
| 568 | | | 1BEB_A |
| 569 | | | 6QPD_A |
| 570 | | | 6QI7_A |
| 571 | | | DAA24277.1 |
| 572 | | | 5HTD_A |
| 573 | | | 6QPE_A |
| 574 | | | 6RWR_A |
| 575 | | | 1BSO_A |
| 576 | | | 6RWQ_A |
| 577 | | | ACG59280.1 |
| 578 | | | 5NUJ_A |
| 579 | | | 5NUM_A |
| 580 | | | 1UZ2_X |
| 581 | | | CAA32835.1 |
| 582 | | | 1CJ5_A |
| 583 | | | 5NUK_A |
| 584 | | | 5NUN_A |
| 585 | | | 732164A |
| 586 | | | XP_024854027.1 |
| 587 | | | AAA30411.1 |
| 588 | Beta Lactoglobulin | Capra hircus | 4OMW_A |
| 589 | | | NP_001272468.1 |
| 590 | | | ABQ51182.1 |
| 591 | Beta Lactoglobulin | Ovis aries | 4NLI_A |
| 592 | | | NP_001009366.1 |
| 593 | | | 4CK4_A |
| 594 | | | 4CK4_B |
| 595 | Beta Lactoglobulin | Bubalus bubalis | 0601265A |
| 596 | | | P02755.2 |
| 597 | | | NP_001277893.1 |
| 598 | | | Q0Q34530.1 |
| 599 | | | APQ30587.1 |
| 600 | | | ABG78270.1 |
| 601 | Beta Lactoglobulin | Bos mutus | XP_005888577.1 |
| 602 | | | MXQ94840.1 |
| 603 | Beta Lactoglobulin | Bos indicus | XP_019826641.1 |
| 604 | Beta Lactoglobulin (lipocalin/fatty-acid binding family protein) | Jeotgalicoccus coquinae | WP_188357550.1 |
| 605 | Beta Lactoglobulin (lipocalin/fatty-acid binding family protei | Jeotgalicoccus schoeneichii | WP_188349305.1 |
| 606 | Beta Lactoglobulin | Bison bison bison | XP_010855058.1 |
| 607 | Beta Lactoglobulin | Ovis sp. | AAA31510.1 |
| 608 | Beta Lactoglobulin | Ovis aries musimon | P67975.1 |
| 609 | Beta Lactoglobulin | Odocoileus virginianus texanus | XP_020744123.1 |
| 610 | Beta Lactoglobulin, Chain A | Rangifer tarandus | 1YUP_A |
| 611 | Beta Lactoglobulin | Rangifer tarandus tarandus | AAZ57420.1 |
| 612 | Beta Lactoglobulin (hypothetical protein FD754_009020) | Muntiacus muntjak | KAB0364864.1 |
| 613 | Beta Lactoglobulin (hypothetical protein FD755_007442) | Muntiacus reevesi | KAB0379658.1 |
| 614 | Beta Lactoglobulin, Chain A | Equus caballus | 3KZA_A |

NUMBERED EMBODIMENTS

Notwithstanding the appended claims, the following numbered embodiments also form part of the instant disclosure.

Embodiment Set 1: Stably Transformed Plant Expressing a Fusion Protein Comprising Bovine Kappa-Casein and Bovine Beta-Lactoglobulin 1. A stably transformed plant, comprising in its genome: a recombinant DNA construct encoding a fusion protein, the fusion protein comprising: a) bovine kappa-casein; and b) bovine beta-lactoglobulin, wherein the fusion protein is stably expressed in the plant.
2. The stably transformed plant of embodiment 1, wherein the fusion protein comprises, in order from N-terminus to C-terminus, the kappa-casein and the beta-lactoglobulin.
3. The stably transformed plant of embodiment 1, wherein the fusion protein comprises a protease cleavage site.
4. The stably transformed plant of embodiment 3, wherein the protease cleavage site is a chymosin cleavage site.
5. The stably transformed plant of embodiment 1, wherein the fusion protein comprises a signal peptide.
6. The stably transformed plant of embodiment 5, wherein the signal peptide is located at the N-terminus of the fusion protein.
7. The stably transformed plant of embodiment 1, wherein the plant is soybean.
8. The stably transformed plant of embodiment 1, wherein the recombinant DNA construct comprises codon-optimized nucleic acids for expression in the plant.
9. The stably transformed plant of embodiment 1, wherein the fusion protein has a molecular weight of 30 kDa to 50 kDa.
10. The stably transformed plant of embodiment 1, wherein the fusion protein is expressed at a level at least 2-fold higher than kappa-casein expressed individually in a plant.
11. The stably transformed plant of embodiment 1, wherein the fusion protein accumulates in the plant at least 2-fold higher than kappa-casein expressed without beta-lactoglobulin.
12. The stably transformed plant of embodiment 1, wherein the fusion protein is stably expressed in the plant in an amount of 1% or higher per total protein weight of soluble protein extractable from the plant.
13. A transgenic soybean plant, comprising: a recombinant DNA construct encoding a fusion protein, the fusion protein comprising: a) bovine kappa-casein; and b) bovine beta-lactoglobulin, wherein the fusion protein is expressed in the soybean plant.
14. The transgenic soybean plant of embodiment 13, wherein the fusion protein comprises, in order from N-terminus to C-terminus, the kappa-casein and the beta-lactoglobulin.
15. The transgenic soybean plant of embodiment 13, wherein the fusion protein comprises a protease cleavage site.
16. The transgenic soybean plant of embodiment 13, wherein the fusion protein comprises a chymosin cleavage site.
17. The transgenic soybean plant of embodiment 13, wherein the fusion protein has a molecular weight of 30 kDa to 50 kDa.
18. A transgenic soybean plant, comprising: a recombinant DNA construct encoding a fusion protein, the fusion protein comprising a bovine casein and bovine beta-lactoglobulin.
19. The transgenic soybean plant of embodiment 18, wherein the fusion protein comprises, in order from N-terminus to C-terminus, the bovine casein and the beta-lactoglobulin.
20. The transgenic soybean plant of embodiment 18, wherein the fusion protein comprises a protease cleavage site.
21. The transgenic soybean plant of embodiment 18, wherein the fusion protein comprises a chymosin cleavage site.
22. The transgenic soybean plant of embodiment 18, wherein the fusion protein has a molecular weight of 30 kDa to 50 kDa.

Embodiment Set 2: Stably Transformed Plant Expressing a Fusion Protein Comprising Kappa-Casein or Para-Kappa-Casein and Beta-Lactoglobulin 1. A recombinant fusion protein, comprising: a) full-length kappa-casein or para-kappa-casein; and b) beta-lactoglobulin.
2. The recombinant fusion protein of embodiment 1, wherein the fusion protein comprises, in order from N-terminus to C-terminus, the full-length kappa-casein or the para-kappa-casein and the beta-lactoglobulin.
3. The recombinant fusion protein of embodiment 1, further comprising a protease cleavage site.
4. The recombinant fusion protein of embodiment 3, wherein the protease cleavage site is a chymosin cleavage site.
5. The recombinant fusion protein of embodiment 1, further comprising a signal peptide.
6. The recombinant fusion protein of embodiment 5, wherein the signal peptide is located at the N-terminus of the fusion protein.
7. The recombinant fusion protein of embodiment 1, wherein the fusion protein comprises the full-length kappa-casein.
8. The recombinant fusion protein of embodiment 1, wherein the fusion protein comprises para-kappa-casein.
9. The recombinant fusion protein of embodiment 1, wherein the fusion protein has a molecular weight of 30 kDa to 50 kDa.
10. A plant transformed to express the recombinant fusion protein of embodiment 1, wherein the fusion protein is expressed in the plant in an amount of 1% or higher per total protein weight of soluble protein extractable from the plant.
11. A plant transformed to express the recombinant fusion protein of embodiment 1, wherein the fusion protein is expressed in the plant at a level at least 2-fold higher than kappa-casein expressed individually in a plant.
12. A plant transformed to express the recombinant fusion protein of embodiment 1, wherein the fusion protein accumulates in the plant at least 2-fold higher than kappa-casein expressed without beta-lactoglobulin.
13. A fusion protein comprising kappa-casein and beta-lactoglobulin, wherein the kappa-casein is full-length kappa-casein comprising an amino acid sequence having at least 90% sequence identity to SEQ ID NO: 4 or the kappa-casein is para-kappa-casein comprising an amino acid sequence having at least 90% sequence identity to SEQ ID NO: 2 and wherein the beta-lactoglobulin is full-length beta-lactoglobulin comprising an amino acid sequence having at least 90% sequence identity to SEQ ID NO: 10.
14. The fusion protein of embodiment 13, wherein the kappa-casein is full-length kappa-casein comprising an amino acid sequence SEQ ID NO: 4.
15. The fusion protein of embodiment 13, wherein the kappa-casein is para-kappa-casein comprising an amino acid sequence SEQ ID NO: 2.
16. The fusion protein of embodiment 13, wherein the beta-lactoglobulin comprises the amino acid sequence SEQ ID NO: 10.
17. The fusion protein of embodiment 13, further comprising a protease cleavage site between the kappa-casein and beta-lactoglobulin.
18. The fusion protein of embodiment 17, wherein the protease cleavage site is a chymosin cleavage site.
19. The fusion protein of embodiment 13, further comprising a signal peptide.
20. A nucleic acid molecule encoding a fusion protein comprising kappa-casein and beta-lactoglobulin, wherein the kappa-casein is full-length kappa-casein comprising an amino acid sequence having at least 90% sequence identity to SEQ ID NO: 4 or the kappa-casein is para-kappa-casein comprising an amino acid sequence having at least 90% sequence identity to SEQ ID NO: 2 wherein the beta-lactoglobulin is full-length beta-lactoglobulin comprising an amino acid sequence having at least 90% sequence identity to SEQ ID NO: 10.
21. The nucleic acid molecule of embodiment 20, wherein the nucleic acid sequence is codon optimized for expression in a plant.
22. The nucleic acid molecule of embodiment 21, wherein the plant is soybean.
23. An expression vector comprising the nucleic acid molecule of embodiment 20.
24. A host cell comprising the expression vector of embodiment 23.
25. The host cell of embodiment 24, wherein the host cell is selected from the group consisting of plant cells, bacterial cells, fungal cells, and mammalian cells.
26. The host cell of embodiment 25, wherein the host cell is a plant cell.
27. A plant stably transformed with the nucleic acid molecule of embodiment 20.
28. The plant of embodiment 27, wherein the plant is a monocot selected from the group consisting of turf grass, maize, rice, oat, wheat, barley, sorghum, orchid, iris, lily, onion, palm, and duckweed.
29. The plant of embodiment 27, wherein the plant is a dicot selected from the group consisting of *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *quinoa*, buckwheat, mung bean, cow pea, lentil, lupin, peanut, fava bean, French beans, mustard, and cactus.
30. The plant of embodiment 29, wherein the plant is soybean.
31. The plant of embodiment 27, wherein the plant is a non-vascular plant selected from the group consisting of moss, liverwort, hornwort, and algae.
32. The plant of embodiment 27, wherein the plant is a vascular plant reproducing from spores.
33. A method for stably expressing a recombinant fusion protein comprising kappa-casein and beta-lactoglobulin in a plant, wherein the kappa-casein is full-length kappa-casein comprising an amino acid sequence having at least 90% sequence identity to SEQ ID NO: 4 or the kappa-casein is para-kappa-casein comprising an amino acid sequence having at least 90% sequence identity to SEQ ID NO: 2 and wherein the beta-lactoglobulin is full-length beta-lactoglobulin comprising an amino acid sequence having at least 90% sequence identity to SEQ ID NO: 10, the method comprising: (i) transforming a plant with a plant transformation vector comprising an expression cassette comprising a nucleic acid molecule encoding the fusion protein; and (ii) growing the transformed plant under conditions wherein the recombinant fusion protein is expressed.
34. The method of embodiment 33, wherein the fusion protein is expressed in an amount of 1% or higher per the total protein weight of the soluble protein extractable from the plant.
35. The method of embodiment 33, wherein the fusion protein is expressed in the plant at a level at least 2-fold higher than kappa-casein expressed individually in a plant.
36. The method of embodiment 33, wherein the fusion protein accumulates in the plant at least 2-fold higher than kappa-casein is expressed without beta-lactoglobulin.
37. A food composition comprising a fusion protein comprising kappa-casein and beta-lactoglobulin, wherein the kappa-casein is full-length kappa-casein comprising an amino acid sequence having at least 90% sequence identity to SEQ ID NO: 4 or the kappa-casein is para-kappa-casein comprising an amino acid sequence having at least 90% sequence identity to SEQ ID NO: 2 and wherein the beta-lactoglobulin is full-length beta-lactoglobulin comprising an amino acid sequence having at least 90% sequence identity to SEQ ID NO: 10.
38. The food composition of embodiment 37, wherein the food composition is selected from the group consisting of cheese and processed cheese products, yogurt and fermented dairy products, directly acidified counterparts of fermented dairy products, cottage cheese dressing, frozen dairy products, frozen desserts, desserts, baked goods, toppings, icings, fillings, low-fat spreads, dairy-based dry mixes, soups, sauces, salad dressing, geriatric nutrition, creams and creamers, analog dairy products, follow-up formula, baby formula, infant formula, milk, dairy beverages, acid dairy drinks, smoothies, milk tea, butter, margarine, butter alternatives, growing up milks, low-lactose products and beverages, medical and clinical nutrition products, protein/nutrition bar applications, sports beverages, confections, meat products, analog meat products, meal replacement beverages, weight management food and beverages, cultured buttermilk, sour cream, yogurt, skyr, leben, lassi, kefir, powder containing a milk protein, and low-lactose products.

Embodiment Set 3: Recombinant Fusion Protein Comprising Beta-Casein and Beta-Lactoglobulin 1. A recombinant fusion protein, comprising: a) beta-casein; and b) beta-lactoglobulin.

2. The recombinant fusion protein of embodiment 1, further comprising a protease cleavage site.
3. The recombinant fusion protein of embodiment 1, further comprising a chymosin cleavage site.
4. A fusion protein, comprising: beta-casein and beta-lactoglobulin, wherein the beta-casein comprises an amino acid sequence having at least 90% sequence identity to SEQ ID NO: 6 and wherein the beta-lactoglobulin comprises an amino acid sequence having at least 90% sequence identity to SEQ ID NO: 10.
5. The fusion protein of embodiment 4, further comprising a protease cleavage site.
6. The fusion protein of embodiment 4, further comprising a chymosin cleavage site.
7. A nucleic acid molecule encoding a fusion protein comprising beta-casein and beta-lactoglobulin, wherein the beta-casein comprises an amino acid sequence having at least 90% sequence identity to SEQ ID NO: 6 and wherein the beta-lactoglobulin comprises an amino acid sequence having at least 90% sequence identity to SEQ ID NO: 10.
8. The nucleic acid molecule of embodiment 7, wherein the nucleic acid sequence is codon optimized for expression in a plant.
9. The nucleic acid molecule of embodiment 8, wherein the plant is a soybean plant.
10. An expression vector comprising the nucleic acid molecule of embodiment 7.
11. A host cell comprising the expression vector of embodiment 10.
12. The host cell of embodiment 11, wherein the host cell is selected from the group consisting of plant cells, bacterial cells, fungal cells, and mammalian cells.
13. The host cell of embodiment 11, wherein the host cell is a plant cell.
14. A plant stably transformed with the nucleic acid molecule of embodiment 7.
15. The plant of embodiment 14, wherein the plant is a monocot selected from the group consisting of turf grass, maize, rice, oat, wheat, barley, sorghum, orchid, iris, lily, onion, palm, and duckweed.
16. The plant of embodiment 14, wherein the plant is a dicot selected from the group consisting of *Arabidopsis*, tobacco, tomato, potato, sweet potato, cassava, alfalfa, lima bean, pea, chick pea, soybean, carrot, strawberry, lettuce, oak, maple, walnut, rose, mint squash, daisy, *quinoa*, buckwheat, mung bean, cow pea, lentil, lupin, peanut, fava bean, French beans, mustard, and cactus.
17. The plant of embodiment 14, wherein the plant is a soybean plant.
18. A food composition, comprising: a fusion protein comprising beta-casein and beta-lactoglobulin.
19. The food composition of embodiment 18, wherein the food composition is a solid.
20. The food composition of embodiment 18, wherein the food composition is a liquid.
21. The food composition of embodiment 18, wherein the food composition is a powder.
22. The food composition of embodiment 18, wherein the food composition is selected from the group consisting of: cheese, processed cheese product, yogurt, fermented dairy product, directly acidified counterpart of fermented dairy product, cottage cheese, dressing, frozen dairy product, frozen dessert, dessert, baked good, topping, icing, filling, low-fat spread, dairy-based dry mix, soup, sauce, salad dressing, geriatric nutrition, cream, creamer, analog dairy product, follow-up formula, baby formula, infant formula, milk, dairy beverage, acid dairy drink, smoothie, milk tea, butter, margarine, butter alternative, growing up milk, low-lactose product, low-lactose beverage, medical and clinical nutrition product, protein bar, nutrition bar, sport beverage, confection, meat product, analog meat product, meal replacement beverage, weight management food and beverage, dairy product, cultured buttermilk, sour cream, yogurt, skyr, leben, lassi, kefir, powder containing a milk protein, and low-lactose product.
23. The food composition of embodiment 18, wherein the food composition is a dairy product.
24. The food composition of embodiment 18, wherein the food composition is an analog dairy product.
25. The food composition of embodiment 18, wherein the food composition is a low lactose product.
26. The food composition of embodiment 18, wherein the food composition is a milk.
27. The food composition of embodiment 18, wherein the food composition is a cheese.
28. The food composition of embodiment 18, wherein the food composition is fermented.

Embodiment Set 4: Seed Processing Composition

1. A seed processing composition, comprising: a) a fusion protein, comprising i) a full-length kappa-casein or para-kappa-casein component; and ii) a beta-lactoglobulin component; and b) plant seed tissue.
2. The seed processing composition of embodiment 1, wherein the plant seed tissue is ground.
3. The seed processing composition of embodiment 1, wherein the plant seed tissue is soybean.
4. The seed processing composition of embodiment 1, further comprising at least one member selected from the group consisting of: enzyme, protease, chymosin, extractant, solvent, phenol, buffer, additive, salt, protease inhibitor, peptidase inhibitor, osmolyte, and reducing agent.
5. A food composition comprising the seed processing composition of embodiment 1.
6. A protein concentrate composition, comprising a protein concentrate of a fusion protein comprising i) a full-length kappa-casein or para-kappa-casein component, and ii) a beta-lactoglobulin component.
7. The protein concentrate composition of embodiment 6, wherein there is no plant seed tissue present.
8. The protein concentrate composition of embodiment 6, further comprising at least one member selected from the group consisting of: enzyme, protease, chymosin, extractant, solvent, phenol, buffer, additive, salt, protease inhibitor, peptidase inhibitor, osmolyte, and reducing agent.
9. The protein concentrate composition of embodiment 6, further comprising chymosin.
10. A food composition comprising the protein concentrate composition of embodiment 6.
11. A food composition, comprising: a fusion protein, comprising i) a full-length kappa-casein or para-kappa-casein component, and ii) a beta-lactoglobulin component.
12. The food composition of embodiment 11, wherein the food composition comprises the fusion protein comprising the full-length kappa-casein component and a beta-lactoglobulin component.

13. The food composition of embodiment 11, wherein the food composition comprises the fusion protein comprising the para-kappa-casein component and a beta-lactoglobulin component.
14. The food composition of embodiment 11, wherein the food composition is a solid.
15. The food composition of embodiment 11, wherein the food composition is a liquid.
16. The food composition of embodiment 11, wherein the food composition is a powder.
17. The food composition of embodiment 11, wherein the food composition is selected from the group consisting of: cheese, processed cheese product, fermented dairy product, directly acidified counterpart of fermented dairy product, cottage cheese, dressing, frozen dairy product, frozen dessert, dessert, baked good, topping, icing, filling, low-fat spread, dairy-based dry mix, soup, sauce, salad dressing, geriatric nutrition, cream, creamer, analog dairy product, follow-up formula, baby formula, infant formula, milk, dairy beverage, acid dairy drink, smoothie, milk tea, butter, margarine, butter alternative, growing up milk, low-lactose product, low-lactose beverage, medical and clinical nutrition product, protein bar, nutrition bar, sport beverage, confection, meat product, analog meat product, meal replacement beverage, weight management food and beverage, dairy product, cultured buttermilk, sour cream, yogurt, skyr, leben, lassi, kefir, powder containing a milk protein, and low-lactose product.
18. The food composition of embodiment 11, wherein the food composition is a dairy product.
19. The food composition of embodiment 11, wherein the food composition is an analog dairy product.
20. The food composition of embodiment 11, wherein the food composition is a low lactose product.
21. The food composition of embodiment 11, wherein the food composition is a milk.
22. The food composition of embodiment 11, wherein the food composition is a cheese.
23. The food composition of embodiment 11, wherein the food composition is fermented.
24. A method of making a food composition, comprising: combining a fusion protein, comprising i) a full-length kappa-casein or para-kappa-casein component, and ii) a beta-lactoglobulin component, into a food composition.
25. The method of embodiment 24, wherein the food composition is selected from the group consisting of: cheese, processed cheese product, yogurt, fermented dairy product, directly acidified counterpart of fermented dairy product, cottage cheese, dressing, frozen dairy product, frozen dessert, dessert, baked good, topping, icing, filling, low-fat spread, dairy-based dry mix, soup, sauce, salad dressing, geriatric nutrition, cream, creamer, analog dairy product, follow-up formula, baby formula, infant formula, milk, dairy beverage, acid dairy drink, smoothie, milk tea, butter, margarine, butter alternative, growing up milk, low-lactose product, low-lactose beverage, medical and clinical nutrition product, protein bar, nutrition bar, sport beverage, confection, meat product, analog meat product, meal replacement beverage, weight management food and beverage, dairy product, cultured buttermilk, sour cream, yogurt, skyr, leben, lassi, kefir, powder containing a milk protein, and low-lactose product.
26. The method of embodiment 24, wherein the food composition is a dairy product.
27. The method of embodiment 24, wherein the food composition is a cheese.
28. A food composition made by the method of embodiment 24.
29. A method for making a fusion protein, comprising: (a) transforming a host cell with a vector comprising an expression cassette comprising a nucleic acid molecule encoding the fusion protein, wherein the fusion protein comprises i) a full-length kappa-casein or para-kappa-casein component, and ii) a beta-lactoglobulin component, and (b) growing the transformed host cell under conditions wherein the fusion protein is expressed.
30. The method of embodiment 29, wherein the host cell is selected from the group consisting of plant cells, bacterial cells, fungal cells, and mammalian cells.
31. The method of embodiment 29, wherein the host cell is a plant cell.
32. A fusion protein made by the method of embodiment 29.

Embodiment Set 5: Transgenic Plant Comprising a Recombinant DNA Encoding a Fusion Protein Comprising Bovine Casein and Bovine Beta-Lactoglobulin 1. A transgenic plant, comprising: a recombinant DNA construct encoding a fusion protein, the fusion protein comprising a bovine casein and bovine beta-lactoglobulin.
2. The transgenic plant of embodiment 1, wherein the fusion protein comprises a protease cleavage site.
3. The transgenic plant of embodiment 1, wherein the fusion protein comprises a chymosin cleavage site.
4. The transgenic plant of embodiment 1, wherein the fusion protein has a molecular weight of 30 kDa to 50 kDa.
5. A method of making a food composition, comprising: a) extracting the bovine casein and bovine beta-lactoglobulin fusion protein from the transgenic plant of embodiment 1; b) optionally separating the bovine casein from the bovine beta-lactoglobulin; and c) combining the fusion protein or the bovine casein or the bovine beta-lactoglobulin into a food composition.
6. The method of embodiment 5, wherein the food composition is selected from the group consisting of: cheese, processed cheese product, fermented dairy product, directly acidified counterpart of fermented dairy product, cottage cheese, dressing, frozen dairy product, frozen dessert, dessert, baked good, topping, icing, filling, low-fat spread, dairy-based dry mix, soup, sauce, salad dressing, geriatric nutrition, cream, creamer, analog dairy product, follow-up formula, baby formula, infant formula, milk, dairy beverage, acid dairy drink, smoothie, milk tea, butter, margarine, butter alternative, growing up milk, low-lactose product, low-lactose beverage, medical and clinical nutrition product, protein bar, nutrition bar, sport beverage, confection, meat product, analog meat product, meal replacement beverage, weight management food and beverage, dairy product, cultured buttermilk, sour cream, yogurt, skyr, leben, lassi, kefir, powder containing a milk protein, and low-lactose product.
7. The method of embodiment 5, wherein the bovine casein is not separated from the bovine beta-lactoglobulin and the food composition comprises the fusion protein.

8. The method of embodiment 5, wherein the bovine casein is separated from the bovine beta-lactoglobulin and the food composition comprises the bovine casein.
9. The method of embodiment 5, wherein the bovine casein is separated from the bovine beta-lactoglobulin and the food composition comprises the bovine beta-lactoglobulin.
10. The method of embodiment 5, wherein the food composition is a solid.
11. The method of embodiment 5, wherein the food composition is a liquid.
12. The method of embodiment 5, wherein the food composition is a powder.
13. The method of embodiment 5, wherein the food composition is a dairy product.
14. The method of embodiment 5, wherein the food composition is an analog dairy product.
15. The method of embodiment 5, wherein the food composition is a low lactose product.
16. The method of embodiment 5, wherein the food composition is a milk.
17. The method of embodiment 5, wherein the food composition is a cheese.

Embodiment Set 6: Recombinant Fusion Protein Comprising Casein and Beta-Lactoglobulin 1. A recombinant fusion protein, comprising: a) casein; and b) beta-lactoglobulin.
2. The recombinant fusion protein of embodiment 1, further comprising a protease cleavage site.
3. The recombinant fusion protein of embodiment 1, further comprising a chymosin cleavage site.
4. The recombinant fusion protein of embodiment 1, wherein the casein is bovine.
5. The recombinant fusion protein of embodiment 1, wherein the β-lactoglobulin is bovine.
6. The recombinant fusion protein of embodiment 1, wherein the casein and β-lactoglobulin are bovine.
7. A nucleic acid molecule encoding the recombinant fusion protein of embodiment 1.
8. The nucleic acid molecule of embodiment 7, wherein the nucleic acid sequence is codon optimized for expression in a plant.
9. The nucleic acid molecule of embodiment 8, wherein the plant is a soybean plant.
10. An expression vector comprising the nucleic acid molecule of embodiment 7.
11. A host cell comprising the expression vector of embodiment 10.
12. The host cell of embodiment 11, wherein the host cell is selected from the group consisting of plant cells, bacterial cells, fungal cells, and mammalian cells.
13. The host cell of embodiment 11, wherein the host cell is a plant cell. 14. A plant stably transformed with the nucleic acid molecule of embodiment 7.
15. The plant of embodiment 14, wherein the plant is a monocot selected from the group consisting of turf grass, maize, rice, oat, wheat, barley, sorghum, orchid, iris, lily, onion, palm, and duckweed.
16. The plant of embodiment 14, wherein the plant is a dicot selected from the group consisting of *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *quinoa*, buckwheat, mung bean, cow pea, lentil, lupin, peanut, fava bean, French beans, mustard, and cactus.
17. The plant of embodiment 14, wherein the plant is a soybean plant.
18. A food composition, comprising: a fusion protein comprising casein and β-lactoglobulin.
19. The food composition of embodiment 18, wherein the food composition is a solid.
20. The food composition of embodiment 18, wherein the food composition is a liquid.
21. The food composition of embodiment 18, wherein the food composition is a powder.
22. The food composition of embodiment 18, wherein the food composition is selected from the group consisting of: cheese, processed cheese product, yogurt, fermented dairy product, directly acidified counterpart of fermented dairy product, cottage cheese, dressing, frozen dairy product, frozen dessert, dessert, baked good, topping, icing, filling, low-fat spread, dairy-based dry mix, soup, sauce, salad dressing, geriatric nutrition, cream, creamer, analog dairy product, follow-up formula, baby formula, infant formula, milk, dairy beverage, acid dairy drink, smoothie, milk tea, butter, margarine, butter alternative, growing up milk, low-lactose product, low-lactose beverage, medical and clinical nutrition product, protein bar, nutrition bar, sport beverage, confection, meat product, analog meat product, meal replacement beverage, weight management food and beverage, dairy product, cultured buttermilk, sour cream, skyr, leben, lassi, kefir, powder containing a milk protein, and low-lactose product.
23. The food composition of embodiment 18, wherein the food composition is a dairy product.
24. The food composition of embodiment 18, wherein the food composition is an analog dairy product.
25. The food composition of embodiment 18, wherein the food composition is a low lactose product.
26. The food composition of embodiment 18, wherein the food composition is a milk.
27. The food composition of embodiment 18, wherein the food composition is a cheese.
28. The food composition of embodiment 18, wherein the food composition is fermented.

Embodiment Set 7: Food Composition Comprising at Least One Component of a Fusion Protein 1. A food composition, comprising: at least one component of a fusion protein, the fusion protein comprising i) a bovine casein component and ii) a bovine β-lactoglobulin component, wherein the component has been separated from the fusion protein.
2. The food composition of embodiment 1, wherein the food composition comprises the bovine casein component.
3. The food composition of embodiment 1, wherein the food composition comprises the bovine β-lactoglobulin component.
4. The food composition of embodiment 1, wherein the food composition is selected from the group consisting of: cheese, processed cheese product, fermented dairy product, directly acidified counterpart of fermented dairy product, cottage cheese, dressing, frozen dairy product, frozen dessert, dessert, baked good, topping, icing, filling, low-fat spread, dairy-based dry mix, soup, sauce, salad dressing, geriatric nutrition, cream, creamer, analog dairy product, follow-up formula, baby formula, infant formula, milk, dairy beverage, acid dairy drink, smoothie, milk tea, butter, margarine, butter alternative, growing up milk, low-lactose product, low-lactose beverage, medical and clinical nutrition product, protein bar, nutrition bar, sport beverage, confection, meat product, analog meat product, meal replacement beverage, weight management food and beverage, dairy product, cultured buttermilk, sour cream, yogurt, skyr, leben, lassi, kefir, powder containing a milk protein, and low-lactose product.

5. The food composition of embodiment 1, wherein the food composition is a solid.
6. The food composition of embodiment 1, wherein the food composition is a liquid.
7. The food composition of embodiment 1, wherein the food composition is a powder.
8. The food composition of embodiment 1, wherein the food composition is a dairy product.
9. The food composition of embodiment 1, wherein the food composition is an analog dairy product.
10. The food composition of embodiment 1, wherein the food composition is a low lactose product.
11. The food composition of embodiment 1, wherein the food composition is a milk.
12. The food composition of embodiment 1, wherein the food composition is a cheese.
13. The food composition of embodiment 1, wherein the food composition is fermented.
14. A food composition, comprising: a fusion protein comprising bovine casein and bovine β-lactoglobulin.
15. The food composition of embodiment 14, wherein the fusion protein comprises a protease cleavage site.
16. The food composition of embodiment 14, wherein the fusion protein comprises a chymosin cleavage site.
17. The food composition of embodiment 14, wherein the fusion protein has a molecular weight of 30 kDa to 50 kDa.
18. The food composition of embodiment 14, wherein the food composition is selected from the group consisting of: cheese, processed cheese product, fermented dairy product, directly acidified counterpart of fermented dairy product, cottage cheese, dressing, frozen dairy product, frozen dessert, dessert, baked good, topping, icing, filling, low-fat spread, dairy-based dry mix, soup, sauce, salad dressing, geriatric nutrition, cream, creamer, analog dairy product, follow-up formula, baby formula, infant formula, milk, dairy beverage, acid dairy drink, smoothie, milk tea, butter, margarine, butter alternative, growing up milk, low-lactose product, low-lactose beverage, medical and clinical nutrition product, protein bar, nutrition bar, sport beverage, confection, meat product, analog meat product, meal replacement beverage, weight management food and beverage, dairy product, cultured buttermilk, sour cream, yogurt, skyr, leben, lassi, kefir, powder containing a milk protein, and low-lactose product.
19. The food composition of embodiment 14, wherein the food composition is a solid.
20. The food composition of embodiment 14, wherein the food composition is a liquid.
21. The food composition of embodiment 14, wherein the food composition is a powder.
22. The food composition of embodiment 14, wherein the food composition is a dairy product.
23. The food composition of embodiment 14, wherein the food composition is an analog dairy product.
24. The food composition of embodiment 14, wherein the food composition is a low lactose product.
25. The food composition of embodiment 14, wherein the food composition is a milk.
26. The food composition of embodiment 14, wherein the food composition is a cheese.
27. The food composition of embodiment 14, wherein the food composition is fermented.
28. The food composition of embodiment 14, wherein the fusion protein is a plant expressed fusion protein.
29. The food composition of embodiment 14, wherein the fusion protein is a soybean expressed fusion protein.

Embodiment Set 8: Alternative Diary Food Composition

1. An alternative dairy food composition comprising: i) a recombinant beta-casein protein, and ii) at least one lipid, wherein the alternative dairy food composition does not comprise any other milk proteins; and wherein the recombinant beta-casein protein confers on the alternative dairy food composition one or more characteristics of a dairy food product selected from the group consisting of: taste, aroma, appearance, handling, mouthfeel, density, structure, texture, elasticity, springiness, coagulation, binding, leavening, aeration, foaming, creaminess and emulsification.
2. The alternative dairy food composition of embodiment 1, wherein the recombinant beta-casein is plant-expressed.
3. The alternative dairy food composition of embodiment 2, wherein the recombinant beta-casein is expressed in a soybean plant.
4. The alternative dairy food composition of embodiment 1, wherein the composition comprises a fusion protein comprising the recombinant beta-casein.
5. The alternative dairy food composition of embodiment 1, wherein the composition is a milk composition, a cream composition, a yogurt composition, an ice cream composition, a frozen custard composition, a frozen dessert composition, a crème fraiche composition, a curd composition, a cottage cheese composition, or a cream cheese composition.
6. The alternative dairy food composition of embodiment 1, wherein the composition comprises at least one salt.
7. The alternative dairy food composition of embodiment 1, wherein the composition comprises calcium.
8. The alternative dairy food composition of embodiment 1, wherein the composition comprises calcium at a concentration of about 0.01% to about 2% by weight.
9. The alternative dairy food composition of embodiment 1, wherein the composition has a pH of about 4 to about 8.
10. The alternative dairy food composition of embodiment 1, wherein the composition comprises a fusion protein comprising the recombinant beta-casein.

Embodiment Set 9: Alternative Diary Food Composition

1. A cheese composition comprising recombinant casein protein; wherein about 32% to 100% by weight of the total casein protein in the cheese composition is beta-casein; and wherein the cheese composition has the ability to stretch to at least 3 cm in length without breaking, as determined by heating a 100 gram mass of the composition at a temperature of 225° C. for 4 minutes and cooling to about 90° C. and pulling with a fork placed beneath the mass.
2. The cheese composition of embodiment 1, wherein the composition does not comprise any casein proteins other than beta-casein.
3. The cheese composition of embodiment 1, wherein the composition comprises at least one additional casein protein.
4. The cheese composition of embodiment 3, wherein at least 80% by weight of the total casein protein in the composition is beta-casein.
5. The cheese composition of embodiment 3, wherein at least 90% by weight of the total casein protein in the composition is beta-casein.
6. The cheese composition of embodiment 3, wherein at least 95% by weight of the total casein protein in the composition is beta-casein.
7. The cheese composition of embodiment 3, wherein the at least one additional casein protein is selected from kappa-casein, para-kappa-casein, beta-casein, alpha-S1-casein and alpha-S2-casein.
8. The cheese composition of embodiment 3, wherein the at least one additional casein protein is kappa-casein.
9. The cheese composition of embodiment 3, wherein the at least one additional casein protein is para-kappa casein.
10. The cheese composition of embodiment 1, wherein the recombinant beta-casein is plant-expressed.
11. The cheese composition of embodiment 10, wherein the recombinant beta-casein is expressed in a soybean plant.
12. The cheese composition of embodiment 3, wherein all caseins in the composition are plant-expressed.
13. The cheese composition of embodiment 1, wherein the recombinant beta-casein protein is derived from a fusion protein.
14. The cheese composition of embodiment 1, wherein the composition does not contain an organoleptically functional amount of beta-lactoglobulin.
15. The cheese composition of embodiment 1, wherein the composition has the ability to stretch to at least 5 cm in length without breaking, as determined by heating a 100 gram mass of the composition at a temperature of 225° C. for 4 minutes and cooling to about 90° C. and pulling with a fork placed beneath the mass.
16. The cheese composition of embodiment 1, wherein the composition has the ability to stretch to at least 3 cm in length without breaking, as determined by heating a 100 gram mass of the composition at a temperature of 225° C. for 4 minutes and cooling to about 90° C. and pulling with a fork placed beneath the mass; and a firmness of at least 150 grams, as determined by compressing a cylindrical-shaped sample of the cheese composition having a height of 3 cm and a diameter of 3 cm to a height of 1.5 cm at 5° C.
17. The cheese composition of embodiment 1, wherein the composition comprises at least one lipid and at least one salt.
18. The cheese composition of embodiment 1, wherein the composition comprises calcium.
19. The cheese composition of embodiment 18, wherein the composition comprises calcium at a concentration of about 0.01% to about 2% by weight.
20. The cheese composition of embodiment 1, wherein the composition has a pH of about 5.2 to about 5.9.
21. The cheese composition of embodiment 1, wherein the composition comprises at least one organoleptic property similar to cheese produced from mammalian milk selected from the group consisting of taste, appearance, mouthfeel, structure, texture, density, elasticity, springiness, coagulation, binding, leavening, aeration, foaming, creaminess, and emulsification.
22. A method of making the cheese composition of embodiment 1, the method comprising expressing the recombinant beta-casein protein in a plant, extracting the beta-casein from the plant, and combining the beta-casein with at least one lipid and/or salt.
23. A cheese composition comprising a recombinant casein protein; wherein about 32% to 100% by weight of the total casein protein in the cheese composition is beta-casein; and wherein the cheese composition has ability to stretch to at least 5 cm in length without breaking, as determined by heating a 100 gram mass of the composition at a temperature of 225° C. for 4 minutes and cooling to about 90° C. and pulling with a fork placed beneath the mass.
24. The cheese composition of embodiment 23, wherein the composition does not comprise any additional casein proteins.
25. The cheese composition of embodiment 23, wherein the composition comprises at least one additional casein protein, and wherein at least 80% by weight of the total casein protein in the composition is beta-casein.
26. The cheese composition of embodiment 25, wherein the at least one additional casein protein is kappa-casein or para-kappa casein.
27. The cheese composition of embodiment 23, wherein the recombinant beta-casein is plant-expressed.
28. The cheese composition of embodiment 23, wherein the recombinant beta-casein protein is derived from a fusion protein.
29. The cheese composition of embodiment 23, wherein the composition has at least one of the following characteristics: i) a firmness of at least 150 grams, as determined by compressing a cylindrical-shaped sample of the cheese composition having a height of 3 cm and a diameter of 3 cm to a height of 1.5 cm at 5° C.; or ii) a melting point of about 35° C. to about 100° C.
30. A method of making the cheese composition of embodiment 23, the method comprising expressing the recombinant beta-casein protein in a plant, extracting the beta-casein from the plant, and combining the beta-casein with at least one lipid and/or salt.

Embodiment Set 10: Fusion Protein Comprising First and Second Milk Proteins, and Transformed Plants Expressing the Same 1. A transformed plant comprising in its genome: a recombinant DNA construct encoding a fusion protein, the fusion protein comprising a first protein and a second protein, wherein the first protein and/or second protein is a milk protein, and wherein the fusion protein is expressed in the plant in an amount of 1% or higher per total protein weight of soluble protein extractable from the plant.
2. The transformed plant of embodiment 1, wherein the fusion protein comprises, from N-terminus to C-terminus, the first protein and the second protein.
3. The transformed plant of embodiment 1, wherein the fusion protein comprises, from N-terminus to C-terminus, the second protein and the first protein.

4. The transformed plant of any one of embodiments 1-3, wherein the milk protein is α-S1 casein, α-S2 casein, β-casein, κ-casein, para-κ-casein, β-lactoglobulin, α-lactalbumin, lysozyme, lactoferrin, lactoperoxidase, or an immunoglobulin.
5. The transformed plant of any one of embodiments 1-3, wherein the milk protein is selected from the group consisting of: SEQ ID NO: 4, or a sequence at least 90% identical thereto; SEQ ID NO: 2, or a sequence at least 90% identical thereto; SEQ ID NO: 6, or a sequence at least 90% identical thereto; SEQ ID NO: 8, or a sequence at least 90% identical thereto; SEQ ID NO: 84, or a sequence at least 90% identical thereto; and SEQ ID NO: 10, or a sequence at least 90% identical thereto.
6. The transformed plant of any one of embodiments 1-5, wherein each of the first protein and the second protein are milk proteins.
7. The transformed plant of any one of embodiments 1-5, wherein the first protein is a milk protein and the second protein is a non-milk protein.
8. The transformed plant of embodiment 7, wherein the non-milk protein is albumin, hemoglobin, collagen, ovalbumin, ovotransferrin, GFP, or ovoglobulin.
9. The transformed plant of embodiment 6, wherein the first protein and the second protein are each casein proteins.
10. The transformed plant of any one of embodiments 1-9, wherein the plant is a dicot.
11. The transformed plant of embodiment 10, wherein the dicot is *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, or cactus.
12. The transformed plant of any one of embodiments 1-9, wherein the plant is soybean.
13. The transformed plant of any one of embodiments 1-12, wherein the fusion protein is stably expressed.
14. The transformed plant of any one of embodiments 1-12, wherein the fusion protein is transiently expressed.
15. The transformed plant of any one of embodiments 1-14, wherein the recombinant DNA construct is codon-optimized for expression in the plant.
16. The transformed plant of any one of embodiments 1-15, wherein the fusion protein comprises a protease cleavage site.
17. The transformed plant of embodiment 16, wherein the protease cleavage site is a chymosin cleavage site.
18. The transformed plant of any one of embodiments 1-17, wherein the fusion protein is expressed at a level at least 2-fold higher than a casein protein expressed individually in a plant.
19. A recombinant fusion protein comprising a first protein and a second protein, wherein at least one of the first protein and the second protein is a milk protein.
20. The recombinant fusion protein of embodiment 19, wherein the fusion protein comprises, from N-terminus to C-terminus, the first protein and the second protein.
21. The recombinant fusion protein of embodiment 19, wherein the fusion protein comprises, from N-terminus to C-terminus, the second protein and the first protein.
22. The recombinant fusion protein of any one of embodiments 19-21, wherein the milk protein is α-S1 casein, α-S2 casein, β-casein, κ-casein, para-κ-casein, β-lactoglobulin, α-lactalbumin, lysozyme, lactoferrin, lactoperoxidase, or an immunoglobulin.
23. The recombinant fusion protein of any one of embodiments 19-21, wherein the milk protein is selected from the group consisting of: SEQ ID NO: 4, or a sequence at least 90% identical thereto; SEQ ID NO: 2, or a sequence at least 90% identical thereto; SEQ ID NO: 6, or a sequence at least 90% identical thereto; SEQ ID NO: 8, or a sequence at least 90% identical thereto; SEQ ID NO: 84, or a sequence at least 90% identical thereto; and SEQ ID NO: 10, or a sequence at least 90% identical thereto.
24. The recombinant fusion protein of any one of embodiments 19-23, wherein the first protein and the second protein are milk proteins.
25. The recombinant fusion protein of any one of embodiments 19-23, wherein the first protein is a milk protein and the second protein is a non-milk protein.
26. The recombinant fusion protein of embodiment 25, wherein the non-milk protein is albumin, hemoglobin, collagen, ovalbumin, ovotransferrin, GFP, or ovoglobulin.
27. The recombinant fusion protein of embodiment 24, wherein the first protein and the second protein are each casein proteins.
28. The recombinant fusion protein of embodiment 27, wherein the first protein and the second protein are the same casein protein.
29. The recombinant fusion protein of embodiment 27, wherein the first protein and the second protein are both α-S1 casein, α-S2 casein, β-casein, κ-casein, or para-κ-casein.
30. The recombinant fusion protein of embodiment 24, wherein the first protein and the second protein are each casein proteins and are different from one another.
31. The recombinant fusion protein of embodiment 30, wherein the first protein and the second protein are each independently selected from α-S1 casein, α-S2 casein, β-casein, κ-casein, and para-κ-casein.
32. A recombinant fusion protein comprising a casein protein and lysozyme, wherein the casein protein is selected from the group consisting of α-S1 casein, α-S2 casein, β-casein, κ-casein, and para-κ-casein.
33. A recombinant fusion protein comprising a casein protein and β-lactoglobulin, wherein the casein protein is selected from the group consisting of α-S1 casein, α-S2 casein, β-casein, κ-casein, and para-κ-casein.
34. The recombinant fusion protein of any one of embodiments 19-33, wherein the fusion protein comprises a protease cleavage site.
35. The recombinant fusion protein of embodiment 34, wherein the protease cleavage site is a chymosin cleavage site.
36. A nucleic acid encoding the recombinant fusion protein of any one of embodiments 19-35.
37. The nucleic acid of embodiment 36, wherein the nucleic acid is codon optimized for expression in a plant species.
38. The nucleic of embodiment 36, wherein the nucleic acid is codon optimized for expression in soybean.
39. A vector comprising a nucleic acid encoding a recombinant fusion protein, wherein the recombinant fusion protein comprises a first protein and a second protein, wherein at least one of the first protein and the second protein is a milk protein.
40. The vector of embodiment 39, wherein the vector is a plasmid.
41. The vector of embodiment 40, wherein the vector is an *Agrobacterium* Ti plasmid.

42. The vector of any one of embodiments 39-41, wherein the nucleic acid comprises, in order from 5' to 3': a promoter; a 5' untranslated region; a sequence encoding the fusion protein of any one of embodiments 19-35; and a terminator.

43. The vector of embodiment 42, wherein the promoter is a seed-specific promoter.

44. The vector of embodiment 43, wherein the seed-specific promoter is selected from the group consisting of PvPhas, BnNap, AtOle1, GmSeed2, GmSeed3, GmSeed5, GmSeed6, GmSeed7, GmSeed8, GmSeed10, GmSeed11, GmSeed12, pBCON, GmCEP1-L, GmTHIC, GmBg7S1, GmGRD, GmOLEA, GmOLER, Gm2S-1, and GmBBld-II.

45. The vector of embodiment 43, wherein the seed-specific promoter is PvPhas and comprises the sequence of SEQ ID NO: 18, or a sequence at least 90% identical thereto.

46. The vector of embodiment 43, wherein the seed-specific promoter is GmSeed2 and comprises the sequence of SEQ ID NO: 19, or a sequence at least 90% identical thereto.

47. The vector of embodiment 42, wherein the 5' untranslated region is selected from the group consisting of Arc5'UTR and glnB1UTR.

48. The vector of embodiment 47, wherein the 5' untranslated region is Arc5'UTR and comprises the sequence of SEQ ID NO: 20, or a sequence at least 90% identical thereto.

49. The vector of embodiment 42, wherein the expression cassette comprises a 3' untranslated region.

50. The vector of embodiment 49, wherein the 3' untranslated region is Arc5-1 and comprises SEQ ID NO: 21, or a sequence at least 90% identical thereto.

51. The vector of embodiment 42, wherein the terminator sequence is a terminator isolated or derived from a gene encoding Nopaline synthase, Arc5-1, an Extensin, Rb7 matrix attachment region, a Heat shock protein, Ubiquitin 10, Ubiquitin 3, and M6 matrix attachment region.

52. The vector of embodiment 42, wherein the terminator sequence is isolated or derived from a Nopaline synthase gene and comprises the sequence of SEQ ID NO: 22, or a sequence at least 90% identical thereto.

53. The vector of embodiment 42, wherein the terminator sequence is a dual terminator and is selected from the group consisting of: SEQ ID NO: 138, or a sequence at least 90% identical thereto; SEQ ID NO: 141, or a sequence at least 90% identical thereto; SEQ ID NO: 144, or a sequence at least 90% identical thereto; and SEQ ID NO: 146, or a sequence at least 90% identical thereto.

54. A plant-expressed recombinant fusion protein, comprising: κ-casein and β-lactoglobulin.

55. The plant-expressed recombinant fusion protein of embodiment 54, wherein the fusion protein comprises, in order from N-terminus to C-terminus, the κ-casein and the β-lactoglobulin.

56. The plant-expressed recombinant fusion protein of embodiment 54 or 55, wherein the fusion protein comprises a protease cleavage site.

57. The plant-expressed recombinant fusion protein of embodiment 56, wherein the protease cleavage site is a chymosin cleavage site.

58. The plant-expressed recombinant fusion protein of any one of embodiments 55-57, wherein the fusion protein comprises a signal peptide.

59. The plant-expressed recombinant fusion protein of embodiment 58, wherein the signal peptide is located at the N-terminus of the fusion protein.

60. The plant-expressed recombinant fusion protein of any one of embodiments 55-59, wherein the fusion protein is encoded by a nucleic acid that is codon optimized for expression in a plant.

61. The plant-expressed recombinant fusion protein of any one of embodiments 55-60, wherein the fusion protein is expressed in a soybean.

62. The plant-expressed recombinant fusion protein of any one of embodiments 55-61, wherein the fusion protein has a molecular weight of 30 kDa to 50 kDa.

63. The plant-expressed recombinant fusion protein of any one of embodiments 55-62, wherein the fusion protein is expressed in a plant in an amount of 1% or higher per total protein weight of soluble protein extractable from the plant.

64. The plant-expressed recombinant fusion protein of any one of embodiments 55-62, wherein the fusion protein is expressed in the plant at a level at least 2-fold higher than κ-casein expressed individually in a plant.

65. The plant-expressed recombinant fusion protein of any one of embodiments 55-62, wherein the fusion protein accumulates in the plant at least 2-fold higher than κ-casein expressed without β-lactoglobulin.

66. A stably transformed plant, comprising in its genome: a recombinant DNA construct encoding a fusion protein, the fusion protein comprising: κ-casein and β-lactoglobulin; wherein the fusion protein is stably expressed in the plant in an amount of 1% or higher per total protein weight of soluble protein extractable from the plant.

67. The stably transformed plant of embodiment 66, wherein the fusion protein comprises, in order from N-terminus to C-terminus, the κ-casein and the β-lactoglobulin.

68. The stably transformed plant of embodiment 66 or 67, wherein the fusion protein comprises a protease cleavage site.

69. The stably transformed plant of embodiment 68, wherein the protease cleavage site is a chymosin cleavage site.

70. The stably transformed plant of any one of embodiments 66-69, wherein the fusion protein comprises a signal peptide.

71. The stably transformed plant of embodiment 70, wherein the signal peptide is located at the N-terminus of the fusion protein.

72. The stably transformed plant of any one of embodiments 66-71, wherein the plant is soybean.

73. The stably transformed plant of any one of embodiments 66-72, wherein the recombinant DNA construct comprises codon-optimized nucleic acids for expression in the plant.

74. The stably transformed plant of any one of embodiments 66-73, wherein the fusion protein has a molecular weight of 30 kDa to 50 kDa.

75. The stably transformed plant of any one of embodiments 66-74, wherein the fusion protein is expressed at a level at least 2-fold higher than κ-casein expressed individually in a plant.

76. The stably transformed plant of any one of embodiments 66-74, wherein the fusion protein accumulates in the plant at least 2-fold higher than κ-casein expressed without β-lactoglobulin.

77. A plant-expressed recombinant fusion protein comprising: a casein protein and β-lactoglobulin.
78. The plant-expressed recombinant fusion protein of embodiment 77, wherein the casein protein is α-S1 casein, α-S2 casein, β-casein, or κ-casein.
79. A stably transformed plant, comprising in its genome: a recombinant DNA construct encoding a fusion protein, the fusion protein comprising: a casein protein and β-lactoglobulin; wherein the fusion protein is stably expressed in the plant in an amount of 1% or higher per total protein weight of soluble protein extractable from the plant.
80. The stably transformed plant of embodiment 79, wherein the casein protein is α-S1 casein, α-S2 casein, β-casein, or κ-casein.
81. A method for stably expressing a recombinant fusion protein in a plant, the method comprising: (a) transforming a plant with a plant transformation vector comprising an expression cassette comprising: a sequence encoding a fusion protein, wherein the fusion protein comprises a first protein and a second protein, wherein at least one of the first protein and the second protein is a milk protein; and (b) growing the transformed plant under conditions wherein the recombinant fusion protein is expressed in an amount of 1% or higher per total protein weight of soluble protein extractable from the plant.
82. The method of embodiment 81, wherein the wherein the milk protein is α-S1 casein, α-S2 casein, β-casein, κ-casein, para-κ-casein, β-lactoglobulin, α-lactalbumin, lysozyme, lactoferrin, lactoperoxidase, or an immunoglobulin.

Embodiment Set 11: Casein Multimers

1. A fusion protein comprising a first, second, third, and fourth protein, wherein the third protein is kappa-casein.
2. The fusion protein of embodiment 1 wherein: the first protein beta-casein; the second protein is beta-casein; and the fourth protein is beta-lactoglobulin.
3. The fusion protein of embodiment 1 or 2, wherein the kappa-casein comprises a chymosin cleavage site.
4. The fusion protein of embodiment 1, wherein cleavage of the fusion protein with chymosin produces the following polypeptides: a first polypeptide comprising the first protein, the second protein, and para-kappa-casein; and a second polypeptide comprising a kappa-casein macropeptide and the fourth protein.
5. A nucleic acid encoding the fusion protein of any one of embodiments 1-4.
6. A transformed plant comprising the fusion protein of any one of embodiments 1~4 or the nucleic acid of embodiment 5.
7. A food composition comprising the fusion protein of any one of embodiments 1-6.
8. A food composition comprising a first, second, third or fourth protein, wherein the first, second, third, our fourth protein is derived from the fusion protein of any one of embodiments 1-7.
9. A method of making a food composition, the method comprising: (i) expressing a fusion protein in a transformed plant; (ii) preparing a food composition comprising the fusion protein and plant protein from the same transformed plant in which the fusion protein was produced.
10. The method of embodiment 9, wherein the transformed plant is soybean.
11. A food composition produced using the method of any one of embodiments 9-10.

Embodiment Set No. 12: Fusion Protein Comprising Milk Protein and a Fusion Partner 1. A fusion protein comprising a first protein and a second protein, wherein the first protein is a milk protein, and the second protein comprises at least one of the following characteristics: a molecular weight of 15 kDa or higher; at least 30% hydrophobic amino acids; and/or less than about 2.5 disulfide bonds per 10 kDa molecular weight.
2. The fusion protein of embodiment 1, wherein the second protein comprises at least two of the characteristics (i), (ii) and (iii).
3. The fusion protein of embodiment 1, wherein the second protein comprises all three of the characteristics (i), (ii) and (iii).
4. The fusion protein of any one of embodiments 1-3, wherein the fusion protein comprises a protease cleavage site located between the first protein and the second protein.
5. The fusion protein of embodiment 4, wherein the protease cleavage site is a chymosin cleavage site.
6. The fusion protein of embodiment 4 or 5, wherein cleavage of the fusion protein with a protease separates the first protein from the second protein.
7. The fusion protein of embodiment 6, wherein after being separated from one another, the first protein and/or the second protein optionally comprise at their N-terminus or C-terminus one or more amino acids that do not occur in the native form of the first protein or the second protein and that are derived from the protease cleavage site.
8. A nucleic acid encoding the fusion protein of any one of embodiments 1-7.
9. A transformed plant comprising the fusion protein of any one of embodiments 1-7 or the nucleic acid of embodiment 8.
10. A food composition comprising the fusion protein of any one of embodiments 1-7.

Embodiment Set 13: Co-Expression of a Milk Protein and a Protein Capable of Forming a Protein Body 1. A composition comprising a first vector and a second vector, wherein the first vector comprises a sequence that encodes a milk protein, and the second vector comprises a sequence that encodes a prolamin.
2. A composition comprising a vector, wherein the vector comprises: a first sequence that encodes a milk protein; and a second sequence that encodes a prolamin.
3. The composition of any one of embodiments 1-2, wherein the milk protein is selected from the group consisting of: α-S1 casein, α-S2 casein, β-casein, κ-casein, para-κ-casein, β-lactoglobulin, α-lactalbumin, lysozyme, lactoferrin, lactoperoxidase, and an immunoglobulin.
4. The composition of embodiment 3, wherein the milk protein is the β-casein.
5. The composition of embodiment 3, wherein the milk protein is the β-lactoglobulin.

6. The composition of any one of embodiments 1-5, wherein the prolamin is selected from the group consisting of: gliadin, a hordein, a secalin, a zein, a kafirin, and an avenin.
7. The composition of embodiment 6, wherein the prolamin is a zein.
8. A plant comprising the composition of any one of embodiments 1-7.
9. A method for stably expressing one or more recombinant proteins in a plant, the method comprising transforming a plant with the composition of any one of embodiments 1-7, thereby stably expressing one or more recombinant proteins in the plant.
10. The method of embodiment 9, wherein the method is effective in: (a) increasing expression of the one or more recombinant proteins in the plant, relative to expression of the milk protein alone, without co-expression of the prolamin; (b) increasing accumulation of the milk protein in the plant, relative to expression of the milk protein alone, without co-expression of the prolamin; or (c) (a) and (b).
11. The method of embodiment 9 or 10, comprising (a), wherein the method is effective in increasing expression of the milk protein by at least about 1-fold, 5-fold, 50-fold, or 100-fold.
12. The method of embodiment 9 or 10, comprising (b), wherein the method is effective in increasing accumulation of the milk protein in the plant by at least about 1-fold, 5-fold, 10-fold, or 50-fold.
13. A food composition that comprises a recombinant protein isolated from the plant of any one of embodiments 9-12.

Embodiment Set 14: Fusion Protein Comprising a Milk Protein and a Protein Capable of Forming a Protein Body 1. A recombinant fusion protein comprising a prolamin protein and a milk protein.
2. The recombinant fusion protein of embodiment 1, wherein the milk protein is a casein protein.
3. The recombinant fusion protein of embodiment 2, wherein the casein protein is α-S1 casein, α-S2 casein, β-casein, κ-casein, or para-κ-casein.
4. The recombinant fusion protein of embodiment 1, wherein the milk protein is β-lactoglobulin, α-lactalbumin, lysozyme, lactoferrin, lactoperoxidase, or an immunoglobulin.
5. The recombinant fusion protein of any one of embodiments 1-4, wherein the prolamin protein is a gliadin, a hordein, a secalin, a zein, a kafirin, or an avenin.
6. The recombinant fusion protein of embodiment 5, wherein the prolamin protein is a zein.
7. The recombinant fusion protein of embodiment 6, wherein the zein has the sequence of any one of SEQ ID NO: 800, 809 or 811, or a sequence at least 90% identical thereto.
8. The recombinant fusion protein of embodiment 1, wherein the prolamin protein is a canein.
9. The recombinant fusion protein of embodiment 8, wherein the canein has the sequence of any one of SEQ ID NO: 800, 809 or 811, or a sequence at least 90% identical thereto.
10. The recombinant fusion protein of embodiment 1, wherein the fusion protein has a sequence of SEQ ID NO: 803 or 807, or a sequence at least 90% identical thereto.
11. A nucleic acid encoding the recombinant fusion protein of any one of embodiments 1-10.
12. A transgenic plant comprising the recombinant fusion protein of any one of embodiments 1-10 or the nucleic acid of embodiment 11.
13. The transgenic plant of embodiment 12, wherein the plant is a dicot.
14. The transgenic plant of embodiment 13, wherein the dicot is *arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, or cactus.
15. The transgenic plant of embodiment 13, wherein dicot is a soybean.
16. A food composition comprising the recombinant fusion protein of any one of embodiments 1-10, or a prolamin protein or milk protein derived therefrom.
17. A protein body comprising a recombinant fusion protein of any one of embodiments 1-10.
18. The protein body of embodiment 17, wherein a transgenic plant comprises the protein body.
19. The protein body of embodiment 18, wherein the transgenic plant is a dicot.
20. The protein body of embodiment 19, wherein the dicot is a soybean.

Embodiment Set 15: Fusion Protein Comprising an Unstructured Milk Protein and a Structured Protein; Transgenic Plants Expressing the Same 1. A stably transformed plant comprising in its genome: a recombinant DNA construct encoding a fusion protein, the fusion protein comprising: (i) an unstructured milk protein, and (ii) a structured animal protein; wherein the fusion protein is stably expressed in the plant in an amount of 1% or higher per total protein weight of soluble protein extractable from the plant.
2. The stably transformed plant of embodiment 1, wherein the fusion protein comprises, from N-terminus to C-terminus, the unstructured milk protein and the animal protein.
3. The stably transformed plant of any one of embodiments 1-2, wherein the unstructured milk protein is α-S1 casein, α-S2 casein, β-casein, or κ-casein.
4. The stably transformed plant of embodiment 1, wherein the unstructured milk protein is κ-casein and comprises the sequence of SEQ ID NO: 4, or a sequence at least 90% identical thereto.
5. The stably transformed plant of embodiment 1, wherein the unstructured milk protein is para-κ-casein and comprises the sequence of SEQ ID NO: 2, or a sequence at least 90% identical thereto.
6. The stably transformed plant of embodiment 1, wherein the unstructured milk protein is β-casein and comprises the sequence of SEQ ID NO: 6, or a sequence at least 90% identical thereto.
7. The stably transformed plant of embodiment 1, wherein the unstructured milk protein is α-S1 casein and comprises the sequence SEQ ID NO: 8, or a sequence at least 90% identical thereto.
8. The stably transformed plant of embodiment 1, wherein the unstructured milk protein is α-S2 casein and comprises the sequence SEQ ID NO: 84, or a sequence at least 90% identical thereto.
9. The stably transformed plant of any one of embodiments 1-8, wherein the structured animal protein is a structured mammalian protein.

10. The stably transformed plant of embodiment 9, wherein the structured mammalian protein is β-lactoglobulin, α-lactalbumin, albumin, lysozyme, lactoferrin, lactoperoxidase, hemoglobin, collagen, or an immunoglobulin.
11. The stably transformed plant of embodiment 9, wherein the structured mammalian protein is β-lactoglobulin and comprises the sequence of SEQ ID NO: 10, or a sequence at least 90% identical thereto.
12. The stably transformed plant of any one of embodiments 1-8, wherein the structured animal protein is a structured avian protein.
13. The stably transformed plant embodiment 12, wherein the structured avian protein is ovalbumin, ovotransferrin, lysozyme or ovoglobulin.
14. The stably transformed plant of embodiment 9, wherein the milk protein is κ-casein and the structured mammalian protein is β-lactoglobulin.
15. The stably transformed plant of embodiment 9, wherein the milk protein is para-κ-casein and the structured mammalian protein is β-lactoglobulin.
16. The stably transformed plant of embodiment 9, wherein the milk protein is β-casein and the structured mammalian protein is β-lactoglobulin.
17. The stably transformed plant of embodiment 9, wherein the milk protein is α-S1 casein or α-S2 casein and the structured mammalian protein is β-lactoglobulin.
18. The stably transformed plant of any one of embodiments 1-17, wherein the plant is a dicot.
19. The stably transformed plant of embodiment 18, wherein the dicot is *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus.
20. The stably transformed plant of any one of embodiments 1-19, wherein the plant is soybean.
21. The stably transformed plant of any one of embodiments 1-20, wherein the recombinant DNA construct is codon-optimized for expression in the plant.
22. The stably transformed plant of any one of embodiments 1-21, wherein the fusion protein comprises a protease cleavage site.
23. The stably transformed plant of embodiment 22, wherein the protease cleavage site is a chymosin cleavage site.
24. The stably transformed plant of any one of embodiments 1-23, wherein the fusion protein is expressed at a level at least 2-fold higher than an unstructured milk protein expressed individually in a plant.
25. The stably transformed plant of any one of embodiments 1-24, wherein the fusion protein accumulates in the plant at least 2-fold higher than an unstructured milk protein expressed without the structured animal protein.
26. A recombinant fusion protein comprising: (i) an unstructured milk protein, and (ii) a structured animal protein.
27. The recombinant fusion protein of embodiment 26, wherein the fusion protein is expressed in a plant.
28. The recombinant fusion protein of embodiment 26 or 27, wherein the unstructured milk protein is α-S1 casein, α-S2 casein, β-casein, or κ-casein.
29. The recombinant fusion protein of embodiment 28, wherein the milk protein is κ-casein and comprises the sequence of SEQ ID NO: 4, or a sequence at least 90% identical thereto.
30. The recombinant fusion protein of embodiment 28, wherein the milk protein is para-κ-casein and comprises the sequence of SEQ ID NO: 2, or a sequence at least 90% identical thereto.
31. The recombinant fusion protein of embodiment 28, wherein the milk protein is β-casein and comprises the sequence of SEQ ID NO: 6, or a sequence at least 90% identical thereto.
32. The recombinant fusion protein of embodiment 28, wherein the milk protein is α-S1 casein and comprises the sequence SEQ ID NO: 8, or a sequence at least 90% identical thereto.
33. The recombinant fusion protein of embodiment 28, wherein the milk protein is α-S2 casein and comprises the sequence SEQ ID NO: 84, or a sequence at least 90% identical thereto.
34. The recombinant fusion protein of any one of embodiments 26-33, wherein the structured animal protein is a structured mammalian protein.
35. The recombinant fusion protein of embodiment 34, wherein the structured mammalian protein is β-lactoglobulin, α-lactalbumin, albumin, lysozyme, lactoferrin, lactoperoxidase, hemoglobin, collagen, or an immunoglobulin.
36. The recombinant fusion protein of embodiment 34, wherein the structured mammalian protein is β-lactoglobulin and comprises the sequence of SEQ ID NO: 10, or a sequence at least 90% identical thereto.
37. The recombinant fusion protein of any one of embodiments 26-33, wherein the structured animal protein is a structured avian protein.
38. The recombinant fusion protein of embodiment 37, wherein the structured avian protein is ovalbumin, ovotransferrin, lysozyme or ovoglobulin.
39. The recombinant fusion protein embodiment 34, wherein the milk protein is κ-casein and the structured mammalian protein is β-lactoglobulin.
40. The recombinant fusion protein of embodiment 34, wherein the milk protein is para-κ-casein and the structured mammalian protein is β-lactoglobulin.
41. The recombinant fusion protein of embodiment 34, wherein the milk protein is β-casein and the structured mammalian protein is β-lactoglobulin.
42. The recombinant fusion protein of embodiment 34, wherein the milk protein is α-S1 casein or α-S2 casein and the structured mammalian protein is β-lactoglobulin.
43. The recombinant fusion protein of embodiment 34, wherein the fusion protein comprises a protease cleavage site.
44. The recombinant fusion protein of embodiment 34, wherein the protease cleavage site is a chymosin cleavage site.
45. A nucleic acid encoding the recombinant fusion protein of any one of embodiments 26 to 44.
46. The nucleic acid of embodiment 45, wherein the nucleic acid is codon optimized for expression in a plant species.
47. The nucleic of embodiment 45 or 46, wherein the nucleic acid is codon optimized for expression in soybean.
48. A vector comprising a nucleic acid encoding a recombinant fusion protein, wherein the recombinant fusion protein comprises: (i) an unstructured milk protein, and (ii) a structured animal protein.
49. The vector of embodiment 48, wherein the vector is a plasmid.
50. The vector of embodiment 49, wherein the vector is an *Agrobacterium* Ti plasmid.
51. The vector of any one of embodiments 48-50, wherein the nucleic acid comprises, in order from 5' to 3': a promoter; a 5' untranslated region; a sequence encoding the fusion protein; and a terminator.
52. The vector of embodiment 51, wherein the promoter is a seed-specific promoter.
53. The vector of embodiment 52, wherein the seed-specific promoter is selected from the group consisting of PvPhas, BnNap, AtOle1, GmSeed2, GmSeed3, GmSeed5, GmSeed6, GmSeed7, GmSeed8, GmSeed10, GmSeed11, GmSeed12, pBCON, GmCEP1-L, GmTHIC, GmBg7S1, GmGRD, GmOLEA, GmOLER, Gm2S-1, and GmBBld-II.
54. The vector of embodiment 53, wherein the seed-specific promoter is PvPhas and comprises the sequence of SEQ ID NO: 18, or a sequence at least 90% identical thereto.
55. The vector of embodiment 53, wherein the seed-specific promoter is GmSeed2 and comprises the sequence of SEQ ID NO: 19, or a sequence at least 90% identical thereto.
56. The vector of any one of embodiments 51-55, wherein the 5' untranslated region is selected from the group consisting of Arc5'UTR and glnB1UTR.
57. The vector of embodiment 56, wherein the 5' untranslated region is Arc5'UTR and comprises the sequence of SEQ ID NO: 20, or a sequence at least 90% identical thereto.
58. The vector of any one of embodiments 51-57, wherein the expression cassette comprises a 3' untranslated region.
59. The vector of embodiment 58, wherein the 3' untranslated region is Arc5-1 and comprises SEQ ID NO: 21, or a sequence at least 90% identical thereto.
60. The vector of any one of embodiments 51-59, wherein the terminator sequence is a terminator isolated or derived from a gene encoding Nopaline synthase, Arc5-1, an Extensin, Rb7 matrix attachment region, a Heat shock protein, Ubiquitin 10, Ubiquitin 3, and M6 matrix attachment region.
61. The vector of embodiment 60, wherein the terminator sequence is isolated or derived from a Nopaline synthase gene and comprises the sequence of SEQ ID NO: 22, or a sequence at least 90% identical thereto.
62. A plant comprising the recombinant fusion protein of any one of embodiments 26-44 or the nucleic acid of any one of embodiments 45-47.
63. A method for stably expressing a recombinant fusion protein in a plant, the method comprising: a) transforming a plant with a plant transformation vector comprising an expression cassette comprising: a sequence encoding a fusion protein, wherein the fusion protein comprises an unstructured milk protein, and a structured animal protein; and b) growing the transformed plant under conditions wherein the recombinant fusion protein is expressed in an amount of 1% or higher per total protein weight of soluble protein extractable from the plant.
64. The method of embodiment 63, wherein the unstructured milk protein is κ-casein.
65. The method of embodiment 63 or 64, wherein the structured animal protein is β-lactoglobulin.
66. A food composition comprising the recombinant fusion protein of any one of embodiments 26-44.
67. A method for making a food composition, the method comprising: expressing the recombinant fusion protein of any one of embodiments 26-44 in a plant; extracting the recombinant fusion protein from the plant; optionally, separating the milk protein from the structured animal protein or the structured plant protein; and creating a food composition using the milk protein or the fusion protein.
68. The method of embodiment 67, wherein the plant stably expresses the recombinant fusion protein.
69. The method of embodiment 68, wherein the plant expresses the recombinant fusion protein in an amount of 1% or higher per total protein weight of soluble protein extractable from the plant.
70. The method of any one of embodiments 67-69, wherein the plant is soybean.
71. The method of any one of embodiments 67-70, wherein the food composition comprises the structured animal or plant protein.
72. The method of any one of embodiments 67-71, wherein the milk protein and the structured animal or plant protein are separated from one another in the plant cell, prior to extraction.
73. The method of any one of embodiments 67-71, wherein the milk protein is separated from the structured animal or plant protein after extraction, by contacting the fusion protein with an enzyme that cleaves the fusion protein.
74. A food composition produced using the method of any one of embodiments 67-73.

Embodiment Set Number 16: Modulation of Post-Translational Modifications by Modifying the Amino Acid Sequence of a Milk Protein 1. A recombinant milk protein, wherein the amino acid sequence of the milk protein is modified to promote addition of one or more post-translational modifications in a plant cell.
2. The recombinant milk protein of embodiment 1, wherein the milk protein is expressed in a plant, and wherein the milk protein comprises one or more post-translational modifications that are not present in a non-modified milk protein expressed in the same type of plant.
3. The recombinant milk protein of embodiment 1, wherein the milk protein is expressed in a plant in an amount of 1% or higher per total protein weight of soluble protein extractable from the plant.
4. The recombinant milk protein of any one of embodiments 1-3, wherein the milk protein is a casein protein selected from α-S1 casein, α-S2 casein, β-casein, κ-casein, and para-κ-casein.
5. The recombinant milk protein of any one of embodiments 1-4, wherein the milk protein is κ-casein or para-κ-casein.
6. The recombinant milk protein of any one of embodiments 1-4, wherein the milk protein is β-casein.
7. The recombinant milk protein of any one of embodiments 1-4, wherein the milk protein is β-lactoglobulin.
8. The recombinant milk protein of any one of embodiments 1-7, wherein the one or more post-translational modifications are selected from glycosylation, phosphorylation, lipidation, ubiquitylation, nitrosylation, methylation, acetylation, amidation, prenylation, alkylation, gamma-carboxylation, biotinylation, oxidation, and sulfation.
9. A nucleic acid encoding the recombinant milk protein of any one of embodiments 1-8.

Embodiment Set Number 17: Modulation of Post-Translational Modifications (PTMs) by Expressing One or More Enzymes which Add/Remove PTMs 1. A method for stably expressing a milk protein in a plant, the method comprising: transforming the plant with a sequence encoding the milk protein and a sequence encoding a kinase.
2. The method of embodiment 1, wherein the milk protein is a casein protein selected from the group consisting of: α-S1 casein, α-S2 casein, β-casein, κ-casein, para-κ-casein.
3. The method of embodiment 1 or 2, wherein the milk protein is fused to a second protein.
4. The method of any one of embodiments 1-3, wherein the kinase is a kinase in the 20C family.
5. The method of any one of embodiments 1-3, wherein the kinase that phosphorylates Ser-X-Glu/pSer motifs.
6. The method of any one of embodiments 1-3, wherein the kinase is a Fam20C kinase, or a fragment or variant thereof.
7. The method of any one of embodiments 1-3, wherein the kinase comprises SEQ ID NO: 821, or a sequence at least 90% or 95% identical thereto.
8. The method of any one of embodiments 1-3, wherein the kinase comprises amino acids 94-586 of SEQ ID NO: 821, or a sequence at least 90% or 95% identical thereto.
9. The method of any one of embodiments 1-8, wherein the sequence encoding the milk protein and the sequence encoding the kinase are in the same vector.
10. The method of embodiment 9, wherein the vector is a binary vector.

Embodiment Set Number 18: Fusion of a Milk Protein to a Glycoprotein Tag

1. A method for stably expressing a milk protein in a plant, the method comprising: transforming the plant with a sequence encoding a milk protein fused to a glycoprotein tag.
2. The method of embodiment 1, wherein the milk protein is a casein protein selected from the group consisting of: α-S1 casein, α-S2 casein, β-casein, κ-casein, para-κ-casein.
3. The method of embodiment 1 or 2, wherein the milk protein is fused to a second protein.
4. The method of any one of embodiments 1-3, wherein the glycoprotein tag is isolated or derived from a hydroxyproline (Hyp)-rich glycoprotein (GRGP).
5. The method of any one of embodiments 1-3, wherein the glycoprotein tag comprises the M domain of CD45.
6. The method of any one of embodiments 1-3, wherein the glycoprotein tag is an (SP) 11 tag.
7. The method of any one of embodiments 1-3, wherein the glycoprotein tag comprises SEQ ID NO: 825, or a sequence at least 90% or 95% identical thereto.
8. The method of any one of embodiments 1-3, wherein the glycoprotein tag comprises SEQ ID NO: 827, or a sequence at least 90% or 95% identical thereto.
9. The method of any one of embodiments 1-8, wherein the sequence encoding the milk protein and the sequence encoding the kinase are in the same vector.
10. The method of embodiment 9, wherein the vector is a binary vector.

Embodiment Set Number 19: Reducing the Expression of One or More Proteases in a Plant Cell 1. A plant cell for expressing recombinant milk proteins, wherein expression of one or more proteases is knocked down or knocked out in the cell.
2. The plant cell of embodiment 1, wherein expression of the one or more proteases is knocked down or knocked out using a gene editing technology or base editing technology.
3. The plant cell of embodiment 1, wherein expression of the one or more proteases is knocked down or knocked out using RNA interference.
4. The plant cell of embodiment 1, wherein the one or more proteases is a cysteine protease, a serine protease, or an aspartyl protease.
5. A transgenic plant comprising the plant cell of any one of embodiments 1-4.
6. A method for stably expressing a recombinant milk protein in a plant, the method comprising: (i) reducing expression of one or more proteases in the plant, (ii) transforming the plant with a plant transformation vector comprising an expression cassette encoding a recombinant milk protein or the fusion protein comprising the recombinant milk protein, (iii) growing the transformed plant under conditions wherein the recombinant milk protein is expressed in an amount of 1% or higher per total weight of soluble protein extractable from the plant.

Embodiment Set Number 20: Food Composition Comprising a Milk Protein Derived from a Fusion Protein 1. A food composition comprising the recombinant milk protein derived from a fusion protein of any one of the embodiment sets above.
2. A method for making a food composition, the method comprising: expressing the recombinant fusion protein of any one of the embodiment sets above; extracting the recombinant fusion protein from the plant; optionally, separating the first protein from the second protein; and creating a food composition using the milk protein or the fusion protein.
3. The method of embodiment 2, wherein the plant stably expresses the recombinant fusion protein.
4. The method of embodiment 2 or 3, wherein the plant expresses the recombinant fusion protein in an amount of 1% or higher per total protein weight of soluble protein extractable from the plant.
5. The method of any one of embodiments 2-4, wherein the plant is soybean.
6. The method of any one of embodiments 2-5, wherein the food composition comprises the first protein and the second protein.

7. The method of embodiment 6, wherein the first protein and the second protein are separated from one another in the plant cell, prior to extraction.
8. The method of embodiment 6, wherein the first protein and the second protein are separated after extraction, by contacting the fusion protein with an enzyme that cleaves the fusion protein.
9. A food composition produced using the method of any one of embodiments 2-8.
10. A food composition comprising a first or second protein, wherein the first or second protein is derived from the fusion protein of any one of the embodiment sets above.

Embodiment Set Number 21: A Solid-Phase Protein Stabilized-Emulsion Comprising a Recombinant Casein Protein 1. A solid phase, protein-stabilized emulsion comprising at least one recombinant casein protein selected from kappa-casein, para-kappa-casein, beta-casein, alpha-S1-casein and alpha-S2-casein; wherein the emulsion has at least one of the following characteristics: a firmness of at least 150 grams, as determined by compressing a cylindrical-shaped sample of the emulsion having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the emulsion to a temperature of about 225° C. for 4 minutes and cooling to about 90° C. and pulling with a fork placed beneath the mass.
2. The solid phase, protein-stabilized emulsion of embodiment 1, wherein the recombinant casein protein is plant-expressed.
3. The solid phase, protein stabilized emulsion of embodiment 1, wherein the recombinant casein protein is yeast-expressed or bacterial-expressed.
4. The solid phase, protein stabilized emulsion of any one of embodiments 1-3, wherein the recombinant casein protein is derived from a fusion protein.
5. The solid phase, protein stabilized emulsion of embodiment 4, wherein the fusion protein comprises a first and a second protein.
6. The solid phase, protein stabilized emulsion of embodiment 5, wherein the first protein comprises β-Casein and the second protein comprises a milk protein.
7. The solid phase, protein stabilized emulsion of embodiment 5, wherein the first protein comprises β-Casein and the second protein comprises a non-milk protein.
8. The solid phase, protein stabilized emulsion of embodiment 6, wherein the milk protein is selected from the group consisting of: β-lactoglobulin, casein, α-lactalbumin, lysozyme, lactoferrin, lactoperoxidase, and immunoglobulin.
9. The solid phase, protein stabilized emulsion of embodiment 8, wherein the milk protein is β-lactoglobulin.
10. The solid phase, protein stabilized emulsion of embodiment 8, wherein the milk protein is casein, and wherein the casein is selected from the group consisting of: α-S1 Casein, α-S2 Casein, β-Casein, κ-Casein, and para-κ-Casein.
11. The solid phase, protein stabilized emulsion of embodiment 10, wherein the milk protein is β-Casein.
12. The solid phase, protein-stabilized emulsion of any one of embodiments 1-11, wherein the emulsion comprises at least one lipid and at least one salt.
13. The solid phase, protein-stabilized emulsion of any one of embodiments 1-5, wherein the emulsion comprises at least two plant-expressed casein proteins each selected from kappa-casein, para-kappa-casein, beta-casein, alpha-S1-casein and alpha-S2-casein.
14. The solid phase, protein-stabilized emulsion of any one of embodiments 1-5, wherein the emulsion comprises at least three plant-expressed casein proteins each selected from kappa-casein, para-kappa-casein, beta-casein, alpha-S1-casein and alpha-S2-casein.
15. The solid phase, protein-stabilized emulsion of any one of embodiments 1-14, wherein the emulsion comprises at least one additional mammalian or plant protein that is not a casein protein.
16. The solid phase, protein-stabilized emulsion of embodiment 2, wherein the plant-expressed casein protein is expressed in a soybean plant.
17. The solid phase, protein-stabilized emulsion of any one of embodiments 1-16, wherein the emulsion has a pH of about 5.2 to about 5.9.
18. The solid phase, protein-stabilized emulsion of any one of embodiments 1-17, wherein the emulsion does not contain an organoleptically functional amount of beta-lactoglobulin.
19. A solid phase, protein-stabilized emulsion comprising one plant-expressed casein protein selected from kappa-casein, para-kappa-casein, beta-casein, alpha-S1-casein, and alpha-S2-casein; wherein the emulsion does not contain any additional casein proteins; wherein the emulsion has at least one of the following characteristics: a firmness of at least 150 grams, as determined by compressing a cylindrical-shaped sample of the emulsion having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the emulsion to a temperature of about 225° C. for 4 minutes and cooling to about 90° C. and pulling with a fork placed beneath the mass.
20. The solid phase, protein-stabilized emulsion of embodiment 19, wherein the emulsion further comprises at least one lipid and at least one salt.
21. The solid phase, protein-stabilized emulsion of embodiment 19 or 20, wherein the plant-expressed casein protein is expressed in soybean plant.
22. The solid phase, protein-stabilized emulsion of any one of embodiments 19-21, wherein the plant-expressed casein protein is derived from a fusion protein.
23. The solid phase, protein stabilized-emulsion of any one of embodiments 19-22, wherein the emulsion has a pH of about 5.2 to about 5.9.
24. The solid phase, protein-stabilized emulsion of any one of embodiments 19-23, wherein the emulsion does not contain an organoleptically functional amount of beta-lactoglobulin.
25. A solid phase, protein-stabilized emulsion comprising: a plant-expressed casein protein selected from kappa-casein, para-kappa-casein, beta-casein, alpha-S1-casein, and alpha-S2-casein; and plant-expressed beta-lactoglobulin; wherein the ratio of the casein protein to the beta-lactoglobulin is about 8:1 to about 1:2.
26. The solid phase, protein-stabilized emulsion of embodiment 25, wherein the emulsion has at least one of the following characteristics: a firmness of at least 150 grams, as determined by compressing a cylindrical-shaped sample of the emulsion having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the emulsion to a temperature of about 225° C. for 4 minutes and cooling to about 90° C. and pulling with a fork placed beneath the mass.

27. The solid phase, protein-stabilized emulsion of embodiment 25 or 26, wherein the emulsion comprises at least at least one additional mammalian or plant protein that is not a casein protein.

28. The solid phase, protein-stabilized emulsion of any one of embodiments 25-27, wherein the ratio of the casein protein to the beta-lactoglobulin is about 2:1.

29. The solid phase, protein-stabilized emulsion of any one of embodiments 25-28, wherein the emulsion has a pH of about 5.2 to about 5.9.

30. The solid phase, protein-stabilized emulsion of any one of embodiments 25-29, wherein the plant-expressed casein protein is derived from a fusion protein.

31. A solid-phase protein-stabilized emulsion comprising about 8% (w/v) to about 25% (w/v) total protein, one or more lipids, and one or more salts; wherein at least 4% of the total protein comprises casein proteins selected from kappa-casein, para-kappa-casein, beta-casein, alpha-S1-casein, and alpha-S2-casein; wherein at least 20% to 100% of the casein protein is kappa casein; wherein the emulsion has at least one of the following characteristics: a firmness of at least 150 grams, as determined by compressing a cylindrical-shaped sample of the emulsion having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the emulsion to a temperature of about 225° C. for 4 minutes and cooling to about 90° C. and pulling with a fork placed beneath the mass.

32. The solid-phase protein-stabilized emulsion of embodiment 31, wherein the kappa casein is expressed in a plant.

33. The solid phase, protein-stabilized emulsion of any one of embodiments 31-32, wherein the kappa casein is derived from a fusion protein.

34. The solid phase, protein-stabilized emulsion of any one of embodiments 31-33, wherein the emulsion has a pH of about 5.2 to about 5.9.

35. The solid phase, protein-stabilized emulsion of any one of embodiments 31-34, wherein the composition comprises only one, only two, only three, or only four casein proteins selected from kappa-casein, para-kappa-casein, beta-casein, alpha-S1-casein, and alpha-S2-casein.

36. The solid phase, protein-stabilized emulsion of any one of embodiments 31-35, wherein the emulsion does not contain an organoleptically functional amount of beta-lactoglobulin.

37. A solid-phase protein-stabilized emulsion comprising about 8% to about 25% total protein, one or more lipids, and one or more salts; wherein at least 4% of the total protein comprises casein proteins selected from kappa-casein, para-kappa-casein, beta-casein, alpha-S1-casein, and alpha-S2-casein; wherein at least 20% to 100% of the casein protein is para-kappa casein; wherein the emulsion has at least one of the following characteristics: a firmness of at least 150 grams, as determined by compressing a cylindrical-shaped sample of the emulsion having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the emulsion to a temperature of about 225° C. for 4 minutes and cooling to about 90° C. and pulling with a fork placed beneath the mass.

38. The solid-phase protein-stabilized emulsion of embodiment 37, wherein the para-kappa casein is expressed in a plant.

39. The solid phase, protein-stabilized emulsion of embodiment 37 or 38, wherein the para-kappa casein is derived from a fusion protein.

40. The solid-phase protein-stabilized emulsion of any one of embodiments 37-39 wherein the para-kappa casein is produced without the use of any enzyme that cleaves kappa-casein to para-kappa casein.

41. The solid phase, protein-stabilized emulsion of any one of embodiments 37-40, wherein the emulsion has a pH of about 5.2 to about 5.9.

42. The solid phase, protein-stabilized emulsion of any one of embodiments 37-41, wherein the composition comprises only one, only two, only three, or only four casein proteins selected from kappa-casein, para-kappa-casein, beta-casein, alpha-S1-casein, and alpha-S2-casein.

43. The solid phase, protein-stabilized emulsion of any one of embodiments 37-42, wherein the emulsion does not contain an organoleptically functional amount of beta-lactoglobulin.

44. A solid-phase protein-stabilized emulsion comprising about 8% to about 25% total protein, one or more lipids, and one or more salts; wherein at least 4% of the total protein comprises casein proteins selected from kappa-casein, para-kappa-casein, beta-casein, alpha-S1-casein, and alpha-S2-casein; wherein at least 50% to 100% of the casein protein is beta-casein; wherein the emulsion has at least one of the following characteristics: a firmness of at least 150 grams, as determined by compressing a cylindrical-shaped sample of the emulsion having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the emulsion to a temperature of about 225° C. for 4 minutes and cooling to about 90° C. and pulling with a fork placed beneath the mass.

45. The solid-phase protein-stabilized emulsion of embodiment 44, wherein the beta-casein is expressed in a plant.

46. The solid phase, protein-stabilized emulsion of any one of embodiments 44-45, wherein the plant-expressed casein protein is derived from a fusion protein.

47. The solid phase, protein-stabilized emulsion of any one of embodiments 44-46, wherein the emulsion has a pH of about 5.2 to about 5.9.

48. The solid phase, protein-stabilized emulsion of any one of embodiments 44-47, wherein the composition comprises only one, only two, only three, or only four casein proteins selected from kappa-casein, para-kappa-casein, beta-casein, alpha-S1-casein, and alpha-S2-casein.

49. The solid phase, protein-stabilized emulsion of any one of embodiments 44-48, wherein the emulsion does not contain an organoleptically functional amount of beta-lactoglobulin.

50. A solid-phase protein-stabilized emulsion comprising about 8% to about 25% total protein, one or more lipids, and one or more salts; wherein at least 4% of the total protein comprises casein proteins selected from kappa-casein, para-kappa-casein, beta-casein, alpha-S1-casein, and alpha-S2-casein; wherein at least 50% to 100% of the casein protein is alpha-S1-casein; wherein the emulsion has at least one of the following characteristics: a firmness of at least 150 grams, as determined by compressing a cylindrical-shaped sample of the emulsion having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the emulsion to a temperature of about 225° C. for 4 minutes and cooling to about 90° C. and pulling with a fork placed beneath the mass.

51. The solid-phase protein-stabilized emulsion of embodiment 50, wherein the alpha-S1-casein is expressed in a plant.

52. The solid phase, protein-stabilized emulsion of any one of embodiments 50-51, wherein the alpha-S1-casein is derived from a fusion protein.

53. The solid phase, protein-stabilized emulsion of any one of embodiments 50-52, wherein the emulsion has a pH of about 5.2 to about 5.9.

54. The solid phase, protein-stabilized emulsion of any one of embodiments 50-53, wherein the composition comprises only one, only two, only three, or only four casein proteins selected from kappa-casein, para-kappa-casein, beta-casein, alpha-S1-casein, and alpha-S2-casein.

55. The solid phase, protein-stabilized emulsion of any one of embodiments 50-54, wherein the emulsion does not contain an organoleptically functional amount of beta-lactoglobulin.

56. A solid-phase protein-stabilized emulsion comprising about 8% to about 25% total protein, one or more lipids, and one or more salts; wherein at least 4% of the total protein comprises casein proteins selected from kappa-casein, para-kappa-casein, beta-casein, alpha-S1-casein, and alpha-S2-casein; wherein at least 20% to 100% of the casein protein is alpha-S2-casein; wherein the emulsion has at least one of the following characteristics: a firmness of at least 150 grams, as determined by compressing a cylindrical-shaped sample of the emulsion having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the emulsion to a temperature of about 225° C. for 4 minutes and cooling to about 90° C. and pulling with a fork placed beneath the mass.

57. The solid-phase protein-stabilized emulsion of embodiment 56, wherein the alpha-S2-casein is expressed in a plant.

58. The solid phase, protein-stabilized emulsion of any one of embodiments 56-57, wherein the plant-expressed casein protein is derived from a fusion protein.

59. The solid phase, protein-stabilized emulsion of any one of embodiments 56-58, wherein the emulsion has a pH of about 5.2 to about 5.9.

60. The solid phase, protein-stabilized emulsion of any one of embodiments 56-59, wherein the composition comprises only one, only two, only three, or only four casein proteins selected from kappa-casein, para-kappa-casein, beta-casein, alpha-S1-casein, and alpha-S2-casein.

61. The solid phase, protein-stabilized emulsion of any one of embodiments 56-60, wherein the emulsion does not contain an organoleptically functional amount of beta-lactoglobulin.

Embodiment Set Number 22: Alternative Dairy Compositions Comprising One or More Recombinant Casein Proteins 1. An alternative dairy composition comprising one or more recombinant casein proteins selected from kappa-casein, para-kappa-casein, beta-casein, alpha-S1-casein, and alpha-S2-casein; wherein the alternative dairy composition has at least one of the following characteristics: a firmness of at least 150 grams, as determined by compressing a cylindrical-shaped sample of the alternative dairy composition having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the alternative dairy composition to a temperature of about 225° C. for 4 minutes and cooling to about 90° C. and pulling with a fork placed beneath the mass.

2. The alternative dairy composition of embodiment 1, wherein the composition further comprises at least one lipid and at least one salt.

3. The alternative dairy composition of embodiment any one of embodiments 1-2, wherein the composition further comprises at least one additional mammalian or plant protein that is not a casein protein.

4. The alternative dairy composition of any one of embodiments 1-3, wherein the one or more recombinant casein proteins are expressed in a plant.

5. The alternative dairy composition of embodiment 4, wherein the one or more recombinant casein proteins are expressed in a soybean plant.

6. The alternative diary composition of any one of embodiments any one of embodiments 1-5, wherein the one or more recombinant casein proteins are derived from one or more fusion proteins.

7. The alternative diary composition of embodiment 6, wherein one of the one or more fusion proteins comprises a first and a second protein.

8. The alternative diary composition of embodiment 7, wherein the first protein comprises β-Casein and the second protein comprises a milk protein.

9. The alternative diary composition of embodiment 7, wherein the first protein comprises β-Casein and the second protein comprises a non-milk protein.

10. The alternative diary composition of embodiment 8, wherein the milk protein is selected from the group consisting of β-lactoglobulin, casein, α-lactalbumin, lysozyme, lactoferrin, lactoperoxidase, and immunoglobulin.

11. The alternative diary composition of embodiment 8, wherein the milk protein is β-lactoglobulin.

12. The alternative diary composition of embodiment 8, wherein the milk protein is casein, and wherein the casein is selected from the group consisting of: α-S1 Casein, α-S2 Casein, β-Casein, κ-Casein, and para-κ-Casein.

13. The alternative diary composition of embodiment 8, wherein the milk protein is β-Casein.

14. The alternative dairy composition of any one of embodiments 1-13, wherein the composition has a pH of about 5.2 to about 5.9.
15. The alternative dairy composition of any one of embodiments 1-9, wherein the composition does not contain an organoleptically functional amount of beta-lactoglobulin.
16. An alternative dairy composition comprising one or more recombinant casein proteins, one or more lipids; and one or more salts; wherein the alternative dairy composition does not contain an organoleptically functional amount of beta-lactoglobulin; wherein the alternative dairy composition has at least one of the following characteristics: a firmness of at least 150 grams, as determined by compressing a cylindrical-shaped sample of the alternative dairy composition having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the alternative dairy composition to a temperature of about 225° C. for 4 minutes and cooling to about 90° C. and pulling with a fork placed beneath the mass.
17. The alternative dairy composition of embodiment 16, wherein the composition comprises at least one additional mammalian or plant protein that is not a casein protein.
18. The alternative dairy composition of embodiment 16 or 17, wherein the one or more recombinant casein proteins are expressed in a plant.
19. The alternative dairy composition of claim 18, wherein the one or more recombinant casein proteins are expressed in a soybean plant.
20. The alternative diary composition of any one of embodiments 16-19, wherein the one or more recombinant casein proteins are derived from one or more fusion proteins.
21. The alternative dairy composition of any one of embodiments 16-20, wherein the composition has a pH of about 5.2 to about 5.9.
22. An alternative dairy composition comprising: a recombinant casein protein selected from kappa-casein, para-kappa-casein, beta-casein, alpha-S1-casein, and alpha-S2-casein; and a recombinant beta-lactoglobulin; wherein the ratio of the casein protein to the beta-lactoglobulin is about 8:1 to about 1:2; wherein the alternative dairy composition has at least one of the following characteristics: a firmness of at least 150 grams, as determined by compressing a cylindrical-shaped sample of the alternative dairy composition having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the alternative dairy composition to a temperature of about 225° C. for 4 minutes and cooling to about 90° C. and pulling with a fork placed beneath the mass.
23. The alternative dairy composition of embodiment 22, wherein the composition comprises at least one additional mammalian or plant protein that is not a casein protein.
24. The alternative dairy composition of embodiment 22 or 23, wherein recombinant casein protein is expressed in a plant.
25. The alternative dairy composition of claim 24, wherein recombinant casein protein is expressed in a soybean plant.
26. The alternative dairy composition of any one of embodiments 22-25, wherein the recombinant casein protein is derived from a fusion protein.
27. The alternative dairy composition of any one of embodiments 22-26, wherein the composition has a pH of about 5.2 to about 5.9.
28. An alternative dairy composition comprising kappa-casein and essentially no para-kappa casein, wherein the alternative dairy composition has at least one of the following characteristics: a firmness of at least 150 grams, as determined by compressing a cylindrical-shaped sample of the alternative dairy composition having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the alternative dairy composition to a temperature of about 225° C. for 4 minutes and cooling to about 90° C. and pulling with a fork placed beneath the mass.
29. The alternative dairy composition of embodiment 28, wherein the composition comprises at least one additional mammalian or plant protein that is not a casein protein.
30. The alternative dairy composition of embodiment 28 or 29, wherein the kappa casein is recombinant.
31. The alternative dairy composition of any one of embodiments 28-30, wherein the kappa casein is expressed in a plant.
32. The alternative dairy composition of embodiment 31, wherein the kappa casein is expressed in a soybean plant.
33. The alternative diary composition of any one of embodiments 28-32, wherein the kappa casein is derived from a fusion protein.
34. The alternative dairy composition of any one of embodiments 28-33, wherein the composition has a pH of about 5.2 to about 5.9.
35. The alternative dairy composition of any one of embodiments 28-33, wherein the composition does not contain an organoleptically functional amount of beta-lactoglobulin.
36. An alternative dairy composition comprising one to four of the milk proteins selected from kappa-casein, para-kappa-casein, beta-casein, alpha-S1-casein, and alpha-S2-casein; wherein the alternative dairy composition has at least one of the following characteristics: a firmness of at least 150 grams, as determined by compressing a cylindrical-shaped sample of the alternative dairy composition having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the alternative dairy composition to a temperature of about 225° C. for 4 minutes and cooling to about 90° C. and pulling with a fork placed beneath the mass.
37. The alternative dairy composition of embodiment 36, wherein at least one milk protein is recombinant.
38. The alternative dairy composition of embodiment 36, wherein the at least one milk protein is plant-expressed.
39. The alternative dairy composition of embodiment 38, wherein the at least one milk protein is expressed in a soybean plant.

40. The alternative dairy composition of embodiment 37, wherein the at least one milk protein is yeast- or bacterial-expressed.
41. The alternative diary composition of any one of embodiments 36-40, wherein at least one milk protein is derived from a fusion protein.
42. The alternative dairy composition of any one of embodiments 36-41, wherein the alternative dairy composition comprises one of the milk proteins selected from kappa-casein, para-kappa-casein, beta-casein, alpha-S1-casein, and alpha-S2-casein.
43. The alternative dairy composition of any one of embodiments 36-41, wherein the alternative dairy composition comprises two of the milk proteins selected from kappa-casein, para-kappa-casein, beta-casein, alpha-S1-casein, and alpha-S2-casein.
44. The alternative dairy composition of any one of embodiments 36-41, wherein the alternative dairy composition comprises three of the milk proteins selected from kappa-casein, para-kappa-casein, beta-casein, alpha-S1-casein, and alpha-S2-casein.
45. The alternative dairy composition of any one of embodiments 36-41, wherein the alternative dairy composition comprises four of the milk proteins selected from kappa-casein, para-kappa-casein, beta-casein, alpha-S1-casein, and alpha-S2-casein.
46. The alternative dairy composition of any one of embodiments 36-45, wherein the composition has a pH of about 5.2 to about 5.9.
47. The alternative dairy composition of any one of embodiments 36-46, wherein the composition does not contain an organoleptically functional amount of beta-lactoglobulin.
48. An alternative dairy composition comprising 2 to 4 casein proteins; wherein the alternative dairy composition has at least one of the following characteristics: a firmness of at least 150 grams, as determined by compressing a cylindrical-shaped sample of the alternative dairy composition having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the alternative dairy composition to a temperature of about 225° C. for 4 minutes and cooling to about 90° C. and pulling with a fork placed beneath the mass.
49. The alternative dairy composition of embodiment 48, wherein the alternative dairy composition does not contain an organoleptically functional amount of beta-lactoglobulin.
50. The alternative dairy composition of embodiment 48 or 49, wherein the casein proteins are selected from kappa-casein, para-kappa-casein, beta-casein, alpha-S1-casein, and alpha-S2-casein.
51. The alternative dairy composition of any one of embodiments 48-50, wherein the composition comprises at least one lipid and at least one salt.
52. The alternative dairy composition of any one of embodiments 48-51, wherein the composition has a pH of about 5.2 to about 5.9.
53. The alternative diary composition of any one of embodiments 48-52, wherein at least one of the casein proteins is derived from a fusion protein.
54. An alternative dairy composition comprising one to four plant-expressed recombinant milk proteins, wherein the alternative dairy composition comprises three or more organoleptic properties similar to a dairy composition selected from the group consisting of taste, appearance, mouthfeel, structure, texture, density, elasticity, springiness, coagulation, binding, leavening, aeration, foaming, creaminess, and emulsification.
55. The alternative dairy composition of embodiment 54, wherein the plant-expressed milk proteins are selected from beta lactoglobulin, kappa-casein, para-kappa-casein, beta-casein, alpha-S1-casein, and alpha-S2-casein.
56. The alternative dairy composition of embodiment 54 or 55, wherein the composition is a milk composition.
57. The alternative dairy composition of embodiment 54 or 55, wherein the composition is a cream composition.
58. The alternative dairy composition of embodiment 54 or 55, wherein the composition is a yogurt composition.
59. The alternative dairy composition of embodiment 54 or 55, wherein the composition is an ice cream composition.
60. The alternative dairy composition of embodiment 54 or 55, wherein the composition is a frozen custard composition.
61. The alternative dairy composition of embodiment 54 or 55, wherein the composition is a frozen desert composition.
62. The alternative dairy composition of embodiment 54 or 55, wherein the composition is a crème fraiche composition.
63. The alternative dairy composition of embodiment 54 or 55, wherein the composition is a curd composition.
64. The alternative dairy composition of embodiment 54 or 55, wherein the composition is a cottage cheese composition.
65. The alternative dairy composition of embodiment 54 or 55, wherein the composition is a cream cheese composition.
66. The alternative dairy composition of any one of embodiments 54-65, wherein at least one of the plant-expressed recombinant milk proteins is derived from a fusion protein.
67. An alternative dairy food composition comprising: a recombinant beta-casein protein, and least one lipid, wherein the alternative dairy food composition does not comprise an organoleptically functional amount of beta-lactoglobulin.
68. The alternative dairy food composition of embodiment 67, wherein the recombinant beta-casein protein confers on the alternative dairy food composition one or more characteristics of a dairy food product selected from the group consisting of: taste, aroma, appearance, handling, mouthfeel, density, structure, texture, elasticity, springiness, coagulation, binding, leavening, aeration, foaming, creaminess and emulsification.
69. The alternative dairy food composition of embodiment 67 or 68, wherein the composition does not comprise any additional casein proteins.
70. The alternative dairy food composition of embodiment 67 or 68, wherein the composition comprises at least one additional casein protein.
71. The alternative dairy food composition of embodiment 70, wherein at least 50% by weight of the total casein protein in the composition is beta-casein.
72. The alternative dairy food composition of embodiment 70, wherein at least 75% by weight of the total casein protein in the composition is beta-casein.
73. The alternative dairy food composition of embodiment 70, wherein at least 90% by weight of the total casein protein in the composition is beta-casein.

74. The alternative dairy food composition of any one of embodiments 70-73, wherein the at least one additional casein protein is selected from kappa-casein, para-kappa-casein, beta-casein, alpha-S1-casein and alpha-S2-casein.
75. The alternative dairy food composition of any one embodiments 70-73, wherein the at least one additional casein protein is kappa-casein or para-kappa casein.
76. The alternative dairy food composition of any one of embodiments 67-75, wherein the recombinant beta-casein is plant-expressed.
77. The alternative dairy food composition of embodiment 76, wherein the recombinant beta-casein is expressed in a soybean.
78. The alternative dairy food composition of any one of embodiments 70-77, wherein all caseins in the composition are plant-expressed.
79. The alternative dairy food composition of any one of embodiments 67-78, wherein the composition comprises a fusion protein comprising the recombinant beta-casein.
80. The alternative dairy food composition any one of embodiments 67-79, wherein the recombinant beta-casein protein confers on the alternative dairy food composition two or more characteristics of a dairy food product selected from the group consisting of: taste, aroma, appearance, handling, mouthfeel, density, structure, texture, elasticity, springiness, coagulation, binding, leavening, aeration, foaming, creaminess and emulsification.
81. The alternative dairy food composition of any one of embodiments 67-80, wherein the composition is a milk composition, a cream composition, a yogurt composition, an ice cream composition, a frozen custard composition, a frozen dessert composition, a crème fraiche composition, a curd composition, a cottage cheese composition, or a cream cheese composition.
82. The alternative dairy food composition of any one of embodiments 67-81, wherein the composition comprises at least one lipid and at least one salt.
83. The alternative dairy food composition any one of embodiments 67-82, wherein the composition comprises calcium.
84. The alternative dairy food composition of embodiment 83, wherein the composition comprises calcium at a concentration of about 0.1% to about 2% by weight.
85. The alternative dairy food composition any one of embodiments 67-84, wherein the composition has a pH of about 4 to about 8.

Embodiment Set Number 23: Colloidal Suspensions Comprising One or More Recombinant Casein Proteins 1. A colloidal suspension comprising: one to four plant-expressed recombinant milk proteins, wherein the recombinant milk proteins comprise between 0.5% (w/v) to 15% (w/v) of the composition; and ash; wherein the colloidal suspension has at least one, at least two, or at least three characteristics that are substantially similar to bovine milk selected from taste, appearance, mouthfeel, structure, texture, density, elasticity, springiness, coagulation, binding, leavening, aeration, foaming, creaminess, and emulsification.
2. The colloidal suspension of embodiment 1, wherein the plant-expressed milk proteins are selected from beta-lactoglobulin, kappa-casein, para-kappa-casein, beta-casein, alpha-S1-casein, and alpha-S2-casein.
3. The colloidal suspension of any one of embodiments 1-2, wherein at least one of the plant-expressed recombinant milk proteins is derived from a fusion protein.
4. A colloidal suspension comprising: one casein protein, wherein the casein protein comprises between 0.5% (w/v) to 15% (w/v); and ash; wherein the colloidal suspension has at least one, at least two, or at least three characteristics that are substantially similar to bovine milk selected from taste, appearance, mouthfeel, structure, texture, density, elasticity, springiness, coagulation, binding, leavening, aeration, foaming, creaminess, and emulsification.
5. The colloidal suspension of embodiment 4, wherein the casein protein is selected from beta lactoglobulin, kappa-casein, para-kappa-casein, beta-casein, alpha-S1-casein, and alpha-S2-casein.
6. The colloidal suspension of embodiment 4 or 5, wherein the casein protein is beta-casein.
7. The colloidal suspension of any one of embodiments 4-6, wherein the casein protein is plant-expressed.
8. The colloidal suspension of any one of embodiments 4-7, wherein the casein protein is derived from a fusion protein.
9. A method of making an alternative dairy composition comprising processing the colloidal suspension of any one of embodiments 1-8.
10. An alternative dairy composition produced from the method of embodiment 9.
11. The alternative dairy composition of embodiment 10, wherein the alternative dairy composition is a cream composition, a yogurt composition, a cheese composition, an ice cream composition, a frozen custard composition, a frozen desert composition, a crème fraiche composition, a curd composition, a cottage cheese composition, or a cream cheese composition.
12. A colloidal suspension comprising: recombinant beta-casein protein, and at least one lipid; wherein the suspension does not contain an organoleptically functional amount of beta-lactoglobulin.
13. The colloidal suspension of embodiment 12, wherein the suspension is a non-Newtonian fluid.
14. The colloidal suspension of embodiment 12 or 13, which is characterized as a shear thinning fluid with an apparent viscosity greater than 10 centipoise, at a shear rate of 1 sec$^{-1}$.
15. The colloidal suspension of any one of embodiments 12-14, wherein the suspension is an aqueous suspension.
16. The colloidal suspension of any one of embodiments 12-15, wherein the suspension does not comprise any additional casein proteins.
17. The colloidal suspension of any one of embodiments 12-15, wherein the composition comprises at least one additional casein protein.
18. The colloidal suspension of embodiment 17, wherein at least 80% by weight of the total casein protein in the composition is beta-casein.
19. The colloidal suspension of embodiment 17 or 18, wherein the at least one additional casein protein is selected from kappa-casein, para-kappa-casein, beta-casein, alpha-S1-casein and alpha-S2-casein.
20. The colloidal suspension of embodiment 17 or 18, wherein the at least one additional casein protein is kappa-casein or para-kappa casein.

21. The colloidal suspension of any one of embodiments 12-20, wherein the recombinant beta-casein is plant-expressed.
22. The colloidal suspension of any one of embodiments 12-21, wherein the composition comprises a fusion protein comprising the recombinant beta-casein.

Embodiment Set Number 24: Cheese Compositions

1. A cheese composition comprising para-kappa-casein produced without the use of any enzyme that cleaves kappa-casein to para-kappa casein.
2. A substantially transparent plant-based cheese composition.
3. A cheese composition comprising a recombinant beta-casein protein; wherein the cheese composition has at least one of the following characteristics: a firmness of at least 150 grams, as determined by compressing a cylindrical-shaped sample of the cheese composition having a height of 3 cm and a diameter of 3 cm to a height of 1.5 cm at 5° C.; a melting point of about 35° C. to about 100° C.; or ability to stretch to at least 3 cm in length without breaking, as determined by heating a 100 gram mass of the cheese composition to a temperature of about 225° C. for 4 minutes and cooling to about 90° C. and pulling with a fork placed beneath the mass.
4. The cheese composition of embodiment 141, wherein the composition does not comprise any additional casein proteins.
5. The cheese composition of embodiment 141, wherein the composition comprises at least one additional casein protein.
6. The cheese composition of embodiment 143, wherein at least 80% by weight of the total casein protein in the composition is beta-casein.
7. The cheese composition of embodiment 143, wherein at least 90% by weight of the total casein protein in the composition is beta-casein.
8. The cheese composition of embodiment 143, wherein at least 95% by weight of the total casein protein in the composition is beta-casein.
9. The cheese composition of embodiment 143, wherein the at least one additional casein protein is selected from kappa-casein, para-kappa-casein, beta-casein, alpha-S1-casein and alpha-S2-casein.
10. The cheese composition of embodiment 143, wherein the at least one additional casein protein is kappa-casein.
11. The cheese composition of embodiment 143, wherein the at least one additional casein protein is para-kappa casein.
12. The cheese composition of any one of embodiments 141-149, wherein the recombinant beta-casein is plant-expressed.
13. The cheese composition of embodiment 150, wherein the recombinant beta-casein is expressed in a soybean.
14. The cheese composition of any one of embodiments 143-149, wherein all caseins in the composition are plant-expressed.
15. The cheese composition of any one of embodiments 141-152, wherein the recombinant casein protein is derived from a fusion protein.
16. The cheese composition of any one of embodiments 141-153, wherein the composition does not contain an organoleptically functional amount of beta-lactoglobulin.
17. The cheese composition of any one of embodiments 141-154, wherein the composition has the ability to stretch to at least 3 cm in length without breaking, as determined by heating a 100 gram mass of the composition at a temperature of 225° C. for 4 minutes and cooling to about 90° C. and pulling with a fork placed beneath the mass.
18. The cheese composition of any one of embodiments 141-155, wherein the composition has the ability to stretch to at least 3 cm in length without breaking, as determined by heating a 100 gram mass of the composition at a temperature of 225° C. for 4 minutes and cooling to about 90° C. and pulling with a fork placed beneath the mass; and a firmness of at least 150 grams, as determined by compressing a cylindrical-shaped sample of the cheese composition having a height of 3 cm and a diameter of 3 cm to a height of 1.5 cm at 5° C.
19. The cheese composition of any one of embodiments 141-156, wherein the composition comprises at least one lipid and at least one salt.
20. The cheese composition of any one of embodiments 141-157, wherein the composition comprises calcium.
21. The cheese composition of embodiment 158, wherein the composition comprises calcium at a concentration of about 0.01% to about 2% by weight.
22. The cheese composition of any one of embodiments 141-159, wherein the composition has a pH of about 5.2 to about 5.9.
23. The cheese composition of any one of embodiments 141-160, wherein the composition comprises at least one organoleptic properties similar to cheese selected from the group consisting of taste, appearance, mouthfeel, structure, texture, density, elasticity, springiness, coagulation, binding, leavening, aeration, foaming, creaminess, and emulsification.
24. A method of making the cheese composition of embodiments 141-161, the method comprising expressing the recombinant beta-casein protein in a plant, extracting the beta-casein from the plant, and combining the beta-casein with at least one lipid and/or salt.
25. A cheese composition comprising a recombinant beta-casein protein; wherein the cheese composition has ability to stretch to at least 3 cm in length without breaking, as determined by heating a 100 gram mass of the composition at a temperature of 225° C. for 4 minutes and cooling to about 90° C. and pulling with a fork placed beneath the mass.
26. The cheese composition of embodiment 163, wherein the composition does not comprise any additional casein proteins.
27. The cheese composition of embodiment 163, wherein the composition comprises at least one additional casein protein, and wherein at least 80% by weight of the total casein protein in the composition is beta-casein.
28. The cheese composition of embodiment 165, wherein the at least one additional casein protein is kappa-casein or para-kappa casein.
29. The cheese composition of any one of embodiments 163-166, wherein the recombinant beta-casein is plant-expressed.
30. The cheese composition of any one of embodiments 165-167, wherein the recombinant casein protein is derived from a fusion protein.
31. The cheese composition of any one of embodiments 163-168, wherein the composition has at least one of the following characteristics: a firmness of at least 150 grams, as determined by compressing a cylindrical-shaped sample of the cheese composition having a height of 3 cm and a diameter of 3 cm to a height of 1.5 cm at 5° C.; or a melting point of about 35° C. to about 100° C.

32. A method of making the cheese composition of any one of embodiments 163-169, the method comprising expressing the recombinant beta-casein protein in a plant, extracting the beta-casein from the plant, and combining the beta-casein with at least one lipid and/or salt.

What is claimed is:

1. A method of making a food composition, said method comprising the steps of:
   a) providing a plant cell expressing:
      i) a heterologous casein protein; and
      ii) a heterologous Fam20C kinase protein;
   b) obtaining the heterologous casein protein from the plant cell; and
   c) processing the heterologous casein protein into a food composition, thereby making the food composition.

2. The method of claim 1, wherein the plant cell is from a dicot.

3. The method of claim 2, wherein the dicot is selected from the group consisting of arabidopsis, tobacco, tomato, potato, sweet potato, cassava, alfalfa, lima bean, pea, chickpea, soybean, carrot, strawberry, lettuce, oak, maple, walnut, rose, mint, squash, daisy, quinoa, buckwheat, mung bean, cow pea, lentil, lupin, peanut, fava bean, French bean, mustard, and cactus.

4. The method of claim 2, wherein the dicot is soybean.

5. The method of claim 1, wherein the plant cell is from a monocot.

6. The method of claim 5, wherein the monocot is selected from the group consisting of maize, rice, oat, wheat, barley, and sorghum.

7. The method of claim 1, wherein the heterologous Fam20C kinase protein comprises a sequence with at least 90% sequence identity to SEQ ID NO: 821.

8. The method of claim 1, wherein the heterologous Fam20C kinase protein comprises SEQ ID NO: 821.

9. The method of claim 1, wherein the heterologous Fam20C kinase protein comprises a sequence with at least 90% sequence identity to amino acids 94-586 of SEQ ID NO: 821.

10. The method of claim 1, wherein the heterologous Fam20C kinase protein comprises amino acids 94-586 of SEQ ID NO: 821.

11. The method of claim 1, wherein the heterologous casein protein is selected from the group consisting of: α-S1 casein, α-S2 casein, β-casein, κ-casein, and para-κ-casein.

12. The method of claim 1, wherein the heterologous casein protein is a mature truncated casein, lacking a signal peptide.

13. The method of claim 1, wherein the heterologous casein protein is within a fusion protein comprising a second milk protein or a zein protein.

14. The method of claim 13, wherein the second milk protein is selected from the group consisting of an α-S1 casein, an α-S2 casein, a β-casein, a κ-casein, a para-κ-casein, a β-lactoglobulin, an α-lactalbumin, a lysozyme, a lactoferrin, a lactoperoxidase, a serum albumin, and an immunoglobulin.

15. The method of claim 1, wherein the heterologous Fam20C kinase protein comprises a plant signal peptide.

16. A method of producing a plant-based casein mimic, said method comprising the steps of:
   a) providing a plant cell expressing:
      i) a heterologous casein protein; and
      ii) a heterologous Fam20C kinase protein; and
   b) separating the heterologous casein protein from the plant cell.

17. The method of claim 16, wherein the plant cell is from a dicot.

18. The method of claim 17, wherein the dicot is selected from the group consisting of arabidopsis, tobacco, tomato, potato, sweet potato, cassava, alfalfa, lima bean, pea, chickpea, soybean, carrot, strawberry, lettuce, oak, maple, walnut, rose, mint, squash, daisy, quinoa, buckwheat, mung bean, cow pea, lentil, lupin, peanut, fava bean, French bean, mustard, and cactus.

19. The method of claim 17, wherein the dicot is soybean.

20. The method of claim 16, wherein the plant cell is from a monocot.

21. The method of claim 20, wherein the monocot is selected from the group consisting of maize, rice, oat, wheat, barley, and sorghum.

22. The method of claim 16, wherein the heterologous Fam20C kinase protein comprises a sequence with at least 90% sequence identity to SEQ ID NO: 821.

23. The method of claim 16, wherein the heterologous Fam20C kinase protein comprises SEQ ID NO: 821.

24. The method of claim 16, wherein the heterologous Fam20C kinase protein comprises a sequence with at least 90% sequence identity to amino acids 94-586 of SEQ ID NO: 821.

25. The method of claim 16, wherein the heterologous Fam20C kinase protein comprises amino acids 94-586 of SEQ ID NO: 821.

26. The method of claim 16, wherein the heterologous casein protein is selected from the group consisting of: α-S1 casein, α-S2 casein, β-casein, κ-casein, and para-κ-casein.

27. The method of claim 16, wherein the heterologous casein protein is a mature truncated casein, lacking a signal peptide.

28. The method of claim 16, wherein the heterologous casein protein is within a fusion protein comprising a second milk protein or a zein protein.

29. The method of claim 28, wherein the second milk protein is selected from the group consisting of an α-S1 casein, an α-S2 casein, a β-casein, a κ-casein, a para-κ-casein, a β-lactoglobulin, an α-lactalbumin, a lysozyme, a lactoferrin, a lactoperoxidase, a serum albumin, and an immunoglobulin.

30. The method of claim 16, wherein the heterologous Fam20C kinase protein comprises a plant signal peptide.

* * * * *

```
                              SEQUENCE LISTING

Sequence total quantity: 860
SEQ ID NO: 1            moltype = DNA  length = 318
FEATURE                 Location/Qualifiers
misc_feature            1..318
                        note = Optimized para-kappa-casein truncated version 1
                          (paraOKC1-T)
source                  1..318
                        mol_type = other DNA
                        organism = synthetic construct
SEQUENCE: 1
caagagcaga atcaagagca gccaatccgt tgtgagaagg acgagaggtt cttctcagac   60
aagatcgcca aatatatacc catacaatat gtactctcac gctaccctag ctacgggctt  120
aactactatc agcaaaaacc tgtagcactg ataaataacc agtttctccc ctatccctat  180
tatgctaaac ctgccgccgt gagggagtcca gcacaaatac ttcagtggca agtgctcagt  240
aacaccgtgc cagcaaaaag ctgccaggct cagcccacca caatggcccg tcatccccat  300
cctcaccttta gcttcatg                                               318

SEQ ID NO: 2            moltype = AA  length = 106
FEATURE                 Location/Qualifiers
REGION                  1..106
                        note = Optimized para-kappa-casein truncated version 1
                          (paraOKC1-T)
source                  1..106
                        mol_type = protein
                        organism = synthetic construct
SEQUENCE: 2
QEQNQEQPIR CEKDERFFSD KIAKYIPIQY VLSRYPSYGL NYYQQKPVAL INNQFLPYPY   60
YAKPAAVRSP AQILQWQVLS NTVPAKSCQA QPTTMARHPH PHLSFM                 106

SEQ ID NO: 3            moltype = DNA  length = 507
FEATURE                 Location/Qualifiers
misc_feature            1..507
                        note = Optimized kappa-casein truncated version 1 (OKC1-T)
source                  1..507
                        mol_type = other DNA
                        organism = synthetic construct
SEQUENCE: 3
caagagcaga atcaagagca gccaatccgt tgtgagaagg acgagaggtt cttctcagac   60
aagatcgcca aatatatacc catacaatat gtactctcac gctaccctag ctacgggctt  120
aactactatc agcaaaaacc tgtagcactg ataaataacc agtttctccc ctatccctat  180
tatgctaaac ctgccgccgt gagggagtcca gcacaaatac ttcagtggca agtgctcagt  240
aacaccgtgc cagcaaaaag ctgccaggct cagcccacca caatggcccg tcatccccat  300
cctcaccttta gcttcatggc aatcccacca aagaagaatc aagacaagac cgaaatacct  360
accatcaaca caattgcatc tggagagcct accagtacac caacaactga ggcagtagag  420
tctactgttg ctacccttga ggacagcccc gaggtttatag agtccccacc tgagataaat  480
accgtgcagg tgacaagtac cgccgta                                     507

SEQ ID NO: 4            moltype = AA  length = 169
FEATURE                 Location/Qualifiers
REGION                  1..169
                        note = Optimized kappa-casein truncated version 1 (OKC1-T)
source                  1..169
                        mol_type = protein
                        organism = synthetic construct
SEQUENCE: 4
QEQNQEQPIR CEKDERFFSD KIAKYIPIQY VLSRYPSYGL NYYQQKPVAL INNQFLPYPY   60
YAKPAAVRSP AQILQWQVLS NTVPAKSCQA QPTTMARHPH PHLSFMAIPP KKNQDKTEIP  120
TINTIASGEP TSTPTTEAVE STVATLEDSP EVIESPPEIN TVQVTSTAV              169

SEQ ID NO: 5            moltype = DNA  length = 627
FEATURE                 Location/Qualifiers
misc_feature            1..627
                        note = Optimized beta-casein truncated version 2 (OBC-T2)
source                  1..627
                        mol_type = other DNA
                        organism = synthetic construct
SEQUENCE: 5
cgcgaactgg aagagttgaa cgtaccagga gagattgtag aatcactgag ctcctcagag   60
gagtctatta ctcgtatcaa caagaagata gagaagttcc aatccgagga gcaacaacaa  120
acagaggacg aattgcagga caagatacat cctttcgcac agaccccagag cctcgtctat  180
cccttttccag gtccaatccc taactctctc ccccagaata tcccacccctt gactcagact  240
cccgtggtcg taccccccttt cttgcaaccc gaggtgatgg gggtttctaa agtcaaagag  300
gctatggctc ctaaacataa ggaaatgcct tttcccaaat atccagtgga gccattcact  360
```

```
gagagccagt ctctgacact tacagatgtg gaaaacttgc acctgccctt gccacttttg  420
cagtcctgga tgcaccaacc acatcaaccc ttgcccccca cagtgatgtt tcctccacaa  480
tcagttctta gtctctccca aagcaaagtc cttccagtgc ctcagaaggc cgtcccatac  540
ccccagagag atatgccaat acaggcattc ttgctttacc aggaaccagt gctcggtcct  600
gtacgtggcc cattccctat catagtg                                      627

SEQ ID NO: 6            moltype = AA  length = 209
FEATURE                 Location/Qualifiers
REGION                  1..209
                        note = Optimized beta-casein truncated version 2 (OBC-T2)
source                  1..209
                        mol_type = protein
                        organism = synthetic construct
SEQUENCE: 6
RELEELNVPG EIVESLSSSE ESITRINKKI EKFQSEEQQQ TEDELQDKIH PFAQTQSLVY   60
PFPGPIPNSL PQNIPPLTQT PVVVPPFLQP EVMGVSKVKE AMAPKHKEMP FPKYPVEPFT  120
ESQSLTLTDV ENLHLPLPLL QSWMHQPHQP LPPTVMFPPQ SVLSLSQSKV LPVPQKAVPY  180
PQRDMPIQAF LLYQEPVLGP VRGPFPIIV                                    209

SEQ ID NO: 7            moltype = DNA  length = 597
FEATURE                 Location/Qualifiers
misc_feature            1..597
                        note = Optimized alpha S1-casein truncated version 1(OaS1-T)
source                  1..597
                        mol_type = other DNA
                        organism = synthetic construct
SEQUENCE: 7
cgcccaaaac atcccataaa acatcaagga ttgccccagg aagtactcaa cgagaatctc   60
ctccgttttt tcgttgctcc tttccccgaa gtgttcggga aggaaaaagt aaacgagctt  120
tcaaaggaca tcggctctga agtaccgag gatcaggcta tggaagatat caagcaaatg  180
gaggccgaat ctataagttc ttcagaagaa atagttccca actcagtgga gcagaagcac  240
attcagaaag aagacgtgcc cagcgagcgc tatctgggat atttggaaca gctgctcaga  300
ctgaaaaagt acaaggtgcc tcagctcgaa atcgtaccca atagtgctga gaaaggttga  360
cactcaatga aagaggggat tcacgcacaa caaaaagcg ctatgatcgg agtaaatcaa  420
gaactggcat acttttatcc cgagttgttt cgccaattct atcaactgga tgcctaccct  480
tccggtgcat ggtactacgt acccctcggt actcaatata ccgatgctcc ctcctttttcc  540
gacattccta atcctatagg ttccgagaat agcgaaaaga ccaccatgcc cttatgg     597

SEQ ID NO: 8            moltype = AA  length = 199
FEATURE                 Location/Qualifiers
REGION                  1..199
                        note = Optimized alpha S1-casein truncated version 1(OaS1-T)
source                  1..199
                        mol_type = protein
                        organism = synthetic construct
SEQUENCE: 8
RPKHPIKHQG LPQEVLNENL LRFFVAPFPE VFGKEKVNEL SKDIGSESTE DQAMEDIKQM   60
EAESISSSEE IVPNSVEQKH IQKEDVPSER YLGYLEQLLR LKKYKVPQLE IVPNSAEERL  120
HSMKEGIHAQ QKEPMIGVNQ ELAYFYPELF RQFYQLDAYP SGAWYYVPLG TQYTDAPSFS  180
DIPNPIGSEN SEKTTMPLW                                                199

SEQ ID NO: 9            moltype = DNA  length = 486
FEATURE                 Location/Qualifiers
misc_feature            1..486
                        note = Optimized Beta Lactoglobulin 1 (OLG1)
source                  1..486
                        mol_type = other DNA
                        organism = synthetic construct
SEQUENCE: 9
ttgatcgtaa cacagactat gaagggtctt gatatacaga aggtggccgg gacttggtac   60
agtttggcaa tggccgcatc cgacatctcc ttgttggacg cacaatcagc cccattgcgt  120
gtgtacgtag aagagcttaa accaactccc gaggggatc tggaaattct gctccagaaa  180
tgggagaacg gtgagtgcgc ccagaagaag atcatcgcag agaagaccaa aattccagca  240
gtattcaaaa tcgacgcatt gaacgaaaat aaggtgctac tactggacac tgattataag  300
aagtatctcc tttctgtat ggagaactca gcagagcctg aacagagtct tgcctgccaa   360
tgccttgttc gtaccccaga ggtagatgat gaagctctgg aaaagttcga taggccctt   420
aaggctctgc ctatgcacat taggctttct ttcaatccaa ctcaacttga ggaacaatgt  480
cacatt                                                             486

SEQ ID NO: 10           moltype = AA  length = 162
FEATURE                 Location/Qualifiers
REGION                  1..162
                        note = Optimized Beta Lactoglobulin 1 (OLG1)
source                  1..162
                        mol_type = protein
                        organism = synthetic construct
SEQUENCE: 10
LIVTQTMKGL DIQKVAGTWY SLAMAASDIS LLDAQSAPLR VYVEELKPTP EGDLEILLQK   60
WENGECAQKK IIAEKTKIPA VFKIDALNEN KVLVLDTDYK KYLLFCMENS AEPEQSLACQ  120
```

```
CLVRTPEVDD EALEKFDKAL KALPMHIRLS FNPTQLEEQC HI                          162

SEQ ID NO: 11              moltype = DNA   length = 486
FEATURE                    Location/Qualifiers
misc_feature               1..486
                           note = Optimized Beta Lactoglobulin 2 (OLG2)
source                     1..486
                           mol_type = other DNA
                           organism = synthetic construct
SEQUENCE: 11
cttattgtga cccaaaccat gaagggcctc gacattcaaa aggttgccgg aacctggtac       60
tcccttgcta tggctgcttc cgatatctcc ttgctcgatg ctcaatccgc tccacttagg      120
gtgtacgtgg aagagttgaa gccaactcca gagggcgatc ttgagatctt gcttcaaaag     180
tgggagaacg atgagtgcgc ccagaagaag attatcgccg aaaagaccaa gattcccgcc     240
gtgttcaaga tcgatgctct caacgagaac aaggtgctcg tgctcgatac cgactacaag     300
aagtaccttc tcgtctgcat ggaaaactcc gctgagccag agcaatctct tgtttgccaa     360
tgccttgtga ggaccccaga ggttgacgat gaagctcttg agaagttcga caaggctctc     420
aaggctttgc ctatgcacat ccgccttagc ttcaacccaa ctcagcttga ggaacagtgc     480
cacatc                                                                 486

SEQ ID NO: 12              moltype = DNA   length = 486
FEATURE                    Location/Qualifiers
misc_feature               1..486
                           note = Optimized Beta Lactoglobulin 3 (OLG3)
source                     1..486
                           mol_type = other DNA
                           organism = synthetic construct
SEQUENCE: 12
ctcattgtta cacaaaccat gaagggtctt gacattcaga aggttgctgg acatggtat       60
tcactagcga tggctgcttc tgatatctcc ctgttggatg cacagtctgc cccctgaga      120
gtgtatgttg aagaactgaa accgacacct gaaggagact ggaaatttt actccagaaa     180
tgggaaaatg atgagtgtgc ccaaaagaag ataatagccg agaagaccaa aattcctgct     240
gtgtttaaga ttgatgcttt gaatgagaac aaagtactag tcctcgacac tgattacaag     300
aaatacttat tagtgtgcat ggaaaacagc gcagagccag aacaatcact tgtttgtcaa     360
tgtttggtcc gtactccaga ggtagatgat gaagcattgg agaaatttga taaagcattg     420
aaggcacttc caatgcatat aaggcttagt ttcaatccta ctcagcttga agagcaatgc     480
cacatc                                                                 486

SEQ ID NO: 13              moltype = DNA   length = 486
FEATURE                    Location/Qualifiers
misc_feature               1..486
                           note = Optimized Beta Lactoglobulin 4 (OLG4)
source                     1..486
                           mol_type = other DNA
                           organism = synthetic construct
SEQUENCE: 13
cttatagtaa ctcaaaccat gaagggactt gatatccaaa aagttgcagg aacctggtac       60
tcactggcta tggcagcttc cgacatctcc ttgttggacg cacaatccgc accattgcgc     120
gtctacgttg aggagttgaa acctacacca gaggggatc ttgagatttt gctccagaaa      180
tgggagaacg acgagtgtgc ccagaaaaaa attatagcag agaagactaa aattcctgct     240
gtttttaaga ttgatgccct gaacgagaat aaggtactgg tcctcgacac tgattataaa     300
aagtatttgc tggtgtgtat ggagaacagt gctgaacctg aacagagcct ggtctgtcaa     360
tgtcttgtaa ggacacctga ggttgatgac gaggcacttg aaaaattcga caaggccctt     420
aaggctctgc ctatgcacat ccgtctgagt ttcaacccta ctcagttgga ggaacaatgt     480
catatt                                                                 486

SEQ ID NO: 14              moltype = DNA   length = 96
FEATURE                    Location/Qualifiers
source                     1..96
                           mol_type = genomic DNA
                           organism = Glycine max
SEQUENCE: 14
atggctactt caaagttgaa aacccagaat gtggttgtat ctctctccct aaccttaacc       60
ttggtactgg tgctactgac cagcaaggca aactca                                96

SEQ ID NO: 15              moltype = AA    length = 32
FEATURE                    Location/Qualifiers
source                     1..32
                           mol_type = protein
                           organism = Glycine max
SEQUENCE: 15
MATSKLKTQN VVVSLSLTLT LVLVLLTSKA NS                                     32

SEQ ID NO: 16              moltype = DNA   length = 57
FEATURE                    Location/Qualifiers
source                     1..57
                           mol_type = genomic DNA
                           organism = Glycine max
SEQUENCE: 16
```

```
atggccaagc tagttttttc cctttgtttt ctgcttttca gtggctgctg cttcgct        57

SEQ ID NO: 17          moltype = AA   length = 19
FEATURE                Location/Qualifiers
source                 1..19
                       mol_type = protein
                       organism = Glycine max
SEQUENCE: 17
MAKLVFSLCF LLFSGCCFA                                                   19

SEQ ID NO: 18          moltype = DNA   length = 1543
FEATURE                Location/Qualifiers
source                 1..1543
                       mol_type = genomic DNA
                       organism = Glycine max
SEQUENCE: 18
cattgtactc ccagtatcat tatagtgaaa gttttggctc tctgccggt ggtttttac        60
ctctatttaa aggggttttc cacctaaaaa ttctggtatc tttctcactt tacttgttac      120
tttaatttct cataatcttt ggttgaaatt atcacgcttc cgcacacgat atccctacaa      180
atttattatt tgttaaacat tttcaaaccg cataaaattt tatgaagtcc cgtctatctt     240
taatgtagtc taacattttc atattgaaat atataattta cttaattttta gcgttggtag    300
aaagcataat gatttattct tattcttctt catatatatc ttaatatac aatataaaca      360
aattctttac cttaagaagg atttcccatt ttatatttta aaaatatatt tatcaaatat     420
ttttcaacca cgtaaatcac ataataataa gttgtttcaa aagtaataaa atttaactcc     480
ataatttttt tatttgactg atcttaaagc aacacccagt gacacaacta gccattttttt   540
tctttgaata aaaaaatcca atatcattg tatttttttt atacaatgaa aatttcacca     600
aacaatgatt tgtggtattt ctgaagcaag tcatgttatg caaaattcta taattcccat    660
ttgacactac ggaagtaact gaagatctgc ttttacatgc gagacacatc ttctaaagta    720
atttttaataa tagttactat attcaagatt tcatatatca aatactcaat attacttcta   780
aaaaattaat tagatataat taaaatatta cttttttttt tttaagttta attgttgaat    840
ttgtgactat tgatttattta ttctactatg tttaaattgt tttataggta gtttaaagta   900
aatataagta atgtagtaga gtgttagagt gttaccctaa accataaaact ataagattta   960
tggtggacta attttcatat atttcttatt gcttttacct tttcttggta tgtaagtccg   1020
taactggaat tactgtgggt tgccatgaca ctctgtggtc ttttggttca tgcatggatg   1080
cttgcgcaag aaaaagacaa agaacaaaga aaaaagacaa aacagagaga caaaacgcaa   1140
tcacacaacc aactcaaatt agtcactggc tgatcaagat cgccgcgtcc atgtatgtct   1200
aaatgccatg caaagcaaca cgtgcttaac atgcacttta aatggctcac ccatcccaac   1260
ccactcacaa acacattgcc tttttcttca tcatcaccac aaccacctgt atatattcat   1320
tctcttccgc cacctcaatt tcttccacttc aacacacgtc aacctgcata tgcgtgtcat   1380
cccatgccca aatctccatg catgttccta ccaccttctc tcttatataa tacctataaa   1440
tacctctaat atcactcact tctttcatca tccatccatc cagagtacta ctactctact   1500
actataatac cccaacccaa ctcatattca atactactct act                     1543

SEQ ID NO: 19          moltype = DNA   length = 1384
FEATURE                Location/Qualifiers
source                 1..1384
                       mol_type = genomic DNA
                       organism = Glycine max
SEQUENCE: 19
aacacaagct tcaagtttta aaggaaaaa tgtcagccaa aaactttaaa taaaatggta      60
acaaggaaat tattcaaaaa ttacaaacct cgtcaaaata ggaaagaaaa aaagtttaaa    120
gatttagaaa aaacatcaat ctagttccac cttattttat agagagaaga aactaatata    180
taagaactaa aaaacagaag aatagaaaaa aaagtattg acaggaaaga aaagtagct     240
gtatgcttat aagtactttg aggatttgaa ttctctcttta taaacacaa acacaatttt    300
tagattttat ttaaataatc atcaatccga ttataattat ttatatattt ttctattttc    360
aaagaagtaa atcatgagct tttccaactc aacatctatt ttttttctct caacctttt    420
cacatcttaa gtagtctcac cctttatata tataacttat ttcttacctt ttacattatg    480
taactttttat caccaaaacc aacaacttta aaatttttatt aaatagactc cacaagtaac    540
ttgacactct tacattcatc gacattaact tttatctgtt ttataaatat tattgtgata    600
taatttaatc aaaataacca caaactttca taaaaggttc ttattaagca tggcatttaa    660
taagcaaaaa caactcaatc acttcatat aggaggtagc ctaagtacgt actcaaaatg     720
ccaacaaata aaaaaaagt tgctttaata atgccaaaac aaattaataa aacacttaca    780
acaccggatt ttttttaatt aaaatgtgcc atttaggata aatagttaat attttttaata  840
attatttaaa aagccgtatc tactaaatg atttttattt ggttgaaaat attaatatgt    900
ttaaatcaac acaatctatc aaaattaaac taaaaaaaaa ataagtgtac gtggttaaca    960
ttagtacagt aatataagag gaaaatgaga aattaagaaa ttgaaagcga gtctaatttt   1020
taaattatga acctgcatat ataaaaggaa agaaagaatc caggaagaaa agaaatgaaa   1080
ccatgcatgg tcccctcgtc atcacgagtt tctgccattt gcaatagaaa cactgaaaca   1140
cctttctctt tgtcacttaa ttgagatgcc gaagccacct cacacgatga acttcatgag   1200
gtgtagcacc caaggcttcc atagccatgc atactgaaga atgtctcaag ctcagcaccc   1260
tacttctgtg acgtgtccct cattcacctt cctctcttcc ctataaataa ccacgcctca   1320
ggttctccgc ttcacaactc aaacattctc tccattggtc cttaaacact catcagtcat   1380
cacc                                                                 1384

SEQ ID NO: 20          moltype = DNA   length = 13
FEATURE                Location/Qualifiers
source                 1..13
                       mol_type = genomic DNA
                       organism = Glycine max
```

```
SEQUENCE: 20
tgaatgcatg atc                                                              13

SEQ ID NO: 21           moltype = DNA   length = 1197
FEATURE                 Location/Qualifiers
source                  1..1197
                        mol_type = genomic DNA
                        organism = Glycine max
SEQUENCE: 21
aataaataaa atgggagcaa taaataaaat gggagctcat atatttacac catttacact            60
gtctattatt caccatgcca attattactt cataatttta aaattatgtc attttaaaa            120
attgcttaat gatggaaagg attattataa gttaaaagta taacatagat aaactaacca           180
caaaacaaat caatataaac taacttactc tcccatctaa tttttattta aatttcttta           240
cacttctctt ccatttctat ttctacaaca ttatttaaca tttttattgt attttcttta           300
ctttctaact ctattcattt caaaaatcaa tatatgttta tcaccacctc tctaaaaaaa           360
actttacaat cattggtcca gaaaagttaa atcacgagat ggtcatttta gcattaaaac           420
aacgattctt gtatcactat ttttcagcat gtagtccatt ctcttcaaac aaagacagcg           480
gctatataat cgttgtgtta tattcagtct aaaacaattg ttatggtaaa agtcgtcatt           540
ttacgccttt ttaaaagata taaaatgaca gttatggtta aaagtcatca tgttagatcc           600
tccttaaaga tataaaatga cagttttgga taaaaagtgg tcattttata cgctcttgaa           660
agatataaaa cgacggttat ggtaaaagct gccattttaa atgaaatatt tttgttttag           720
ttcattttgt ttaatgctaa tcccatttaa attgacttgt acaattaaaa ctcacccacc           780
cagatacaat ataaactaac ttactctcac agctaagttt tatttaaatt tctttacact           840
tcttttccat ttctatttct atgacattaa ctaacatttt tctcgtaatt tttttttctta          900
ttttctaact ctatccattt caaatcgata tatgtttatc accaccactt taaaaagaaa           960
atttacaatt tctcgtgcaa aaaagctaaa tcatgaccgt catttttagca ttaaaacaac         1020
gattcttgta tcgttgtttt tcagcatgta gtccattctt ttcaagcaaa gacaacagct         1080
atataatcat cgtgttatat tcagtctaaa acaacagtaa tgataaaagt catcatttta         1140
ggcctttctg aaatatatag aacgacattc atggtaaaaa atcgtcatttt tagatcc          1197

SEQ ID NO: 22           moltype = DNA   length = 253
FEATURE                 Location/Qualifiers
source                  1..253
                        mol_type = genomic DNA
                        organism = Glycine max
SEQUENCE: 22
gatcgttcaa acatttggca ataaagtttc ttaagattga atcctgttgc cggtcttgcg            60
atgattatca tataatttct gttgaattac gttaagcatg taataattaa catgtaatgc           120
atgcgttat ttatgagatg ggttttatg attagagtcc cgcaattata catttaatac            180
gcgatagaaa acaaaatata gcgcgcaaac taggataaat tatcgcgcgc ggtgtcatct           240
atgttactag atc                                                              253

SEQ ID NO: 23           moltype = AA    length = 4
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 23
KDEL                                                                          4

SEQ ID NO: 24           moltype = AA    length = 4
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 24
HDEL                                                                          4

SEQ ID NO: 25           moltype = AA    length = 4
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 25
HDEF                                                                          4

SEQ ID NO: 26           moltype = AA    length = 4
FEATURE                 Location/Qualifiers
REGION                  1..4
                        note = Carboxy-terminal endoplasmic reticulum
```

```
                         retention/retrieval signal
source                   1..4
                         mol_type = protein
                         organism = unidentified
SEQUENCE: 26
RDEF                                                                       4

SEQ ID NO: 27            moltype = AA  length = 4
FEATURE                  Location/Qualifiers
REGION                   1..4
                         note = Carboxy-terminal endoplasmic reticulum
                         retention/retrieval signal
source                   1..4
                         mol_type = protein
                         organism = unidentified
SEQUENCE: 27
RDEL                                                                       4

SEQ ID NO: 28            moltype = AA  length = 4
FEATURE                  Location/Qualifiers
REGION                   1..4
                         note = Carboxy-terminal endoplasmic reticulum
                         retention/retrieval signal
source                   1..4
                         mol_type = protein
                         organism = unidentified
SEQUENCE: 28
WDEL                                                                       4

SEQ ID NO: 29            moltype = AA  length = 4
FEATURE                  Location/Qualifiers
REGION                   1..4
                         note = Carboxy-terminal endoplasmic reticulum
                         retention/retrieval signal
source                   1..4
                         mol_type = protein
                         organism = unidentified
SEQUENCE: 29
YDEL                                                                       4

SEQ ID NO: 30            moltype = AA  length = 4
FEATURE                  Location/Qualifiers
REGION                   1..4
                         note = Carboxy-terminal endoplasmic reticulum
                         retention/retrieval signal
source                   1..4
                         mol_type = protein
                         organism = unidentified
SEQUENCE: 30
HEEF                                                                       4

SEQ ID NO: 31            moltype = AA  length = 4
FEATURE                  Location/Qualifiers
REGION                   1..4
                         note = Carboxy-terminal endoplasmic reticulum
                         retention/retrieval signal
source                   1..4
                         mol_type = protein
                         organism = unidentified
SEQUENCE: 31
HEEL                                                                       4

SEQ ID NO: 32            moltype = AA  length = 4
FEATURE                  Location/Qualifiers
REGION                   1..4
                         note = Carboxy-terminal endoplasmic reticulum
                         retention/retrieval signal
source                   1..4
                         mol_type = protein
                         organism = unidentified
SEQUENCE: 32
KEEL                                                                       4

SEQ ID NO: 33            moltype = AA  length = 4
FEATURE                  Location/Qualifiers
REGION                   1..4
                         note = Carboxy-terminal endoplasmic reticulum
                         retention/retrieval signal
source                   1..4
```

```
                              mol_type = protein
                              organism = unidentified
SEQUENCE: 33
REEL                                                                          4

SEQ ID NO: 34                 moltype = AA  length = 4
FEATURE                       Location/Qualifiers
REGION                        1..4
                              note = Carboxy-terminal endoplasmic reticulum
                                retention/retrieval signal
source                        1..4
                              mol_type = protein
                              organism = unidentified
SEQUENCE: 34
KAEL                                                                          4

SEQ ID NO: 35                 moltype = AA  length = 4
FEATURE                       Location/Qualifiers
REGION                        1..4
                              note = Carboxy-terminal endoplasmic reticulum
                                retention/retrieval signal
source                        1..4
                              mol_type = protein
                              organism = unidentified
SEQUENCE: 35
KCEL                                                                          4

SEQ ID NO: 36                 moltype = AA  length = 4
FEATURE                       Location/Qualifiers
REGION                        1..4
                              note = Carboxy-terminal endoplasmic reticulum
                                retention/retrieval signal
source                        1..4
                              mol_type = protein
                              organism = unidentified
SEQUENCE: 36
KFEL                                                                          4

SEQ ID NO: 37                 moltype = AA  length = 4
FEATURE                       Location/Qualifiers
REGION                        1..4
                              note = Carboxy-terminal endoplasmic reticulum
                                retention/retrieval signal
source                        1..4
                              mol_type = protein
                              organism = unidentified
SEQUENCE: 37
KGEL                                                                          4

SEQ ID NO: 38                 moltype = AA  length = 4
FEATURE                       Location/Qualifiers
REGION                        1..4
                              note = Carboxy-terminal endoplasmic reticulum
                                retention/retrieval signal
source                        1..4
                              mol_type = protein
                              organism = unidentified
SEQUENCE: 38
KHEL                                                                          4

SEQ ID NO: 39                 moltype = AA  length = 4
FEATURE                       Location/Qualifiers
REGION                        1..4
                              note = Carboxy-terminal endoplasmic reticulum
                                retention/retrieval signal
source                        1..4
                              mol_type = protein
                              organism = unidentified
SEQUENCE: 39
KLEL                                                                          4

SEQ ID NO: 40                 moltype = AA  length = 4
FEATURE                       Location/Qualifiers
REGION                        1..4
                              note = Carboxy-terminal endoplasmic reticulum
                                retention/retrieval signal
source                        1..4
                              mol_type = protein
                              organism = unidentified
```

```
SEQUENCE: 40
KNEL                                                                      4

SEQ ID NO: 41            moltype = AA  length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 41
KQEL                                                                      4

SEQ ID NO: 42            moltype = AA  length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 42
KREL                                                                      4

SEQ ID NO: 43            moltype = AA  length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 43
KSEL                                                                      4

SEQ ID NO: 44            moltype = AA  length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 44
KVEL                                                                      4

SEQ ID NO: 45            moltype = AA  length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 45
KWEL                                                                      4

SEQ ID NO: 46            moltype = AA  length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 46
KYEL                                                                      4

SEQ ID NO: 47            moltype = AA  length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 47
KEDL                                                                      4
```

```
SEQ ID NO: 48            moltype = AA   length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 48
KIEL                                                                    4

SEQ ID NO: 49            moltype = AA   length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 49
DKEL                                                                    4

SEQ ID NO: 50            moltype = AA   length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 50
FDEL                                                                    4

SEQ ID NO: 51            moltype = AA   length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 51
KDEF                                                                    4

SEQ ID NO: 52            moltype = AA   length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 52
KKEL                                                                    4

SEQ ID NO: 53            moltype = AA   length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 53
HADL                                                                    4

SEQ ID NO: 54            moltype = AA   length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 54
HAEL                                                                    4

SEQ ID NO: 55            moltype = AA   length = 4
```

```
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 55
HIEL                                                                    4

SEQ ID NO: 56           moltype = AA  length = 4
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 56
HNEL                                                                    4

SEQ ID NO: 57           moltype = AA  length = 4
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 57
HTEL                                                                    4

SEQ ID NO: 58           moltype = AA  length = 4
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 58
KTEL                                                                    4

SEQ ID NO: 59           moltype = AA  length = 4
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 59
HVEL                                                                    4

SEQ ID NO: 60           moltype = AA  length = 4
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 60
NDEL                                                                    4

SEQ ID NO: 61           moltype = AA  length = 4
FEATURE                 Location/Qualifiers
REGION                  1..4
                        note = Carboxy-terminal endoplasmic reticulum
                         retention/retrieval signal
source                  1..4
                        mol_type = protein
                        organism = unidentified
SEQUENCE: 61
QDEL                                                                    4

SEQ ID NO: 62           moltype = AA  length = 4
FEATURE                 Location/Qualifiers
REGION                  1..4
```

```
                        note = Carboxy-terminal endoplasmic reticulum
                          retention/retrieval signal
source                  1..4
                        mol_type = protein
                        organism = unidentified
SEQUENCE: 62
REDL                                                                        4

SEQ ID NO: 63           moltype = AA   length = 4
FEATURE                 Location/Qualifiers
REGION                  1..4
                        note = Carboxy-terminal endoplasmic reticulum
                          retention/retrieval signal
source                  1..4
                        mol_type = protein
                        organism = unidentified
SEQUENCE: 63
RNEL                                                                        4

SEQ ID NO: 64           moltype = AA   length = 4
FEATURE                 Location/Qualifiers
REGION                  1..4
                        note = Carboxy-terminal endoplasmic reticulum
                          retention/retrieval signal
source                  1..4
                        mol_type = protein
                        organism = unidentified
SEQUENCE: 64
RTDL                                                                        4

SEQ ID NO: 65           moltype = AA   length = 4
FEATURE                 Location/Qualifiers
REGION                  1..4
                        note = Carboxy-terminal endoplasmic reticulum
                          retention/retrieval signal
source                  1..4
                        mol_type = protein
                        organism = unidentified
SEQUENCE: 65
RTEL                                                                        4

SEQ ID NO: 66           moltype = AA   length = 4
FEATURE                 Location/Qualifiers
REGION                  1..4
                        note = Carboxy-terminal endoplasmic reticulum
                          retention/retrieval signal
source                  1..4
                        mol_type = protein
                        organism = unidentified
SEQUENCE: 66
SDEL                                                                        4

SEQ ID NO: 67           moltype = AA   length = 4
FEATURE                 Location/Qualifiers
REGION                  1..4
                        note = Carboxy-terminal endoplasmic reticulum
                          retention/retrieval signal
source                  1..4
                        mol_type = protein
                        organism = unidentified
SEQUENCE: 67
TDEL                                                                        4

SEQ ID NO: 68           moltype = AA   length = 4
FEATURE                 Location/Qualifiers
REGION                  1..4
                        note = Carboxy-terminal endoplasmic reticulum
                          retention/retrieval signal
source                  1..4
                        mol_type = protein
                        organism = unidentified
SEQUENCE: 68
SKEL                                                                        4

SEQ ID NO: 69           moltype = AA   length = 4
FEATURE                 Location/Qualifiers
REGION                  1..4
                        note = Carboxy-terminal endoplasmic reticulum
                          retention/retrieval signal
```

```
source                   1..4
                         mol_type = protein
                         organism = unidentified
SEQUENCE: 69
STEL                                                                    4

SEQ ID NO: 70            moltype = AA  length = 4
FEATURE                  Location/Qualifiers
REGION                   1..4
                         note = Carboxy-terminal endoplasmic reticulum
                          retention/retrieval signal
source                   1..4
                         mol_type = protein
                         organism = unidentified
SEQUENCE: 70
EDEL                                                                    4

SEQ ID NO: 71            moltype = AA  length = 367
FEATURE                  Location/Qualifiers
REGION                   1..367
                         note = Fusion protein sig10:OKC1-T:OLG1:KDEL
source                   1..367
                         mol_type = protein
                         organism = synthetic construct
SEQUENCE: 71
MATSKLKTQN VVVSLSLTLT LVLVLLTSKA NSQEQNQEQP IRCEKDERFF SDKIAKYIPI        60
QYVLSRYPSY GLNYYQQKPV ALINNQFLPY PYYAKPAAVR SPAQILQWQV LSNTVPAKSC       120
QAQPTTMARH PHPHLSFMAI PPKKNQDKTE IPTINTIASG EPTSTPTTEA VESTVATLED       180
SPEVIESPPE INTVQVTSTA VLIVTQTMKG LDIQKVAGTW YSLAMAASDI SLLDAQSAPL       240
RVYVEELKPT PEGDLEILLQ KWENGECAQK KIIAEKTKIP AVPKIDALNE NKVLVLDTDY       300
KKYLLFCMEN SAEPEQSLAC QCLVRTPEVD DEALEKFDKA LKALPMHIRL SFNPTQLEEQ       360
CHIKDEL                                                                367

SEQ ID NO: 72            moltype = DNA  length = 1104
FEATURE                  Location/Qualifiers
misc_feature             1..1104
                         note = Nucleic acid sequence encoding fusion protein
                          sig10:OKC1-T:OLG1:KDEL
source                   1..1104
                         mol_type = other DNA
                         organism = synthetic construct
SEQUENCE: 72
atggctactt caaagttgaa aacccagaat gtggttgtat ctctctccct aaccttaacc        60
ttggtactgg tgctactgac cagcaaggca aactcacaag agcagaatca agagcagcca       120
atccgttgtg agaaggacga gaggttcttc tcagacaaga tcgccaaata tatccccata       180
caatatgtac tctcacgcta ccctagctac gggcttaact actatcagca aaaacctgta       240
gcactgataa ataaccagtt tctccccta t ccctattgc ctaaacctgc cgccgtgagg       300
agtccagcac aaatacttca gtggcaagtg ctcagtaaca ccgtgccagc aaaaagctgc       360
caggctcagc ccaccacaat ggcccgtcat ccccatcctc accttagctt catggcaatc       420
ccaccaaaga agaatcaaga caagaccgaa atacctacca tcaacacaat tgcatctgga       480
gagcctacca gtacaccaac aactgaggca gtagagtcta ctgttgctac ccttgaggac       540
agccccgagg ttatagagtc ccccacctga g ataaatacc g tgcaggtgac aagtaccgcc       600
gtattgatcg taacacagac tatgaagggt cttgatatac agaaggtggc cgggacttgg       660
tacagtttgc caatggccgc atccgacatc tccttgttgg acgcacaatc agccccattg       720
cgtctgtacg tagaagagct taaaccaact cccgagggga tctgtaacat tctgctccag       780
aaatgggaga acggtgagtg cgcccagaag aagatcatcg cagagaagac caaaattcca       840
gcagtattca aaatcgacgc attgaacgaa aataaggtgc tcgtactgga cactgattat       900
aagaagtatc tcctttttctg tatggagaac tcagcagagc ctgaacagag tcttgcctgc       960
caatgccttg ttcgtacccc agaggtagat gatgaagctc tggaaaagtt cgataaggcc      1020
cttaaggctc tgcctatgca cattaggctt tctttcaatc caactcaact tgaggaacaa      1080
tgtcacatta aggatgagct taa                                              1104

SEQ ID NO: 73            moltype = AA  length = 405
FEATURE                  Location/Qualifiers
REGION                   1..405
                         note = Fusion protein sig10:OBC-T2:FM:OLG1
source                   1..405
                         mol_type = protein
                         organism = synthetic construct
SEQUENCE: 73
MATSKLKTQN VVVSLSLTLT LVLVLLTSKA NSRELEELNV PGEIVESLSS SEESITRINK        60
KIEKFQSEEQ QQTEDELQDK IHPFAQTQSL VYPFPGPIPN SLPQNIPPLT QTPVVVPPFL       120
QPEVMGVSKV KEAMAPKHKE MPFPKYPVEP FTESQSLTLT DVENLHLPLP LLQSWMHQPH       180
QPLPPTVMFP PQSVLSLSQS KVLPVPQKAV PYPQRDMPIQ AFLLYQEPVL GPVRGPFPII       240
VFMLIVTQTM KGLDIQKVAG TWYSLAMAAS DISLLDAQSA PLRVYVEELK PTPEGDLEIL       300
LQKWENGECA QKKIIAEKTK IPAVPKIDAL NENKVLVLDT DYKKYLLFCM ENSAEPEQSL       360
ACQCLVRTPE VDDEALEKFD KALKALPMHI RLSFNPTQLE EQCHI                      405

SEQ ID NO: 74            moltype = DNA  length = 1218
```

| FEATURE | Location/Qualifiers |
|---|---|
| misc_feature | 1..1218 |
| | note = Nucleic acid encoding fusion protein |
| | sig10:OBC-T2:FM:OLG1 |
| source | 1..1218 |
| | mol_type = other DNA |
| | organism = synthetic construct |

SEQUENCE: 74

```
atggctactt caaagttgaa aacccagaat gtggttgtat ctctctccct aaccttaacc   60
ttggtactgg tgctactgac cagcaaggca aactcacgcg aactggaaga gttgaacgta  120
ccaggagaga ttgtagaatc actgagctcc tcagaggagt ctattactcg tatcaacaag  180
aagatagaga agttccaatc cgaggagcaa caacaaacag aggacgaatt gcaggacaag  240
atacatcctt tcgcacagac ccagagcctc gtctatccct ttccaggtcc aatccctaac  300
tctctccccc agaatatccc acccttgact cagactcccg tggtcgtacc cccttttcttg  360
caacccgagg tgatgggggt ttctaaagtc aaagaggcta tggctcctaa acataaggaa  420
atgcctttc ccaaatatcc agtggagcca ttcactgaga ccagtctct gacacttaca  480
gatgtggaaa acttgcacct gcccttgcca cttttgcagt cctggatgca ccaaccacat  540
caaccctgc ccccacagt gatgtttcct ccacaatcga ttcttagtct ctcccaaagc  600
aaagtcctc cagtgcctca gaaggccgtc ccatacccc agagagatat gccaatacag  660
gcattcttgc tttaccagga accagtgctc ggtcctgtac gtggcccatt ccctatcata  720
gtgttcatgt tgatcgtaac acagactatg aagggtcttg atatacagaa ggtggccggg  780
acttggtaca gtttggcaat ggccgcatcc gacatctcct tgttggacgc acaatcagcc  840
ccattgcgtg tgtacgtaga agagcttaaa ccaactcccg aggggatct ggaaattctg  900
ctccagaaat gggagaacgg tgagtgcgcc cagaagaaga tcatcgcaga aagaccaaa   960
attccagcag tattcaaaat cgacgcattg aacgaaaata aggtgctcgt actggacact 1020
gattataaga agtatctcct tttctgtatg gagaactcag cagagcctga acagagtctt 1080
gcctgccaat gccttgttcg taccccagag gtagatgatg aagctctgga aaagttcgat 1140
aaggcccta aggctctgcc tatgcacatt aggctttctt tcaatccaac tcaacttgag 1200
gaacaatgtc acatttaa                                                1218
```

| SEQ ID NO: 75 | moltype = AA length = 395 |
|---|---|
| FEATURE | Location/Qualifiers |
| REGION | 1..395 |
| | note: Fusion protein sig10:OaS1-T:FM:OLG1 |
| source | 1..395 |
| | mol_type = protein |
| | organism = synthetic construct |

SEQUENCE: 75

```
MATSKLKTQN VVVSLSLTLT LVLVLLTSKA NSRPKHPIKH QGLPQEVLNE NLLRFFVAPF   60
PEVFGKEKVN ELSKDIGSES TEDQAMEDIK QMEAESISSS EEIVPNSVEQ KHIQKEDVPS  120
ERYLGYLEQL LRLKKYKVPQ LEIVPNSAEE RLHSMKEGIH AQQKEPMIGV NQELAYFYPE  180
LFRQFYQLDA YPSGAWYYVP LGTQYTDAPS FSDIPNPIGS ENSEKTTMPL WFMLIVTQTM  240
KGLDIQKVAG TWYSLAMAAS DISLLDAQSA PLRVYVEELK PTPEGDLEIL LQKWENGECA  300
QKKIIAEKTK IPAVFKIDAL NENKVLVLDT DYKKYLLFCM ENSAEPEQSL ACQCLVRTPE  360
VDDEALEKFD KALKALPMHI RLSFNPTQLE EQCHI                             395
```

| SEQ ID NO: 76 | moltype = DNA length = 1188 |
|---|---|
| FEATURE | Location/Qualifiers |
| misc_feature | 1..1188 |
| | note = Nucleic acid encoding fusion protein |
| | sig10:OaS1-T:FM:OLG1 |
| source | 1..1188 |
| | mol_type = other DNA |
| | organism = synthetic construct |

SEQUENCE: 76

```
atggctactt caaagttgaa aacccagaat gtggttgtat ctctctccct aaccttaacc   60
ttggtactgg tgctactgac cagcaaggca aactcacgcc aaaacatcc cataaaacat  120
caaggattgc cccaggaagt actcaacgag aatctcctcc gttttttcgt tgctcctttc  180
cccgaagtgt tcgggaagga aaaagtaaac gagctttcaa aggacatcgg ctctgaaagt  240
accgaggatc aggctatgga agatatcaag caaatggagg ccgaatctat aagttcttca  300
gaagaaatag ttcccaactc agtggagcag aagcacattc agaaagaaga cgtgcccagc  360
gagcgctatc tgggatattt ggaacagctg ctcagactga aaaagtacaa ggtgcctcag  420
ctcgaaatcg taccaaatag tgctgaagaa aggttgcact caatgaaaga ggggattcac  480
gcacaacaaa aagagcctat gatcggagta aatcaagaac tggcatactt ttatcccgag  540
ttgtttcgcc aattctatca actggatgcc tacccttccg gtgcatggta ctacgtaccc  600
ctcggtactc aatataccga tgctccctcc ttttccgaca ttcctaatcc tataggttcc  660
gagaatagcc aaaagaccac catgcccttta tggttcatgt tgatcgtaac acagactatg  720
aagggtcttg atatacagaa ggtggccggg acttggtaca gtttggcaat ggccgcatcc  780
gacatctcct tgttggacgc acaatcagcc ccaactcccg aggggatct ggaaattctg   840
ctccagaaat gggagaacgg tgagtgcgcc cagaagaaga tcatcgcaga aagaccaaa   900
attccagcag tattcaaaat cgacgcattg aacgaaaata aggtgctcgt actggacact  960
gattataaga agtatctcct tttctgtatg gagaactcag cagagcctga acagagtctt 1020
gcctgccaat gccttgttcg taccccagag gtagatgatg aagctctgga aaagttcgat 1080
aaggcccta aggctctgcc tatgcacatt aggctttctt tcaatccaac tcaacttgag 1140
gaacaatgtc acatttaa                                                1188
```

| SEQ ID NO: 77 | moltype = AA length = 304 |
|---|---|
| FEATURE | Location/Qualifiers |
| REGION | 1..304 |

```
                        note = Fusion protein sig10:paraOKC1-T:FM:OLG1:KDEL
source                  1..304
                        mol_type = protein
                        organism = synthetic construct
SEQUENCE: 77
MATSKLKTQN VVVSLSLTLT LVLVLLTSKA NSQEQNQEQP IRCEKDERFF SDKIAKYIPI   60
QYVLSRYPSY GLNYYQQKPV ALINNQFLPY PYYAKPAAVR SPAQILQWQV LSNTVPAKSC  120
QAQPTTMARH PHPHLSFMLI VTQTMKGLDI QKVAGTWYSL AMAASDISLL DAQSAPLRVY  180
VEELKPTPEG DLEILLQKWE NGECAQKKII AEKTKIPAVF KIDALNENKV LVLDTDYKKY  240
LLFCMENSAE PEQSLACQCL VRTPEVDDEA LEKFDKALKA LPMHIRLSFN PTQLEEQCHI  300
KDEL                                                               304

SEQ ID NO: 78           moltype = DNA  length = 915
FEATURE                 Location/Qualifiers
misc_feature            1..915
                        note = Nucleic acid encoding fusion protein
                          sig10:paraOKC1-T:FM:OLG1:KDEL
source                  1..915
                        mol_type = other DNA
                        organism = synthetic construct
SEQUENCE: 78
atggctactt caaagttgaa aacccagaat gtggttgtat ctctctccct aaccttaacc   60
ttggtactgg tgctactgac cagcaaggca aactcacaag agcagaatca agagcagcca  120
atccgttgtg agaaggacga gaggttcttc tcagacaaga tcgccaaata tacccata   180
caatatgtac tctcacgcta ccctagctac gggcttaact actatcagca aaaacctgta  240
gcactgataa ataaccagtt tctccccta cccatattg ctaaacctgc cgccgtgagg   300
agtccagcac aaatacttca gtggcaagtg ctcagtaaca ccgtgccagc aaaaagctgc  360
caggctcagc ccaccacaat ggcccgtcat ccccatcctc accttagctt catgttgatc  420
gtaacacaga ctatgaaggg tcttgatata cagaaggtgg ccgggacttg gtacagtttg  480
gcaatggccg catccgacat ctccttgttg gacgcacaat cagccccatt gcgtgtgtac  540
gtagaagagc ttaaaccaac tcccgagggg atctggaaa ttctgctcca gaatgggag   600
aacggtgagt gcgcccagaa aagatcatc gcagagaaga ccaaaattcc agcagtattc  660
aaaatcgacg cattgaacga aaataaggtg ctcgtactgg acactgatta taagaagtat  720
ctccttttct gtatggagaa ctcagcgag cctgaacaga gtcttgcctg ccaatgcctt  780
gttcgtaccc cagaggtaga tgatgaagct ctggaaaagt tcgataaggc ccttaaggct  840
ctgcctatgc acattaggct ttctttcaat ccaactcaac ttgaggaaca atgtcacatt  900
aaggatgagc tttaa                                                   915

SEQ ID NO: 79           moltype = AA  length = 300
FEATURE                 Location/Qualifiers
REGION                  1..300
                        note = Fusion protein sig10:paraOKC1-T:FM:OLG1
source                  1..300
                        mol_type = protein
                        organism = synthetic construct
SEQUENCE: 79
MATSKLKTQN VVVSLSLTLT LVLVLLTSKA NSQEQNQEQP IRCEKDERFF SDKIAKYIPI   60
QYVLSRYPSY GLNYYQQKPV ALINNQFLPY PYYAKPAAVR SPAQILQWQV LSNTVPAKSC  120
QAQPTTMARH PHPHLSFMLI VTQTMKGLDI QKVAGTWYSL AMAASDISLL DAQSAPLRVY  180
VEELKPTPEG DLEILLQKWE NGECAQKKII AEKTKIPAVF KIDALNENKV LVLDTDYKKY  240
LLFCMENSAE PEQSLACQCL VRTPEVDDEA LEKFDKALKA LPMHIRLSFN PTQLEEQCHI  300

SEQ ID NO: 80           moltype = DNA  length = 903
FEATURE                 Location/Qualifiers
misc_feature            1..903
                        note = Nucleic acid encoding fusion protein
                          sig10:paraOKC1-T:FM:OLG1
source                  1..903
                        mol_type = other DNA
                        organism = synthetic construct
SEQUENCE: 80
atggctactt caaagttgaa aacccagaat gtggttgtat ctctctccct aaccttaacc   60
ttggtactgg tgctactgac cagcaaggca aactcacaag agcagaatca agagcagcca  120
atccgttgtg agaaggacga gaggttcttc tcagacaaga tcgccaaata tacccata   180
caatatgtac tctcacgcta ccctagctac gggcttaact actatcagca aaaacctgta  240
gcactgataa ataaccagtt tctccccta cccatattg ctaaacctgc cgccgtgagg   300
agtccagcac aaatacttca gtggcaagtg ctcagtaaca ccgtgccagc aaaaagctgc  360
caggctcagc ccaccacaat ggcccgtcat ccccatcctc accttagctt catgttgatc  420
gtaacacaga ctatgaaggg tcttgatata cagaaggtgg ccgggacttg gtacagtttg  480
gcaatggccg catccgacat ctccttgttg gacgcacaat cagccccatt gcgtgtgtac  540
gtagaagagc ttaaaccaac tcccgagggg atctggaaa ttctgctcca gaatgggag   600
aacggtgagt gcgcccagaa aagatcatc gcagagaaga ccaaaattcc agcagtattc  660
aaaatcgacg cattgaacga aaataaggtg ctcgtactgg acactgatta taagaagtat  720
ctccttttct gtatggagaa ctcagcgag cctgaacaga gtcttgcctg ccaatgcctt  780
gttcgtaccc cagaggtaga tgatgaagct ctggaaaagt tcgataaggc ccttaaggct  840
ctgcctatgc acattaggct ttctttcaat ccaactcaac ttgaggaaca atgtcacatt  900
taa                                                                903

SEQ ID NO: 81           moltype = AA  length = 354
```

```
FEATURE                 Location/Qualifiers
REGION                  1..354
                        note = Fusion protein sig2:OKC1-T:OLG1:KDEL
source                  1..354
                        mol_type = protein
                        organism = synthetic construct
SEQUENCE: 81
MAKLVFSLCF LLFSGCCFAQ EQNQEQPIRC EKDERFFSDK IAKYIPIQYV LSRYPSYGLN    60
YYQQKPVALI NNQFLPYPYY AKPAAVRSPA QILQWQVLSN TVPAKSCQAQ PTTMARHPHP   120
HLSFMAIPPK KNQDKTEIPT INTIASGEPT STPTTEAVES TVATLEDSPE VIESPPEINT   180
VQVTSTAVLI VTQTMKGLDI QKVAGTWYSL AMAASDISLL DAQSAPLRVY VEELKPTPEG   240
DLEILLQKWE NGECAQKKII AEKTKIPAVF KIDALNENKV LVLDTDYKKY LLFCMENSAE   300
PEQSLACQCL VRTPEVDDEA LEKFDKALKA LPMHIRLSFN PTQLEEQCHI KDEL         354

SEQ ID NO: 82           moltype = DNA  length = 1065
FEATURE                 Location/Qualifiers
misc_feature            1..1065
                        note = Nucleic acid encoding fusion protein
                        sig2:OKC1-T:OLG1:KDEL
source                  1..1065
                        mol_type = other DNA
                        organism = synthetic construct
SEQUENCE: 82
atggccaagc tagtttttc ctttgtttt ctgcttttca gtggctgctg cttcgctcaa      60
gagcagaatc aagagcagcc aatccgttgt gagaaggacg agaggttctt ctcagacaag   120
atcgccaaat atatacccat acaatgtgta ctctcacgct accctagcta cgggcttaac   180
tactatcagc aaaaacctgt agcactgata ataaccagt ttctccccta tccctattat    240
gctaaacctg ccgccgtgag gagtccagca caaatacttc agtggcaagt gctcagtaac   300
accgtgccag caaaaagctg ccaggctcag cccaccaca tggcccgtca tccccatcct    360
caccttagct tcatggcaat cccaccaaag aagaatacaa acaagaccga aatacctacc   420
atcaacacaa ttgcatctgg agagcctacc agtacaccaa caactgaggc agtagagtct   480
actgttgcta cccttgagga cagccccgag gttatagagt ccccacctga gataaatacc   540
gtgcaggtga caagtaccgc cgtattgatc gtaacacaga ctatgaaggg tcttgatata   600
cagaaggtgg ccgggacttg gtacagtttg gcaatggccg catccgacat ctccttgttg   660
gacgcacaat cagccccatt gcgtgtgtac gtagaagagc ttaaaccaac tcccgagggg   720
gatctggaaa ttctgctcca gaaatgggag aacggtgagt gcgcccagaa gaagatcatc   780
gcagagaaga ccaaaattcc agcagtattc aaaatcgacg cattgaacga aaataaggtg   840
ctcgtactgg acactgatta taagaagtat ctccttttct gtatggagaa ctcagcagag   900
cctgaacaga gtcttgcctg ccaatgcctt gttcgtaccc cagaggtaga tgatgaagct   960
ctggaaaagt tcgataaggc ccttaaggct ctgcctatgc acattaggct ttctttcaat  1020
ccaactcaac ttgaggaaca atgtcacatt aaggatgagc tttaa                  1065

SEQ ID NO: 83           moltype = AA  length = 621
FEATURE                 Location/Qualifiers
REGION                  1..621
                        note = Optimized alpha S2-casein truncated version 1(OaS2-T)
source                  1..621
                        mol_type = protein
                        organism = synthetic construct
SEQUENCE: 83
AAGAATACTA TGGAACACGT AAGCTCAAGT GAAGAATCTA TAATAAGTCA AGAGACATAT    60
AAGCAAGAGA AAAACATGGC AATAAATCCC TCCAAGGAGA ATCTTTGTAG CACTTTTTGC   120
AAAGAAGTTG TGAGAAATGC AAATGAGGAA GAATACTCAA TAGGCAGCTC TTCCGAAGAA   180
TCTGCTGAAG TCGCTACTGA AGAGGTCAAA ATAACAGTTG ACGACAAGCA TTATCAAAAA   240
GCCCTGAATG AAATAAACCA GTTCTACCAA AAATTTCCCC AATACCTCCA GTACCTTTAT   300
CAAGGACCCA TAGTCCTCAA CCCCTTGGAT CAGGTCAAGC GTAATGCTGT TCCAATAACA   360
CCAACACTCA ATCGTGAACA ACTGTCTACC TCAAGAAAA ATTCCAAAAA AACTGTGGAT    420
ATGGAAAGTA CAGAAGTTTT TACTAAAAAG ACCAAGCTCA CCGAGGAGGA AAAAAATAGA   480
TTGAATTTTC TTAAGAAGAT CAGTCAACGC TATCAGAAGT TCGCCCTTCC ACAATACCTC   540
AAGACTGTAT ACCAACATCA GAAGGCCATG AAGCCTTGGA TTCAGCCCAA AACAAAGGTA   600
ATCCCCTATG TTAGATACTT G                                            621

SEQ ID NO: 84           moltype = AA  length = 207
FEATURE                 Location/Qualifiers
REGION                  1..207
                        note = Optimized alpha S2-casein truncated version 1(OaS2-T)
source                  1..207
                        mol_type = protein
                        organism = synthetic construct
SEQUENCE: 84
KNTMEHVSSS EESIISQETY KQEKNMAINP SKENLCSTFC KEVVRNANEE EYSIGSSSEE    60
SAEVATEEVK ITVDDKHYQK ALNEINQFYQ KFPQYLQYLY QGPIVLNPWD QVKRNAVPIT   120
PTLNREQLST SEENSKKTVD MESTEVFTKK TKLTEEEKNR LNFLKKISQR YQKFALPQYL   180
KTVYQHQKAM KPWIQPKTKV IPYVRYL                                      207

SEQ ID NO: 85           moltype = AA  length = 171
FEATURE                 Location/Qualifiers
source                  1..171
                        mol_type = protein
```

```
                            organism = Capra hircus
SEQUENCE: 85
QEQNQEQPIC CEKDERFFDD KIAKYIPIQY VLSRYPSYGL NYYQQRPVAL INNQFLPYPY    60
YAKPVAVRSP AQTLQWQVLP NTVPAKSCQD QPTTLARHPH PHLSFMAIPP KKDQDKTEVP   120
AINTIASAEP TVHSTPTTEA IVNTVDNPEA SSESIASASE TNTAQVTSTE V            171

SEQ ID NO: 86           moltype = AA  length = 171
FEATURE                 Location/Qualifiers
source                  1..171
                        mol_type = protein
                        organism = Ovis aries
SEQUENCE: 86
QEQNQEQRIC CEKDERFFDD KIAKYIPIQY VLSRYPSYGL NYYQQRPVAL INNQFLPYPY    60
YAKPVAVRSP AQTLQWQVLP NAVPAKSCQD QPTAMARHPH PHLSFMAIPP KKDQDKTEIP   120
AINTIASAEP TVHSTPTTEA VVNAVDNPEA SSESIASAPE TNTAQVTSTE V            171

SEQ ID NO: 87           moltype = AA  length = 165
FEATURE                 Location/Qualifiers
source                  1..165
                        mol_type = protein
                        organism = Bubalus bubalis
SEQUENCE: 87
QEQNQEQPIR CEKEERFFND KIAKYIPIQY VLSRYPSYGL NYYQQKPVAL INNQFLPYPY    60
YAKPAAVRSP AQILQWQVLP NTVPAKSCQA QPTTMTRHPH PHLSFMAIPP KKNQDKTEIP   120
TINTIVSVEP TSTPTTEAIE NTVATLEASS EVIESVPETN TAQVT                   165

SEQ ID NO: 88           moltype = AA  length = 162
FEATURE                 Location/Qualifiers
source                  1..162
                        mol_type = protein
                        organism = Camelus dromedarius
SEQUENCE: 88
EVQNQEQPTC FEKVERLLNE KTVKYFPIQF VQSRYPSYGI NYYQHRLAVP INNQFIPYPN    60
YAKPVAIRLH AQIPQCQALP NIDPPTVERR PRPRPSFIAI PPKKTQDKTV NPAINTVATV   120
EPPVIPTAEP AVNTVVIAEA SSEFITTSTP ETTTVQITST EI                      162

SEQ ID NO: 89           moltype = AA  length = 162
FEATURE                 Location/Qualifiers
source                  1..162
                        mol_type = protein
                        organism = Camelus bactrianus
SEQUENCE: 89
EVQNQEQPTC CEKVERLLNE KTVKYFPIQF VQSRYPSYGI NYYQHRLAVP INNQFIPYPN    60
YAKPVAIRLH AQIPQCQALP NIDPPTVERR PRPRPSFIAI PPKKTQDKTV NPAINTVATV   120
EPPVIPTAEP AVNTVVIAEA SSEFITTSTP ETTTVQITST EI                      162

SEQ ID NO: 90           moltype = AA  length = 173
FEATURE                 Location/Qualifiers
source                  1..173
                        mol_type = protein
                        organism = Bos mutus
SEQUENCE: 90
QEQNQEQPIR CEKDERFFSD KIAKYIPIQY VLSRYPSYGL NYYQQKPVAL INNQFLPYPY    60
YAKPAAVRSP AQILQWQVLS NTVPAKSCQA QPTTMARHPH PHLSFMAIPP KKNQDKTEIP   120
TINTIASGEP TSTPTTEAVE STVATLEASP EASPEVIESP PEINTVQVTS TAV          173

SEQ ID NO: 91           moltype = AA  length = 165
FEATURE                 Location/Qualifiers
source                  1..165
                        mol_type = protein
                        organism = Equus caballus
SEQUENCE: 91
EVQNQEQPTC HKNDERFFDL KTVKYIPIYY VLNSSPRYEP IYYQHRLALL INNQHMPYQY    60
YARPAAVRPH VQIPQWQVLP NIYPSTVVRH PCPHPSFIAI PPKKLQEITV IPKINTIATV   120
EPTPIPTPEP TVNNAVIPDA SSEFIIASTP ETTTVPVTSP VVQKL                   165

SEQ ID NO: 92           moltype = AA  length = 162
FEATURE                 Location/Qualifiers
source                  1..162
                        mol_type = protein
                        organism = Equus asinus
SEQUENCE: 92
EVQNQEQPTC RKNDERFFDL KTVKYIPIYY VLNSSPRNEP IYYQHRLAVL INNQHMPYQY    60
YARPAAVRPH VQIPQWQVLP NIYPSTVVRH PRPHPSFIAI PPKKLQEKTV IPKINTIATV   120
EPTPIPTPEP TVNNAVIPDA SSEFIIASTP ETTTVPVTSP VV                      162

SEQ ID NO: 93           moltype = AA  length = 122
FEATURE                 Location/Qualifiers
source                  1..122
```

```
                    mol_type = protein
                    organism = Rangifer tarandus
SEQUENCE: 93
VALINNQFLP YPYYAKPGAV RSPAQILQWQ VLPNTVPAKS CQAQPTTLAR HPHPRLSFMA    60
IPPKKNQDKT DIPTINTIAT VESTITPTTE AIVDTVATLE ASSEVIESAP ETNTDQVTST   120
VV                                                                 122

SEQ ID NO: 94       moltype = AA  length = 141
FEATURE             Location/Qualifiers
source              1..141
                    mol_type = protein
                    organism = Alces alces
SEQUENCE: 94
KIVKYIPIQY ALSRYPSYGL SYYQHRPVAL INNQFLPYPY YAKPGAVRSP AQILQWQVLP    60
NTVPAKSCQA QPTTMARHPR PRLSFMAIPP KKNQDKTDIP TINTIATVES TITPTTEAIE   120
DNVATLEASS EVIESAPETN T                                            141

SEQ ID NO: 95       moltype = AA  length = 162
FEATURE             Location/Qualifiers
source              1..162
                    mol_type = protein
                    organism = Vicugna pacos
SEQUENCE: 95
EVQNQEQPTC CEKVERLLNE KTVKYFPIQF VQSRYPSYGI NYYQHRLAVP INNQFIPYPN    60
YAKPVAIRLH AQIPQCQALP NIDPPTVERR PRPRPSFIAI PPKKTQDKTV IPAINTVATA   120
EPPVIPTAEP VVNTVVIAEA SSEFITTSTP ETTTVQITST EI                     162

SEQ ID NO: 96       moltype = AA  length = 160
FEATURE             Location/Qualifiers
source              1..160
                    mol_type = protein
                    organism = Bos indicus
SEQUENCE: 96
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                        160

SEQ ID NO: 97       moltype = AA  length = 162
FEATURE             Location/Qualifiers
source              1..162
                    mol_type = protein
                    organism = Lama glama
SEQUENCE: 97
EVQNQEQPTC CEKVERLLNE KTVKYFPIQF VQSRYPSYGI NYYQHRLAVP INNQFIPYPN    60
YAKPVAIRLH AQIPQCQALP NIDPPTVERR PRPRPSFIAI PPKKTQDKTV IPAINTVATV   120
EPPVIPTAEP VVNTVVIAEA SSEFITTSTP ETTTVQITST EI                     162

SEQ ID NO: 98       moltype = AA  length = 162
FEATURE             Location/Qualifiers
source              1..162
                    mol_type = protein
                    organism = Homo sapiens
SEQUENCE: 98
EVQNQKQPAC HENDERPFYQ KTAPYVPMYY VPNSYPYYGT NLYQRRPAIA INNPYVPRTY    60
YANPAVVRPH AQIPQRQYLP NSHPPTVVRR PNLHPSFIAI PPKKIQDKII IPTINTIATV   120
EPTPAPATEP TVDSVVTPEA FSESIITSTP ETTTVAVTPP TA                     162

SEQ ID NO: 99       moltype = AA  length = 199
FEATURE             Location/Qualifiers
source              1..199
                    mol_type = protein
                    organism = Capra hircus
SEQUENCE: 99
RPKHPINHRG LSPEVPNENL LRFVVAPFPE VFRKENINEL SKDIGSESTE DQAMEDAKQM    60
KAGSSSSSEE IVPNSAEQKY IQKEDVPSER YLGYLEQLLR LKKYNVPQLE IVPKSAEEQL   120
HSMKEGNPAH QKQPMIAVNQ ELAYFYPQLF RQFYQLDAYP SGAWYYLPLG TQYTDAPSFS   180
DIPNPIGSEN SGKTTMPLW                                               199

SEQ ID NO: 100      moltype = AA  length = 199
FEATURE             Location/Qualifiers
source              1..199
                    mol_type = protein
                    organism = Ovis aries
SEQUENCE: 100
RPKHPIKHQG LSSEVLNENL LRFVVAPFPE VFRKENINEL SKDIGSESIE DQAMEDAKQM    60
KAGSSSSSEE IVPNSAEQKY IQKEDVPSER YLGYLEQLLR LKKYNVPQLE IVPKSAEEQL   120
HSMKEGNPAH QKQPMIAVNQ ELAYFYPQLF RQFYQLDAYP SGAWYYLPLG TQYTDAPSFS   180
DIPNPIGSEN SGKITMPLW                                               199
```

```
SEQ ID NO: 101            moltype = AA  length = 199
FEATURE                   Location/Qualifiers
source                    1..199
                          mol_type = protein
                          organism = Bubalus bubalis
SEQUENCE: 101
RPKQPIKHQG LPQGVLNENL LRFFVAPFPE VFGKEKVNEL STDIGSESTE DQAMEDIKQM    60
EAESISSSEE IVPISVEQKH IQKEDVPSER YLGYLEQLLR LKKYNVPQLE IVPNLAEEQL   120
HSMKEGIHAQ QKEPMIGVNQ ELAYFYPQLF RQFYQLDAYP SGAWYYVPLG TQYPDAPSFS   180
DIPNPIGSEN SGKTTMPLW                                                199

SEQ ID NO: 102            moltype = AA  length = 154
FEATURE                   Location/Qualifiers
source                    1..154
                          mol_type = protein
                          organism = Camelus dromedarius
SEQUENCE: 102
DTERKESGSS SSEEVVSSTT EQKDILKEDM PSQRYLEELH RLNKYKLLQL EAIRDQKLIP    60
RVKLSSHPYL EQLYRINEDN HPQLGEPVKV VTQEQAYFHL EPFPQFFQLG ASPYVAWYYP   120
PQVMQYIAHP SSYDTPEGIA SEDGGKTDVM PQWW                               154

SEQ ID NO: 103            moltype = AA  length = 207
FEATURE                   Location/Qualifiers
source                    1..207
                          mol_type = protein
                          organism = Camelus bactrianus
SEQUENCE: 103
RPKYPLRYPE VFQNEPDSIE EVLNKRKILE LAVVSPIQFR QENIDELKDT RNEPTEDHIM    60
EDTERKESGS SSEEVVSST TEQKDILKED MPSQRYLEEL HRLNKYKLLQ LEAIRDQKLI   120
PRVKLSSHPY LEQLYRINED NHPQLGEPVK VVTQPFPQFF QLGASPYVAW YYPPQVMQYI   180
AHPSSYDTPE GIASEDGGKT DVMPQWW                                       207

SEQ ID NO: 104            moltype = AA  length = 199
FEATURE                   Location/Qualifiers
source                    1..199
                          mol_type = protein
                          organism = Bos mutus
SEQUENCE: 104
RPKHPIKHQG LPQEVLNENL LRFFVAPFPE VFGKEKVNEL SKDIGSESTE DQAMEDIKQM    60
EAESISSSEE IVPNSVEQKH IQKEDVPSEH YLGYLEQLLR LKKYKVPQLE IVPNSAEERL   120
HSMKEGIHAQ QKEPMIGVNQ ELAYFYPELF RQFYQLDAYP SGAWYYVPLG TQYTDAPSFS   180
DIPNPIGSEN SGKTTMPLW                                                199

SEQ ID NO: 105            moltype = AA  length = 226
FEATURE                   Location/Qualifiers
source                    1..226
                          mol_type = protein
                          organism = Equus caballus
SEQUENCE: 105
REKEELNVSS ETVESLSSNE PDSSSEESIT HINKEKLQKF KHEGQQQREV ERQDKISRFV    60
QPQPVVYPYA EPVPYAVVPQ SILPLAQPPI LPFLQPEIME VSQAKETILP KRKVMPFLKS   120
PIVPFSERQI LNPTNGENLR LPVHLIQPFM HQVPQSLLQT LMLPSQPVLS PPQSKVAPFP   180
QPVVPYPQRD TPVQAFLLYQ DPRLGPTGEL DPATQPIVAV HNPVIV                   226

SEQ ID NO: 106            moltype = AA  length = 202
FEATURE                   Location/Qualifiers
source                    1..202
                          mol_type = protein
                          organism = Equus asinus
SEQUENCE: 106
RPKLPHRHPE IIQNEQDSRE KVLKERKFPS FALHTPREEY INELNRQREL LKEKQKDEHK    60
EYLIEDPEQQ ESSSTSSSEE VVPINTEQKR IPREDMLYQH TLEQLRRLSK YNQLQLQAIY   120
AQEQLIRMKE NSQRKPMRVV NQEQAYFYLE PFQPSYQLDV YPYAAWFHPA QIMQHVAYSP   180
FHDTAKLIAS ENSEKTDIIP EW                                            202

SEQ ID NO: 107            moltype = AA  length = 199
FEATURE                   Location/Qualifiers
VARIANT                   84
                          note = X can be any naturally occurring amino acid
source                    1..199
                          mol_type = protein
                          organism = Bos indicus
SEQUENCE: 107
RPKHPIKHQG LPQEVLNENL LRFFVAPFPE VFGKEKVNEL SKDIGSESTE DQAMEDIKQM    60
EAESISSSEE IVPNSVEQKH IQKXDVPSER YLGYLEQLLR LKKYKVPQLE IVPNSAEERL   120
HSMKEGIHAQ QKEPMIGVNQ ELAYFYPELF RQFYQLDAYP SGAWYYVPLG TQYTDAPSFS   180
DIPNPIGSEN SGKTTMPLW                                                199

SEQ ID NO: 108            moltype = AA  length = 215
```

```
FEATURE              Location/Qualifiers
source               1..215
                     mol_type = protein
                     organism = Lama glama
SEQUENCE: 108
RPKYPLRYPE VFQNEPDSIQ EVLNKRKILE LAVVSPIQFR QENIDELKDT RNEPTEDHIM    60
EDTERTVSGS SSSEEVVSST TEQKDILKED MPSQRILEEL HRLNKYKLLQ LEAIRDQKLI   120
PRVKLSSHPY LEQLYRINED NHPQLGEPVK VVTQEQAYFH LEPFQQFFQL GASPYVAWYY   180
PPQVMQYIAH PSSHDTPEGI ASEDGGKTDV MPQWW                              215

SEQ ID NO: 109       moltype = AA  length = 170
FEATURE              Location/Qualifiers
source               1..170
                     mol_type = protein
                     organism = Homo sapiens
SEQUENCE: 109
RPKLPLRYPE RLQNPSESSE PIPLESREEY MNGMNRQRNI LREKQTDEIK DTRNESTQNC    60
VVAEPEKMES SISSSSEEMS LSKCAEQFCR LNEYNQLQLQ AAHAQEQIRR MNENSHVQVP   120
FQQLNQLAAY PYAVWYYPQI MQYVPFPPFS DISNPTAHEN YEKNNVMLQW              170

SEQ ID NO: 110       moltype = AA  length = 208
FEATURE              Location/Qualifiers
source               1..208
                     mol_type = protein
                     organism = Capra hircus
SEQUENCE: 110
KHKMEHVSSS EEPINIFQEI YKQEKNMAIH PRKEKLCTTS CEEVVRNANE EEYSIRSSSE    60
ESAEVAPEEI KITVDDKHYQ KALNEINQFY QKFPQYLQYP YQGPIVLNPW DQVKRNAGPF   120
TPTVNREQLS TSEENSKKTI DMESTEVFTK KTKLTEEEKN RLNFLKKISQ YYQKFAWPQY   180
LKTVDQHQKA MKPWTQPKTN AIPYVRYL                                      208

SEQ ID NO: 111       moltype = AA  length = 208
FEATURE              Location/Qualifiers
source               1..208
                     mol_type = protein
                     organism = Ovis aries
SEQUENCE: 111
KHKMEHVSSS EEPINISQEI YKQEKNMAIH PRKEKLCTTS CEEVVRNADE EEYSIRSSSE    60
ESAEVAPEEV KITVDDKHYQ KALNEINQFY QKFPQYLQYL YQGPIVLNPW DQVKRNAGPF   120
TPTVNREQLS TSEENSKKTI DMESTEVFTK KTKLTEEEKN RLNFLKKISQ YYQKFAWPQY   180
LKTVDQHQKA MKPWTQPKTN AIPYVRYL                                      208

SEQ ID NO: 112       moltype = AA  length = 207
FEATURE              Location/Qualifiers
source               1..207
                     mol_type = protein
                     organism = Bubalus bubalis
SEQUENCE: 112
KHTMEHVSSS EESIISQETY KQEKNMAIHP SKENLCSTFC KEVIRNANEE EYSIGSSSEE    60
SAEVATEEVK ITVDDKHYQK ALNEINQFYQ KFPQYLQYLY QGPIVLNPWD QVKRNAVPIT   120
PTLNREQLST SEENSKKTVD MESTEVITKK TKLTEEDKNR LNFLKKISQH YQKFTWPQYL   180
KTVYQYQKAM KPWTQPKTNV IPYVRYL                                       207

SEQ ID NO: 113       moltype = AA  length = 178
FEATURE              Location/Qualifiers
source               1..178
                     mol_type = protein
                     organism = Camelus dromedarius
SEQUENCE: 113
KHEMDQGSSS EESINVSQQK FKQVKKVAIH PSKEDICSTF CEEAVRNIKE VESAEVPTEN    60
KISQFYQKWK FLQYLQALHQ GQIVMNPWDQ GKTRAYPFIP TVNTEQLSIS EESTEVPTEE   120
STEVFTKKTE LTEEEKDHQK FLNKIYQYYQ TFLWPEYLKT VYQYQKTMTP WNHIKRYF     178

SEQ ID NO: 114       moltype = AA  length = 178
FEATURE              Location/Qualifiers
source               1..178
                     mol_type = protein
                     organism = Camelus bactrianus
SEQUENCE: 114
KHEMDQGSSS EESINVSQQK FKQVKKVAIH PSKEDICSTF CEEAVRNIKE VESAEVPTEN    60
KISQFYQKWK FLQYLQALHQ GQIVMNPWDQ GKTRAYPFIP TVNTEQLSIS EESTEVPTEE   120
STEVFNKKTE LTEEEKDHQK FLNKIYQYYQ TFLWPEYLKT VYQYQKTMTP WNHIKRYF     178

SEQ ID NO: 115       moltype = AA  length = 204
FEATURE              Location/Qualifiers
source               1..204
                     mol_type = protein
                     organism = Bos mutus
SEQUENCE: 115
```

```
KNTMEHVSSS EESIISQETY KQEKNMAINP SKGNLCSTFC KEVVRNANEE EYSIGSSSEE      60
SAEVATEEVK ITVDDKHYQK ALNEINQFYQ KFPQYLQYLY QGPIVLNPWD QVKRNAVPIT     120
PTLNREQLST SEENSKKTVD MESTEVFTKK TKLTEEEKNR LNFLKKISQR YQKFALPQYL     180
KTVYQHQKAM KPWIQPKTKV IPYV                                           204

SEQ ID NO: 116          moltype = AA   length = 216
FEATURE                 Location/Qualifiers
source                  1..216
                        mol_type = protein
                        organism = Equus caballus
SEQUENCE: 116
KHNMEHRSSS EDSVNISQEK FKQEKYVVIP TSKESICSTS CEEATRNINE MESAKFPTEV      60
YSSSSSSEES AKFPTEREEK EVEEKHHLKQ LNKINQFYEK LNFLQYLQAL RQPRIVLTPW     120
DQTKTGDSPF IPIVNTEQLF TSEEIPKKTV DMESTEVVTE KTELTEEEKN YLKLLYYEKF     180
TLPQYFKIVR QHQTTMDPRS HRKTNSYQII PVLRYF                              216

SEQ ID NO: 117          moltype = AA   length = 221
FEATURE                 Location/Qualifiers
source                  1..221
                        mol_type = protein
                        organism = Equus asinus
SEQUENCE: 117
KHNMEHRSSS EDSVNISQEK FKQEKYVVIP TSKESICSTS CEEATRNINE MESAKFPTEV      60
YSSSSSSEES AKFPTEREEK EVEEKHHLKQ LNKINQFYEK LNFLQYLQAL RQPRIVLTPW     120
DQTKTGASPF IPIVNTEQLF TSEEIPKKTV DMESTEVVTE KTELTEEEKN YLKLLNKINQ     180
YYEKFTLPQY FKIVHQHQTT MDPQSHSKTN SYQIIPVLRY F                        221

SEQ ID NO: 118          moltype = AA   length = 192
FEATURE                 Location/Qualifiers
source                  1..192
                        mol_type = protein
                        organism = Vicugna pacos
SEQUENCE: 118
KHEMDQGSSS EESINVSQQK LKQVKKVAIH PSKEDICSTF CEEAVRNIKE VESVEVPTEN      60
KISQFYQKWK FLQYLQALHQ GQIVMNPWDQ GKTMVYPFIP TVNTEQLSIS EESTEVPTEE     120
STEVFTKKTE LTEEEKDHQK FLNKIYQYYQ TFLWPEYLKT VYQYQKTMTP WNHIKVKAYQ     180
IIPNLVSSTF YL                                                        192

SEQ ID NO: 119          moltype = AA   length = 207
FEATURE                 Location/Qualifiers
source                  1..207
                        mol_type = protein
                        organism = Bos indicus
SEQUENCE: 119
KNTMEHVSSS EESIISQETY KQEKNMAINP SKENLCSTFC KEVVRNANEE EYSIGSSSEE      60
SAEVATEEVK ITVDDKHYQK ALNEINQFYQ KFPQYLQYLY QGPIVLNPWD QVKRNAVPIT     120
PTLNREQLST SEENSKKTVD MESTEVFTKK TKLTEEEKNR LNFLKKISQR YQKFALPQYL     180
KTVYQHQKAM KPWIQPKTKV IPYVRYL                                        207

SEQ ID NO: 120          moltype = AA   length = 187
FEATURE                 Location/Qualifiers
source                  1..187
                        mol_type = protein
                        organism = Lama glama
SEQUENCE: 120
KHEMDQGSSS EESINVSQQK LKQVKKVAIH PSKEDICSTF CEEAVRNIKE VESVEVPTEN      60
KISQFYQKWK FLQYLQALHQ GQIVMNPWDQ GKTMVYPFIP TVNTEQLSIS EESTEVPTEE     120
NSKKTVDTES TEVFTKKTEL TEEEKDHQKF LNKIYQYYQT FLWPEYLKTV YQYQKTMTPW     180
NHIKRYF                                                              187

SEQ ID NO: 121          moltype = AA   length = 207
FEATURE                 Location/Qualifiers
source                  1..207
                        mol_type = protein
                        organism = Capra hircus
SEQUENCE: 121
REQEELNVVG ETVESLSSSE ESITHINKKI EKFQSEEQQQ TEDELQDKIH PFAQAQSLVY      60
PFTGPIPNSL PQNILPLTQT PVVVPPFLQP EIMGVPKVKE TMVPKHKEMP FPKYPVEPFT     120
ESQSLTLTDV EKLHLPLPLV QSWMHQPPQP LSPTVMFPPQ SVLSLSQPKV LPVPQKAVPQ     180
RDMPIQAFLL YQEPVLGPVR GPFPILV                                        207

SEQ ID NO: 122          moltype = AA   length = 207
FEATURE                 Location/Qualifiers
source                  1..207
                        mol_type = protein
                        organism = Ovis aries
SEQUENCE: 122
REQEELNVVG ETVESLSSSE ESITHINKKI EKFQSEEQQQ TEDELQDKIH PFAQAQSLVY      60
PFTGPIPNSL PQNILPLTQT PVVVPPFLQP EIMGVPKVKE TMVPKHKEMP FPKYPVEPFT     120
```

```
ESQSLTLTDV EKLHLPLPLV QSWMHQPPQP LPPTVMFPPQ SVLSLSQPKV LPVPQKAVPQ    180
RDMPIQAFLL YQEPVLGPVR GPFPILV                                        207

SEQ ID NO: 123          moltype = AA  length = 209
FEATURE                 Location/Qualifiers
source                  1..209
                        mol_type = protein
                        organism = Bubalus bubalis
SEQUENCE: 123
RELEELNVPG EIVESLSSSE ESITHINKKI EKFQSEEQQQ MEDELQDKIH PFAQTQSLVY     60
PPPGPIPKSL PQNIPPLTQT PVVVPPFLQP EIMGVSKVKE AMAPKHKEMP FPKYPVEPFT    120
ESQSLTLTDV ENLHLPLPLL QSWMHQPPQP LPPTVMFPPQ SVLSLSQSKV LPVPQKAVPY    180
PQRDMPIQAF LLYQEPVLGP VRGPFPIIV                                      209

SEQ ID NO: 124          moltype = AA  length = 217
FEATURE                 Location/Qualifiers
source                  1..217
                        mol_type = protein
                        organism = Camelus dromedarius
SEQUENCE: 124
REKEEFKTAG EALESISSSE ESITHINKQK IEKFKIEEQQ QTEDEQQDKI YTFPQPQSLV     60
YSHTEPIPYP ILPQNFLPPL QPAVMVPFLQ PKVMDVPKTK ETIIPKRKEM PLLQSPVVPF    120
TESQSLTLTD LENLHLPLPL LQSLMYQIPQ PVPQTPMIPP QSLLSLSQFK VLPVPQQMVP    180
YPQRAMPVQA VLPFQEPVPD PVRGLHPVPQ PLVPVIA                             217

SEQ ID NO: 125          moltype = AA  length = 217
FEATURE                 Location/Qualifiers
source                  1..217
                        mol_type = protein
                        organism = Camelus bactrianus
SEQUENCE: 125
REKEEFKTAG EALESISSSE ESITHINKQK IEKFKIEEQQ QTEDEQQDKI YTFPQPQSLV     60
YSHTEPIPYP ILPQNFLPPL QPAVMVPFLQ PKVMDVPKTK ETIIPKRKEM PLLQSPVVPF    120
TESQSLTLTD LENLHLPLPL LQSLMYQIPQ PVPQTPMIPP QSLLSLSQFK VLPVPQQMVP    180
YPQRAIPVQA VLPFQEPVPD PVRGLHPVPQ PLVPVIA                             217

SEQ ID NO: 126          moltype = AA  length = 209
FEATURE                 Location/Qualifiers
source                  1..209
                        mol_type = protein
                        organism = Bos mutus
SEQUENCE: 126
RELEELNVPG EIVESLSSSE ESITRINKKI EKFQSEEQQQ TEDELQDKIH PFAQTQSLVY     60
PPPGPIPNSL PQNIPPLTQT PVVVPPFLQP EVMGVSKVKE AMAPKHKEMP FPKYPVEPFT    120
ESQSLTLTDV ENLHLPLPLL QSWMHQPHQP LPPTVMFPPQ SVLSLSQSKV LPVPQKAVPY    180
PQRDMPIQAF LLYQEPVLGP VRGPFPIIV                                      209

SEQ ID NO: 127          moltype = AA  length = 226
FEATURE                 Location/Qualifiers
source                  1..226
                        mol_type = protein
                        organism = Equus caballus
SEQUENCE: 127
REKEELNVSS ETVESLSSNE PDSSSEESIT HINKEKLQKF KHEGQQQREV ERQDKISRFV     60
QPQPVVYPYA EPVPYAVVPQ SILPLAQPPI LPFLQPEIME VSQAKETILP KRKVMPFLKS    120
PIVPFSERQI LNPTNGENLR LPVHLIQPFM HQVPQSLLQT LMLPSQPVLS PPQSKVAPFP    180
QPVVPYPQRD TPVQAFLLYQ DPRLGPTGEL DPATQPIVAV HNPVIV                   226

SEQ ID NO: 128          moltype = AA  length = 226
FEATURE                 Location/Qualifiers
source                  1..226
                        mol_type = protein
                        organism = Equus asinus
SEQUENCE: 128
REKEELNVSS ETVESLSSNE PDSSSEESIT HINKEKSQKF KHEGQQQREV EHQDKISRFV     60
QPQPVVYPYA EPVPYAVVPQ NILVLAQPPI VPFLQPEIME VSQAKETILP KRKVMPFLKS    120
PIVPFSERQI LNPTNGENLR LPVHLIQPFM HQVPQSLLQT LMLPSQPVLS PPQSKVAPFP    180
QPVVPYPQRD TPVQAFLLYQ DPQLGLTGEF DPATQPIVPV HNPVIV                   226

SEQ ID NO: 129          moltype = AA  length = 141
FEATURE                 Location/Qualifiers
VARIANT                 6
                        note = X can be any naturally occurring amino acid
VARIANT                 17
                        note = X can be any naturally occurring amino acid
VARIANT                 65
                        note = X can be any naturally occurring amino acid
source                  1..141
                        mol_type = protein
```

```
                          organism = Alces alces
SEQUENCE: 129
IHPFAXTQSL VYPFTGXIPY SLPQNFLPLP QTPGMVPPFL QPEIMGVSEV KETMVPKNKE      60
MPFPXYPVEP FAEGQSLTLT DVENLHLPLP LLQSWMHQTP QPLPPTVMFP PQSVLSLSQP     120
KVLSVPQKAV PYPQRDMPIQ A                                               141

SEQ ID NO: 130            moltype = AA   length = 173
FEATURE                   Location/Qualifiers
source                    1..173
                          mol_type = protein
                          organism = Vicugna pacos
SEQUENCE: 130
DEQQDKIYTF PQPQSLVYSH TEPIPYPILP QNFLPPLQPA VMVPFLQPKV MDVPKTKEIV      60
IPKRKEMPLL QSPLVPFTES QSLTLTDLEN LHLPLPLLQS LMHQIPQPVP QTPMIPPQSL     120
LSLSQFKVLP VPQQMVPYPQ RAMPVQALLP FQEPIPDPVR GLHPVPQPLV PVI            173

SEQ ID NO: 131            moltype = AA   length = 209
FEATURE                   Location/Qualifiers
source                    1..209
                          mol_type = protein
                          organism = Bos indicus
SEQUENCE: 131
RELEELNVPG EIVESLSSSE ESITRINKKI EKFQSEEQQQ TEDELQDKIH PFAQTQSLVY      60
PFPPGPIPNSL PQNIPPLTQT PVVVPPFLQP EVMGVSKVKE AMAPKHKEMP FPKYPVEPFT   120
ESQSLTLTDV ENLHLPLPLL QSWMHQPHQP LPPTVMFPPQ SVLSLSQSKV LPVPQKAVPY    180
PQRDMPIQAF LLYQEPVLGP VRGPFPIIV                                      209

SEQ ID NO: 132            moltype = AA   length = 217
FEATURE                   Location/Qualifiers
source                    1..217
                          mol_type = protein
                          organism = Lama glama
SEQUENCE: 132
REKEEFKTAG EAVESISSSE ESITHINKQK IEKFKIEEQQ QTEDEQQDKI YTFPQPQSLV      60
YSHTEPIPYP ILPQNFLPPL QPAVMVPFLQ PKVMDVPKTK EIVIPKRKEM PLLQSPLVPF    120
TESQSLTLTD LENLHLPLPL LQSLMHQIPQ PVPQTPMIPP QSLLSLSQFK VLPVPQQMVP    180
YPQRAMPVQA LLPFQEPIPD PVRGLHPVPQ PLVPVIA                             217

SEQ ID NO: 133            moltype = AA   length = 211
FEATURE                   Location/Qualifiers
source                    1..211
                          mol_type = protein
                          organism = Homo sapiens
SEQUENCE: 133
RETIESLSSS EESITEYKQK VEKVKHEDQQ QGEDEHQDKI YPSFQPQPLI YPFVEPIPYG      60
FLPQNILPLA QPAVVLPVPQ PEIMEVPKAK DTVYTKGRVM PVLKSPTIPF FDPQIPKLTD    120
LENLHLPLPL LQPLMQQVPQ PIPQTLALPP QPLWSVPQPK VLPIPQQVVP YPQRAVPQA     180
LLLNQELLLN PTHQIYPVTQ PLAPVHNPIS V                                   211

SEQ ID NO: 134            moltype = DNA   length = 1059
FEATURE                   Location/Qualifiers
misc_feature              1..1059
                          note = Nucleic acid encoding fusion protein
                          sig2:OKC1-T:FM:OLG1
source                    1..1059
                          mol_type = other DNA
                          organism = synthetic construct
SEQUENCE: 134
atggccaagc tagtttttc cctttgtttt ctgcttttca gtggctgctg cttcgctcaa      60
gagcagaatc aagagcagcc aatccgttgt gagaaggacg agaggttctt ctcagacaag    120
atcgccaaat atatacccat acaatatgta ctctcacgct accctagcta cgggcttaac    180
tactatcagc aaaaacctgt agcactgata ataaccagt ttctccccta tcctatat       240
gctaaacctg ccgccgtgag gagtccagca caaatacttc agtggcaagt gctcagtaac    300
accgtgccag caaaaagctg ccaggctcag cccaccacag tgcccgtca tccccatcct     360
caccttagct tcatggcaat cccaccaaag aagaatcaag acaagaccga atacctacc     420
atcaacacaa ttgcatctgg agagcctacc agtacaccaa caactgaggc agtagagtct    480
actgttgcta cccttgagga cagccccgag gttatagagt ccccacctga gataaatacc    540
gtgcaggtga caagtaccgc cgtattcatg ttgatcgtaa cacagactac gaagggtctt    600
gatatacaga aggtggccgg gacttggtac agtttgcaa tggccgcatc cgacatctcc     660
ttgttggacg cacaatcagc cccattgcgt gtgtacgtag aagagcttaa accaactccc    720
gaggggggatc tggaaattct gctccagaaa tgggagaacg tgagtgcgc ccagaagaag    780
atcatcgcga agaagaccaa aattccagca gtattcaaaa tcgacgcatt gaacgaaaat    840
aaggtgctcg tactggacac tgattataag agtatctcc ttttctgtat ggagaactca    900
gcagagcctg aacagagtct tgcctgccaa tgccttgttc gtaccccaga ggtagatgat    960
gaagctctgg aaaagttcga taaggccctt aaggctctgc ctatgcacat taggctttct   1020
ttcaatccaa ctcaacttga ggaacaatgt cacatttaa                          1059

SEQ ID NO: 135            moltype = AA   length = 352
FEATURE                   Location/Qualifiers
```

```
REGION                  1..352
                        note = Fusion protein sig2:OKC1-T:FM:OLG1
source                  1..352
                        mol_type = protein
                        organism = synthetic construct
SEQUENCE: 135
MAKLVFSLCF LLFSGCCFAQ EQNQEQPIRC EKDERFFSDK IAKYIPIQYV LSRYPSYGLN      60
YYQQKPVALI NNQFLPYPYY AKPAAVRSPA QILQWQVLSN TVPAKSCQAQ PTTMARHPHP     120
HLSFMAIPPK KNQDKTEIPT INTIASGEPT STPTTEAVES TVATLEDSPE VIESPPEINT     180
VQVTSTAVFM LIVTQTMKGL DIQKVAGTWY SLAMAASDIS LLDAQSAPLR VYVEELKPTP     240
EGDLEILLQK WENGECAQKK IIAEKTKIPA VFKIDALNEN KVLVLDTDYK KYLLFCMENS     300
AEPEQSLACQ CLVRTPEVDD EALEKFDKAL KALPMHIRLS FNPTQLEEQC HI             352

SEQ ID NO: 136          moltype = DNA  length = 1071
FEATURE                 Location/Qualifiers
misc_feature            1..1071
                        note = Nucleic acid encoding fusion protein
                        sig2:OKC1-T:FM:OLG1:KDEL
source                  1..1071
                        mol_type = other DNA
                        organism = synthetic construct
SEQUENCE: 136
atggccaagc tagttttttc cctttgtttt ctgcttttca gtggctgctg cttcgctcaa      60
gagcagaatc aagagcagcc aatccgttgt gagaaggacg agaggttctt ctcagacaag     120
atcgcaaat atatacccat acaatatgta ctctcacgct accctagcta cgggcttaac     180
tactatcagc aaaaacctgt agcactgata aataaccagt ttctccccta tccctattat     240
gctaaacctg ccgccgtgag gagtccagca caaatacttc agtggcaagt gctcagtaac     300
accgtgccag caaaaagctg ccaggctcag cccaccacaa tggcccgtca tccccatcct     360
caccttagct tcatggcaat cccaccaaag aagaatcaag acaagaccga atacctacc     420
atcaacacaa ttgcatctgg agagcctacc agtacaccaa caactgaggc agtagatgt     480
actgttgcta cccttgagga cagccccgag gttatagagt ccccacctga gataaatacc     540
gtgcaggtga caagtaccgc cgtattcatg ttgatcgtaa cacagactat gaagggtctt     600
gatatacaga aggtggccgg gacttggtac agttttgcaa tggccgcatc cgacatctcc     660
ttgttggacg cacaatcagc cccattgcgt gtgtacgtag aagagcttaa accaactccc     720
gagggggatc tggaaattct gctccagaaa tgggagaacg gtgagtgcgc ccagaagaag     780
atcatcgcag agaagaccaa aattccagca gtattcaaaa tcgacgcatt gaacgaaaat     840
aaggtgctcg tactggacac tgattataag aagtatctcc ttttctgtat ggagaactca     900
gcagagcctg aacagagtct tgcctgccaa tgccttgttc gtaccccaga ggtagatgat     960
gaagctctgg aaaagttcga taaggccctt aaggctctgc ctatgcacat taggctttct    1020
ttcaatccaa ctcaacttga ggaacaatgt cacattaagg atgagcttta a             1071

SEQ ID NO: 137          moltype = AA  length = 356
FEATURE                 Location/Qualifiers
REGION                  1..356
                        note = Fusion protein sig2:OKC1-T:FM:OLG1:KDEL
source                  1..356
                        mol_type = protein
                        organism = synthetic construct
SEQUENCE: 137
MAKLVFSLCF LLFSGCCFAQ EQNQEQPIRC EKDERFFSDK IAKYIPIQYV LSRYPSYGLN      60
YYQQKPVALI NNQFLPYPYY AKPAAVRSPA QILQWQVLSN TVPAKSCQAQ PTTMARHPHP     120
HLSFMAIPPK KNQDKTEIPT INTIASGEPT STPTTEAVES TVATLEDSPE VIESPPEINT     180
VQVTSTAVFM LIVTQTMKGL DIQKVAGTWY SLAMAASDIS LLDAQSAPLR VYVEELKPTP     240
EGDLEILLQK WENGECAQKK IIAEKTKIPA VFKIDALNEN KVLVLDTDYK KYLLFCMENS     300
AEPEQSLACQ CLVRTPEVDD EALEKFDKAL KALPMHIRLS FNPTQLEEQC HIKDEL        356

SEQ ID NO: 138          moltype = DNA  length = 1647
FEATURE                 Location/Qualifiers
misc_feature            1..1647
                        note = EU:Rb7 dual terminator
source                  1..1647
                        mol_type = other DNA
                        organism = synthetic construct
SEQUENCE: 138
aaagcagaat gctgagctaa agaaaaggct tttccatttt cgagagacaa tgaaaaag       60
aagaagaaga agaagaagaa gaagaagaag aaaagagtaa ataataaagc cccacaggag    120
gcgaagttct gtagctccaa tgttatctaa gttattgata ttgtttgccc tatattttat    180
ttctgtcatt gtgtatgttt tgttcagttt cgatctcctt gcaaaatgca gagattatga    240
gatgaataaa ctaagttata ttattatacg tgttaatatt ctcctcctct ctctagctag    300
cctttttgttt tctctttttc ttatttgatt ttctttaaat caatccattt taggagaggg    360
ccagggagtg atccagcaaa acatgaagat tagaagaaac ttccctcttt tttttcctga    420
aaacaattta acgtcgagat ttatctcttt ttgtaatgga atcatttcta cagttatgac    480
tcgattaaaa tcccaattat atttggtcta atttagtttg gtattgagta aaacaaattc    540
gaaccaaacc aaaaatataa tatatagttt ttatatatgt gccttttaaga tctttttaga    600
aatttttcttt aaaaaatatc tagaaatatt tgcgactctt ctggcatgta atatttcgtt    660
aaatatgaag tgctccattt ttattaactt taaataattg gttgtacgat cactttctta    720
tcaagtgtta ctaaaatgcg tcaatctctt gttcttccta tattcatatg tcaaaatcta    780
tcaaaattct tatatatctt tttcgaattt gaagtgaaat ttcgataatt aaaattaaa    840
tagaacatat cattatttag gtatcatatt gattttata cttaattact aaatttggtt    900
```

```
aactttgaaa gtgtacatca acgaaaaatt agtcaaacga ctaaaataaa taaatatcat    960
gtgttattaa gaaaattctc ctataagaat attttaatag atcatatgtt tgtaaaaaaa   1020
attaatttt  actaacacat atatttactt atcaaaaatt tgacaaagta agattaaaat   1080
aatattcatc taacaaaaaa aaaaccgaaa aatgctgaaa acccggcaaa accgaaccaa   1140
tccaaaccga tatagttggt ttggtttgat tttgatataa accgaaccaa ctcggtccat   1200
ttgcacccct aatcataata gctttaatat ttcaagatat tattaagtta acgttgtcaa   1260
tatcctggaa attttgcaaa atgaatcaag cctatatggc tgtaatatga atttaaaagc   1320
agctcgatgt ggtggtaata tgtaatttac ttgattctaa aaaaatatcc caagtattaa   1380
taatttctgc taggaagaag gttagctacg atttacagca aagccagaat acaaagaacc   1440
ataaagtgat tgaagctcga aatatacgaa ggaacaaata ttttttaaaaa aatacgcaat   1500
gacttggaac aaaagaaagt gatatatttt ttgttcttaa acaagcatcc cctctaaaga   1560
atggcagttt tcctttgcat gtaactatta tgctcccttc gttacaaaaa ttttggacta   1620
ctattgggaa cttcttctga aaatagt                                       1647

SEQ ID NO: 139         moltype = DNA  length = 480
FEATURE                Location/Qualifiers
source                 1..480
                       mol_type = genomic DNA
                       organism = Nicotiana tabacum
SEQUENCE: 139
aaagcagaat gctgagctaa aagaaaggct ttttccattt tcgagagaca atgagaaaag    60
aagaagaaga agaagaagaa gaagaagaag aaaagagtaa ataataaagc cccacaggag   120
gcgaagttct tgtagctcca tgttatctaa gttattgata ttgttgccc  tatatttat    180
ttctgtcatt gtgtatgttt tgttcagttt cgatctcctt gcaaaatgca gagattatga   240
gatgaataaa ctaagttata ttattatacg tgttaatatt ctcctcctct ctctagctag   300
cctttgttt  tctctttttc ttatttgatt ttctttaaat caatccattt taggagaggg   360
ccagggagtg atccagcaaa acatgaagat tagaagaaac ttccctcttt tttttcctga   420
aaacaatttta acgtcgagat ttatctcttt ttgtaatgga atcatttcta cagttatgac   480

SEQ ID NO: 140         moltype = DNA  length = 1167
FEATURE                Location/Qualifiers
source                 1..1167
                       mol_type = genomic DNA
                       organism = Nicotiana tabacum
SEQUENCE: 140
tcgattaaaa tcccaattat atttggtcta atttagtttg gtattgagta aaacaaattc    60
gaaccaaacc aaaatataaa tatatagttt ttatatatat gcctttaaga cttttttatag   120
aattttcttt aaaaaaatatc tagaaatatt tgcgactctt ctggcatgta atatttcgtt   180
aaatatgaag tgctccattt ttattaactt taaataattg gttgtacgat cactttctta   240
tcaagtgtta ctaaaatgcg tcaatctctt tgttcttcca tattcatatg tcaaaatcta   300
tcaaaattct tatatatctt tttcgaattt gaagtgaaat ttcgataatt taaaattaaa   360
tagaacatat cattatttag gtatcatatt gattttata  cttaattact aaatttggtt   420
aactttgaaa gtgtacatca acgaaaaatt agtcaaacga ctaaaataaa taaatatcat   480
gtgttattaa gaaaattctc ctataagaat attttaatag atcatatgtt tgtaaaaaaa   540
attaatttt  actaacacat atatttactt atcaaaaatt tgacaaagta agattaaaat   600
aatattcatc taacaaaaaa aaaaccgaaa aatgctgaaa acccggcaaa accgaaccaa   660
tccaaaccga tatagttggt ttggtttgat tttgatataa accgaaccaa ctcggtccat   720
ttgcacccct aatcataata gctttaatat ttcaagatat tattaagtta acgttgtcaa   780
tatcctggaa attttgcaaa atgaatcaag cctatatggc tgtaatatga atttaaaagc   840
agctcgatgt ggtggtaata tgtaatttac ttgattctaa aaaaatatcc caagtattaa   900
taatttctgc taggaagaag gttagctacg atttacagca aagccagaat acaaagaacc   960
ataaagtgat tgaagctcga aatatacgaa ggaacaaata ttttttaaaaa aatacgcaat  1020
gacttggaac aaaagaaagt gatatatttt ttgttcttaa acaagcatcc cctctaaaga  1080
atggcagttt tcctttgcat gtaactatta tgctcccttc gttacaaaaa ttttggacta  1140
ctattgggaa cttcttctga aaatagt                                      1167

SEQ ID NO: 141         moltype = DNA  length = 625
FEATURE                Location/Qualifiers
misc_feature           1..625
                       note = AtHSP:AtUbi10 Dual Terminator
source                 1..625
                       mol_type = other DNA
                       organism = synthetic construct
SEQUENCE: 141
atatgaagat gaagatgaaa tatttggtgt gtcaaataaa aagcttgtgt gcttaagttt    60
gtgttttttt cttggcttgt tgtgttatga atttgtggct ttttctaata tcaaatgaat   120
gtaagatctc attataatga ataaacaaat gtttctataa tccattgtga atgttttgtt   180
ggatctcttc tgcagcatat aactactgta tgtgctatgg tatggactat ggaatatgat   240
taaagataaa tctcgtctct gttatgctta agaagttcaa tgtttcgttt catgtaaaac   300
tttggtggtt tgtgttttgg ggccttgtat aatccctgat gaataagtgt tctactatgt   360
ttccgttcct gttatctctt tctttctaat gacaagtcga acttcttctt tatcatcgct   420
tcgtttttat tatctgtgct tcttttgttt aatacgcctg caaagtgact cgactctgtt   480
tagtgcagtt ctgcgaaact tgtaaatagt ccaattgttg gcctctagta atagatgtag   540
cgaaagtgtt gagctgttgg gttctaagga tggcttgaac atgttaatct tttaggttct   600
gagtatgatg aacattcgtt gttgc                                         625

SEQ ID NO: 142         moltype = DNA  length = 249
FEATURE                Location/Qualifiers
source                 1..249
```

```
                        mol_type = genomic DNA
                        organism = Arabidopsis thaliana
SEQUENCE: 142
atatgaagat gaagatgaaa tatttggtgt gtcaaataaa aagcttgtgt gcttaagttt    60
gtgttttttt cttggcttgt tgtgttatga atttgtgct ttttctaata tcaaatgaat    120
gtaagatctc attataatga ataaacaaat gtttctataa tccattgtga atgttttgtt    180
ggatctcttc tgcagcatat aactactgta tgtgctatgg tatggactat ggaatatgat    240
taaagataa                                                            249

SEQ ID NO: 143          moltype = DNA   length = 376
FEATURE                 Location/Qualifiers
source                  1..376
                        mol_type = genomic DNA
                        organism = Arabidopsis thaliana
SEQUENCE: 143
atctcgtctc tgttatgctt aagaagttca atgtttcgtt tcatgtaaaa ctttggtggt    60
ttgtgttttg gggccttgta taatccctga tgaataagtg ttctactatg tttccgttcc    120
tgttatctct ttcttttctaa tgacaagtcg aacttcttct ttatcatcgc ttcgttttta   180
ttatctgtgc ttcttttgtt taatacgcct gcaaagtgac tcgactcgt ttagtgcagt    240
tctgcgaaac ttgtaaatag tccaattgtt ggcctctagt aatagatgta gcgaaagtgt   300
tgagctgttg ggttctaagg atggcttgaa catgttaatc ttttaggttc tgagtatgat   360
gaacattcgt tgttgc                                                    376

SEQ ID NO: 144          moltype = DNA   length = 894
FEATURE                 Location/Qualifiers
misc_feature            1..894
                        note = EU:StUbi3 Dual Terminator
source                  1..894
                        mol_type = other DNA
                        organism = synthetic construct
SEQUENCE: 144
aaagcagaat gctgagctaa aagaaaggct ttttccattt tcgagagaca atgagaaaag    60
aagaagaaga agaagaagaa gaagaagaag aaaagagtaa ataataaagc cccacaggag   120
gcgaagttct tgtagctcca tgttatctaa gttattgata ttgtttgccc tatattttat   180
ttctgtcatt gtgtatgttt tgttcagttt cgatctcctt gcaaaatgca gagattatga   240
gatgaataaa ctaagttata ttattatacg tgttaatatt ctcctcctct ctctagctag   300
ccttttgttt tctctttttc ttatttgatt ttctttaaat caatccattt taggagaggg   360
ccagggagtg atccagcaaa acatgaagat tagaagaaac ttccctcttt tttttcctga   420
aaacaattta acgtcgagat ttatctcttt ttgtaatgga atcatttcta cagttatgac   480
ctgatttttaa tgtttagcaa atgtcttatc agttttctct ttttgtcgaa cggtaattta   540
gagttttttt tgctatatgg attttcgttt ttgatgtatg tgacaaccct cgggattgtt   600
gatttatttc aaaactaaga gttttgtct tattgttctc gtctattttg gaatatcaat    660
cttagtttta tatcttttct agttctctac gtgttaaatg ttcaacacac tagcaatttg   720
gcctgccagc gtatggatta tggaactatc aagtgtgtgg gatcgataaa tatgcttctc   780
aggaatttga gattttacag tctttatgct cattgggttg agtataatat agtaaaaaaa   840
tagtaaattt aagcaataat gttaggtgct atgtgtctgt cgagactatt ggcc         894

SEQ ID NO: 145          moltype = DNA   length = 414
FEATURE                 Location/Qualifiers
source                  1..414
                        mol_type = genomic DNA
                        organism = Solanum tuberosum
SEQUENCE: 145
ctgatttttaa tgtttagcaa atgtcttatc agttttctct ttttgtcgaa cggtaattta   60
gagttttttt tgctatatgg attttcgttt ttgatgtatg tgacaaccct cgggattgtt   120
gatttatttc aaaactaaga gttttgtct tattgttctc gtctattttg gaatatcaat   180
cttagtttta tatcttttct agttctctac gtgttaaatg ttcaacacac tagcaatttg   240
gcctgccagc gtatggatta tggaactatc aagtgtgtgg gatcgataaa tatgcttctc   300
aggaatttga gattttacag tctttatgct cattgggttg agtataatat agtaaaaaaa   360
tagtaaattt aagcaataat gttaggtgct atgtgtctgt cgagactatt ggcc         414

SEQ ID NO: 146          moltype = DNA   length = 1670
FEATURE                 Location/Qualifiers
misc_feature            1..1670
                        note = EU:TM6 Dual Terminator
source                  1..1670
                        mol_type = other DNA
                        organism = synthetic construct
SEQUENCE: 146
aaagcagaat gctgagctaa aagaaaggct ttttccattt tcgagagaca atgagaaaag    60
aagaagaaga agaagaagaa gaagaagaag aaaagagtaa ataataaagc cccacaggag   120
gcgaagttct tgtagctcca tgttatctaa gttattgata ttgtttgccc tatattttat   180
ttctgtcatt gtgtatgttt tgttcagttt cgatctcctt gcaaaatgca gagattatga   240
gatgaataaa ctaagttata ttattatacg tgttaatatt ctcctcctct ctctagctag   300
ccttttgttt tctctttttc ttatttgatt ttctttaaat caatccattt taggagaggg   360
ccagggagtg atccagcaaa acatgaagat tagaagaaac ttccctcttt tttttcctga   420
aaacaattta acgtcgagat ttatctcttt ttgtaatgga atcatttcta cagttatgac   480
gacatcctag gttcaatcaa attttactcg catattgtag actttatcct tttgtaattg   540
ttgcaaattt cttataaaat tgattatcta tattttaatc aaacatatat atacacttcc   600
```

```
aaataataaa atataatgac aacaaaacaa tcaagcacaa aaaatgccta taacaaataa   660
aaattacaac atacttttac cctgattcaa atcttcaaac actatgccag acaccataat   720
ccttctggat ataggataaa aatttaaagt gattttttac caattactat ttcataaatt   780
gttcaaatac aaaatatgat attttaatta ttcccaactt tttgagcctc ctataactaa   840
tcaatataaa aaaataattt atcgattaag actaaagcaa aaaatattac cgatttgagt   900
tacaataaaa agttttatat cacgttatgg tattgtgaat tactctaact tcctagttct   960
tgggttctag cttttcttgg ctctctgaat cttcaaaacc tatatttgat aaagccataa  1020
catacactaa tgctcccatg caaagtgctt ctaaaactcc ttaacttggt ctacggtaaa  1080
atttcttcta aaacaaaagc gactatcaac ttctaatcgt tgaacaaata attcatctcc  1140
aataaaggat tttaacaata aatatgaaat aagaagtcta tttctagtta ataaccaac   1200
aatatcccaa acatttatga atcaatata tgactgcatt acaatttgat cccaaaatgc  1260
aaaaataaaa ttgcatctct attatagagt aaaaataatg catcatcaat tactaaccga  1320
ttttactaac acgagaatct aattctcttc cacaaagtaa aactcaatgt caccgtcaat  1380
tatttaagaa tttgaattat attccaacaa ctgagtaaga actatataa ttgtgggggg   1440
agggggggcc aaccctaaaa gtttacttct cataaaaggc tattagaaag gaaaggatac  1500
ataaaaagaa gagcaaagag agatcggaga agagagaaaa agtatatgaa tttattagaa  1560
gtacttttac ttattagagg taagagagtt ctagactgat ttggatacca tattagagtt  1620
attaccgata taaaaatcct tggttatgtt aattaaattt ctaaatatta              1670

SEQ ID NO: 147         moltype = DNA  length = 1190
FEATURE                Location/Qualifiers
source                 1..1190
                       mol_type = genomic DNA
                       organism = Nicotiana tabacum
SEQUENCE: 147
gacatcctag gttcaatcaa attttactcg catattgtag actttatcct tttgtaattg    60
ttgcaaattt cttataaaat tgattatcta tattttaatc aaacatatat atacacttcc   120
aaataataaa atataatgac aacaaaacaa tcaagcacaa aaaatgccta taacaaataa   180
aaattacaac atacttttac cctgattcaa atcttcaaac actatgccag acaccataat   240
ccttctggat ataggataaa aatttaaagt gattttttac caattactat ttcataaatt   300
gttcaaatac aaaatatgat attttaatta ttcccaactt tttgagcctc ctataactaa   360
tcaatataaa aaaataattt atcgattaag actaaagcaa aaaatattac cgatttgagt   420
tacaataaaa agttttatat cacgttatgg tattgtgaat tactctaact tcctagttct   480
tgggttctag cttttcttgg ctctctgaat cttcaaaacc tatatttgat aaagccataa   540
catacactaa tgctcccatg caaagtgctt ctaaaactcc ttaacttggt ctacggtaaa   600
atttcttcta aaacaaaagc gactatcaac ttctaatcgt tgaacaaata attcatctcc   660
aataaaggat tttaacaata aatatgaaat aagaagtcta tttctagtta ataaccaac    720
aatatcccaa acatttatga atcaatata tgactgcatt acaatttgat cccaaaatgc    780
aaaaataaaa ttgcatctct attatagagt aaaaataatg catcatcaat tactaaccga   840
ttttactaac acgagaatct aattctcttc cacaaagtaa aactcaatgt caccgtcaat   900
tatttaagaa tttgaattat attccaacaa ctgagtaaga actatataa ttgtgggggg    960
agggggggcc aaccctaaaa gtttacttct cataaaaggc tattagaaag gaaaggatac  1020
ataaaaagaa gagcaaagag agatcggaga agagagaaaa agtatatgaa tttattagaa  1080
gtacttttac ttattagagg taagagagtt ctagactgat ttggatacca tattagagtt  1140
attaccgata taaaaatcct tggttatgtt aattaaattt ctaaatatta              1190

SEQ ID NO: 148         moltype = AA   length = 190
FEATURE                Location/Qualifiers
source                 1..190
                       mol_type = protein
                       organism = Bos taurus
SEQUENCE: 148
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTTEAV ESTVATLEDS PEVIESPPEI   180
NTVQVTSTAV                                                          190

SEQ ID NO: 149         moltype = AA   length = 190
FEATURE                Location/Qualifiers
source                 1..190
                       mol_type = protein
                       organism = Bos taurus
SEQUENCE: 149
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTIEAV ESTVATLEAS PEVIESPPEI   180
NTVQVTSTAV                                                          190

SEQ ID NO: 150         moltype = AA   length = 190
FEATURE                Location/Qualifiers
source                 1..190
                       mol_type = protein
                       organism = Bos taurus
SEQUENCE: 150
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTIEAV ESTVATLEAS PEVTESPPEI   180
NTVQVTSTAV                                                          190
```

```
SEQ ID NO: 151          moltype = AA  length = 169
FEATURE                 Location/Qualifiers
source                  1..169
                        mol_type = protein
                        organism = Bos taurus
SEQUENCE: 151
QEQNQEQPIR CEKDERFFSD KIAKYIPIQY VLSRYPSYGL NYYQQKPVAL INNQFLPYPY   60
YAKPAAVRSP AQILQWQVLS NTVPAKSCQA QPTTMAHHPH PHLSFMAIPP KKNQDKTEIP  120
TINTIASGEP TSTPITEAVE STVATLEASP EVIESPPEIN TVQVTSTAV             169

SEQ ID NO: 152          moltype = AA  length = 190
FEATURE                 Location/Qualifiers
source                  1..190
                        mol_type = protein
                        organism = Bos taurus
SEQUENCE: 152
MMKSFFLVVT ILALTLPFLG AQEQNQEQPI RCEKDERFFS DKIAKYIPIQ YVLSRYPSYG   60
LNYYQQKPVA LINNQFLPYP YYAKPAAVRS PAQILQWQVL SNTVPAKSCQ AQPTTMARHP  120
HPHLSFMAIP PKKNQDKTGI PTINTIASGE PTSTPTIEAV ESTVATLEAS PEVTESPPEI  180
NTVQVTSTAV                                                        190

SEQ ID NO: 153          moltype = AA  length = 160
FEATURE                 Location/Qualifiers
source                  1..160
                        mol_type = protein
                        organism = Bos taurus
SEQUENCE: 153
RCEKDERFFS DKIAKYIPIQ YVLSRYPSYG LNYYQQKPVA LINNQFLPYP YYAKPAAVRS   60
PAQILQWQVL SNTVPAKSCQ AQPTTMARHP HPHLSFMAIP PKKNQDKTEI PTINTIASGE  120
PTSTPITEAV ESTVATLEDS PEVIESPPEI NTVQVTSTAV                        160

SEQ ID NO: 154          moltype = AA  length = 160
FEATURE                 Location/Qualifiers
source                  1..160
                        mol_type = protein
                        organism = Bos taurus
SEQUENCE: 154
HCEKDERFFS DKIAKYIPIQ YVLSRYPSYG LNYYQQKPVA LINNQFLPYP YYAKPAAVRS   60
PAQILQWQVL SNTVPAKSCQ AQPTTMARHP HPHLSFMAIP PKKNQDKTEI PTINTIASGE  120
PTSTPTTEAV ESTVATLEDS PEVIESPPEI NTVQVTSTAV                        160

SEQ ID NO: 155          moltype = AA  length = 179
FEATURE                 Location/Qualifiers
source                  1..179
                        mol_type = protein
                        organism = Bos taurus
SEQUENCE: 155
MMKSFFLVVT ILALTLPFLR CEKDERFFSD KIAKYIPIQY VLSRYPSYGL NYYQQKPVAL   60
INNQFLPYPY YAKPAAVRSP AQILQWQVLS NTVPAKSCQA QPTTMARHPH PHLSFMAIPP  120
KKNQDKTEIP TINTIASGEP TSTPTIEAVE STVATLEASP EVIESPPEIN TVQVTSTAV  179

SEQ ID NO: 156          moltype = AA  length = 159
FEATURE                 Location/Qualifiers
source                  1..159
                        mol_type = protein
                        organism = Bos taurus
SEQUENCE: 156
CEKDERFFSD KIAKYIPIQY VLSRYPSYGL NYYQQKPVAL INNQFLPYPY YAKPAAVRSP   60
AQILQWQVLS NTVPAKSCQA QPTTMAHHPH PHLSFMAIPP KKNQDKTEIP TINTIASGEP  120
TSTPTTEAVE STVATLEDSP EVIESPPEIN TVQVTSTAV                         159

SEQ ID NO: 157          moltype = AA  length = 160
FEATURE                 Location/Qualifiers
source                  1..160
                        mol_type = protein
                        organism = Bos taurus
SEQUENCE: 157
RCEKDERFFS DKIAKYIPIQ YVLSRYPSYG LNYYQQKPVA LINNQFLPYP YYAKPAAVRS   60
PAQILQWQVL SNTVPAKSCQ AQPTTMARHP HPHLSFMAIP PKKNQDKTEI PTINTIASGE  120
PTSTPTIEAV ESTVATLEAS PEVIESPPEI NTVQVTSTAV                        160

SEQ ID NO: 158          moltype = AA  length = 160
FEATURE                 Location/Qualifiers
source                  1..160
                        mol_type = protein
                        organism = Bos taurus
SEQUENCE: 158
RCEKDERFFS DKIAKYIPIQ YVLSRYPSYG LNYYQQKPVA LINNQFLPYP YYAKPAAVRS   60
PAQILQWQVL SNTVPAKSCQ AQPTTMACHP HPHLSFMAIP PKKNQDKTEI PTINTIASGE  120
```

```
PTSTPITEAV ESTVATLEDS PEVIESPPEI NTVQVTSTAV                              160

SEQ ID NO: 159          moltype = AA   length = 145
FEATURE                 Location/Qualifiers
source                  1..145
                        mol_type = protein
                        organism = Bos taurus
SEQUENCE: 159
YIPIQYVLSR YPSYGLNYYQ QKPVALINNQ FLPYPYYAKP AAVRSPAQIL QWQVLSNTVP         60
AKSCQAQPTT MARHPHPHLS FMAIPPKKNQ DKTEIPTINT IASGEPTSTP TTEAVESTVA        120
TLEDSPEVIE SPPEINTVQV TSTAV                                             145

SEQ ID NO: 160          moltype = AA   length = 160
FEATURE                 Location/Qualifiers
source                  1..160
                        mol_type = protein
                        organism = Bos taurus
SEQUENCE: 160
MMKSFFLVVT ILALTLPFLG AQEQNQEQPI RCEKDERFFS DKIAKYIPIQ YVLSRYPSYG         60
LNYYQQKPVA LINNQFLPYP YYAKPAAVRS PAQILQWQVL SNTVPAKSCQ AQPTTMARHP        120
HPHLSFMAIP PKKNQDKTEI PTINTIASGE PTSTPTTEAV                             160

SEQ ID NO: 161          moltype = AA   length = 142
FEATURE                 Location/Qualifiers
source                  1..142
                        mol_type = protein
                        organism = Bos taurus
SEQUENCE: 161
IQYVLSRYPS YGLNYYQQKP VALINNQFLP YPYYAKPAAV RSPAQILQWQ VLSNTVPAKS         60
CQAQPTTMAR HPHPHLSFMA IPPKKNQDKT EIPTINTIAS GEPTSTPITE AVESTVATLE        120
DSPEVIESPP EINTVQVTST AV                                                142

SEQ ID NO: 162          moltype = AA   length = 141
FEATURE                 Location/Qualifiers
source                  1..141
                        mol_type = protein
                        organism = Bos taurus
SEQUENCE: 162
QYVLSRYPSY GLNYYQQKPV ALINNQFLPY PYYAKPAAVR SPAQILQWQV LSNTVPAKSC         60
QAQPTTMARH PHPHLSFMAI PPKKNQDKTE IPTINTIASG EPTSTPTTEA VESTVATLED        120
SPEVIEGPPE INTVQVTSTA V                                                 141

SEQ ID NO: 163          moltype = AA   length = 139
FEATURE                 Location/Qualifiers
source                  1..139
                        mol_type = protein
                        organism = Bos taurus
SEQUENCE: 163
VLSRYPSYGL NYYQQKPVAL INNQFLPYPY YAKPAAVRSP AQILQWQVLS NTVPAKSCQA         60
QPTTMARHPH PHLSFMAIPP KKNQDKTEIP TINTIASGEP TSTPTTEAVE STVATLEDSP        120
EVIESPPEIN TVQVTSTAV                                                    139

SEQ ID NO: 164          moltype = AA   length = 140
FEATURE                 Location/Qualifiers
source                  1..140
                        mol_type = protein
                        organism = Bos taurus
SEQUENCE: 164
YVLSRYPSYG LNYYQQKPVA LINNQFLPYP YYAKPAAVRS PAQILQWQVL SNTVPAKSCQ         60
AQPTTMARHP HPHLSFMAIP PKKNQDKTEI PTINTIASGE PTSTPTIEAV ESTVATLEAS        120
PEVIESPPEI NTVQVTSTAV                                                   140

SEQ ID NO: 165          moltype = AA   length = 192
FEATURE                 Location/Qualifiers
source                  1..192
                        mol_type = protein
                        organism = Capra hircus
SEQUENCE: 165
MMKSFFLVVT ILALTLPFLG AQEQNQEQPI CCEKDERFFD DKIAKYIPIQ YVLSRYPSYG         60
LNYYRQRPVA LINNQFLPYP YYAKPIAVRS PAQTLQWQVL PNTVPAKSCQ DQPTTLARHP        120
HPHLSFMAIP PKKDQDKTEI PAINTIASAE PTVHSTPTTE AIVNTVDNPE ASSESIASAP        180
ETNTAQVTST EV                                                           192

SEQ ID NO: 166          moltype = AA   length = 192
FEATURE                 Location/Qualifiers
source                  1..192
                        mol_type = protein
                        organism = Capra hircus
SEQUENCE: 166
```

```
MMKSFFLVVT ILALTLPFLG AQEQNQEQPI CCEKDERFFD DKIAKYIPIQ YVLSRYPSYG   60
LNYYQQRPVA LINNQFLPYP YYAKPVAVRS PAQTLQWQVL PNTVPAKSCQ DQPTTLARHP  120
HPHLSFMAIP PKKDQDKTEI PAINTIASAE PTVHSTPTTE AIVNTVDNPE ASSESIASAS  180
ETNTAQVTST EV                                                     192

SEQ ID NO: 167           moltype = AA   length = 162
FEATURE                  Location/Qualifiers
source                   1..162
                         mol_type = protein
                         organism = Capra hircus
SEQUENCE: 167
CCEKDERFFD DKIAKYIPIQ YVLSRYPSYG LNYYQQRPVA LINNQFLPYP YYAKPVAVRS   60
PAQTLQWQVL PNTVPAKSCQ DQPTTLARHP HPHLSFMAIP PKKDQDKTEI PAINTIASAE  120
PTVHSTPTTE AIVNTVDNPE ASSESIASAP ETNTAQVTST EV                    162

SEQ ID NO: 168           moltype = AA   length = 161
FEATURE                  Location/Qualifiers
source                   1..161
                         mol_type = protein
                         organism = Capra hircus
SEQUENCE: 168
CEKDERFFDD KIAKYIPIQY VLSRYPSYGL NYYQQRPVAL INNQFLPYPY YAKPIAVRSP   60
AQTLQWQVLP NTVPAKSCQD QPTTLARHPH PHLSFMAIPP KKDQDKTEIP AINTIASAEP  120
TVHSTPTTEA IVNTVDNPEA SSESIASAPE TNTAQVTSTE V                     161

SEQ ID NO: 169           moltype = AA   length = 192
FEATURE                  Location/Qualifiers
source                   1..192
                         mol_type = protein
                         organism = Capra hircus
SEQUENCE: 169
MMKSFFLVVT ILALTLPFLG AQEQNQEQPI CCEKDERFFD DKIAKYIPIQ YVLSRYPSYG   60
LNYYQQRPVA LINNQFLPYP YYAKPVAVRS PAQTLQWQVL PNTVPAKSCQ DQPTTLARHP  120
HPHLSFMAIP PKKDQDKTEV PAINTIASAE PTVHSTPTTE AIVNTVDNPE ASSESIASAS  180
ETNTAQVTST EV                                                     192

SEQ ID NO: 170           moltype = AA   length = 162
FEATURE                  Location/Qualifiers
source                   1..162
                         mol_type = protein
                         organism = Capra hircus
SEQUENCE: 170
CCEKDERFFD DKIAKYIPIQ YVLSRYPSYG LNYYQQRPVA LINNQFLPYP YYAKPIAVRS   60
PAQTLQWQVL PNTVPAKSCQ DQPTTLARHP HPHLSFMAIP PKKDQDKTEI PAINTIASAE  120
PTVHSTPTTE AIVNTVDNPE ASSESIASAP ETNTAQVTST EV                    162

SEQ ID NO: 171           moltype = AA   length = 161
FEATURE                  Location/Qualifiers
source                   1..161
                         mol_type = protein
                         organism = Capra hircus
SEQUENCE: 171
CEKDERFFDD KIAKYIPIQY VLSRYPSYGL NYYQQRPVAL INNQFLPYPY YAKPIAVRSP   60
AQTLQWQVLP NTVPAKSCQD QPTTLARHPH PHLSFMAIPP KKDQDKTEIP AINTIASAEP  120
TVHSTPTTEA IVNTVDNPEA SSESIVSAPE TNTAQVTSTE V                     161

SEQ ID NO: 172           moltype = AA   length = 162
FEATURE                  Location/Qualifiers
source                   1..162
                         mol_type = protein
                         organism = Capra hircus
SEQUENCE: 172
CCEKDERFFD DKIAKYIPIQ YVLSRYPSYG LNYYQQRPVA LINNQFLPYP YYAKPIAVRS   60
PAQTLQWQVL PNTVPAKSCQ DQPTTLARHP HPHLSFMAIP PKKDQDKTEI PAINTIASAE  120
PTVHSTPTTE AIVNTVDNPE ASSESIVSAP ETNTAQVTST EV                    162

SEQ ID NO: 173           moltype = AA   length = 161
FEATURE                  Location/Qualifiers
source                   1..161
                         mol_type = protein
                         organism = Capra hircus
SEQUENCE: 173
CEKDERFFDD KIAKYIPIQY VLSRYPSYGL NYYRQRPVAL INNQFLPYPY YAKPIAVRSP   60
AQTLQWQVLP NTVPAKSCQD QPTTLARHPH PHLSFMAIPP KKDQDKTEIP AINTIASAEP  120
TVHSTPTTEA IVNTVDNPEA SSESIASAPE TNTAQVTSTE V                     161

SEQ ID NO: 174           moltype = AA   length = 192
FEATURE                  Location/Qualifiers
source                   1..192
```

```
                        mol_type = protein
                        organism = Capra hircus
SEQUENCE: 174
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKDQDKTEI PAINTIASAE PTVHSTPITE AIVNTVDNPE ASSESIASAS   180
ETNTAQVTST EV                                                       192

SEQ ID NO: 175          moltype = AA   length = 162
FEATURE                 Location/Qualifiers
source                  1..162
                        mol_type = protein
                        organism = Capra hircus
SEQUENCE: 175
CCEKDERFFD DKIAKYIPIQ YVLSRYPSYG LNYYQQRPVA LINNQFLPYP YYAKPVAVRS    60
PAQTLQWQVL PNTVPAKSCQ NQPTTLARHP HPHLSFMAIP PKKDQDKTEI PAINTIASAE   120
PTVHSTPTTE AIVNTADNPE ASSESIASAP ETNTAQVTST EV                      162

SEQ ID NO: 176          moltype = AA   length = 162
FEATURE                 Location/Qualifiers
source                  1..162
                        mol_type = protein
                        organism = Capra hircus
SEQUENCE: 176
CCEKDERFFD DKIAKYIPIQ YVLSRYPSYG LNYYRQRPVA LINNQFLPYP YYAKPIAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAP ETNTAQVTST EV                      162

SEQ ID NO: 177          moltype = AA   length = 162
FEATURE                 Location/Qualifiers
source                  1..162
                        mol_type = protein
                        organism = Capra hircus
SEQUENCE: 177
CCEKDERFFD DKIAKYIPIQ YVLSRYPSYG LNYYQQRPVA LINNQFLPYP YYAKPVAVRS    60
PAQTLQWQVL PNTVPAKSCQ GQPTTLARHP HPHLSFMAIP PKKDQDKTEI PAINTIASAE   120
PTVHSTPTTE AIVNTVDNPE ASSESIASAS ETNTAQVTST EV                      162

SEQ ID NO: 178          moltype = AA   length = 161
FEATURE                 Location/Qualifiers
source                  1..161
                        mol_type = protein
                        organism = Capra hircus
SEQUENCE: 178
CEKDERFFDD KIAKYIPIQY VLSRYPSYGL NYYQQRPVAL INNQFLPYPY YAKPVAVRSP    60
AQTLQWQVLP NTVPAKSCQD QPTTLARHPH PHLSFMAIPP KKDQDKTEIP AINTIASAEP   120
TVHSTPTTEA IVNTVDNPEA SSESIASASE TNTAQVTSTE V                       161

SEQ ID NO: 179          moltype = AA   length = 162
FEATURE                 Location/Qualifiers
source                  1..162
                        mol_type = protein
                        organism = Capra hircus
SEQUENCE: 179
CCEKDERFFD DKIAKYIPIQ YVLSRYPSYG LNYYQQRPVA LINNQFLPYP YYAKPVAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAS ETNTAQVTST EV                      162

SEQ ID NO: 180          moltype = AA   length = 161
FEATURE                 Location/Qualifiers
source                  1..161
                        mol_type = protein
                        organism = Capra hircus
SEQUENCE: 180
CEKDERFFDD KIAKYIPIQY VLSRYPSYGL NYYQQRPVAL INNQFLPYPY YAKPVAVRSP    60
AQTLQWQVLP NTVPAKSCQD QPTTLARHPH PHLSFMAIPP KKDQDKTEVP AINTIASAEP   120
TVHSTPTTEA IVNTVDNPEA SSESIASASE TNTAQVTSTE V                       161

SEQ ID NO: 181          moltype = AA   length = 162
FEATURE                 Location/Qualifiers
source                  1..162
                        mol_type = protein
                        organism = Capra hircus
SEQUENCE: 181
CCEKDERFFD DKIAKYIPIQ YVLSRYPSYG LNYYQQRPVA LINNQFLPYP YYAKPIAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAS ETNTAQVTST EV                      162

SEQ ID NO: 182          moltype = AA   length = 162
```

```
FEATURE                 Location/Qualifiers
source                  1..162
                        mol_type = protein
                        organism = Capra hircus
SEQUENCE: 182
CCEKDERFFD DKIAKYIPIQ YVLSRYPSYG LNYYQRPVA  LINNQFLPYP YYAKPVAVRS    60
PAQTLQWQVL PNTVPAKSCQ DQPTTLARHP HPHLSFMAIP PKKDQDKTEV PAINTIASAE   120
PTVHSTPTTE AIVNTVDNPE ASSESIASAS ETNTAQVTST EV                      162

SEQ ID NO: 183          moltype = AA   length = 162
FEATURE                 Location/Qualifiers
source                  1..162
                        mol_type = protein
                        organism = Capra hircus
SEQUENCE: 183
CCEKDERFFD DKIAKYIPIQ YVLSRYPSYG LNYYRQRPVA LINNQFLPYP YYAKPVAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAS ETNTAQVTST EV                      162

SEQ ID NO: 184          moltype = AA   length = 192
FEATURE                 Location/Qualifiers
source                  1..192
                        mol_type = protein
                        organism = Ovis aries
SEQUENCE: 184
MMKSFFLVVT ILALTLPFLG AQEQNQEQRI CCEKDERFFD DKIAKYIPIQ YVLSRYPSYG    60
LNYYQQRPVA LINNQFLPYP YYAKPVAVRS PAQTLQWQVL PNAVPAKSCQ DQPTAMARHP   120
HPHLSFMAIP PKKDQDKTEI PAINTIASAE PTVHSTPTTE AVVNAVDNPE ASSESIASAP   180
ETNTAQVTST EV                                                       192

SEQ ID NO: 185          moltype = AA   length = 162
FEATURE                 Location/Qualifiers
source                  1..162
                        mol_type = protein
                        organism = Ovis aries
SEQUENCE: 185
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE   120
PTVHSTPTTE AVVNAVDNPE ASSESIASAP ETNTAQVTST EV                      162

SEQ ID NO: 186          moltype = AA   length = 190
FEATURE                 Location/Qualifiers
source                  1..190
                        mol_type = protein
                        organism = Bubalus bubalis
SEQUENCE: 186
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSVE PTSTPTTEAI ENTVATLEAS SEVIESVPET   180
NTAQVTSTVV                                                          190

SEQ ID NO: 187          moltype = AA   length = 190
FEATURE                 Location/Qualifiers
source                  1..190
                        mol_type = protein
                        organism = Bubalus bubalis
SEQUENCE: 187
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSIE PTSTPTTEAI ENTVATLEAS SEVIESVPET   180
NTAQVTSTVV                                                          190

SEQ ID NO: 188          moltype = AA   length = 190
FEATURE                 Location/Qualifiers
source                  1..190
                        mol_type = protein
                        organism = Bubalus bubalis
SEQUENCE: 188
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSVE PTSTPTTEAI ENTVATLEAS SDVIESVPET   180
NTAQVTSTVV                                                          190

SEQ ID NO: 189          moltype = AA   length = 190
FEATURE                 Location/Qualifiers
source                  1..190
                        mol_type = protein
                        organism = Bubalus bubalis
SEQUENCE: 189
```

```
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSIE PTSTPTTEAI ENTVATLEAS SDVIESVPET   180
NTAQVTSTVV                                                          190

SEQ ID NO: 190             moltype = AA  length = 190
FEATURE                    Location/Qualifiers
source                     1..190
                           mol_type = protein
                           organism = Bubalus bubalis
SEQUENCE: 190
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSVE PTSTPITEAI ENTVATLEAS SEVIESVPET   180
NTAQVTSTVV                                                          190

SEQ ID NO: 191             moltype = AA  length = 190
FEATURE                    Location/Qualifiers
source                     1..190
                           mol_type = protein
                           organism = Bubalus bubalis
SEQUENCE: 191
MMKSFFLVVT ILALTLPFLG AQEQNQEQLI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSVE PTSTPTTEAI ENTVATLEAS SDVIESVPET   180
NTAQVTSTVV                                                          190

SEQ ID NO: 192             moltype = AA  length = 194
FEATURE                    Location/Qualifiers
source                     1..194
                           mol_type = protein
                           organism = Bos mutus
SEQUENCE: 192
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTTEAV ESTVATLEAS PEASPEVIES   180
PPEINTVQVT STAV                                                     194

SEQ ID NO: 193             moltype = AA  length = 183
FEATURE                    Location/Qualifiers
source                     1..183
                           mol_type = protein
                           organism = Bos mutus
SEQUENCE: 193
MMKSFFLVVT ILALTLPFLR CEKDERFFSD KIAKYIPIQY VLSRYPSYGL NYYQQKPVAL    60
INNQFLPYPY YAKPAAVRSP AQILQWQVLS NTVPAKSCQA QPTTMARHPH PHLSFMAIPP   120
KKNQDKTEIP TINTIASGEP TSTPTTEAVE STVATLEASP EASPEVIESP PEINTVQVTS   180
TAV                                                                 183

SEQ ID NO: 194             moltype = AA  length = 976
FEATURE                    Location/Qualifiers
source                     1..976
                           mol_type = protein
                           organism = Bos mutus
SEQUENCE: 194
MTSGTAVQRA DSSEEKRHRK RKKHHLIKSQ ILSYTEDRGF NEGQMKEDEQ EKADSSEEVR    60
HFHSLQKDKV NMKFFIFTCL LAVALAKNVK SLLKSKKHGT ITRTSFKVQE SHRENVDSQT   120
ISSICQNFII LDCRSSATRI LCKRFKITVD DKHYQKALNE INQFYQKFPQ YLQYLYQGPI   180
VLNPWDQVKR NAVPITPTLV IKLIFIFFPH KESTEVFTKK LKLTEEEKNR LNFLKKISQR   240
YQKFALPQYL KTVYQHQKAM KPWIQPKTKV IPYVDYSDNI GSPYPVNPSA SISYPVTPSA   300
SIPCPVNPSA SIPCPMPDRD FTPPVYLTKT NLPNDPAVPS NPLVFTALGA PLYSIAGLPI   360
SPFSGQLPPT GVFRLVPVSS RPIGPLYSPN EAAPSANTYI VEILVPPTTP PHTVPDVQPL   420
TITEPDEAEP AADALAAPEP QSSISFDQLI PQHLMSASNS NELLLNLNNA QLRPLQLQGP   480
FNPWIPPFPG ILQQQQQNQV PGLSPFSLST REWFAGLVPN QIFVPGQVSF AQGTQAGQLD   540
PSQPQTPQQT QRGPKNVMPS VFFKMPQEQA QMLQYYPVYM FLPWEQPQQT VAQSPPQTRE   600
QLFEEQMPFY TEFGYIPQQV EPVMPVEQQQ PVFDPFLGTA PEIAAMDRKA VIVITIKRQL   660
APFVRTILEP VTSISYNTIP EKDRTGKFEV SQDTEGEARS VSGSDELSSQ FFFPPYQYPR   720
SHYSRFLCPW WAYFYPPIPV PASVSATTPL NEKKKYQIHV NKVERPTEPT AKQELTVTRK   780
GAMMKSFFLV VTILALTLPF LGAQEQNQEQ PIRCEKDERF FSDKIAKYIP IQYVLSRYPS   840
YGLNYYQQKP VALINNQFLP YPYYAKPAAV RSPAQILQWQ VLSNTVPAKS CQAQPTTMAR   900
HPHPHLSFMA IPPKKNQDKT EIPTINTIAS GEPTSTPTTE AVESTVATLE ASPEASPEVI   960
ESPPEINTVQ VTSTAV                                                   976

SEQ ID NO: 195             moltype = AA  length = 190
FEATURE                    Location/Qualifiers
source                     1..190
                           mol_type = protein
                           organism = Bos indicus
SEQUENCE: 195
```

```
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPITEAV ESTVATLEDS PEVIESPPEI   180
NTVQVTSTAV                                                         190

SEQ ID NO: 196          moltype = AA  length = 160
FEATURE                 Location/Qualifiers
source                  1..160
                        mol_type = protein
                        organism = Bos indicus
SEQUENCE: 196
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTIEAV ESTVATLEDS PEVIESPPEI NTVQVTSTAV                         160

SEQ ID NO: 197          moltype = AA  length = 160
FEATURE                 Location/Qualifiers
source                  1..160
                        mol_type = protein
                        organism = Bos indicus
SEQUENCE: 197
RCEKDERFFS DKIAKYIPIQ YVLSRYPSYG LNYYQQKPVA LINNQFLPYP YYAKPAAVRS    60
SAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                         160

SEQ ID NO: 198          moltype = AA  length = 160
FEATURE                 Location/Qualifiers
source                  1..160
                        mol_type = protein
                        organism = Bos indicus
SEQUENCE: 198
RCEKDERFFS DKIAKYIPIQ YVLSRYPSYG LNYYQQKPVA LINNQFLPYP YYAKPAAVRS    60
SAQILQWQVL SNTVPAKSCQ AQPTTMARHP HPHLSFMAIP PKKNQDKTEI PTINTIASGE   120
PTSTPTIEAV ESTVATLEAS PEVIESPPEI NTVQVTSTAV                         160

SEQ ID NO: 199          moltype = AA  length = 171
FEATURE                 Location/Qualifiers
source                  1..171
                        mol_type = protein
                        organism = Bos indicus
SEQUENCE: 199
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPITEAV ESTVATLEDS PEVIESPPEI NTVQVRQLQS KNLRRHQRRQ R            171

SEQ ID NO: 200          moltype = AA  length = 171
FEATURE                 Location/Qualifiers
source                  1..171
                        mol_type = protein
                        organism = Bos indicus
SEQUENCE: 200
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPITEAV ESTVATLEDS PEVIESPPEI NTVQVLNLQS KNLRRHQRRQ R            171

SEQ ID NO: 201          moltype = AA  length = 156
FEATURE                 Location/Qualifiers
source                  1..156
                        mol_type = protein
                        organism = Bos indicus
SEQUENCE: 201
DERFFSDKIA KYIPIQYVLS RYPSYGLNYY QQKPVALINN QFLPYPYYAK PAAVRSPAQI    60
LQWQVLSNTV PAKSCQAQPT TMARHPHPHL SFMAIPPKKN QDKTEIPTIN TIASGEPTST   120
PTIEAVESTV ATLEASPEVI ESPPEINTVQ VTSTAV                             156

SEQ ID NO: 202          moltype = AA  length = 144
FEATURE                 Location/Qualifiers
source                  1..144
                        mol_type = protein
                        organism = Bos indicus
SEQUENCE: 202
IPIQYVLSRY PSYGLNYYQQ KPVALINNQF LPYPYYAKPA AVRSPAQILQ WQVLSNTVPA    60
KSCQAQPTTM ARHPHPHLSF MAIPPKKNQD KTEIPTINTI ASGEPTSTPT TEAVESTVAT   120
LEDSPEVIES PPEINTVQVT STAV                                          144

SEQ ID NO: 203          moltype = AA  length = 144
FEATURE                 Location/Qualifiers
source                  1..144
                        mol_type = protein
```

```
                                    organism = Bos indicus
SEQUENCE: 203
IPIQYVLSRY PSYGLNYYQQ KPVALINNQF LPYPYYAKPA AVRSPAQILQ WQVLSNTVPA        60
KSCQAQPTTM ARHPHPHLSF MAIPPKKNQD KTEIPTINTI ASGEPTSTPI TEAVESTVAT       120
LEDSPEVIES PPEINTVQVT STAV                                              144

SEQ ID NO: 204          moltype = AA  length = 141
FEATURE                 Location/Qualifiers
source                  1..141
                        mol_type = protein
                        organism = Bos indicus
SEQUENCE: 204
QYVLSRYPSY GLNYYQQKPV ALINNQFLPY PYYAKPAAVR SPAQILQWQV LSNTVPAKSC        60
QAQPTTMARH PHPHLSFMAI PPKKNQDKTE IPTINTIASG EPTSTPTIEA VESTVATLEA       120
SPEVIESPPE INTVQVTSTA V                                                 141

SEQ ID NO: 205          moltype = AA  length = 139
FEATURE                 Location/Qualifiers
source                  1..139
                        mol_type = protein
                        organism = Bos indicus
SEQUENCE: 205
VLSRYPSYGL NYYQQKPVAL INNQFLPYPY YAKPAAVRSP AQILQWQVLS NTVPAKSCQA        60
QPTTMARHPH PHLSFMAIPP KKNQDKTEIP TINTIASGEP TSTPITEAVE STVATLEDSP       120
EVIESPPEIN TVQVTSTAV                                                    139

SEQ ID NO: 206          moltype = AA  length = 210
FEATURE                 Location/Qualifiers
source                  1..210
                        mol_type = protein
                        organism = Jeotgalicoccus coquinae
SEQUENCE: 206
MERPTEPTAK QELTVTRKGA MMKSFFLVVT ILALTLPFLG AQEQNQEQPI RCEKDERFFS        60
DKIAKYIPIQ YVLSRYPSYG LNYYQQKPVA LINNQFLPYP YYAKPAAVRS PAQILQWQVL       120
SNTVPAKSCQ AQPTTMARHP HLSFMAIP PKKNQDKTEI PTINTIASGE PTSTPTIEAV        180
ESTVATLEAS PEVIESPPEI NTVQVTSTAV                                        210

SEQ ID NO: 207          moltype = AA  length = 184
FEATURE                 Location/Qualifiers
source                  1..184
                        mol_type = protein
                        organism = Jeotgalicoccus coquinae
SEQUENCE: 207
LVVTILALTL PFLGAQEQNQ EQLIRCEKEE RFFNDKIAKY IPIQYVLSRY PSYGLNYYQQ        60
KPVALINNQF LPYPYYAKPA AVRSPAQILQ WQVLPNTVPA KSCQAQPTTM TRHPHPHLSF       120
MAIPPKKNQD KTEIPTINTI VSVEPTSTPT TEAIENTVAT LEASSEVIES VPETNTAQVT       180
STVV                                                                    184

SEQ ID NO: 208          moltype = AA  length = 190
FEATURE                 Location/Qualifiers
source                  1..190
                        mol_type = protein
                        organism = Bison bison
SEQUENCE: 208
MMKSFFLVVT ILALTLPFLG AQEQNQEQPI RCEKDERFFS DKIAKYIPIQ YVLSRYPSYG        60
LNAYQQKPVA LINNQFLPYP YYAKPAAVRS PAQILQWQVL SNTVPAKSCQ AQPTTMARHP       120
HPHLSFMAIP PKKNQDKTEI PTINTIASGE PTSTPTTEAV ESTVATLEAS PEVIESPPEI       180
NTVQVTSTVV                                                              190

SEQ ID NO: 209          moltype = AA  length = 179
FEATURE                 Location/Qualifiers
source                  1..179
                        mol_type = protein
                        organism = Bison bison
SEQUENCE: 209
MMKSFFLVVT ILALTLPFLR CEKDERFFSD KIAKYIPIQY VLSRYPSYGL NAYQQKPVAL        60
INNQFLPYPY YAKPAAVRSP AQILQWQVLS NTVPAKSCQA QPTTMARHPH PHLSFMAIPP       120
KKNQDKTEIP TINTIASGEP TSTPTTEAVE STVATLEASP EVIESPPEIN TVQVTSTVV        179

SEQ ID NO: 210          moltype = AA  length = 190
FEATURE                 Location/Qualifiers
source                  1..190
                        mol_type = protein
                        organism = Bos grunniens
SEQUENCE: 210
MMKSFFLVVT ILALTLPFLG AQEQNQEQPI RCEKDERFFS DKIAKYIPIQ YVLSRYLSYG        60
LNYYQQKPVA LINNQFLPYP YYAKPAAVRS PAQILQWQVL SNTVPAKSCQ AQPTTMARHP       120
HPHLSFMAIP PKKNQDKTEI PTINTIASGE RTSTPTTEAV ESTVATLEAS PEVIESPPEI       180
NTVQVTSTAV                                                              190
```

```
SEQ ID NO: 211           moltype = AA   length = 194
FEATURE                  Location/Qualifiers
source                   1..194
                         mol_type = protein
                         organism = Bos grunniens
SEQUENCE: 211
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SSTVPAKSCQ AQPTTMARHP   120
HPHLSFMAIP PKKNQDKTEI PTINTIASGE PTSTPTTEAV ESTVATLEAS PEASPEVIES   180
PPEINTVQVT STAV                                                    194

SEQ ID NO: 212           moltype = AA   length = 160
FEATURE                  Location/Qualifiers
source                   1..160
                         mol_type = protein
                         organism = Bos grunniens
SEQUENCE: 212
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEVIESPPEI NTVQVTSTAV                        160

SEQ ID NO: 213           moltype = AA   length = 160
FEATURE                  Location/Qualifiers
source                   1..160
                         mol_type = protein
                         organism = Bos grunniens
SEQUENCE: 213
RCEKDERFFS DKIAKYIPIQ YVLSRYLSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEVIESPPEI NTVQVTSTAV                        160

SEQ ID NO: 214           moltype = AA   length = 164
FEATURE                  Location/Qualifiers
source                   1..164
                         mol_type = protein
                         organism = Bos grunniens
SEQUENCE: 214
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEASPEVIES PPEINTVQVT STAV                   164

SEQ ID NO: 215           moltype = AA   length = 160
FEATURE                  Location/Qualifiers
source                   1..160
                         mol_type = protein
                         organism = Bos grunniens
SEQUENCE: 215
RCEKDERFFS DKIAKYIPIQ YVLSRYLSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
RTSTPTTEAV ESTVATLEAS PEVIESPPEI NTVQVTSTAV                        160

SEQ ID NO: 216           moltype = AA   length = 160
FEATURE                  Location/Qualifiers
REGION                   1..160
                         note = Bos indicus x Bos taurus
source                   1..160
                         mol_type = protein
                         organism = unidentified
SEQUENCE: 216
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                        160

SEQ ID NO: 217           moltype = AA   length = 160
FEATURE                  Location/Qualifiers
REGION                   1..160
                         note = Bos indicus x Bos taurus
source                   1..160
                         mol_type = protein
                         organism = unidentified
SEQUENCE: 217
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLAFMAIP PKKNQDKTEI PTINTIASGE   120
PTSTPTTEAV ESTVATLEDS PEVIESPPEI NTVQVTSTAV                        160

SEQ ID NO: 218           moltype = AA   length = 192
FEATURE                  Location/Qualifiers
source                   1..192
```

```
                        mol_type = protein
                        organism = Oreamnos americanus
SEQUENCE: 218
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQILQWQVL PNTAPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 219          moltype = AA   length = 192
FEATURE                 Location/Qualifiers
source                  1..192
                        mol_type = protein
                        organism = Naemorhedus goral
SEQUENCE: 219
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTAPAKSCQ DQPTTMARHP   120
HPHLSFMAIP PKKDQDKTEI PTINTIASAE PTVHSTPTTE AIVNTVDNPE ASSESIASAP   180
ETNTAQVTST EV                                                      192

SEQ ID NO: 220          moltype = AA   length = 190
FEATURE                 Location/Qualifiers
source                  1..190
                        mol_type = protein
                        organism = Odocoileus virginianus
SEQUENCE: 220
MMKSFSLVVT ILALTLPFLV AQEQNQEQPT GCEKDERFFN DKIVKYIPIQ YVLSRYPSYG    60
LSYYQHRPVA LINNQFLPYP YYAKPGAVRS PAQILQWQVL PNTVPAKSCQ AQPTTLARHP   120
HPRLSFMAIP PKKNQDKTDI PTINTIATVE STITPTTEAI VDTVATPEAS SEVIESAPET   180
KTDQVTSTVV                                                         190

SEQ ID NO: 221          moltype = AA   length = 192
FEATURE                 Location/Qualifiers
source                  1..192
                        mol_type = protein
                        organism = Capricornis sumatraensis
SEQUENCE: 221
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTAPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 222          moltype = AA   length = 192
FEATURE                 Location/Qualifiers
source                  1..192
                        mol_type = protein
                        organism = Capricornis crispus
SEQUENCE: 222
MMKSFFLAVT ILALTLPFLG AQEQNQEQPI CCEKDETFFD DKIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 223          moltype = AA   length = 192
FEATURE                 Location/Qualifiers
source                  1..192
                        mol_type = protein
                        organism = Capricornis crispus
SEQUENCE: 223
MMKSFFLVVT ILALTLPFLG AQEQNQEQPI CCEKDETFFD DKIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 224          moltype = AA   length = 192
FEATURE                 Location/Qualifiers
source                  1..192
                        mol_type = protein
                        organism = Capricornis swinhoei
SEQUENCE: 224
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTAPAKSCQ DQPTTMARHP   120
HPHLSFMAIP PKKDQDKTEI PTINTIASAE TTVHSTPTTE AIVNTVDNRE ASSESIVSAP   180
ETNTAQVTST EV                                                      192

SEQ ID NO: 225          moltype = AA   length = 202
FEATURE                 Location/Qualifiers
source                  1..202
                        mol_type = protein
                        organism = Saiga tatarica
```

```
SEQUENCE: 225
MMKSFFLVVT ILALTLPFLD AQERNQEQPI CCEKDERFFN DRIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKDQDKTEI PTINTVASAE PASTPTTEAI VNTEAIVNTE AIVNTVDNPE   180
ASSEIIASVP ETNTAQVTST EV                                           202

SEQ ID NO: 226          moltype = AA  length = 192
FEATURE                 Location/Qualifiers
source                  1..192
                        mol_type = protein
                        organism = Rupicapra rupicapra
SEQUENCE: 226
MMKSFFLVAT ILALTLPFLG AQEQNQEQSI CCEKDERFFE DKIAKYIPIQ YVLSRYPSYG    60
LNYYQQRPVA LINNQFLPYP YYAKPVAVRS PAQTLQWQVL PNTAPAKSCQ DQPTTMAHHP   120
HPHLSFMAIP PKKDQDKTEI PTINTIASAE PTVHSTPTTE AIVNTVDNPE ASSESIASAP   180
ETNTAQVTST EV                                                      192

SEQ ID NO: 227          moltype = AA  length = 190
FEATURE                 Location/Qualifiers
source                  1..190
                        mol_type = protein
                        organism = Cervus nippon
SEQUENCE: 227
MMKSFFLAVT ILALTLPFLV AQEQIQEQPT GCEKDERFFN DKIVKYIPIQ YALSRYPSYG    60
LNYYQHRPVA LINNQFLPYP YYVKPGAVRS PAQILQWQVL PNTVPAKFCQ AQPTTMARHP   120
HPRLSFMAIP PKKNQDKTDI PSINTIATAE STITPTTEAI VDTVATQEAF SEVIESAPEA   180
KTDQVTSTVV                                                         190

SEQ ID NO: 228          moltype = AA  length = 139
FEATURE                 Location/Qualifiers
source                  1..139
                        mol_type = protein
                        organism = Bos frontalis
SEQUENCE: 228
VLSRYPSYGL NYYQQKPVAL INNQFLPYPY YAKPAAVRSP AQILQWQVLS NTVPAKSCQA    60
QPTTMARHPH PHLSFMAIPP KKNQDKTEIP TINTIASGEP TSTPTTEAVE STVATLEASP   120
EVIESPPEIN TVQVTSTAV                                                139

SEQ ID NO: 229          moltype = AA  length = 170
FEATURE                 Location/Qualifiers
source                  1..170
                        mol_type = protein
                        organism = Muntiacus reevesi
SEQUENCE: 229
AQELNQEQPT GCEKDERFFN DKIVKYIPIQ YALSRYPSYG LNYYQHRPVA LISNQFLPYP    60
YYAKPGAVRS PAQILQWQAL PNTVPATSCQ AQPATVARHP HPRLSFMAIP PKKSQDKTDH   120
PTINTIATVE STATPTTEAV VDTAATQEAS PEVIASAPEA STDQVTSTAV              170

SEQ ID NO: 230          moltype = AA  length = 170
FEATURE                 Location/Qualifiers
source                  1..170
                        mol_type = protein
                        organism = Muntiacus muntjak
SEQUENCE: 230
AQELNQEQPT GCEKDERFFN DKIVKYIPIQ YALSRYPSYG LNYYQHRPVA LISNQFLPYP    60
YYAKPGAVRS PAQTLQWQAL PNTVPATSCQ AQPATMARHP HPRLSFMAIP PKKTQDKTDH   120
PTFNTIATAE STATPTTEAV VDTVATQEAS SEVTASAPEA NTDQVTSTAV              170

SEQ ID NO: 231          moltype = AA  length = 160
FEATURE                 Location/Qualifiers
source                  1..160
                        mol_type = protein
                        organism = Madoqua saltiana
SEQUENCE: 231
CCEKDERFFN DKIAKYIPIQ YVLSRYPSYG LNYYQQRPVA LINNQFLPYP YFAKPVAVRS    60
PAQTLQWQVL PNTVPAKSCQ DQPTTMARHP HPHLSFMAIP PKKDQDKPEI PTINTIASAE   120
LTSTPTTEAI VNTVDNPEAS SEIIASVPET NTAEVTSTEV                         160

SEQ ID NO: 232          moltype = AA  length = 172
FEATURE                 Location/Qualifiers
source                  1..172
                        mol_type = protein
                        organism = Gazella dorcas
SEQUENCE: 232
CCEKDERFFN DKIAKYIPIQ YVLSRYPSYG LNYYQQRPVA LINNQFLPYP YYAKPVAVRS    60
PAQTLQWQVL PNTVPAKSCQ DQPTTMARHP HPHLSFMAIP PKKDQDKTEI PTINTIASAE   120
PASTPTTEAI VNTEAIVNTE PIVNTVDNPE ASSEIIASVP ETNTAQVTST EV           172

SEQ ID NO: 233          moltype = AA  length = 178
```

```
FEATURE                    Location/Qualifiers
VARIANT                    178
                           note = X can be any naturally occurring amino acid
source                     1..178
                           mol_type = protein
                           organism = Gazella arabica
SEQUENCE: 233
CCEKDERFFN DKIAKYIPIQ YVLSRYPSYG LNYYQQRPVA LINNQFLPYP YYAKPVAVRS    60
PAQTLQWQVL PNTVPAKSCQ DQPTTMARHP HPHLSFMAIP KKDQDKTEI PTINTIASAE   120
PASTPTTEAI VNTEAVVNTE AIVNTEAIVN TVDNPEASSE IIASVPETNT AQVTSTEX    178

SEQ ID NO: 234             moltype = AA  length = 162
FEATURE                    Location/Qualifiers
source                     1..162
                           mol_type = protein
                           organism = Capra ibex
SEQUENCE: 234
CCEKDERFFD DKIAKYIPIQ YVLNRYPTYG LNYYQQRPVA LINNQFLPYP YYAKPVAVRS    60
PAQTLQWQVL PNTVPAKSCQ DQPTTLARHP HPHLSFMAIP PKKDQDKTEI PAINTIASAE  120
PTVHSTPTTE AIVNTVDNPE ASSESIASAP ETNTAQVTST EV                     162

SEQ ID NO: 235             moltype = AA  length = 162
FEATURE                    Location/Qualifiers
VARIANT                    73
                           note = X can be any naturally occurring amino acid
source                     1..162
                           mol_type = protein
                           organism = Ovis ammon
SEQUENCE: 235
CCEKDERFFD DKIAKYIPIQ YVLSRYPSYG LNYYQQRPVA LINNQFLPYP YYAKPVAVRS    60
PAQTLQWQVL PNXVPAKSCQ DQPTAMARHP HPHLSFMAIP PKKDQDKTEI PAINTIASAE  120
PTVHSTPTTE AVVNAVDNPE ASSESIASAP ETNTAQVTST EV                     162

SEQ ID NO: 236             moltype = AA  length = 162
FEATURE                    Location/Qualifiers
source                     1..162
                           mol_type = protein
                           organism = Ovis orientalis
SEQUENCE: 236
CCEKDERFFD DKIAKYIPIQ YVLSRYPSYG LNYYQQRPVA LINNQFLPYP YYAKPVAVRS    60
PAQTLQWQVL PNTVPAKSCQ DQPTAMARHP HPHLSFMAIP PKKDQDKTEI PAINTIASAE  120
PTVHSTPTTE AVVNAVDNPE ASSESIASAP ETNTAQVTST EV                     162

SEQ ID NO: 237             moltype = AA  length = 162
FEATURE                    Location/Qualifiers
source                     1..162
                           mol_type = protein
                           organism = Ovis orientalis
SEQUENCE: 237
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE  120
PTVHSTPTTE AVVNAVDNPE ASSESIASAP ETNTAQITST EV                     162

SEQ ID NO: 238             moltype = AA  length = 463
FEATURE                    Location/Qualifiers
source                     1..463
                           mol_type = protein
                           organism = Cervus hanglu
SEQUENCE: 238
QEVKVTVDNK HYQKVLNEIS QFYQKFPQYL QYLYQGPIVM NPWEQVKRTA GPFIPTVVSA    60
AFLYVSCLFG FLFKTKLTEE EKNRLNFLKK ISQYYQKFAW PQYLKTVYQY QKAMKPWTQP  120
KTNAIPYVLI PQRLMSASNS NELLLNLNNA QLQPLQLQGP FNSWIPPFPG ILQQQQQDQI  180
PGLSPFSLST LERFAGLVPN QIFVPGQVGF AQGTQAGQLD PSQPQTPQQT QRGPKNVMPS  240
LLSLKMPQEQ AQLLQYYPVY MFLPWEQPQQ TVAQSPPQTR LQLFEEQMPY YTEFGYIPQQ  300
VEPGCEKDER FFNDKIVKYI PIQYALSRYP SYGLNYYQHR PVALINNQFL PYPYYVKPGA  360
VRSPAQILQW QVLPNTVPAK FCQAQPTTMA RHPHPRLSFM AIPPKKNQDK TDIPSINTIA  420
TAESTITPTT EAIVDTVATQ EASSEVIESA PEAKTDQVTS TVV                    463

SEQ ID NO: 239             moltype = AA  length = 160
FEATURE                    Location/Qualifiers
source                     1..160
                           mol_type = protein
                           organism = Procapra gutturosa
SEQUENCE: 239
CCEKDERFFN DKIAKYIPIQ YVMSRYPSYG LNYYQQRPVA LINNQFLPYP YYAKPVAVRS    60
PAQTLQWQVL PNTVPAKSCQ DQPTTMARHP HPHLSFMAIP PKKDQDKTEI PTINTIASAE  120
PTSTPTTEAI VNTVDNPEAT SEIIASVPET NTAQVTSTEV                        160

SEQ ID NO: 240             moltype = AA  length = 160
```

```
FEATURE                 Location/Qualifiers
VARIANT                 111
                        note = X can be any naturally occurring amino acid
VARIANT                 121
                        note = X can be any naturally occurring amino acid
VARIANT                 125
                        note = X can be any naturally occurring amino acid
VARIANT                 139
                        note = X can be any naturally occurring amino acid
source                  1..160
                        mol_type = protein
                        organism = Procapra gutturosa
SEQUENCE: 240
CCEKDERFFN DKIAKYIPIQ YVMSRYPSYG LNYYQQRPVA LINNQFLPYP YYAKPVAVRS    60
PAQTLQWQVL PNTVPAKSCQ DQPTTMARHP HPHLSFMAIP PKKDQDKTEI XTINTIASAE   120
XTSTXTTEAI VNTVDNPEXT SEIIASVPET NTAQVTSTEV                         160

SEQ ID NO: 241          moltype = AA  length = 190
FEATURE                 Location/Qualifiers
source                  1..190
                        mol_type = protein
                        organism = Bos taurus
SEQUENCE: 241
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTIEAV ESTVATLEAS PEVTESPPEI   180
NTVQVTSTAV                                                          190

SEQ ID NO: 242          moltype = AA  length = 190
FEATURE                 Location/Qualifiers
source                  1..190
                        mol_type = protein
                        organism = Bos taurus
SEQUENCE: 242
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTGI PTINTIASGE PTSTPTIEAV ESTVATLEAS PEVTESPPEI   180
NTVQVTSTAV                                                          190

SEQ ID NO: 243          moltype = AA  length = 190
FEATURE                 Location/Qualifiers
source                  1..190
                        mol_type = protein
                        organism = Bos taurus
SEQUENCE: 243
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTIEAV ESTVATLEAS PEVIESPPEI   180
NTVQVTSTAV                                                          190

SEQ ID NO: 244          moltype = AA  length = 190
FEATURE                 Location/Qualifiers
source                  1..190
                        mol_type = protein
                        organism = Bos taurus
SEQUENCE: 244
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTTEAV ESTVATLEDS PEVIESPPEI   180
NTVQVTSTAV                                                          190

SEQ ID NO: 245          moltype = AA  length = 160
FEATURE                 Location/Qualifiers
source                  1..160
                        mol_type = protein
                        organism = Bos taurus
SEQUENCE: 245
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTTEAV                         160

SEQ ID NO: 246          moltype = AA  length = 169
FEATURE                 Location/Qualifiers
source                  1..169
                        mol_type = protein
                        organism = Bos taurus
SEQUENCE: 246
QEQNQEQPIR CEKDERFFSD KIAKYIPIQY VLSRYPSYGL NYYQQKPVAL INNQFLPYPY    60
YAKPAAVRSP AQILQWQVLS NTVPAKSCQA QPTTMAHHPH PHLSFMAIPP KKNQDKTEIP   120
```

-continued

```
TINTIASGEP TSTPITEAVE STVATLEASP EVIESPPEIN TVQVTSTAV           169

SEQ ID NO: 247            moltype = AA  length = 179
FEATURE                   Location/Qualifiers
source                    1..179
                          mol_type = protein
                          organism = Bos taurus
SEQUENCE: 247
MMKSFFLVVT ILALTLPFLR CEKDERFFSD KIAKYIPIQY VLSRYPSYGL NYYQQKPVAL  60
INNQFLPYPY YAKPAAVRSP AQILQWQVLS NTVPAKSCQA QPTTMARHPH PHLSFMAIPP  120
KKNQDKTEIP TINTIASGEP TSTPIEAVE STVATLEASP EVIESPPEIN TVQVTSTAV   179

SEQ ID NO: 248            moltype = AA  length = 160
FEATURE                   Location/Qualifiers
source                    1..160
                          mol_type = protein
                          organism = Bos taurus
SEQUENCE: 248
RCEKDERFFS DKIAKYIPIQ YVLSRYPSYG LNYYQQKPVA LINNQFLPYP YYAKPAAVRS  60
PAQILQWQVL SNTVPAKSCQ AQPTTMARHP HPHLSFMAIP PKKNQDKTEI PTINTIASGE  120
PTSTPTIEAV ESTVATLEAS PEVIESPPEI NTVQVTSTAV                      160

SEQ ID NO: 249            moltype = AA  length = 160
FEATURE                   Location/Qualifiers
source                    1..160
                          mol_type = protein
                          organism = Bos taurus
SEQUENCE: 249
RCEKDERFFS DKIAKYIPIQ YVLSRYPSYG LNYYQQKPVA LINNQFLPYP YYAKPAAVRS  60
PAQILQWQVL SNTVPAKSCQ AQPTTMARHP HPHLSFMAIP PKKNQDKTEI PTINTIASGE  120
PTSTPITEAV ESTVATLEDS PEVIESPPEI NTVQVTSTAV                      160

SEQ ID NO: 250            moltype = AA  length = 106
FEATURE                   Location/Qualifiers
source                    1..106
                          mol_type = protein
                          organism = Bos taurus
SEQUENCE: 250
AEQQNEEEPI RCEKDERFFS DKIAKYIPIQ YVLSRYPSYG LNYYQQKPVA LINNQFLPYP  60
YYAKPAAVRS PAQILQWQVL SNTVPAKSCQ AQPTTMARHP PHHLSF                106

SEQ ID NO: 251            moltype = AA  length = 160
FEATURE                   Location/Qualifiers
source                    1..160
                          mol_type = protein
                          organism = Bos taurus
SEQUENCE: 251
HCEKDERFFS DKIAKYIPIQ YVLSRYPSYG LNYYQQKPVA LINNQFLPYP YYAKPAAVRS  60
PAQILQWQVL SNTVPAKSCQ AQPTTMARHP HPHLSFMAIP PKKNQDKTEI PTINTIASGE  120
PTSTPTTEAV ESTVATLEDS PEVIESPPEI NTVQVTSTAV                      160

SEQ ID NO: 252            moltype = AA  length = 160
FEATURE                   Location/Qualifiers
source                    1..160
                          mol_type = protein
                          organism = Bos taurus
SEQUENCE: 252
RCEKDERFFS DKIAKYIPIQ YVLSRYPSYG LNYYQQKPVA LINNQFLPYP YYAKPAAVRS  60
PAQILQWQVL SNTVPAKSCQ AQPTTMACHP HPHLSFMAIP PKKNQDKTEI PTINTIASGE  120
PTSTPITEAV ESTVATLEDS PEVIESPPEI NTVQVTSTAV                      160

SEQ ID NO: 253            moltype = AA  length = 159
FEATURE                   Location/Qualifiers
source                    1..159
                          mol_type = protein
                          organism = Bos taurus
SEQUENCE: 253
CEKDERFFSD KIAKYIPIQY VLSRYPSYGL NYYQQKPVAL INNQFLPYPY YAKPAAVRSP  60
AQILQWQVLS NTVPAKSCQA QPTTMAHHPH PHLSFMAIPP KKNQDKTEIP TINTIASGEP  120
TSTPTTEAVE STVATLEDSP EVIESPPEIN TVQVTSTAV                       159

SEQ ID NO: 254            moltype = AA  length = 210
FEATURE                   Location/Qualifiers
source                    1..210
                          mol_type = protein
                          organism = Jeotgalicoccus coquinae
SEQUENCE: 254
MERPTEPTAK QELTVTRKGA MMKSFFLVVT ILALTLPFLG AQEQNQEQPI RCEKDERFFS  60
DKIAKYIPIQ YVLSRYPSYG LNYYQQKPVA LINNQFLPYP YYAKPAAVRS PAQILQWQVL  120
```

```
SNTVPAKSCQ AQPTTMARHP HPHLSFMAIP PKKNQDKTEI PTINTIASGE PTSTPTIEAV    180
ESTVATLEAS PEVIESPPEI NTVQVTSTAV                                    210

SEQ ID NO: 255           moltype = AA  length = 184
FEATURE                  Location/Qualifiers
source                   1..184
                         mol_type = protein
                         organism = Jeotgalicoccus coquinae
SEQUENCE: 255
LVVTILALTL PFLGAQEQNQ EQLIRCEKEE RFFNDKIAKY IPIQYVLSRY PSYGLNYYQQ    60
KPVALINNQF LPYPYYAKPA AVRSPAQILQ WQVLPNTVPA KSCQAQPTTM TRHPHPHLSF    120
MAIPPKKNQD KTEIPTINTI VSVEPTSTPT TEAIENTVAT LEASSEVIES VPETNTAQVT    180
STVV                                                                184

SEQ ID NO: 256           moltype = AA  length = 194
FEATURE                  Location/Qualifiers
source                   1..194
                         mol_type = protein
                         organism = Bos mutus
SEQUENCE: 256
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP    120
HPHLSFMAIP PKKNQDKTEI PTINTIASGE PTSTPTTEAV ESTVATLEAS PEASPEVIES    180
PPEINTVQVT STAV                                                     194

SEQ ID NO: 257           moltype = AA  length = 183
FEATURE                  Location/Qualifiers
source                   1..183
                         mol_type = protein
                         organism = Bos mutus
SEQUENCE: 257
MMKSFFLVVT ILALTLPFLR CEKDERFFSD KIAKYIPIQY VLSRYPSYGL NYYQQKPVAL    60
INNQFLPYPY YAKPAAVRSP AQILQWQVLS NTVPAKSCQA QPTTMARHPH PHLSFMAIPP    120
KKNQDKTEIP TINTIASGEP TSTPTTEAVE STVATLEASP EASPEVIESP PEINTVQVTS    180
TAV                                                                 183

SEQ ID NO: 258           moltype = AA  length = 976
FEATURE                  Location/Qualifiers
source                   1..976
                         mol_type = protein
                         organism = Bos mutus
SEQUENCE: 258
MTSGTAVQRA DSSEEKRHRK RKKHHLIKSQ ILSYTEDRGF NEGQMKEDEQ EKADSSEEVR    60
HFHSLQKDKV NMKFFIFTCL LAVALAKNVK SLLKSKKHGT ITRTSFKVQE SHRENVDSQT    120
ISSICQNFII LDCRSSATRI LCKRFKITVD DKHYQKALNE INQFYQKFPQ YLQYLYQGPI    180
VLNPWDQVKR NAVPITPTLV IKLIFIFFFH KESTEVFTKK TKLTEEEKNR LNFLKKISQR    240
YQKFALPQYL KTVYQHQKAM KPWIQPKTKV IPYVDYSDNI GSPYVNPSA SISYPVTPSA     300
SIPCPVNPSA SIPCPMPDRD FTPPVYLTKT NLPNDPAVPS NPLVFTALGA PLYSIAGLPI    360
SPFSGQLPPT GVFRLVPVSS RPIGPLYSPN EAAPSANTYI VEILVPPTTP PHTVPDVQPL    420
TITEPDEAEP AADALAAPEP QSSISFDQLI PQHLMSASNS NELLLNLNNA QLRPLQLQGP    480
FNPWIPPFPG ILQQQQQNQV PGLSPFSLST REWFAGLVPN QIFVPGQVSF AGTQAGQLD     540
PSQPQTPQQT QRGPKNVMPS VFFKMPQEQA QMLQYYPVYM FLPWEQPQQT VAQSPPQTRE    600
QLFEEQMPFY TEFGYIPQQV EPVMPVEQQQ PVFDPFLGTA PEIAAMDRKA VIVITIKRQL    660
APFVRTILEP VTSISYNTIP EKDRTGKFEV SQDTEGEARS VSGSDELSSQ FFFPPYQYPR    720
SHYSRFLCPW WAYFYPPIPV PASVSATTPL NEKKKYQIHV NKVERPTEPT AKQELTVTRK    780
GAMMKSFFLV VTILALTLPF LGAQEQNQEQ PIRCEKDERF FSDKIAKYIP IQYVLSRYPS    840
YGLNYYQQKP VALINNQFLP YPYYAKPAAV RSPAQILQWQ VLSNTVPAKS CQAQPTTMAR    900
HPHPHLSFMA IPPKKNQDKT EIPTINTIAS GEPTSTPTTE AVESTVATLE ASPEASPEVI    960
ESPPEINTVQ VQSTAV                                                   976

SEQ ID NO: 259           moltype = AA  length = 190
FEATURE                  Location/Qualifiers
source                   1..190
                         mol_type = protein
                         organism = Bos indicus
SEQUENCE: 259
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP    120
HPHLSFMAIP PKKNQDKTEI PTINTIASGE PTSTPITEAV ESTVATLEDS PEVIESPPEI    180
NTVQVTSTAV                                                          190

SEQ ID NO: 260           moltype = AA  length = 160
FEATURE                  Location/Qualifiers
source                   1..160
                         mol_type = protein
                         organism = Bos indicus
SEQUENCE: 260
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE    120
```

```
PTSTPTIEAV ESTVATLEDS PEVIESPPEI NTVQVTSTAV                         160

SEQ ID NO: 261          moltype = AA  length = 171
FEATURE                 Location/Qualifiers
source                  1..171
                        mol_type = protein
                        organism = Bos indicus
SEQUENCE: 261
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPITEAV ESTVATLEDS PEVIESPPEI NTVQVRQLQS KNLRRHQRRQ R            171

SEQ ID NO: 262          moltype = AA  length = 171
FEATURE                 Location/Qualifiers
source                  1..171
                        mol_type = protein
                        organism = Bos indicus
SEQUENCE: 262
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPITEAV ESTVATLEDS PEVIESPPEI NTVQVLNLQS KNLRRHQRRQ R            171

SEQ ID NO: 263          moltype = AA  length = 160
FEATURE                 Location/Qualifiers
source                  1..160
                        mol_type = protein
                        organism = Bos indicus
SEQUENCE: 263
RCEKDERFFS DKIAKYIPIQ YVLSRYPSYG LNYYQQKPVA LINNQFLPYP YYAKPAAVRS    60
SAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                         160

SEQ ID NO: 264          moltype = AA  length = 160
FEATURE                 Location/Qualifiers
source                  1..160
                        mol_type = protein
                        organism = Bos indicus
SEQUENCE: 264
RCEKDERFFS DKIAKYIPIQ YVLSRYPSYG LNYYQQKPVA LINNQFLPYP YYAKPAAVRS    60
SAQILQWQVL SNTVPAKSCQ AQPTTMARHP HPHLSFMAIP PKKNQDKTEI PTINTIASGE   120
PTSTPTIEAV ESTVATLEAS PEVIESPPEI NTVQVTSTAV                         160

SEQ ID NO: 265          moltype = AA  length = 156
FEATURE                 Location/Qualifiers
source                  1..156
                        mol_type = protein
                        organism = Bos indicus
SEQUENCE: 265
DERFFSDKIA KYIPIQYVLS RYPSYGLNYY QQKPVALINN QFLPYPYYAK PAAVRSPAQI    60
LQWQVLSNTV PAKSCQAQPT TMARHPHPHL SFMAIPPKKN QDKTEIPTIN TIASGEPTST   120
PTIEAVESTV ATLEASPEVI ESPPEINTVQ VTSTAV                             156

SEQ ID NO: 266          moltype = AA  length = 194
FEATURE                 Location/Qualifiers
source                  1..194
                        mol_type = protein
                        organism = Bos grunniens
SEQUENCE: 266
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SSTVPAKSCQ AQPTTMARHP   120
HPHLSFMAIP PKKNQDKTEI PTINTIASGE PTSTPTTEAV ESTVATLEAS PEASPEVIES   180
PPEINTVQVT STAV                                                    194

SEQ ID NO: 267          moltype = AA  length = 190
FEATURE                 Location/Qualifiers
source                  1..190
                        mol_type = protein
                        organism = Bos grunniens
SEQUENCE: 267
MMKSFFLVVT ILALTLPFLG AQEQNQEQPI RCEKDERFFS DKIAKYIPIQ YVLSRYLSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE RTSTPTTEAV ESTVATLEAS PEVIESPPEI   180
NTVQVTSTAV                                                         190

SEQ ID NO: 268          moltype = AA  length = 160
FEATURE                 Location/Qualifiers
source                  1..160
                        mol_type = protein
                        organism = Bos grunniens
```

-continued

```
SEQUENCE: 268
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEVIESPPEI NTVQVTSTAV                         160

SEQ ID NO: 269          moltype = AA   length = 164
FEATURE                 Location/Qualifiers
source                  1..164
                        mol_type = protein
                        organism = Bos grunniens
SEQUENCE: 269
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEASPEVIES PPEINTVQVT STAV                    164

SEQ ID NO: 270          moltype = AA   length = 160
FEATURE                 Location/Qualifiers
source                  1..160
                        mol_type = protein
                        organism = Bos grunniens
SEQUENCE: 270
RCEKDERFFS DKIAKYIPIQ YVLSRYLSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEVIESPPEI NTVQVTSTAV                         160

SEQ ID NO: 271          moltype = AA   length = 190
FEATURE                 Location/Qualifiers
source                  1..190
                        mol_type = protein
                        organism = Bison bison
SEQUENCE: 271
MMKSFFLVVT ILALTLPFLG AQEQNQEQPI RCEKDERFFS DKIAKYIPIQ YVLSRYPSYG    60
LNAYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTTEAV ESTVATLEAS PEVIESPPEI   180
NTVQVTSTVV                                                          190

SEQ ID NO: 272          moltype = AA   length = 179
FEATURE                 Location/Qualifiers
source                  1..179
                        mol_type = protein
                        organism = Bison bison
SEQUENCE: 272
MMKSFFLVVT ILALTLPFLR CEKDERFFSD KIAKYIPIQY VLSRYPSYGL NAYQQKPVAL    60
INNQFLPYPY YAKPAAVRSP AQILQWQVLS NTVPAKSCQA QPTTMARHPH PHLSFMAIPP   120
KKNQDKTEIP TINTIASGEP TSTPTTEAVE STVATLEASP EVIESPPEIN TVQVTSTVV    179

SEQ ID NO: 273          moltype = AA   length = 190
FEATURE                 Location/Qualifiers
source                  1..190
                        mol_type = protein
                        organism = Bubalus bubalis
SEQUENCE: 273
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSVE PTSTPTTEAI ENTVATLEAS SEVIESVPET   180
NTAQVTSTVV                                                          190

SEQ ID NO: 274          moltype = AA   length = 190
FEATURE                 Location/Qualifiers
source                  1..190
                        mol_type = protein
                        organism = Bubalus bubalis
SEQUENCE: 274
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSVE PTSTPITEAI ENTVATLEAS SEVIESVPET   180
NTAQVTSTVV                                                          190

SEQ ID NO: 275          moltype = AA   length = 190
FEATURE                 Location/Qualifiers
source                  1..190
                        mol_type = protein
                        organism = Bubalus bubalis
SEQUENCE: 275
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSIE PTSTPTTEAI ENTVATLEAS SEVIESVPET   180
NTAQVTSTVV                                                          190
```

```
SEQ ID NO: 276            moltype = AA   length = 190
FEATURE                   Location/Qualifiers
source                    1..190
                          mol_type = protein
                          organism = Bubalus bubalis
SEQUENCE: 276
MMKSFFLVVT ILALTLPFLG AQEQNQEQPI RCEKEERFFN DKIAKYIPIQ YVLSRYPSYG   60
LNYYQQKPVA LINNQFLPYP YYAKPAAVRS PAQILQWQVL PNTVPAKSCQ AQPTTMTRHP  120
HPHLSFMAIP PKKNQDKTEI PTINTIVSIE PTSTPTTEAI ENTVATLEAS SDVIESVPET  180
NTAQVTSTVV                                                        190

SEQ ID NO: 277            moltype = AA   length = 190
FEATURE                   Location/Qualifiers
source                    1..190
                          mol_type = protein
                          organism = Bubalus bubalis
SEQUENCE: 277
MMKSFFLVVT ILALTLPFLG AQEQNQEQPI RCEKEERFFN DKIAKYIPIQ YVLSRYPSYG   60
LNYYQQKPVA LINNQFLPYP YYAKPAAVRS PAQILQWQVL PNTVPAKSCQ AQPTTMTRHP  120
HPHLSFMAIP PKKNQDKTEI PTINTIVSVE PTSTPTTEAI ENTVATLEAS SDVIESVPET  180
NTAQVTSTVV                                                        190

SEQ ID NO: 278            moltype = AA   length = 190
FEATURE                   Location/Qualifiers
source                    1..190
                          mol_type = protein
                          organism = Bubalus bubalis
SEQUENCE: 278
MMKSFFLVVT ILALTLPFLG AQEQNQEQLI RCEKEERFFN DKIAKYIPIQ YVLSRYPSYG   60
LNYYQQKPVA LINNQFLPYP YYAKPAAVRS PAQILQWQVL PNTVPAKSCQ AQPTTMTRHP  120
HPHLSFMAIP PKKNQDKTEI PTINTIVSVE PTSTPTTEAI ENTVATLEAS SDVIESVPET  180
NTAQVTSTVV                                                        190

SEQ ID NO: 279            moltype = AA   length = 192
FEATURE                   Location/Qualifiers
source                    1..192
                          mol_type = protein
                          organism = Oreamnos americanus
SEQUENCE: 279
MMKSFFLVVT ILALTLPFLG AQEQNQEQPI CCEKDERFFD DKIAKYIPIQ YVLSRYPSYG   60
LNYYQQRPVA LINNQFLPYP YYAKPVAVRS PAQILQWQVL PNTAPAKSCQ DQPTTMARHP  120
HPHLSFMAIP PKKDQDKTEI PTINTIASAE PTVHSTPTTE AIVNTVDNPE ASSESIVSAP  180
ETNTAQVTST EV                                                     192

SEQ ID NO: 280            moltype = AA   length = 192
FEATURE                   Location/Qualifiers
source                    1..192
                          mol_type = protein
                          organism = Capricornis swinhoei
SEQUENCE: 280
MMKSFFLVVT ILALTLPFLG AQEQNQEQPI CCEKDERFFD DKIAKYIPIQ YVLSRYPSYG   60
LNYYQQRPVA LINNQFLPYP YYAKPVAVRS PAQTLQWQVL PNTAPAKSCQ DQPTTMARHP  120
HPHLSFMAIP PKKDQDKTEI PTINTIASAE TTVHSTPTTE AIVNTVDNRE ASSESIVSAP  180
ETNTAQVTST EV                                                     192

SEQ ID NO: 281            moltype = AA   length = 192
FEATURE                   Location/Qualifiers
source                    1..192
                          mol_type = protein
                          organism = Naemorhedus goral
SEQUENCE: 281
MMKSFFLVVT ILALTLPFLG AQEQNQEQPI CCEKDERFFD DKIAKYIPIQ YVLSRYPSYG   60
LNYYQQRPVA LINNQFLPYP YYAKPVAVRS PAQTLQWQVL PNTAPAKSCQ DQPTTMARHP  120
HPHLSFMAIP PKKDQDKTEI PTINTIASAE PTVHSTPTTE AIVNTVDNPE ASSESIASAP  180
ETNTAQVTST EV                                                     192

SEQ ID NO: 282            moltype = AA   length = 192
FEATURE                   Location/Qualifiers
source                    1..192
                          mol_type = protein
                          organism = Capricornis sumatraensis
SEQUENCE: 282
MMKSFFLVVT ILALTLPFLG AQEQNQEQPI CCEKDERFFD DKIAKYIPIQ YVLSRYPSYG   60
LNYYQQRPVA LINNQFLPYP YYAKPVAVRS PAQTLQWQVL PNTAPAKSCQ DQPTTMARHP  120
HPHLSFMAIP PKKDQDKTEI PTINTIASAE PTVHSTPTTE AIVNTVDNPE ASSESIVSAP  180
ETNTAQVTST EV                                                     192

SEQ ID NO: 283            moltype = AA   length = 192
FEATURE                   Location/Qualifiers
```

```
source                  1..192
                        mol_type = protein
                        organism = Capricornis crispus
SEQUENCE: 283
MMKSFFLAVT ILALTLPFLG AQEQNQEQPI CCEKDETFFD DKIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKQDKTEI  PTINTIASAE PTVHSTPTTE AIVNTVDNPE ASSESIVSAP   180
ETNTAQVTST EV                                                      192

SEQ ID NO: 284          moltype = AA   length = 192
FEATURE                 Location/Qualifiers
source                  1..192
                        mol_type = protein
                        organism = Capricornis crispus
SEQUENCE: 284
MMKSFFLVVT ILALTLPFLG AQEQNQEQPI CCEKDETFFD DKIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKQDKTEI  PTINTIASAE PTVHSTPTTE AIVNTVDNPE ASSESIVSAP   180
ETNTAQVTST EV                                                      192

SEQ ID NO: 285          moltype = AA   length = 202
FEATURE                 Location/Qualifiers
source                  1..202
                        mol_type = protein
                        organism = Saiga tatarica
SEQUENCE: 285
MMKSFFLVVT ILALTLPFLD AQERNQEQPI CCEKDERFFN DRIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKQDKTEI  PTINTVASAE PASTPTTEAI VNTEAIVNTE AIVNTVDNPE   180
ASSEIIASVP ETNTAQVTST EV                                           202

SEQ ID NO: 286          moltype = AA   length = 160
FEATURE                 Location/Qualifiers
REGION                  1..160
                        note = Bos indicus x Bos taurus
source                  1..160
                        mol_type = protein
                        organism = unidentified
SEQUENCE: 286
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                         160

SEQ ID NO: 287          moltype = AA   length = 160
FEATURE                 Location/Qualifiers
REGION                  1..160
                        note = Bos indicus x Bos taurus
source                  1..160
                        mol_type = protein
                        organism = unidentified
SEQUENCE: 287
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLAFMAIP PKKNQDKTEI PTINTIASGE   120
PTSTPTTEAV ESTVATLEDS PEVIESPPEI NTVQVTSTAV                         160

SEQ ID NO: 288          moltype = AA   length = 192
FEATURE                 Location/Qualifiers
source                  1..192
                        mol_type = protein
                        organism = Capra hircus
SEQUENCE: 288
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKQDKTEV PAINTIASAE PTVHSTPTTE AIVNTVDNPE ASSESIASAS   180
ETNTAQVTST EV                                                      192

SEQ ID NO: 289          moltype = AA   length = 192
FEATURE                 Location/Qualifiers
source                  1..192
                        mol_type = protein
                        organism = Capra hircus
SEQUENCE: 289
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKQDKTEI PAINTIASAE PTVHSTPTTE AIVNTVDNPE ASSESIASAS   180
ETNTAQVTST EV                                                      192

SEQ ID NO: 290          moltype = AA   length = 192
FEATURE                 Location/Qualifiers
```

```
source                        1..192
                              mol_type = protein
                              organism = Capra hircus
SEQUENCE: 290
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKDQDKTEI PAINTIASAE PTVHSTPITE AIVNTVDNPE ASSESIASAS   180
ETNTAQVTST EV                                                      192

SEQ ID NO: 291                moltype = AA  length = 192
FEATURE                       Location/Qualifiers
source                        1..192
                              mol_type = protein
                              organism = Capra hircus
SEQUENCE: 291
MMKSFFLVVT ILALTLPFLG AQEQNQEQPI CCEKDERFFD DKIAKYIPIQ YVLSRYPSYG    60
LNYYRQRPVA LINNQFLPYP YYAKPIAVRS PAQTLQWQVL PNTVPAKSCQ DQPTTLARHP   120
HPHLSFMAIP PKKDQDKTEI PAINTIASAE PTVHSTPTTE AIVNTVDNPE ASSESIASAP   180
ETNTAQVTST EV                                                      192

SEQ ID NO: 292                moltype = AA  length = 161
FEATURE                       Location/Qualifiers
source                        1..161
                              mol_type = protein
                              organism = Capra hircus
SEQUENCE: 292
CEKDERFFDD KIAKYIPIQY VLSRYPSYGL NYYQQRPVAL INNQFLPYPY YAKPIAVRSP    60
AQTLQWQVLP NTVPAKSCQD QPTTLARHPH PHLSFMAIPP KKDQDKTEIP AINTIASAEP   120
TVHSTPTTEA IVNTVDNPEA SSESIASAPE TNTAQVTSTE V                      161

SEQ ID NO: 293                moltype = AA  length = 161
FEATURE                       Location/Qualifiers
source                        1..161
                              mol_type = protein
                              organism = Capra hircus
SEQUENCE: 293
CEKDERFFDD KIAKYIPIQY VLSRYPSYGL NYYQQRPVAL INNQFLPYPY YAKPIAVRSP    60
AQTLQWQVLP NTVPAKSCQD QPTTLARHPH PHLSFMAIPP KKDQDKTEIP AINTIASAEP   120
TVHSTPTTEA IVNTVDNPEA SSESIVSAPE TNTAQVTSTE V                      161

SEQ ID NO: 294                moltype = AA  length = 162
FEATURE                       Location/Qualifiers
source                        1..162
                              mol_type = protein
                              organism = Capra hircus
SEQUENCE: 294
CCEKDERFFD DKIAKYIPIQ YVLSRYPSYG LNYYQQRPVA LINNQFLPYP YYAKPVAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAP ETNTAQVTST EV                     162

SEQ ID NO: 295                moltype = AA  length = 162
FEATURE                       Location/Qualifiers
source                        1..162
                              mol_type = protein
                              organism = Capra hircus
SEQUENCE: 295
CCEKDERFFD DKIAKYIPIQ YVLSRYPSYG LNYYQQRPVA LINNQFLPYP YYAKPVAVRS    60
PAQTLQWQVL PNTVPAKSCQ GQPTTLARHP HPHLSFMAIP PKKDQDKTEI PAINTIASAE   120
PTVHSTPTTE AIVNTVDNPE ASSESIASAS ETNTAQVTST EV                     162

SEQ ID NO: 296                moltype = AA  length = 162
FEATURE                       Location/Qualifiers
source                        1..162
                              mol_type = protein
                              organism = Capra hircus
SEQUENCE: 296
CCEKDERFFD DKIAKYIPIQ YVLSRYPSYG LNYYQQRPVA LINNQFLPYP YYAKPVAVRS    60
PAQTLQWQVL PNTVPAKSCQ NQPTTLARHP HPHLSFMAIP PKKDQDKTEI PAINTIASAE   120
PTVHSTPTTE AIVNTADNPE ASSESIASAP ETNTAQVTST EV                     162

SEQ ID NO: 297                moltype = AA  length = 161
FEATURE                       Location/Qualifiers
source                        1..161
                              mol_type = protein
                              organism = Capra hircus
SEQUENCE: 297
CEKDERFFDD KIAKYIPIQY VLSRYPSYGL NYYQQRPVAL INNQFLPYPY YAKPVAVRSP    60
AQTLQWQVLP NTVPAKSCQD QPTTLARHPH PHLSFMAIPP KKDQDKTEVP AINTIASAEP   120
TVHSTPTTEA IVNTVDNPEA SSESIASASE TNTAQVTSTE V                      161
```

```
SEQ ID NO: 298            moltype = AA   length = 162
FEATURE                   Location/Qualifiers
source                    1..162
                          mol_type = protein
                          organism = Capra hircus
SEQUENCE: 298
CCEKDERFFD DKIAKYIPIQ YVLSRYPSYG LNYYQQRPVA LINNQFLPYP YYAKPIAVRS   60
PAQTLQWQVL PNTVPAKSCQ DQPTTLARHP HPHLSFMAIP PKKDQDKTEI PAINTIASAE  120
PTVHSTPTTE AIVNTVDNPE ASSESIASAP ETNTAQVTST EV                    162

SEQ ID NO: 299            moltype = AA   length = 162
FEATURE                   Location/Qualifiers
source                    1..162
                          mol_type = protein
                          organism = Capra hircus
SEQUENCE: 299
CCEKDERFFD DKIAKYIPIQ YVLSRYPSYG LNYYQQRPVA LINNQFLPYP YYAKPIAVRS   60
PAQTLQWQVL PNTVPAKSCQ DQPTTLARHP HPHLSFMAIP PKKDQDKTEI PAINTIASAE  120
PTVHSTPTTE AIVNTVDNPE ASSESIVSAP ETNTAQVTST EV                    162

SEQ ID NO: 300            moltype = AA   length = 161
FEATURE                   Location/Qualifiers
source                    1..161
                          mol_type = protein
                          organism = Capra hircus
SEQUENCE: 300
CEKDERFFDD KIAKYIPIQY VLSRYPSYGL NYYQQRPVAL INNQFLPYPY YAKPVAVRSP   60
AQTLQWQVLP NTVPAKSCQD QPTTLARHPH PHLSFMAIPP KKDQDKTEIP AINTIASAEP  120
TVHSTPTTEA IVNTVDNPEA SSESIASASE TNTAQVTSTE V                     161

SEQ ID NO: 301            moltype = AA   length = 162
FEATURE                   Location/Qualifiers
source                    1..162
                          mol_type = protein
                          organism = Capra hircus
SEQUENCE: 301
CCEKDERFFD DKIAKYIPIQ YVLSRYPSYG LNYYQQRPVA LINNQFLPYP YYAKPVAVRS   60
PAQTLQWQVL PNTVPAKSCQ DQPTTLARHP HPHLSFMAIP PKKDQDKTEV PAINTIASAE  120
PTVHSTPTTE AIVNTVDNPE ASSESIASAS ETNTAQVTST EV                    162

SEQ ID NO: 302            moltype = AA   length = 162
FEATURE                   Location/Qualifiers
source                    1..162
                          mol_type = protein
                          organism = Capra hircus
SEQUENCE: 302
CCEKDERFFD DKIAKYIPIQ YVLSRYPSYG LNYYQQRPVA LINNQFLPYP YYAKPVAVRS   60
PAQTLQWQVL PNTVPAKSCQ DQPTTLARHP HPHLSFMAIP PKKDQDKTEI PAINTIASAE  120
PTVHSTPTTE AIVNTVDNPE ASSESIASAS ETNTAQVTST EV                    162

SEQ ID NO: 303            moltype = AA   length = 159
FEATURE                   Location/Qualifiers
source                    1..159
                          mol_type = protein
                          organism = Capra hircus
SEQUENCE: 303
CCEKDERFFD DKIAKYIPIQ YVLSRYPSYG LNYYQQRPVA LINNQFLPYP YYAKPVAVRS   60
PAQTLQWQVL PNTVPAKSCQ DQPTTLARHP HPHLSFMAIP PKKDQDKTEI PAINTIASAE  120
PTVHSTPTTE AIVNTVDNPE ASSESIASAS ETNTAQVTS                        159

SEQ ID NO: 304            moltype = AA   length = 159
FEATURE                   Location/Qualifiers
source                    1..159
                          mol_type = protein
                          organism = Capra hircus
SEQUENCE: 304
CCEKDERFFD DKIAKYIPIQ YVLSRYPSYG LNYYQQRPVA LINNQFLPYP YYAKPVAVRS   60
PAQTLQWQVL PNTVPAKSCQ DQPTTLARHP HPHLSFMAIP PKKDQDKTEV PAINTIASAE  120
PTVHSTPTTE AIVNTVDNPE ASSESIASAS ETNTAQVTS                        159

SEQ ID NO: 305            moltype = AA   length = 141
FEATURE                   Location/Qualifiers
VARIANT                   110
                          note = X can be any naturally occurring amino acid
source                    1..141
                          mol_type = protein
                          organism = Capra hircus
SEQUENCE: 305
```

```
CCEKDERFFD DKIAKYIPIQ YVLSRYPSYG LNYYQQRPVA LINNQFLPYP YYAKPVAVRS      60
PAQTLQWQVL PNTVPAKSCQ DQPTTLARHP HPHLSFMAIP PKKDQDKTEX PAINTIASAE    120
PTVHSTPTTE AIVNTVDNPE A                                              141

SEQ ID NO: 306          moltype = AA   length = 162
FEATURE                 Location/Qualifiers
source                  1..162
                        mol_type = protein
                        organism = Capra hircus
SEQUENCE: 306
CCEKDERFFD DKIAKYIPIQ YVLSRYPSYG LNYYQQRPVA LINNQFLPYP YYAKPIAVRS     60
PAQTLQWQVL PNTVPAKSCQ DQPTTLARHP HPHLSFMAIP PKKDQDKTEI PAINTIASAE    120
PTVHSTPTTE AIVNTVDNPE ASSESIASAS ETNTAQVTST EV                       162

SEQ ID NO: 307          moltype = AA   length = 161
FEATURE                 Location/Qualifiers
source                  1..161
                        mol_type = protein
                        organism = Capra hircus
SEQUENCE: 307
CEKDERFFDD KIAKYIPIQY VLSRYPSYGL NYYRQRPVAL INNQFLPYPY YAKPIAVRSP     60
AQTLQWQVLP NTVPAKSCQD QPTTLARHPH PHLSFMAIPP KKDQDKTEIP AINTIASAEP    120
TVHSTPTTEA IVNTVDNPEA SSESIASAPE TNTAQVTSTE V                        161

SEQ ID NO: 308          moltype = AA   length = 162
FEATURE                 Location/Qualifiers
source                  1..162
                        mol_type = protein
                        organism = Capra hircus
SEQUENCE: 308
CCEKDERFFD DKIAKYIPIQ YVLSRYPSYG LNYYRQRPVA LINNQFLPYP YYAKPIAVRS     60
PAQTLQWQVL PNTVPAKSCQ DQPTTLARHP HPHLSFMAIP PKKDQDKTEI PAINTIASAE    120
PTVHSTPTTE AIVNTVDNPE ASSESIASAP ETNTAQVTST EV                       162

SEQ ID NO: 309          moltype = AA   length = 162
FEATURE                 Location/Qualifiers
source                  1..162
                        mol_type = protein
                        organism = Capra hircus
SEQUENCE: 309
CCEKDERFFD DKIAKYIPIQ YVLSRYPSYG LNYYRQRPVA LINNQFLPYP YYAKPVAVRS     60
PAQTLQWQVL PNTVPAKSCQ DQPTTLARHP HPHLSFMAIP PKKDQDKTEI PAINTIASAE    120
PTVHSTPTTE AIVNTVDNPE ASSESIASAS ETNTAQVTST EV                       162

SEQ ID NO: 310          moltype = AA   length = 162
FEATURE                 Location/Qualifiers
source                  1..162
                        mol_type = protein
                        organism = Capra hircus
SEQUENCE: 310
CCEKDERFFD DKIAKYIPIQ YVLSRYPSYG LNYYQQRPVA LINSQFLPYP YYAKPVAVRS     60
PAQTLQWQVL PNTVPAKSCQ DQPTTLARHP HPHLSFMAIP PKKDQDKTEI PAINTIASAE    120
PTVHSTPTTE AIVNTVDNPE ASSESIASAS ETNTAQVTST EV                       162

SEQ ID NO: 311          moltype = AA   length = 190
FEATURE                 Location/Qualifiers
source                  1..190
                        mol_type = protein
                        organism = Odocoileus virginianus
SEQUENCE: 311
MMKSFSLVVT ILALTLPFLV AQEQNQEQPT GCEKDERFFN DKIVKYIPIQ YVLSRYPSYG     60
LSYYQHRPVA LINNQFLPYP YYAKPGAVRS PAQILQWQVL PNTVPAKSCQ AQPTTLARHP    120
HPRLSFMAIP PKKNQDKTDI PTINTIATVE STITPTTEAI VDTVATPEAS SEVIESAPET    180
KTDQVTSTVV                                                           190

SEQ ID NO: 312          moltype = AA   length = 192
FEATURE                 Location/Qualifiers
source                  1..192
                        mol_type = protein
                        organism = Rupicapra rupicapra
SEQUENCE: 312
MMKSFFLVAT ILALTLPFLG AQEQNQEQSI CCEKDERFFE DKIAKYIPIQ YVLSRYPSYG     60
LNYYQQRPVA LINNQFLPYP YYAKPVAVRS PAQTLQWQVL PNTAPAKSCQ DQPTTMAHHP    120
HPHLSFMAIP PKKDQDKTEI PTINTIASAE PTVHSTPTTE AIVNTVDNPE ASSESIASAP    180
ETNTAQVTST EV                                                        192

SEQ ID NO: 313          moltype = AA   length = 192
FEATURE                 Location/Qualifiers
source                  1..192
```

```
                              mol_type = protein
                              organism = Ovis aries
SEQUENCE: 313
MMKSFFLVVT ILALTLPFLG AQEQNQEQRI CCEKDERFFD DKIAKYIPIQ YVLSRYPSYG     60
LNYYQQRPVA LINNQFLPYP YYAKPVAVRS PAQTLQWQVL PNAVPAKSCQ DQPTAMARHP    120
HPHLSFMAIP PKKDQDKTEI PAINTIASAE PTVHSTPTTE AVVNAVDNPE ASSESIASAP    180
ETNTAQVTST EV                                                       192

SEQ ID NO: 314               moltype = AA   length = 162
FEATURE                      Location/Qualifiers
source                       1..162
                             mol_type = protein
                             organism = Ovis aries
SEQUENCE: 314
CCEKDERFFD DKIAKYIPIQ YVLSRYPSYG LNYYQQRPVA LINNQFLPYP YYAKPVAVRS     60
PAQTLQWQVL PNAVPAKSCQ DQPTAMARHP HPHLSFMAIP PKKDQDKTEI PAINTIASAE    120
PTVHSTPTTE AVVNAVDNPE ASSESIASAP ETNTAQVTST EV                       162

SEQ ID NO: 315               moltype = AA   length = 190
FEATURE                      Location/Qualifiers
source                       1..190
                             mol_type = protein
                             organism = Cervus nippon
SEQUENCE: 315
MMKSFFLAVT ILALTLPFLV AQEQIQEQPT GCEKDERFFN DKIVKYIPIQ YALSRYPSYG     60
LNYYQHRPVA LINNQFLPYP YYVKPGAVRS PAQILQWQVL PNTVPAKFCQ AQPTTMARHP    120
HPRLSFMAIP PKKNQDKTDI PSINTIATAE STITPTTEAI VDTVATQEAF SEVIESAPEA    180
KTDQVTSTVV                                                           190

SEQ ID NO: 316               moltype = AA   length = 178
FEATURE                      Location/Qualifiers
VARIANT                      178
                             note = X can be any naturally occurring amino acid
source                       1..178
                             mol_type = protein
                             organism = Gazella arabica
SEQUENCE: 316
CCEKDERFFN DKIAKYIPIQ YVLSRYPSYG LNYYQQRPVA LINNQFLPYP YYAKPVAVRS     60
PAQTLQWQVL PNTVPAKSCQ DQPTTMARHP HPHLSFMAIP PKKDQDKTEI PTINTIASAE    120
PASTPTTEAI VNTEAVVNTE AIVNTEAIVN TVDNPEASSE IIASVPETNT AQVTSTEX      178

SEQ ID NO: 317               moltype = AA   length = 170
FEATURE                      Location/Qualifiers
source                       1..170
                             mol_type = protein
                             organism = Muntiacus muntjak
SEQUENCE: 317
AQELNQEQPT GCEKDERFFN DKIVKYIPIQ YALSRYPSYG LNYYQHRPVA LISNQFLPYP     60
YYAKPGAVRS PAQTLQWQAL PNTVPATSCQ AQPATMARHP HPRLSFMAIP PKKTQDKTDH    120
PTFNTIATAE STATPTTEAV VDTVATQEAS SEVTASAPEA NTDQVTSTAV                170

SEQ ID NO: 318               moltype = AA   length = 170
FEATURE                      Location/Qualifiers
source                       1..170
                             mol_type = protein
                             organism = Muntiacus reevesi
SEQUENCE: 318
AQELNQEQPT GCEKDERFFN DKIVKYIPIQ YALSRYPSYG LNYYQHRPVA LISNQFLPYP     60
YYAKPGAVRS PAQILQWQAL PNTVPATSCQ AQPATVARHP HPRLSFMAIP PKKSQDKTDH    120
PTINTIATVE STATPTTEAV VDTAATQEAS PEVIASAPEA STDQVTSTAV                170

SEQ ID NO: 319               moltype = AA   length = 172
FEATURE                      Location/Qualifiers
VARIANT                      136
                             note = X can be any naturally occurring amino acid
VARIANT                      151
                             note = X can be any naturally occurring amino acid
VARIANT                      154
                             note = X can be any naturally occurring amino acid
VARIANT                      161
                             note = X can be any naturally occurring amino acid
VARIANT                      168
                             note = X can be any naturally occurring amino acid
source                       1..172
                             mol_type = protein
                             organism = Gazella dorcas
SEQUENCE: 319
CCEKDERFFN DKIAKYIPIQ YVLSRYPSYG LNYYQQRPVA LINNQFLPYP YYAKPVAVRS     60
PAQTLQWQVL PNTVPAKSCQ DQPTTMARHP HPHLSFMAIP PKKDQDKTEI PTINTIASAE    120
```

```
PASTPTTEAI VNTEPXVNTE PIVNTVDNPE XSSXIIASVP XTNTAQVXST EV            172

SEQ ID NO: 320              moltype = AA  length = 160
FEATURE                     Location/Qualifiers
source                      1..160
                            mol_type = protein
                            organism = Procapra gutturosa
SEQUENCE: 320
CCEKDERFFN DKIAKYIPIQ YVMSRYPSYG LNYYQQRPVA LINNQFLPYP YYAKPVAVRS    60
PAQTLQWQVL PNTVPAKSCQ DQPTTMARHP HPHLSFMAIP PKKDQDKTEI PTINTIASAE    120
PTSTPTTEAI VNTVDNPEAT SEIIASVPET NTAQVTSTEV                          160

SEQ ID NO: 321              moltype = AA  length = 160
FEATURE                     Location/Qualifiers
VARIANT                     111
                            note = X can be any naturally occurring amino acid
VARIANT                     121
                            note = X can be any naturally occurring amino acid
VARIANT                     125
                            note = X can be any naturally occurring amino acid
VARIANT                     139
                            note = X can be any naturally occurring amino acid
source                      1..160
                            mol_type = protein
                            organism = Procapra gutturosa
SEQUENCE: 321
CCEKDERFFN DKIAKYIPIQ YVMSRYPSYG LNYYQQRPVA LINNQFLPYP YYAKPVAVRS    60
PAQTLQWQVL PNTVPAKSCQ DQPTTMARHP HPHLSFMAIP PKKDQDKTEI XTINTIASAE    120
XTSTXTTEAI VNTVDNPEXT SEIIASVPET NTAQVTSTEV                          160

SEQ ID NO: 322              moltype = AA  length = 160
FEATURE                     Location/Qualifiers
source                      1..160
                            mol_type = protein
                            organism = Madoqua saltiana
SEQUENCE: 322
CCEKDERFFN DKIAKYIPIQ YVLSRYPSYG LNYYQQRPVA LINNQFLPYP YFAKPVAVRS    60
PAQTLQWQVL PNTVPAKSCQ DQPTTMARHP HPHLSFMAIP PKKDQDKPEI PTINTIASAE    120
LTSTPTTEAI VNTVDNPEAS SEIIASVPET NTAEVTSTEV                          160

SEQ ID NO: 323              moltype = AA  length = 155
FEATURE                     Location/Qualifiers
VARIANT                     138
                            note = X can be any naturally occurring amino acid
source                      1..155
                            mol_type = protein
                            organism = Ammotragus lervia
SEQUENCE: 323
CCEKDERFFD DKIAKYIPIQ YVLSRYPSYG LNYYQQRPVA LINNQFLPYP YYAKPVAVRS    60
PAQTLQWQVL PNTAPAKSCQ DQPTTMARHP HPHLSFMAIP PKKDQDKTEI PAINTIASVE    120
PTVHSTPTAE AIVNTVDXPE ASSESIASAP ETNTA                               155

SEQ ID NO: 324              moltype = AA  length = 155
FEATURE                     Location/Qualifiers
source                      1..155
                            mol_type = protein
                            organism = Ammotragus lervia
SEQUENCE: 324
CCEKDERFFD DKIAKYIPIQ YVLSRYPSYG LNYYQQRPVA LINNQFLPYP YYAKPVAVRS    60
PAQTLQWQVL PNTAPAKSCQ DQPTTMARHP HPHLSFMAIP PKKDQDKTEI PAINTIASVE    120
PTVHSTPTAE AIVNTVDSPE ASSESIASAP ETNTA                               155

SEQ ID NO: 325              moltype = AA  length = 155
FEATURE                     Location/Qualifiers
source                      1..155
                            mol_type = protein
                            organism = Ammotragus lervia
SEQUENCE: 325
CCEKDERFFD DKIAKYIPIQ YVLSRYPSYG LNYYQQRPVA LINNQFLPYP YYAKPVAVRS    60
PAQTLQWQVL PNTAPAKSCQ DQPTTMARHP HPHLSFMAIP PKKDQDKTEI PAINTIASVE    120
PTVHSTPTAE AIVNTVDNPE ASSESIASAP ETNTA                               155

SEQ ID NO: 326              moltype = AA  length = 162
FEATURE                     Location/Qualifiers
source                      1..162
                            mol_type = protein
                            organism = Capra sibirica
SEQUENCE: 326
CCEKDERFFD DKIAKYIPIQ YVLSRYPSYG LNYYQQRPVA LINNQFLPYP YYAKPVAVRS    60
```

```
PAQTLQWQVL PNTVPAKSCQ DQPTTLARHP HPHLSFMAIP PKKDQDKTEV PAINTIASAE    120
PTVHSTPTTE AIVNTVDNPE ASSESIASAS ETNTGQVTST EV                      162

SEQ ID NO: 327              moltype = AA  length = 162
FEATURE                     Location/Qualifiers
source                      1..162
                            mol_type = protein
                            organism = Ovis canadensis
SEQUENCE: 327
CCEKDERFFD DKIAKYIPIQ YVLSRYPSYG LNYYQQRPVA LINNQFLPYP YYAKPVAVRS    60
PAQTLQWQVL PNTVPAKSCQ DQPTTMAHHP HPHLSFMAIP PKKDQDKTEI PAINTIASVE    120
PTVHSTPTTE AVVNTVDNPE ASSESIASAP ETNAAQVTTT EV                       162

SEQ ID NO: 328              moltype = AA  length = 162
FEATURE                     Location/Qualifiers
VARIANT                     155..156
                            note = X can be any naturally occurring amino acid
source                      1..162
                            mol_type = protein
                            organism = Ovis canadensis
SEQUENCE: 328
CCEKDERFFD DKIAKYIPIQ YVLSRYPSYG LNYYQQRPVA LINNQFLPYP YYAKPVAVRS    60
PAQTLQWQVL PNTVPAKSCQ DQPTTMAHHP HPHLSFMAIP PKKDQDKTEI PAINTIASVE    120
PTVHSTPTTE AVVNTVDNPE ASSESIASAP ETNAXXVTTT EV                       162

SEQ ID NO: 329              moltype = AA  length = 178
FEATURE                     Location/Qualifiers
source                      1..178
                            mol_type = protein
                            organism = Gazella subgutturosa
SEQUENCE: 329
CCEKNERFFN DKIAKYIPIQ YVLSRYPSYG LNYYQQRPVA LINNQFLPYP YYVKPVAVRS    60
PAQTLQWQVL PNTVPAKSCQ DQPTTMARHP HPHLSFMAIP PKKDQDKTEI PTINTIASAE    120
PASTPTTEAI VNTEAVVNTE AIVNTEAIVN TVDNPEASSE IIASVPETNT AQVTSTEV      178

SEQ ID NO: 330              moltype = AA  length = 172
FEATURE                     Location/Qualifiers
VARIANT                     33
                            note = X can be any naturally occurring amino acid
VARIANT                     135
                            note = X can be any naturally occurring amino acid
source                      1..172
                            mol_type = protein
                            organism = Antilope cervicapra
SEQUENCE: 330
GCEKDERFFN DKIAKYIPIQ YVLSRYPSYG LNXYQQRPVA LINNQFLPYP YYVKPVAVRS    60
PAQTLQWQVL PNTVPAKSCQ DQPTTMARHP HPHLSFMAIP PKKDQDKTEI PTINTIASAE    120
PASTPTTEAI VNTEXIVNTE PIVNTVDNPE ASSEIIASVP ETNTAQVTST EV            172

SEQ ID NO: 331              moltype = AA  length = 162
FEATURE                     Location/Qualifiers
source                      1..162
                            mol_type = protein
                            organism = Capra ibex
SEQUENCE: 331
CCEKDERFFD DKIAKYIPIQ YVLNRYPTYG LNYYQQRPVA LINNQFLPYP YYAKPVAVRS    60
PAQTLQWQVL PNTVPAKSCQ DQPTTLARHP HPHLSFMAIP PKKDQDKTEI PAINTIASAE    120
PTVHSTPTTE AIVNTVDNPE ASSESIASAP ETNAQVTST EV                        162

SEQ ID NO: 332              moltype = AA  length = 162
FEATURE                     Location/Qualifiers
source                      1..162
                            mol_type = protein
                            organism = Ovis vignei
SEQUENCE: 332
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE    120
PTVHSTPTTE AVVNAVDNPE ASSESIASAP ETNAQVTST ES                        162

SEQ ID NO: 333              moltype = AA  length = 162
FEATURE                     Location/Qualifiers
VARIANT                     73
                            note = X can be any naturally occurring amino acid
VARIANT                     162
                            note = X can be any naturally occurring amino acid
source                      1..162
                            mol_type = protein
                            organism = Ovis vignei
SEQUENCE: 333
```

```
CCEKDERFFD DKIAKYIPIQ YVLSRYPSYG LNYYQQRPVA LINNQFLPYP YYAKPVAVRS    60
PAQTLQWQVL PNXVPAKSCQ DQPTAMARHP HPHLSFMAIP PKKDQDKTEI PAINTIASAE   120
PTVHSTPTTE AVVNAVDNPE ASSESIASAP ETNTAQVTST EX                      162

SEQ ID NO: 334          moltype = AA  length = 162
FEATURE                 Location/Qualifiers
VARIANT                 156
                        note = X can be any naturally occurring amino acid
source                  1..162
                        mol_type = protein
                        organism = Ovis ammon
SEQUENCE: 334
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE   120
PTVHSTPTTE AVVNAVDNPE ASSESIASAP ETNTAXVTST EV                      162

SEQ ID NO: 335          moltype = AA  length = 162
FEATURE                 Location/Qualifiers
VARIANT                 112
                        note = X can be any naturally occurring amino acid
source                  1..162
                        mol_type = protein
                        organism = Ovis vignei
SEQUENCE: 335
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PXINTIASAE   120
PTVHSTPTTE AVVNAVDNPE ASSESIASAP ETNTAQVTST EV                      162

SEQ ID NO: 336          moltype = AA  length = 162
FEATURE                 Location/Qualifiers
source                  1..162
                        mol_type = protein
                        organism = Ovis orientalis
SEQUENCE: 336
CCEKDERFFD DKIAKYIPIQ YVLSRYPSYG LNYYQQRPVA LINNQFLPYP YYAKPVAVRS    60
PAQTLQWQVL PNTVPAKSCQ DQPTAMARHP HPHLSFMAIP PKKDQDKTEI PAINTIASAE   120
PTVHSTPTTE AVVNAVDNPE ASSESIASAP ETNTAQVTST EV                      162

SEQ ID NO: 337          moltype = AA  length = 162
FEATURE                 Location/Qualifiers
source                  1..162
                        mol_type = protein
                        organism = Ovis orientalis
SEQUENCE: 337
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE   120
PTVHSTPTTE AVVNAVDNPE ASSESIASAP ETNTAQITST EV                      162

SEQ ID NO: 338          moltype = AA  length = 162
FEATURE                 Location/Qualifiers
REGION                  1..162
                        note = Ovis orientalis x vignei
VARIANT                 107
                        note = X can be any naturally occurring amino acid
source                  1..162
                        mol_type = protein
                        organism = unidentified
SEQUENCE: 338
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDXTEI PAINTIASAE   120
PTVHSTPTTE AVVNAVDNPE ASSESIASAP ETNTAQVTST EV                      162

SEQ ID NO: 339          moltype = AA  length = 162
FEATURE                 Location/Qualifiers
VARIANT                 154
                        note = X can be any naturally occurring amino acid
source                  1..162
                        mol_type = protein
                        organism = Ovis vignei
SEQUENCE: 339
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE   120
PTVHSTPTTE AVVNAVDNPE ASSESIASAP ETNXAQVTST EV                      162

SEQ ID NO: 340          moltype = AA  length = 162
FEATURE                 Location/Qualifiers
VARIANT                 73
                        note = X can be any naturally occurring amino acid
source                  1..162
```

```
                        mol_type = protein
                        organism = Ovis ammon
SEQUENCE: 340
CCEKDERFFD DKIAKYIPIQ YVLSRYPSYG LNYYQQRPVA LINNQFLPYP YYAKPVAVRS    60
PAQTLQWQVL PNXVPAKSCQ DQPTAMARHP HPHLSFMAIP PKKDQDKTEI PAINTIASAE   120
PTVHSTPTTE AVVNAVDNPE ASSESIASAP ETNTAQVTST EV                     162

SEQ ID NO: 341          moltype = AA  length = 205
FEATURE                 Location/Qualifiers
source                  1..205
                        mol_type = protein
                        organism = Bos taurus
SEQUENCE: 341
VSAALARPKH PIKHQGLPQE VLNENLLRFF VAPFPEVFGK EKVNELSKDI GSESTEDQAM    60
EDIKQMEAES ISSSEEIVPN SVEQKHIQKE DVPSERYLGY LEQLLRLKKY KVPQLEIVPN   120
SAEERLHSMK EGIHAQQKEP MIGVNQELAY FYPELFRQFY QLDAYPSGAW YYVPLGTQYT   180
DAPSFSDIPN PIGSENSEKT TMPLW                                        205

SEQ ID NO: 342          moltype = AA  length = 215
FEATURE                 Location/Qualifiers
source                  1..215
                        mol_type = protein
                        organism = Bos taurus
SEQUENCE: 342
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSEKTT MPLWW                             215

SEQ ID NO: 343          moltype = AA  length = 206
FEATURE                 Location/Qualifiers
source                  1..206
                        mol_type = protein
                        organism = Bos taurus
SEQUENCE: 343
LVAVALARPK HPIKHQGLPQ EVLNENLLRF FVAPFPEVFG KEKVNELSKD IGSESTEDQA    60
MEDIKQMEAE SISSSEEIVP NSVEQKHIQK EDVPSERYLG YLEQLLRLKK YKVPQLEIVP   120
NSAEERLHSM KEGIHAQQKE PMIGVNQELA YFYPELFRQF YQLDAYPSGA WYYVPLGTQY   180
TDAPSFSDIP NPIGSENSEK TTMPLW                                       206

SEQ ID NO: 344          moltype = AA  length = 214
FEATURE                 Location/Qualifiers
source                  1..214
                        mol_type = protein
                        organism = Bos taurus
SEQUENCE: 344
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKDD VPSERYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSGKTT MPLW                              214

SEQ ID NO: 345          moltype = AA  length = 213
FEATURE                 Location/Qualifiers
source                  1..213
                        mol_type = protein
                        organism = Bos taurus
SEQUENCE: 345
MKLLILTCLV AVALARPKHP IKHQGLPQEV LNENLLRFFV APFPEVFGKE KVNELSKDIG    60
SESTEDQAME DIKQMEAESI SSSEEIVPNS VEKHIQKEDV PSERYLGYLE QLLRLKKYKV   120
PQLEIVPNSA EERLHSMKEG IHAQQKEPMI GVNQELAYFY PELFRQFYQL DAYPSGAWYY   180
VPLGTQYTDA PSFSDIPNPI GSENSEKTTM PLW                               213

SEQ ID NO: 346          moltype = AA  length = 214
FEATURE                 Location/Qualifiers
source                  1..214
                        mol_type = protein
                        organism = Bos taurus
SEQUENCE: 346
MKLLILTCLV AVALARPKHP IKHQGLPQEV LNENLLRFFV APFPEVFGKE KVNELSKDIG    60
SESTEDQAME DIKQMEAESI SSSEEIVPNS VEKHIQKEDV PSERYLGYLE QLLRLKKYKV   120
PQLEIVPNSA EERLHSMKEG IHAQQKEPMI GVNQELAYFY PELFRQFYQL DAYPSGAWYY   180
VPLGTQYTDA PSFSDIPNPI GSENSEKTTM PLWW                              214

SEQ ID NO: 347          moltype = AA  length = 214
FEATURE                 Location/Qualifiers
source                  1..214
                        mol_type = protein
                        organism = Bos taurus
SEQUENCE: 347
```

```
MKLLILTCLV AVALARPKHP IKHQGLPQEV LNENLLRFFV APFPEVFGKE KVNELSKDIG     60
SESTEDQAME DIKEMEAESI SSSGEIVPNS VEQKHIQKED VPSERYLGYL EQLLRLKKYK    120
VPQLEIVPNS AEERLHSMKE GIDAQQKEPM IGVNQELAYF YPELFRQFYQ LDAYPSGAWY   180
YVPLGTQYTD APSFSDIPNP IGSENSEKTT MPLW                                214

SEQ ID NO: 348         moltype = AA   length = 195
FEATURE                Location/Qualifiers
source                 1..195
                       mol_type = protein
                       organism = Bos taurus
SEQUENCE: 348
PIKHQGLPQE VLNENLLRFF VAPFPEVFGK EKVNELSKDI GSESTEDQAM EDIKQMEAES     60
ISSSEEIVPN SVEQKHIQKE DVPSERYLGY LEQLLRLKKY KVPQLEIVPN SAEERLHSMK    120
EGIHAQQKEP MIGVNQELAY FYPELFRQFY QLDAYPSGAW YVPLGTQYT DAPSFSDIPN    180
PIGSENSEKT TMPLW                                                     195

SEQ ID NO: 349         moltype = AA   length = 214
FEATURE                Location/Qualifiers
source                 1..214
                       mol_type = protein
                       organism = Bos taurus
SEQUENCE: 349
MKLLILTCLV AVALARPKHP IKHQGLPQEV LNENLLRFFV ALFPEVFGKE KVNELSKDIG     60
SESTEDQAME DIKQMEAESI SSSEEIVPNS VEQKHIQKED VPSERYLGYL EQLLRLKKYK    120
VPQLEIVPNS AEERLHSMKE GIDAQQKEPM IGVNQELAYF YPELFRQFYQ LDAYPSGAWY   180
YVPLGTQYTD APSFSDIPNP IGSENSEKTT ISLW                                214

SEQ ID NO: 350         moltype = AA   length = 206
FEATURE                Location/Qualifiers
source                 1..206
                       mol_type = protein
                       organism = Bos taurus
SEQUENCE: 350
MKLLILTCLV AVALARPKHP IKHQGLPQEV LNENLLRFFV APFPEVFGKE KVNELSKDIG     60
SESTEDQAME DIKQMEAESI SSSEEQKHIQK EDVPSERYLG YLEQLLRLKK YKVPQLEIVP   120
NSAEERLHSM KEGIHAQQKE PMIGVNQELA YFYPELFRQF YQLDAYPSGA WYYVPLGTQY   180
TDAPSFSDIP NPIGSENSEK TTMPLW                                         206

SEQ ID NO: 351         moltype = AA   length = 206
FEATURE                Location/Qualifiers
source                 1..206
                       mol_type = protein
                       organism = Bos taurus
SEQUENCE: 351
MKLLILTCLV AVALARPKHP IKHQGLPQEV LNENLLRFFV APFPEVFGKE KVNELSKDIG     60
SESTEDQAME DIKQMEAESI SSSEEIVPNS VEQKHIQKED VPSERYLGYL EQLLRLKKYK    120
VPQLERLHSM KEGIHAQQKE PMIGVNQELA YFYPELFRQF YQLDAYPSGA WYYVPLGTQY   180
TDAPSFSDIP NPIGSENSEK TTMPLW                                         206

SEQ ID NO: 352         moltype = AA   length = 207
FEATURE                Location/Qualifiers
source                 1..207
                       mol_type = protein
                       organism = Bos taurus
SEQUENCE: 352
MKLLILTCLV AVALARPKHP IKHQGLPQEV LNENLLRFFV APFPEVFGKE KVNELSKDIG     60
SESTEDQAME DIKQMEAESI SSSEEQKHIQ EDVPSERYLG YLEQLLRLKK YKVPQLEIVP   120
NSAEERLHSM KEGIHAQQKE PMIGVNQELA YFYPELFRQF YQLDAYPSGA WYYVPLGTQY   180
TDAPSFSDIP NPIGSENSEK TTMPLWW                                        207

SEQ ID NO: 353         moltype = AA   length = 206
FEATURE                Location/Qualifiers
source                 1..206
                       mol_type = protein
                       organism = Bos taurus
SEQUENCE: 353
MKLLILTCLV AVALARPKHP IKHQGLPQEV LNENLLRFFV APFPEVFGKE KVNELSKDIG     60
SESTEDQAME DIKQMEAESI SSSEEIVPNS VEQKHIQKED VPSERYLGYL EQLLRLKKYK    120
VPQLEIVPNS AEERLHSMKE GIHAQQKEPM IGVNQLFRQF YQLDAYPSGA WYYVPLGTQY   180
TDAPSFSDIP NPIGSENSEK TTMPLW                                         206

SEQ ID NO: 354         moltype = AA   length = 205
FEATURE                Location/Qualifiers
source                 1..205
                       mol_type = protein
                       organism = Bos taurus
SEQUENCE: 354
MKLLILTCLV AVALARPKHP IKHQGLPQEV LNENLLRFFV APFPEVFGKE KVNELSKDIG     60
SESTEDQAME DIKQMEAESI SSSEEIVPNS VEKHIQKEDV PSERYLGYLE QLLRLKKYKV   120
```

```
PQLERLHSMK EGIHAQQKEP MIGVNQELAY FYPELFRQFY QLDAYPSGAW YYVPLGTQYT    180
DAPSFSDIPN PIGSENSEKT TMPLW                                         205

SEQ ID NO: 355          moltype = AA  length = 201
FEATURE                 Location/Qualifiers
source                  1..201
                        mol_type = protein
                        organism = Bos taurus
SEQUENCE: 355
MKLLILTCLV AVALARPKHP IKHQGLPQPF PEVFGKEKVN ELSKDIGSES TEDQAMEDIK    60
QMEAESISSS EEIVPNSVEQ KHIQKEDVPS ERYLGYLEQL LRLKKYKVPQ LEIVPNSAEE    120
RLHSMKEGIH AQQKEPMIGV NQELAYFYPE LFRQFYQLDA YPSGAWYYVP LGTQYTDAPS    180
FSDIPNPIGS ENSEKTTMPL W                                             201

SEQ ID NO: 356          moltype = AA  length = 202
FEATURE                 Location/Qualifiers
source                  1..202
                        mol_type = protein
                        organism = Bos taurus
SEQUENCE: 356
MKLLILTCLV AVALARPKHP IKHQGLPQPF PEVFGKEKVN ELSKDIGSES TEDQAMEDIK    60
QMEAESISSS EEIVPNSVEQ KHIQKEDVPS ERYLGYLEQL LRLKKYKVPQ LEIVPNSAEE    120
RLHSMKEGIH AQQKEPMIGV NQELAYFYPE LFRQFYQLDA YPSGAWYYVP LGTQYTDAPS    180
FSDIPNPIGS ENSEKTTMPL WW                                            202

SEQ ID NO: 357          moltype = AA  length = 200
FEATURE                 Location/Qualifiers
source                  1..200
                        mol_type = protein
                        organism = Bos taurus
SEQUENCE: 357
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EIVPNSAEER    120
LHSMKEGIHA QQKEPMIGVN QELAYFYPEL FRQFYQLDAY PSGAWYYVPL GTQYTDAPSF    180
SDIPNPIGSE NSEKTTMPLW                                               200

SEQ ID NO: 358          moltype = AA  length = 201
FEATURE                 Location/Qualifiers
source                  1..201
                        mol_type = protein
                        organism = Bos taurus
SEQUENCE: 358
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EIVPNSAEER    120
LHSMKEGIHA QQKEPMIGVN QELAYFYPEL FRQFYQLDAY PSGAWYYVPL GTQYTDAPSF    180
SDIPNPIGSE NSEKTTMPLW W                                             201

SEQ ID NO: 359          moltype = AA  length = 200
FEATURE                 Location/Qualifiers
source                  1..200
                        mol_type = protein
                        organism = Bos taurus
SEQUENCE: 359
MKLLILTCLV AVALARPKHP IKHQGLPQPF PEVFGKEKVN ELSKDIGSES TEDQAMEDIK    60
QMEAESISSS EEIVPNSVEK HIQKEDVPSE RYLGYLEQLL RLKKYKVPQL EIVPNSAEER    120
LHSMKEGIHA QQKEPMIGVN QELAYFYPEL FRQFYQLDAY PSGAWYYVPL GTQYTDAPSF    180
SDIPNPIGSE NSEKTTMPLW                                               200

SEQ ID NO: 360          moltype = AA  length = 199
FEATURE                 Location/Qualifiers
source                  1..199
                        mol_type = protein
                        organism = Bos taurus
SEQUENCE: 360
MKLLILTCLV AVALARPKHP IKHQGLPQEV LNENLLRFFV APFPEVFGKE KVNELSKDIG    60
SESTEDQAME DIKQMEAESI SSSEEIVPNS VEKHIQKEDV PSERYLGYLE IVPNSAEERL    120
HSMKEGIHAQ QKEPMIGVNQ ELAYFYPELF RQFYQLDAYP SGAWYYVPLG TQYTDAPSFS    180
DIPNPIGSEN SEKTTMPLW                                                199

SEQ ID NO: 361          moltype = AA  length = 200
FEATURE                 Location/Qualifiers
source                  1..200
                        mol_type = protein
                        organism = Bos taurus
SEQUENCE: 361
MKLLILTCLV AVALARPKHP IKHQGLPQEV LNENLLRFFV APFPEVFGKE KVNELSKDIG    60
SESTEDQAME DIKQMEAESI SSSEEIVPNS VEKHIQKEDV PSERYLGYLE IVPNSAEERL    120
HSMKEGIHAQ QKEPMIGVNQ ELAYFYPELF RQFYQLDAYP SGAWYYVPLG TQYTDAPSFS    180
DIPNPIGSEN SEKTTMPLWW                                               200
```

```
SEQ ID NO: 362          moltype = AA  length = 198
FEATURE                 Location/Qualifiers
source                  1..198
                        mol_type = protein
                        organism = Bos taurus
SEQUENCE: 362
MKLLILTCLV AVALARPKHP IKHQGLPQEV LNENLLRFFV APFPEVFGKE KVNELSKDIG    60
SESTEDQAME DIKQMEAESI SSSEQKHIQK EDVPSERYLG YLEQLLRLKK YKVPQLERLH   120
SMKEGIHAQQ KEPMIGVNQE LAYFYPELFR QFYQLDAYPS GAWYYVPLGT QYTDAPSFSD   180
IPNPIGSENS EKTTMPLW                                                 198

SEQ ID NO: 363          moltype = AA  length = 198
FEATURE                 Location/Qualifiers
source                  1..198
                        mol_type = protein
                        organism = Bos taurus
SEQUENCE: 363
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLERLHSM KEGIHAQQKE PMIGVNQLFR QFYQLDAYPS GAWYYVPLGT QYTDAPSFSD   180
IPNPIGSENS EKTTMPLW                                                 198

SEQ ID NO: 364          moltype = AA  length = 214
FEATURE                 Location/Qualifiers
VARIANT                 111..124
                        note = X can be any naturally occurring amino acid
source                  1..214
                        mol_type = protein
                        organism = Bos taurus
SEQUENCE: 364
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL XXXXXXXXXX   120
XXXXEIVPNS AEERLHSMKE GIHAQQKEPM IGVNQELAYF YPELFRQFYQ LDAYPSGAWY   180
YVPLGTQYTD APSFSDIPNP IGSENSEKTT MPLW                               214

SEQ ID NO: 365          moltype = AA  length = 193
FEATURE                 Location/Qualifiers
source                  1..193
                        mol_type = protein
                        organism = Bos taurus
SEQUENCE: 365
MKLLILTCLV AVALARPKHP IKHQGLPQPF PEVFGKEKVN ELSKDIGSES TEDQAMEDIK    60
QMEAESISSS EEIVPNSVEQ KHIQKEDVPS ERYLGYLEQL LRLKKYKVPQ LERLHSMKEG   120
IHAQQKEPMI GVNQELAYFY PELFRQFYQL DAYPSGAWYY VPLGTQYTDA PSFSDIPNPI   180
GSENSEKTTM PLW                                                      193

SEQ ID NO: 366          moltype = AA  length = 194
FEATURE                 Location/Qualifiers
source                  1..194
                        mol_type = protein
                        organism = Bos taurus
SEQUENCE: 366
MKLLILTCLV AVALARPKHP IKHQGLPQPF PEVFGKEKVN ELSKDIGSES TEDQAMEDIK    60
QMEAESISSS EQKHIQKEDV PSERYLGYLE QLLRLKKYKV PQLEIVPNSA EERLHSMKEG   120
IHAQQKEPMI GVNQELAYFY PELFRQFYQL DAYPSGAWYY VPLGTQYTDA PSFSDIPNPI   180
GSENSEKTTM PLWW                                                     194

SEQ ID NO: 367          moltype = AA  length = 192
FEATURE                 Location/Qualifiers
source                  1..192
                        mol_type = protein
                        organism = Bos taurus
SEQUENCE: 367
MKLLILTCLV AVALARPKHP IKHQGLPQEV LNENLLRFFV APFPEVFGKE KVNELSKDIG    60
SESTEDQAME DIKQMEAESI SSSEQKHIQK EDVPSERYLG YLEIVPNSAE ERLHSMKEGI   120
HAQQKEPMIG VNQELAYFYP ELFRQFYQLD AYPSGAWYYV PLGTQYTDAP SFSDIPNPIG   180
SENSEKTTMP LW                                                       192

SEQ ID NO: 368          moltype = AA  length = 193
FEATURE                 Location/Qualifiers
source                  1..193
                        mol_type = protein
                        organism = Bos taurus
SEQUENCE: 368
MKLLILTCLV AVALARPKHP IKHQGLPQEV LNENLLRFFV APFPEVFGKE KVNELSKDIG    60
SESTEDQAME DIKQMEAESI SSSEQKHIQK EDVPSERYLG YLEIVPNSAE ERLHSMKEGI   120
HAQQKEPMIG VNQELAYFYP ELFRQFYQLD AYPSGAWYYV PLGTQYTDAP SFSDIPNPIG   180
SENSEKTTMP LWW                                                      193
```

```
SEQ ID NO: 369          moltype = AA   length = 192
FEATURE                 Location/Qualifiers
source                  1..192
                        mol_type = protein
                        organism = Bos taurus
SEQUENCE: 369
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EIVPNSAEER   120
LHSMKEGIHA QQKEPMIGVN QLFRQFYQLD AYPSGAWYYV PLGTQYTDAP SFSDIPNPIG   180
SENSEKTTMP LW                                                      192

SEQ ID NO: 370          moltype = AA   length = 172
FEATURE                 Location/Qualifiers
source                  1..172
                        mol_type = protein
                        organism = Bos taurus
SEQUENCE: 370
FSEVFGKEKV NELSKDIGSE STEDQAMEDI KQMEAESISS SEEIVPNSVE QKHIQKEDVP    60
SERYLGYLEQ LLRLKKYKVP QLEIVPNSAE ERLHSMKEGI HAQQKEPMIG VNQELAYFYP   120
ELFRQFYQLD AYPSGAWYYV PLGTQYTDAP SFSDIPNPIG SENSEKTTMP LW           172

SEQ ID NO: 371          moltype = AA   length = 187
FEATURE                 Location/Qualifiers
source                  1..187
                        mol_type = protein
                        organism = Bos taurus
SEQUENCE: 371
MKLLILTCLV AVALARPKHP IKHQGLPQPF PEVFGKEKVN ELSKDIGSES TEDQAMEDIK    60
QMEAESISSS EEIVPNSVEQ KHIQKEDVPS ERYLGYLEIV PNSAEERLHS MKEGIHAQQK   120
EPMIGVNQEL AYFYPELFRQ FYQLDAYPSG AWYYVPLGTQ YTDAPSFSDI PNPIGSENSE   180
KTTMPLW                                                            187

SEQ ID NO: 372          moltype = AA   length = 166
FEATURE                 Location/Qualifiers
VARIANT                 118
                        note = X can be any naturally occurring amino acid
source                  1..166
                        mol_type = protein
                        organism = Bos taurus
SEQUENCE: 372
KEKVNELSKD IGSESTEDQA MEDIKQMEAE SISSSEEIVP NSVEQKHIQK EDVPSERYLG    60
YLEQLLRLKK YKVPQLEIVP NSAEERLHSM KEGIHAQQKE PMIGVNQELA YFYPELFXQF   120
YQLDAYPSGA WYYVPLGTQY TDAPSFSDIP NPIGSENSEK TTMPLW                  166

SEQ ID NO: 373          moltype = AA   length = 177
FEATURE                 Location/Qualifiers
source                  1..177
                        mol_type = protein
                        organism = Bos taurus
SEQUENCE: 373
MKLLILTCLV AVALARPKHP IKHQGLPQEV LNENLLRFFV APFPEVFGKE KVNELSKDIG    60
SESTEDQAME DIKEQLLRLK KYKVPQLEIV PNSAEERLHS MKEGIHAQQK EPMIGVNQEL   120
AYFYPELFRQ FYQLDAYPSG AWYYVPLGTQ YTDAPSFSDI PNPIGSENSE KTTMPLW      177

SEQ ID NO: 374          moltype = AA   length = 178
FEATURE                 Location/Qualifiers
source                  1..178
                        mol_type = protein
                        organism = Bos taurus
SEQUENCE: 374
MKLLILTCLV AVALARPKHP IKHQGLPQEV LNENLLRFFV APFPEVFGKE KVNELSKDIG    60
SESTEDQAME DIKEQLLRLK KYKVPQLEIV PNSAEERLHS MKEGIHAQQK EPMIGVNQEL   120
AYFYPELFRQ FYQLDAYPSG AWYYVPLGTQ YTDAPSFSDI PNPIGSENSE KTTMPLWW     178

SEQ ID NO: 375          moltype = AA   length = 155
FEATURE                 Location/Qualifiers
source                  1..155
                        mol_type = protein
                        organism = Bos taurus
SEQUENCE: 375
GSESTEDQAM EDIKQMEAES ISSSEEIVPN SVEQKHIQKE DVPSERYLGY LEQLLRLKKY    60
KVPQLEIVPN SAEERLHSMK EGIHAQQKEP MIGVNQELAY FYPELFRQFY QLDAYPSGAW   120
YYVPLGTQYT DAPSFSDIPN PIGSENSEKT TMPLW                              155

SEQ ID NO: 376          moltype = AA   length = 163
FEATURE                 Location/Qualifiers
source                  1..163
                        mol_type = protein
```

```
                             organism = Bos taurus
SEQUENCE: 376
MKLLILTCLV AVALARPKHP IKHQGLPQEV LNENLLRFFV APFPEVFGKE KVNELSKDIG   60
SESTEDQAME DIKQMEAESI SSSEEIVPNS VEQKHIQKED VPSERYLGYL EQLLRLKKYK  120
VPQLEIVPNS AEERLHSMKE GIHAQQKEPM IGVNQELAYF YPE                   163

SEQ ID NO: 377              moltype = AA   length = 177
FEATURE                     Location/Qualifiers
source                      1..177
                            mol_type = protein
                            organism = Bos taurus
SEQUENCE: 377
MKLLILTCLV AVALARPKHP IKHQGLPQEV LNENLLRFFV APFPEVFGKE KVNELSKDIG   60
SESTEDQAME DIKQMEAESI SSSEEIVPNS VEQKHIQKED VPSERYLGYL EQLLRLKKYK  120
VPQLEIVPNS AEERLHSMKE GIHAQQKEPM IGVNQELAYF YPEKSQVNSE GLHSYGL    177

SEQ ID NO: 378              moltype = AA   length = 141
FEATURE                     Location/Qualifiers
source                      1..141
                            mol_type = protein
                            organism = Bos taurus
SEQUENCE: 378
QMEAESISSS EEIVPNSVEQ KHIQKEDVPS ERYLGYLEQL LRLKKYKVPQ LEIVPNSAEE   60
RLHSMKEGIH AQQKEPMIGV NQELAYFYPE LFRQFYQLDA YPSGAWYYVP LGTQYTDAPS  120
FSDIPNPIGS ENSEKTTMPL W                                           141

SEQ ID NO: 379              moltype = AA   length = 136
FEATURE                     Location/Qualifiers
source                      1..136
                            mol_type = protein
                            organism = Bos taurus
SEQUENCE: 379
SISSSEEIVP NSVEQKHIQK EDVPSERYLG YLEQLLRLKK YKVPQLEIVP NSAEERLHSM   60
KEGIHAQQKE PMIGVNQELA YFYPELFRQF YQLDAYPSGA WYYVPLGTQY TDAPSFSDIP  120
NPIGSENSEK TTMPLW                                                 136

SEQ ID NO: 380              moltype = AA   length = 138
FEATURE                     Location/Qualifiers
VARIANT                     10
                            note = X can be any naturally occurring amino acid
VARIANT                     90
                            note = X can be any naturally occurring amino acid
VARIANT                     128
                            note = X can be any naturally occurring amino acid
source                      1..138
                            mol_type = protein
                            organism = Bos taurus
SEQUENCE: 380
AESISSSEEX VPNSVEQKHI QKEDVPSERY LGYLEQLLRL KKYKVPQLEI VPNSAEERLH   60
SMKEGIHAQQ KEPMIGVNQE LAYFYPELFX QFYQLDAYPS GAWYYVPLGT QYTDAPSFSD  120
IPNPIGSXNS EKTTMPLW                                               138

SEQ ID NO: 381              moltype = AA   length = 126
FEATURE                     Location/Qualifiers
source                      1..126
                            mol_type = protein
                            organism = Bos taurus
SEQUENCE: 381
NSVEQKHIQK EDVPSERYLG YLEQLLRLKK YKVPQLEIVP NSAEERLHSM KEGIHAQQKE   60
PMIGVNQELA YFYPELFRQF YQLDAYPSGA WYYVPLGTQY TDAPSFSDIP NPIGSENSEK  120
TTMPLW                                                            126

SEQ ID NO: 382              moltype = AA   length = 129
FEATURE                     Location/Qualifiers
VARIANT                     81
                            note = X can be any naturally occurring amino acid
source                      1..129
                            mol_type = protein
                            organism = Bos taurus
SEQUENCE: 382
IVPNSVEQKH IQKEDVPSER YLGYLEQLLR LKKYKVPQLE IVPNSAEERL HSMKEGIHAQ   60
QKEPMIGVNQ ELAYFYPELF XQFYQPDAYP SGAWYYVPLG TQYTDAPSFS DIPNPIGSEN  120
SEKTTMPLW                                                         129

SEQ ID NO: 383              moltype = AA   length = 111
FEATURE                     Location/Qualifiers
source                      1..111
                            mol_type = protein
                            organism = Bos taurus
```

```
SEQUENCE: 383
ERYLGYLEQL LRLKKYKVPQ LEIVPNSAEE RLHSMKEGIH AQQKEPMIGV NQELAYFYPE    60
LFRQFYQLDA YPSGAWYYVP LGTQYTDAPS FSDIPNPIGS ENSEKTTMPL W            111

SEQ ID NO: 384          moltype = AA  length = 103
FEATURE                 Location/Qualifiers
source                  1..103
                        mol_type = protein
                        organism = Bos taurus
SEQUENCE: 384
QLLRLKKYKV PQLEIVPNSA EERLHSMKEG IHAQQKEPMI GVNQELAYFY PELFRQFYQL    60
DAYPSGAWYY VPLGTQYTDA PSFSDIPNPI GSENSEKTTM PLW                     103

SEQ ID NO: 385          moltype = AA  length = 214
FEATURE                 Location/Qualifiers
source                  1..214
                        mol_type = protein
                        organism = Capra hircus
SEQUENCE: 385
MKLLILTCLV AVALARPKHP INHQGLSPEV LNENLLRFVV APFPEVFRKE NINELSKDIG    60
SESTEDQAME DAKQMKAGSS SSSEEIVPNS AQQKYIQKED VPSERYLGYL EQLLRLKKYN   120
VPQLEIVPKS AEEQLHSMKE GNPAHQKQPM IAVNQELAYF YPLFRQFYQ LDAYPSGAWY   180
YLPLGTQYTD APSFSDIPNP IGSENSGKTT MPLW                              214

SEQ ID NO: 386          moltype = AA  length = 214
FEATURE                 Location/Qualifiers
source                  1..214
                        mol_type = protein
                        organism = Capra hircus
SEQUENCE: 386
MKLLILTCLV AVALARPKHP INHQGLSPEV LNENLLRFVV APFPEVFRKE NINELSKDIG    60
SESTEDQAME DAKQMKAGSS SSSEEIVPNS AEQKYIQKED VPSERYLGYL EQLLKLKKYN   120
VPQLEIVPKS AEEQLHSMKE GNPAHQKQPM IAVNQELAYF YPLFRQFYQ LDAYPSGAWY   180
YLPLGTQYTD APSFSDIPNP IGSENSGKTA MPLW                              214

SEQ ID NO: 387          moltype = AA  length = 213
FEATURE                 Location/Qualifiers
source                  1..213
                        mol_type = protein
                        organism = Capra hircus
SEQUENCE: 387
KLLILTCLVA VALARPKHPI NHQGLSPEVP NENLLRFVVA PFPEVFRKEN INELSKDIGS    60
ESTEDQAMED AKQMKAGSSS SEEIVPNSA EQKYIQKEDV PSERYLGYLE QLLRLKKYNV   120
PQLEIVPKSA EEQLHSMKEG NPAHQKQPMI AVNQELAYFY PQLFRQFYQL DAYPSGAWYY   180
LPLGTQYTDA PSFSDIPNPI GSENSGKTTM PLW                                213

SEQ ID NO: 388          moltype = AA  length = 214
FEATURE                 Location/Qualifiers
source                  1..214
                        mol_type = protein
                        organism = Capra hircus
SEQUENCE: 388
MKLLILTCLV AVALARPKHP INHRGLSPEV PNENLLRFVV APFPEVFRKE NINELSKDIG    60
SESTEDQAME DAKQMKAGSS SSSEEIVPNS AEQKYIQKED VPSERYLGYL EQLLRLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKTT MPLW                              214

SEQ ID NO: 389          moltype = AA  length = 213
FEATURE                 Location/Qualifiers
source                  1..213
                        mol_type = protein
                        organism = Capra hircus
SEQUENCE: 389
MKLLILTCLV AVALARPKHP INHQGLSPEV LNENLLRFVV APFPEVFRKE NINELSKDIG    60
SESTEDQAME DAKQMKAGSS SSSEEIVPNS AQKYIQKEDV PSERYLGYLE QLLRLKKYNV   120
PQLEIVPKSA EEQLHSMKEG NPAHQKQPMI AVNQELAYFY PQLFRQFYQL DAYPSGAWYY   180
LPLGTQYTDA PSFSDIPNPI GSENSGKTTM PLW                                213

SEQ ID NO: 390          moltype = AA  length = 213
FEATURE                 Location/Qualifiers
source                  1..213
                        mol_type = protein
                        organism = Capra hircus
SEQUENCE: 390
MKLLILTCLV VVALARPKHP INHQGLSPEV LNENLLRFVV APFPEVFRKE NINELSKDIG    60
SESTEDQAME DAKQMKAGSS SSSEEIVPNS AQKYIQKEDV PSERYLGYLE QLLRLKKYNV   120
PQLEIVPKSA EEQLHSMKEG NPAHQKQPMI AVNQELAYFY PQLFRQFYQL DAYPSGAWYY   180
LPLGTQYTDA PSFSDIPNPI GSENSGKTTM PLW                                213
```

| SEQ ID NO: 391 | moltype = AA  length = 214 |
| --- | --- |
| FEATURE | Location/Qualifiers |
| source | 1..214 |
|  | mol_type = protein |
|  | organism = Capra hircus |

SEQUENCE: 391
```
MKLLILTCLV AVALARPKHP INHQGLSPEV PNENLLRFVV APFPEVFRKE NINELSKDIG    60
SESTEDQAME DAKQMKAGSS SSSEEIVPNS AEQKYIQKED VPSERYLGYL EQLLKLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKTA MPLW                               214
```

| SEQ ID NO: 392 | moltype = AA  length = 214 |
| --- | --- |
| FEATURE | Location/Qualifiers |
| source | 1..214 |
|  | mol_type = protein |
|  | organism = Capra hircus |

SEQUENCE: 392
```
MKLLILTCLV AVALARPKHP INHQGLSPEV PNENLLRFVV APFPEVFRKE NINELSKDIG    60
SESTEDQAME DAKQMKAGSS SSSEEIVPNS AEQKYIQKED VPSERYLGYL EQLLKLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKAA MPLW                               214
```

| SEQ ID NO: 393 | moltype = AA  length = 213 |
| --- | --- |
| FEATURE | Location/Qualifiers |
| source | 1..213 |
|  | mol_type = protein |
|  | organism = Capra hircus |

SEQUENCE: 393
```
MKLLILTCLV AVALARPKHP INHQGLSPEV PNENLLRFVV APFPEVFRKE NINELSKDIG    60
SESTEDQAME DAKQMKAGSS SSSEEIVPNS AEKYIQKEDV PSERYLGYLE QLLRLKKYNV   120
PQLETVPNSA EEQLHSMKEG NPAHQKQPMI AVNQELAYFY PQLFRQFYQL DAYPSGAWYY   180
LPLGTQYTDA PSFSDIPNPI GSENSGKTTM PLW                                213
```

| SEQ ID NO: 394 | moltype = AA  length = 212 |
| --- | --- |
| FEATURE | Location/Qualifiers |
| source | 1..212 |
|  | mol_type = protein |
|  | organism = Capra hircus |

SEQUENCE: 394
```
KLLILTCLVA VALARPKHPI NHQGLSPEVP NENLLRFVVA PFPEVFRKEN INELSKDIGS    60
ESTEDQAMED AKQMKAGSSS SSEEIVPNSA EKYIQKEDVP SERYLGYLEQ LLRLKKYNVP   120
QLEIVPKSAE EQLHSMKEGN PAHQKQPMIA VNQELAYFYP QLFRQFYQLD AYPSGAWYYL   180
PLGTQYTDAP SFSDIPNPIG SENSGKTTMP LW                                 212
```

| SEQ ID NO: 395 | moltype = AA  length = 214 |
| --- | --- |
| FEATURE | Location/Qualifiers |
| source | 1..214 |
|  | mol_type = protein |
|  | organism = Capra hircus |

SEQUENCE: 395
```
MKLLILTCLV AVALARPKHP INIQGLSPEV PNENLLRFVV APFPEVFRKE NINELSKDIG    60
SESTEDQAME DAKQMKAGSS SSSEEIVPNS AEQKYIQKED VPSERYLGYL EQLLKLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKTA MPLW                               214
```

| SEQ ID NO: 396 | moltype = AA  length = 215 |
| --- | --- |
| FEATURE | Location/Qualifiers |
| source | 1..215 |
|  | mol_type = protein |
|  | organism = Capra hircus |

SEQUENCE: 396
```
MKLLILTCLV AVALARPKHP INHQGLSPVS EVLNENLLRF VVAPFPEVFR RENINELSKD    60
IGSESTEDQA MEDAKQMKAG SSSSSEEIVP NSAQKYIQKE GVPSERYLGY LEQLLRLKKY   120
NVPQLEIVPK SAEEQLHSMK EGNPAHQKQP MIAVNQELAY FYPQLFRQFY QLDAYPSGAW   180
YYLPLGTQYT DAPSFSDIPN PIGSENSGKT TMPLW                              215
```

| SEQ ID NO: 397 | moltype = AA  length = 213 |
| --- | --- |
| FEATURE | Location/Qualifiers |
| source | 1..213 |
|  | mol_type = protein |
|  | organism = Capra hircus |

SEQUENCE: 397
```
MKLLILTCLV AVALARPKHP INIQGLSPEV PNENLLRFVV APFPEVFRKE NINELSKDIG    60
SESTEDQAME DAKQMKAGSS SSSEEIVPNS AEKYIQKEDV PSERYLGYLE QLLKLKKYNV   120
PQLEIVPKSA EEQLHSMKEG NPAHQKQPMI AVNQELAYFY PQLFRQFYQL DAYPSGAWYY   180
LPLGTQYTDA PSFSDIPNPI GSENSGKTAM PLW                                213
```

| SEQ ID NO: 398 | moltype = AA  length = 206 |
| --- | --- |
| FEATURE | Location/Qualifiers |

```
                         source          1..206
                                         mol_type = protein
                                         organism = Capra hircus
SEQUENCE: 398
MKLLILTCLV AVALARPKHP INHQGLSPEV LNENLLRFVV APFPEVFRKE NINELSKDIG       60
SESTEDQAME DAKQMKAGSS SSSEEIVPNS AQQKYIQKED VPSERYLGYL EQLLRLKKYN      120
VPQLEQLHSM KEGNPAHQKQ PMIAVNQELA YFYPQLFRQF YQLDAYPSGA WYYLPLGTQY      180
TDAPSFSDIP NPIGSENSGK TTMPLW                                          206

SEQ ID NO: 399          moltype = AA    length = 203
FEATURE                 Location/Qualifiers
source                  1..203
                        mol_type = protein
                        organism = Capra hircus
SEQUENCE: 399
MKLLILTCLV AVALARPEVL NENLLRFVVA PFPEVFRKEN INELSKDIGS ESTEDQAMED       60
AKQMKAGSSS SSEEIVPNSA QQKYIQKEDV PSERYLGYLE QLLRLKKYNV PQLEIVPKSA      120
EEQLHSMKEG NPAHQKQPMI AVNQELAYFY PQLFRQFYQL DAYPSGAWYY LPLGTQYTDA      180
PSFSDIPNPI GSENSGKTTM PLW                                             203

SEQ ID NO: 400          moltype = AA    length = 206
FEATURE                 Location/Qualifiers
source                  1..206
                        mol_type = protein
                        organism = Capra hircus
SEQUENCE: 400
MKLLILTCLV AVALARPKHP INHQGLSPEV LNENLLRFVV APFPEVFRKE NINELSKDIG       60
SESTEDQAME DAKQMKAGSS SSSEEIVPNS AQQKYIQKED VPSERYLGYL EQLLRLKKYN      120
VPQLEIVPKS AEEQLHSMKE GNPAHQKQPM IAVNQLFRQF YQLDAYPSGA WYYLPLGTQY      180
TDAPSFSDIP NPIGSENSGK TTMPLW                                          206

SEQ ID NO: 401          moltype = AA    length = 198
FEATURE                 Location/Qualifiers
source                  1..198
                        mol_type = protein
                        organism = Capra hircus
SEQUENCE: 401
MKLLILTCLV AVALARPKHP INHQGLSPEV LNENLLRFVV APFPEVFRKE NINELSKDIG       60
SESTEDQAME DAKQMKAGSS SSSEEIVPNS AQQKYIQKED VPSERYLGYL EQLLRLKKYN      120
VPQLEQLHSM KEGNPAHQKQ PMIAVNQLFR QFYQLDAYPS GAWYYLPLGT QYTDAPSFSD      180
IPNPIGSENS GKTTMPLW                                                   198

SEQ ID NO: 402          moltype = AA    length = 177
FEATURE                 Location/Qualifiers
source                  1..177
                        mol_type = protein
                        organism = Capra hircus
SEQUENCE: 402
MKLLILTCLV AVALARPKHP INHQGLSPEV LNENLLRFVV APFPEVFRKE NINELSKDIG       60
SESTEDQAME DAKEQLLRLK KYNVPQLEIV PKSAEEQLHS MKEGNPAHQK QPMIAVNQEL      120
AYFYPQLFRQ FYQLDAYPSG AWYYLPLGTQ YTDAPSFSDI PNPIGSENSG KTTMPLW         177

SEQ ID NO: 403          moltype = AA    length = 214
FEATURE                 Location/Qualifiers
source                  1..214
                        mol_type = protein
                        organism = Ovis aries
SEQUENCE: 403
MKLLILTCLV AVALARPKHP IKHQGLSPEV LNENLLRFVV APFPEVFRKE NINELSKDIG       60
SESIEDQAME DAKQMKAGSS SSSEEIVPNS AEQKYIQKED VPSERYLGYL EQLLRLKKYN      120
VPQLEIVPKS AEEQLHSMKE GNPAHQKQPM IAVNQELAYF YPQLFRQFYQ LDAYPSGAWY      180
YLPLGTQYTD APSFSDIPNP IGSENSGKTT MPLW                                 214

SEQ ID NO: 404          moltype = AA    length = 214
FEATURE                 Location/Qualifiers
source                  1..214
                        mol_type = protein
                        organism = Ovis aries
SEQUENCE: 404
MKLLILTCLV AVALARPKHP IKHQGLSSEV LNENLLRFVV APFPEVFRKE NINELSKDIG       60
SESIEDQAME DAKQMKAGSS SSSEEIVPNS AEQKYIQKED VPSERYLGYL EQLLRLKKYN      120
VPQLEIVPKS AEEQLHSMKE GNPAHQKQPM IAVNQELAYF YPQLFRQFYQ LDAYPSGAWY      180
YLPLGTQYTD APSFSDIPNP IGSENSGKIT MPLW                                 214

SEQ ID NO: 405          moltype = AA    length = 199
FEATURE                 Location/Qualifiers
source                  1..199
                        mol_type = protein
                        organism = Ovis aries
```

```
SEQUENCE: 405
RPKHPIKHQG LSSEVLNENL LRFVVAPFPE VFRKENINEL SKDIGSESIE DQAMEDAKQM    60
KAGSSSSSEE IVPNSAEQKY IQKEDVPSER YLGYLEQLLR LKKYNVPQLE IVPKSAEEQL   120
HSMKEGNPAH QKQPMIAVNQ ELAYFYPQLF RQFYQLDAYP SGAWYYLPLG TQYTDAPSFS   180
DIPNPIGSEN SGKITMPLW                                                199

SEQ ID NO: 406           moltype = AA  length = 214
FEATURE                  Location/Qualifiers
source                   1..214
                         mol_type = protein
                         organism = Ovis aries
SEQUENCE: 406
MKLLILTCLV AVALARPKHP IKHQGLSPEV LNENLLRFVV APFPEVFRKE NINELSKDIG    60
SESIEDQAME DAKQMKAGSS SSEEIVPNS AEQKYIQKED VPSERYLGYL EQLLRLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKIT MPLW                               214

SEQ ID NO: 407           moltype = AA  length = 206
FEATURE                  Location/Qualifiers
source                   1..206
                         mol_type = protein
                         organism = Ovis aries
SEQUENCE: 407
MKLLILTCLV AVALARPKHP IKHQGLSPEV LNENLLRFVV APFPEVFRKE NINELSKDQA    60
MEDAKQMKAG SSSSEEIVP NSAEQKYIQK EDVPSERYLG YLEQLLRLKK YNVPQLEIVP   120
KSAEEQLHSM KEGNPAHQKQ PMIAVNQELA YFYPQLFRQF YQLDAYPSGA WYYLPLGTQY   180
TDAPSFSDIP NPIGSENSGK TTMPLW                                        206

SEQ ID NO: 408           moltype = AA  length = 206
FEATURE                  Location/Qualifiers
source                   1..206
                         mol_type = protein
                         organism = Ovis aries
SEQUENCE: 408
MKLLILTCLV AVALARPKHP IKHQGLSPEV LNENLLRFVV APFPEVFRKE NINELSKDIG    60
SESIEQMKAG SSSSEEIVP NSAEQKYIQK EDVPSERYLG YLEQLLRLKK YNVPQLEIVP   120
KSAEEQLHSM KEGNPAHQKQ PMIAVNQELA YFYPQLFRQF YQLDAYPSGA WYYLPLGTQY   180
TDAPSFSDIP NPIGSENSGK TTMPLW                                        206

SEQ ID NO: 409           moltype = AA  length = 206
FEATURE                  Location/Qualifiers
source                   1..206
                         mol_type = protein
                         organism = Ovis aries
SEQUENCE: 409
MKLLILTCLV AVALARPKHP IKHQGLSPEV LNENLLRFVV APFPEVFRKE NINELSKDQA    60
MEDAKQMKAG SSSSEEIVP NSAEQKYIQK EDVPSERYLG YLEQLLRLKK YNVPQLEIVP   120
KSAEEQLHSM KEGNPAHQKQ PMIAVNQELA YFYPQLFRQF YQLDAYPSGA WYYLPLGTQY   180
TDAPSFSDIP NPIGSENSGK ITMPLW                                        206

SEQ ID NO: 410           moltype = AA  length = 206
FEATURE                  Location/Qualifiers
source                   1..206
                         mol_type = protein
                         organism = Ovis aries
SEQUENCE: 410
MKLLILTCLV AVALARPKHP IKHQGLSPEV LNENLLRFVV APFPEVFRKE NINELSKDIG    60
SESIEQMKAG SSSSEEIVP NSAEQKYIQK EDVPSERYLG YLEQLLRLKK YNVPQLEIVP   120
KSAEEQLHSM KEGNPAHQKQ PMIAVNQELA YFYPQLFRQF YQLDAYPSGA WYYLPLGTQY   180
TDAPSFSDIP NPIGSENSGK ITMPLW                                        206

SEQ ID NO: 411           moltype = AA  length = 191
FEATURE                  Location/Qualifiers
source                   1..191
                         mol_type = protein
                         organism = Ovis aries
SEQUENCE: 411
RPKHPIKHQG LSSEVLNENL LRFVVAPFPE VFRKENINEL SKDIGSESIE DQAMEDAKQM    60
KAGSSSSSEE IVPNSAEQKY IQKEDVPSER YLGYLEQLLR LKKYNVPQLE IVPKSAEEQL   120
HSMKEGNPAH QKQPMIAVNQ LFRQFYQLDA YPSGAWYYLP LGTQYTDAPS FSDIPNPIGS   180
ENSGKITMPL W                                                        191

SEQ ID NO: 412           moltype = AA  length = 206
FEATURE                  Location/Qualifiers
source                   1..206
                         mol_type = protein
                         organism = Ovis aries
SEQUENCE: 412
MKLLILTCLV AVALARPKHP IKHQGLSPEV LNENLLRFVV APFPEVFRKE NINELSKDIG    60
```

```
SESIEDQAME DAKQMKAGSS SSSEEIVPNS AEQKYIQKED VPSERYLGYL EQLLRLKKYN    120
VPQLEIVPKS AEEQLHSMKE GNPAHQKQPM IAVNQLFRQF YQLDAYPSGA WYYLPLGTQY    180
TDAPSFSDIP NPIGSENSGK ITMPLW                                        206

SEQ ID NO: 413          moltype = AA   length = 214
FEATURE                 Location/Qualifiers
source                  1..214
                        mol_type = protein
                        organism = Bubalus bubalis
SEQUENCE: 413
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APSFSDIPNP IGSENSEKTT MPLW                               214

SEQ ID NO: 414          moltype = AA   length = 214
FEATURE                 Location/Qualifiers
source                  1..214
                        mol_type = protein
                        organism = Bubalus bubalis
SEQUENCE: 414
MKLLVLTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APSFSDIPNP IGSENSGKTT MPLW                               214

SEQ ID NO: 415          moltype = AA   length = 214
FEATURE                 Location/Qualifiers
source                  1..214
                        mol_type = protein
                        organism = Bubalus bubalis
SEQUENCE: 415
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APSFSDIPNP IGSENSGKTT MPLW                               214

SEQ ID NO: 416          moltype = AA   length = 214
FEATURE                 Location/Qualifiers
source                  1..214
                        mol_type = protein
                        organism = Bubalus bubalis
SEQUENCE: 416
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APLFSDIPNP IGSENSGKTT MPLW                               214

SEQ ID NO: 417          moltype = AA   length = 214
FEATURE                 Location/Qualifiers
source                  1..214
                        mol_type = protein
                        organism = Bubalus bubalis
SEQUENCE: 417
MKLLILTCLV AVALARPKQP IKHQGLPQGV LNENLLRFFV APFPEVFGKE KVNELSTDVG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APSLSDIPNP IGSENSGKTT MPLW                               214

SEQ ID NO: 418          moltype = AA   length = 215
FEATURE                 Location/Qualifiers
source                  1..215
                        mol_type = protein
                        organism = Bubalus bubalis
SEQUENCE: 418
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APLFSDIPNP IGSENSGKTT MPLWW                              215

SEQ ID NO: 419          moltype = AA   length = 214
FEATURE                 Location/Qualifiers
source                  1..214
                        mol_type = protein
                        organism = Bubalus bubalis
SEQUENCE: 419
MKLLILTCLV AVALARPKQP IKHQGLPQGV LNENLLRFFV APFPEMFGKE KVNELSTDVG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
```

```
YVPLGTQYPD APLFSDIPNP IGSENSGKTT MPLW                          214

SEQ ID NO: 420            moltype = AA  length = 214
FEATURE                   Location/Qualifiers
source                    1..214
                          mol_type = protein
                          organism = Bubalus bubalis
SEQUENCE: 420
MKLLILTCLV AVALARPKQP IKHQGLPQGV LNENLLRFFV APFPEVFGKE KVNELSTDIG   60
SESTEDQAME DIKQMEAESI SSSEEIVPIS VEKHIQKEDV PSERYLGYLE QLLRLKKYNV  120
PQLEIVPNLA EEQLHSMKEG IHAQQKEPMI GVNQELAYFY PQLFRQFYQL DAYPSGAWYY  180
VPLGTQYPDA PLFSDIPNPI GSENSGKTTM PLWW                             214

SEQ ID NO: 421            moltype = AA  length = 206
FEATURE                   Location/Qualifiers
source                    1..206
                          mol_type = protein
                          organism = Bubalus bubalis
SEQUENCE: 421
MKLLILTCLV AVALARPKQP IKHQGLPQGV LNENLLRFFV APFPEMFGKD VGSESTEDQA   60
MEDIKQMEAE SISSSEEIVP ISVEQKHIQK EDVPSERYLG YLEQLLRLKK YNVPQLEIVP  120
NLAEEQLHSM KEGIHAQQKE PMIGVNQELA YFYPQLFRQF YQLDAYPSGA WYYVPLGTQY  180
PDAPSFSDIP NPIGSENSGK TTMPLW                                      206

SEQ ID NO: 422            moltype = AA  length = 206
FEATURE                   Location/Qualifiers
source                    1..206
                          mol_type = protein
                          organism = Bubalus bubalis
SEQUENCE: 422
MKLLILTCLV AVALARPKQP IKHQGLPQGV LNENLLRFFV APFPEVFGKD IGSESTEDQA   60
MEDIKQMEAE SISSSEEIVP ISVEQKHIQK EDVPSERYLG YLEQLLRLKK YNVPQLEIVP  120
NLAEEQLHSM KEGIHAQQKE PMIGVNQELA YFYPQLFRQF YQLDAYPSGA WYYVPLGTQY  180
PDAPLFSDIP NPIGSENSGK TTMPLW                                      206

SEQ ID NO: 423            moltype = AA  length = 207
FEATURE                   Location/Qualifiers
source                    1..207
                          mol_type = protein
                          organism = Bubalus bubalis
SEQUENCE: 423
MKLLILTCLV AVALARPKQP IKHQGLPQGV LNENLLRFFV APFPEVFGKD IGSESTEDQA   60
MEDIKQMEAE SISSSEEIVP ISVEQKHIQK EDVPSERYLG YLEQLLRLKK YNVPQLEIVP  120
NLAEEQLHSM KEGIHAQQKE PMIGVNQELA YFYPQLFRQF YQLDAYPSGA WYYVPLGTQY  180
PDAPLFSDIP NPIGSENSGK TTMPLWW                                     207

SEQ ID NO: 424            moltype = AA  length = 207
FEATURE                   Location/Qualifiers
source                    1..207
                          mol_type = protein
                          organism = Bubalus bubalis
SEQUENCE: 424
MKLLILTCLV AVALARPKQP IKHQGLPQGV LNENLLRFFV APFPEVFGKE KVNELSTDIG   60
SESTEDQAME DIKQMEAESI SSSEEIVPIS VEQKHIQKED VPSERYLGYL EQLLRLKKYN  120
VPQLEIVPNL AEEQLHSMKE GIHAQQKEPM IGVNQLFRQF YQLDAYPSGA WYYVPLGTQY  180
PDAPLFSDIP NPIGSENSGK TTMPLWW                                     207

SEQ ID NO: 425            moltype = AA  length = 207
FEATURE                   Location/Qualifiers
source                    1..207
                          mol_type = protein
                          organism = Bubalus bubalis
SEQUENCE: 425
MKLLILTCLV AVALARPKQP IKHQGLPQGV LNENLLRFFV APFPEVFGKE KVNELSTDQA   60
MEDIKQMEAE SISSSEEIVP ISVEQKHIQK EDVPSERYLG YLEQLLRLKK YNVPQLEIVP  120
NLAEEQLHSM KEGIHAQQKE PMIGVNQELA YFYPQLFRQF YQLDAYPSGA WYYVPLGTQY  180
PDAPLFSDIP NPIGSENSGK TTMPLWW                                     207

SEQ ID NO: 426            moltype = AA  length = 206
FEATURE                   Location/Qualifiers
source                    1..206
                          mol_type = protein
                          organism = Bubalus bubalis
SEQUENCE: 426
MKLLILTCLV AVALARPKQP IKHQGLPQGV LNENLLRFFV APFPEVFGKE KVNELSTDQA   60
MEDIKQMEAE SISSSEEIVP ISVEKHIQKE DVPSERYLGY LEQLLRLKKY NVPQLEIVPN  120
LAEEQLHSMK EGIHAQQKEP MIGVNQELAY FYPQLFRQFY QLDAYPSGAW YYVPLGTQYP  180
DAPLFSDIPN PIGSENSGKT TMPLWW                                      206
```

```
SEQ ID NO: 427            moltype = AA  length = 202
FEATURE                   Location/Qualifiers
source                    1..202
                          mol_type = protein
                          organism = Bubalus bubalis
SEQUENCE: 427
MKLLILTCLV AVALARPKQP IKHQGLPQPF PEVFGKEKVN ELSTDIGSES TEDQAMEDIK   60
QMEAESISSS EEIVPISVEQ KHIQKEDVPS ERYLGYLEQL LRLKKYNVPQ LEIVPNLAEE  120
QLHSMKEGIH AQQKEPMIGV NQELAYFYPQ LFRQFYQLDA YPSGAWYYVP LGTQYPDAPL  180
FSDIPNPIGS ENSGKTTMPL WW                                           202

SEQ ID NO: 428            moltype = AA  length = 194
FEATURE                   Location/Qualifiers
source                    1..194
                          mol_type = protein
                          organism = Bubalus bubalis
SEQUENCE: 428
MKLLILTCLV AVALARPKQP IKHQGLPQPF PEVFGKDIGS ESTEDQAMED IKQMEAESIS   60
SSEEIVPISV EQKHIQKEDV PSERYLGYLE QLLRLKKYNV PQLEIVPNLA EEQLHSMKEG  120
IHAQQKEPMI GVNQELAYFY PQLFRQFYQL DAYPSGAWYY VPLGTQYPDA PLFSDIPNPI  180
GSENSGKTTM PLWW                                                    194

SEQ ID NO: 429            moltype = AA  length = 194
FEATURE                   Location/Qualifiers
source                    1..194
                          mol_type = protein
                          organism = Bubalus bubalis
SEQUENCE: 429
MKLLILTCLV AVALARPKQP IKHQGLPQPF PEVFGKEKVN ELSTDQAMED IKQMEAESIS   60
SSEEIVPISV EQKHIQKEDV PSERYLGYLE QLLRLKKYNV PQLEIVPNLA EEQLHSMKEG  120
IHAQQKEPMI GVNQELAYFY PQLFRQFYQL DAYPSGAWYY VPLGTQYPDA PLFSDIPNPI  180
GSENSGKTTM PLWW                                                    194

SEQ ID NO: 430            moltype = AA  length = 178
FEATURE                   Location/Qualifiers
source                    1..178
                          mol_type = protein
                          organism = Bubalus bubalis
SEQUENCE: 430
MKLLILTCLV AVALARPKQP IKHQGLPQGV LNENLLRFFV APFPEVFGKE KVNELSTDIG   60
SESTEDQAME DIKEQLLRLK KYNVPQLEIV PNLAEEQLHS MKEGIHAQQK EPMIGVNQEL  120
AYFYPQLFRQ FYQLDAYPSG AWYYVPLGTQ YPDAPLFSDI PNPIGSENSG KTTMPLWW    178

SEQ ID NO: 431            moltype = AA  length = 214
FEATURE                   Location/Qualifiers
source                    1..214
                          mol_type = protein
                          organism = Bos mutus
SEQUENCE: 431
MKLLILTCLV AVALARPKHP IKHQGLPQEV LNENLLRFFV APFPEVFGKE KVNELSKDIG   60
SESTEDQAME DIKKMEAESI SSSEEIVPNS VEQKHIQKED VPSERYLGYL EQLLRLKKYK  120
VPQLEIVPNS AEERLHSMKE GIHAQQKEPM IGVNQELAYF YPELFRQFYQ LDAYPSGAWY  180
YVPLGTQYTD APSFSDIPNP IGSENSGKTT MPLW                              214

SEQ ID NO: 432            moltype = AA  length = 214
FEATURE                   Location/Qualifiers
VARIANT                   99
                          note = X can be any naturally occurring amino acid
source                    1..214
                          mol_type = protein
                          organism = Bos indicus
SEQUENCE: 432
MKLLILTCLV AVALARPKHP IKHQGLPQEV LNENLLRFFV APFPEVFGKE KVNELSKDIG   60
SESTEDQAME DIKQMEAESI SSSEEIVPNS VEQKHIQKXD VPSERYLGYL EQLLRLKKYK  120
VPQLEIVPNS AEERLHSMKE GIHAQQKEPM IGVNQELAYF YPELFRQFYQ LDAYPSGAWY  180
YVPLGTQYTD APSFSDIPNP IGSENSGKTT MPLW                              214

SEQ ID NO: 433            moltype = AA  length = 205
FEATURE                   Location/Qualifiers
source                    1..205
                          mol_type = protein
                          organism = Jeotgalicoccus coquinae
SEQUENCE: 433
MAVALARPKH PIKHQGLPQE VLNENLLRFF VAPFPEVFGK EKVNELSKDI GSESTEDQAM   60
EDIKQMEAES ISSSEEIVPN SVEQKHIQKE DVPSERYLGY LEQLLRLKKY KVPQLEIVPN  120
SAEERLHSMK EGIHAQQKEP MIGVNQELAY FYPELFRQFY QLDAYPSGAW YYVPLGTQYT  180
DAPSFSDIPN PIGSENSEKT TMPLW                                        205

SEQ ID NO: 434            moltype = AA  length = 146
```

```
FEATURE                 Location/Qualifiers
source                  1..146
                        mol_type = protein
                        organism = Jeotgalicoccus coquinae
SEQUENCE: 434
MEDIKQMEAE SISSSEEIVP NSVEQKHIQK EDVPSERYLG YLEQLLRLKK YKVPQLEIVP    60
NSAEERLHSM KEGIHAQQKE PMIGVNQELA YFYPELFRQF YQLDAYPSGA WYYVPLGTQY   120
TDAPSFSDIP NPIGSENSEK TTMPLW                                       146

SEQ ID NO: 435          moltype = AA  length = 214
FEATURE                 Location/Qualifiers
source                  1..214
                        mol_type = protein
                        organism = Bison bison
SEQUENCE: 435
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSGKTT MPLW                              214

SEQ ID NO: 436          moltype = AA  length = 214
FEATURE                 Location/Qualifiers
source                  1..214
                        mol_type = protein
                        organism = Bos grunniens
SEQUENCE: 436
MRLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSEHYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSGKTT MPLW                              214

SEQ ID NO: 437          moltype = AA  length = 214
FEATURE                 Location/Qualifiers
source                  1..214
                        mol_type = protein
                        organism = Jeotgalicoccus aerolatus
SEQUENCE: 437
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSEKTT MPLW                              214

SEQ ID NO: 438          moltype = AA  length = 196
FEATURE                 Location/Qualifiers
source                  1..196
                        mol_type = protein
                        organism = Jeotgalicoccus aerolatus
SEQUENCE: 438
LVAVALARPK QPIKHQGLPQ GVLNENLLRF FVAPFPEVFG KEKVNELSTD IGSESTEDQA    60
MEDIKQMEAE SISSSEEIVP ISVEQKHIQK EDVPSERYLG YLEQLLRLKK YNVPQLEIVP   120
NLAEEQLHSM KEGIHAQQKE PMIGVNQELA YFYPQLFRQF YQLDAYPSGA WYYVPLGTQY   180
PDAPSFSDIP NPIGSE                                                  196

SEQ ID NO: 439          moltype = AA  length = 229
FEATURE                 Location/Qualifiers
source                  1..229
                        mol_type = protein
                        organism = Muntiacus muntjak
SEQUENCE: 439
KHPIGHQGLP QEVLNENLLR LFVVPFPEVF GKESINELSK DTESESTEDH AMEDTKQVES    60
GSSSSSEEIV SNIAEQKQVQ KEDVPSERYL GYLEQLLKLQ KYNLPQLEQK IRSPRELLDY   120
FPPDMKHRFF VLPNYSKYNT ELNIFSKELL HSMKEGIHAQ QKKPMKGVSQ ELAYFYPQLF   180
RQFYQLDAYP SGAWYYLPLG IQYTDVPSFS DIPNPIGSEN SGKATMPLW               229

SEQ ID NO: 440          moltype = AA  length = 229
FEATURE                 Location/Qualifiers
source                  1..229
                        mol_type = protein
                        organism = Muntiacus reevesi
SEQUENCE: 440
KHPIGHQGLP QEVLNENLLR LFVVPFPEVF GKESISELSK DTESESTEDH AMEDTKQVES    60
GSSSSSEEIV SNIAEQKQVQ KEDVPSERYL GYLEQLLKLQ KYNLPQLEQK IRSPRELLDY   120
FPPDMKHRFF VLPNYSKYNT ELNIFSKELL HSMKEGIHAQ QKKPMKGVSQ ELAYFYPQLF   180
RQFYQLDAYP SGAWYYLPLG IQYTDAPSFS DIPNPIGSEN SGKATMPLW               229

SEQ ID NO: 441          moltype = AA  length = 222
FEATURE                 Location/Qualifiers
source                  1..222
                        mol_type = protein
```

-continued

```
                           organism = Bos taurus
SEQUENCE: 441
MKFFIFTCLL AVALAKNTME HVSSSEESII SQETYKQEKN MDINPSKENL CSTFCKEVVR    60
NANEEEYSIG SSSEESAEVA TEEVKITVDD KHYQKALNEI NQFYRKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMKPWIQ PKTKVIPYVR YL                     222

SEQ ID NO: 442             moltype = AA  length = 213
FEATURE                    Location/Qualifiers
source                     1..213
                           mol_type = protein
                           organism = Bos taurus
SEQUENCE: 442
MKFFIFTCLL AVALAKNTME HVSSSEESII SQETYKQEKN MAINPSKENL CSTFCKEVVR    60
NANEEEYSIG SSSEESAEVA TEEVKITVDD KHYQKALNEI NQFYQKFPQY LQYLYQGPIV   120
LNPWDQVKRN AVPITPTLNR EQLSTSEEST EVFTKKTKLT EEEKNRLNFL KKISQRYQKF   180
ALPQYLKTVY QHQKAMKPWI QPKTKVIPYV RYL                               213

SEQ ID NO: 443             moltype = AA  length = 213
FEATURE                    Location/Qualifiers
source                     1..213
                           mol_type = protein
                           organism = Bos taurus
SEQUENCE: 443
MKFFIFTCLL AVALAKNTME HVSSSEESII SQETYKQEKN MAINPSKEVV RNANEEEYSI    60
GSSSEESAEV ATEEVKITVD DKHYQKALNE INQFYQKFPQ YLQYLYQGPI VLNPWDQVKR   120
NAVPITPTLN REQLSTSEEN SKKTVDMEST EVFTKKTKLT EEEKNRLNFL KKISQRYQKF   180
ALPQYLKTVY QHQKAMKPWI QPKTKVIPYV RYL                               213

SEQ ID NO: 444             moltype = AA  length = 223
FEATURE                    Location/Qualifiers
source                     1..223
                           mol_type = protein
                           organism = Capra hircus
SEQUENCE: 444
MKFFIFTCLL AVALAKHKME HVSSSEEPIN ILQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                    223

SEQ ID NO: 445             moltype = AA  length = 223
FEATURE                    Location/Qualifiers
source                     1..223
                           mol_type = protein
                           organism = Capra hircus
SEQUENCE: 445
MKFFIFTCLL AVALAKHKME HVSSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                    223

SEQ ID NO: 446             moltype = AA  length = 223
FEATURE                    Location/Qualifiers
source                     1..223
                           mol_type = protein
                           organism = Capra hircus
SEQUENCE: 446
MKFFIFTCLL AVALAKHKME HISSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                    223

SEQ ID NO: 447             moltype = AA  length = 223
FEATURE                    Location/Qualifiers
source                     1..223
                           mol_type = protein
                           organism = Capra hircus
SEQUENCE: 447
MKFFIFTCLL AVALAKHKME HVSSSEEPIN IFQEIYKQEK NMAIHPRKEK LCTTSCEEVV    60
RNANEEEYSI RSSSEESAKV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                    223

SEQ ID NO: 448             moltype = AA  length = 223
FEATURE                    Location/Qualifiers
source                     1..223
                           mol_type = protein
                           organism = Capra hircus
SEQUENCE: 448
```

```
MKFFIFTCLL AVALAKHKME HVSSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KIISQYYQKF AWPQYLKTVD QHQKAMKPWT QPKTNAIPYV RYL                    223

SEQ ID NO: 449            moltype = AA   length = 223
FEATURE                   Location/Qualifiers
source                    1..223
                          mol_type = protein
                          organism = Capra hircus
SEQUENCE: 449
MKFFIFTCLL AVALATHKME HVSSSEEPIN IFQEIYKQEK NMAIHPRKEK LCTTSCEEVV    60
RNANEEEYSI RSSSEESAKV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                    223

SEQ ID NO: 450            moltype = AA   length = 223
FEATURE                   Location/Qualifiers
source                    1..223
                          mol_type = protein
                          organism = Capra hircus
SEQUENCE: 450
MKFFIFTCLL AVALAKHKME HVSSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGAFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                    223

SEQ ID NO: 451            moltype = AA   length = 223
FEATURE                   Location/Qualifiers
source                    1..223
                          mol_type = protein
                          organism = Capra hircus
SEQUENCE: 451
MKFFIFTCLL AVALAKHKME HVSSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEEN SKKTIDMEST EVFTKKAKLT EEEKNRLNFL   180
KIISQYYQKF AWPQYLKTVE QHQKAMKPWT QPKTNAIPYV RYL                    223

SEQ ID NO: 452            moltype = AA   length = 222
FEATURE                   Location/Qualifiers
source                    1..222
                          mol_type = protein
                          organism = Capra hircus
SEQUENCE: 452
MKFFIFTCLL AVALAKHMEH VSSSEEPINI FQEIYKQEKN MAIHPRKEKL CTTSCEEVVR    60
NANEEEYSIR SSSEESAEVA PEEIKITVDD KHYQKALNEI NQFYQKFPQY LQYPYQGPIV   120
LNPWDQVKRN AGAFTPTVNR EQLSTSEENS KKTIDMESTE VFTKKTKLTE EEKNRLNFLK   180
KISQYYQKFA WPQYLKTVDQ HQKAMKPWTQ PKTNAIPYVR YL                     222

SEQ ID NO: 453            moltype = AA   length = 223
FEATURE                   Location/Qualifiers
source                    1..223
                          mol_type = protein
                          organism = Capra hircus
SEQUENCE: 453
MKFFIFTCLL AVALAKHKME HVSSSEEPIN IFQEIYKQEK NMAIRPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPRT QPKTNAIPYV RYL                    223

SEQ ID NO: 454            moltype = AA   length = 223
FEATURE                   Location/Qualifiers
source                    1..223
                          mol_type = protein
                          organism = Capra hircus
SEQUENCE: 454
MKFFIFTCLL AVALAKHKME HVSSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KIISQYYQKF AWPQYLKTVD QHQKAMKRWT QPKTNAIPYV RYL                    223

SEQ ID NO: 455            moltype = AA   length = 223
FEATURE                   Location/Qualifiers
source                    1..223
                          mol_type = protein
                          organism = Capra hircus
SEQUENCE: 455
MKFFIFTCLL AVALAKHKME HVSSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
```

```
VLNPWDQVKR NAGPFTPTVN REQLSTSEEN SKKTIDMEST KVFTKKTKLT EEEKNRLNFL    180
KIISQYYQKF AWPQYLKTVD QHQKAMKRWT QPKTNAIPYV RYL                     223

SEQ ID NO: 456            moltype = AA  length = 215
FEATURE                   Location/Qualifiers
source                    1..215
                          mol_type = protein
                          organism = Capra hircus
SEQUENCE: 456
MKFFIFTCLL AVALAKHKME HVSSSEEPIN IFQEIYKQEK NMAIHPRKEK LCTTSCEEVV    60
RNANEEEYSI RSSSEEIKIT VDDKHYQKAL NEINQFYQKF PQYLQYPYQG PIVLNPWDQV    120
KRNAGPFTPT VNREQLSTSE ENSKKTIDME STEVFTKKTK LTEEEKNRLN FLKKISQYYQ    180
KFAWPQYLKT VDQHQKAMKP WTQPKTNAIP YVRYL                              215

SEQ ID NO: 457            moltype = AA  length = 214
FEATURE                   Location/Qualifiers
source                    1..214
                          mol_type = protein
                          organism = Capra hircus
SEQUENCE: 457
MKFFIFTCLL AVALAKHEPI NIFQEIYKQE KNMAIHPRKE KLCTTSCEEV VRNANEEEYS    60
IRSSSEESAE VAPEEIKITV DDKHYQKALN EINQFYQKFP QYLQYPYQGP IVLNPWDQVK    120
RNAGAFTPTV NREQLSTSEE NSKKTIDMES TEVFTKKTKL TEEEKNRLNF LKKISQYYQK    180
FAWPQYLKTV DQHQKAMKPW TQPKTNAIPY VRYL                               214

SEQ ID NO: 458            moltype = AA  length = 214
FEATURE                   Location/Qualifiers
source                    1..214
                          mol_type = protein
                          organism = Capra hircus
SEQUENCE: 458
MKFFIFTCLL AVALAKHKME HVSSSEEPIN IFQEIYKQEK NMAIHPRKEV VRNANEEEYS    60
IRSSSEESAE VAPEEIKITV DDKHYQKALN EINQFYQKFP QYLQYPYQGP IVLNPWDQVK    120
RNAGPFTPTV NREQLSTSEE NSKKTIDMES TEVFTKKTKL TEEEKNRLNF LKKISQYYQK    180
FAWPQYLKTV DQHQKAMKPW TQPKTNAIPY VRYL                               214

SEQ ID NO: 459            moltype = AA  length = 214
FEATURE                   Location/Qualifiers
source                    1..214
                          mol_type = protein
                          organism = Capra hircus
SEQUENCE: 459
MKFFIFTCLL AVALAKHEPI NIFQEIYKQE KNMAIHPRKE KLCTTSCEEV VRNANEEEYS    60
IRSSSEESAK VAPEEIKITV DDKHYQKALN EINQFYQKFP QYLQYPYQGP IVLNPWDQVK    120
RNAGPFTPTV NREQLSTSEE NSKKTIDMES TEVFTKKTKL TEEEKNRLNF LKKISQYYQK    180
FAWPQYLKTV DQYQKAMKPW TQPKTNAIPY VRYL                               214

SEQ ID NO: 460            moltype = AA  length = 215
FEATURE                   Location/Qualifiers
source                    1..215
                          mol_type = protein
                          organism = Capra hircus
SEQUENCE: 460
MKFFIFTCLL AVALAKHKME HVSSSEEPIN IFQEIYKQEK NMAIHPRKEK LCTTSCEEVV    60
RNANEEEYSI RSSSEEIKIT VDDKHYQKAL NEINQFYQKF PQYLQYPYQG PIVLNPWDQV    120
KRNAGAFTPT VNREQLSTSE ENSKKTIDME STEVFTKKTK LTEEEKNRLN FLKKISQYYQ    180
KFAWPQYLKT VDQHQKAMKP WTQPKTNAIP YVRYL                              215

SEQ ID NO: 461            moltype = AA  length = 214
FEATURE                   Location/Qualifiers
source                    1..214
                          mol_type = protein
                          organism = Capra hircus
SEQUENCE: 461
MKFFIFTCLL AVALAKHKME HVSSSEEPIN IFQEIYKQEK NMAIHPRKEV VRNANEEEYS    60
IRSSSEESAE VAPEEIKITV DDKHYQKALN EINQFYQKFP QYLQYPYQGP IVLNPWDQVK    120
RNAGPFTPTV NREQLSTSEE NSKKTIDMES TEVFTKKTKL TEEEKNRLNF LKIISQYYQK    180
FAWPQYLKTV DQHQKAMKPW TQPKTNAIPY VRYL                               214

SEQ ID NO: 462            moltype = AA  length = 214
FEATURE                   Location/Qualifiers
source                    1..214
                          mol_type = protein
                          organism = Capra hircus
SEQUENCE: 462
MKFFIFTCLL AVALAKHKME HVSSSEEPIN IFQEIYKQEK NMAIHPRKEV VRNANEEEYS    60
IRSSSEESAE VAPEEIKITV DDKHYQKALN EINQFYQKFP QYLQYPYQGP IVLNPWDQVK    120
RNAGAFTPTV NREQLSTSEE NSKKTIDMES TEVFTKKTKL TEEEKNRLNF LKKISQYYQK    180
FAWPQYLKTV DQHQKAMKPW TQPKTNAIPY VRYL                               214
```

```
SEQ ID NO: 463          moltype = AA   length = 214
FEATURE                 Location/Qualifiers
source                  1..214
                        mol_type = protein
                        organism = Capra hircus
SEQUENCE: 463
MKFFIFTCLL AVALAKHKME HVSSSEEPIN IFQEIYKQEK NMAIHPRKEV VRNANEEEYS    60
IRSSSEESAK VAPEEIKITV DDKHYQKALN EINQFYQKFL QYLQYPYQGP IVLNPWDQVK   120
RNAGPFTPTV NREQLSTSEE NSKKTIDMES TEVFTKKTKL TEEEKNRLNF LKKISQYYQK   180
FAWPQYLKTV DQHQKAMKPW TQPKTNAIPY VRYL                              214

SEQ ID NO: 464          moltype = AA   length = 214
FEATURE                 Location/Qualifiers
source                  1..214
                        mol_type = protein
                        organism = Capra hircus
SEQUENCE: 464
MKFFIFTCLL AVALAKHKME HVSSSEEPIN IFQEIYKQEK NMAIHPRKEV VRNANEEEYS    60
IRSSSEESAE VAPKEIKITV DDKHYQKALN EINQFYQKFP QYLQYPYQGP IVLNPWDQVK   120
RNAGPFTPTV NREQLSTSEE NSKKTIDMES TEVFTKKTKL TEEEKNRLNF LKIISQYYQK   180
FAWPQYLKTV DQHQKAMKAW TQPKTNAIPY VRYL                              214

SEQ ID NO: 465          moltype = AA   length = 214
FEATURE                 Location/Qualifiers
source                  1..214
                        mol_type = protein
                        organism = Capra hircus
SEQUENCE: 465
MKFFIFTCLL AVALAKHKME HVSSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEES TEVFTKKTKL TEEEKNRLNF LKIISRYYQK   180
FAWPQYLKTV DQHQKAMKPW TQPKTNAIPY VRYL                              214

SEQ ID NO: 466          moltype = AA   length = 205
FEATURE                 Location/Qualifiers
source                  1..205
                        mol_type = protein
                        organism = Capra hircus
SEQUENCE: 466
MKFFIFTCLL AVALAKHEPI NIFQEIYKQE KNMAIHPRKE VVRNANEEEY SIRSSSEESA    60
EVAPEEIKIT VDDKHYQKAL NEINQFYQKF PQYLQYPYQG PIVLNPWDQV KRNAGAFTPT   120
VNREQLSTSE ENSKKTIDME STEVFTKKTK LTEEEKNRLN FLKKISQYYQ KFAWPQYLKT   180
VDQHQKAMKP WTQPKTNAIP YVRYL                                        205

SEQ ID NO: 467          moltype = AA   length = 206
FEATURE                 Location/Qualifiers
source                  1..206
                        mol_type = protein
                        organism = Capra hircus
SEQUENCE: 467
MKFFIFTCLL AVALAKHKME HVSSSEEPIN IFQEIYKQEK NMAIHPRKEV VRNANEEEYS    60
IRSSSEEIKI TVDDKHYQKA LNEINQFYQK FPQYLQYPYQ GPIVLNPWDQ VKRNAGAFTP   120
TVNREQLSTS EENSKKTIDM ESTEVFTKKT KLTEEEKNRL NFLKKISQYY QKFAWPQYLK   180
TVDQHQKAMK PWTQPKTNAI PYVRYL                                       206

SEQ ID NO: 468          moltype = AA   length = 223
FEATURE                 Location/Qualifiers
source                  1..223
                        mol_type = protein
                        organism = Ovis aries
SEQUENCE: 468
MKFFIFTCLL AVALAKHKME HVSSSEEPIN ISQEIYKQEK NMAIHPRKEK LCTTSCEEVV    60
RNANEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                    223

SEQ ID NO: 469          moltype = AA   length = 223
FEATURE                 Location/Qualifiers
source                  1..223
                        mol_type = protein
                        organism = Ovis aries
SEQUENCE: 469
MKFFIFTCLL AVALAKHKME HVSSSEEPIN ISQEIYKQEK NMAIHPRKEK LCTTSCEEVV    60
RNADEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                    223

SEQ ID NO: 470          moltype = AA   length = 223
```

```
FEATURE                 Location/Qualifiers
source                  1..223
                        mol_type = protein
                        organism = Ovis aries
SEQUENCE: 470
MKFFIFTCLL AVALAKHKME HVSSSEEPIN ISQEIYKQEK NMAIHPRKEK LCTTSCEEVI    60
RNSNEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 471          moltype = AA   length = 223
FEATURE                 Location/Qualifiers
source                  1..223
                        mol_type = protein
                        organism = Ovis aries
SEQUENCE: 471
MKFFIFTCLL AVALAKHKME HVSSSEEPIN ISQEIYKQEK NMAIHPRKEK LCTTSCEEVV    60
RNANEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNHLNFL   180
KKISQYYQKF AWPQYLKTVD QHQKAMKPWT QPKTNAIPYV RYL                     223

SEQ ID NO: 472          moltype = AA   length = 223
FEATURE                 Location/Qualifiers
source                  1..223
                        mol_type = protein
                        organism = Ovis aries
SEQUENCE: 472
MKFFIFTCLL AVALAKHKME HVSSSEEPIN ISQEIYKQEK NMAIHPRKEK LCTTSCEEVV    60
SNANEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 473          moltype = AA   length = 223
FEATURE                 Location/Qualifiers
source                  1..223
                        mol_type = protein
                        organism = Ovis aries
SEQUENCE: 473
MKFFIFTCLL AVALAKHKME HVSSSEEPIN ISQEIYKQEK NMAIHPRKEK LCTTSCEEVV    60
RNANEEEYSI RSSSEESAEV APEEVKITVY DKHYQKALNE INQFYQKFPQ YLQYLYQGPV   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 474          moltype = AA   length = 222
FEATURE                 Location/Qualifiers
source                  1..222
                        mol_type = protein
                        organism = Bubalus bubalis
SEQUENCE: 474
MKFFIFTCLL AVALAKHTME HVSSSEESII SQETYKQEKN MAIHPSKENL CSTFCKEVIR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EDKNRLNFLK   180
KISQHYQKFA WPQYLKTVYQ YQKAMKPWTQ PKTNVIPYVR YL                      222

SEQ ID NO: 475          moltype = AA   length = 222
FEATURE                 Location/Qualifiers
source                  1..222
                        mol_type = protein
                        organism = Bubalus bubalis
SEQUENCE: 475
MKFFIFTCLL AVALAKHTME HVSSSEESII SQETYKQEKN MAIHPSKENL CSTFCKEVIR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VITKKTKLTE EDKNRLNFLK   180
KISQHYQKFT WPQYLKTVYQ YQKAMKPWTQ PKTKVIPYVR YL                      222

SEQ ID NO: 476          moltype = AA   length = 210
FEATURE                 Location/Qualifiers
source                  1..210
                        mol_type = protein
                        organism = Bubalus bubalis
SEQUENCE: 476
ALAKHTMEHV SSSEESIISQ ETYKQEKNMA IHPSKENLCS TFCKEVIRNA NEEEYSIGSS    60
SEESAEVATE EVKITVDDKH YQKALNEINQ FYQKFPQYLQ YLYQGPIVLN PWDQVKRNAV   120
PITPTLNREQ LSTSEENSKK TVDMESTEVI TKKTKLTEED KNRLNFLKKI SQHYQKFTWP   180
QYLKTVYQYQ KAMKPWTQPK TNVIPYVRYL                                    210

SEQ ID NO: 477          moltype = AA   length = 215
FEATURE                 Location/Qualifiers
source                  1..215
```

```
                        mol_type = protein
                        organism = Bubalus bubalis
SEQUENCE: 477
CLLAVALAKH TMEHVSSEE  SIISQETYKQ EKNMAIHPSK ENLCSTFCKE VIRNANEEEY  60
SIGSSSEESA EVATEEVKIT VDDKHYQKAL NEINQFYQKF PQYLQYLYQG PIVLNPWDQV  120
KRNAVPITPT LNREQLSTSE ENSKKTVDME STEVITKKTK LTEEDKNRLN FLKKISQHYQ  180
KFTWPQYLKT VYQYQKAMKP WTQPKTNVIP YVRYL                            215

SEQ ID NO: 478          moltype = AA  length = 222
FEATURE                 Location/Qualifiers
source                  1..222
                        mol_type = protein
                        organism = Bubalus bubalis
SEQUENCE: 478
MKFFIFTCLL AVALAKHTME HVSSSEESII SQETYKQEKN MAIHPSKENL CSTFCKEVIR  60
NANEEEYSIG SSSEESAEVA TEEVKITVDD KHYQKALNEI NQFYQKFPQY LQYLYQGPIV  120
LNPWDQVKRN AVPITPTLNR EQLSTSEENS KKTVDMESTE VITKKTKLTE EDKNRLNFLK  180
KISQHYQKFT WPQYLKTVYQ YQKAMKPWTQ PKTNVIPYVR YL                    222

SEQ ID NO: 479          moltype = AA  length = 222
FEATURE                 Location/Qualifiers
source                  1..222
                        mol_type = protein
                        organism = Bubalus bubalis
SEQUENCE: 479
MKFFIFTCLL AVALAKHTME HVSSSEESII SQETYKQEKN MAIHPSKENL CSTFCKEVIR  60
NANEEEYSIG SSSEESAEVA TEEVKITVDD KHYQKALNEI NQFYQKFPQY LQYLYQGPIV  120
LNPWDQVERN AVPITPTLNR EQLSTSEENS KKTVDMESTE VITKKTKLTE EDKNRLNFLK  180
KISQHYQKFT WPQYLKTVYQ YQKAMKPWTQ PKTNVIPYVR YL                    222

SEQ ID NO: 480          moltype = AA  length = 213
FEATURE                 Location/Qualifiers
source                  1..213
                        mol_type = protein
                        organism = Bubalus bubalis
SEQUENCE: 480
MKFFIFTCLL AVALAKHTME HVSSSEESII SQETYKQEKN MAIHPSKENL CSTFCKEYSI  60
GSSSEESAEV ATEEVKITVD DKHYQKALNE INQFYQKFPQ YLQYLYQGPI VLNPWDQVKR  120
NAVPITPTLN REQLSTSEEN SKKTVDMEST EVFTKKTKLT EEDKNRLNFL KKISQHYQKF  180
AWPQYLKTVY QYQKAMKPWT QPKTNVIPYV RYL                              213

SEQ ID NO: 481          moltype = AA  length = 213
FEATURE                 Location/Qualifiers
source                  1..213
                        mol_type = protein
                        organism = Bubalus bubalis
SEQUENCE: 481
MKFFIFTCLL AVALAKHTME HVSSSEESII SQETYKQEKN MAIHPSKENL CSTFCKEVIR  60
NANEEEYSIG SSSEESAEVA TEEVKITVDD KHYQKALNEI NQFYQKFPQY LQYLYQGPIV  120
LNPWDQVKRN AVPITPTLNR EQLSTSEEST EVITKKTKLT EEDKNRLNFL KKISQHYQKF  180
TWPQYLKTVY QYQKAMKPWT QPKTNVIPYV RYL                              213

SEQ ID NO: 482          moltype = AA  length = 213
FEATURE                 Location/Qualifiers
source                  1..213
                        mol_type = protein
                        organism = Bubalus bubalis
SEQUENCE: 482
MKFFIFTCLL AVALAKHTME HVSSSEESII SQETYKQEKN MAIHPSKEVI RNANEEEYSI  60
GSSSEESAEV ATEEVKITVD DKHYQKALNE INQFYQKFPQ YLQYLYQGPI VLNPWDQVKR  120
NAVPITPTLN REQLSTSEEN SKKTVDMEST EVITKKTKLT EEDKNRLNFL KKISQHYQKF  180
TWPQYLKTVY QYQKAMKPWT QPKTNVIPYV RYL                              213

SEQ ID NO: 483          moltype = AA  length = 222
FEATURE                 Location/Qualifiers
source                  1..222
                        mol_type = protein
                        organism = Bos mutus
SEQUENCE: 483
MKFFIFTCLL AVALAKNTME HVSSSEESII SQETYKQEKN MAINPSKGNL CSTFCKEVVR  60
NANEEEYSIG SSSEESAEVA TEEVKITVDD KHYQKALNEI NQFYQKFPQY LQYLYQGPIV  120
LNPWDQVKRN AVPITPTLNR EQLSTSEENS KKTVDMESTE VFTKKTKLTE EKNRLNFLK   180
KISQRYQKFA LPQYLKTVYQ HQKAMKPWIQ PKTKVIPYVR YL                    222

SEQ ID NO: 484          moltype = AA  length = 219
FEATURE                 Location/Qualifiers
source                  1..219
                        mol_type = protein
                        organism = Bos mutus
```

-continued

```
SEQUENCE: 484
MKFFIFTCLL AVALAKNTME HVSSSEESII SQETYKQEKN MAINPSKGNL CSTFCKEVVR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMKPWIQ PKTKVIPYV                         219

SEQ ID NO: 485          moltype = AA  length = 222
FEATURE                 Location/Qualifiers
source                  1..222
                        mol_type = protein
                        organism = Jeotgalicoccus aerolatus
SEQUENCE: 485
MKFFIFTCLL AVALAKNTME HVSSSEESII SQETYKQEKN MAINPSKENL CSTFCKEVVR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMKPWIQ PKTKVIPYVR YL                     222

SEQ ID NO: 486          moltype = AA  length = 182
FEATURE                 Location/Qualifiers
source                  1..182
                        mol_type = protein
                        organism = Jeotgalicoccus aerolatus
SEQUENCE: 486
MAINPSKENL CSTFCKEVVR NANEEEYSIG SSSEESAEVA TEEVKITVDD KHYQKALNEI    60
NQFYQKFPQY LQYLYQGPIV LNPWDQVKRN AVPITPTLNR EQLSTSEENS KKTVDMESTE   120
VFTKKTKLTE EEKNRLNFLK KISQRYQKFA LPQYLKTVYQ HQKAMKPWIQ PKTKVIPYVR   180
YL                                                                 182

SEQ ID NO: 487          moltype = AA  length = 237
FEATURE                 Location/Qualifiers
source                  1..237
                        mol_type = protein
                        organism = Jeotgalicoccus coquinae
SEQUENCE: 487
PGLLVFLLGN EDKVNMKFFI FTCLLAVALA KNTMEHVSSS EESIISQETY KQEKNMAINP    60
SKENLCSTFC KEVVRNANEE EYSIGSSSEE SAEVATEEVK ITVDDKHYQK ALNEINQFYQ   120
KFPQYLQYLY QGPIVLNPWD QVKRNAVPIT PTLNREQLST SEENSKKTVD MESTEVFTKK   180
TKLTEEEKNR LNFLKKISQR YQKFALPQYL KTVYQHQKAM KPWIQPKTKV IPYVRYL     237

SEQ ID NO: 488          moltype = AA  length = 222
FEATURE                 Location/Qualifiers
source                  1..222
                        mol_type = protein
                        organism = Bos grunniens
SEQUENCE: 488
MKFFIFTCLL AVALAKNTME HVSSSEESII SQETYKQEKN MAINPSKENL CSTFCKEVVR    60
NANEEEYSIG SSSEESAVVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMEPWIQ PKTKVIPYVR YL                     222

SEQ ID NO: 489          moltype = AA  length = 222
FEATURE                 Location/Qualifiers
source                  1..222
                        mol_type = protein
                        organism = Bison bison
SEQUENCE: 489
MKFFIFTCLL AVALAKNTME HVSSSEESII SQETYKQEKN MAINPSKENL CSTFCKEVVR    60
NVNEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ RQKAMKPWIQ PKTKVIPYVR YL                     222

SEQ ID NO: 490          moltype = AA  length = 414
FEATURE                 Location/Qualifiers
REGION                  1..414
                        note = Bos indicus x Bos taurus
source                  1..414
                        mol_type = protein
                        organism = unidentified
SEQUENCE: 490
MKFFIFTCLL AVALAKNTME HVSSSEESII SQETYKQEKN MAINPSKENL CSTFCKEVVR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMKPWIQ PKTKVIPYVD YSDNIGSPYP VNPSASISYP   240
VIPSASIPYP FNPSASISYP VTPSASIPCP VNPSASIPCP MPDRDFTPPV YLTKTNLPND   300
PAVPSNPLVF TALGAPLYSI AGLPISPFSG QLPPTGVFRL VPVSSRPIGP LYSPNEAAPS   360
ANTYIVEILV PPTTPPHTVP DVQPLTITEP DEAEPAADAL AAPEPQSSIS FDRE         414

SEQ ID NO: 491          moltype = AA  length = 222
FEATURE                 Location/Qualifiers
```

```
source                  1..222
                        mol_type = protein
                        organism = Odocoileus virginianus
SEQUENCE: 491
MKFFIFTCLL AVALAKHKME HVSSSEESIN IQETYKQEKN MAIHPSKENL CSTSCKEVVR     60
NANEEEYSIS SSSEESAEVA TEEVKVTVDD KHYQKILNEI SQFYQKFPQY LQYLYQGPIV    120
MNPWEQVKRT AVPFTPTVNR EQLSTSEENS EKIVDMESTE VFTKKTKLTE EEKNHLNLLK    180
KISQYYQKFA WPQYLKTVYQ YQKAMKPWTQ PKTNAIPYVK YL                      222

SEQ ID NO: 492          moltype = AA   length = 210
FEATURE                 Location/Qualifiers
source                  1..210
                        mol_type = protein
                        organism = Muntiacus muntjak
SEQUENCE: 492
MKNSAKHHKM EHVSSSEESI NIQETYKQEK NMAIHPSKEN LCSTSCKEVV RNANEEEYSI     60
SSSSEESAEV ATEEVKVTVD DKHYQKVLNE ISQLYQKFPQ YLQYLYQGPI VMNPWEQVKR    120
TAGPFTPTVN RDHLSTSEEN SKKIVDMEST EVFTKKTKLT EEEKNRLNFL KKISQYYQKF    180
AWPQYLKTVY QYQKAMKPWT QPKTNAIPYV                                    210

SEQ ID NO: 493          moltype = AA   length = 210
FEATURE                 Location/Qualifiers
source                  1..210
                        mol_type = protein
                        organism = Muntiacus reevesi
SEQUENCE: 493
MKNSAKHHKM EHVSSSEESI NIQETYKQEK NMAIHPSKEN LCSTSCKEVV RNANEEEYSI     60
SSSSEESAEV ATEEAKVTVD DKHYQKVLNE ISQLYQKFPQ YLQYLYQGPI VMNPWEQVKR    120
TAGPFTPTVN RDHLSTSEEN SKKIVDMEST EVFTKKTKLT EEEKNRLNFL KKISQYYQKF    180
AWPQYLKTVY QYQKAMKPWT QPKTNAIPYV                                    210

SEQ ID NO: 494          moltype = AA   length = 235
FEATURE                 Location/Qualifiers
source                  1..235
                        mol_type = protein
                        organism = Cervus elaphus
SEQUENCE: 494
MKFFIFTCLL AVALAKHKME HVSSSEESIN IQETYKQEKN MAIHPSKEVV RNANEEESAD     60
VATEEVKVTV DNKHYQKVLN EISQFYQKFP QYLQYLYQGP IVMNPWEQVK RTAGPFIPTV    120
NRDHLSTSEE NSKKIVDMES TEVFTKKTKL TEEEKNRLNF LKKISQYYQK FAWPQYLKTV    180
YQYQKAMKPW TQPKTNAIPY VVELENLSST VSYLPLSTTS MFGVAHQQDK SQSIS         235

SEQ ID NO: 495          moltype = AA   length = 224
FEATURE                 Location/Qualifiers
source                  1..224
                        mol_type = protein
                        organism = Bos taurus
SEQUENCE: 495
MKVLILACLV ALALARELEE LNVPGEIVES LSSSEESITR INKKIEKFQS EEQQQTEDEL     60
QDKIHPFAQT QSLVYPFPGP IPNSLPQNIP PLTQTPVVVP PFLQPEVMGV SKVKEAMAPK    120
QKEMPFPKYP VEPFTESQSL TLTDVENLHL PLPLLQSWMH QHQPLPPTV MFPPQSVLSL    180
SQSKVLPVPQ KAVPYPQRDM PIQAFLLYQE PVLGPVRGPF PIIV                     224

SEQ ID NO: 496          moltype = AA   length = 224
FEATURE                 Location/Qualifiers
source                  1..224
                        mol_type = protein
                        organism = Bos taurus
SEQUENCE: 496
MKVLILACLV ALALARELEE LNVPGEIVES LSSSEESITR INKKIEKFQS EEQQQTEDEL     60
QDKIHPFAQT QSLVYPFPGP IHNSLPQNIP PLTQTPVVVP PFLQPEVMGV SKVKEAMAPK    120
HKEMPFPKYP VEPFTESQSL TLTDVENLHL PLPLLQSWMH QHQPLPPTV MFPPQSVLSL    180
SQSKVLPVPQ KAVPYPQRDM PIQAFLLYQE PVLGPVRGPF PIIV                     224

SEQ ID NO: 497          moltype = AA   length = 209
FEATURE                 Location/Qualifiers
source                  1..209
                        mol_type = protein
                        organism = Bos taurus
SEQUENCE: 497
RELEELNVPG EIVESLSSSE ESITRINKKI EKFQSEEQQQ TEDELQDKIH PFAQTQSLVY     60
PFPGPIHNSL PQNIPPLTQT PVVVPPFLQP EVMGVSKVKE AMAPKHKEMP FPKYPVEPFT    120
ESQSLTLTDV ENLHLPLPLL QSWMHQHQP LPPTVMFPPQ SVLSLSQSKV LPVPQKAVPY    180
PQRDMPIQAF LLYQEPVLGP VRGPFPIIV                                     209

SEQ ID NO: 498          moltype = AA   length = 224
FEATURE                 Location/Qualifiers
source                  1..224
                        mol_type = protein
```

```
                             organism = Bos taurus
SEQUENCE: 498
MKVLILACLV ALALARELEE LNVPGEIVES LSSSEESITR INKKIEKFQS EEQQQTEDEL    60
QDKIHPFAQT QSLVYPFPGP IPNSLPQNIP PLTQTPVVVP PFLQPEVMGV SKVKGAMAPK   120
HKEMPFPKYP VEPLTESQSL TLTDVENLHL PLPLLQSWMH QPHQPLPPTV MFPPQSVLSL   180
SQSKVLPVPQ KAVPYPQRDM PIQAFLLYQE PVLGPVRGPF PIIV                    224

SEQ ID NO: 499           moltype = AA  length = 224
FEATURE                  Location/Qualifiers
source                   1..224
                         mol_type = protein
                         organism = Bos taurus
SEQUENCE: 499
MKVLILACLV ALALARELEE LNVPGEIVES LSSSEESITR INKKIEKFQS EEQQQTEDEL    60
QDKIHPFAQT QSLVYPFPGP IHNSLPQNIP PLTQTPVVVP PFLQPEVMGV SKVKEAMAPK   120
HKEMPFPKYP VEPFTERQSL TLTDVENLHL PLPLLQSWMH QPHQPLPPTV MFPPQSVLSL   180
SQSKVLPVPQ KAVPYPQRDM PIQAFLLYQE PVLGPVRGPF PIIV                    224

SEQ ID NO: 500           moltype = AA  length = 259
FEATURE                  Location/Qualifiers
source                   1..259
                         mol_type = protein
                         organism = Bos taurus
SEQUENCE: 500
MPLNTIYKQP QNQIIIHSAP PSLLVLYFGK KELRAMKVLI LACLVALALA RELEELNVPG    60
EIVESLSSSE ESITRINKKI EKFQSEEQQQ TEDELQDKIH PFAQTQSLVY PFPGPIHNSL   120
PQNIPPLTQT PVVVPPFLQP EVMGVSKVKE AMAPKHKEMP FPKYPVEPFT ERQSLTLTDV   180
ENLHLPLPLL QSWMHQPHQP LPPTVMFPPQ SVLSLSQSKV LPVPQKAVPY PQRDMPIQAF   240
LLYQEPVLGP VRGPFPIIV                                                259

SEQ ID NO: 501           moltype = AA  length = 224
FEATURE                  Location/Qualifiers
source                   1..224
                         mol_type = protein
                         organism = Bos taurus
SEQUENCE: 501
MKVLILACLV ALALARELEE LNVPGEIVES LSSSEESITR INKKIEKFQS EEQQQTEDEL    60
QDKIHPFAQT QSLVYPFPGP IPNSLPQNIP PLTQTPVVVP PFLQPEVLGV SKVKEAMAPK   120
HKEMPFPKYP VEPFTESQSL TLTDVENLHL PPLLLQSWMH QPHQPLPPTV MFPPQSVLSL   180
SQSKVLPVPQ KAVPYPQRDM PIQAFLLYQQ PVLGPVRGPF PIIV                    224

SEQ ID NO: 502           moltype = AA  length = 216
FEATURE                  Location/Qualifiers
source                   1..216
                         mol_type = protein
                         organism = Bos taurus
SEQUENCE: 502
MKVLILACLV ALALARELEE LNVPGEIVES LSSSEKIEKF QSEEQQQTED ELQDKIHPFA    60
QTQSLVYPFP GPIHNSLPQN IPPLTQTPVV VPPFLQPEVM GVSKVKEAMA PKHKEMPFPK   120
YPVEPFTERQ SLTLTDVENL HLPLPLLQSW MHQPHQPLPP TVMFPPQSVL SLSQSKVLPV   180
PQKAVPYPQR DMPIQAFLLY QEPVLGPVRG PFPIIV                             216

SEQ ID NO: 503           moltype = AA  length = 166
FEATURE                  Location/Qualifiers
source                   1..166
                         mol_type = protein
                         organism = Bos taurus
SEQUENCE: 503
DELQDKIHPF AQTQSLVYPF PGPIPNSLPQ NIPPLTQTPV VVPPFLQPEV MGVSKVKEAM    60
APKHKEMPFP KYPVEPFTES QSLTLTDVEN LHLPLPLLQS WMHQPHQPLP PTVMFPPQSV   120
LSLSQSKVLP VPQKAVPYPQ RDMPIQAFLL YQEPALGPVR GPFPII                  166

SEQ ID NO: 504           moltype = AA  length = 165
FEATURE                  Location/Qualifiers
source                   1..165
                         mol_type = protein
                         organism = Bos taurus
SEQUENCE: 504
DELQDKIPPL PEQSLVYPFP GPIHNSLPQN IPPLTQTPVV VPPFLQPEVM GVSRVKEAMA    60
PKHKEMPFPK YPVEPFTESQ SLTLTDVENL HLPLPLLQSW MHQPHQPLPP TVMFPPQSVL   120
SLSQSKVLPV PQKAVPYPQR DMPIQAFLLY QEPVLGPVRG PFPII                   165

SEQ ID NO: 505           moltype = AA  length = 149
FEATURE                  Location/Qualifiers
source                   1..149
                         mol_type = protein
                         organism = Bos taurus
SEQUENCE: 505
DELQDKIHPF AQTQSLVYPF PGPIPNSLPQ NIPPLTQTPV VVPPFLQPEV MGVSKVKEAM    60
```

```
APKHKEMPFP KYPVEPFTES QSLTLTDVEN LHLPLPLLQS WMHQPHQPLP PTVMFPPQSV    120
LSLSQSKVLP VPQKAVPYPQ RDMPIQAFL                                    149

SEQ ID NO: 506         moltype = AA  length = 149
FEATURE                Location/Qualifiers
source                 1..149
                       mol_type = protein
                       organism = Bos taurus
SEQUENCE: 506
DELQDKIHPF AQTQSLVYPF PGPIHNSLPQ NIPPLTQTPV VVPPFLQPEV MGVSKVKEAM    60
APKHKEMPFP KYPVEPFTES QSLTLTDVEN LHLPLPLLQS WMHQPHQPLP PTVMFPPQSV   120
LSLSQSKVLP VPQKAVPYPQ RDMPIQAFL                                    149

SEQ ID NO: 507         moltype = AA  length = 146
FEATURE                Location/Qualifiers
source                 1..146
                       mol_type = protein
                       organism = Bos taurus
SEQUENCE: 507
KIHPFAQTQS LVYPFPGPIH NSLPQNIPPL TQTPVVVPPF LQPEVMGVSK VKEAMAPKHK    60
EMPFPKYPVE PFTERQSLTL TDVENLHLPL PLLQSWMHQP HQPLPPTVMF PPQSVLSLSQ   120
SKVLPVPQKA VPYPQRDMPI QAFLLV                                       146

SEQ ID NO: 508         moltype = AA  length = 222
FEATURE                Location/Qualifiers
source                 1..222
                       mol_type = protein
                       organism = Capra hircus
SEQUENCE: 508
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KAVPQRDMPI QAFLLYQEPV LGPVRGPFPI LV                      222

SEQ ID NO: 509         moltype = AA  length = 222
FEATURE                Location/Qualifiers
source                 1..222
                       mol_type = protein
                       organism = Capra hircus
SEQUENCE: 509
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KVVPQRDMPI QAFLLYQEPV LGPVRGPFPI LV                      222

SEQ ID NO: 510         moltype = AA  length = 222
FEATURE                Location/Qualifiers
source                 1..222
                       mol_type = protein
                       organism = Capra hircus
SEQUENCE: 510
MKVLILACLV ALALAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KAVPQRDMPI QAFLLYQEPV LGPVRGPFPI LV                      222

SEQ ID NO: 511         moltype = AA  length = 223
FEATURE                Location/Qualifiers
source                 1..223
                       mol_type = protein
                       organism = Capra hircus
SEQUENCE: 511
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KVVPQRDMPI QAFLLYQEPV LGPVRGPFPI LVV                     223

SEQ ID NO: 512         moltype = AA  length = 257
FEATURE                Location/Qualifiers
source                 1..257
                       mol_type = protein
                       organism = Capra hircus
SEQUENCE: 512
MPLNTIYKQP LNQIIIHSAS PSLLLLYFGK KESRAMKVLI LACLVALAIA REQEELNVVG    60
ETVESLSSSE ESITHINKKI EKFQSEEQQQ TEDELQDKIH PFAQAQSLVY PFTGPIPNSL   120
PQNILPLTQT PVVVPPFLQP EIMGVPKVKE TMVPKHKEMP FPKYPVEPFT ESQSLTLTDV   180
EKLHLPLPLV QSWMHQPPQP LSPTVMFPPQ SVLSLSQPKV LPVPQKVVPQ RDMPIQAFLL   240
YQEPVLGPVR GPFPILV                                                 257
```

```
SEQ ID NO: 513           moltype = AA   length = 222
FEATURE                  Location/Qualifiers
source                   1..222
                         mol_type = protein
                         organism = Capra hircus
SEQUENCE: 513
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KVVPQRDMPI QAFLLYQEPV LGPVRGPFPI LN                     222

SEQ ID NO: 514           moltype = AA   length = 257
FEATURE                  Location/Qualifiers
source                   1..257
                         mol_type = protein
                         organism = Capra hircus
SEQUENCE: 514
MPLNTIYKQP LNQIIIHSAS PSLLLLYFGK KESRAMKVLI LACLVALAIA REQEELNVVG    60
ETVESLSSSE ESITHINKKI EKFQSEEQQQ TEDELQDKIH PFAQAQSLVY PFTGPIPNSL   120
PQNILPLTQT PVVVPPFLQP EIMGVPKVKE TMVPKHKEMP FPKYPVEPFT ESQSLTLTDV   180
EKLHLPLPLV QSWMHQPPQP LSPTVMFPPQ SVLSLSQPKV LPVPQKVVPQ RDMPIQAFLL   240
YQEPVLGPVR GPFPILN                                                 257

SEQ ID NO: 515           moltype = AA   length = 222
FEATURE                  Location/Qualifiers
source                   1..222
                         mol_type = protein
                         organism = Capra hircus
SEQUENCE: 515
MKVLILACLV ALDIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KVVPQRDMPI QAFLLYQEPV LGPVRGPFPI LN                     222

SEQ ID NO: 516           moltype = AA   length = 160
FEATURE                  Location/Qualifiers
source                   1..160
                         mol_type = protein
                         organism = Capra hircus
SEQUENCE: 516
DELQDKIHPF AQAQSLVYPF TGPIPNSLPQ NILPLTQTPV VVPPFLQPEI MGVPKVKETM    60
VPKHKEMPFP KYPVEPFTES QSLTLTDVEK LHLPLPLVQS WMHQPPQPLS PTVMFPPQSV   120
LSLSQPKVLP VPQKAVPQRD MPIQAFLLYQ EPVLGPVRGP                        160

SEQ ID NO: 517           moltype = AA   length = 188
FEATURE                  Location/Qualifiers
source                   1..188
                         mol_type = protein
                         organism = Capra hircus
SEQUENCE: 517
MKVLILACLV ALALAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPV                                                           188

SEQ ID NO: 518           moltype = AA   length = 160
FEATURE                  Location/Qualifiers
source                   1..160
                         mol_type = protein
                         organism = Capra hircus
SEQUENCE: 518
DELQDKIHPF AQAQSLVYPF TGPIPNSLPQ NILPLTQTPV VVPPFLQPEI MGVPKVKETM    60
VPKHKEMPFP KYPVEPFTES QSLTLTDVEK LHLPLPLVQS WMHQPPQPLS PTVMFPPQSV   120
LSLSQPKVLP VPQKVVPQRD MPIQAFLLYQ EPVLGPVRGP                        160

SEQ ID NO: 519           moltype = AA   length = 181
FEATURE                  Location/Qualifiers
source                   1..181
                         mol_type = protein
                         organism = Capra hircus
SEQUENCE: 519
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
S                                                                  181

SEQ ID NO: 520           moltype = AA   length = 149
FEATURE                  Location/Qualifiers
source                   1..149
```

```
                            mol_type = protein
                            organism = Capra hircus
SEQUENCE: 520
QAQSLVYPFT GPIPNSLPQN ILPLTQTPVV VPPFLQPEIM GVPKVKETMV PKHKEMPFPK    60
YPVEPFTESQ SLTLTDVEKL HLPLPLVQSW MHQPPQPLSP TVMFPPQSVL SLSQPKVLPV   120
PQKAVPQRDM PIQAFLLYQE PVLGPVRGP                                    149

SEQ ID NO: 521              moltype = AA  length = 148
FEATURE                     Location/Qualifiers
source                      1..148
                            mol_type = protein
                            organism = Capra hircus
SEQUENCE: 521
DEVQDKIHPF AQAQSLVYPF TGPIPNSLPQ NILPLTQTPV VVPPFLQPEI MGVPKVKETM    60
VPKHKEMPFP KYPVEPFTES QSLTLTDVEK LHLPLPLVQS WMHQPPQPLS PTVMFPPQSV   120
LSLSQPKVLP VPQKAVPQRD MPIQAFLL                                     148

SEQ ID NO: 522              moltype = AA  length = 222
FEATURE                     Location/Qualifiers
source                      1..222
                            mol_type = protein
                            organism = Ovis aries
SEQUENCE: 522
MKVLILACLV ALALAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLPPTV MFPPQSVLSL   180
SQPKVLPVPQ KAVPQRDMPI QAFLLYQEPV LGPVRGPFPI LV                     222

SEQ ID NO: 523              moltype = AA  length = 222
FEATURE                     Location/Qualifiers
VARIANT                     7
                            note = X can be any naturally occurring amino acid
source                      1..222
                            mol_type = protein
                            organism = Ovis aries
SEQUENCE: 523
MKVLILXCLV ALALAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLPPTV MFPPQSVLSL   180
SQPKVLPVPQ KAVPQRDMPI QAFLLYQEPV LGPVRGPFPI LV                     222

SEQ ID NO: 524              moltype = AA  length = 224
FEATURE                     Location/Qualifiers
source                      1..224
                            mol_type = protein
                            organism = Bubalus bubalis
SEQUENCE: 524
MKVLILACLV ALALARELEE LNVPGEIVES LSSSEESITH INKKIEKFQS EEQQQTEDEL    60
QDKIHPFAQT QSLVYPFGP IPNSLPQNIP PLTQTPVVVP PFLQPEIMGV SKVKEAMAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                   224

SEQ ID NO: 525              moltype = AA  length = 259
FEATURE                     Location/Qualifiers
source                      1..259
                            mol_type = protein
                            organism = Bubalus bubalis
SEQUENCE: 525
MPLNTIYKQP QNQIIIHSAP PSLLVLYFGK KKLRVMKVLI LACLVALALA RELEELNVPG    60
EIVESLSSSE ESITHINKKI EKFQSEEQQQ TEDELQDKIH PFAQTQSLVY PFPGPIPNSL   120
PQNIPPLTQT PVVVPPFLQP EIMGVSKVKE AMAPKHKEMP FPKYPVEPFT ESQSLTLTDV   180
ENLHLPLPLL QSWMHQPPQP LPPTVMFPPQ SVLSLSQSKV LPVPQKAVPY PQRDMPIQAF   240
LLYQEPVLGP VRGPFPIIV                                               259

SEQ ID NO: 526              moltype = AA  length = 224
FEATURE                     Location/Qualifiers
source                      1..224
                            mol_type = protein
                            organism = Bubalus bubalis
SEQUENCE: 526
MKVLILACLV ALALARELEE LNVPGEIVES LSSSEESITH INKKIEKFQS EEQQQTEDEL    60
QDKIHPFAQT QSLVYPFPGP IPNSLPQNIP PLTQTPVVVP PFLQPEIMGV SKVKEAMAPK   120
HKEMPFPKYP FEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                   224

SEQ ID NO: 527              moltype = AA  length = 224
FEATURE                     Location/Qualifiers
source                      1..224
                            mol_type = protein
```

```
                           organism = Bubalus bubalis
SEQUENCE: 527
MKVLILACLV ALALARELEE LNVPSEIVES LSSSEESITH INKKIEKFQS EEQQQTEDEL    60
QDKIHPFAQT QSLVYPFPGP IPNSLPQNIP PLTQTPVVVP PFLQPEIMGV SKVKEAMAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 528          moltype = AA  length = 224
FEATURE                 Location/Qualifiers
source                  1..224
                        mol_type = protein
                        organism = Bubalus bubalis
SEQUENCE: 528
MKVLILACLV ALALARELEE LNVPSEIVES LSSSEESITH INKKIEKFQS EEQRQTEDEL    60
QDKIHPFAQT QSLVYPFPGP IPNSLPQNIP PLTQTPVVVP PFLQPEIMGV SKVKEAMAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 529          moltype = AA  length = 224
FEATURE                 Location/Qualifiers
source                  1..224
                        mol_type = protein
                        organism = Bubalus bubalis
SEQUENCE: 529
MKVLILACLV ALALARELEE LNVPGEIVES LSSSEESITH INKKIEKFQS EEQQQMEDEL    60
QDKIHPFAQT QSLVYPFPGP IPKSLPQNIP PLTQTPVVVP PFLQPEIMGV SKVKEAMAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 530          moltype = AA  length = 259
FEATURE                 Location/Qualifiers
source                  1..259
                        mol_type = protein
                        organism = Bubalus bubalis
SEQUENCE: 530
MPLNTIYKQP QNQIIIHSAP PSLLVLYFGK KKLRAMKVLI LACLVALALA RELEELNVPG    60
EIVESLSSSE ESITHINKKI EKFQSEEQQQ MEDELQDKIH PFAQTQSLVY PFPGPIPKSL   120
PQNIPPLTQT PVVVPPFLQP EIMGVSKVKE AMAPKHKEMP FPKYPVEPFT ESQSLTLTDV   180
ENLHLPLPLL QSWMHQPPQP LPPTVMFPPQ SVLSLSQSKV LPVPQKAVPY PQRDMPIQAF   240
LLYQEPVLGP VRGPFPIIV                                                259

SEQ ID NO: 531          moltype = AA  length = 224
FEATURE                 Location/Qualifiers
source                  1..224
                        mol_type = protein
                        organism = Bubalus bubalis
SEQUENCE: 531
MKVLILACLV ALALARELEE LNVPGEIVES LSSSEESITH INKKIEKFQS EEQQQMEDEL    60
QDKIHPFAQT QSLVYPFPGP IPKSLPQNIP PLTQTPVVVP PFLQPEIMGV SKVKEATAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 532          moltype = AA  length = 209
FEATURE                 Location/Qualifiers
source                  1..209
                        mol_type = protein
                        organism = Bubalus bubalis
SEQUENCE: 532
RELEELNVPG EIVESLSSSE ESITHINKKI EKFQSEEQQQ TEDELQDKIH PFAQTQSLVY    60
PFPGPIPKSL PQNIPPLTQT PVVVPPFLQP EIMGVSKVKE AMAPKHKEMP FPKYPVQPET   120
ESQSLTLTDV ENLHLPPLLL QSWMHQPHQP LPPTVMFPPQ SVLSLSQSKV LPVPEKAVPY   180
PQRDMPIQAF LLYQEPVLGP VRGPFPIIV                                     209

SEQ ID NO: 533          moltype = AA  length = 166
FEATURE                 Location/Qualifiers
source                  1..166
                        mol_type = protein
                        organism = Bubalus bubalis
SEQUENCE: 533
DELQDKIHPF AQTQSLVYPF PGPIPNSLPQ NIPPLTQTPV VVPPFLQPEI MGVSKVKEAM    60
APKHKEMPFP KYPVEPFTES QSLTLTDVEN LHLPLPLLQS WMHQPPQPLP PTVMFPPQSV   120
LSLSQSKVLP VPQKAVPYPQ RDMPIQAFLL YQEPVLGPVR GPFPII                  166

SEQ ID NO: 534          moltype = AA  length = 166
FEATURE                 Location/Qualifiers
source                  1..166
                        mol_type = protein
                        organism = Bubalus bubalis
SEQUENCE: 534
```

```
DELQDKIHPF AQTQSLVYPF PGPIPKSLPQ NIPPLTQTPV VVPPFLQPEI MGVSKVKEAM    60
APKHKEMPFP KYPVEPFTES QSLTLTDVEN LHLPLPLLQS WMHQPPQPLP PTVMFPPQSV   120
LSLSQSKVLP VPQKAVPYPQ RDMPIQAFLL YQEPVLGPVR GPFPII                 166

SEQ ID NO: 535          moltype = AA   length = 166
FEATURE                 Location/Qualifiers
source                  1..166
                        mol_type = protein
                        organism = Bubalus bubalis
SEQUENCE: 535
DELQDKNHPF AQTQSLVYPF PGPIPKSLPQ NIPPLTQTPV VVPPFLQPEI MGVSKVKEAM    60
APKHKEMPFP KYPVEPFTES QSLTLTDVEN LHLPLPLLQS WMHQPPQPLP PTVMFPPQSV   120
LSLSQSKVLP VPQKAVPYPQ RDMPIQAFLL YQEPVLGPVR GPFPII                 166

SEQ ID NO: 536          moltype = AA   length = 165
FEATURE                 Location/Qualifiers
source                  1..165
                        mol_type = protein
                        organism = Bubalus bubalis
SEQUENCE: 536
DELQDKIPPL PEQSLVYPFP APIPKSLPQN IPPLTQTPVV VPPFLQPEIM GVSKVKEAMA    60
PKHKEMPFPK YPVEPFTESQ SLTLTDVENL HLPLPLLQSW MHQPPQPLPP TVMFPPQSVL   120
SLSQSKVLPV PQKAVPYPQR DMPIQAFLLY QEPVLGPVRG PFPII                  165

SEQ ID NO: 537          moltype = AA   length = 155
FEATURE                 Location/Qualifiers
source                  1..155
                        mol_type = protein
                        organism = Bubalus bubalis
SEQUENCE: 537
IHPFAQTQSL VYPFPGPIPN SLPQNIPPLT QTPVVPPFL QPEIMGVSKV KEAMAPKHKE     60
MPFPKYPVEP FTESQSLTLT DVENLHLPLP LLQSWMHQPP QPLPPTVMFP PQSVLSLSQS   120
KVLPVPQKAV PYPQRDMPIQ AFLLYQEPVL GPVRG                             155

SEQ ID NO: 538          moltype = AA   length = 155
FEATURE                 Location/Qualifiers
source                  1..155
                        mol_type = protein
                        organism = Bubalus bubalis
SEQUENCE: 538
IHPFAQTQSL VYPFPGPIPK SLPQNIPPLT QTPVVPPFL QPEIMGVSKV KEAMAPKHKE     60
MPFPKYPVEP FTESQSLTLT DVENLHLPLP LLQSWMHQPP QPLPPTVMFP PQSVLSLSQS   120
KVLPVPQKAV PYPQRDMPIQ AFLLYQEPVL GPVRG                             155

SEQ ID NO: 539          moltype = AA   length = 235
FEATURE                 Location/Qualifiers
source                  1..235
                        mol_type = protein
                        organism = Bos mutus
SEQUENCE: 539
MKVLILACLV ALALARELEE LNVPGEIVES LSSSEESITR INKKIEKFQS EEQQQTEDEL    60
QDKIHPFAQT QSLVYPFPGP IPNSLPQNIP PLTQTPVVVP PFLQPEVMGV SKVKEAMAPK   120
HKEMPFPKYP VEPFTESQSL TLTDVENLHL PLPLLQSWMH QPHQPLPPTV MFPPQSVLSL   180
SQSKVLPVPQ KAVPYPQRDM PIQAFLLYQE PVLGPVRGPF PIIVSLNLLT VLFNF        235

SEQ ID NO: 540          moltype = AA   length = 270
FEATURE                 Location/Qualifiers
source                  1..270
                        mol_type = protein
                        organism = Bos mutus
SEQUENCE: 540
MPLNTIYKQP QNQIIIHSAP PSLLVLYFGK KELRAMKVLI LACLVALALA RELEELNVPG    60
EIVESLSSSE ESITRINKKI EKFQSEEQQQ TEDELQDKIH PFAQTQSLVY PFPGPIPNSL   120
PQNIPPLTQT PVVVPPFLQP EVMGVSKVKE AMAPKHKEMP FPKYPVEPFT ESQSLTLTDV   180
ENLHLPLPLL QSWMHQPHQP LPPTVMFPPQ SVLSLSQSKV LPVPQKAVPY PQRDMPIQAF   240
LLYQEPVLGP VRGPFPIIVS LNLLTVLFNF                                   270

SEQ ID NO: 541          moltype = AA   length = 259
FEATURE                 Location/Qualifiers
source                  1..259
                        mol_type = protein
                        organism = Bos mutus
SEQUENCE: 541
MPLNTIYKQP QNQIIIHSAP PSLLVLYFGK KELRAMKVLI LACLVALALA RELEELNVPG    60
EIVESLSSSE ESITRINKKI EKFQSEEQQQ TEDELQDKIH PFAQTQSLVY PFPGPIPNSL   120
PQNIPPLTQT PVVVPPFLQP EVMGVSKVKE AMAPKHKEMP FPKYPVEPFT ESQSLTLTDV   180
ENLHLPLPLL QSWMHQPHQP LPPTVMFPPQ SVLSLSQSKV LPVPQKAVPY PQRDMPIQAF   240
LLYQEPVLGP VRGPFPIIV                                               259
```

```
SEQ ID NO: 542              moltype = AA  length = 216
FEATURE                     Location/Qualifiers
source                      1..216
                            mol_type = protein
                            organism = Bos mutus
SEQUENCE: 542
MKVLILACLV ALALARELEE LNVPGEIVES LSSSEKIEKF QSEEQQQTED ELQDKIHPFA    60
QTQSLVYPFP GPIPNSLPQN IPPLTQTPVV VPPFLQPEVM GVSKVKEAMA PKHKEMPFPK   120
YPVEPFTESQ SLTLTDVENL HLPLPLLQSW MHQPHQPLPP TVMFPPQSVL SLSQSKVLPV   180
PQKAVPYPQR DMPIQAFLLY QEPVLGPVRG PFPIIV                             216

SEQ ID NO: 543              moltype = AA  length = 227
FEATURE                     Location/Qualifiers
source                      1..227
                            mol_type = protein
                            organism = Bos mutus
SEQUENCE: 543
MKVLILACLV ALALARELEE LNVPGEIVES LSSSEKIEKF QSEEQQQTED ELQDKIHPFA    60
QTQSLVYPFP GPIPNSLPQN IPPLTQTPVV VPPFLQPEVM GVSKVKEAMA PKHKEMPFPK   120
YPVEPFTESQ SLTLTDVENL HLPLPLLQSW MHQPHQPLPP TVMFPPQSVL SLSQSKVLPV   180
PQKAVPYPQR DMPIQAFLLY QEPVLGPVRG PFPIIVSLNL LTVLFNF                 227

SEQ ID NO: 544              moltype = AA  length = 224
FEATURE                     Location/Qualifiers
VARIANT                     197
                            note = X can be any naturally occurring amino acid
source                      1..224
                            mol_type = protein
                            organism = Bos indicus
SEQUENCE: 544
MKVLILACLV ALALARELEE LNVPGEIVES LSSSEESITR INKKIEKFQS EEQQQTEDEL    60
QDKIHPFAQT QSLVYPFPGP IPNSLPQNIP PLTQTPVVVP PFLQPEVMGV SKVKEAMAPK   120
HKEMPFPKYP VEPFTESQSL TLTDVENLHL PLPLLQSWMH QPHQPLPPTV MFPPQSVLSL   180
SQSKVLPVPQ KAVPYPXRDM PIQAFLLYQE PVLGPVRGPF PIIV                    224

SEQ ID NO: 545              moltype = AA  length = 224
FEATURE                     Location/Qualifiers
VARIANT                     197
                            note = X can be any naturally occurring amino acid
source                      1..224
                            mol_type = protein
                            organism = Bos indicus
SEQUENCE: 545
MKVLILACLV ALALARELEE LNVPGEIVES LSSSEESITR INKKIEKFQS EEQQQTEDEL    60
QDKIHPFAQT QSLVYPFPGP IHNSLPQNIP PLTQTPVVVP PFLQPEVMGV SKVKEAMAPK   120
HKEMPFPKYP VEPFTESQSL TLTDVENLHL PLPLLQSWMH QPHQPLPPTV MFPPQSVLSL   180
SQSKVLPVPQ KAVPYPXRDM PIQAFLLYQE PVLGPVRGPF PIIV                    224

SEQ ID NO: 546              moltype = AA  length = 165
FEATURE                     Location/Qualifiers
source                      1..165
                            mol_type = protein
                            organism = Bos indicus
SEQUENCE: 546
DELQDKIPPL PEQSLVYPFP GPIPNSLPQN IPPLTQTPVV VPPFLQPEVM GVSKVKEAMA    60
PKHKEMPFPK YPVEPFTESQ SLTLTDVENL HLPLPLLQSW MHQPHQPLPP TVMFPPQSVL   120
SLSQSKVLPV PQKAVPYPQR DMPIQAFLLY QEPVLGPVRG PFPII                   165

SEQ ID NO: 547              moltype = AA  length = 155
FEATURE                     Location/Qualifiers
source                      1..155
                            mol_type = protein
                            organism = Bos indicus
SEQUENCE: 547
IHPFAQTQSL VYPFPGPIPN SLPQNIPPLT QTPVVVPPFL QPEVMGVSKV KEAMAPKHKE    60
MPFPKYPVEP FTESQSLTLT DVENLHLPLP LLQSWMHQPH QPLPPTVMFP PQSVLSLSQS   120
KVLPVPQKAV YPQRDMPIQ AFLLYQEPVL GPVRG                               155

SEQ ID NO: 548              moltype = AA  length = 152
FEATURE                     Location/Qualifiers
source                      1..152
                            mol_type = protein
                            organism = Bos indicus
SEQUENCE: 548
QSLVYPFPGP IPNSLPQNIP PLTQTPVVVP PFLQPEVMGV SKVKEAMAPK HKEMPFPKYP    60
VEPFTESQSL TLTDVENLHL PLPLLQSWMH QPHQPLPPTV MFPPQSVLSL SQSKVLPVPQ   120
KAVPYPQRDM PIQAFLLYQE PVLGPVRGPF PI                                 152

SEQ ID NO: 549              moltype = AA  length = 154
```

```
FEATURE                 Location/Qualifiers
source                  1..154
                        mol_type = protein
                        organism = Bos indicus
SEQUENCE: 549
LPDQSLVYPF PGPIPNSLPQ NIPPLTQTPV VVPPFLQPEV MGVSKVKEAM APKHKEMPFP    60
KYPVEPFTES QSLTLTDVEN LHLPLPLLQS WMHQPHQPLP PTVMFPPQSV LSLSQSKVLP   120
VPQKAVPYPQ RDMPIQAFLL YQEPVLGPVR GPFP                               154

SEQ ID NO: 550          moltype = AA   length = 224
FEATURE                 Location/Qualifiers
source                  1..224
                        mol_type = protein
                        organism = Bison bison
SEQUENCE: 550
MKVLILACLV ALARELEE LNVPGEIVES LSSSEESITR INKKIEKFQS EEQQQTEDEL      60
QDKIHPFAQT QSLVYPFPGP IPNSLPQNIP PLTQTPVVVP PFLQPEVMGV SKVKEAMAPK   120
HKEMPFPKYP VEPFTESQSL TLTDVENLHL PLPLLQSWMH QPHQPLPPTV MFPPQSVLSL   180
SQSKVLPVPQ KAVPYPQRDM PIQAFLLYQE PVLGPVRGPF PIIV                    224

SEQ ID NO: 551          moltype = AA   length = 177
FEATURE                 Location/Qualifiers
source                  1..177
                        mol_type = protein
                        organism = Jeotgalicoccus aerolatus
SEQUENCE: 551
FQSEEQQQTE DELQDKIHPF AQTQSLVYPF PGPIPNSLPQ NIPPLTQTPV VVPPFLQPEV    60
MGVSKVKEAM APKHKEMPFP KYPVEPFTES QSLTLTDVEN LHLPLPLLQS WMHQPHQPLP   120
PTVMFPPQSV LSLSQSKVLP VPQKAVPYPQ RDMPIQAFLL YQEPVLGPVR GPFPIIV      177

SEQ ID NO: 552          moltype = AA   length = 240
FEATURE                 Location/Qualifiers
source                  1..240
                        mol_type = protein
                        organism = Jeotgalicoccus coquinae
SEQUENCE: 552
PPSLLVLYFG KKELRAMKVL ILACLVALAL ARELEELNVP GEIVESLSSS EESITRINKK    60
IEKFQSEEQQ QTEDELQDKI HPFAQTQSLV YPFPGPIPNS LPQNIPPLTQ TPVVVPPFLQ   120
PEVMGVSKVK EAMAPKHKEM PFPKYPVEPF TESQSLTLTD VENLHLPLPL LQSWMHQPHQ   180
PLPPTVMFPP QSVLSLSQSK VLPVPQKAVP YPQRDMPIQA FLLYQEPVLG PVRGPFPIIV   240

SEQ ID NO: 553          moltype = AA   length = 224
FEATURE                 Location/Qualifiers
REGION                  1..224
                        note = Bos indicus x Bos taurus
source                  1..224
                        mol_type = protein
                        organism = unidentified
SEQUENCE: 553
MKVLILACLV ALARELEE LNVPGEIVES LSSSEESITR INKKIEKFQS EEQQQTEDEL      60
QEKIHPFAQT QSLVYPFPGP IPNSLPQNIP PLTQTPVVVP PFLQPEVMGV SKVKEAMAPK   120
HKEMPFPKYP VEPFTESQSL TLTDVENLHL PLPLLQSWMH QPHQPLPPTV MFPPQSVLSL   180
SQSKVLPVPQ KAVPYPQRDM PIQAFLLYQE PVLGPVRGPF PIIV                    224

SEQ ID NO: 554          moltype = AA   length = 153
FEATURE                 Location/Qualifiers
REGION                  1..153
                        note = Bos indicus x Bos taurus
source                  1..153
                        mol_type = protein
                        organism = unidentified
SEQUENCE: 554
QSLVYPFPGP IPNSLPQNIP PLTQTPVVVP PFLQPEVMGV SKVKEAMAPK HKEMPFPKYP    60
VEPFTESQSL TLTDVENLHL PLPLLQSWMH QPHQPLPPTV MFPPQSVLSL SQSKVLPVPQ   120
KAVPYPQRDM PIQAFLLYQE PVLGPVRGPF PIL                                153

SEQ ID NO: 555          moltype = AA   length = 150
FEATURE                 Location/Qualifiers
REGION                  1..150
                        note = Bos indicus x Bos taurus
source                  1..150
                        mol_type = protein
                        organism = unidentified
SEQUENCE: 555
DEVQDKIHPF AQTQSLVYPF PGPIPNSLPQ NIPPLTQTPV VVPPFLQPEV MGVSKVKEAM    60
APKHKEMPFP KYPVEPFTES QSLTLTDVEN LHLPLPLLQS WMHQPHQPLP PTVMFPPQSV   120
LSLSQSKVLP VPQKAVPYPQ RDMPIQAFLL                                    150

SEQ ID NO: 556          moltype = AA   length = 259
```

```
FEATURE                 Location/Qualifiers
source                  1..259
                        mol_type = protein
                        organism = Bos grunniens
SEQUENCE: 556
MPLNTIYKQP QNQIIIHSAP PSLLVLYFGK KELGAMKVLI LACLVALALA RELEELNVPG    60
EIVEGLSSSE ESITRINKKI EKFQSEEQQQ TEDGLQDKIH PFAQTQSLVY PFPGPIPNSL   120
PQNIPPLTQT PVVVPPFLQP EVMGVSKVKE AMAPKHKEMP FPKYPVEPFT ESQSLTLTDV   180
ENLHLPLPLL QSWMHQPHQP LPPTVMFPPQ SVLSLSQSKV LPVPQKAVPY PQRDMPIQAF   240
LLYQEPVLGP VRGPFPIIV                                                259

SEQ ID NO: 557          moltype = AA  length = 166
FEATURE                 Location/Qualifiers
source                  1..166
                        mol_type = protein
                        organism = Bos grunniens
SEQUENCE: 557
DELQDKIHPF AQTQSLVYPF PGPIPNSLPQ NIPPLTQTPV VVPPFLQPEV MGVSKVKEAM    60
APKHKEMPFP KYPVEPFTES QSLTLTDVEN LHLPLPLLQS WMHQPHQPLP PTVMFPPQSV   120
LSLSQSKVLP VPQKAVPYPQ RDMPIQAFLL YQEPVLGPVR GPFPII                  166

SEQ ID NO: 558          moltype = AA  length = 166
FEATURE                 Location/Qualifiers
source                  1..166
                        mol_type = protein
                        organism = Bos grunniens
SEQUENCE: 558
DELQDKIHPF AQTQSLVYPF PGPIPNSLPQ NIPPLTQTPV VVPPFLQPEV MGVSKVKEAM    60
APKHEEMPFP KYPVEPFTES QSLTLTDVEN LHLPLPLLQS WMHQPHQPLP PTVMFPPQSV   120
LSLSQSKVLP VPQKAVPYPQ RDMPIQAFLL YQEPVLGPVR GPFPII                  166

SEQ ID NO: 559          moltype = AA  length = 155
FEATURE                 Location/Qualifiers
source                  1..155
                        mol_type = protein
                        organism = Bos grunniens
SEQUENCE: 559
QSLVYPFPGP IPNSLPQNIP PLTQTPVVVP PFLQPEVMGV SKVKEAMAPK HKEMPFPKYP    60
VEPFTESQSL TLTDVENLHL PLPLLQSWMH QPHQPLPPTV MFPPQSVLSL SQSKVLPVPQ   120
KAVPYPQRDM PIQAFLLYQE PVLGPVRGPF PIFVS                              155

SEQ ID NO: 560          moltype = AA  length = 224
FEATURE                 Location/Qualifiers
source                  1..224
                        mol_type = protein
                        organism = Neophocaena asiaeorientalis
SEQUENCE: 560
MKVLILACLL ALALAREKEE LIVSGETVKS LSSSEESVTH INEKIEKFKH EEQQQTEDER    60
QDRIHHFSQP QPLVYSYTGP IPYPILPKNI LPLAQPPVVV PPFQPEIMEV PKAKETILPK   120
HKEMRFPKSP VEPFIESQSL TLTDLENLHL PLPLLQSLMH QPPHRLPPTL MFPPQPLQSL   180
SQSKVLPIPQ QVVPYLQRDM PIQTLLLYQE PVLGPIQGLY PVIV                    224

SEQ ID NO: 561          moltype = AA  length = 258
FEATURE                 Location/Qualifiers
source                  1..258
                        mol_type = protein
                        organism = Odocoileus virginianus
SEQUENCE: 561
MPLNTIYKQP QNQIIIHSGS PSLLVLYVGK EELRAMKVLI LACLVALALA KEEELNVSSE    60
IVESISSSEE SITHITKKIE KLQSEGQQQA EDELQDKIHP FAQTQSLVYP FTGPIPYSLP   120
QNFLPLPQTP VMVPPFLQPE IMGVSEVKET MVPKHKEMPF PKYPVEPFAE GQSLTLTEAE   180
NLHFPLPLPQ SWMHQTPQPL PPAVMFPPQS VLSLSQPKVL SVPQKAVPYP QRDMPIQAFL   240
LYQEPVPGPV RGPFPFIV                                                 258

SEQ ID NO: 562          moltype = AA  length = 222
FEATURE                 Location/Qualifiers
source                  1..222
                        mol_type = protein
                        organism = Muntiacus reevesi
SEQUENCE: 562
MKVLILACLV ALAREEEL NVSGERLSSS SKAESITHIT KKIEKLQSEG QQQTEAELQD      60
KIHPFAQTQP LVYPFTGPIP YSLPQNFLPL PQTPMVVPPF LQPEIMGVSE VKETMVPKHK   120
EMPFPKYPVE PFAEGQSLTL TDVENLHLPL PVLQPWMHQT PQPLPPTVMF PPQSVLSLSQ   180
PKVLSVPQKA VPYPQREMPI QAFLLYQEPV PGPVPGPFPI IV                      222

SEQ ID NO: 563          moltype = AA  length = 230
FEATURE                 Location/Qualifiers
source                  1..230
                        mol_type = protein
```

```
                              organism = Muntiacus muntjak
SEQUENCE: 563
MKVLILACLV ALALAREEEL NVSGESRTLL KRLSSSSSSK AESITHITKK IEKLPSEGQQ    60
QTEAELQDKI HPFAQTQPLV YPFTGPIPYS LPQNFLPLPQ TPMVVPPFLQ PEIMGVSEVK   120
ETMVPKHKEM PFPKYPVEPF AEGQSLTLTD VENLHLPLPV LQPWMHQTPQ PLPPTVMFPP   180
QSVLSLSQPK VLSVPQKAVP YPQREMPIQA FLLYQEPVPG PVPGPFPIIV              230

SEQ ID NO: 564           moltype = AA  length = 163
FEATURE                  Location/Qualifiers
source                   1..163
                         mol_type = protein
                         organism = Bos taurus
SEQUENCE: 564
MLIVTQTMKG LDIQKVAGTW YSLAMAASDI SLLDAQSAPL RVYVEELKPT PEGDLEILLQ    60
KWENGECAQK KIIAEKTKIP AVFKIDALNE NKVLVLDTDY KKYLLFCMEN SAEPEQSLAC   120
QCLVRTPEVD DEALEKFDKA LKALPMHIRL SFNPTQLEEQ CHI                     163

SEQ ID NO: 565           moltype = AA  length = 162
FEATURE                  Location/Qualifiers
source                   1..162
                         mol_type = protein
                         organism = Bos taurus
SEQUENCE: 565
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HI                      162

SEQ ID NO: 566           moltype = AA  length = 178
FEATURE                  Location/Qualifiers
source                   1..178
                         mol_type = protein
                         organism = Bos taurus
SEQUENCE: 566
MKCLLLALAL TCGAQALIVT QTMKGLDIQK VAGTWYSLAM AASDISLLDA QSAPLRVYVE    60
ELKPTPEGDL EILLQKWENG ECAQKKIIAE KTKIPAVFKI DALNENKVLV LDTDYKKYLL   120
FCMENSAEPE QSLACQCLVR TPEVDDEALE KFDKALKALP MHIRLSFNPT QLEEQCHI     178

SEQ ID NO: 567           moltype = AA  length = 161
FEATURE                  Location/Qualifiers
source                   1..161
                         mol_type = protein
                         organism = Bos taurus
SEQUENCE: 567
IVTQTMKGLD IQKVAGTWYS LAMAASDISL LDAQSAPLRV YVEELKPTPE GDLEILLQKW    60
ENGECAQKKI IAEKTKIPAV FKIDALNENK VLVLDTDYKK YLLFCMENSA EPEQSLACQC   120
LVRTPEVDDE ALEKFDKALK ALPMHIRLSF NPTQLEEQCH I                       161

SEQ ID NO: 568           moltype = AA  length = 162
FEATURE                  Location/Qualifiers
source                   1..162
                         mol_type = protein
                         organism = Bos taurus
SEQUENCE: 568
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLVCQ   120
CLVRTPEVDD EALEKFDKAL KALPMHIRLS FNPTQLEEQC HI                      162

SEQ ID NO: 569           moltype = AA  length = 162
FEATURE                  Location/Qualifiers
source                   1..162
                         mol_type = protein
                         organism = Bos taurus
SEQUENCE: 569
LIVTQTMKGL DIQKVAGTWY SLAMAASDIS LLDAQSAPLR VYVEELKPTP EGDLEFLLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HI                      162

SEQ ID NO: 570           moltype = AA  length = 162
FEATURE                  Location/Qualifiers
source                   1..162
                         mol_type = protein
                         organism = Bos taurus
SEQUENCE: 570
LIVTQTMKGL DIQKVAGTWY SLAMAASDIS LLDAQSAPYR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HI                      162

SEQ ID NO: 571           moltype = AA  length = 178
FEATURE                  Location/Qualifiers
```

```
                                 -continued source                  1..178
                        mol_type = protein
                        organism = Bos taurus
SEQUENCE: 571
MKCLLLALAL TCGAQALIVT QTMKGLDIQK VAGTWYSLAM AASDISLLDA QSAPLRVYVE      60
ELKPTPEGDL EILLQKWENG ECAQKKIIAE KTKIPAVFKI DALNENKVLV LDTDYKKYLL     120
FCMENSAEPE QSLVCQCLVR TPEVDDEALE KFDKALKALP MHIRLSFNPT QLEEQCHI      178

SEQ ID NO: 572          moltype = AA  length = 162
FEATURE                 Location/Qualifiers
source                  1..162
                        mol_type = protein
                        organism = Bos taurus
SEQUENCE: 572
ASVTQTMKGL DIQKVAGTWY SLAMAASDIS LLDAQSAPLR VYVEELKPTP EGDLEILLQK      60
WENGECAQKK IIAEKTKIPA VFKIDALNEN KVLVLDTDYK KYLLFCMENS AEPEQSLACQ     120
CLVRTPEVDD EALEKFDKAL KALPMHIRLS FNPTQLEEQC HI                        162

SEQ ID NO: 573          moltype = AA  length = 162
FEATURE                 Location/Qualifiers
source                  1..162
                        mol_type = protein
                        organism = Bos taurus
SEQUENCE: 573
ASVTQTMKGL DIQKVAGTWY SLAMAASDIS LLDAQSAPLR VYVEELKPTP EGDLEILFQK      60
WENGECAQKK IIAEKTKIPA VFKIDALNEN KVLVLDTDYK KYLLFCMENS AEPEQSLACQ     120
CLVRTPEVDD EALEKFDKAL KALPMHIRLS FNPTQLEEQC HI                        162

SEQ ID NO: 574          moltype = AA  length = 162
FEATURE                 Location/Qualifiers
source                  1..162
                        mol_type = protein
                        organism = Bos taurus
SEQUENCE: 574
ASVTQTMKGL DIQKVAGTWY SLAMAASDIS LLDAQSAPLR VYVEELKPTP EGDLEILLQK      60
WENGECAQKK IIAEKTKIPA VFKIDALNEN KVLVLDTDYK KYLLFCLENS AEPEQSLACQ     120
CLVRTPEVDD EALEKFDKAL KALPMHIRLS FNPTQLEEQC HI                        162

SEQ ID NO: 575          moltype = AA  length = 162
FEATURE                 Location/Qualifiers
source                  1..162
                        mol_type = protein
                        organism = Bos taurus
SEQUENCE: 575
LIVTQTMKGL DIQKVAGTWY SLAMAASDIS LLDAQSAPLR VYVEELKPTP EGDLEILLQK      60
WENDECAQKK IIAEKTKIPA VFKIDALNEN KVLVLDTDYK KYLLFCMENS AEPEQSLVCQ     120
CLVRTPEVDD EALEKFDKAL KALPMHIRLS FNPTQLEEQC HI                        162

SEQ ID NO: 576          moltype = AA  length = 162
FEATURE                 Location/Qualifiers
source                  1..162
                        mol_type = protein
                        organism = Bos taurus
SEQUENCE: 576
ASVTQTMKGL DIQKVAGTWY SLAMAASDIS LLDAQSAPLR VYVEELKPTP EGDLEILLQK      60
WENGECAQKK IIAEKTKIPA VFKIDALNEN KVLVLDTDYK KYLLLCMENS AEPEQSLACQ     120
CLVRTPEVDD EALEKFDKAL KALPMHIRLS FNPTQLEEQC HI                        162

SEQ ID NO: 577          moltype = AA  length = 178
FEATURE                 Location/Qualifiers
source                  1..178
                        mol_type = protein
                        organism = Bos taurus
SEQUENCE: 577
MKCLLLALAL TCGAQALIVT QTMKGLDIQK VAGTWYSLAM AASDISLLDA QSAPLRVYVE      60
ELKPTPEGDL EILLQKWEND ECAQKKIIAE KTKIPAVFKI DALNENKVLV LDTDYKKYLL     120
FCMENSAEPE QSLVCQCLVR TPEVDDEALE KFDKALKALP MHIRLSFNPT QLEEQCHI      178

SEQ ID NO: 578          moltype = AA  length = 162
FEATURE                 Location/Qualifiers
source                  1..162
                        mol_type = protein
                        organism = Bos taurus
SEQUENCE: 578
ASVTQTMKGL DIQKVAGTWY SLAMAASDIS LLDAQSAPAR VYVEELKPTP EGDLEFLLQK      60
WENGECAQKK IIAEKTKIPA VFKIDALNEN KVLVLDTDYK KYLLFCMENS AEPEQSLACQ     120
CLVRTPEVDD EALEKFDKAL KALPMHIRLS FNPTQLEEQC HI                        162

SEQ ID NO: 579          moltype = AA  length = 162
```

```
FEATURE                 Location/Qualifiers
source                  1..162
                        mol_type = protein
                        organism = Bos taurus
SEQUENCE: 579
ASVTQTMKGL DIQKVAGTWY SLAMAASDIS LLDAQSAPAR VYVEELKPTP EGDLEILLQK    60
WENGECAQKK IIAEKTKIPA VFKIDALNEN KVLVLDTDYK KYLLLCMENS AEPEQSLACQ   120
CLVRTPEVDD EALEKFDKAL KALPMHIRLS FNPTQLEEQC HI                      162

SEQ ID NO: 580          moltype = AA  length = 162
FEATURE                 Location/Qualifiers
source                  1..162
                        mol_type = protein
                        organism = Bos taurus
SEQUENCE: 580
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLVCQ   120
SLVRTPEVDD EALEKFDKAL KALPMHIRLS FNPTQLEEQC HI                      162

SEQ ID NO: 581          moltype = AA  length = 178
FEATURE                 Location/Qualifiers
source                  1..178
                        mol_type = protein
                        organism = Bos taurus
SEQUENCE: 581
MKCLLLALAL TCGAQALIVT QTMKGLDIQK VAGTWYSLAM AASDISLLDA QSAPLRVYVE    60
ELKPTPEGDL EILLQKWEND ECAQKKIIAE KTKIPAVFKI DALNENKVLV LDTDYKKYLL   120
VCMENSAEPE QSLVCQCLVR TPEVDDEALE KFDKALKALP MHIRLSFNPT QLEEQCHI    178

SEQ ID NO: 582          moltype = AA  length = 163
FEATURE                 Location/Qualifiers
source                  1..163
                        mol_type = protein
                        organism = Bos taurus
SEQUENCE: 582
AAYVTQTMKG LDIQKVAGTW YSLAMAASDI SLLDAQSAPL RVYVEELKPT PEGDLEILLQ    60
KWENDECAQK KIIAEKTKIP AVFKIDALNE NKVLVLDTDY KKYLLFCMEN SAEPEQSLVC   120
QCLVRTPEVD DEALEKFDKA LKALPMHIRL SFNPTQLEEQ CHI                     163

SEQ ID NO: 583          moltype = AA  length = 162
FEATURE                 Location/Qualifiers
source                  1..162
                        mol_type = protein
                        organism = Bos taurus
SEQUENCE: 583
ASVTQTMKGL DIQKVAGTWY SLAMAASDIS LLDAQSAPAR VYVEELKPTP EGDLEFLLQK    60
WENGECAQKK IIAEKTKIPA VFKIDALNEN KVLVLDTDYK KYLLFCFENS AEPEQSLACQ   120
CLVRTPEVDD EALEKFDKAL KALPMHIRLS FNPTQLEEQC HI                      162

SEQ ID NO: 584          moltype = AA  length = 162
FEATURE                 Location/Qualifiers
source                  1..162
                        mol_type = protein
                        organism = Bos taurus
SEQUENCE: 584
ASVTQTMKGL DIQKVAGTWY SLAMAASDIS LLDAQSAPAR VYVEELKPTP EGDLEILLQK    60
WENGECAQKK IIAEKTKIPA VFKIDALNEN KVLVLDTDYK KYLLLCFENS AEPEQSLACQ   120
CLVRTPEVDD EALEKFDKAL KALPMHIRLS FNPTQLEEQC HI                      162

SEQ ID NO: 585          moltype = AA  length = 162
FEATURE                 Location/Qualifiers
source                  1..162
                        mol_type = protein
                        organism = Bos taurus
SEQUENCE: 585
LIVTQTMKGL DIQKVAGTWY SLAMAASDIS LLDAQSAPLR VYVEELKPTP EGDLEILLQK    60
WENGECAQKK IIAEKTKIPA VFKLDAINEN KVLVLDTDYK KYLLFCMENS AEPEQSLVCQ   120
CLVRTPEVDD EALEKFDKAL KALPMHIRLS FNPTLQEEQC HI                      162

SEQ ID NO: 586          moltype = AA  length = 252
FEATURE                 Location/Qualifiers
source                  1..252
                        mol_type = protein
                        organism = Bos taurus
SEQUENCE: 586
MKCLLLALAL TCGAQALIVT QTMKGLDIQK VAGTWYSLAM AASDISLLDA QSAPLRVYVE    60
ELKPTPEGDL EILLQKWENG ECAQKKIIAE KTKIPAVFKI DALNENKVLV LDTDYKKYLL   120
FCMENSAEPE QSLACQCLVR TPEVDDEALE KFDKALKALP MHIRLSFNPT QLEGEHPGPT   180
LLLGQEATRP RTTSSHGDPQ LPRPPGRMET GCRAPRWPPP HPLPSSLCPG VSSPILTLPR   240
```

```
HGSPSPTEQC HI                                                                 252

SEQ ID NO: 587           moltype = AA  length = 151
FEATURE                  Location/Qualifiers
source                   1..151
                         mol_type = protein
                         organism = Bos taurus
SEQUENCE: 587
IQKVAGTWYS LAMAASDISL LDAQSAPLRV YVEELKPTPE GDLEILLQKW ENDECAQKKI    60
IAEKTKIPAV FKIDALNENK VLVLDTDYKK YLLFCMENSA EPEQSLVCQC LVRTPEVDDE   120
ALEKFDKALK ALPMHIRLSF NPTQLEEQCH I                                  151

SEQ ID NO: 588           moltype = AA  length = 162
FEATURE                  Location/Qualifiers
source                   1..162
                         mol_type = protein
                         organism = Capra hircus
SEQUENCE: 588
IIVTQTMKGL DIQKVAGTWY SLAMAASDIS LLDAQSAPLR VYVEELKPTP EGNLEILLQK    60
WENGECAQKK IIAEKTKIPA VFKIDALNEN KVLVLDTDYK KYLLFCMENS AEPEQSLACQ   120
CLVRTPEVDK EALEKFDKAL KALPMHIRLA FNPTQLEGQC HV                      162

SEQ ID NO: 589           moltype = AA  length = 180
FEATURE                  Location/Qualifiers
source                   1..180
                         mol_type = protein
                         organism = Capra hircus
SEQUENCE: 589
MKCLLLALGL ALACGIQAII VTQTMKGLDI QKVAGTWYSL AMAASDISLL DAQSAPLRVY    60
VEELKPTPEG NLEILLQKWE NGECAQKKII AEKTKIPAVF KIDALNENKV LVLDTDYKKY   120
LLFCMENSAE PEQSLACQCL VRTPEVDKEA LEKFDKALKA LPMHIRLAFN PTQLEGQCHV   180

SEQ ID NO: 590           moltype = AA  length = 169
FEATURE                  Location/Qualifiers
source                   1..169
                         mol_type = protein
                         organism = Capra hircus
SEQUENCE: 590
MKCLLLALGL ALACGIQAII VTQTMKGLDI QKVAGTWYSL AMAASDISLL DAQSAPLRVY    60
VEELKPTPEG NLEILLQKWE NGECAQKKII AEKTKIPAVF KIDALNENKV LVLDTDYKKY   120
LLFCMENSAE PEQSLACQCL VRTPEVDKEA LEKFDKALKA LPMHIRLAF               169

SEQ ID NO: 591           moltype = AA  length = 162
FEATURE                  Location/Qualifiers
source                   1..162
                         mol_type = protein
                         organism = Ovis aries
SEQUENCE: 591
IIVTQTMKGL DIQKVAGTWY SLAMAASDIS LLDAQSAPLR VYVEELKPTP EGNLEILLQK    60
WENGECAQKK IIAEKTKIPA VFKIDALNEN KVLVLDTDYK KYLLFCMENS AEPEQSLACQ   120
CLVRTPEVDN EALEKFDKAL KALPMHIRLA FNPTQLEGQC HV                      162

SEQ ID NO: 592           moltype = AA  length = 180
FEATURE                  Location/Qualifiers
source                   1..180
                         mol_type = protein
                         organism = Ovis aries
SEQUENCE: 592
MKCLLLALGL ALACGVQAII VTQTMKGLDI QKVAGTWHSL AMAASDISLL DAQSAPLRVY    60
VEELKPTPEG NLEILLQKWE NGECAQKKII AEKTKIPAVF KIDALNENKV LVLDTDYKKY   120
LLFCMENSAE PEQSLACQCL VRTPEVDNEA LEKFDKALKA LPMHIRLAFN PTQLEGQCHV   180

SEQ ID NO: 593           moltype = AA  length = 161
FEATURE                  Location/Qualifiers
source                   1..161
                         mol_type = protein
                         organism = Ovis aries
SEQUENCE: 593
VTQTMKGLDI QKVAGTWYHS LAMAASDISL LDAQSAPLRV YVEELKPTPE GNLEILLQKW    60
ENGECAQKKI IAEKTKIPAV FKIDALNENK VLVLDTDYKK YLLFCMENSA EPEQSLACQC   120
LVRTPEVDNE ALEKFDKALK ALPMHIRLAF NPTQLEGQCH V                       161

SEQ ID NO: 594           moltype = AA  length = 162
FEATURE                  Location/Qualifiers
source                   1..162
                         mol_type = protein
                         organism = Ovis aries
SEQUENCE: 594
IIVTQTMKGL DIQKVAGTWY HSLAMAASDI SLLDAQSAPL RVYVEELKPT PEGNLEILLQ    60
```

```
KWEGECAQKK IIAEKTKIPA VFKIDALNEN KVLVLDTDYK KYLLFCMENS AEPEQSLACQ    120
CLVRTPEVDN EALEKFDKAL KALPMHIRLA FNPTQLEGQC HV                      162

SEQ ID NO: 595          moltype = AA  length = 162
FEATURE                 Location/Qualifiers
source                  1..162
                        mol_type = protein
                        organism = Bubalus bubalis
SEQUENCE: 595
IIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ    120
CLVRTPEVDD EALEKFDKAL KALPMHIRLS FNPTQLEEQC HV                      162

SEQ ID NO: 596          moltype = AA  length = 180
FEATURE                 Location/Qualifiers
source                  1..180
                        mol_type = protein
                        organism = Bubalus bubalis
SEQUENCE: 596
MKCLLLALGL ALACAAQAII VTQTMKGLDI QKVAGTWYSL AMAASDISLL DAQSAPLRVY    60
VEELKPTPEG DLEILLQKWE NGECAQKKII AEKTKIPAVF KIDALNENKV LVLDTDYKKY    120
LLFCMENSAE PEQSLACQCL VRTPEVDDEA LEKFDKALKA LPMHIRLSFN PTQLEEQCHV    180

SEQ ID NO: 597          moltype = AA  length = 180
FEATURE                 Location/Qualifiers
source                  1..180
                        mol_type = protein
                        organism = Bubalus bubalis
SEQUENCE: 597
MKCLLLALGL ALACGAQAII VTQTMKGLDI QKVAGTWYSL AMAASDISLL DAQSAPLRVY    60
VEELKPTPEG DLEILLQKWE NGECAQKKII AEKTKIPAVF KIDALNENKV LVLDTDYKKY    120
LLFCMENSAE PEQSLACQCL VRTPEVDDEA LEKFDKALKA LPMHIRLSFN PTQLEEQCHV    180

SEQ ID NO: 598          moltype = AA  length = 180
FEATURE                 Location/Qualifiers
source                  1..180
                        mol_type = protein
                        organism = Bubalus bubalis
SEQUENCE: 598
MKCLLLALGL ALACGTQAII VTQTMKGLDI QKVAGTWYSL AMAASDISLL DAQSAPLRVY    60
VEELKPTPEG DLEILLQKWE NGECAQKKII AEKTKIPAVF KIDALNENKV LVLDTDYKKY    120
LLFCMENSAE PEQSLACQCL VRTPEVDDEA LEKFDKALKA LPMHIRLSFN PTQLEEQCHV    180

SEQ ID NO: 599          moltype = AA  length = 180
FEATURE                 Location/Qualifiers
source                  1..180
                        mol_type = protein
                        organism = Bubalus bubalis
SEQUENCE: 599
MKCLLLALGL ALACGTQAII VTQTMKGLDI QKVAGTWYSL AMAVSDISLL DAQSAPLRVY    60
VEELKPTPEG DLEILLQKWE NGECAQKKII AEKTKIPAVF KIDALNENKV LVLDTDYKKY    120
LLFCMENSAE PEQSLACQCL VRTPEVDDEA LEKFDKALKA LPMHIRLSFN PTQLEEQCHV    180

SEQ ID NO: 600          moltype = AA  length = 178
FEATURE                 Location/Qualifiers
source                  1..178
                        mol_type = protein
                        organism = Bubalus bubalis
SEQUENCE: 600
MKCLLLALAL ACGAQAIIVT QTMKGLDIQK VAGTWYSLAM AASDISLLDA QSAPLRVYVE    60
ELKPTPEGDL EILLQKWENG ECAQKKIIAE KTKIPAVFKI DALNENKVLV LDTDYKKYLL    120
FCMENSAEPE KAWPASAWVR TPEVDDEALE KFDKALKALP MHIRLSFNPT QLEEQCHI     178

SEQ ID NO: 601          moltype = AA  length = 178
FEATURE                 Location/Qualifiers
source                  1..178
                        mol_type = protein
                        organism = Bos mutus
SEQUENCE: 601
MKCLLLALAL TCGAQALIVT QTMKGLDIQK VAGTWYSLAM AASDISLLDA QSAPLRVYVE    60
ELKPTPEGDL EILLQKWENG ECAQKKIIAE KTKIPAVFKI DALNENKVLV LDTDYKKYLL    120
FCMENSAEPE QSLACQCLVR TPEVDDEALE KFDKALKALP MHIRLSFNPT QLEGQCHI     178

SEQ ID NO: 602          moltype = AA  length = 298
FEATURE                 Location/Qualifiers
source                  1..298
                        mol_type = protein
                        organism = Bos mutus
SEQUENCE: 602
```

```
MQLKVPPQVA GMWHTVAMAA SNMLLLDAES GPLRVYVEEL KPTPEGDLEI LLQKRENHEC   60
VEKTLMAQKT EDPAVFTPGP EMDDEAMEKF AGALASLLEH VQMVLGLRQG AELRSVTPAA  120
AMKCLLLALA LTCGAQALIV TQTMKGLDIQ KVAGTWYSLA MAASDISLLD AQSAPLRVYV  180
EELKPTPEGD LEILLQKWEN GECAQKKIIA EKTKIPAVFK IDALNENKVL VLDTDYKKYL  240
LFCMENSAEP EQSLACQCLV RTPEVDDEAL EKFDKALKAL PMHIRLSFNP TQLEGKPS    298

SEQ ID NO: 603          moltype = AA  length = 178
FEATURE                 Location/Qualifiers
VARIANT                 80
                        note = X can be any naturally occurring amino acid
VARIANT                 134
                        note = X can be any naturally occurring amino acid
source                  1..178
                        mol_type = protein
                        organism = Bos indicus
SEQUENCE: 603
MKCLLLALAL TCGAQALIVT QTMKGLDIQK VAGTWYSLAM AASDISLLDA QSAPLRVYVE   60
ELKPTPEGDL EILLQKWENX ECAQKKIIAE KTKIPAVFKI DALNENKVLV LDTDYKKYLL  120
FCMENSAEPE QSLXCQCLVR TPEVDDEALE KFDKALKALP MHIRLSFNPT QLEEQCHI    178

SEQ ID NO: 604          moltype = AA  length = 184
FEATURE                 Location/Qualifiers
source                  1..184
                        mol_type = protein
                        organism = Jeotgalicoccus coquinae
SEQUENCE: 604
MTPAAAMKCL LLALALTCGA QALIVTQTMK GLDIQKVAGT WYSLAMAASD ISLLDAQSAP   60
LRVYVEELKP TPEGDLEILL QKWENGECAQ KKIIAEKTKI PAVFKIDALN ENKVLVLDTD  120
YKKYLLFCME NSAEPEQSLA CQCLVRTPEV DDEALEKFDK ALKALPMHIR LSFNPTQLEE  180
QCHI                                                               184

SEQ ID NO: 605          moltype = AA  length = 181
FEATURE                 Location/Qualifiers
source                  1..181
                        mol_type = protein
                        organism = Jeotgalicoccus schoeneichii
SEQUENCE: 605
LRSVIPAAAM KCLLLALALT CGAQALIVTQ TMKGLDIQKV AGTWYSLAMA ASDISLLDAQ   60
SAPLRVYVEE LKPTPEGDLE ILLQKWENGE CAQKKIIAEK TKIPAVFKID ALNENKVLVL  120
DTDYKKYLLF CMENSAEPEQ SLACQCLVRT GVQDRCLERE QSPCAGHRLQ KVPALLHGEQ  180
C                                                                  181

SEQ ID NO: 606          moltype = AA  length = 178
FEATURE                 Location/Qualifiers
source                  1..178
                        mol_type = protein
                        organism = Bison bison
SEQUENCE: 606
MKCLLLALAL TCGAQALIVT QTMKGLDIQK VAGTWYSLAM AASDISLLDA QSAPLRVYVE   60
ELKPTPEGNL EILLQKWENG ECAQKKIIAE KTKVPAVFKI DALNENKVLV LDTDYKKYLL  120
FCMENSAEPE QSLACQCLVR TPEVDDEALE KFDKALKALP MHIRLSFNPT QLEGQCHI    178

SEQ ID NO: 607          moltype = AA  length = 180
FEATURE                 Location/Qualifiers
REGION                  1..180
                        note = Ovis sp.
source                  1..180
                        mol_type = protein
                        organism = unidentified
SEQUENCE: 607
MKCLLLALGL ALACGVQAII VTQTMKGLDI QKVAGTWYSL AMAASDISLL DAQSAPLRVY   60
VEELKPTPEG NLEILLQKWE NGECAQKKII AEKTKIPAVF KIDALNENKV LVLDTDYKKY  120
LLFCMENSAE PEQSLACQCL VRTPEVDNEA LEKFDKALKA LPMHIRLAFN PTQLEGQCHV  180

SEQ ID NO: 608          moltype = AA  length = 162
FEATURE                 Location/Qualifiers
source                  1..162
                        mol_type = protein
                        organism = Ovis aries
SEQUENCE: 608
IIVTQTMKGL DIQKVAGTWH SLAMAASDIS LLDAQSAPLR VYVEELKPTP EGNLEILLQK   60
WENGECAQKK IIAEKTKIPA VFKIDALNEN KVLVLDTDYK KYLLFCMENS AEPEQSLACQ  120
CLVRTPEVDN EALEKFDKAL KALPMHIRLA FNPTQLEGQC HV                     162

SEQ ID NO: 609          moltype = AA  length = 180
FEATURE                 Location/Qualifiers
source                  1..180
                        mol_type = protein
                        organism = Odocoileus virginianus
```

```
SEQUENCE: 609
MKCLLLALGL ALACGVQAAH IPQTAEDLDV RKVVGTWHVV AMAASDMSLL DAESGPLRVY    60
VEELKPTPQG DLEVLLQKRE NGKCAQKKII AEKTEIPAVF KIDALNENKV LVLDTDYKKY   120
LLFCMENSAE PEQSLACQCL VRTPEVDDEA MEKFDKALKA LPMHIRLSFN PTQLEEQCRI   180

SEQ ID NO: 610          moltype = AA   length = 162
FEATURE                 Location/Qualifiers
source                  1..162
                        mol_type = protein
                        organism = Rangifer tarandus
SEQUENCE: 610
IIVTQTMKDL DVQKVAGTWY SLAMAASDIS LLDAQSAPLR VYVEELKPTP GGDLEILLQK    60
WENGKCAQKK IIAEKTEIPA VFKIDALNEN KVLVLDTDYK KYLLFCMENS AEPEQSLACQ   120
CLVRTPEVDD EAMEKFDKAL KALPMHIRLS FNPTQLEEQC RV                      162

SEQ ID NO: 611          moltype = AA   length = 180
FEATURE                 Location/Qualifiers
source                  1..180
                        mol_type = protein
                        organism = Rangifer tarandus
SEQUENCE: 611
MKCLLITLGL ALACGAQAII VTQTMKDLDV QKVAGTWYSL AMAASDISLL DAQSAPLRVY    60
VEELKPTPGG DLEILLQKWE NGKCAQKKII AEKTEIPAVF KIDALNENKV LVLDTDYKKY   120
LLFCMENSAE PEQSLACQCL VRTPEVDDEA MEKFDKALKA LPMHIRLSFN PTQLEEQCRV   180

SEQ ID NO: 612          moltype = AA   length = 180
FEATURE                 Location/Qualifiers
source                  1..180
                        mol_type = protein
                        organism = Muntiacus muntjak
SEQUENCE: 612
MKCLLLALGL ALACGAQAIV VTQTMKDLDI QKVAGTWYSL AMAASDISLL DAQSAPLRVY    60
VEELKPTPEG DLEILLQKWE NGECAQKKIT AEKTEIPAVF KIDALNENEV LVLDTDYEKY   120
LLFCMDNSAE PEQSLACQCL VRTPEVDAEA MEKFDKALEA LPMHIRLSFN PTQLEEQCHV   180

SEQ ID NO: 613          moltype = AA   length = 180
FEATURE                 Location/Qualifiers
source                  1..180
                        mol_type = protein
                        organism = Muntiacus reevesi
SEQUENCE: 613
MKCLLLALGL ALACGAQAII VTQTMKDLDI QKVAGTWYSL AMAASDISLL DAQSAPLRVY    60
VEELKPTPEG DLEILLQKWE NGECAQKKIT AEKTEIPAVF KIDALNENNV LVLDTDYEKY   120
LLFCMDNSAE PEQSLACQCL VRTPEVDAEA MEKFDKALEA LPMHIRLSFN PTQLEEHCHV   180

SEQ ID NO: 614          moltype = AA   length = 162
FEATURE                 Location/Qualifiers
source                  1..162
                        mol_type = protein
                        organism = Equus caballus
SEQUENCE: 614
TNIPQTMQDL DLQEVAGTWY SLAMAASDIS LLDSESAPLR VYVEELKPTP EGDLEILLQK    60
WENKGCAQKK IIAEKTESPA EFKIDALDEN KVLVLDTDYK NYLLFCMENA ATPGQSLACQ   120
ALVRTQMVDD EALEKFDKAL QPLPMHIRLS FNPTRMAERC RI                      162

SEQ ID NO: 615          moltype = DNA   length = 807
FEATURE                 Location/Qualifiers
misc_feature            1..807
                        note = fusion protein (paraOKC1-T:FM:OLG1)
source                  1..807
                        mol_type = other DNA
                        organism = synthetic construct
SEQUENCE: 615
caagagcaga atcaagagca gccaatccgt tgtgagaagg acgagaggtt cttctcagac    60
aagatcgcca aatatatacc catacaatat gtactctcac gctaccctag ctacgggctt   120
aactactatc agcaaaaacc tgtagcactg ataaataacc agtttctccc ctatccctat   180
tatgctaaac ctgccgccgt gaggagtcca gcacaaatac ttcagtggca agtgctcagt   240
aacaccgtgc cagcaaaaag ctgccaggct cagcccacca caatggcccg tcatccccat   300
cctcacctta gcttcatgtt gatcgtaaca cagactgca agggtcttga tatacagaag   360
gtggccggga cttggtacag tttggcaatg gccgcatccg acatctcctt gttggacgca   420
caatcagccc cattgcgtgt gtacgtgaaa gagcttaaac caactcccga ggggatctg    480
gaaattctgc tccagaaatg gcagaacggt gagtgcgccc agaagaagat catcgcgag   540
aagaccaaaa ttcagcagt attcaaaatc gacgcattga cgaaaataa ggtgctcgta   600
ctggacactg attataagaa gtatctcctt ttctgtatgg agaactcagc agagcctgaa   660
cagagtcttg cctgccaatg ccttgttcgt accccagagg tagatgatga agctctgaa   720
aagttcgata aggcccttaa ggctctgcct atgcacatta ggctttcttt caatccaact   780
caacttgagg aacaatgtca catttaa                                        807

SEQ ID NO: 616          moltype = AA   length = 268
```

```
FEATURE                 Location/Qualifiers
REGION                  1..268
                        note = fusion protein (paraOKC1-T:FM:OLG1)
source                  1..268
                        mol_type = protein
                        organism = synthetic construct
SEQUENCE: 616
QEQNQEQPIR CEKDERFFSD KIAKYIPIQY VLSRYPSYGL NYYQQKPVAL INNQFLPYPY    60
YAKPAAVRSP AQILQWQVLS NTVPAKSCQA QPTTMARHPH PHLSFMLIVT QTMKGLDIQK   120
VAGTWYSLAM AASDISLLDA QSAPLRVYVE ELKPTPEGDL EILLQKWENG ECAQKKIIAE   180
KTKIPAVFKI DALNENKVLV LDTDYKKYLL FCMENSAEPE QSLACQCLVR TPEVDDEALE   240
KFDKALKALP MHIRLSFNPT QLEEQCHI                                      268

SEQ ID NO: 617          moltype = DNA  length = 819
FEATURE                 Location/Qualifiers
misc_feature            1..819
                        note = fusion protein (paraOKC1-T:FM:OLG1:KDEL)
source                  1..819
                        mol_type = other DNA
                        organism = synthetic construct
SEQUENCE: 617
caagagcaga atcaagagca gccaatccgt tgtgagaagg acgagaggtt cttctcagac    60
aagatcgcca aatatatacc catacaatat gtactctcac gctaccctag ctacgggctt   120
aactactatc agcaaaaacc tgtagcactg ataaataacc agtttctccc ctatccctat   180
tatgctaaac ctgccgccgt gaggagtcca gcacaaatac ttcagtggca agtgctcagt   240
aacaccgtgc cagcaaaaag ctgccaggct cagcccacca caatggcccg tcatcccat    300
cctcaccttta gcttcatgtt gatcgtaaca cagactatga agggtcttga tacacagaag   360
gtggccggga cttggtacag tttggcaatg gccgcatccg acatctcctt gttggacgca   420
caatcagccc cattgcgtgt gtacgtagaa gagcttaaac aactcccga ggggggatctg   480
gaaattctgc tccagaaatg ggagaacggt gagtgcgccc agaagaagat catcgcagag   540
aagaccaaaa ttccagcagt attcaaaatc gacgcattga acgaaaataa ggtgctcgta   600
ctggacactg attataagaa gtatctcctt ttctgtatgg agaactcagc agagcctgaa   660
cagagtcttg cctgccaatg ccttgttcgt acccccagagg tagatgatga agctctggaa   720
aagttcgata aggccttaa ggctctgcct atgcacatta ggctttcttt caatccaact   780
caacttgagg aacaatgtca cattaaggat gagctttaa                          819

SEQ ID NO: 618          moltype = AA  length = 272
FEATURE                 Location/Qualifiers
REGION                  1..272
                        note = fusin protein (paraOKC1-T:FM:OLG1:KDEL)
source                  1..272
                        mol_type = protein
                        organism = synthetic construct
SEQUENCE: 618
QEQNQEQPIR CEKDERFFSD KIAKYIPIQY VLSRYPSYGL NYYQQKPVAL INNQFLPYPY    60
YAKPAAVRSP AQILQWQVLS NTVPAKSCQA QPTTMARHPH PHLSFMLIVT QTMKGLDIQK   120
VAGTWYSLAM AASDISLLDA QSAPLRVYVE ELKPTPEGDL EILLQKWENG ECAQKKIIAE   180
KTKIPAVFKI DALNENKVLV LDTDYKKYLL FCMENSAEPE QSLACQCLVR TPEVDDEALE   240
KFDKALKALP MHIRLSFNPT QLEEQCHIKD EL                                 272

SEQ ID NO: 619          moltype = DNA  length = 804
FEATURE                 Location/Qualifiers
misc_feature            1..804
                        note = fusion protein (paraOKC1-T:OLG1)
source                  1..804
                        mol_type = other DNA
                        organism = synthetic construct
SEQUENCE: 619
caagagcaga atcaagagca gccaatccgt tgtgagaagg acgagaggtt cttctcagac    60
aagatcgcca aatatatacc catacaatat gtactctcac gctaccctag ctacgggctt   120
aactactatc agcaaaaacc tgtagcactg ataaataacc agtttctccc ctatccctat   180
tatgctaaac ctgccgccgt gaggagtcca gcacaaatac ttcagtggca agtgctcagt   240
aacaccgtgc cagcaaaaag ctgccaggct cagcccacca caatggcccg tcatcccat    300
cctcaccttta gcttcttgat cgtaacacag actatgaagg gtcttgatat acagaaggt   360
gccgggactt ggtacagttt ggcaatggcc gcatccgaca tctccttgtt ggacgcacaa   420
tcagccccat tgcgtgtgta cgtagaagag cttaaaccaa ctcccgaggg gatctggaa   480
attctgctcc agaaatggga gaacggtgag tgcgcccaga gaagatcat cgcagagaag   540
accaaaaattc cagcagtatt caaaatcgac gcattgaaca aataaggt gctcgtactg   600
gacactgatt ataagaagta tctccttttc tgtatggaga actcagcaga gcctgaacag   660
agtcttgcct gccaatgcct tgttcgtacc ccagaggtag atgatgaagc tctgaaaag   720
ttcgataagg cccttaaggc tctgcctatg cacattaggc tttctttcaa tccaactcaa   780
cttgaggaac aatgtcacat ttaa                                          804

SEQ ID NO: 620          moltype = AA  length = 267
FEATURE                 Location/Qualifiers
REGION                  1..267
                        note = fusion protein (paraOKC1-T:OLG1)
source                  1..267
                        mol_type = protein
```

```
                        organism = synthetic construct
SEQUENCE: 620
QEQNQEQPIR CEKDERFFSD KIAKYIPIQY VLSRYPSYGL NYYQQKPVAL INNQFLPYPY    60
YAKPAAVRSP AQILQWQVLS NTVPAKSCQA QPTTMARHPH PHLSFLIVTQ TMKGLDIQKV   120
AGTWYSLAMA ASDISLLDAQ SAPLRVYVEE LKPTPEGDLE ILLQKWENGE CAQKKIIAEK   180
TKIPAVFKID ALNENKVLVL DTDYKKYLLF CMENSAEPEQ SLACQCLVRT PEVDDEALEK   240
FDKALKALPM HIRLSFNPTQ LEEQCHI                                      267

SEQ ID NO: 621          moltype = DNA  length = 816
FEATURE                 Location/Qualifiers
misc_feature            1..816
                        note = fusion protein (paraOKC1-T:OLG1:KDEL)
source                  1..816
                        mol_type = other DNA
                        organism = synthetic construct
SEQUENCE: 621
caagagcaga atcaagagca gccaatccgt tgtgagaagg acgagaggtt cttctcagac    60
aagatcgcca aatatatacc catacaatat gtactctcac gctaccctag ctacgggctt   120
aactactatc agcaaaaacc tgtagcactg ataaataacc agtttctccc ctatccctat   180
tatgctaaac ctgccgccgt gaggagtcca gcacaaatac ttcagtggca agtgctcagt   240
aacaccgtgc cagcaaaaag ctgccaggct cagcccacca caatgcccg tcatcccat    300
cctcaccta gcttcttgat cgtaacacag actatgaagg tcttgatat acagaaggtg    360
gccgggactt ggtacagttt ggcaatggcc gcatccgaca tctccttgtt ggacgcacaa   420
tcagccccat tgcgtgtgta cgtagaagag cttaaaccaa ctcccgaggg ggatctggaa   480
attctgctcc agaaatggga gaacggtgag tgcgcccaga agaagatcat cgcagagaag   540
accaaaaattc cagcagtatt caaaatcgac gcattgaaca aaataaggt gctcgtactg   600
gacactgatt ataagaagta tctccttttc tgtatggaga actcagcaga gcctgaacag   660
agtcttgcct gccaatgcct tgttcgtacc ccagaggtag atgatgaagc tctggaaaag   720
ttcgataagg cccttaaggc tctgcctatg cacattaggc tttctttcaa tccaactcaa   780
cttgaggaac aatgtcacat taaggatgag ctttaa                             816

SEQ ID NO: 622          moltype = AA  length = 271
FEATURE                 Location/Qualifiers
REGION                  1..271
                        note = fusion protein (paraOKC1-T:OLG1:KDEL)
source                  1..271
                        mol_type = protein
                        organism = synthetic construct
SEQUENCE: 622
QEQNQEQPIR CEKDERFFSD KIAKYIPIQY VLSRYPSYGL NYYQQKPVAL INNQFLPYPY    60
YAKPAAVRSP AQILQWQVLS NTVPAKSCQA QPTTMARHPH PHLSFLIVTQ TMKGLDIQKV   120
AGTWYSLAMA ASDISLLDAQ SAPLRVYVEE LKPTPEGDLE ILLQKWENGE CAQKKIIAEK   180
TKIPAVFKID ALNENKVLVL DTDYKKYLLF CMENSAEPEQ SLACQCLVRT PEVDDEALEK   240
FDKALKALPM HIRLSFNPTQ LEEQCHIKDE L                                  271

SEQ ID NO: 623          moltype = DNA  length = 810
FEATURE                 Location/Qualifiers
misc_feature            1..810
                        note = fusion protein (OLG:FM:paraOKC1-T)
source                  1..810
                        mol_type = other DNA
                        organism = synthetic construct
SEQUENCE: 623
ttgatcgtaa cacagactat gaagggtctt gatatacaga aggtggccgg gacttggtac    60
agtttggcaa tggccgcatc cgacatctcc ttgttggacg cacaatcagc cccattgcgt   120
gtgtacgtag aagagcttaa accaactccc gagggggatc tggaaattct gctccagaaa   180
tgggagaacg tgagtgcgc ccagaagaag atcatcgcag agaagaccaa aattccagca   240
gtattcaaaa tcgacgcatt gaacgaaaat aaggtgctcg tactggacac tgattataag   300
aagtatctcc ttttctgtat ggagaactca gcagagcctg aacagagtct tgcctgccaa   360
tgccttgttc gtaccccaga ggtagatgat gaagctctgg aaaagttcga taaggccctt   420
aaggctctgc ctatgcacat taggctttct ttcaatccaa ctcaacttga ggaacaatgt   480
cacattttca tgcaagagca gaatcaagag cagccaatcc gttgtgagaa ggacgagagg   540
ttcttctcag acaagatcgc caaatatata cccatacaat atgtactctc acgctaccct   600
agctacgggc ttaactacta tcagcaaaaa cctgtagcac tgataaataa ccagtttctc   660
ccctatccct attatgctaa acctgccgcc gtgaggagtc cagcacaaat acttcagtgg   720
caagtgctca gtaacaccgt gccagcaaaa agctgccagg ctcagcccac acaatggcc   780
cgtcatcccc atcctcacct tagcttctaa                                    810

SEQ ID NO: 624          moltype = AA  length = 269
FEATURE                 Location/Qualifiers
REGION                  1..269
                        note = fusion protein (OLG:FM:paraOKC1-T)
source                  1..269
                        mol_type = protein
                        organism = synthetic construct
SEQUENCE: 624
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HIFMQEQNQE QPIRCEKDER   180
```

```
FFSDKIAKYI PIQYVLSRYP SYGLNYYQQK PVALINNQFL PYPYYAKPAA VRSPAQILQW   240
QVLSNTVPAK SCQAQPTTMA RHPHPHLSF                                    269

SEQ ID NO: 625             moltype = DNA  length = 822
FEATURE                    Location/Qualifiers
misc_feature               1..822
                           note = fusion protein (OLG:FM:paraOKC1-T:KDEL)
source                     1..822
                           mol_type = other DNA
                           organism = synthetic construct
SEQUENCE: 625
ttgatcgtaa cacagactat gaagggtctt gatatacaga aggtggccgg gacttggtac   60
agtttggcaa tggccgcatc cgacatctcc ttgttggacg cacaatcagc cccattgcgt  120
gtgtacgtag aagagcttaa accaactccc gaggggatc tggaaattct gctccagaaa   180
tgggagaacg gtgagtgcgc ccagaagaag atcatcgcag agaagaccaa aattccagca  240
gtattcaaaa tcgacgcatt gaacgaaaat aaggtgctcg tactgacac tgattataag   300
aagtatctcc ttttctgtat ggagaactca gcagagcctg aacagagtct tgcctgccaa  360
tgccttgttc gtaccccaga ggtagatgat gaagctctgg aaaagttcga taggcccttt  420
aaggctctgc ctatgcacat taggcttttct ttcaatccaa ctcaacttga ggaacaatgt  480
cacattttca tgcaagagca gaatcaagag cagccaatcc gttgtgagaa ggacgagagg  540
ttcttctcag acaagatcgc caaatatata cccttacaat atgtactctc acgctaccct  600
agctacgggc ttaactacta tcagcaaaaa cctgtagcac tgataaataa ccagtttctc  660
ccctatccct attatgctaa acctgccgcc gtgaggagtc cagcacaaat acttcagtgg  720
caagtgctca gtaacaccgt gccagcaaaa agctgccagg ctcagcccac cacaatggcc  780
cgtcatcccc atcctcacct tagcttcaag gatgagcttt aa                     822

SEQ ID NO: 626             moltype = AA  length = 273
FEATURE                    Location/Qualifiers
REGION                     1..273
                           note = fusion protein (OLG:FM:paraOKC1-T:KDEL)
source                     1..273
                           mol_type = protein
                           organism = synthetic construct
SEQUENCE: 626
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HIFMQEQNQE QPIRCEKDER   180
FFSDKIAKYI PIQYVLSRYP SYGLNYYQQK PVALINNQFL PYPYYAKPAA VRSPAQILQW   240
QVLSNTVPAK SCQAQPTTMA RHPHPHLSFK DEL                               273

SEQ ID NO: 627             moltype = DNA  length = 804
FEATURE                    Location/Qualifiers
misc_feature               1..804
                           note = fusion protein (OLG:paraOKC1-T)
source                     1..804
                           mol_type = other DNA
                           organism = synthetic construct
SEQUENCE: 627
ttgatcgtaa cacagactat gaagggtctt gatatacaga aggtggccgg gacttggtac   60
agtttggcaa tggccgcatc cgacatctcc ttgttggacg cacaatcagc cccattgcgt  120
gtgtacgtag aagagcttaa accaactccc gaggggatc tggaaattct gctccagaaa   180
tgggagaacg gtgagtgcgc ccagaagaag atcatcgcag agaagaccaa aattccagca  240
gtattcaaaa tcgacgcatt gaacgaaaat aaggtgctcg tactgacac tgattataag   300
aagtatctcc ttttctgtat ggagaactca gcagagcctg aacagagtct tgcctgccaa  360
tgccttgttc gtaccccaga ggtagatgat gaagctctgg aaaagttcga taggcccttt  420
aaggctctgc ctatgcacat taggcttttct ttcaatccaa ctcaacttga ggaacaatgt  480
cacattcaag agcagaatca gagcagcca atccgttgtg agaaggacga ggttcttc     540
tcagacaaga tcgccaaata tacccata caatatgtac tctcacgcta ccctagctac   600
gggcttaact actatcagca aaacctgta gcactgataa ataaccagtt tctcccctat   660
cccattatg ctaaacctgc cgccgtgagg agtccagcac aaatacttca gtggcaagtg   720
ctcagtaaca ccgtgccagc aaaaagctgc caggctcagc ccaccacaat ggcccgtcat   780
ccccatcctc accttagctt ctaa                                         804

SEQ ID NO: 628             moltype = AA  length = 271
FEATURE                    Location/Qualifiers
REGION                     1..271
                           note = fusion protein (OLG:paraOKC1-T)
source                     1..271
                           mol_type = protein
                           organism = synthetic construct
SEQUENCE: 628
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HIQEQNQEQP IRCEKDERFF   180
SDKIAKYIPI QYVLSRYPSY GLNYYQQKPV ALINNQFLPY PYYAKPAAVR SPAQILQWQV   240
LSNTVPAKSC QAQPTTMARH PHPHLSFKDE L                                 271

SEQ ID NO: 629             moltype = DNA  length = 816
FEATURE                    Location/Qualifiers
```

```
misc_feature            1..816
                        note = fusion protein (OLG:paraOKC1-T:KDEL)
source                  1..816
                        mol_type = other DNA
                        organism = synthetic construct
SEQUENCE: 629
ttgatcgtaa cacagactat gaagggtctt gatatacaga aggtggccgg gacttggtac   60
agtttggcaa tggccgcatc cgacatctcc ttgttggacg cacaatcagc cccattgcgt  120
gtgtacgtag aagagcttaa accaactccc gagggggatc tggaaattct gctccagaaa  180
tgggagaacg gtgagtgcgc ccagaagaag atcatcgcag agaagaccaa aattccagca  240
gtattcaaaa tcgacgcatt gaacgaaaat aaggtgctcg tactggacac tgattataag  300
aagtatctcc ttttctgtat ggagaactca gcagagcctg aacagagtct tgcctgccaa  360
tgccttgttc gtaccccaga ggtagatgat gaagctctgg aaaagttcga taaggccctt  420
aaggctctgc ctatgcacat taggctttct ttcaatccaa ctcaacttga ggaacaatgt  480
cacattcaag agcagaatca agagcagcca atccgttgtg agaaggacga gaggttcttc  540
tcagacaaga tcgccaaata tacccata caatatgtac tctcacgcta ccctagctac  600
gggcttaact actatcagca aaaacctgta gcactgataa ataaccagtt tctcccctat  660
ccctattatg ctaaacctgc cgccgtgagg agtccagcaa taaccagtt tctccccat  720
ctcagtaaca ccgtgccagc aaaaagctgc caggctcagc ccaccacaat ggcccgtcat  780
ccccatcctc accttagctt caaggatgag ctttaa                            816

SEQ ID NO: 630          moltype = AA  length = 271
FEATURE                 Location/Qualifiers
REGION                  1..271
                        note = fusion protein (OLG:paraOKC1-T:KDEL)
source                  1..271
                        mol_type = protein
                        organism = synthetic construct
SEQUENCE: 630
LIVTQTMKGL DIQKVAGTWY SLAMAASDIS LLDAQSAPLR VYVEELKPTP EGDLEILLQK   60
WENGECAQKK IIAEKTKIPA VFKIDALNEN KVLVLDTDYK KYLLFCMENS AEPEQSLACQ  120
CLVRTPEVDD EALEKFDKAL KALPMHIRLS FNPTQLEEQC HIQEQNQEQP IRCEKDERFF  180
SDKIAKYIPI QYVLSRYPSY GLNYYQQKPV ALINNQFLPY PYYAKPAAVR SPAQILQWQV  240
LSNTVPAKSC QAQPTTMARH PHPHLSFKDE L                                  271

SEQ ID NO: 631          moltype = DNA  length = 1092
FEATURE                 Location/Qualifiers
misc_feature            1..1092
                        note = fusion protein (OaS1-T:FM:OLG1)
source                  1..1092
                        mol_type = other DNA
                        organism = synthetic construct
SEQUENCE: 631
cgccccaaaac atcccataaa acatcaagga ttgccccagg aagtactcaa cgagaatctc   60
ctccgttttt tcgttgctcc tttccccgaa gtgttcggga aggaaaaagt aaacgagctt  120
tcaaaggaca tcggctctga agtaccgag atcaggcta tggaagatat caagcaaatg  180
gaggccgaat ctataagttc ttcagaagaa atagttccca actcagtga gcagaagcac  240
attcagaaag aagacgtgcc cagcgagcgc tatctgggat attggaaca gctgctcaga  300
ctgaaaaagt acaaggtgcc tcagctcgaa atcgtaccca atagtgctga gaaaggttg  360
cactcaatga agagggat tcacgcacaa caaaagagc ctatgatcgg agtaaatcaa  420
gaactggcat acttttatcc cgagttgttt cgccaattct atcaactgga tgcctacct  480
tccggtgcat ggtactacgt accccctcgg actcaatata ccgatgctcc ctcctttccc  540
gacattccta atcctatagg ttccgagaat agcgaaaaga ccaccatgcc cttatggttc  600
atgttgatcg taacacagac tatgaagggt cttgatatac agaaggtggc cgggacttgg  660
tacagtttgg caatggccgc atccgacatc tccttgttg acgcacaatc agcccccattg  720
cgtgtgtacg tagaagagct taaaccaact cccgagggggg atctggaaat tctgctccaa  780
aaatggggaga acggtgagtg cgcccagaag aagatcatcg cagagaagac caaaattcca  840
gcagtattca aaatcgacgc attgaacgaa aataaggtgc tcgtactgga cactgattat  900
aagaagtatc tccttttctg tatggagaac tcagcagagc tgaacagag tcttgcctgc  960
caatgccttg ttcgtacccc agaggtagat gatgaagctc tggaaaagtt cgataaggcc  1020
cttaaggctc tgcctatgca cattaggctt tctttcaatc caactcaact tgaggaacaa  1080
tgtcacattt aa                                                       1092

SEQ ID NO: 632          moltype = AA  length = 363
FEATURE                 Location/Qualifiers
REGION                  1..363
                        note = fusion protein (OaS1-T:FM:OLG1)
source                  1..363
                        mol_type = protein
                        organism = synthetic construct
SEQUENCE: 632
RPKHPIKHQG LPQEVLNENL LRFFVAPFPE VFGKEKVNEL SKDIGSESTE DQAMEDIKQM   60
EAESISSSEE IVPNSVEQKH IQKEDVPSER YLGYLEQLLR LKKYKVPQLE IVPNSAEERL  120
HSMKEGIHAQ QKEPMIGVNQ ELAYFYPELF RQFYQLDAYP SGAWYYVPLG TQYTDAPSFS  180
DIPNPIGSEN SEKTTMPLWF MLIVTQTMKG LDIQKVAGTW YSLAMAASDI SLLDAQSAPL  240
RVYVEELKPT PEGDLEILLQ KWENGECAQK KIIAEKTKIP AVFKIDALNE NKVLVLDTDY  300
KKYLLFCMEN SAEPEQSLAC QCLVRTPEVD DEALEKFDKA LKALPMHIRL SFNPTQLEEQ  360
CHI                                                                  363
```

| SEQ ID NO: 633 | moltype = DNA length = 1104 |
|---|---|
| FEATURE | Location/Qualifiers |
| misc_feature | 1..1104 |
| | note = fusion protein (OaS1-T:FM:OLG1:KDEL) |
| source | 1..1104 |
| | mol_type = other DNA |
| | organism = synthetic construct |

SEQUENCE: 633

```
cgcccaaaac atcccataaa acatcaagga ttgccccagg aagtactcaa cgagaatctc   60
ctccgttttt tcgttgctcc tttccccgaa gtgttcggga aggaaaaagt aaacgagctt  120
tcaaaggaca tcggctctga aagtaccgag atcaggcta tggaagatat caagcaaatg  180
gaggccgaat ctataagttc ttcagaagaa atagttccca actcagtgga gcagaagcac  240
attcagaaag aagacgtgcc cagcgagcgc tatctgggat atttggaaca gctgctcaga  300
ctgaaaaagt acaaggtgcc tcagctcgaa atcgtaccca atagtgctga agaaaggttg  360
cactcaatga agaggggat tcacgcacaa caaaaagagc ctatgatcgg agtaaatcaa  420
gaactggcat acttttatcc cgagttgttt cgccaattct atcaactgga tgcctaccct  480
tccggtgcat ggtactacgt accctcggt actcaatata ccgatgctcc ctccttttcc  540
gacattccta atcctatagg ttccgagaat agcgaaaaga ccaccatgcc cttatggttc  600
atgttgatcg taacacagac tatgaaggt cttgatatac agaaggtggc cgggacttgg  660
tacagtttgg caatggccgc atccgacatc tccttgttgg acgcacaatc agccccattg  720
cgtgtgtacg tagaagagct taaaccaact cccgaggggg atctgaaaat tctgctccag  780
aaatgggaga acggtgagtg cgcccagaag aagatcatcg cagagaagac caaaattcca  840
gcagtattca aaatcgacgc attgaacgaa aataaggtgc tcgtactgga cactgattat  900
aagaagtatc tcttttctg tatggagaac tcagcagagc ctgaacagag tcttgcctgc  960
caatgccttg ttcgtacccc agaggtagat gatgaagctc tggaaaagtt cgataaggcc 1020
cttaaggctc tgcctatgca cattaggctt tctttcaatc caactcaact tgaggaacaa 1080
tgtcacatta aggatgagct ttaa                                        1104
```

| SEQ ID NO: 634 | moltype = AA length = 367 |
|---|---|
| FEATURE | Location/Qualifiers |
| REGION | 1..367 |
| | note = fusion protein (OaS1-T:FM:OLG1:KDEL) |
| source | 1..367 |
| | mol_type = protein |
| | organism = synthetic construct |

SEQUENCE: 634

```
RPKHPIKHQG LPQEVLNENL LRFFVAPFPE VFGKEKVNEL SKDIGSESTE DQAMEDIKQM   60
EAESISSSEE IVPNSVEQKH IQKEDVPSER YLGYLEQLLR LKKYKVPQLE IVPNSAEERL  120
HSMKEGIHAQ QKEPMIGVNQ ELAYFYPELF RQFYQLDAYP SGAWYYVPLG TQYTDAPSFS  180
DIPNPIGSEN SEKTTMPLWF MLIVTQTMKG LDIQKVAGTW YSLAMAASDI SLLDAQSAPL  240
RVYVEELKPT PEGDLEILLQ KWENGECAQK KIIAEKTKIP AVFKIDALNE NKVLVLDTDY  300
KKYLLFCMEN SAEPEQSLAC QCLVRTPEVD DEALEKFDKA LKALPMHIRL SFNPTQLEEQ  360
CHIKDEL                                                           367
```

| SEQ ID NO: 635 | moltype = DNA length = 1086 |
|---|---|
| FEATURE | Location/Qualifiers |
| misc_feature | 1..1086 |
| | note = fusion protein (OaS1-T:OLG1) |
| source | 1..1086 |
| | mol_type = other DNA |
| | organism = synthetic construct |

SEQUENCE: 635

```
cgcccaaaac atcccataaa acatcaagga ttgccccagg aagtactcaa cgagaatctc   60
ctccgttttt tcgttgctcc tttccccgaa gtgttcggga aggaaaaagt aaacgagctt  120
tcaaaggaca tcggctctga aagtaccgag atcaggcta tggaagatat caagcaaatg  180
gaggccgaat ctataagttc ttcagaagaa atagttccca actcagtgga gcagaagcac  240
attcagaaag aagacgtgcc cagcgagcgc tatctgggat atttggaaca gctgctcaga  300
ctgaaaaagt acaaggtgcc tcagctcgaa atcgtaccca atagtgctga agaaaggttg  360
cactcaatga agaggggat tcacgcacaa caaaaagagc ctatgatcgg agtaaatcaa  420
gaactggcat acttttatcc cgagttgttt cgccaattct atcaactgga tgcctaccct  480
tccggtgcat ggtactacgt accctcggt actcaatata ccgatgctcc ctccttttcc  540
gacattccta atcctatagg ttccgagaat agcgaaaaga ccaccatgcc cttatggttg  600
atcgtaacac agactatgaa gggtcttgat atacagaagg tggccgggac ttggtacagt  660
ttggccgatc cgcatccga catctccttg ttggacgcac aatcagcccc attgcgtgta  720
tacgtagaag agcttaaacc aactcccgag gggatctgg aaattctgct ccagaaatgg  780
gagaacggtg agtgcgccca agaagatc atcgcagaga gaccaaaat tccagcagta  840
ttcaaaatcg acgcattgaa cgaaataag gtgctcgtac tggacactga ttataagaag  900
tatctccttt tctgtatgga gaactcagca gagcctgaac agagtcttgc ctgccaatgc  960
cttgttcgta ccccagaggt agatgatgaa gctctgaaa agttcgataa ggcccttaag 1020
gctctgccta tgcacattag gctttctttc aatccaactc aacttgagga acaatgtcac 1080
atttaa                                                           1086
```

| SEQ ID NO: 636 | moltype = AA length = 361 |
|---|---|
| FEATURE | Location/Qualifiers |
| REGION | 1..361 |
| | note = fusion protein (OaS1-T:OLG1) |
| source | 1..361 |
| | mol_type = protein |
| | organism = synthetic construct |

```
SEQUENCE: 636
RPKHPIKHQG LPQEVLNENL LRFFVAPFPE VFGKEKVNEL SKDIGSESTE DQAMEDIKQM    60
EAESISSSEE IVPNSVEQKH IQKEDVPSER YLGYLEQLLR LKKYKVPQLE IVPNSAEERL   120
HSMKEGIHAQ QKEPMIGVNQ ELAYFYPELF RQFYQLDAYP SGAWYYVPLG TQYTDAPSFS   180
DIPNPIGSEN SEKTTMPLWL IVTQTMKGLD IQKVAGTWYS LAMAASDISL LDAQSAPLRV   240
YVEELKPTPE GDLEILLQKW ENGECAQKKI IAEKTKIPAV FKIDALNENK VLVLDTDYKK   300
YLLFCMENSA EPEQSLACQC LVRTPEVDDE ALEKFDKALK ALPMHIRLSF NPTQLEEQCH   360
I                                                                  361

SEQ ID NO: 637         moltype = DNA   length = 1098
FEATURE                Location/Qualifiers
misc_feature           1..1098
                       note = fusion protein (OaS1-T:OLG1:KDEL)
source                 1..1098
                       mol_type = other DNA
                       organism = synthetic construct
SEQUENCE: 637
cgcccaaaac atcccataaa acatcaagga ttgccccagg aagtactcaa cgagaatctc    60
ctccgttttt tcgttgctcc ttttccccgaa gtgttcggga aggaaaaagt aaacgagctt   120
tcaaaggaca tcggctctga agtaccgag gatcaggcta tggaagatat caagcaaatg    180
gaggccgaat ctataagttc ttcagaagaa atagttccca actcagtgga gcagaagcac    240
attcagaaag aagacgtgcc cagcgagcgc tatctgggta atttggaaca gctgctcaga    300
ctgaaaaagt acaaggtgcc tcagctcgaa atcgtaccca atagtgctga gaaaggttga    360
cactcaatga agaggggat tcacgcacaa caaaaagagc ctatgatcgg agtaaatcaa     420
gaactggcat acttttatcc cgagttgttt cgccaattct atcaactgga tgcctaccct    480
tccggtgcat ggtactacgt accccctcggt actcaatata ccgatgctcc ctcctttttcc  540
gacattccta atcctatagg ttccgagaat agcgaaaaga ccaccatgcc cttatgggttta  600
atcgtaacac agactatgaa gggtcttgat atacagaagg tggccgggac ttggtacagt    660
ttggcaatgc cgcatccga catctccttg ttggacgcac aatcagcccc attgcgtgtg    720
tacgtagaag agcttaaacc aactcccgag ggggatctgg aaattctgct ccagaaatgt   780
gagaacggtg agtgcgccca agaagatc atcgcagaa agaccaaaat tccagcagta     840
ttcaaaatcg acgcattgaa cgaaataag gtgctcgtac tggacactga ttataagaag    900
tatctccttt tctgtatgga gaactcagca gagcctgaac agagtcttgc ctgccaatgc   960
cttgttcgta ccccagaggt agatgatgaa gctctggaaa agttcgataa ggcccttaag  1020
gctctgccta tgcacattag gctttctttc aatccaactc aacttgagga caatgtcac   1080
attaaggatg agcttttaa                                               1098

SEQ ID NO: 638         moltype = AA   length = 365
FEATURE                Location/Qualifiers
REGION                 1..365
                       note = fusion protein (OaS1-T:OLG1:KDEL)
source                 1..365
                       mol_type = protein
                       organism = synthetic construct
SEQUENCE: 638
RPKHPIKHQG LPQEVLNENL LRFFVAPFPE VFGKEKVNEL SKDIGSESTE DQAMEDIKQM    60
EAESISSSEE IVPNSVEQKH IQKEDVPSER YLGYLEQLLR LKKYKVPQLE IVPNSAEERL   120
HSMKEGIHAQ QKEPMIGVNQ ELAYFYPELF RQFYQLDAYP SGAWYYVPLG TQYTDAPSFS   180
DIPNPIGSEN SEKTTMPLWL IVTQTMKGLD IQKVAGTWYS LAMAASDISL LDAQSAPLRV   240
YVEELKPTPE GDLEILLQKW ENGECAQKKI IAEKTKIPAV FKIDALNENK VLVLDTDYKK   300
YLLFCMENSA EPEQSLACQC LVRTPEVDDE ALEKFDKALK ALPMHIRLSF NPTQLEEQCH   360
IKDEL                                                              365

SEQ ID NO: 639         moltype = DNA   length = 1092
FEATURE                Location/Qualifiers
misc_feature           1..1092
                       note = fusion protein (OLG1:FM:OaS1-T)
source                 1..1092
                       mol_type = other DNA
                       organism = synthetic construct
SEQUENCE: 639
ttgatcgtaa cacagactat gaagggtctt gatatacaga aggtggccgg gacttggtac    60
agtttggcaa tggccgcatc cgacatctcc ttgttggacg cacaatcagc cccattgcgt   120
gtgtacgtag aagagcttaa accaactccc gaggggatc tggaaattct gctccagaaa    180
tgggagaacg gtgagtgcgc ccagaagaag atcatcgcag agaagaccaa aattccagca    240
gtattcaaaa tcgacgcatt gaacgaaaat aaggtgctcg tactggacac tgattataag    300
aagtatctcc ttttctgtat ggagaactca gcagagcctg aacagagtct tgcctgccaa    360
tgccttgttc gtaccccaga ggtagatgat gaagctctgg aaaagttcga taaggcccttt   420
aaggctctgc ctatgcacat taggctttct ttcaatccaa ctcaacttga ggacaatgtct   480
cacattttca tgcgcccaaa acatcccata aacatcaag gattgcccca ggaagtactc    540
aacgagaatc tcctccgttt tttcgttgct ccttttcccg aagtgttcgg aaggaaaaa    600
gtaaacgagc tttcaaagga catcggctct gaagtaccg aggatcaggc tatggaagat    660
atcaagcaaa tggaggccga atctataagt tcttcagaag aaatagttcc caactcagtg    720
gagcagaagc acattcagaa agaagacgtg cccagcgagc gctatctggg tatatttggaa  780
cagctgctca gactgaaaaa gtacaaggtg cctcagctcg aaatcgtacc caatagtgct    840
gaagaaaaggt tgcactcaat gaagaggggt attcacgcac aacaaaaaga gcctatgatc    900
ggagtaaatc aagaactggc atactttat cccgagttgt tcgccaatt ctatcaactg     960
gatgcctacc cttccggtgc atggtactac gtaccccctcg gtactcaata taccgatgct  1020
ccctcctttt ccgacattcc taatcctata ggttccgaga atagcgaaaa gaccaccatg  1080
```

```
cccttatggt aa                                                      1092

SEQ ID NO: 640           moltype = AA   length = 363
FEATURE                  Location/Qualifiers
REGION                   1..363
                         note = fusion protein (OLG1:FM:OaS1-T)
source                   1..363
                         mol_type = protein
                         organism = synthetic construct
SEQUENCE: 640
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HIFMRPKHPI KHQGLPQEVL   180
NENLLRFFVA PFPEVFGKEK VNELSKDIGS ESTEDQAMED IKQMEAESIS SSEEIVPNSV   240
EQKHIQKEDV PSERYLGYLE QLLRLKKYKV PQLEIVPNSA EERLHSMKEG IHAQQKEPMI   300
GVNQELAYFY PELFRQFYQL DAYPSGAWYY VPLGTQYTDA PSFSDIPNPI GSENSEKTTM   360
PLW                                                                 363

SEQ ID NO: 641           moltype = DNA   length = 1104
FEATURE                  Location/Qualifiers
misc_feature             1..1104
                         note = fusion protein (OLG1:FM:OaS1-T:KDEL)
source                   1..1104
                         mol_type = other DNA
                         organism = synthetic construct
SEQUENCE: 641
ttgatcgtaa cacagactat gaagggtctt gatatacaga aggtggccgg gacttggtac    60
agtttggcaa tggccgcatc cgacatctcc ttgttggacg cacaatcagc cccattgcgt   120
gtgtacgtag aagagcttaa accaactccc gagggggatc tggaaattct gctccagaaa   180
tgggagaacg gtgagtgcgc ccagaagaag atcatcgcag agaagaccaa aattccagca   240
gtattcaaaa tcgacgcatt gaacgaaaat aaggtgctcg tactggacac tgattataag   300
aagtatctcc ttttctgtat ggagaactca gcagagcctg aacagagtct tgcctgccaa   360
tgccttgttc gtaccccaga ggtagatgat gaagctctgg aaaagttcga taaggccctt   420
aaggctctgc ctatgcacat taggcttttct ttcaatccaa ctcaacttga ggaacaatgt   480
cacattttca tgcgcccaaa acatcccata aaacatcaag gattgcccca ggaagtactc   540
aacgagaatc tcctccgttt tttcgttgct ccttttcccg aagtgttcgg aaggaaaaa    600
gtaaacgagc tttcaaagga catcggctct gaaagtaccg aggatcaggc tatggaagat   660
atcaagcaaa tggaggccga atctataagt tcttcagaag aaatagttcc caactcagtg   720
gagcagaagc acattcagaa agaagacgtg cccagcgagc gctatctggg atatttggaa   780
cagctgctca gactgaaaaa gtacaaggtg cctcagctcg aaatcgtacc caatagtgct   840
gaagaaaggt tgcactcaat gaaagagggg attcacgcac aacaaaaaga gcctatgatc   900
ggagtaaatc aagaactggc atacttttat cccgagttgt ttcgccaatt ctatcaactg   960
gatgcctacc cttccggtgc atggtactac gtacccctcg gtactcaata taccgatgct  1020
ccctcctttt ccgacattcc taatcctata ggttccgaga atagcgaaaa gaccaccatg  1080
cccttatgga aggatgagct ttaa                                         1104

SEQ ID NO: 642           moltype = AA   length = 367
FEATURE                  Location/Qualifiers
REGION                   1..367
                         note = fusion protein (OLG1:FM:OaS1-T:KDEL)
source                   1..367
                         mol_type = protein
                         organism = synthetic construct
SEQUENCE: 642
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HIFMRPKHPI KHQGLPQEVL   180
NENLLRFFVA PFPEVFGKEK VNELSKDIGS ESTEDQAMED IKQMEAESIS SSEEIVPNSV   240
EQKHIQKEDV PSERYLGYLE QLLRLKKYKV PQLEIVPNSA EERLHSMKEG IHAQQKEPMI   300
GVNQELAYFY PELFRQFYQL DAYPSGAWYY VPLGTQYTDA PSFSDIPNPI GSENSEKTTM   360
PLWKDEL                                                             367

SEQ ID NO: 643           moltype = DNA   length = 1086
FEATURE                  Location/Qualifiers
misc_feature             1..1086
                         note = fusion protein (OLG1:OaS1-T)
source                   1..1086
                         mol_type = other DNA
                         organism = synthetic construct
SEQUENCE: 643
ttgatcgtaa cacagactat gaagggtctt gatatacaga aggtggccgg gacttggtac    60
agtttggcaa tggccgcatc cgacatctcc ttgttggacg cacaatcagc cccattgcgt   120
gtgtacgtag aagagcttaa accaactccc gagggggatc tggaaattct gctccagaaa   180
tgggagaacg gtgagtgcgc ccagaagaag atcatcgcag agaagaccaa aattccagca   240
gtattcaaaa tcgacgcatt gaacgaaaat aaggtgctcg tactggacac tgattataag   300
aagtatctcc ttttctgtat ggagaactca gcagagcctg aacagagtct tgcctgccaa   360
tgccttgttc gtaccccaga ggtagatgat gaagctctgg aaaagttcga taaggccctt   420
aaggctctgc ctatgcacat taggcttttct ttcaatccaa ctcaacttga ggaacaatgt   480
cacattcgcc caaacatcc cataaaacat caaggattgc cccaggaagt actcaacgag   540
```

```
aatctcctcc gttttttcgt tgctcctttc cccgaagtgt tcgggaagga aaaagtaaac    600
gagctttcaa aggacatcgg ctctgaaagt accgaggatc aggctatgga agatatcaag    660
caaatggagg ccgaatctat aagttcttca gaagaaatag ttcccaactc agtggagcag    720
aagcacattc agaaagaaga cgtgcccagc gagcgctatc tgggatattt ggaacagctg    780
ctcagactga aaaagtacaa ggtgcctcag ctcgaaatcg tacccaatag tgctgaagaa    840
aggttgcact caatgaaaga ggggattcac gcacaacaaa aagagcctat gatcggagta    900
aatcaagaac tggcatactt ttatcccgag ttgtttcgcc aattctatca actggatgcc    960
tacccttccg gtgcatggta ctacgtaccc ctcggtactc aatataccga tgctccctcc   1020
ttttccgaca ttcctaatcc tataggttcc gagaatagcg aaaagaccac catgccctta   1080
tggtaa                                                              1086
```

SEQ ID NO: 644        moltype = AA   length = 361
FEATURE               Location/Qualifiers
REGION                1..361
                      note = fusion protein (OLG1:OaS1-T)
source                1..361
                      mol_type = protein
                      organism = synthetic construct
SEQUENCE: 644
LIVTQTMKGL DIQKVAGTWY SLAMAASDIS LLDAQSAPLR VYVEELKPTP EGDLEILLQK     60
WENGECAQKK IIAEKTKIPA VFKIDALNEN KVLVLDTDYK KYLLFCMENS AEPEQSLACQ    120
CLVRTPEVDD EALEKFDKAL KALPMHIRLS FNPTQLEEQC HIRPKHPIKH QGLPQEVLNE    180
NLLRFFVAPF PEVFGKEKVN ELSKDIGSES TEDQAMEDIK QMEAESISSS EEIVPNSVEQ    240
KHIQKEDVPS ERYLGYLEQL LRLKKYKVPQ LEIVPNSAEE RLHSMKEGIH AQQKEPMIGV    300
NQELAYFYPE LFRQFYQLDA YPSGAWYYVP LGTQYTDAPS FSDIPNPIGS ENSEKTTMPL    360
W                                                                   361

SEQ ID NO: 645        moltype = DNA   length = 1098
FEATURE               Location/Qualifiers
misc_feature          1..1098
                      note = fusion protein (OLG1:OaS1-T:KDEL)
source                1..1098
                      mol_type = other DNA
                      organism = synthetic construct
SEQUENCE: 645
ttgatcgtaa cacagactat gaagggtctt gatatacaga aggtggccgg gacttggtac     60
agtttggcaa tggccgcatc cgacatctcc ttgttggacg cacaatcagc cccattgcgt    120
gtgtacgtag aagagcttaa accaactccc gaggggggatc tggaaattct gctccagaaa    180
tgggagaacg gtgagtgcgc ccagaagaag atcatcgcag agaagaccaa aattccagca    240
gtattcaaaa tcgacgcatt gaacgaaaat aaggtgctcg tactggacac tgattataag    300
aagtatctcc ttttctgtat ggagaactca gcagagcctg aacagagtct tgcctgccaa    360
tgccttgttc gtaccccaga ggtagatgat gaagctctgg aaaagtttga taaggcccttg   420
aaggcctgc ctatgcacat taggctttct ttcaatccaa ctcaacttga ggaacaatgc    480
cacattcgcc caaaacatcc cataaaacat caaggattgc cccaggaagt actcaacgag    540
aatctcctcc gttttttcgt tgctcctttc cccgaagtgt tcgggaagga aaaagtaaac    600
gagctttcaa aggacatcgg ctctgaaagt accgaggatc aggctatgga agatatcaag    660
caaatggagg ccgaatctat aagttcttca gaagaaatag ttcccaactc agtggagcag    720
aagcacattc agaaagaaga cgtgcccagc gagcgctatc tgggatattt ggaacagctg    780
ctcagactga aaaagtacaa ggtgcctcag ctcgaaatcg tacccaatag tgctgaagaa    840
aggttgcact caatgaaaga ggggattcac gcacaacaaa aagagcctat gatcggagta    900
aatcaagaac tggcatactt ttatcccgag ttgtttcgcc aattctatca actggatgcc    960
tacccttccg gtgcatggta ctacgtaccc ctcggtactc aatataccga tgctccctcc   1020
ttttccgaca ttcctaatcc tataggttcc gagaatagcg aaaagaccac catgccctta   1080
tggaaggatg agctttaa                                                 1098

SEQ ID NO: 646        moltype = AA   length = 365
FEATURE               Location/Qualifiers
REGION                1..365
                      note = fusion protein (OLG1:OaS1-T:KDEL)
source                1..365
                      mol_type = protein
                      organism = synthetic construct
SEQUENCE: 646
LIVTQTMKGL DIQKVAGTWY SLAMAASDIS LLDAQSAPLR VYVEELKPTP EGDLEILLQK     60
WENGECAQKK IIAEKTKIPA VFKIDALNEN KVLVLDTDYK KYLLFCMENS AEPEQSLACQ    120
CLVRTPEVDD EALEKFDKAL KALPMHIRLS FNPTQLEEQC HIRPKHPIKH QGLPQEVLNE    180
NLLRFFVAPF PEVFGKEKVN ELSKDIGSES TEDQAMEDIK QMEAESISSS EEIVPNSVEQ    240
KHIQKEDVPS ERYLGYLEQL LRLKKYKVPQ LEIVPNSAEE RLHSMKEGIH AQQKEPMIGV    300
NQELAYFYPE LFRQFYQLDA YPSGAWYYVP LGTQYTDAPS FSDIPNPIGS ENSEKTTMPL    360
WKDEL                                                               365

SEQ ID NO: 647        moltype = DNA   length = 1122
FEATURE               Location/Qualifiers
misc_feature          1..1122
                      note = fusion protein (OLG1:FM:OBC-T2)
source                1..1122
                      mol_type = other DNA
                      organism = synthetic construct
SEQUENCE: 647

```
ttgatcgtaa cacagactat gaagggtctt gatatacaga aggtggccgg gacttggtac    60
agtttggcaa tggccgcatc cgacatctcc ttgttggacg cacaatcagc cccattgcgt   120
gtgtacgtag aagagcttaa accaactccc gaggggatc tggaaattct gctccagaaa   180
tgggagaacg tgagtgcgc ccagaagaag atcatcgcag agaagaccaa aattccagca   240
gtattcaaaa tcgacgcatt gaacgaaaat aaggtgctca tactggacac tgattataag   300
aagtatctcc ttttctgtat ggagaactca gcagagcctg aacagagtct tgcctgccaa   360
tgccttgttc gtaccccaga ggtagatgat gaagctctgg aaaagttcga taaggccctt   420
aaggctctgc ctatgcacat taggctttct ttcaatccaa ctcaacttga ggaacaatgt   480
cacatttca tgcgcgaact ggaagagttg aactaccagg agagagattgt agaatcactg   540
agctcctcag aggagtctat tactcgtatc aacaagaaga tagagaagtt ccaatccgag   600
gagcaacaac aaacagagga cgaattgcag gacaagatac atcctttcgc acagacccag   660
agcctcgtct atccctttcc aggtccaatc cctaactctc tccccccagaa tatcccaccc   720
ttgactcaga ctcccgtggt cgtacccct tcttgcaac ccgaggtgat gggggttct   780
aaagtcaaag aggctatggc tcctaaacat aaggaaatgc cttttcccaa atatccagtg   840
gagccattca ctgagagcca gtctctgaca cttacagatg tggaaaactt gcacctgccc   900
ttgccacttt tgcagtcctg gatgcaccaa ccacatcaac ccttgccccc cacagtgatg   960
tttcctccac aatcagttct tagtctctcc caaagcaaag tccttccagt gcctcagaag  1020
gccgtcccat accccagag agatatgcca tacaggcagt tctgcttta ccaggaacca  1080
gtgctcggtc ctgtacgtgg cccattccct atcatagtgt aa                    1122

SEQ ID NO: 648         moltype = AA  length = 373
FEATURE                Location/Qualifiers
REGION                 1..373
                       note = fusion protein (OLG1:FM:OBC-T2)
source                 1..373
                       mol_type = protein
                       organism = synthetic construct
SEQUENCE: 648
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HIFMRELEEL NVPGEIVESL   180
SSSEESITRI NKKIEKFQSE EQQQTEDELQ DKIHPFAQTQ SLVYPFPGPI PNSLPQNIPP   240
LTQTPVVVPP FLQPEVMGVS KVKEAMAPKH KEMPFPKYPV EPFTESQSLT LTDVENLHLP   300
LPLLQSWMHQ PHQPLPPTVM FPPQSVLSLS QSKVLPVPQK AVPYPQRDMP IQAFLLYQEP   360
VLGPVRGPFP IIV                                                      373

SEQ ID NO: 649         moltype = DNA  length = 1623
FEATURE                Location/Qualifiers
misc_feature           1..1623
                       note = fusion protein (OBC-T2:OKC1-T:OLG1)
source                 1..1623
                       mol_type = other DNA
                       organism = synthetic construct
SEQUENCE: 649
cgcgaactgg aagagttgaa cgtaccagga gagattgtag aatcactgag ctcctcagag    60
gagtctatta ctcgtatcaa caagaagata gagaagttcc aatccgagga gcaacaacaa   120
acagaggacg aattgcagga caagatacat cctttcgcac agacccagag cctcgtctat   180
ccctttccag gtccaatccc taactctctc ccccagaata tcccacctt gactcagact   240
cccgtggtcg tacccctttt cttgcaaccc gaggtgatgg gggttctaa agtcaaagag   300
gctatggctc ctaaacataa ggaaatgcct tttcccaaat atccagtgga gccattcact   360
gagagccagt ctctgacact tacagatgtg gaaaacttgc acctgcccct tgccactttg   420
cagtcctgga tgcaccaacc acatcaaccc ttgcccccca gtgatgttt cctccacaa   480
tcagttctta gtctctccca aagcaaagtc cttccagtgc ctcagaaggc cgtcccatac   540
ccccagagag atatgccaat acaggcattc tgctttacc aggaaccagt gctcggtcct   600
gtacgtggcc cattccctat catagtgcaa gagcagaatc aagagcagtc aatccgttgt   660
gagaaggacg agaggttctt ctcagacaag atcgccaaat atatacccat acaatatgta   720
ctctcacgct acccctagcta cgggcttaac tactatcagc aaaaacctgt agcactgata   780
aataaccagt ttctccccta tccctattat gctaaacctg ccgccgtgag gagtccagca   840
caaatactc agtggcaagt gctcagtaac accgtgcaac caaaaagctg ccaggctcag   900
cccaccacaa tggccgtca tccccatcct caccttagct tcatggcaat cccaccaaag   960
aagaatcaag acaagaccga atacctacc atcaacacaa ttgcatctgg agagcctacc  1020
agtacaccaa caactgaggc agtagagtct actgttgcta cccttgagga cagccccgag  1080
gttatagagt ccccacctga gataaatacc gtgcaggtga caagtaccgc cgtattgatc  1140
gtaacacaga ctatgaaggg tcttgatata cagaaggttg ccgggacttg gtacagtttg  1200
gcaatggccg catccgacat ctccttgttg gacgcacaat cagccccatt gcgtgtgtac  1260
gtagaagagc ttaaaccaac tcccgagggg atctggaaa ttctgctcca gaaatgggag  1320
aacgtgagtg cgcccagaa gaagatcatc gcagagaaga ccaaaattcc agcagtattc  1380
aaaatcgacg cattgaacga aaataaggtg ctcgtactgg acactgatta taagaagtat  1440
ctccttttct gtatggagaa ctcagcagag cctgaacaga gtcttgcctg ccaatgcctt  1500
gttcgtaccc cagaggtaga tgatgaagct ctggaaaagt tcgataaggc ccttaaggct  1560
ctgcctatgc acattaggct ttctttcaat ccaactcaac ttgaggaaca atgtcacatt  1620
taa                                                                1623

SEQ ID NO: 650         moltype = AA  length = 540
FEATURE                Location/Qualifiers
REGION                 1..540
                       note = fusion protein (OBC-T2:OKC1-T:OLG1)
source                 1..540
                       mol_type = protein
```

```
                        organism = synthetic construct
SEQUENCE: 650
RELEELNVPG EIVESLSSSE ESITRINKKI EKFQSEEQQQ TEDELQDKIH PFAQTQSLVY    60
PFPGPIPNSL PQNIPPLTQT PVVVPPFLQP EVMGVSKVKE AMAPKHKEMP FPKYPVEPFT   120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIVQ EQNQEQPIRC EKDERFFSDK IAKYIPIQYV   240
LSRYPSYGLN YYQQKPVALI NNQFLPYPYY AKPAAVRSPA QILWQVLSN  TVPAKSCQAQ   300
PTTMARHPHP HLSFMAIPPK KNQDKTEIPT INTIASGEPT STPTTEAVES TVATLEDSPE   360
VIESPPEINT VQVTSTAVLI VTQTMKGLDI QKVAGTWYSL AMAASDISLL DAQSAPLRVY   420
VEELKPTPEG DLEILLQKWE NGECAQKKII AEKTKIPAVF KIDALNENKV LVLDTDYKKY   480
LLFCMENSAE PEQSLACQCL VRTPEVDDEA LEKFDKALKA LPMHIRLSFN PTQLEEQCHI   540

SEQ ID NO: 651            moltype = DNA  length = 2250
FEATURE                   Location/Qualifiers
misc_feature              1..2250
                          note = fusion protein (OBC-T3:OBC-T2:OKC1-T:OLG1)
source                    1..2250
                          mol_type = other DNA
                          organism = synthetic construct
SEQUENCE: 651
agggaactcg aggaacttaa cgttccaggt gagatcgtcg agtccctctc atcttccgaa     60
gagtccatta ccaggatcaa caagaagatc gagaagttcc agtccgagga acaacagcaa    120
accgaggatg agcttcagga caagattcac ccattcgctc agacccagtc tctcgtgtat    180
ccatttccag ggccaattcc aaacagcctg ccacagaaca ttccaccact tactcagacc    240
ccagttgtgt tgccaccatt ccttcaacca gaggttatgg gagtgtccaa ggtgaaagaa    300
gccatggcac caaagcacaa agagatgccc tttccaaagt accccgttga gccattcact    360
gagtctcagt ctcttaccct caccgacgtt gagaacttca accttccact tccattgctc    420
cagtcttgga tgcatcaacc acatcagcca cttccaccaa ccgttatgtt cccacctcag    480
tccgtgctta gcctctctca gtctaaggtt ttgccagtgc ctcagaaggc cgttccatat    540
ccacaaaggg atatgccaat ccaggccttc ttgctctacc agagccagt  tcttggacca    600
gtgagaggcc catttccaat cattgtgcgc gaactggaag agttgaacgt accaggagag    660
attgtagaat cactgagctc ctcagaggag tctattactc gtatcaacaa gaagatagag    720
aagttccaat ccgaggagca caacaaaca  gaggacgaat gcaggacaa  gatacatcct    780
ttcgcacaga cccagagcct cgtctatccc tttccaggtc caatccctaa ctctctccca    840
cagaatatcc caccctttga ctcagactcc gtggtcgtac cccctttctt gcaacccgag    900
gtgatggggg tttctaaagt caaagaggct atggctccta acataagga  aatgcctttt    960
cccaaatatc cagtggagcc attcactgag agccagtctc tgacacttac agatgtggaa   1020
aacttgcacc tgcccttgcc actttgcag  tcctggatgc accaaccaca tcaaccctg   1080
cccccacagt tgatgttccc tccacaatca gttcttagtc tctcccaaag caagtgcctt   1140
ccagtgcctc agaaggccgt cccatacccc cagagagata tgccaataca ggcattcttg   1200
ctttaccagg aaccagtgct cggtcctgta cgtggcccat ccctatcat  agtgcaagag   1260
cagaatcaag agcagccaat ccgttgtgag aaggacgaga ggttcttctc agacaagatc   1320
gccaaatata taccocataca atatgtactc tcacgctacg gcttaactac             1380
tatcagcaaa aacctgtagc actgataaat aaccagtttc tccccatacc ctattatgct   1440
aaacctgccg ccgtgaggag tccagcacaa atacttcagt ggcaagtgct cagtaacacc   1500
gtgccagcaa aagctgccca ggctcagccc accacaatgg cccgtcatcc catcctcac   1560
cttagcttca tggcaatccc  accaaagaag aatcaagaca agaccgaaat acctaccatc   1620
aacacaattg catctggaga gcctaccagt acaccaacag ctgaggcagt agagtctact   1680
gttgctaccc ttgaggacag ccccgaggtt atagagtccc cacctgagat aaataccgtg   1740
caggtgacaa gtaccgccgt attgatcgta acacagacta gaagggtct  tgatatacag   1800
aaggtgccg  ggacttggta cagtttggca atggccgcat ccgacatctc cttgttggac   1860
gcacaatcag ccccattgcg tgtgtacgta gaagagctta aaccaactcc cgaggggat   1920
ctggaaattc tgctccagaa atgggagaac ggtgagtgcg cccagaagaa gatcatcgca   1980
gagaagacca aaattccagc agtattcaaa atcgacgcat gaacgaaaa  taaggtgctc   2040
gtactggaca ctgattataa gaagtatctc cttttctgtt gaaatgggc  ggctcaacag   2100
gaacagagtc ttgcctgcca atgccttgtt cgtaccccag aggtagatga tgaagctctg   2160
gaaaagttcg ataaggccct taaggctctg cctatgcaca ttaggctttc tttcaatcca   2220
actcaacttg aggaacaatg tcacattaa                                     2250

SEQ ID NO: 652            moltype = AA  length = 749
FEATURE                   Location/Qualifiers
REGION                    1..749
                          note = fusion protein (OBC-T3:OBC-T2:OKC1-T:OLG1)
source                    1..749
                          mol_type = protein
                          organism = synthetic construct
SEQUENCE: 652
RELEELNVPG EIVESLSSSE ESITRINKKI EKFQSEEQQQ TEDELQDKIH PFAQTQSLVY    60
PFPGPIPNSL PQNIPPLTQT PVVVPPFLQP EVMGVSKVKE AMAPKHKEMP FPKYPVEPFT   120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIVR ELEELNVPGE IVESLSSSEE SITRINKKIE   240
KFQSEEQQQT EDELQDKIHP FAQTQSLVYP FPGPIPNSLP QNIPPLTQTP VVVPPFLQPE   300
VMGVSKVKEA MAPKHKEMPF PKYPVEPFTE SQSLTLTDVE NLHLPLPLLQ SWMHQPHQPL   360
PPTVMFPPQS VLSLSQSKVL PVPQKAVPYP QRDMPIQAFL LYQEPVLGPV RGPFPIIVQE   420
QNQEQPIRCE KDERFFSDKI AKYIPIQYVL SRYPSYGLNY YQQKPVALIN NQFLPYPYYA   480
KPAAVRSPAQ ILWQVLSNT  VPAKSCQAQP TTMARHPHPH LSFMAIPPKK NQDKTEIPTI   540
NTIASGEPTS TPTTEAVEST VATLEDSPEV IESPPEINTV QVTSTAVLIV TQTMKGLDIQ   600
KVAGTWYSLA MAASDISLLD AQSAPLRVYV EELKPTPEGD LEILLQKWEN GECAQKKIIA   660
EKTKIPAVFK IDALNENKVL VLDTDYKKYL LFCMENSAEP EQSLACQCLV RTPEVDDEAL   720
```

-continued

EKFDKALKAL PMHIRLSFNP TQLEEQCHI                                                  749

SEQ ID NO: 653          moltype = DNA   length = 2877
FEATURE                 Location/Qualifiers
misc_feature            1..2877
                        note = fusion protein (OBC-T4:OBC-T3:OBC-T2:OKC1-T:OLG1)
source                  1..2877
                        mol_type = other DNA
                        organism = synthetic construct
SEQUENCE: 653
agggagctcg aggagttgaa cgtgcctggc gagattgtag agtcattgag ctctagtgag    60
gagagtataa caaggatcaa taaaaagatt gaaaaatttc aaagcgaaga gcagcaacaa   120
acagaagatg aactgcaaga caaaattcat ccttttgctc agacacagag cttggtgtat   180
cccttcccag ggccaattcc caatagtctg ccccaaaaca tccctcccct gacccaaacc   240
cccgtagtag tacctccatt cttgcagcct gaagtgatgg gggtgagtaa agtgaaggag   300
gcaatggccc ctaagcataa agagatgcca ttccctaaat atcccgttga gccattcacc   360
gaatcacaat ccttgacact tactgatgtc gagaatttgc acttgccact gcccttgctc   420
caaagctgga tgcaccaacc acaccaacct ctgcctccca cagtgatgtt cccaccccaa   480
tccgtcttgt ctctgtccca gtcaaaggtg ttgcctgttc ctcagaaagc agttccctat   540
ccccaacgcg atatgcccat ccaggctttt ctcttgtatc aagaaccagt gctcggtcct   600
gtcagaggcc ccttccccat tatcgtgagg gaactcgagg aacttaacgt tccaggtgag   660
atcgtgagt ccctctcatc ttccgaagag tccattacca ggatcaacaa gaagatcgaa   720
aagttccagt ccgaggaaca acagcaaacc gaggatgagc ttcaggacaa gattcaccca   780
ttcgctcaga cccagtctct cgtgtatcca tttccagggc caattccaaa cagcctgcca   840
cagaacattc caccacttac tcagacccca gttgtggtgc caccattcct caaccagag    900
gttatgggag tgtccaaggt gaaagaagcc atggccacaa agcacaaaga gatgcctttc   960
ccaaagtacc ccgttgagcc attcactgag tctcagtctc ttaccctcac cgacgttgag  1020
aaccttcacc ttccacttcc attgctccag tcttggatgc atcaaccaca tcagccactt  1080
ccaccaaccg ttatgttccc acctcagtcc gtgcttagcc tctctcagtc taaggttttg  1140
ccagtgcctc agaaggccgt tccatatcca caaagggata tgccaatcca ggccttcttg  1200
ctctaccaag agccagttct tggaccagtg agaggcccat ttccaatcat tgtgcgcgaa  1260
ctggaagagt tgaacgtacc aggagagatt gtagaatcac tgagctcctc agaggagtct  1320
attactcgta tcaacaagaa gatagagaag ttccaatccg aggagcaaca caaacagag   1380
gacgaattgc aggacaagat acatcctttc gcacagaccc agagcctcgt ctatcccatt  1440
ccaggtccaa tccctaactc tctccccccag aatatcccac ccttgactca gactcccgtg  1500
gtcgtacccc cttttcttgca acccgaggtg atggggggttt ctaaagtcaa agaggctatg  1560
gctcctaaac ataaggaaat gccttttccc aaatatccag tggagccatt cactgagagc  1620
cagtctctga cacttacaga tgtggaaaac ttgcacctgc ccttgccact tttgcagtcc  1680
tggatgcacc aaccacatca cccctgcc cccacagttg tgtttcctcc acaatcagtt  1740
cttagtctct cccaaagcaa agtccttcca gtgcctcaga aggccgtccc ataccccag   1800
agagatatgc caatacaggc attcttgctt taccaggaaac cagtgctcgg tcctgtacgt  1860
ggcccattcc ctatcatagt gcaagagcag aatcaagagc agccaatccg ttgtgagaag  1920
gacgagaggt tcttctcaga caagatcgcc aaatatatac ccatacaata tgtactcta   1980
cgctaccota gctacgggct taactactat cagcaaaaac ctgtagcact gataaataac  2040
cagtttctcc cctatcccta ttatgctaaa cctgccgccg tgaggagtcc agcacaaata  2100
cttcagtggc aagtgctcag taacaccgtg ccagcaaaaa gctgccaggc tcagcccacc  2160
acaatggccc gtcatcccca tcctcacctt agcttcatgg caatcccacc aaagaagaat  2220
caagacaaga ccgaaatacc taccatcaac acaattgcat ctggagagcc taccagtaca  2280
ccaacaactg aggcagtaga gtctactgtt gctacccttg aggacagccc cgaggttata  2340
gagtccccac ctgagataaa taccgtgcag gtgacaagta ccgccgtatt gatcgtaaca  2400
cagactatga agggtcttga tatacagaag gtggccggga cttggtacag tttggcaaag  2460
gccgcatccg acatctcctt gttggacgca caatcagccc cattgcgtgt gtacgtagaa  2520
gagcttaaac caactcccga ggggggatctg gaaattctgc tccagaaatg ggagaacggt  2580
gagtgcgccc agaagaagat catcgcgagg aagaccaaaa ttccagcagt attcaaaatc  2640
gacgcattga acgaaaataa ggtgctcgta ctggacactg attataagaa gtatctcctt  2700
ttctgtatgg agaactcagc agagcctgaa cagagtcttg cctgccaatg ccttgttcgt  2760
accccagagg tagatgatga agctctgaaa aagttcgata aggcccttaa ggctctgcct  2820
atgcacatta ggctttcttt caatccaact caacttgagg aacaatgtca catttaa      2877

SEQ ID NO: 654          moltype = AA    length = 958
FEATURE                 Location/Qualifiers
REGION                  1..958
                        note = fusion protein (OBC-T4:OBC-T3:OBC-T2:OKC1-T:OLG1)
source                  1..958
                        mol_type = protein
                        organism = synthetic construct
SEQUENCE: 654
RELEELNVPG EIVESLSSSE ESITRINKKI EKFQSEEQQQ TEDELQDKIH PFAQTQSLVY    60
PFPGPIPNSL PQNIPPLTQT PVVVPPFLQP EVMGVSKVKE AMAPKHKEMP FPKYPVEPFT   120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIVR ELEELNVPGE IVESLSSSEE SITRINKKIE   240
KFQSEEQQQT EDELQDKIHP FAQTQSLVYP FPGPIPNSLP QNIPPLTQTP VVVPPFLQPE   300
VMGVSKVKEA MAPKHKEMPF PKYPVEPFTE SQSLTLTDVE NLHLPLPLLQ SWMHQPHQPL   360
PPTVMFPPQS VLSLSQSKVL PVPQKAVPYP QRDMPIQAFL LYQEPVLGPV RGPFPIIVRE   420
LEELNVPGEI VESLSSSEES ITRINKKIEK FQSEEQQQTE DELQDKIHPF AQTQSLVYPF   480
PGPIPNSLPQ NIPPLTQTPV VVPPFLQPEV MGVSKVKEAM APKHKEMPFP KYPVEPFTES   540
QSLTLTDVEN LHLPLPLLQS WMHQPHQPLP PTVMFPPQSV LSLSQSKVLP VPQKAVPYPQ   600
RDMPIQAFLL YQEPVLGPVR GPFPIIVQEQ NQEQPIRCEK DERFFSDKIA KYIPIQYVLS   660
RYPSYGLNYY QQKPVALINN QFLPYPYYAK PAAVRSPAQI LQWQVLSNTV PAKSCQAQPT   720

```
TMARHPHPHL SFMAIPPKKN QDKTEIPTIN TIASGEPTST PTTEAVESTV ATLEDSPEVI  780
ESPPEEINTVQ VTSTAVLIVT QTMKGLDIQK VAGTWYSLAM AASDISLLDA QSAPLRVYVE  840
ELKPTPEGDL EILLQKWENG ECAQKKIIAE KTKIPAVFKI DALNENKVLV LDTDYKKYLL  900
FCMENSAEPE QSLACQCLVR TPEVDDEALE KFDKALKALP MHIRLSFNPT QLEEQCHI    958

SEQ ID NO: 655           moltype = DNA   length = 3504
FEATURE                  Location/Qualifiers
misc_feature             1..3504
                         note = fusion protein
                         (OBC-T5:OBC-T4:OBC-T3:OBC-T2:OKC1-T:OLG1)
source                   1..3504
                         mol_type = other DNA
                         organism = synthetic construct
SEQUENCE: 655
agggagcttg aggagttgaa tgttcccggg gaaatagtag aatccctgtc atcaagtgaa    60
gaaagcataa cacgaatcaa caagaagatt gagaaatttc agtctgaaga gcagcaacaa   120
actgaagatg aacttcaaga taaaattcat ccatttgctc aaacacagtc tctagtgtac   180
ccattcccg gccctatacc caacagttta ccccaaaata ttcctccatt aacccaaacc    240
ccggtagttg ttccacccct ccttcagcct gaggtcatgg gtgtttccaa agtgaaggag   300
gcaatggctc caaaacacaa ggaaatgcct tttccaaagt atccggttga gcctttcaca   360
gagtctcagt cgcttacgct cactgatgtg gaaaatttac atctcccact gcctttgttg   420
caatcatgga tgcatcaacc tcaccagccc ttgccaccaa ctgtcatgtt tcctcctcaa   480
tcagttttga gcctctctca gagtaaggtt ctgcctgtgc cacagaaagc cgtgccttat   540
cctcagagac acatgccaat tcaagcattt cttctttacc aagaacctgt tttgggacca   600
gtacgtggac cgttcccaat cattgtcagg agctcgagg agttgaacgt gcctggcgag    660
attgtagagt cattgagctc tagtgaggag agtataacag gatcaataa aaagattgaa    720
aaatttcaaa gcgaagagca gcaacaaaca gaagatgaac tgcaagacaa aattcatcct   780
tttgctcaga cacagagctt ggtgtatccc ttcccagggc caattcccaa tagtctgccc   840
caaaacatcc ctcccttgac ccaaaccccc gtagtagtac ctccattctt gcagcctgaa   900
gtgatggggg tgagtaaagt gaaggaggca atggccccta agcataaaga gatgccattc   960
cctaaatatc ccgttgagcc attcaccgaa tcaacaatcct tgacacttac tgatgtcgag  1020
aatttgcact tgccactgcc cttgctccaa agctggatgc accaaccaca ccaacctctg  1080
cctcccacag tgatgttccc accccaatcc gtcttgtctc tgtcccagtc aaaggtgttg  1140
cctgttcctc agaaagcagt tccctatccc caacgcgata tgcccatcca ggcttttctc  1200
ttgtatcaag aaccagtgct cggtcctgtc agaggcccct tcccccattat cgtgagggaa  1260
ctcgaggaac ttaacgttcc aggtgagatc gtcgagtccc tctcatcttc cgaagagtcc  1320
attaccagga tcaacaagaa gatcgagaag ttccagtccg aggaacaaca gcaaaccgag  1380
gatgagcttc aggacaagat tcaccccattc gctcagaccc agtctctcgt gtatccattt  1440
ccagggccaa ttccaaacag cctgccacag aacattccac cacttactca gaccccagtt  1500
gtggtgccac cattccttca accagaggtt atgggagtgt ccaaggtgaa agaagcccatg  1560
gcaccaaagc acaagagat gccctttcca aagtaccccg ttgagccatt cactgagtct  1620
cagtctctta ccctcaccga cgttgagaac cttcacttc cacttccatt gctccagtct   1680
tggatgcatc aaccacatca gccacttcca ccaaccgtta tgttcccacc tcagtccgtg  1740
cttagcctct ctcagtctaa ggttttgcca gtgcctcaga aggccgttcc atatccacaa  1800
agggatatgc caatccaggc cttcttgctc taccaagagc cagttcttgg accagtgaga  1860
ggcccattc caatcattgt gcgcgaactg gaagagttga acgtaccagg agagattgta  1920
gaatcactga gctcctcaga ggagtctatt actcgtatca acaagaagat agagaagttc  1980
caatccgagg agcaacaaca aacagaggac gaattgcagg acaagataca tcctttcgca  2040
cagacccaga gcctcgtcta tcccttttcca ggtccaatcc ctaactctct ccccccagaat  2100
atcccaccct tgactcagac tcccgtggtc gtaccccctt tcttgcaacc cgaggtgatg  2160
ggggtttcta aagtcaaaga ggctatggct cctaaacata aggaaatgcc ttttccccaaa  2220
tatccagtgg agccattcac tgagagccag tctctgacac ttacagatgt ggaaaacttg  2280
cacctgccct tgccactttt gcagtcctgg atgcaccaaac cacatcaaacc cttgcccccc  2340
acagtgatgt ttcctccaca atcagttctt agtctctccc aaagcaaagt ccttccagtg  2400
cctcagaagg ccgtcccata ccccagaga gatatgccaa caggccatt cttgctttac  2460
caggaaccag tgctcggtcc tgtacgtggc ccattcccta tcatagtgca agagcagaat  2520
caagagcagc caatccgttg tgagaaggac gagaggttct tctcagacaa gatcgccaaa  2580
tatatacccca acaatatgt actctcacgc taccctagct acgggcttaa ctactatcag  2640
caaaaacctg tagcactgat aaataaccag ttttctccct atcccctata tgctaaacct  2700
gccgccgtga ggagtccagc acaaatactt cagtggcaag tgctcagtaa caccgtgcca  2760
gcaaaaagct gccaggctca gcccaccaca atggcccgtc atcccatcc tcaccttagc  2820
ttcatggcaa tccaccaaa gaagaatcaa gacaagaccg aaatacctac catcaacaca  2880
attgcatctg gagagcctac cagtacacca caaactgagg cagtagagtc tactgttgct  2940
acccttgagg acagcccga ggttatagag tccccacctg agataaatac cgtgcaggtg  3000
acaagtaccg ccgtattgat cgtaacacag actatgaagg tcttgatat acagaaggtg  3060
gccgggactt ggtacagttt ggcaatggcc gcatccgaca tctccttgtt ggacgcacaa  3120
tcagcccat tgcgtgtgta cgtagaagag cttaaaccaa ctcccgaggg ggatctgaaa  3180
attctgctcc agaaatggga gaacggtgag tgcgcccaga agaagatcat cgcagagaag  3240
accaaaattc cagcagtatt caaaatcgac gcattgaacg aaaataagg gtcgtactg  3300
gacactgatt ataagaagta tctccttttc tgtatgagga actcagcaga gcctgaacag  3360
agtcttgcct gccaatgcct tgttcgtacc ccagaggtag atgatgaagc tctgaaaaag  3420
ttcgataagg cccttaaggc tctgcctatg cacattaggc tttctttcaa tccaactcaa  3480
cttgaggaac aatgtcacat ttaa                                          3504

SEQ ID NO: 656           moltype = AA   length = 1167
FEATURE                  Location/Qualifiers
REGION                   1..1167
                         note = fusion protein
                         (OBC-T5:OBC-T4:OBC-T3:OBC-T2:OKC1-T:OLG1)
```

-continued

```
source                  1..1167
                        mol_type = protein
                        organism = synthetic construct
SEQUENCE: 656
RELEELNVPG EIVESLSSSE ESITRINKKI EKFQSEEQQQ TEDELQDKIH PFAQTQSLVY    60
PFPGPIPNSL PQNIPPLTQT PVVVPPFLQP EVMGVSKVKE AMAPKHKEMP FPKYPVEPFT   120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIVR ELEELNVPGE IVESLSSSEE SITRINKKIE   240
KFQSEEQQQT EDELQDKIHP FAQTQSLVYP FPGPIPNSLP QNIPPLTQTP VVVPPFLQPE   300
VMGVSKVKEA MAPKHKEMPF PKYPVEPFTE SQSLTLTDVE NLHLPLPLLQ SWMHQPHQPL   360
PPTVMFPPQS VLSLSQSKVL PVPQKAVPYP QRDMPIQAFL LYQEPVLGPV RGPFPIIVRE   420
LEELNVPGEI VESLSSSEES ITRINKKIEK FQSEEQQQTE DELQDKIHPF AQTQSLVYPF   480
PGPIPNSLPQ NIPPLTQTPV VVPPFLQPEV MGVSKVKEAM APKHKEMPFP KYPVEPFTES   540
QSLTLTDVEN LHLPLPLLQS WMHQPHQPLP PTVMFPPQSV LSLSQSKVLP VPQKAVPYPQ   600
RDMPIQAFLL YQEPVLGPVR GPFPIIVREL EELNVPGEIV ESLSSSEESI TRINKKIEKF   660
QSEEQQQTED ELQDKIHPFA QTQSLVYPFP GPIPNSLPQN IPPLTQTPVV VPPFLQPEVM   720
GVSKVKEAMA PKHKEMPFPK YPVEPFTESQ SLTLTDVENL HLPLPLLQSW MHQPHQPLPP   780
TVMFPPQSVL SLSQSKVLPV PQKAVPYPQR DMPIQAFLLY QEPVLGPVRG PFPIIVQEQN   840
QEQPIRCEKD ERFFSDKIAK YIPIQYVLSR YPSYGLNYYQ QKPVALINNQ FLPYPYYAKP   900
AAVRSPAQIL QWQVLSNTVP AKSCQAQPTT MARHPHPHLS FMAIPPKKNQ DKTEIPTINT   960
IASGEPTSTP TTEAVESTVA TLEDSPEVIE SPPEINTQVV TSTAVLIVTQ TMKGLDIQKV  1020
AGTWYSLAMA ASDISLLDAQ SAPLRVVEE LKPTPEGDLE ILLQKWENGE CAQKKIIAEK  1080
TKIPAVFKID ALNENKVLVL DTDYKKYLLF CMENSAEPEQ SLACQCLVRT PEVDDEALEK  1140
FDKALKALPM HIRLSFNPTQ LEEQCHI                                     1167

SEQ ID NO: 657         moltype = DNA   length = 2997
FEATURE                Location/Qualifiers
misc_feature           1..2997
                       note = fusion protein (OBC-T5:OBC-T4:OBC-T3:OBC-T2:OLG1)
source                 1..2997
                       mol_type = other DNA
                       organism = synthetic construct
SEQUENCE: 657
agggagcttg aggagttgaa tgttcccggg gaaatagtag aatccctgtc atcaagtgaa    60
gaaagcataa cacgaatcaa caagaagatt gagaaatttc agtctgaaga gcagcaacaa   120
actgaagatg aacttcaaga taaaattcat ccatttgctc aaacacagtc tctagtgtac   180
ccattccccg gccctatacc caacagttta ccccaaaata ttcctccatt aacccaaacc   240
ccggtagttg ttccacccct ccttcagcct gaggtcatgg gtgtttccaa agtgaaggag   300
gcaatggctc caaaacacaa ggaaatgcct tttccaaagt atccggttga gccttttcaca  360
gagtctcagt cgcttacgct cactgatgtg gaaaatttac atctcccact gcctttgttg   420
caatcatgga tgcatcaacc tcaccagccc ttgccaccaa ctgtcatgtt tcctcctcaa   480
tcagttttga gcctctctca gagtaaggtt ctgcctgtgc cacagaaagc cgtgccttat   540
cctcagagag acatgccaat tcaagcattt cttctttacc aagaacctgt tttgggacca   600
gtacgtggac cgttcccaat cattgtcagg gagctcgagg agttgaacgt gcctggcgag   660
attgtagagt cattgagctc tagtgaggag agtataacaa ggatcaataa aaagattgaa   720
aaatttcaaa gcgaagagca gcaacaaaca gaagatgaac tgcaagacaa aattcatcct   780
tttgctcaga cacagagtct ggtgtatccc ttcccagcca caattcccaa tagtctgccc   840
caaaacatcc ctcccttgac ccaaaccccc gtagtagtac ctccattctt cagcctgaa    900
gtgatggggg tgagtaaagt gaaggaggca atgccccta agcataaga gatgccattc    960
cctaaatatc ccgttgagcc attcaccgaa tcacaatcct tgacacttac tgatgtcgag  1020
aatttgcact tgccactgcc cttgctcaaa agctggatgc accaaccaca ccaacctctg  1080
cctcccacag tgatgttccc accccaatcc gtcttgtctc tgtcccagtc aaaggtgttg  1140
cctgttcctc agaaagcagt tcccatccc caacgcgata tgcccatcca ggcttttctc   1200
ttgtatcaag aaccagtgct cggtcctgtc agaggcccct tccccattat cgtgagggaa  1260
ctcgaggaac ttaacgttcc aggtgagatc gtcgagtccc tctcatcttc cgaagagtcc  1320
attaccagga tcaacaagaa gatcgagaag ttccagtccg aggaacaaca gcaaacggag  1380
gatgagcttc aggacaagat tcacccattc gctcagaccc agtctctcgt gtatccattt  1440
ccagggccaa ttccaaacag cctgccacag aacattccac cacttactca gaccccagtt  1500
gtggtgccac cattccttca accagaggtt atggagagtg tccaaggtga agaagccatg  1560
gcaccaaagc acaaagagat gcccttttca aagtacccg ttgagccatt cactgagtcc   1620
cagtctctta ccctcaccga cgttgagaac cttacccttc cacttccatt gctccagtct  1680
tggatgcatc aaccacatca gccacttcca ccaaccgtta tgttcccacc tcagtccgtg  1740
cttagcctct ctcagtctaa ggttttgcca gtgcctcaga aggccgttcc atatccacaa  1800
agggatatgc caattcaggc cttcttgctc taccaagagc cagttcttgg accagtgaga  1860
ggcccatttc caatcattgt gcgcgaactg gaagagttga acgtaccagg agagattgta  1920
gaatcactga gctcctcaga ggagtctatt actcgtatca acaagaagat agaagttc    1980
caatccgagg agcaacaaca aacagaggac gaattgcagg acaagataca tcctttcgca  2040
cagacccaga gcctcgtcta tccctttcca ggtccaatcc ctaactctct ccccagaat   2100
atccccaccct tgactcagac tcccgtggtc gtaccccctt tcttgcaacc cgaggtgatg  2160
gggggttcta aagtcaaaga ggctatggct cctaaacata ggaaatgcc tttccccaaa   2220
tatccagtgg agccattcac tgagagccag tctctgacac ttagagatgt ggaaaacttg  2280
cacctgcct gcactttt gcagtcctgg atgaccaac acatcaacc cttgccccc     2340
acagtgatgt ttcctccaca atcagttctt agtctctccc aaagcaaagt ccttccagtg  2400
cctcaaaagg ccgtgcccata cccccagaga gatatgccaa tacaggcatt cttgctttac  2460
caggaaccag tgctccggtcc tgtacgtggg ccattcccta tcatagtgtt gatcgtaaca  2520
cagactatga agggtcttga tatacagaag gtggccggga cttggtacag tttggcaatg  2580
gccgcatccg acatctcctt gttggacgca caatcagcc cattgcgtgt gtacgtgaa    2640
gagcttaaac caactcccga gggggatctg gaaattctgc tccagaaatg ggagaacggt  2700
gagtgcgccc agaagaagat catcgcagag aagaccaaaa ttccagcagt attcaaaatc  2760
```

```
gacgcattga acgaaaataa ggtgctcgta ctggacactg attataagaa gtatctcctt 2820
ttctgtatgg agaactcagc agagcctgaa cagagtcttg cctgccaatg ccttgttcgt 2880
accccagagg tagatgatga agctctggaa aagttcgata aggcccttaa ggctctgcct 2940
atgcacatta ggctttcttt caatccaact caacttgagg aacaatgtca catttaa    2997
```

| SEQ ID NO: 658 | moltype = AA  length = 998 |
|---|---|
| FEATURE | Location/Qualifiers |
| REGION | 1..998 |
| | note = fusion protein (OBC-T5:OBC-T4:OBC-T3:OBC-T2:OLG1) |
| source | 1..998 |
| | mol_type = protein |
| | organism = synthetic construct |

```
SEQUENCE: 658
RELEELNVPG EIVESLSSSE ESITRINKKI EKFQSEEQQQ TEDELQDKIH PFAQTQSLVY  60
PFPGPIPNSL PQNIPPLTQT PVVVPPFLQP EVMGVSKVKE AMAPKHKEMP FPKYPVEPFT 120
ESQSLTLTDV ENLHLPLPLL QSWMHQPHQP LPPTVMFPPQ SVLSLSQSKV LPVPQKAVPY 180
PQRDMPIQAF LLYQEPVLGP VRGPFPIIVR ELEELNVPGE IVESLSSSEE SITRINKKIE 240
KFQSEEQQQT EDELQDKIHP FAQTQSLVYP FPGPIPNSLP QNIPPLTQTP VVVPPFLQPE 300
VMGVSKVKEA MAPKHKEMPF PKYPVEPFTE SQSLTLTDVE NLHLPLPLLQ SWMHQPHQPL 360
PPTVMFPPQS VLSLSQSKVL PVPQKAVPYP QRDMPIQAFL LYQEPVLGPV RGPFPIIVRE 420
LEELNVPGEI VESLSSSEES ITRINKKIEK FQSEEQQQTE DELQDKIHPF AQTQSLVYPF 480
PGPIPNSLPQ NIPPLTQTPV VVPPFLQPEV MGVSKVKEAM APKHKEMPFP KYPVEPFTES 540
QSLTLTDVEN LHLPLPLLQS WMHQPHQPLP PTVMFPPQSV LSLSQSKVLP VPQKAVPYPQ 600
RDMPIQAFLL YQEPVLGPVR GPFPIIVREL EELNVPGEIV ESLSSSEESI TRINKKIEKF 660
QSEEQQQTED ELQDKIHPFA QTQSLVYPFP GPIPNSLPQN IPPLTQTPVV VPPFLQPEVM 720
GVSKVKEAMA PKHKEMPFPK YPVEPFTESQ SLTLTDVENL HLPLPLLQSW MHQPHQPLPP 780
TVMFPPQSVL SLSQSKVLPV PQKAVPYPQR DMPIQAFLLY QEPVLGPVRG PFPIIVLIVT 840
QTMKGLDIQK VAGTWYSLAM AASDISLLDA QSAPLRVYVE ELKPTPEGDL EILLQKWENG 900
ECAQKKIIAE KTKIPAVFKI DALNENKVLV LDTDYKKYLL FCMENSAEPE QSLACQCLVR 960
TPEVDDEALE KFDKALKALP MHIRLSFNPT QLEEQCHI                        998
```

| SEQ ID NO: 659 | moltype = DNA  length = 2508 |
|---|---|
| FEATURE | Location/Qualifiers |
| misc_feature | 1..2508 |
| | note = fusion protein (OBC-T5:OBC-T4:OBC-T3:OBC-T2) |
| source | 1..2508 |
| | mol_type = other DNA |
| | organism = synthetic construct |

```
SEQUENCE: 659
agggagcttg aggagttgaa tgttcccggg gaaatagtag aatccctgtc atcaagtgaa  60
gaaagcataa cacgaatcaa caagaagatt gagaaatttc agtctgaaga gcagcaacaa 120
actgaagatg aacttcaaga taaaattcat ccatttgctc aaacacagtc tctagtgtac 180
ccattcccg gccctatacc caacagttta ccccaaaata ttcctccata acccaaacc  240
ccggtagttg ttccacccett ccttcagect gaggtcatgg gtgttccaa agtgaaggag 300
gcaatggctc aaaacacaa ggaaatgcct tttccaaagt atccggttga gccttcaca  360
gagtctcagt cgcttacgct cactgatgtg gaaaattac atctcccact gccttgttg  420
caatcatgga tgcatcaacc tcaccagccc ttgccaccaa ctgtcatgtt tcctcctcaa 480
tcagttttga gcctctctca gagtaaggtt ctgcctgtgc cacagaaagc cgtgccttat 540
cctcagagac acatgccaat tcaagcattt cttctttacc aagaacctgt tttgggacca 600
gtacgtggac cgttcccaat cattgtcagg agctcgagg agttgaacgt gcctggcgag  660
attgtagagt cattgagctc tagtgaggag agtataacaa ggatcaataa aaagattgaa 720
aaatttcaaa gcgaagagca gcaacaaaca gaagatgaac tgcaagacaa aattcatcct 780
tttgctcaga cacagagctt ggtgtatccc ttcccagggc caattccaa tagtctgccc 840
caaaacatcc ctcccttgac ccaaaccccc gtagtagtac ctccattctt gcagcctgaa 900
gtgatggggg tgagtaaagt gaaggaggca atggcccccta agcataaaga gatgccattc 960
cctaaatatc ccgttgagcc attcaccgaa tcacaatcct tgacacttac tgatgtcgag 1020
aatttgcact tgccactgcc cttgctccaa agctggatgc accaaccaca ccaacctctg 1080
cctcccacag tgatgtttcc accccaatcc gtcttgtctc tgtcccagtc aaaggtgttg 1140
cctgttcctc agaaagcagt tcctatccc caacgcgata tgcccatcca ggcttttctc 1200
ttgtatcaag aaccagtgct cggtcctgtc agaggcccct tcccattat cgtgagggaa 1260
ctcgaggaac ttaacgttcc aggtgagatc gtcgagtccc tctcatcttc cgaagagtcc 1320
attaccagga tcaacaagaa gatcgagaag ttccagtccg aggaacaaca gcaaaccgag 1380
gatgagcttc aggacaagat tcacccattc gctcagaccc agtctctcgt gtatccattt 1440
ccagggccaa ttccaaacag cctgccacag aacattccaa cacttactca gacccccagtt 1500
gtggtgccac cattccttca accagaggtt atgggagtgt ccaaggtgaa agaagccatg 1560
gcaccaaagc acaagagat gcccttcca aagtaccccg ttgagccatt cactgagtct 1620
cagtctctta ccctcaccga cgttgagaac cttaccttc acttccatt gctccagtct 1680
tggatgcatc aaccacatca gccacttcca caaccgtta tgttcccacc tcagtccgtg 1740
cttagcctct ctcagtctaa ggttttgcca gtgcctcaga aggccgttcc atatccacaa 1800
agggatatgc caatccaggc cttcttgctc taccaagagc cagttcttgg accagtgaga 1860
ggcccatttc caatcattgt gcgcgaactg gaagagttga acgtaccagg agagattgta 1920
gaatcactga gctcctcaga ggagtctatt actcgtatca acaagaagat agagaagttc 1980
caatccgagg agcaacaaca aacagaggac gaattgcagg acaagataca tcctttcgca 2040
cagacccaga gcctcgtcta tccttttcca gggccgcaat ctaactctcc ccccagaat  2100
atccaccct tgactcagac tcccgtggtc gtaccccctt tcttgcaacc cgaggtgatg 2160
gggggttcta aagtcaaaga ggctatggct cctaaacata ggaaatgcc ttttcccaaa  2220
tatccagtga agccattcac tgagagccag tctctgacac ttacgatgt ggaaacttg  2280
cacctgcct tgcactttt gcagtcctgg atgcaccaac cacatcaacc cttgcccccc 2340
acagtgatgt ttcctccaca atcagttctt agtctctccc aaagcaaagt ccttccagtg 2400
```

```
cctcagaagg ccgtcccata cccccagaga gatatgccaa tacaggcatt cttgctttac 2460
caggaaccag tgctcggtcc tgtacgtggc ccattccta tcatagtg                2508

SEQ ID NO: 660          moltype = AA  length = 836
FEATURE                 Location/Qualifiers
REGION                  1..836
                        note = fusion protein (OBC-T5:OBC-T4:OBC-T3:OBC-T2)
source                  1..836
                        mol_type = protein
                        organism = synthetic construct
SEQUENCE: 660
RELEELNVPG EIVESLSSSE ESITRINKKI EKFQSEEQQQ TEDELQDKIH PFAQTQSLVY   60
PPFPGPIPNSL PQNIPPLTQT PVVVPPFLQP EVMGVSKVKE AMAPKHKEMP FPKYPVEPFT  120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIVR ELEELNVPGE IVESLSSSEE SITRINKKIE   240
KFQSEEQQQT EDELQDKIHP FAQTQSLVYP FPGPIPNSLP QNIPPLTQTP VVVPPFLQPE   300
VMGVSKVKEA MAPKHKEMPF PKYPVEPFTE SQSLTLTDVE NLHLPLPLLQ SWMHQPHQPL   360
PPTVMFPPQS VLSLSQSKVL PVPQKAVPYP QRDMPIQAFL LYQEPVLGPV RGPFPIIVRE   420
LEELNVPGEI VESLSSSEES ITRINKKIEK FQSEEQQQTE DELQDKIHPF AQTQSLVYPF   480
PGPIPNSLPQ NIPPLTQTPV VVPPFLQPEV MGVSKVKEAM APKHKEMPFP KYPVEPFTES   540
QSLTLTDVEN LHLPLPLLQS WMHQPHQPLP PTVMFPPQSV LSLSQSKVLP VPQKAVPYPQ   600
RDMPIQAFLL YQEPVLGPVR GPFPIIVREL EELNVPGEIV ESLSSSEESI TRINKKIEKF   660
QSEEQQQTED ELQDKIHPFA QTQSLVYPFP GPIPNSLPQN IPPLTQTPVV VPPFLQPEVM   720
GVSKVKEAMA PKHKEMPFPK YPVEPFTESQ SLTLTDVENL HLPLPLLQSW MHQPHQPLPP   780
TVMFPPQSVL SLSQSKVLPV PQKAVPYPQR DMPIQAFLLY QEPVLGPVRG PFPIIV       836

SEQ ID NO: 661          moltype = DNA  length = 3021
FEATURE                 Location/Qualifiers
misc_feature            1..3021
                        note = fusion protein
                        (OBC-T5:FM:OBC-T4:FM:OBC-T3:FM:OBC-T2:FM:OLG1)
source                  1..3021
                        mol_type = other DNA
                        organism = synthetic construct
SEQUENCE: 661
agggagcttg aggagttgaa tgttcccggg gaaatagtag aatccctgtc atcaagtgaa   60
gaaagcataa cacgaatcaa caagaagatt gagaaatttc agtctgaaga gcagcaacaa   120
actgaagatg aacttcaaga taaaattcat ccatttgctc aaacacagtc tctagtgtac   180
ccattcccg gccctatacc caacagttta ccccaaaata ttcctccatt aacccaaacc   240
ccggtagttg ttccacccct ccttcagcct gaggtcatgg gtgtttccaa agtgaaggag   300
gcaatggctc caaaacacaa ggaaatgcct tttccaaagt atccggttga gccttcaca   360
gagtctcagt cgcttacgct cactgatgtg gaaaatttac atctcccact gcctttgttg   420
caatcatgga tgcatcaacc tcaccagccc ttgccaccaa ctgtcatgtt tcctcctcaa   480
tcagttttga gcctctctca gagtaaggtt ctgcctgtgc cacagaaagc cgtgccttat   540
cctcagagag acatgccaat tcaagcattt cttctttacc aagaacctgt tttgggacca   600
gtacgtggac cgttcccaat cattgtcttc atgagggagc tcgaggagtt gaacgtgcct   660
ggcgagattg tagagtcatt gagctctagt gaggagagta taacaaggat caataaaaag   720
attgaaaaat ttcaaagcga agagcagcaa caaacagaag atgaactgca agacaaaatt   780
catccttttg ctcagacaca gagcttggtg tatcccttcc cagggccaat tcccaatagt   840
ctgccccaaa acatccctcc cttgacccaa accccgtag tagtacctcc attcttgcag   900
cctgagtga tggggtgag taaagtgaag gaggcaatgg cccctaagca taaagagatg   960
ccattcccta aatatcccgt tgagccattc accgaatcac aatccttgac acttactgat   1020
gtcgagaatt tgcacttgcc actgcccttg ctccaaagct ggatgcacca accacaccaa   1080
cctctgcctc ccacagtgat gttcccaccc caatccgtct tgtctctgtc ccagtcaaag   1140
gtgttgcctg ttcctcagaa agcagttccc tatcccaac gcgatatgcc catccaggct   1200
tttctcttgt atcaagaacc agtgctcggt cctgtcagag gcccttccc cattatcgtg   1260
ttcatgaggg aactcgagga acttaacgtt ccaggtgaga tcgtcgagtc cctctcatct   1320
tccgaagagt ccattaccag gatcaacaag aagatcgaga gttccagtc cgaggaacaa   1380
cagcaaaccg aggatgagct tcaggacaag attcacccat tcgctcagac ccagtctctc   1440
gtgtatccat ttccagggcc aattccaaac agcctgccac agaacattcc accacttact   1500
cagaccccag ttgtggtgcc accattcctt caaccagagg ttatgggagt gtccaaggtg   1560
aaagaagcca tggcaccaaa gcacaaagag atgcccttc caaagtaccc cgttgagcca   1620
ttcactgagt ctcagtctct taccctcacc gacgttgaga accttcacct tccacttcca   1680
ttgctccagt cttggatgca tcaaccacat cagccacttc caccaaccgt tatgttccca   1740
cctcagtccg tgcttagcct ctctcagtct aaggttttgc cagtgcctca gaaggccgtt   1800
ccatatccac aaagggatat gccaatccag gccttcttgc tctaccaaga gccagttctt   1860
ggaccagtga gaggcccatt tccaatcatt gtgttcatgc gcgaactgga gagttgaac   1920
gtaccaggag agattgtaga atcactgagc tcctcagagg agtctattac tcgtatcaac   1980
aagaagatag agaagttcca atccgaggag caacaacaga cagagacga attgcaggac   2040
aagatacatc ctttcgcaca gacccagagc tcgtctatc cctttccagg tccaatccct   2100
aactctctcc cccagaatat cccacccttg actcagactc ccgtggtcgt acccccttc   2160
ttgcaacccg aggtgatggg ggtttctaaa gtcaaagagg ctatggctcc taaacataag   2220
gaaatgcctt ttcccaaata tccagtggag ccattcactg agagccagtc tctgacactt   2280
acagatgtgg aaaacttgca cctgcccttg cactttgga gtcctggat gcaccaaacca   2340
catcaaccct tgcccccac agtgatgttt cctccacaat cagttcttag tctctcccaa   2400
agcaaagtcc ttccagtgcc tcagaaggcc gtcccatacc cccagagaga tatgccaata   2460
caggcattct tgctttacca ggaaccagtg ctcggtcctg tacgtggccc attccctatc   2520
atagtgttca tgttgatcgt aacacagact atgaagggtc ttgatataca gaaggtggcc   2580
gggacttggt acagtttggc aatggccgca tccgacatct ccttgttgga cgcacaatca   2640
```

-continued

```
gccccattgc gtgtgtacgt agaagagctt aaaccaactc ccgagggggga tctggaaatt    2700
ctgctccaga aatgggagaa cggtgagtgc gcccagaaga agatcatcgc agagaagacc    2760
aaaattccag cagtattcaa aatcgacgca ttgaacgaaa ataaggtgct cgtactggac    2820
actgattata agaagtatct cctttttctgt atggagaact cagcagagcc tgaacagagt    2880
cttgcctgcc aatgccttgt tcgtacccca gaggtagatg atgaagctct ggaaaagttc    2940
gataaggccc ttaaggctct gcctatgcac attaggcttt ctttcaatcc aactcaactt    3000
gaggaacaat gtcacattta a                                              3021

SEQ ID NO: 662           moltype = AA  length = 1006
FEATURE                  Location/Qualifiers
REGION                   1..1006
                         note = fusion protein
                         (OBC-T5:FM:OBC-T4:FM:OBC-T3:FM:OBC-T2:FM:OLG1)
source                   1..1006
                         mol_type = protein
                         organism = synthetic construct
SEQUENCE: 662
RELEELNVPG EIVESLSSSE ESITRINKKI EKFQSEEQQQ TEDELQDKIH PFAQTQSLVY       60
PFPGPIPNSL PQNIPPLTQT PVVVPPFLQP EVMGVSKVKE AMAPKHKEMP FPKYPVEPFT      120
ESQSLTLTDV ENLHLPLPLL QSWMHQPHQP LPPTVMFPPQ SVLSLSQSKV LPVPQKAVPY      180
PQRDMPIQAF LLYQEPVLGP VRGPFPIIVF MRELEELNVP GEIVESLSSS EESITRINKK      240
IEKFQSEEQQ QTEDELQDKI HPFAQTQSLV YPFPGPIPNS LPQNIPPLTQ TPVVVPPFLQ      300
PEVMGVSKVK EAMAPKHKEM PFPKYPVEPF TESQSLTLTD VENLHLPLPL LQSWMHQPHQ      360
PLPPTVMFPP QSVLSLSQSK VLPVPQKAVP YPQRDMPIQA FLLYQEPVLG PVRGPFPIIV      420
FMRELEELNV PGEIVESLSS SEESITRINK KIEKFQSEEQ QQTEDELQDK IHPFAQTQSL      480
VYPFPGPIPN SLPQNIPPLT QTPVVVPPFL QPEVMGVSKV KEAMAPKHKE MPFPKYPVEP      540
FTESQSLTLT DVENLHLPLP LLQSWMHQPH QPLPPTVMFP PQSVLSLSQS KVLPVPQKAV      600
PYPQRDMPIQ AFLLYQEPVL GPVRGPFPII VFMRELEELN VPGEIVESLS SSEESITRIN      660
KKIEKFQSEE QQQTEDELQD KIHPFAQTQS LVYPFPGPIP NSLPQNIPPL TQTPVVVPPF      720
LQPEVMGVSK VKEAMAPKHK EMPFPKYPVE PFTESQSLTL TDVENLHLPL PLLQSWMHQP      780
HQPLPPTVMF PPQSVLSLSQ SKVLPVPQKA VPYPQRDMPI QAFLLYQEPV LGPVRGPFPI      840
IVFMLIVTQT MKGLDIQKVA GTWYSLAMAA SDISLLDAQS APLRVYVEEL KPTPEGDLEI      900
LLQKWENGEC AQKKIIAEKT KIPAVFKIDA LNENKVLVLD TDYKKYLLFC MENSAEPEQS      960
LACQCLVRTP EVDDEALEKF DKALKALPMH IRLSFNPTQL EEQCHI                    1006

SEQ ID NO: 663           moltype = DNA  length = 2529
FEATURE                  Location/Qualifiers
misc_feature             1..2529
                         note = fusion protein (OBC-T5:FM:OBC-T4:FM:OBC-T3:FM:OBC-T2)
source                   1..2529
                         mol_type = other DNA
                         organism = synthetic construct
SEQUENCE: 663
agggagcttg aggagttgaa tgttcccggg gaaatagtag aatccctgtc atcaagtgaa      60
gaaagcataa cacgaatcaa caagaagatt gagaaatttc agtctgaaga gcagcaacaa     120
actgaagatg aacttcaaga taaaattcat ccatttgctc aaacacagtc tctagtgtac     180
ccattcccg gccctatacc caacagttta ccccaaaata ttcctccatt aacccaaacc      240
ccggtagttg ttccacccct ccttcagcct gaggtcatgg gtgtttccaa agtgaaggag     300
gcaatggctc aaaaacacaa ggaaatgcct tttccaaagt atccggttga gccttttcaca    360
gagtctcagt cgcttacgct cactgatgtg gaaaatttac atctcccact gcctttgttg     420
caatcatgga tgcatcaacc tcaccagccc ttgccaccaa ctgtcatgtt tcctcctcaa     480
tcagttttga gcctctctca gagtaaggtt ctgcctgtgc cacagaaagc cgtgccttat     540
cctcagagag acatgccaat tcaagcattt cttctttacc aagaacctgt tttgggacca     600
gtacgtggac cgttcccaat cattgtcttc atgagggagc tcgaggagtt gaacgtgcct     660
ggcgagattg tagagtcatt gagctctagt gaggagagta taacaaggat caataaaaag     720
attgaaaaat ttcaaagcga agagcagcaa caaacagaag atgaactgca agacaaaatt     780
catccttttg ctcagacaca gagcttggtt tatcccttcc cagggccaat tcccaatagt     840
ctgccccaaa acatccctcc cttgacccaa acccccgtag tagtacctcc attcttgcag     900
cctgaagtga tgggggtgag taaagtgaag gaggcaatgg cccctaagca taaagagatg     960
ccattcccta aatatcccgt tgagccattc accgaatcac aatccttgac acttactgat    1020
gtcgagaatt tgcacttgcc actgcccttg ctccaaagct ggatgcacca accacaccaa    1080
cctctgcctc ccacagtgat gttcccaccc caatccgtct tgtctctgtc ccagtcaaag    1140
gtgttgcctg ttcctcagaa agcagttccc tatcccaac gcgatatgcc catccaggct    1200
tttctcttgt atcaagaacc agtgctcggt ccctgtgcag gcccttccc cattatcgtg   1260
ttcatgaggg aactcgagga acttaacgtt ccaggtgaga tcgtcgagtc cctctcatct    1320
tccgaagagt ccattaccag gatcaacaag aagatcgaga agttccagtc cgaggaacaa    1380
cagcaaaccg aggatgagct tcaggacaag attcacccat cgctcagac ccagtctctc    1440
gtgtatccat ttccagggcc aattccaaac agcctgccaa agaacattcc accacttact    1500
cagacccag ttgtggtgcc accattcctt caaccagagg ttatgggagt gtccaaggtg   1560
aaagaagcca tggcaccaaa gcacaaagag atgcccttc caaagtaccc cgttgagcca    1620
ttcactgagt ctcagtctct taccctcacc gacgttgaga accttcacct tccacttcca    1680
ttgctccagt cttggatgca tcaaccacat cagccacttc caccaaccgt tatgttccca   1740
cctcagtccg tgcttagcct ctctcagtct aaggttttgc cagtgcctca gaaggccgtt    1800
ccatatccac aaagggatat gccaatccag ccttctgtc tctaccaaga gccagttctt     1860
ggaccagtga gagggcccatt tccaatcatt gtgttcatgc gcgaactgga agagttgaac   1920
gtaccaggag agattgtaga atcactgagc tcctcagagg agtctattac tcgtatcaac    1980
aagaagatat agaagttcca atccgaggag caacaacaaa cagaggacga attgcaggac    2040
aagatacatc ctttcgcaca gacccagagc ctcgtctatc ccttcccagg tccaatccct    2100
aactctctcc cccagaatat cccaccctg actcagactc ccgtggtcgt acccccttc     2160
```

```
ttgcaacccg aggtgatggg ggtttctaaa gtcaaagagg ctatggctcc taaacataag    2220
gaaatgcctt ttcccaaata tccagtggag ccattcactg agagccagtc tctgacactt    2280
acagatgtgg aaaacttgca cctgcccttg ccacttttgc agtcctggat gcaccaacca    2340
catcaaccct gcccccccac agtgatgttt cctccacaat cagttcttag tctctcccaa    2400
agcaaagtcc ttccagtgcc tcagaaggcc gtcccatacc cccagagaga tatgccaata    2460
caggcattct tgctttacca ggaaccagtg ctcggtcctg tacgtggccc attccctatc    2520
atagtgtaa                                                            2529

SEQ ID NO: 664          moltype = AA   length = 842
FEATURE                 Location/Qualifiers
REGION                  1..842
                        note = fusion protein (OBC-T5:FM:OBC-T4:FM:OBC-T3:FM:OBC-T2)
source                  1..842
                        mol_type = protein
                        organism = synthetic construct
SEQUENCE: 664
RELEELNVPG EIVESLSSSE ESITRINKKI EKFQSEEQQQ TEDELQDKIH PFAQTQSLVY     60
PFPGPIPNSL PQNIPPLTQT PVVVPPFLQP EVMGVSKVKE AMAPKHKEMP FPKYPVEPFT    120
ESQSLTLTDV ENLHLPLPLL QSWMHQPHQP LPPTVMFPPQ SVLSLSQSKV LPVPQKAVPY    180
PQRDMPIQAF LLYQEPVLGP VRGPFPIIVF MRELEELNVP GEIVESLSSS EESITRINKK    240
IEKFQSEEQQ QTEDELQDKI HPFAQTQSLV YPFPGPIPNS LPQNIPPLTQ TPVVVPPFLQ    300
PEVMGVSKVK EAMAPKHKEM PFPKYPVEPF TESQSLTLTD VENLHLPLPL LQSWMHQPHQ    360
PLPPTVMFPP QSVLSLSQSK VLPVPQKAVP YPQRDMPIQA FLLYQEPVLG PVRGPFPIIV    420
FMRELEELNV PGEIVESLSS SEESITRINK KIEKFQSEEQ QQTEDELQDK IHPFAQTQSL    480
VYPFPGPIPN SLPQNIPPLT QTPVVVPPFL QPEVMGVSKV KEAMAPKHKE MPFPKYPVEP    540
FTESQSLTLT DVENLHLPLP LLQSWMHQPH QPLPPTVMFP PQSVLSLSQS KVLPVPQKAV    600
PYPQRDMPIQ AFLLYQEPVL GPVRGPFPII VFMRELEELN VPGEIVESLS SSEESITRIN    660
KKIEKFQSEE QQQTEDELQD KIHPFAQTQS LVYPFPGPIP NSLPQNIPPL TQTPVVVPPF    720
LQPEVMGVSK VKEAMAPKHK EMPFPKYPVE PFTESQSLTL TDVENLHLPL PLLQSWMHQP    780
HQPLPPTVMF PPQSVLSLSQ SKVLPVPQKA VPYPQRDMPI QAFLLYQEPV LGPVRGPFPI    840
IV                                                                   842

SEQ ID NO: 665          moltype = AA   length = 16
FEATURE                 Location/Qualifiers
REGION                  1..16
                        note = Protease cleavage site
source                  1..16
                        mol_type = protein
                        organism = synthetic construct
SEQUENCE: 665
RHPHPHLSFM AIPPKK                                                     16

SEQ ID NO: 666          moltype = AA   length = 14
FEATURE                 Location/Qualifiers
REGION                  1..14
                        note = Protease cleavage site
source                  1..14
                        mol_type = protein
                        organism = synthetic construct
SEQUENCE: 666
HPHPHLSFMA IPPK                                                       14

SEQ ID NO: 667          moltype = AA   length = 10
FEATURE                 Location/Qualifiers
REGION                  1..10
                        note = Protease cleavage site
source                  1..10
                        mol_type = protein
                        organism = synthetic construct
SEQUENCE: 667
RHPHPHLSFM                                                            10

SEQ ID NO: 668          moltype = AA   length = 16
FEATURE                 Location/Qualifiers
REGION                  1..16
                        note = Protease cleavage site
source                  1..16
                        mol_type = protein
                        organism = synthetic construct
SEQUENCE: 668
EDFLQKQQYG ISSKFR                                                     16

SEQ ID NO: 669          moltype = AA   length = 16
FEATURE                 Location/Qualifiers
REGION                  1..16
                        note = Protease cleavage site
source                  1..16
                        mol_type = protein
                        organism = synthetic construct
```

```
SEQUENCE: 669
RHPHPHLSFM AIPPKK                                                          16

SEQ ID NO: 670          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 670
HHPHPHLSFM AIPPKK                                                          16

SEQ ID NO: 671          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 671
RHPHPRLSFM AIPPKK                                                          16

SEQ ID NO: 672          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 672
RRPRPHLSFM AIPPKK                                                          16

SEQ ID NO: 673          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 673
HQTFQHASFI ATPPQK                                                          16

SEQ ID NO: 674          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 674
RRPNLHPSFI AIPPKK                                                          16

SEQ ID NO: 675          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 675
PYAIPNPSFL AMPTNE                                                          16

SEQ ID NO: 676          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 676
PHPIPNPSFL AIPTNE                                                          16

SEQ ID NO: 677          moltype = AA  length = 16
FEATURE                 Location/Qualifiers
REGION                  1..16
                        note = Protease cleavage site
source                  1..16
                        mol_type = protein
```

```
                            -continued

SEQUENCE: 677              organism = synthetic construct
RHPCHPSFI AIPPKK                                                     16

SEQ ID NO: 678             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 678
ARRPPHASFI AIPPKK                                                    16

SEQ ID NO: 679             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 679
VGRHSHPFFM AILPNK                                                    16

SEQ ID NO: 680             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 680
RRPRPRPSFI AIPPKK                                                    16

SEQ ID NO: 681             moltype = AA   length = 16
FEATURE                    Location/Qualifiers
REGION                     1..16
                           note = Protease cleavage site
VARIANT                    16
                           note = X can be any naturally occurring amino acid
source                     1..16
                           mol_type = protein
                           organism = synthetic construct
SEQUENCE: 681
RHPRPHPSFI AIPPKX                                                    16

SEQ ID NO: 682             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 682
RHPYRRPSFI AIPPKK                                                    16

SEQ ID NO: 683             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 683
RHPHLPASFI VIPPKK                                                    16

SEQ ID NO: 684             moltype = AA   length = 16
FEATURE                    Location/Qualifiers
REGION                     1..16
                           note = Protease cleavage site
VARIANT                    15
                           note = X can be any naturally occurring amino acid
source                     1..16
                           mol_type = protein
                           organism = synthetic construct
SEQUENCE: 684
CRRRPHPSFL AIPPXK                                                    16

SEQ ID NO: 685             moltype = AA   length = 16
```

```
FEATURE                 Location/Qualifiers
REGION                  1..16
                        note = Protease cleavage site
source                  1..16
                        mol_type = protein
                        organism = synthetic construct
SEQUENCE: 685
HRPNLHPSFI AIPPKK                                                               16

SEQ ID NO: 686          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 686
HRPQLHPSFI AIPPKK                                                               16

SEQ ID NO: 687          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 687
HRPHIHPSFI AIPPKK                                                               16

SEQ ID NO: 688          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 688
HRPHLHPSFI AIPPKK                                                               16

SEQ ID NO: 689          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 689
HRPHLHPSFI AIPAKK                                                               16

SEQ ID NO: 690          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 690
HHPHPCPSFL AIPPKK                                                               16

SEQ ID NO: 691          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 691
HRPHLHPSFT AIPAKK                                                               16

SEQ ID NO: 692          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 692
HHPHPRPSFT AIPPKK                                                               16
```

```
SEQ ID NO: 693          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 693
HHPHPRPSFL AIPPKK                                                          16

SEQ ID NO: 694          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 694
HRPHLHPSFI AIPTKK                                                          16

SEQ ID NO: 695          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 695
HHKYLKPSFI VIPPTK                                                          16

SEQ ID NO: 696          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 696
RHPRHPSFI AIPPKK                                                           16

SEQ ID NO: 697          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 697
YHQAKHPSFM AILSKK                                                          16

SEQ ID NO: 698          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 698
PHTYLKPPFI VIPPKK                                                          16

SEQ ID NO: 699          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 699
HRPKLHPSFI AVPPKK                                                          16

SEQ ID NO: 700          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 700
RRPHPRLSFM AIPPKK                                                          16
```

```
SEQ ID NO: 701          moltype = AA   length = 8
FEATURE                 Location/Qualifiers
REGION                  1..8
                        note = Protease cleavage site
source                  1..8
                        mol_type = protein
                        organism = synthetic construct
SEQUENCE: 701
KPAEFFRL                                                                    8

SEQ ID NO: 702          moltype = AA   length = 8
FEATURE                 Location/Qualifiers
REGION                  1..8
                        note = Protease cleavage site
source                  1..8
                        mol_type = protein
                        organism = synthetic construct
SEQUENCE: 702
KPAEFKRL                                                                    8

SEQ ID NO: 703          moltype = AA   length = 8
FEATURE                 Location/Qualifiers
REGION                  1..8
                        note = Protease cleavage site
source                  1..8
                        mol_type = protein
                        organism = synthetic construct
SEQUENCE: 703
KPAEFERL                                                                    8

SEQ ID NO: 704          moltype = AA   length = 8
FEATURE                 Location/Qualifiers
REGION                  1..8
                        note = Protease cleavage site
source                  1..8
                        mol_type = protein
                        organism = synthetic construct
SEQUENCE: 704
KPAEFTRL                                                                    8

SEQ ID NO: 705          moltype = AA   length = 8
FEATURE                 Location/Qualifiers
REGION                  1..8
                        note = Protease cleavage site
source                  1..8
                        mol_type = protein
                        organism = synthetic construct
SEQUENCE: 705
KPAEFGRL                                                                    8

SEQ ID NO: 706          moltype = AA   length = 8
FEATURE                 Location/Qualifiers
REGION                  1..8
                        note = Protease cleavage site
source                  1..8
                        mol_type = protein
                        organism = synthetic construct
SEQUENCE: 706
KPAEFARL                                                                    8

SEQ ID NO: 707          moltype = AA   length = 8
FEATURE                 Location/Qualifiers
REGION                  1..8
                        note = Protease cleavage site
source                  1..8
                        mol_type = protein
                        organism = synthetic construct
SEQUENCE: 707
KPAEFVRL                                                                    8

SEQ ID NO: 708          moltype = AA   length = 8
FEATURE                 Location/Qualifiers
REGION                  1..8
                        note = Protease cleavage site
source                  1..8
                        mol_type = protein
                        organism = synthetic construct
SEQUENCE: 708
```

```
KPAEFLRL                                                                        8

SEQ ID NO: 709          moltype = AA   length = 8
FEATURE                 Location/Qualifiers
REGION                  1..8
                        note = Protease cleavage site
source                  1..8
                        mol_type = protein
                        organism = synthetic construct
SEQUENCE: 709
KPAEFIRL                                                                        8

SEQ ID NO: 710          moltype = AA   length = 9
FEATURE                 Location/Qualifiers
REGION                  1..9
                        note = Protease cleavage site
source                  1..9
                        mol_type = protein
                        organism = synthetic construct
SEQUENCE: 710
HPHLSFMAI                                                                       9

SEQ ID NO: 711          moltype = AA   length = 9
FEATURE                 Location/Qualifiers
REGION                  1..9
                        note = Protease cleavage site
source                  1..9
                        mol_type = protein
                        organism = synthetic construct
SEQUENCE: 711
HPHLSFEAI                                                                       9

SEQ ID NO: 712          moltype = AA   length = 7
FEATURE                 Location/Qualifiers
REGION                  1..7
                        note = Protease cleavage site
source                  1..7
                        mol_type = protein
                        organism = synthetic construct
SEQUENCE: 712
YGIFLRF                                                                         7

SEQ ID NO: 713          moltype = AA   length = 7
FEATURE                 Location/Qualifiers
REGION                  1..7
                        note = Protease cleavage site
source                  1..7
                        mol_type = protein
                        organism = synthetic construct
SEQUENCE: 713
YGIFKRF                                                                         7

SEQ ID NO: 714          moltype = AA   length = 7
FEATURE                 Location/Qualifiers
REGION                  1..7
                        note = Protease cleavage site
source                  1..7
                        mol_type = protein
                        organism = synthetic construct
SEQUENCE: 714
YGAFLRF                                                                         7

SEQ ID NO: 715          moltype = AA   length = 9
FEATURE                 Location/Qualifiers
REGION                  1..9
                        note = Protease cleavage site
source                  1..9
                        mol_type = protein
                        organism = synthetic construct
SEQUENCE: 715
KYSSWYVAL                                                                       9

SEQ ID NO: 716          moltype = AA   length = 9
FEATURE                 Location/Qualifiers
REGION                  1..9
                        note = Protease cleavage site
source                  1..9
                        mol_type = protein
                        organism = synthetic construct
```

```
SEQUENCE: 716
KYSSWKVAL                                                                        9

SEQ ID NO: 717         moltype = AA  length = 9
FEATURE                Location/Qualifiers
REGION                 1..9
                       note = Protease cleavage site
source                 1..9
                       mol_type = protein
                       organism = synthetic construct
SEQUENCE: 717
KYSSWEVAL                                                                        9

SEQ ID NO: 718         moltype = AA  length = 9
FEATURE                Location/Qualifiers
REGION                 1..9
                       note = Protease cleavage site
source                 1..9
                       mol_type = protein
                       organism = synthetic construct
SEQUENCE: 718
KYSSWLVAL                                                                        9

SEQ ID NO: 719         moltype = AA  length = 11
FEATURE                Location/Qualifiers
REGION                 1..11
                       note = Protease cleavage site
source                 1..11
                       mol_type = protein
                       organism = synthetic construct
SEQUENCE: 719
RPKPQQFFGL M                                                                    11

SEQ ID NO: 720         moltype = AA  length = 11
FEATURE                Location/Qualifiers
REGION                 1..11
                       note = Protease cleavage site
source                 1..11
                       mol_type = protein
                       organism = synthetic construct
SEQUENCE: 720
RPKPQQFKGL M                                                                    11

SEQ ID NO: 721         moltype = AA  length = 10
FEATURE                Location/Qualifiers
REGION                 1..10
                       note = Protease cleavage site
source                 1..10
                       mol_type = protein
                       organism = synthetic construct
SEQUENCE: 721
APLEFKREL                                                                       10

SEQ ID NO: 722         moltype = AA  length = 10
FEATURE                Location/Qualifiers
REGION                 1..10
                       note = Protease cleavage site
source                 1..10
                       mol_type = protein
                       organism = synthetic construct
SEQUENCE: 722
APLEFKREL                                                                       10

SEQ ID NO: 723         moltype = AA  length = 10
FEATURE                Location/Qualifiers
REGION                 1..10
                       note = Protease cleavage site
source                 1..10
                       mol_type = protein
                       organism = synthetic construct
SEQUENCE: 723
APLEFEREL                                                                       10

SEQ ID NO: 724         moltype = AA  length = 10
FEATURE                Location/Qualifiers
REGION                 1..10
                       note = Protease cleavage site
source                 1..10
                       mol_type = protein
```

```
                       organism = synthetic construct
SEQUENCE: 724
APPLEFEREL                                                             10

SEQ ID NO: 725         moltype = AA  length = 10
FEATURE                Location/Qualifiers
REGION                 1..10
                       note = Protease cleavage site
source                 1..10
                       mol_type = protein
                       organism = synthetic construct
SEQUENCE: 725
APPLEFIREL                                                             10

SEQ ID NO: 726         moltype = AA  length = 10
FEATURE                Location/Qualifiers
REGION                 1..10
                       note = Protease cleavage site
source                 1..10
                       mol_type = protein
                       organism = synthetic construct
SEQUENCE: 726
APPLEFFREL                                                             10

SEQ ID NO: 727         moltype = AA  length = 10
FEATURE                Location/Qualifiers
REGION                 1..10
                       note = Protease cleavage site
source                 1..10
                       mol_type = protein
                       organism = synthetic construct
SEQUENCE: 727
KIPYILKRQL                                                             10

SEQ ID NO: 728         moltype = AA  length = 10
FEATURE                Location/Qualifiers
REGION                 1..10
                       note = Protease cleavage site
source                 1..10
                       mol_type = protein
                       organism = synthetic construct
SEQUENCE: 728
KIPYILRRQL                                                             10

SEQ ID NO: 729         moltype = AA  length = 10
FEATURE                Location/Qualifiers
REGION                 1..10
                       note = Protease cleavage site
source                 1..10
                       mol_type = protein
                       organism = synthetic construct
SEQUENCE: 729
KIPYILERQL                                                             10

SEQ ID NO: 730         moltype = AA  length = 10
FEATURE                Location/Qualifiers
REGION                 1..10
                       note = Protease cleavage site
source                 1..10
                       mol_type = protein
                       organism = synthetic construct
SEQUENCE: 730
KIPYILSRQL                                                             10

SEQ ID NO: 731         moltype = AA  length = 10
FEATURE                Location/Qualifiers
REGION                 1..10
                       note = Protease cleavage site
source                 1..10
                       mol_type = protein
                       organism = synthetic construct
SEQUENCE: 731
KIPYILARQL                                                             10

SEQ ID NO: 732         moltype = AA  length = 10
FEATURE                Location/Qualifiers
REGION                 1..10
                       note = Protease cleavage site
source                 1..10
```

```
                        mol_type = protein
                        organism = synthetic construct
SEQUENCE: 732
KIPYILIRQL                                                              10

SEQ ID NO: 733          moltype = AA  length = 10
FEATURE                 Location/Qualifiers
REGION                  1..10
                        note = Protease cleavage site
source                  1..10
                        mol_type = protein
                        organism = synthetic construct
SEQUENCE: 733
KIPYILFRQL                                                              10

SEQ ID NO: 734          moltype = AA  length = 10
FEATURE                 Location/Qualifiers
REGION                  1..10
                        note = Protease cleavage site
source                  1..10
                        mol_type = protein
                        organism = synthetic construct
SEQUENCE: 734
KIPYILFRQL                                                              10

SEQ ID NO: 735          moltype = AA  length = 10
FEATURE                 Location/Qualifiers
REGION                  1..10
                        note = Protease cleavage site
source                  1..10
                        mol_type = protein
                        organism = synthetic construct
SEQUENCE: 735
KIPYILWRQL                                                              10

SEQ ID NO: 736          moltype = AA  length = 19
FEATURE                 Location/Qualifiers
REGION                  1..19
                        note = Protease cleavage site
source                  1..19
                        mol_type = protein
                        organism = synthetic construct
SEQUENCE: 736
EDFLQKQQYG ISSKYSGFG                                                    19

SEQ ID NO: 737          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 737
EDFLQKQQYG ISSKFM                                                       16

SEQ ID NO: 738          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 738
EDFLQKQQYG ISSKFA                                                       16

SEQ ID NO: 739          moltype = AA  length = 16
FEATURE                 Location/Qualifiers
REGION                  1..16
                        note = Protease cleavage site
source                  1..16
                        mol_type = protein
                        organism = synthetic construct
SEQUENCE: 739
EDFLQKQQYG ISSKFC                                                       16

SEQ ID NO: 740          moltype = AA  length = 16
FEATURE                 Location/Qualifiers
REGION                  1..16
                        note = Protease cleavage site
```

```
source                     1..16
                           mol_type = protein
                           organism = synthetic construct
SEQUENCE: 740
EDFLQKQQYG ISSKFF                                                    16

SEQ ID NO: 741             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 741
EDFLQKQQYG ISSKFH                                                    16

SEQ ID NO: 742             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 742
EDFLQKQQYG ISSKFI                                                    16

SEQ ID NO: 743             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 743
EDFLQKQQYG ISSKFK                                                    16

SEQ ID NO: 744             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 744
EDFLQKQQYG ISSKFL                                                    16

SEQ ID NO: 745             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 745
EDFLQKQQYG ISSKFN                                                    16

SEQ ID NO: 746             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 746
EDFLQKQQYG ISSKFR                                                    16

SEQ ID NO: 747             moltype = AA   length = 16
FEATURE                    Location/Qualifiers
REGION                     1..16
                           note = Protease cleavage site
source                     1..16
                           mol_type = protein
                           organism = synthetic construct
SEQUENCE: 747
EDFLQKQQYG ISSKFT                                                    16

SEQ ID NO: 748             moltype = AA   length = 16
FEATURE                    Location/Qualifiers
REGION                     1..16
```

```
                    note = Protease cleavage site
source              1..16
                    mol_type = protein
                    organism = synthetic construct
SEQUENCE: 748
EDFLQKQQYG ISSKFV                                               16

SEQ ID NO: 749      moltype = AA  length = 16
FEATURE             Location/Qualifiers
REGION              1..16
                    note = Protease cleavage site
source              1..16
                    mol_type = protein
                    organism = synthetic construct
SEQUENCE: 749
EDFLQKQQYG ISSKFW                                               16

SEQ ID NO: 750      moltype = AA  length = 19
FEATURE             Location/Qualifiers
REGION              1..19
                    note = Protease cleavage site
source              1..19
                    mol_type = protein
                    organism = synthetic construct
SEQUENCE: 750
EDFLQKQQYG ISSKYSGFV                                            19

SEQ ID NO: 751      moltype = AA  length = 19
FEATURE             Location/Qualifiers
REGION              1..19
                    note = Protease cleavage site
source              1..19
                    mol_type = protein
                    organism = synthetic construct
SEQUENCE: 751
EDFLQKQQYG ISSKYSGFV                                            19

SEQ ID NO: 752      moltype = AA  length = 19
FEATURE             Location/Qualifiers
REGION              1..19
                    note = Protease cleavage site
source              1..19
                    mol_type = protein
                    organism = synthetic construct
SEQUENCE: 752
EDFLQKQQYG ISSKYSGFM                                            19

SEQ ID NO: 753      moltype = AA  length = 19
FEATURE             Location/Qualifiers
REGION              1..19
                    note = Protease cleavage site
source              1..19
                    mol_type = protein
                    organism = synthetic construct
SEQUENCE: 753
EDFLQKQQYG ISSKYSGFM                                            19

SEQ ID NO: 754      moltype = AA  length = 19
FEATURE             Location/Qualifiers
REGION              1..19
                    note = Protease cleavage site
source              1..19
                    mol_type = protein
                    organism = synthetic construct
SEQUENCE: 754
EDFLQKQQYG ISSKYSGFS                                            19

SEQ ID NO: 755      moltype = AA  length = 19
FEATURE             Location/Qualifiers
REGION              1..19
                    note = Protease cleavage site
source              1..19
                    mol_type = protein
                    organism = synthetic construct
SEQUENCE: 755
EDFLQKQQYG ISSKSSGFV                                            19

SEQ ID NO: 756      moltype = AA  length = 19
FEATURE             Location/Qualifiers
```

```
REGION                    1..19
                          note = Protease cleavage site
source                    1..19
                          mol_type = protein
                          organism = synthetic construct
SEQUENCE: 756
EDFLQKQQYG ISSKSSGFV                                                        19

SEQ ID NO: 757            moltype = AA  length = 19
FEATURE                   Location/Qualifiers
REGION                    1..19
                          note = Protease cleavage site
source                    1..19
                          mol_type = protein
                          organism = synthetic construct
SEQUENCE: 757
EDFLQKQQYG ISSKSSGFV                                                        19

SEQ ID NO: 758            moltype = AA  length = 16
FEATURE                   Location/Qualifiers
REGION                    1..16
                          note = Protease cleavage site
source                    1..16
                          mol_type = protein
                          organism = synthetic construct
SEQUENCE: 758
EDFLQKQQYG ISSKYV                                                           16

SEQ ID NO: 759            moltype = AA  length = 16
FEATURE                   Location/Qualifiers
REGION                    1..16
                          note = Protease cleavage site
source                    1..16
                          mol_type = protein
                          organism = synthetic construct
SEQUENCE: 759
EDFLQKQQYG ISSKFS                                                           16

SEQ ID NO: 760            moltype = AA  length = 5
FEATURE                   Location/Qualifiers
REGION                    1..5
                          note = Protease cleavage site
source                    1..5
                          mol_type = protein
                          organism = synthetic construct
SEQUENCE: 760
DDDDK                                                                        5

SEQ ID NO: 761            moltype = AA  length = 9
FEATURE                   Location/Qualifiers
REGION                    1..9
                          note = Protease cleavage site
source                    1..9
                          mol_type = protein
                          organism = synthetic construct
SEQUENCE: 761
HPHLSFMAI                                                                    9

SEQ ID NO: 762            moltype = AA  length = 9
FEATURE                   Location/Qualifiers
REGION                    1..9
                          note = Protease cleavage site
source                    1..9
                          mol_type = protein
                          organism = synthetic construct
SEQUENCE: 762
HPHLSFEAI                                                                    9

SEQ ID NO: 763            moltype = AA  length = 5
FEATURE                   Location/Qualifiers
REGION                    1..5
                          note = Protease cleavage site
source                    1..5
                          mol_type = protein
                          organism = synthetic construct
SEQUENCE: 763
LVPRG                                                                        5

SEQ ID NO: 764            moltype = AA  length = 11
```

```
FEATURE                 Location/Qualifiers
REGION                  1..11
                        note = Protease cleavage site
source                  1..11
                        mol_type = protein
                        organism = synthetic construct
SEQUENCE: 764
ELSLSRLRDS A                                                              11

SEQ ID NO: 765          moltype = AA  length = 8
FEATURE                 Location/Qualifiers
REGION                  1..8
                        note = Protease cleavage site
source                  1..8
                        mol_type = protein
                        organism = synthetic construct
SEQUENCE: 765
ELSLSRLR                                                                   8

SEQ ID NO: 766          moltype = AA  length = 8
FEATURE                 Location/Qualifiers
REGION                  1..8
                        note = Protease cleavage site
source                  1..8
                        mol_type = protein
                        organism = synthetic construct
SEQUENCE: 766
DNYTRLRK                                                                   8

SEQ ID NO: 767          moltype = AA  length = 8
FEATURE                 Location/Qualifiers
REGION                  1..8
                        note = Protease cleavage site
source                  1..8
                        mol_type = protein
                        organism = synthetic construct
SEQUENCE: 767
YTRLRKQM                                                                   8

SEQ ID NO: 768          moltype = AA  length = 8
FEATURE                 Location/Qualifiers
REGION                  1..8
                        note = Protease cleavage site
source                  1..8
                        mol_type = protein
                        organism = synthetic construct
SEQUENCE: 768
APSGRVSM                                                                   8

SEQ ID NO: 769          moltype = AA  length = 8
FEATURE                 Location/Qualifiers
REGION                  1..8
                        note = Protease cleavage site
source                  1..8
                        mol_type = protein
                        organism = synthetic construct
SEQUENCE: 769
VSMIKNLQ                                                                   8

SEQ ID NO: 770          moltype = AA  length = 8
FEATURE                 Location/Qualifiers
REGION                  1..8
                        note = Protease cleavage site
source                  1..8
                        mol_type = protein
                        organism = synthetic construct
SEQUENCE: 770
RIRPKLKW                                                                   8

SEQ ID NO: 771          moltype = AA  length = 8
FEATURE                 Location/Qualifiers
REGION                  1..8
                        note = Protease cleavage site
source                  1..8
                        mol_type = protein
                        organism = synthetic construct
SEQUENCE: 771
AMAPRERK                                                                   8
```

-continued

| | | |
|---|---|---|
| SEQ ID NO: 772<br>FEATURE<br>REGION<br>source | moltype = AA  length = 8<br>Location/Qualifiers<br>1..8<br>note = Protease cleavage site<br>1..8<br>mol_type = protein<br>organism = synthetic construct | |
| SEQUENCE: 772<br>NFFWKTFT | | 8 |
| SEQ ID NO: 773<br>FEATURE<br>REGION<br>source | moltype = AA  length = 8<br>Location/Qualifiers<br>1..8<br>note = Protease cleavage site<br>1..8<br>mol_type = protein<br>organism = synthetic construct | |
| SEQUENCE: 773<br>KMYPRGNH | | 8 |
| SEQ ID NO: 774<br>FEATURE<br>REGION<br>source | moltype = AA  length = 8<br>Location/Qualifiers<br>1..8<br>note = Protease cleavage site<br>1..8<br>mol_type = protein<br>organism = synthetic construct | |
| SEQUENCE: 774<br>QTYPRTNT | | 8 |
| SEQ ID NO: 775<br>FEATURE<br>REGION<br>source | moltype = AA  length = 4<br>Location/Qualifiers<br>1..4<br>note = Protease cleavage site<br>1..4<br>mol_type = protein<br>organism = synthetic construct | |
| SEQUENCE: 775<br>IQGR | | 4 |
| SEQ ID NO: 776<br>FEATURE<br>REGION<br>source | moltype = AA  length = 4<br>Location/Qualifiers<br>1..4<br>note = Protease cleavage site<br>1..4<br>mol_type = protein<br>organism = synthetic construct | |
| SEQUENCE: 776<br>IEGR | | 4 |
| SEQ ID NO: 777<br>FEATURE<br>REGION<br>SITE<br>source | moltype = AA  length = 7<br>Location/Qualifiers<br>1..7<br>note = Protease cleavage site<br>7<br>note = SVARIANT - X is G or S<br>1..7<br>mol_type = protein<br>organism = synthetic construct | |
| SEQUENCE: 777<br>ENLYFQX | | 7 |
| SEQ ID NO: 778<br>SEQUENCE: 778<br>000 | moltype =    length = | |
| SEQ ID NO: 779<br>FEATURE<br>REGION<br>VARIANT<br>source | moltype = AA  length = 6<br>Location/Qualifiers<br>1..6<br>note = Protease cleavage site<br>6<br>note = X is any amino acid<br>1..6<br>mol_type = protein<br>organism = synthetic construct | |
| SEQUENCE: 779<br>VDVADX | | 6 |
| SEQ ID NO: 780 | moltype =    length = | |

```
SEQUENCE: 780
000

SEQ ID NO: 781        moltype =    length =
SEQUENCE: 781
000

SEQ ID NO: 782        moltype = AA   length = 170
FEATURE               Location/Qualifiers
REGION                1..170
                      note = Modified kappa-casein (OKC1-T with extra M)
source                1..170
                      mol_type = protein
                      organism = synthetic construct
SEQUENCE: 782
MQEQNQEQPI RCEKDERFFS DKIAKYIPIQ YVLSRYPSYG LNYYQQKPVA LINNQFLPYP   60
YYAKPAAVRS PAQILQWQVL SNTVPAKSCQ AQPTTMARHP HPHLSFMAIP PKKNQDKTEI  120
PTINTIASGE PTSTPTTEAV ESTVATLEDS PEVIESPPEI NTVQVTSTAV             170

SEQ ID NO: 783        moltype = AA   length = 170
FEATURE               Location/Qualifiers
REGION                1..170
                      note = Modified kappa-casein (OKC1-T with extra F)
source                1..170
                      mol_type = protein
                      organism = synthetic construct
SEQUENCE: 783
QEQNQEQPIR CEKDERFFSD KIAKYIPIQY VLSRYPSYGL NYYQQKPVAL INNQFLPYPY   60
YAKPAAVRSP AQILQWQVLS NTVPAKSCQA QPTTMARHPH PHLSFMAIPP KKNQDKTEIP  120
TINTIASGEP TSTPTTEAVE STVATLEDSP EVIESPPEIN TVQVTSTAVF             170

SEQ ID NO: 784        moltype = AA   length = 210
FEATURE               Location/Qualifiers
REGION                1..210
                      note = Modified beta-casein (OBC-T2 with extra M)
source                1..210
                      mol_type = protein
                      organism = synthetic construct
SEQUENCE: 784
MRELEELNVP GEIVESLSSS EESITRINKK IEKFQSEEQQ QTEDELQDKI HPFAQTQSLV   60
YPFPGPIPNS LPQNIPPLTQ TPVVVPPFLQ PEVMGVSKVK EAMAPKHKEM PFPKYPVEPF  120
TESQSLTLTD VENLHLPLPL LQSWMHQPHQ PLPPTVMFPP QSVLSLSQSK VLPVPQKAVP  180
YPQRDMPIQA FLLYQEPVLG PVRGPFPIIV                                   210

SEQ ID NO: 785        moltype = AA   length = 210
FEATURE               Location/Qualifiers
REGION                1..210
                      note = Modified beta-casein (OBC-T2 with extra F)
source                1..210
                      mol_type = protein
                      organism = synthetic construct
SEQUENCE: 785
RELEELNVPG EIVESLSSSE ESITRINKKI EKFQSEEQQQ TEDELQDKIH PFAQTQSLVY   60
PFPGPIPNSL PQNIPPLTQT PVVVPPFLQP EVMGVSKVKE AMAPKHKEMP FPKYPVEPFT  120
ESQSLTLTDV ENLHLPLPLL QSWMHQPHQP LPPTVMFPPQ SVLSLSQSKV LPVPQKAVPY  180
PQRDMPIQAF LLYQEPVLGP VRGPFPIIVF                                   210

SEQ ID NO: 786        moltype = AA   length = 200
FEATURE               Location/Qualifiers
REGION                1..200
                      note = Modified alpha S1-casein (OAS1-T with extra M)
source                1..200
                      mol_type = protein
                      organism = synthetic construct
SEQUENCE: 786
MRPKHPIKHQ GLPQEVLNEN LLRFFVAPFP EVFGKEKVNE LSKDIGSEST EDQAMEDIKQ   60
MEAESISSSE EIVPNSVEQK HIQKEDVPSE RYLGYLEQLL RLKKYKVPQL EIVPNSAEER  120
LHSMKEGIHA QQKEPMIGVN QELAYFYPEL FRQFYQLDAY PSGAWYYVPL GTQYTDAPSF  180
SDIPNPIGSE NSEKTTMPLW                                              200

SEQ ID NO: 787        moltype = AA   length = 200
FEATURE               Location/Qualifiers
REGION                1..200
                      note = Modified alpha S1-casein (OAS1-T with extra F)
source                1..200
                      mol_type = protein
                      organism = synthetic construct
SEQUENCE: 787
RPKHPIKHQG LPQEVLNENL LRFFVAPFPE VFGKEKVNEL SKDIGSESTE DQAMEDIKQM   60
```

```
EAESISSSEE IVPNSVEQKH IQKEDVPSER YLGYLEQLLR LKKYKVPQLE IVPNSAEERL    120
HSMKEGIHAQ QKEPMIGVNQ ELAYFYPELF RQFYQLDAYP SGAWYYVPLG TQYTDAPSFS    180
DIPNPIGSEN SEKTTMPLWF                                                200

SEQ ID NO: 788           moltype = AA   length = 163
FEATURE                  Location/Qualifiers
REGION                   1..163
                         note = modified beta-lactogloublin (OLG1 with extra M)
source                   1..163
                         mol_type = protein
                         organism = synthetic construct
SEQUENCE: 788
MLIVTQTMKG LDIQKVAGTW YSLAMAASDI SLLDAQSAPL RVYYEELKPT PEGDLEILLQ     60
KWENGECAQK KIIAEKTKIP AVFKIDALNE NKVLVLDTDY KKYLLFCMEN SAEPEQSLAC    120
QCLVRTPEVD DEALEKFDKA LKALPMHIRL SFNPTQLEEQ CHI                      163

SEQ ID NO: 789           moltype = AA   length = 163
FEATURE                  Location/Qualifiers
REGION                   1..163
                         note = modified beta-lactogloublin (OLG1 with extra F)
source                   1..163
                         mol_type = protein
                         organism = synthetic construct
SEQUENCE: 789
LIVTQTMKGL DIQKVAGTWY SLAMAASDIS LLDAQSAPLR VYVEELKPTP EGDLEILLQK     60
WENGECAQKK IIAEKTKIPA VFKIDALNEN KVLVLDTDYK KYLLFCMENS AEPEQSLACQ    120
CLVRTPEVDD EALEKFDKAL KALPMHIRLS FNPTQLEEQ HIF                       163

SEQ ID NO: 790           moltype = AA   length = 208
FEATURE                  Location/Qualifiers
REGION                   1..208
                         note = Modified alpha S1-casein (OAS2-T with extra M)
source                   1..208
                         mol_type = protein
                         organism = synthetic construct
SEQUENCE: 790
MKNTMEHVSS SEESIISQET YKQEKNMAIN PSKENLCSTF CKEVVRNANE EEYSIGSSSE     60
ESAEVATEEV KITVDDKHYQ KALNEINQFY QKFPQYLQYL YQGPIVLNPW DQVKRNAVPI    120
TPTLNREQLS TSEENSKKTV DMESTEVFTK KTKLTEEEKN RLNFLKKISQ RYQKFALPQY    180
LKTVYQHQKA MKPWIQPKTK VIPYVRYL                                       208

SEQ ID NO: 791           moltype = AA   length = 208
FEATURE                  Location/Qualifiers
REGION                   1..208
                         note = Modified alpha S1-casein (OAS2-T with extra F)
source                   1..208
                         mol_type = protein
                         organism = synthetic construct
SEQUENCE: 791
KNTMEHVSSS EESIISQETY KQEKNMAINP SKENLCSTFC KEVVRNANEE EYSIGSSSEE     60
SAEVATEEVK ITVDDKHYQK ALNEINQFYQ KFPQYLQYLY QGPIVLNPWD QVKRNAVPIT    120
PTLNREQLST SEENSKKTVD MESTEVFTKK TKLTEEEKNR LNFLKKISQR YQKFALPQYL    180
KTVYQHQKAM KPWIQPKTKV IPYVRYLF                                       208

SEQ ID NO: 792           moltype = DNA   length = 1896
FEATURE                  Location/Qualifiers
misc_feature             1..1896
                         note = fusion protein (OBC-T4:FM:OBC-T3:FM:OBC-T2)
source                   1..1896
                         mol_type = other DNA
                         organism = synthetic construct
SEQUENCE: 792
agggagctcg aggagttgaa cgtgcctggc gagattgtag agtcattgag ctctagtgag     60
gagagtataa caaggatcaa taaaaagatt gaaaaatttc aaagcgaaga gcagcaacaa    120
acagaagatg aactgcaaga caaaattcat ccttttgctc agacacagag cttggtgtat    180
cccttcccag ggccaattcc caatagtctg ccccaaaaca tccctccctt gacccaaacc    240
cccgtagtag tacctccatt cttgcagcct gaagtgatgg gggtgagtaa agtgaaggag    300
gcaatggccc ctaagcataa agagatgcca ttccctaaat atcccgttga gccattcacc    360
gaatcacaat ccttgacact tactgatgtc gagaatttgc acttgccact gcccttgctc    420
caaagctgga tgcaccaacc acaccaacct ctgcctccca cagtgatgtt cccacccaa    480
tccgtcttgt ctctgtccca gtcaaaggtg ttgcctgttc ctcagaaagc agttccctat    540
ccccaacgcg atatgcccat ccaggctttt ctcttgtatc aagaaccagt gctcggtcct    600
gtcagaggcc ccttccccat tatcgtgttc atgagggaac tcgaggaact taacgttcca    660
ggtgagctcg tcgagtccct ctcatcttcc gaagatcca ttaccaggat caacaagaag    720
atcgagaagt tccagtccga ggaacaacag caaaccgagg atgagcttca ggacaagatt    780
cacccattcg ctcagaccca gtctctcgtg tatccatttc cagggccaat tccaaacagc    840
ctgccacaga acattccacc acttactcag accccgttgt ggtgccacc attccttcaa    900
ccagaggtta tgggagtgtc caaggtgaaa gaagccatgg caccaaagca caagagatg    960
cccttttcaa agtacccgt tgagccattc actgagtctc agtctcttac cctcaccgac   1020
```

```
gttgagaacc ttcaccttcc acttccattg ctccagtctt ggatgcatca accacatcag   1080
ccacttccac caaccgttat gttcccacct cagtccgtgc ttagcctctc tcagtctaag   1140
gttttgccag tgcctcagaa ggccgttcca tatccacaaa gggatatgcc aatccaggcc   1200
ttcttgctct accaagagcc agttcttgga ccagtgagag gcccatttcc aatcattgtg   1260
ttcatgcgcg aactggaaga gttgaacgta ccaggagaga ttgtagaatc actgagctcc   1320
tcagaggagt ctattactcg tatcaacaag aagatagaga gttccaatc cgaggagcaa   1380
caacaaacag aggacgaatt gcaggacaag atacatcctt tcgcacagac ccagagcctc   1440
gtctatccct ttccaggtcc aatccctaac tctctccccc agaatatccc acccttgact   1500
cagactcccg tggtcgtacc ccctttcttg caacccgagg tgatgggggt ttctaaagtc   1560
aaagaggcta tggctcctaa acataaggaa atgcctttc ccaaatatcc agtggagcca   1620
ttcactgaga gccagtctct gacacttaca gatgtggaaa acttgcacct gcccttgcca   1680
cttttgcagt cctggatgca ccaaccacat caacccttgc ccccacagt gatgtttcct   1740
ccacaatcag ttcttagtct ctcccaaagc aaagtccttc cagtgcctca gaaggccgtc   1800
ccatacccc agagagatat gccaatacag gcattcttgc tttaccagga accagtgctc   1860
ggtcctgtac gtggcccatt ccctatcata gtgtaa                             1896

SEQ ID NO: 793        moltype = AA   length = 631
FEATURE               Location/Qualifiers
REGION                1..631
                      note = fusion protein (OBC-T4:FM:OBC-T3:FM:OBC-T2)
source                1..631
                      mol_type = protein
                      organism = synthetic construct
SEQUENCE: 793
RELEELNVPG EIVESLSSSE ESITRINKKI EKFQSEEQQQ TEDELQDKIH PFAQTQSLVY    60
PPFPGPIPNSL PQNIPPLTQT PVVVPPFLQP EVMGVSKVE AMAPKHKEMP FPKYPVEPFT   120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIVF MRELEELNVP GEIVESLSSS EESITRINKK   240
IEKFQSEEQQ QTEDELQDKI HPFAQTQSLV YPFPGPIPNS LPQNIPPLTQ TPVVVPPFLQ   300
PEVMGVSKVK EAMAPKHKEM PFPKYPVEPF TESQSLTLTD VENLHLPLPL LQSWMHQPHQ   360
PLPPTVMFPP QSVLSLSQSK VLPVPQKAVP YPQRDMPIQA FLLYQEPVLG PVRGPFPIIV   420
FMRELEELNV PGEIVESLSS SEESITRINK KIEKFQSEEQ QQTEDELQDK IHPFAQTQSL   480
VYPFPGPIPN SLPQNIPPLT QTPVVVPPFL QPEVMGVSKV KEAMAPKHKE MPFPKYPVEP   540
FTESQSLTLT DVENLHLPLP LLQSWMHQPH QPLPPTVMFP PQSVLSLSQS KVLPVPQKAV   600
PYPQRDMPIQ AFLLYQEPVL GPVRGPFPII V                                  631

SEQ ID NO: 794        moltype = DNA   length = 2388
FEATURE               Location/Qualifiers
misc_feature          1..2388
                      note = fusion protein (OBC-T4:FM:OBC-T3:FM:OBC-T2:FM:OLG1)
source                1..2388
                      mol_type = other DNA
                      organism = synthetic construct
SEQUENCE: 794
agggagctcg aggagttgaa cgtgcctggc gagattgtag agtcattgag ctctagtgag    60
gagagtataa caaggatcaa taaaaagatt gaaaaatttc aaagcgaaga gcagcaacaa   120
acagaagatg aactgcaaga caaaattcat ccttttgctc agacacagag cttggtgtat   180
cccttcccag ggccaattcc caatagtctg ccccaaaaca tccctccctt gacccaaacc   240
cccgtagtag tacctccatt cttgcagcct gaagtgatgg gggtgagtaa agtgaaggag   300
gcaatggccc ctaagcataa agagatgcca ttccctaaat atcccgttga gccattcacc   360
gaatcacaat ccttgacact tactgatgtc gagaatttgc acttgccact gcccttgctc   420
caaagctgga tgcaccaacc acaccaacct ctgcctccca cagtgatgtt cccacccaa   480
tccgtcttgt ctctgtccca gtcaaaggtg ttgcctgttc ctcagaaagc agttcctat   540
ccccaacgcg atatgcccat ccaggctttt ctcttgtatc aagaaccagt gctcggtcct   600
gtcagaggcc ccttcccat tatcgtgttc atgagggaac tcgaggaact taacgttcca   660
ggtgagatcg tcgagtccct ctcatcttcc gaagagtcca ttaccaggat caacaagaag   720
atcgagaagt tccagtccga ggaacaacag caaaccgagg atgagcttca ggacaagatt   780
cacccattcg ctcagaccca gtctctcgtg tatccatttc cagggccaat tccaacagc    840
ctgccacaga acattccacc acttactcag accccagttg tggtgccacc attccttcaa   900
ccagaggtta tgggagtgtc caaggtgaaa gaagcccatgg caccaaagca caaagagatg   960
cccttccaa agtaccccgt tgagccattc actgagtctc agtctcttac cctcaccgac  1020
gttgagaacc ttcaccttcc acttccattg ctccagtctt ggatgcatca accacatcag  1080
ccacttccac caaccgttat gttcccacct cagtccgtgc ttagcctctc tcagtctaag  1140
gttttgccag tgcctcagaa ggccgttcca tatccacaaa gggatatgcc aatccaggcc  1200
ttcttgctct accaagagcc agttcttgga ccagtgagag gcccatttcc aatcattgtg  1260
ttcatgcgcg aactggaaga gttgaacgta ccaggagaga ttgtagaatc actgagctcc  1320
tcagaggagt ctattactcg tatcaacaag aagatagaga gttccaatc cgaggagcaa  1380
caacaaacag aggacgaatt gcaggacaag atacatcctt tcgcacagac ccagagcctc  1440
gtctatccct ttccaggtcc aatccctaac tctctccccc agaatatccc acccttgact  1500
cagactcccg tggtcgtacc ccctttcttg caacccgagg tgatgggggt ttctaaagtc  1560
aaagaggcta tggctcctaa acataaggaa atgcctttc ccaaatatcc agtggagcca  1620
ttcactgaga gccagtctct gacacttaca gatgtggaaa acttgcacct gcccttgcca  1680
cttttgcagt cctggatgca ccaaccacat caacccttgc ccccacagt gatgtttcct  1740
ccacaatcag ttcttagtct ctcccaaagc aaagtccttc cagtgcctca gaaggccgtc  1800
ccatacccc agagagatat gccaatacag gcattcttgc tttaccagga accagtgctc  1860
ggtcctgtac gtggcccatt ccctatcata gtgttcatgt tgatcgtaac acagactatg  1920
aagggtcttg atatacagaa ggtggccggg acttggtaca gtttggcaat ggccgcatcc  1980
gacatctcct tgttggacgc acaatcagcc ccattgcgtg tgtacgtaga agagcttaaa  2040
ccaactcccg aggggatct ggaaattctg ctccagaaat gggagaacgg tgagtgcgcc  2100
```

```
cagaagaaga tcatcgcaga gaagaccaaa attccagcag tattcaaaat cgacgcattg 2160
aacgaaaata aggtgctcgt actggacact gattataaga agtatctcct tttctgtatg 2220
gagaactcag cagagcctga acagagtctt gcctgccaat gccttgttcg tacccccagag 2280
gtagatgatg aagctctgga aaagttcgat aaggccctta aggctctgcc tatgcacatt 2340
aggctttctt tcaatccaac tcaacttgag gaacaatgtc acatttaa            2388

SEQ ID NO: 795         moltype = AA   length = 795
FEATURE                Location/Qualifiers
REGION                 1..795
                       note = fusion protein (OBC-T4:FM:OBC-T3:FM:OBC-T2:FM:OLG1)
source                 1..795
                       mol_type = protein
                       organism = synthetic construct
SEQUENCE: 795
RELEELNVPG EIVESLSSSE ESITRINKKI EKFQSEEQQQ TEDELQDKIH PFAQTQSLVY    60
PFPGPIPNSL PQNIPPLTQT PVVVPPFLQP EVMGVSKVKE AMAPKHKEMP FPKYPVEPFT   120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIVF MRELEELNVP GEIVESLSSS EESITRINKK   240
IEKFQSEEQQ QTEDELQDKI HPFAQTQSLV YPFPGPIPNS LPQNIPPLTQ TPVVVPPFLQ   300
PEVMGVSKVK EAMAPKHKEM PFPKYPVEPF TESQSLTLTD VENLHLPLPL LQSWMHQPHQ   360
PLPPTVMFPP QSVLSLSQSK VLPVPQKAVP YPQRDMPIQA FLLYQEPVLG PVRGPFPIIV   420
FMRELEELNV PGEIVESLSS SEESITRINK KIEKFQSEEQ QQTEDELQDK IHPFAQTQSL   480
VYPFPGPIPN SLPQNIPPLT QTPVVVPPFL QPEVMGVSKV KEAMAPKHKE MPFPKYPVEP   540
FTESQSLTLT DVENLHLPLP LLQSWMHQPH QPLPPTVMFP PQSVLSLSQS KVLPVPQKAV   600
PYPQRDMPIQ AFLLYQEPVL GPVRGPFPII VFMLIVTQTM KGLDIQKVAG TWYSLAMAAS   660
DISLLDAQSA PLRVYVEELK PTPEGDLEIL LQKWENGECA QKKIIAEKTK IPAVFKIDAL   720
NENKVLVLDT DYKKYLLFCM ENSAEPEQSL ACQCLVRTPE VDDEALEKFD KALKALPMHI   780
RLSFNPTQLE EQCHI                                                   795

SEQ ID NO: 796         moltype = DNA   length = 1884
FEATURE                Location/Qualifiers
misc_feature           1..1884
                       note = fusion protein (OBC-T4:OBC-T3:OBC-T2)
source                 1..1884
                       mol_type = other DNA
                       organism = synthetic construct
SEQUENCE: 796
agggagctcg aggagttgaa cgtgcctggc gagattgtag agtcattgag ctctagtgag    60
gagagtataa caaggatcaa taaaaagatt gaaaaatttc aaagcgaaga gcagcaacaa   120
acagaagatg aactgcaaga caaaattcat ccttttgctc agacacagag cttggtgtat   180
cccttcccag ggccaattcc caatagtctg ccccaaaaca tccctccctt gacccaaacc   240
cccgtagtag tacctccatt cttgcagcct gaagtgatgg gggtgagtaa agtgaaggag   300
gcaatggccc ctaagcataa agagatgcca ttccctaaat atcccgttga gccattcacc   360
gaatcacaat ccttgacact tactgatgtc gagaatttgc acttgccact gcccttgctc   420
caaagctgga tgcaccaacc acaccaacct ctgcctccca cagtgatgtt cccaccccaa   480
tccgtctctg tctctgtccca gtcaaggtg ttgcctgttc ctcagaaagc agttccctat   540
ccccaacgcg atatgccaat ccaggctttt ctcttgtatc agaaaccagt gctcggtcct   600
gtcagaggcc ccttccccat tatcgtgagg gaactcgagg aacttaacgt tccaggtgag   660
atcgtcgagt ccctctcatc ttccgaagag tccattacca ggatcaacaa gaagatcgag   720
aagttccagt ccgaggaaca cagcaaacc gaggatgagc ttcaggacaa gattcaccca   780
ttcgctcaga cccagtctct cgtgtatcca tttccagggc caattccaaa cagcctgcca   840
cagaacattc caccacttac tcagaccccca gttgtggtgc caccattcct tcaaccagag   900
gttatgggag tgtccaaggt gaaagaagcc atggcaccaa agcacaaaga gatgcccttt   960
ccaaagtacc ccgttgagcc attcactgag tctcagtctc ttaccctcac cgacgttgag  1020
aaccttcacc ttccacttcc attgctccag tcttggatgc atcaaccagt cagccactt  1080
ccaccaaccg ttatgttccc acctcagtcc gtgcttagcc tctctcagtc taaggttttg  1140
ccagtgcctc agaaggccgt tccatatcca caaagggata tgccaatcca ggccttcttg  1200
ctctaccaag agccagttct tggaccagtg agaggcccat ttccaatcat tgtgcgcgaa  1260
ctggaagagt tgaactacc aggagagatt gtagaatgac tgagctcctc agaggagtct  1320
attactcgta tcaacaagaa gatagaaag ttccaatccg aggagcaaca acaaacagag  1380
gacgaattgc aggacaagat acatccttc gcacagaccc agagcctcgt ctatcccttt  1440
ccaggtccaa tccctaactc tctccccag aatatcccac ccttgactca gactcccgtg  1500
gtcgtacccc ctttcttgca acccgaggtg atggggttt ctaaagtcaa agaggctatg  1560
gctcctaaac ataaggaaat gcctttccc aaatatccag tggagccatt cactgagagc  1620
cagtctctga cacttacaga tgtggaaaac ttgcacctga ccttgccact tttgcagtcc  1680
tggatgcacc aaccacatca accttgccc ccacagtga tgtttcctcc acaatcagtt  1740
cttagtctct cccaaagcaa agtccttcca gtgcctcaga aggccgtccc ataccccag  1800
agagatatgc caatacaggc attcttgctt taccaggaac cagtgctcgg tcctgtacgt  1860
ggcccattcc ctatcatagt gtaa                                        1884

SEQ ID NO: 797         moltype = AA   length = 627
FEATURE                Location/Qualifiers
REGION                 1..627
                       note = fusion protein (OBC-T4:OBC-T3:OBC-T2)
source                 1..627
                       mol_type = protein
                       organism = synthetic construct
SEQUENCE: 797
RELEELNVPG EIVESLSSSE ESITRINKKI EKFQSEEQQQ TEDELQDKIH PFAQTQSLVY    60
```

```
PFPGPIPNSL PQNIPPLTQT PVVVPPFLQP EVMGVSKVKE AMAPKHKEMP FPKYPVEPFT    120
ESQSLTLTDV ENLHLPLPLL QSWMHQPHQP LPPTVMFPPQ SVLSLSQSKV LPVPQKAVPY    180
PQRDMPIQAF LLYQEPVLGP VRGPFPIIVR ELEELNVPGE IVESLSSSEE SITRINKKIE    240
KFQSEEQQQT EDELQDKIHP FAQTQSLVYP FPGPIPNSLP QNIPPLTQTP VVVPPFLQPE    300
VMGVSKVKEA MAPKHKEMPF PKYPVEPFTE SQSLTLTDVE NLHLPLPLLQ SWMHQPHQPL    360
PPTVMFPPQS VLSLSQSKVL PVPQKAVPYP QRDMPIQAFL LYQEPVLGPV RGPFPIIVRE    420
LEELNVPGEI VESLSSSEES ITRINKKIEK FQSEEQQQTE DELQDKIHPF AQTQSLVYPF    480
PGPIPNSLPQ NIPPLTQTPV VVPPFLQPEV MGVSKVKEAM APKHKEMPFP KYPVEPFTES    540
QSLTLTDVEN LHLPLPLLQS WMHQPHQPLP PTVMFPPQSV LSLSQSKVLP VPQKAVPYPQ    600
RDMPIQAFLL YQEPVLGPVR GPFPIIV                                       627

SEQ ID NO: 798           moltype = DNA   length = 2370
FEATURE                  Location/Qualifiers
misc_feature             1..2370
                         note = fusion protein (OBC-T4:OBC-T3:OBC-T2:OLG1)
source                   1..2370
                         mol_type = other DNA
                         organism = synthetic construct
SEQUENCE: 798
agggagctcg aggagttgaa cgtgcctggc gagattgtag agtcattgag ctctagtgag     60
gagagtataa caaggatcaa taaaaagatt gaaaaatttc aaagcgaaga gcagcaacaa    120
acagaagatg aactgcaaga caaaattcat ccttttgctc agacacagag cttggtgtat    180
cccttcccag ggccaattcc caatagtctg ccccaaaaca tccctccctt gacccaaacc    240
cccgtagtag tacctccatt cttgcagcct gaagtgatgg gggtgagtaa agtgaaggag    300
gcaatggccc ctaagcataa agagatgcca ttccctaaat atcccgttga gccattcacc    360
gaatcacaat ccttgacact tactgatgtc gagaatttgc acttgccact gcccttgctc    420
caaagctgga tgcaccaacc acaccaacct ctgcctccca cagtgatgtt cccaccccaa    480
tccgtcttgt ctctgtccca gtcaaaggtg ttgcctgttc ctcagaaagc agttccctat    540
ccccaacgcg atatgcccat ccaggctttt ctcttgtatc aagaaccagt gctcggtcct    600
gtcagaggcc ccttcccat tatcgtgagg gaactcgagg aacttaacgt tccaggtgag    660
atcgtcgagt ccctctcatc ttccgaagag tccattacca ggatcaacaa gaagatcgag    720
aagttccagt ccgaggaaca acagcaaacc gaggatgagc ttcaggacaa gattcaccca    780
ttcgctcaga cccagtctct cgtgtatcca tttccagggc caattccaaa cagcctgcca    840
cagaacattc caccacttac tcagaccccca caccattcct caaccagag                900
gttatgggag tgtccaaggt gaaagaagcc atggccacaa agcacaaaga gatgcccttt    960
ccaaagtacc ccgttgagcc attcactgag tctcagtctc ttaccctcac cgacgttgag   1020
aaccttaccc ttccacttcc attgctccag tcttggatgc atcaaccaca tcagccactt   1080
ccaccaaccg ttatgttccc acctcagtcc gtgcttagcc tctctcagtc taaggttttg   1140
ccagtgcctc agaaggccgt tccatatcca caagggata tgccaatcca ggccttcttg   1200
ctctaccaag agccagttct tggaccagtg agggccccat ttccaatcat tgtgcgcgaa   1260
ctggaagagt tgaacgtacc aggagagatt gtagaatcac tgagctcctc agaggagtct   1320
attactcgta tcaacaagaa gatagagaag ttccaatccg aggagcaaca aacaaacgag   1380
gacgaattgc aggacaagat acatccttc gcacagacca gagcctcgt ctatccctct   1440
ccaggtccaa tccctaactc tctccccag aatatcccac ccttgactca gactcccgtg   1500
gtcgtacccc ctttcttgca acccgaggtg atggggtt ctaaagtcaa agaggctatg   1560
gctcctaaac ataaggaaat gccttttccc aaatatccag tggagccatt cactgagagc   1620
cagtctctga cacttacaga tgtggaaaac ttgcacctgc ccttgccact tttgcagtcc   1680
tggatgcacc aaccacatca acccttgccc ccacagtga tgtttcctcc acaatcagtt   1740
cttagtctct cccaaagcaa agtccttcca gtgcctcaga aggccgtccc ataccccag   1800
agagatatgc caatacaggc attcttgctt taccaggaac cagtgctcgg tcctgtacgt   1860
ggcccattcc ctatcatagt gttgatcgta acacagacta tgaagggtct tgatatacag   1920
aaggtggccg ggactgggta cagtttggca atggccgcat ccgacatctc cttgttggac   1980
gcacaatcag ccccattgcg tgtgtacgta aagagctta aaccaactcc cgaggggat   2040
ctggaaattc tgctccagaa atgggagaac ggtgagtgcg cccagaagaa gatcatcgca   2100
gagaagacca aaattccagc agtattcaaa atcgacgcat tgaacgaaaa taaggtgctc   2160
gtactggaca ctgattataa gaagtatctc ctttctgta tggagaactc agcagagcct   2220
gaacagagtc ttgcctgcca atgccttgtt cgtaccccag aggtagatga tgaagctctg   2280
gaaaagttcg ataaggccct taaggctctg cctatgcaca ttaggctttc tttcaatcca   2340
actcaacttg aggaacaatg tcacatttaa                                    2370

SEQ ID NO: 799           moltype = AA   length = 789
FEATURE                  Location/Qualifiers
REGION                   1..789
                         note = fusion protein (OBC-T4:OBC-T3:OBC-T2:OLG1)
source                   1..789
                         mol_type = protein
                         organism = synthetic construct
SEQUENCE: 799
RELEELNVPG EIVESLSSSE ESITRINKKI EKFQSEEQQQ TEDELQDKIH PFAQTQSLVY     60
PFPGPIPNSL PQNIPPLTQT PVVVPPFLQP EVMGVSKVKE AMAPKHKEMP FPKYPVEPFT    120
ESQSLTLTDV ENLHLPLPLL QSWMHQPHQP LPPTVMFPPQ SVLSLSQSKV LPVPQKAVPY    180
PQRDMPIQAF LLYQEPVLGP VRGPFPIIVR ELEELNVPGE IVESLSSSEE SITRINKKIE    240
KFQSEEQQQT EDELQDKIHP FAQTQSLVYP FPGPIPNSLP QNIPPLTQTP VVVPPFLQPE    300
VMGVSKVKEA MAPKHKEMPF PKYPVEPFTE SQSLTLTDVE NLHLPLPLLQ SWMHQPHQPL    360
PPTVMFPPQS VLSLSQSKVL PVPQKAVPYP QRDMPIQAFL LYQEPVLGPV RGPFPIIVRE    420
LEELNVPGEI VESLSSSEES ITRINKKIEK FQSEEQQQTE DELQDKIHPF AQTQSLVYPF    480
PGPIPNSLPQ NIPPLTQTPV VVPPFLQPEV MGVSKVKEAM APKHKEMPFP KYPVEPFTES    540
QSLTLTDVEN LHLPLPLLQS WMHQPHQPLP PTVMFPPQSV LSLSQSKVLP VPQKAVPYPQ    600
RDMPIQAFLL YQEPVLGPVR GPFPIIVLIV TQTMKGLDIQ KVAGTWYSLA MAASDISLLD    660
```

```
AQSAPLRVYV EELKPTPEGD LEILLQKWEN GECAQKKIIA EKTKIPAVFK IDALNENKVL    720
VLDTDYKKYL LFCMENSAEP EQSLACQCLV RTPEVDDEAL EKFDKALKAL PMHIRLSFNP    780
TQLEEQCHI                                                            789

SEQ ID NO: 800          moltype = AA  length = 237
FEATURE                 Location/Qualifiers
source                  1..237
                        mol_type = protein
                        organism = Saccharum officinarum
SEQUENCE: 800
MPGLPTRSAA YLLAYLLQNR EELDTMKVLL VALALLALAA SAASTLTSGG CGCQTPHLPP     60
PVHLPPPVDL PPPVHLPPPV HLPPSVHVPP PPPSCHYPTL QPRPQPPHPC PCHPTSPCHP    120
GHLVGSPPIL GQCIEFLRHQ CSPAATPYCS PQCQALQQQC CQQLRQVEPL HRYQAIFGVV    180
LQFIQQQQPQ GQSPLGTLMA AANSAPTDGD VRSATKYKSL PFCSAPAGVS HTEETMS       237

SEQ ID NO: 801          moltype = AA  length = 223
FEATURE                 Location/Qualifiers
source                  1..223
                        mol_type = protein
                        organism = Zea mays
SEQUENCE: 801
MRVLLVALAL LALAASATST HTSGGCGCQP PPPVHLPPPV HLPPPVHLPP PVHLPPPVHL     60
PPPVHLPPPV HVPPPVHLPP PPCHYPTQPP RPQPHPQPHP CPCQQPHPSP CQLQGTCGVG    120
STPILGQCVE FLRHQCSPTA TPYCSPQCQS LRQQCCQQLR QVEPHRYQA IFGLVLQSIL     180
QQQPQSGQVA GLLAAQIAQQ LTAMCGLQQP TPCPYAAAGG VPH                     223

SEQ ID NO: 802          moltype = DNA  length = 1224
FEATURE                 Location/Qualifiers
misc_feature            1..1224
                        note = fusion protein (gcan27:FM:OBC-T2)
source                  1..1224
                        mol_type = other DNA
                        organism = synthetic construct
SEQUENCE: 802
gccgccagca cactcacatc cggcggctgc ggctgccaaa ctcctcatct ccctccacca     60
gtgcacctgc caccaccagt tgatctgcct cctcctgtac acctcccacc tcccgtgcat    120
ttgcctccaa gcgtgcacgt accccccacct ccaccttcat gccattatcc cactctgcaa   180
ccaagaccac aaccccacac ccctgcccc tgtcacccca cttctccttg tcatcctggc    240
caccttgtcg ggagccccc catccttggt caatgcattg agttccttag gcatcaatgc    300
agtcctgctg ccaccccata ttgttcccct cagtgccagg ctttgcaaca acagtgttgc    360
cagcagttga ggcaagtgga gcctcttcat cgctaccaag caatatttgg agtagtattg    420
cagttcatac aacaacagca gccccaaggc cagtcccccc ttggtactct gatggcagca    480
gccaattctg caccaaccga cggcgatgta agaagtgcta ccaagtacaa atccctgcca    540
ttttgctcag caccagcagg agtatctcac acagaagaaa ctatgtcctt catgcgcgaa    600
ctggaagagt tgaacgtacc aggagagatt tagaatcac tgagctcctc agaggagtct     660
attactcgta tcaacaagaa gatagagaag ttccaatccg aggagcaaca caaacagag     720
gacgaattgc aggacaagat acatccttc gcacagaacc agagcctcgt ctatcccttt    780
ccaggtccaa tccctaactc tctccccag aatatcccac ccttgactca gactcccgtg    840
gtcgtacccc ctttcttgca acccgaggtg atggggggttt ctaaagtcaa agaggctatg   900
gctcctaaac ataaggaaat gcctttccc aaatatccag tggagccatt cactgagagc    960
cagtcctctga cacttacaga tgtggaaaaac ttgcacctgc ccttgccact tttgcagtcc  1020
tggatgcacc aaccacatca accctttgccc ccacagtga tgtttcctcc acaatcagtt   1080
cttagtctct cccaaagcaa agtccttcca gtgcctcaga aggccgtccc ataccccag    1140
agagatatgc caatacaggc attcttgctt taccaggaac cagtgctcgg tcctgtacgt   1200
ggcccattcc ctatcatagt gtaa                                          1224

SEQ ID NO: 803          moltype = AA  length = 407
FEATURE                 Location/Qualifiers
REGION                  1..407
                        note = fusion protein (gcan27:FM:OBC-T2)
source                  1..407
                        mol_type = protein
                        organism = synthetic construct
SEQUENCE: 803
AASTLTSGGC GCQTPHLPPP VHLPPPVDLP PPVHLPPPVH LPPSVHVPPP PPSCHYPTLQ     60
PRPQPPHPCP CHPTSPCHPG HLVGSPPILG QCIEFLRHQC SPAATPYCSP QCQALQQQCC    120
QQLRQVEPLH RYQAIFGVVL QFIQQQQPQG QSPLGTLMAA ANSAPTDGDV RSATKYKSLP    180
FCSAPAGVSH TEETMSFMRE LEELNVPGEI VESLSSSEES ITRINKKIEK FQSEEQQQTE    240
DELQDKIHPF AQTQSLVYPF PGIPNSLPQ NIPPLTQTPV VVPPFLQPEV MGVSKVKEAM     300
APKHKEMPFP KYPVEPFTES QSLTLTDVEN LHLPLPLLQS WMQPHQPLP PTVMFPPQSV    360
LSLSQSKVLP VPQKAVPYPQ RDMPIQAFLL YQEPVLGPVR GPFPIIV                 407

SEQ ID NO: 804          moltype = DNA  length = 588
FEATURE                 Location/Qualifiers
misc_feature            1..588
                        note = codon optimized gcan27
source                  1..588
                        mol_type = other DNA
                        organism = synthetic construct
```

-continued

```
SEQUENCE: 804
gccgccagca cactcacatc cggcggctgc ggctgccaaa ctcctcatct ccctccacca    60
gtgcacctgc caccaccagt tgatctgcct cctcctgtac acctcccacc tcccgtgcat   120
ttgcctccaa gcgtgcacgt accccccacct ccaccttcat gccattatcc cactctgcaa  180
ccaagaccac aacccccaca cccctgcccc tgtcacccca cttctccttg tcatcctggc   240
caccttgtcg ggagccccc catccttggt caatgcattg agttccttag gcatcaatgc   300
agtcctgctg ccaccccata ttgttcccct cagtgccagg ctttgcaaca acagtgttgc   360
cagcagttga ggcaagtgga gcctcttcat cgctaccaag caatatttgg agtagtattg   420
cagttcatac aacaacagca gccccaaggc cagtccccc ttggtactct gatggcagca    480
gccaattctg caccaaccga cggcgaatgta agaagtgcta ccaagtacaa atccctgcca   540
ttttgctcag caccagcagg agtatctcac acagaagaaa ctatgtcc               588

SEQ ID NO: 805          moltype = AA  length = 196
FEATURE                 Location/Qualifiers
REGION                  1..196
                        note = gcan27
source                  1..196
                        mol_type = protein
                        organism = synthetic construct
SEQUENCE: 805
AASTLTSGGC GCQTPHLPPP VHLPPPVDLP PPVHLPPPVH LPPSVHVPPP PPSCHYPTLQ    60
PRPQPPHPCP CHPTSPCHPG HLVGSPPILG QCIEFLRHQC SPAATPYCSP QCQALQQQCC   120
QQLRQVEPLH RYQAIFGVVL QFIQQQQPQG QSPLGTLMAA ANSAPTDGDV RSATKYKSLP   180
FCSAPAGVSH TEETMS                                                   196

SEQ ID NO: 806          moltype = DNA  length = 918
FEATURE                 Location/Qualifiers
misc_feature            1..918
                        note = fusion protein (yZein:OBC-T2)
source                  1..918
                        mol_type = other DNA
                        organism = synthetic construct
SEQUENCE: 806
gcaacatcta cacatacttc cggaggatgt ggttgtcagc ctccacctcc agtacatttg    60
cctcccccag ttcacctgcc cccaccagtc caccttcctc cacctgttca tctgccacca   120
cccgtacact tgccacctcc tgtccatctc ccaccacccg tgcatgtccc tcccccagtg   180
catctgcccc cacctccatg tcattatcca cccagccac cccgtcctca accccatcca   240
cagcctcatc cctgtccttg tcagcaacct cacccatcac catgtcaacg cgaactggaa   300
gagttgaacg taccaggaga gattgtgaaa tcactgagct cctcagagga gtctattact   360
cgtatcaaca agaagataga gaagttccaa tccgaggagc aacaacaaac agaggacgaa   420
ttgcaggaca agatacatcc tttgcacag cccagagcc tcgtctatcc ctttccaggt    480
ccaatccta actctctccc ccagaatatc ccacccttga ctcagactcc gtggtcgta    540
ccccctttct tgcaacccga ggtgatgggg gtttctaaag tcaaagaggc tatggctcct   600
aaacataagg aaatgccttt tcccaaatat ccagtggagc cattcactga gagccagtct   660
ctgacactta cagatgtgga aaacttgcac ctgcccttgc cactttttca gtcctggatg   720
caccaaccac atcaaccctt gcccccaca gtgatgtttc ctccacaatc agttcttagt   780
ctctcccaaa gcaaagtcct tccagtgcct cagaaggccg tcccatacc ccagagagat   840
atgccaatac aggcattctt gctttaccag gaaccagtgc tcggtcctgt acgtggccca   900
ttccctatca tagtgtaa                                                 918

SEQ ID NO: 807          moltype = AA  length = 305
FEATURE                 Location/Qualifiers
REGION                  1..305
                        note = fusion protein (yZein:OBC-T2)
source                  1..305
                        mol_type = protein
                        organism = synthetic construct
SEQUENCE: 807
ATSTHTSGGC GCQPPPPVHL PPPVHLPPPV HLPPPVHLPP PVHLPPPVHL PPPVHVPPPV    60
HLPPPPCHYP TQPPRPQPHP QHPCPCQQP HPSPCQRELE ELNVPGEIVE SLSSSEESIT   120
RINKKIEKFQ SEEQQQTEDE LQDKIHPFAQ TQSLVYPPPG PIPNSLPQNI PPLTQTPVVV   180
PPFLQPEVMG VSKVKEAMAP KHKEMPFPKY PVEPFTESQS LTLTDVENLH LPLPLLQSWM   240
HQPHQPLPPT VMFPPQSVLS LSQSKVLPVP QKAVPYPQRD MPIQAFLLYQ EPVLGPVRGP   300
FPIIV                                                                305

SEQ ID NO: 808          moltype = DNA  length = 288
FEATURE                 Location/Qualifiers
misc_feature            1..288
                        note = codon optimized zein fragment (yZein 17-112)
source                  1..288
                        mol_type = other DNA
                        organism = synthetic construct
SEQUENCE: 808
gcaacatcta cacatacttc cggaggatgt ggttgtcagc ctccacctcc agtacatttg    60
cctcccccag ttcacctgcc cccaccagtc caccttcctc cacctgttca tctgccacca   120
cccgtacact tgccacctcc tgtccatctc ccaccacccg tgcatgtccc tcccccagtg   180
catctgcccc cacctccatg tcattatcca cccagccac cccgtcctca accccatcca   240
cagcctcatc cctgtccttg tcagcaacct cacccatcac catgtcaa               288
```

| | | |
|---|---|---|
| SEQ ID NO: 809 | moltype = AA length = 96 | |
| FEATURE | Location/Qualifiers | |
| REGION | 1..96 | |
| | note = zein fragment protein sequence (yZein 17-112) | |
| source | 1..96 | |
| | mol_type = protein | |
| | organism = synthetic construct | |

SEQUENCE: 809
```
ATSTHTSGGC GCQPPPPVHL PPPVHLPPPV HLPPPVHLPP PVHLPPPVHL PPPVHVPPPV    60
HLPPPPCHYP TQPPRPQPHP QPHPCPCQQP HPSPCQ                             96
```

| | | |
|---|---|---|
| SEQ ID NO: 810 | moltype = DNA length = 612 | |
| FEATURE | Location/Qualifiers | |
| misc_feature | 1..612 | |
| | note = codon optimized zein fragment (yZein 20-223) | |
| source | 1..612 | |
| | mol_type = other DNA | |
| | organism = synthetic construct | |

SEQUENCE: 810
```
acacatactt ccggaggatg tggttgtcag cctccacctc cagtacattt gcctccccca    60
gttcacctgc ccccaccagt ccaccttcct ccacctgttc atctgccacc acccgtacac   120
ttgccacctc ctgtccatct cccaccaccc gtgcatgtcc ctcccccagt gcatctgccc   180
ccacctccat gtcattatcc aacccagcca cccgtcctc aaccccatcc acagcctcat   240
ccctgtcctt gtcagcaacc tcacccatca ccatgtcaac ttcaaggaac ttgtggggtg   300
gggagcaccc ctattctggg gcagtgtgtg gagttcttc gtcaccaatg ttctcctacc    360
gccacacctt attgctcacc acagtgtcag tcactccgtc agcaatgctg tcaacaactt   420
aggcaggtcg aaccacagca taggtatcag gctattttcg gattggtcct ccaatctata   480
ttgcaacagc aacctcaaag cggacaagta gctgggctgt tggctgctca gattgcccaa   540
caactgacag ctatgtgcgg cttgcagcag cctacccctt gtccttatgc tgccgcagga   600
ggggtgcctc at                                                       612
```

| | | |
|---|---|---|
| SEQ ID NO: 811 | moltype = AA length = 204 | |
| FEATURE | Location/Qualifiers | |
| REGION | 1..204 | |
| | note = zein fragment protein sequence (yZein 20-223) | |
| source | 1..204 | |
| | mol_type = protein | |
| | organism = synthetic construct | |

SEQUENCE: 811
```
THTSGGCGCQ PPPPVHLPPP VHLPPPVHLP PPVHLPPPVH LPPPVHLPPP VHVPPPVHLP    60
PPPCHYPTQP PRPQPHPQPH PCPCQQPHPS PCQLQGTCGV GSTPILGQCV EFLRHQCSPT   120
ATPYCSPQCQ SLRQQCCQQL RQVEPQHRYQ AIFGLVLQSI LQQQPQSGQV AGLLAAQIAQ   180
QLTAMCGLQQ PTPCPYAAAG GVPH                                         204
```

| | | |
|---|---|---|
| SEQ ID NO: 812 | moltype = AA length = 6 | |
| FEATURE | Location/Qualifiers | |
| REGION | 1..6 | |
| | note = Zein peptide repeat sequence | |
| source | 1..6 | |
| | mol_type = protein | |
| | organism = synthetic construct | |

SEQUENCE: 812
```
PPPVHL                                                               6
```

| | | |
|---|---|---|
| SEQ ID NO: 813 | moltype = DNA length = 1384 | |
| FEATURE | Location/Qualifiers | |
| misc_feature | 1..1384 | |
| | note = GmSeed2 promoter | |
| source | 1..1384 | |
| | mol_type = other DNA | |
| | organism = synthetic construct | |

SEQUENCE: 813
```
aacacaagct tcaagtttta aaaggaaaaa tgtcagccaa aaactttaaa taaaatggta    60
acaaggaaat tattcaaaaa ttacaaacct cgtcaaaata ggaaagaaaa aaagtttagg   120
gatttagaaa aaacatcaat ctagttccac cttatttat agagagaaga aactaatata    180
taagaactaa aaaacagaag aatagaaaaa aaagtattg acaggaaaga aaaagtagct    240
gtatgcttat aagtactttg aggatttgaa ttctctctta taaacacaa acacaatttt    300
tagattttat ttaaataatc atcaatccga ttataattat ttatatattt ttctattttc   360
aaagaagtaa atcatgagct tttccaactc aacatctatt ttttttctct caaccttttt   420
cacatcttaa gtagtctcac cctttatata taacttat ttcttacctt ttacattatg     480
taactttttat caccaaaacc aacaactta aatttatt aaatagactc cacaagtaac     540
ttgcacactct tacattcatc gacattaact tttatctgtt ttataaatat tattgtgata   600
taatttaatc aaaataacca caaactttca taaaaggttc ttattaagca tggcatttaa   660
aaaaaaaa caactcaatc actttcatat aggaggtagc ctaagtacgt actcaaaatg    720
ccaacaaata aaaaaaagt tgctttaata atgccaaaac aaattaataa aacacttaca   780
acaccggatt tttttttaatt aaaatgtgcc atttaggata aatagttaat atttttaata   840
attattaaa aagccgtatc tactaaaatg atttttattt ggttgaaaat attaatatgt    900
ttaaatcaac acaatctatc aaaattaaac taaaaaaaa ataagtgtac gtggttaaca    960
ttagtacagt aatataagag gaaatgaga aattaagaaa ttgaaagcga gtctaatttt   1020
```

```
taaattatga acctgcatat ataaaaggaa agaaagaatc caggaagaaa agaaatgaaa   1080
ccatgcatgg tccctcgtc atcacgagtt tctgccattt gcaatagaaa cactgaaaca    1140
cctttctctt tgtcacttaa ttgagatgcc gaagccacct cacaccatga acttcatgag   1200
gtgtagcacc caaggcttcc atagccatgc atactgaaga atgtctcaag ctcagcaccc   1260
tacttctgtg acgtgtccct cattcacctt cctctcttcc ctataaataa ccacgcctca   1320
ggttctccgc ttcacaactc aaacattctc tccattggtc cttaaacact catcagtcat   1380
cacc                                                                1384

SEQ ID NO: 814         moltype = DNA  length = 57
FEATURE                Location/Qualifiers
misc_feature           1..57
                       note = sig2 signal peptide
source                 1..57
                       mol_type = other DNA
                       organism = synthetic construct
SEQUENCE: 814
atggccaagc tagttttttc cctttgtttt ctgcttttca gtggctgctg cttcgct       57

SEQ ID NO: 815         moltype = DNA  length = 249
FEATURE                Location/Qualifiers
misc_feature           1..249
                       note = AtHSP T terminator
source                 1..249
                       mol_type = other DNA
                       organism = synthetic construct
SEQUENCE: 815
atatgaagat gaagatgaaa tatttggtgt gtcaaataaa aagcttgtgt gcttaagttt    60
gtgttttttt cttggcttgt tgtgttatga atttgtggct ttttctaata tcaaatgaat   120
gtaagatctc attataatga ataaacaaat gtttctataa tccattgtga atgttttgtt   180
ggatctcttc tgcagcatat aactactgta tgtgctatgg tatggactat ggaatatgat   240
taaagataa                                                           249

SEQ ID NO: 816         moltype = DNA  length = 376
FEATURE                Location/Qualifiers
misc_feature           1..376
                       note = AtUbi10T terminator
source                 1..376
                       mol_type = other DNA
                       organism = synthetic construct
SEQUENCE: 816
atctcgtctc tgttatgctt aagaagttca atgtttcgtt tcatgtaaaa ctttggtggt    60
ttgtgttttg gggccttgta taatccctga tgaataagtg ttctactatg tttccgttcc   120
tgttatctct ttcttttctaa tgacaagtcg aacttcttgc ttcgttttta              180
ttatctgtgc ttcttttgtt taatacgcct gcaaagtgac tcgactcgt ttagtgcagt    240
tctgcgaaac ttgtaaatag tccaattgtt ggcctctagt aatagatgta gcgaaagtgt   300
tgagctgttg ggttctaagg atggcttgaa catgttaatc ttttaggttc tgagtatgat   360
gaacattcgt tgttgc                                                   376

SEQ ID NO: 817         moltype = DNA  length = 1543
FEATURE                Location/Qualifiers
misc_feature           1..1543
                       note = PvPhas promoter
source                 1..1543
                       mol_type = other DNA
                       organism = synthetic construct
SEQUENCE: 817
cattgtactc ccagtatcat tatagtgaaa gttttggctc tctcgccggt ggttttttac    60
ctctatttaa aggggttttc cacctaaaaa ttctggtatc attctcactt tacttgttac   120
tttaatttct cataatcttt ggttgaaatt atcacgcttc cgcacacgat atccctacaa   180
atttattatt tgttaaacat tttcaaaccg cataaaattt tatgaagtcc cgtctatctt   240
taatgtagtc taacattttc atattgaaat atataattta cttaattttta gcgttggtag   300
aaagcataat gatttattct tattcttctt catataaatg tttaatatac aatataaaca   360
aattctttac cttaagaagg attttcccatt ttatattta aaaatatatt tatcaaatat   420
ttttcaacca cgtaaatcac ataataataa gttgtttcaa aagtaataaa atttaactta   480
ataattttt tatttgactg atcttaaagc aacaccagt gacacaacta gccattttt     540
tctttgaata aaaaaatcca attatcattg tattttttt atacaatgaa atttccacca   600
aacaatgatt tgtggtattt ctgaagcaag tcatgttatg caaattctta taattcccat   660
ttgacactac ggaagtaact gaagatctgc ttttacatgc gagacacatc ttctaaagta   720
atttaataa tagttactat attcaagatt tcatatatca aagtaataaa atttacttcta   780
aaaaattaat tagatataat taaaatatta ctttttttaat tttaagttta attgttgaat   840
ttgtgactat tgatttatta ttctactatg tttaaattgt tttataggta gtttaaagta   900
aatataagta atgtagtaga gtgttagagt gttaccctaa accataaact ataagattta   960
tggtggacta atttcatat atttcttatt gcttttaacct tttcttggta tgtaagtccg    1020
taactggaat tactgtgggt tgccatgaca ctctgtggtc ttttggtttca tgcatggatg   1080
cttgcgcaag aaaagacaa agaacaaaga aaaagacaa aacagagaga caaaacgcaa     1140
tcacacaacc aactcaaatt agtcactggc tgatcaagat cgccgcgtcc atgtatgtct   1200
aaatgccatg caaagcaaca cgtgcttaac atgcactttta aatggctcac ccatcccaac    1260
ccactcacaa acacattgcc ttttttcttca tcatccacac aaccacctgt atatattcat    1320
tctcttccgc cacctcaatt tcttcacttc aacacacgtc aacctgcata tgcgtgtcat    1380
```

```
cccatgccca aatctccatg catgttccta ccaccttctc tcttatataa tacctataaa   1440
tacctctaat atcactcact tctttcatca tccatccatc cagagtacta ctactctact   1500
actataatac cccaacccaa ctcatattca atactactct act                     1543

SEQ ID NO: 818         moltype = DNA  length = 13
FEATURE                Location/Qualifiers
misc_feature           1..13
                       note = arc5UTR 5'utr
source                 1..13
                       mol_type = other DNA
                       organism = synthetic construct
SEQUENCE: 818
tgaatgcatg atc                                                      13

SEQ ID NO: 819         moltype = DNA  length = 96
FEATURE                Location/Qualifiers
misc_feature           1..96
                       note = sig10 signal peptide
source                 1..96
                       mol_type = other DNA
                       organism = synthetic construct
SEQUENCE: 819
atggctactt caaagttgaa aacccagaat gtggttgtat ctctctccct aaccttaacc   60
ttggtactgg tgctactgac cagcaaggca aactca                             96

SEQ ID NO: 820         moltype = DNA  length = 1479
FEATURE                Location/Qualifiers
misc_feature           1..1479
                       note = Fam20C protein coding sequence
source                 1..1479
                       mol_type = other DNA
                       organism = synthetic construct
SEQUENCE: 820
gacttttcca gtgaccccctc tagcaatttg acctctcact ccttggagaa acttccaccc   60
gcagccgaag cagcagaagg agccccacct gggcaagacc cagggtgtcag acgccctcca  120
gatcctgctc atagacctct tccacgcgat cctggaccaa gaggtcctgt actgcctcct   180
gggctttcag gggatggctc attgctcacc cgtctgttcc agcacccact ctatcaagtg   240
cctatccctc cacttaccga gggcgatgta ctctttaacg taaacagcga catccgcttc   300
aaccccaaag ctgcaactgc tgaaaatccc gattggccac acgaaggtcc tgaggacgag   360
ttcctcccta ccggagaagc tgccgtggac agttatccta actggttgaa gtttcatatt   420
ggcatcaata ggtatgagct ctacagtaga cacaaccccg ctgtaggtgc acttctgcaa   480
gatttgggga cccaaaagat aacctccgta gccatgaaat ccgaggaac tcagttgaag   540
ctcattatga cttttccagaa ttacgggcag gcctgttta aacctatgaa acaaacaaga   600
gaacaggaaa cccctcccga ttttttttac tttagcgact atgaacgcca taacgctgaa   660
atagccgctt tccatctcga cagaatcctg gacttcagga gggtgcctcc agtgccgga    720
cgccttgtca atatgaccaa agagatcaga gacgtaacaa gagataagaa gctgtggcgt   780
accttcttca tttctcctgc aaataacgtg tgtttctacg gggaatgctc ttattactgt   840
agcaccgagc acgctctgtg cggaaagcct gaccagatag aaggtagctt ggcagctttc   900
ttgccagacc ttgcccttgc taagcgcaag acctggagaa atccctggag gaggtcttat   960
cacaagagaa aaaagcaga gtgggaggtc gatccagatt attgtgagga ggtgaggcag  1020
acccctccat acgattcaag tcacaggctt ttggacgtga tggacatgac tatcttcgat  1080
tttctcatgg gaaacatgga tcgccaccat tatgagacct ttgaaaaatt cggaaatgaa  1140
accttcatta tacatttgga taatggtcgc ggtttcggga agcactctca cgatgagctt  1200
tctatccttg ttcccttgca acaatgttgt aggattgaaa ggtccacata cctcagattg  1260
caacttctcg ctcaggagga acaccgtctt tctctcttga tggctgaagc cctgcgcgca  1320
gatcgcgtcg ctccagtgtt gtttcaaccc cacctggaag cactggaccg ccgcttgagg  1380
atcgttctca gagctgtcgg cgattgtgtg gagaaagacg gtctgcattc agtcgtggag  1440
gatgacttgg gaccagaaca ccgtgctgct gcagggagg                         1479

SEQ ID NO: 821         moltype = AA   length = 493
FEATURE                Location/Qualifiers
REGION                 1..493
                       note = Fam20C protein coding sequence
source                 1..493
                       mol_type = protein
                       organism = synthetic construct
SEQUENCE: 821
DFSSDPSSNL TSHSLEKLPP AAEAAEGAPP GQDPGVRRPP DPAHRPLPRD PGPRGPVLPP   60
GLSGDGSLLT RLFQHPLYQV PIPPLTEGDV LFNVNSDIRF NPKAATAENP DWPHEGPEDE  120
FLPTGEAAVD SYPNWLKFHI GINRYELYSR HNPAVGALLQ DLGTQKITSV AMKSGGTQLK  180
LIMTFQNYGQ ALFKPMKQTR EQETPPDFFY FSDYERHNAE IAAFHLDRIL DFRRVPPVAG  240
RLVNMTKEIR DVTRDKKLWR TFFISPANNV CFYGECSYYC STEHALCGKP DQIEGSLAAF  300
LPDLALAKRK TWRNPWRRSY HKRKKAEWEV DPDYCEEVRQ TPPYDSSHRL LDVMDMTIFD  360
FLMGNMDRHH YETFEKFGNE TFIIHLDNGR GFGKHSHDEL SILVPLQQCC RIRRSTYLRL  420
QLLAQEEHRL SLLMAEALRA DRVAPVLFQP HLEALDRRLR IVLRAVGDCV EKDGLHSVVE  480
DDLGPEHRAA AGR                                                     493

SEQ ID NO: 822         moltype = DNA  length = 1197
FEATURE                Location/Qualifiers
```

```
misc_feature         1..1197
                     note = 3arc terminator
source               1..1197
                     mol_type = other DNA
                     organism = synthetic construct
SEQUENCE: 822
aataaataaa atgggagcaa taaataaaat gggagctcat atatttacac catttacact    60
gtctattatt caccatgcca attattactt cataatttta aaattatgtc atttttaaaa   120
attgcttaat gatggaaagg attattataa gttaaaagta taacatagat aaactaacca   180
caaaacaaat caatataaac taacttactc tcccatctaa ttttttattta aatttctttta  240
cacttctctt ccatttctat ttctacaaca ttatttaaca ttttttattgt attttttctta  300
cttttctaact ctattcattt caaaaatcaa tatatgttta tcaccacctc tctaaaaaaa   360
actttacaat cattggtcca gaaaagttaa atcacgagat ggtcatttta gcattaaaac   420
aacgattctt gtatcactat ttttcagcat gtagtccatt ctcttcaaac aaagacagcg   480
gctatataat cgttgtgtta tattcagtct aaaacaattg ttatggtaaa agtcgtcatt   540
ttacgccttt ttaaaagata taaaatgaca gttatggtta aaagtcatca tgttagatcc   600
tccttaaaga tataaaatga cagttttgga taaaagtgg tcattttata cgctcttgaa   660
agatataaaa cgacggttat ggtaaaagct gccattttaa atgaaatatt tttgttttag   720
ttcattttgt ttaatgctaa tcccatttaa attgacttgt acaattaaaa ctcacccacc   780
cagatacaat ataaactaac ttactctcac agctaagttt tatttaaatt tctttacact   840
tcttttccat ttctattct atgacattaa ctaacattt tctcgtaatt ttttttctta   900
ttttctaact ctatccattt caaatcgata tatgttttatc accaccactt taaaaagaaa   960
atttacaatt tctcgtgcaa aaaagctaaa tcatgaccgt catttagca ttaaaacaac   1020
gattcttgta tcgttgtttt tcagcatgta gtccattctt ttcaagcaaa gacaacagct   1080
atataatcat cgtgttatat tcagtctaaa acaacgtaa tgataaaagt catcattta   1140
ggcctttctg aaatatatag aacgacattc atggtaaaaa atcgtcattt tagatcc     1197

SEQ ID NO: 823        moltype = DNA  length = 69
FEATURE               Location/Qualifiers
misc_feature         1..69
                     note = pat21ss signal peptide
source               1..69
                     mol_type = other DNA
                     organism = synthetic construct
SEQUENCE: 823
atggcaacta ctaaatcttt tttaatttta tttttttatga tattagcaac tactagttca   60
acatgtgct                                                            69

SEQ ID NO: 824        moltype = DNA  length = 66
FEATURE               Location/Qualifiers
misc_feature         1..66
                     note = (SP)11 hydroxyproline-rich glycoprotein tag
source               1..66
                     mol_type = other DNA
                     organism = synthetic construct
SEQUENCE: 824
tcaccatcac catcaccttc acccagtcct agccctagtc ctagcccaag ccatctccc    60
tcgcct                                                               66

SEQ ID NO: 825        moltype = AA  length = 22
FEATURE               Location/Qualifiers
REGION               1..22
                     note = (SP)11 hydroxyproline-rich glycoprotein tag
source               1..22
                     mol_type = protein
                     organism = synthetic construct
SEQUENCE: 825
SPSPSPSPSP SPSPSPSPSP SP                                             22

SEQ ID NO: 826        moltype = DNA  length = 180
FEATURE               Location/Qualifiers
misc_feature         1..180
                     note = CD45 protein coding sequence
source               1..180
                     mol_type = other DNA
                     organism = synthetic construct
SEQUENCE: 826
gcaaacataa ccgtcgacta cctttacaat aaagagacta agttgtttac tgccaagctc   60
aacgtaaacg agaacgtgga gtgcggtaat aataccctgca ctaataatga ggttcacaat  120
cttacagaat gtaagaatgc ctccgtaagc attagccata atagctgcac agctcccgat  180

SEQ ID NO: 827        moltype = AA  length = 60
FEATURE               Location/Qualifiers
REGION               1..60
                     note = CD45 protein
source               1..60
                     mol_type = protein
                     organism = synthetic construct
SEQUENCE: 827
```

ANITVDYLYN KETKLFTAKL NVNENVECGN NTCTNNEVHN LTECKNASVS ISHNSCTAPD  60

```
SEQ ID NO: 828         moltype = AA  length = 7
FEATURE                Location/Qualifiers
REGION                 1..7
                       note = repeat sequence
source                 1..7
                       mol_type = protein
                       organism = synthetic construct
SEQUENCE: 828
PPPPVHL                                                              7

SEQ ID NO: 829         moltype = AA  length = 7
FEATURE                Location/Qualifiers
REGION                 1..7
                       note = repeat sequence
VARIANT                6
                       note = X is S, Y, Q or F
source                 1..7
                       mol_type = protein
                       organism = synthetic construct
SEQUENCE: 829
PPPPVXS                                                              7

SEQ ID NO: 830         moltype = AA  length = 4
FEATURE                Location/Qualifiers
REGION                 1..4
                       note = repeat sequence
source                 1..4
                       mol_type = protein
                       organism = synthetic construct
SEQUENCE: 830
PPPV                                                                 4

SEQ ID NO: 831         moltype = AA  length = 5
FEATURE                Location/Qualifiers
REGION                 1..5
                       note = repeat sequence
VARIANT                5
                       note = X is S or F
source                 1..5
                       mol_type = protein
                       organism = synthetic construct
SEQUENCE: 831
PPVHX                                                                5

SEQ ID NO: 832         moltype = AA  length = 6
FEATURE                Location/Qualifiers
REGION                 1..6
                       note = repeat sequence
source                 1..6
                       mol_type = protein
                       organism = synthetic construct
SEQUENCE: 832
PPPVHS                                                               6

SEQ ID NO: 833         moltype = AA  length = 6
FEATURE                Location/Qualifiers
REGION                 1..6
                       note = repeat sequence
VARIANT                5
                       note = X is Y, H or F
source                 1..6
                       mol_type = protein
                       organism = synthetic construct
SEQUENCE: 833
PPPVXS                                                               6

SEQ ID NO: 834         moltype = AA  length = 6
FEATURE                Location/Qualifiers
REGION                 1..6
                       note = repeat sequence
VARIANT                5
                       note = X is H or D
source                 1..6
                       mol_type = protein
                       organism = synthetic construct
SEQUENCE: 834
PPPVXL                                                               6
```

```
SEQ ID NO: 835          moltype = AA  length = 6
FEATURE                 Location/Qualifiers
REGION                  1..6
                        note = repeat sequence
source                  1..6
                        mol_type = protein
                        organism = synthetic construct
SEQUENCE: 835
PPPVHL                                                                     6

SEQ ID NO: 836          moltype = AA  length = 8
FEATURE                 Location/Qualifiers
REGION                  1..8
                        note = repeat sequence
source                  1..8
                        mol_type = protein
                        organism = synthetic construct
SEQUENCE: 836
PPPPPVYS                                                                   8

SEQ ID NO: 837          moltype = AA  length = 7
FEATURE                 Location/Qualifiers
REGION                  1..7
                        note = repeat sequence
source                  1..7
                        mol_type = protein
                        organism = synthetic construct
SEQUENCE: 837
PPPPVHS                                                                    7

SEQ ID NO: 838          moltype = AA  length = 6
FEATURE                 Location/Qualifiers
REGION                  1..6
                        note = repeat sequence
source                  1..6
                        mol_type = protein
                        organism = synthetic construct
SEQUENCE: 838
PPPVHL                                                                     6

SEQ ID NO: 839          moltype = DNA  length = 252
FEATURE                 Location/Qualifiers
source                  1..252
                        mol_type = genomic DNA
                        organism = Glycine max
SEQUENCE: 839
gcacgcatgg aactgagctt cttcaaaagt gatcagtcat caagttatga tgatgatgag          60
tattcaaaac catgctgtga tctctgcatg tgcacacgct caatgcctcc tcaatgcagc         120
tgtgaagata ttaggctgaa ttcatgccac tcagattgta agagctgtat gtgcacacgc         180
tcacagccag gacagtgtcg ttgtcttgac accaacgact tctgctacaa accttgcaag         240
tccagagatg ac                                                             252

SEQ ID NO: 840          moltype = AA  length = 84
FEATURE                 Location/Qualifiers
source                  1..84
                        mol_type = protein
                        organism = Glycine max
SEQUENCE: 840
ARMELSFFKS DQSSSYDDDE YSKPCCDLCM CTRSMPPQCS CEDIRLNSCH SDCKSCMCTR          60
SQPGQCRCLD TNDFCYKPCK SRDD                                                84

SEQ ID NO: 841          moltype = DNA  length = 282
FEATURE                 Location/Qualifiers
source                  1..282
                        mol_type = genomic DNA
                        organism = Glycine max
SEQUENCE: 841
gccagcttga ggctgagtga gcttggcctg tcatgaaaaa gtgatcatca tcaacactca          60
aatgatgatg actcttcaaa accatgctgt gatcaatgcg catgcacaaa gtcaaaccct         120
cctcaatgcc gctgttcaga tatgaggctg aattcgtgcc attcagcttg caaatcttgt         180
atttgcgcat atcgtatcc  tgcacagtgt ttttgtgttg acataacgga tttctgctat         240
gaaccttgca agcccagtga ggatgacaag gaaaactact aa                            282

SEQ ID NO: 842          moltype = AA  length = 93
FEATURE                 Location/Qualifiers
source                  1..93
                        mol_type = protein
                        organism = Glycine max
```

```
SEQUENCE: 842
ASLRLSELGL LMKSDHHQHS NDDDSSKPCC DQCACTKSNP PQCRCSDMRL NSCHSACKSC    60
ICALSYPAQC FCVDITDFCY EPCKPSEDDK ENY                                93

SEQ ID NO: 843          moltype = DNA  length = 537
FEATURE                 Location/Qualifiers
source                  1..537
                        mol_type = genomic DNA
                        organism = Glycine max
SEQUENCE: 843
cagttcgtgc tcgacactga tgatgatcct cttcaaaacg gtggcacata ctatatgttg    60
ccagttatga gaggaaaggg cggtggaata gaagtagatt caactggaaa agaaatatgc   120
cctctcactg ttgtgcaatc acccaatgag ctcgataagg ggattggact agtctttaca   180
tctccattac atgcccttt tatcgccgaa ggctatcatt tgagcattaa gtttggttca    240
tttgcagtta taacgctgtg tgccggcatg cctactgagt gggctattgt ggagagagag   300
ggtctacaag ctgttaaact tgctgcacgc gatacagtag atggttggtt taatattgag   360
agagtttccc gtgaatacaa tgactataag cttgtgttct gtccacagca agctgaagat   420
aacaaatgcg aggatattgg gattcagatc gacgatgga gaatcaggcg tttagtgctg    480
tctaagaaca aaccattagt ggttcagttt cagaaattta gatcatcaac tgcatga      537

SEQ ID NO: 844          moltype = AA  length = 178
FEATURE                 Location/Qualifiers
source                  1..178
                        mol_type = protein
                        organism = Glycine max
SEQUENCE: 844
QFVLDTDDDP LQNGGTYYML PVMRGKGGGI EVDSTGKEIC PLTVVQSPNE LDKGIGLVFT    60
SPLHALFIAE GYPLSIKFGS FAVITLCAGM PTEWAIVERE GLQAVKLAAR DTVDGWFNIE   120
RVSREYNDYK LVFCPQQAED NKCEDIGIQI DDDGIRRLVL SKNKPLVVQF QKFRSSTA     178

SEQ ID NO: 845          moltype = DNA  length = 540
FEATURE                 Location/Qualifiers
source                  1..540
                        mol_type = genomic DNA
                        organism = Glycine max
SEQUENCE: 845
cagttcgtgc tcgacactga tgatgatcct cttcaaaacg gtggcacata ctatatgttg    60
ccagttatga gaggaaagag cggtggaata gaaggaaatt caactggaaa agaaatatgc   120
cctctcactg ttgtgcaatc acccaataag cacaataagg ggattggact agtctttaaa   180
tctccattac atgcccttt tatcgccgaa cggtatcctt tgagcattaa gtttgattca    240
tttgcagtta taccgctgtg tggcgtcatg cctactaagt gggctattgt ggagagagag   300
ggtctacaag ctgttacact tgctgcacgc gatacagtag atggttggtt taatattgag   360
agagtttccc gtgaatacaa tgactactat aagcttgtgt tctgtccaca ggaagctgaa   420
gataacaaat gcgaggatat tgggattcag atcgacaatg atggaatcag gcgtttagtg   480
ctgtctaaga acaaaccatt agtggttgag tttcagaaaat ttagatcatc aactgcatga  540

SEQ ID NO: 846          moltype = AA  length = 179
FEATURE                 Location/Qualifiers
source                  1..179
                        mol_type = protein
                        organism = Glycine max
SEQUENCE: 846
QFVLDTDDDP LQNGGTYYML PVMRGKSGGI EGNSTGKEIC PLTVVQSPNK HNKGIGLVFK    60
SPLHALFIAE RYPLSIKFDS FAVIPLCGVM PTKWAIVERE GLQAVTLAAR DTVDGWFNIE   120
RVSREYNDYY KLVFCPQEAE DNKCEDIGIQ IDNDGIRRLV LSKNKPLVVE FQKFRSSTA    179

SEQ ID NO: 847          moltype = DNA  length = 576
FEATURE                 Location/Qualifiers
source                  1..576
                        mol_type = genomic DNA
                        organism = Glycine max
SEQUENCE: 847
gatttcgtgc tcgataatga aggtaaccct cttgaaaatg gtggcacata ttatatcttg    60
tcagacataa cagcatttgg tggaataaga gcagcccca gaaatgaa aagatgccct      120
ctcactgtgg tgcaatctcg caatgagctc gacaaaggga ttggaacaat catctcgtcc   180
ccatatcgaa tccgttttat cgccgaaggc catcctttga gccttaagtt cgattcattt   240
gcagttataa tgctgtgtgt tggaattcct accgagtggt ctgttgtgga ggatctacca   300
gaaggacctg ctgttaaaat tggtgagaac aaagatgcaa tggatggttg gtttagacta  360
gagagagttt ctgatgtga attcaataac tataagcttg tgttctgtcc acagcaagct   420
gaggatgaca aatgtgggga tattgggatt agtattgatc atgatgatgg aaccaggcgt   480
ttggtggtgt ctaagaacaa accgttagtg gttcagtttc aaaaacttga taagaatca    540
ctggccaaga aaaatcatgg cctttctcgc agtgag                             576

SEQ ID NO: 848          moltype = AA  length = 192
FEATURE                 Location/Qualifiers
source                  1..192
                        mol_type = protein
                        organism = Glycine max
SEQUENCE: 848
```

```
DFVLDNEGNP LENGGTYYIL SDITAFGGIR AAPTGNERCP LTVVQSRNEL DKGIGTIISS    60
PYRIRFIAEG HPLSLKFDSF AVIMLCVGIP TEWSVVEDLP EGPAVKIGEN KDAMDGWFRL   120
ERVSDDEFNN YKLVFCPQQA EDDKCGDIGI SIDHDDGTRR LVVSKNKPLV VQFQKLDKES   180
LAKKNHGLSR SE                                                      192

SEQ ID NO: 849             moltype = DNA   length = 468
FEATURE                    Location/Qualifiers
source                     1..468
                           mol_type = genomic DNA
                           organism = Glycine max
SEQUENCE: 849
gctcatcttg aatacgttga gaacctcaat gtaaaggaac aactcgtagc aggaaccctc    60
tattacataa ccttggtggc aactgacgct ggcaaaaaga aaatctatga aaccaaaatt   120
tgggttaaag agtgggaaga cttcaagaaa gtggtagaat ttaagttggt cggtgacgat   180
agtccaaatc caggcggaat taccaacgtc ccattcccaa accttcctca gttcaaggac   240
ctcgcacgct tgccgtaca ggactataat aagaaggaaa atgctcacct tgaatttgtt    300
gagaacctta atgttaaaga acaagtagtt gcaggcataa tctactatat caccttggtc   360
gcaacagacg caggtaagaa gaagatttat gagacaaaa tccttgtaaa aggttgggaa    420
aacttcaaag aagtccagga gttcaaattg gtgggagacg caacaaaa                468

SEQ ID NO: 850             moltype = AA    length = 156
FEATURE                    Location/Qualifiers
source                     1..156
                           mol_type = protein
                           organism = Glycine max
SEQUENCE: 850
AHLEYVENLN VKEQLVAGTL YYITLVATDA GKKKIYETKI WVKEWEDFKK VVEFKLVGDD    60
SPNPGGITNV PFPNLPQFKD LARFAVQDYN KKENAHLEFV ENLNVKEQVV AGIIYYITLV   120
ATDAGKKKIY ETKILVKGWE NFKEVQEFKL VGDATK                             156

SEQ ID NO: 851             moltype = DNA   length = 1323
FEATURE                    Location/Qualifiers
source                     1..1323
                           mol_type = genomic DNA
                           organism = Glycine max
SEQUENCE: 851
atggaggcta agttggccac caccataata cttattttct ccgtaatttg gcttatgagg    60
gtgaatggca tagaccctg tgcctctcaa gcggataatt ccgaccctga acgtgattcc   120
atctacagca aatgctcacc gttcaaacca ccaaagtcag actcatcgtg ggacaacaga   180
attataaaca tggccctcaaa agacccactc cgattcaaat acttgtccac cttagtgggc   240
caaaagaccg tgtccacggc cccaatcgct tcgggccaga ccttcaacat cggcaactac   300
gtcgtcaggg tcaaattggg aacccctggt caacttttgt tcatggtcct cgacaccagc   360
accgacgagg ccttcgttcc atgctcgggc tgcacgggct gtccgacac cacttttctcg   420
cccaaagcct ccaccagcta tgggccattg gactgctctg ttcccagtg cggtcaggtc   480
cgcgggcttt cgtgccccgc cacaggtacc ggcgcgtgct ccttcaacca atcctacgcg   540
ggctcatctt tctccgccac cctagtccaa gactcgttaa gattagccac tgatgttatc   600
cccaactact ccttcggctg cgtcaacgcc atcaccggcg cgtcgtccc ggcccaaggg    660
cttttgggcc tgggccgtgg cccgctgtcc ttgctctccc aatccgggtc aaattactcg   720
gcatcttct cttactgtct ccccagcttc aagtcctact acttctctgg gtcgctcaag    780
ctcgggcccg tgggccagcc caagagcatt cgcaccaccc gcttcttcg cagccctcac   840
cgtccttctc tttactacgt gaacttcacc ggaatcgtgt gggacgtgt cctggtaccc   900
tttcccagcg agtatcttgg gtttaacccg aatacaggat ccggaaccat aattgattcc   960
ggcacggtta taacccggtt cgtggagccc gtttacaacg cggtgaggga ggagttcagg   1020
aagcaggtgg gaggcactac attcacgagc attggagcct cgatacgtg ttttgtgaaa    1080
acctacgaaa ctctggcgcc gccaattacg ctgcacttcg aggggttgga cctgaaactg   1140
ccgttggaaa acagcttgat ccacagcagc gcgggttcgc tggcgtgtct tgcaatggca   1200
gcggcacccg acaatgtgaa ctcggtgttg aacgtcatcg ccaactttca gcaacagaac   1260
cttaggattt tgtttgatac cgtcaataat aaggttggca tagcccgtga ggtttgtaac   1320
tag                                                                 1323

SEQ ID NO: 852             moltype = AA    length = 440
FEATURE                    Location/Qualifiers
source                     1..440
                           mol_type = protein
                           organism = Glycine max
SEQUENCE: 852
MEAKLATTII LIFSVIWLMR VNGIDPCASQ ADNSDLNVIP IYSKCSPFKP PKSDSSWDNR    60
IINMASKDPL RFKYLSTLVG QKTVSTAPIA SGQTFNIGNY VVRVKLGTPG QLLFMVLDTS   120
TDEAFVPCSG CTGCSDTTFS PKASTSYGPL DCSVPQCGQV RGLSCPATGT GACSFNQSYA   180
GSSFSATLVQ DSLRLATDVI PNYSFGCVNA ITGASVPAQG LLGLGRGPLS LLSQSGSNYS   240
GIFSYCLPSF KSYYFSGSLK LGPVGQPKSI RTTPLLRSPH RPSLYYVNFT GISVGRVLVP   300
FPSEYLGFNP NTGSGTIIDS GTVITRFVEP VYNAVREEFR KQVGGTTFTS IGAFDTCFVK   360
TYETLAPPIT LHFEGLDLKL PLENSLIHSS AGSLACLAMA AAPDNVNSVL NVIANFQQQN   420
LRILFDTVNN KVGIAREVCN                                              440

SEQ ID NO: 853             moltype = DNA   length = 1143
FEATURE                    Location/Qualifiers
source                     1..1143
                           mol_type = genomic DNA
```

```
                   organism = Glycine max
SEQUENCE: 853
atggaggcaa agcgaggcca tgccctcatg tgcttggcac gtgtttcact cttcctctgc   60
gctctaaccc tatccgctgc tcacggaagc accacggttc aagacatcgc gagaaagttg  120
aaactcgggg acaacgagct tctgcgcacg gagaagaagt tcaaggtttt catggagaat  180
tacgggagga gctactccac agaggaggag tatttgcgcc gtttggggat tttcgcccag  240
aacatggtca gagcggcgga gcatcaggcg ctggacccca ccgccgtcca cggcgtcacg  300
cagttctccg atctcaccga ggacgagttt gagaagctct acactggcgt caatggcggc  360
ttcccgtcat cgaataatgc cgccggcggt attgcgccgc cgttggaggt ggacgggctg  420
ccggagaatt ttgattggag agagaaagga gctgtcaccg aagttaagtt acagggtaga  480
tgtggatcat gctgggcttt cagcaccaca ggatctatag aaggagccaa ttttcttgcc  540
accgaaaagc tcgtcagtct tagtgaacaa cagctccttg actgtgacaa caagtgtgac  600
ataacagaaa agacttcatg tgacaatggg tgtaatggag gtcttatgac aaatgcctac  660
aattatttgc tcgagtctgg tgggttggaa gaggagtctt catatcccta cactggggag  720
agaggtgaat gcaagtttga tccagagaaa atagcagtta gatcacaaa tttcaccaat   780
atccctgctg atgagaacca aattgccgca tatttagtaa aaaatggtcc acttgctatg  840
ggcgtgaatg caattttcat gcaaacatac attggtggtg tctcatgccc tctcatatgt  900
agcaagaaaa ggctgaacca tggtcgtgta cttgtgggat atggtgcaaa aggcttctca  960
attcttaggc ttggcaacaa accatactgg atcatcaaga attcgtgggg ggagaaatgg 1020
ggagaagatg gctattacaa gctctgcaga gggcatggca tgtgtggaat aaacactatg 1080
gtttctgctg caatggtgcc tcaaccacaa acaacaccta aagaatta tgcttcttat 1140
tag                                                                1143

SEQ ID NO: 854      moltype = AA  length = 380
FEATURE             Location/Qualifiers
source              1..380
                    mol_type = protein
                    organism = Glycine max
SEQUENCE: 854
MEAKRGHALM CLARVSLFLC ALTLSAAHGS TTVQDIARKL KLGDNELLRT EKKFKVFMEN   60
YGRSYSTEEE YLRRLGIFAQ NMVRAAEHQA LDPTAVHGVT QFSDLTEDEF EKLYTGVNGG  120
FPSSNNAAGG IAPPLEVDGL PENFDWREKG AVTEVKLQGR CGSCWAFSTT GSIEGANFLA  180
TGKLVSLSEQ QLLDCDNKCD ITEKTSCDNG CNGGLMTNAY NYLLESGGLE EESSYPYTGE  240
RGECKFDPEK IAVKITNFTN IPADENQIAA YLVKNGPLAM GVNAIFMQTY IGGVSCPLIC  300
SKKRLNHGVL LVGYGAKGFS ILRLGNKPYW IIKNSWGEKW GEDGYYKLCR GHGMCGINTM  360
VSAAMVPQPQ TTPTKNYASY                                              380

SEQ ID NO: 855      moltype = DNA  length = 1140
FEATURE             Location/Qualifiers
source              1..1140
                    mol_type = genomic DNA
                    organism = Glycine max
SEQUENCE: 855
atgggtttcc ttgtgttgct tctttctcc ctcttaggtc tctcttctag ttccagcata    60
tcaactcatc gttccatatt ggaccttgac ctaaccaagt ttaccacaca gaaacaggtg  120
tcttcactgt tccaactatg gaagagtgag catggacgtg tctaccataa ccacgaagaa  180
gaggcaaaga gacttgagat tttcaagaat aacttgaact atcaggga catgaatgca   240
aacagaaaat caccccattc tcatcgttta ggattgaaca agtttgctga catcactcct  300
caagagttca gcaaaaagta cttgcaagct cccaaggatg tgtcgcagca aatcaaaatg  360
gccaacaaga aaatgaagaa ggaacaatat tcttgtgacc atccacctgc atcatgggat  420
tggagggaaa aaggtgtcat cacccaagta aagtaccagg ggggctgtgg aagcggttgg  480
gcgttttctg ccacgggagc catagaagca gcacatgcaa tagcaacagg agaccttgtt  540
agcctttctg aacaagaact cgtagactgt gtggaagaaa gcgaaggttg ttacaatgga  600
tggcactatc aatcgttcga atgggttta gaacatggtg ggattgccac tgatgatgat  660
tatccttaca gagctaaaga gggtagatgc aaagccataa agatacaaga caaggttaca  720
attgacggat atgaaactct aataatgtca gatgagagta cagaatcaga gacagagcaa  780
gcgttcttaa gcgccatcct tgagcaacca attagtgtct ccattgatgc aaaagatttt  840
catttataca ccgggggaat ttatgatgga gaaaactgta caagtccgta tgggattaat  900
cactttgttt tacttgtggg ttatggttca gcggatggtg tagattcgaa gatagcgaaa  960
aattcatggg gagaagattg gggagaagat ggttacattt ggatccaaag aaacacgggt 1020
aatttattag gagtgtgtgg gatgaattat ttcgcttcat acccaaccaa agaggaatca 1080
gaaacactgg tgtctgctcg cgttaaaggt catcgaagag ttgatcactc tcctctttga 1140

SEQ ID NO: 856      moltype = AA  length = 379
FEATURE             Location/Qualifiers
source              1..379
                    mol_type = protein
                    organism = Glycine max
SEQUENCE: 856
MGFLVLLLFS LLGLSSSSSI STHRSILDLD LTKFTTQKQV SSLFQLWKSE HGRVYHNHEE   60
EAKRLEIFKN NLNYIRDMNA NRKSPHSHRL GLNKFADITP QEFSKKYLQA PKDVSQQIKM  120
ANKKMKKEQY SCDHPPASWD WRKKGVITQV KYQGGCGSGW AFSATGAIEA AHAIATGDLV  180
SLSEQELVDC VEESEGCYNG WHYQSFEWVL EHGGIATDDD YPYRAKEGRC KANKIQDKVT  240
IDGYETLIMS DESTESETEQ AFLSAILEQP ISVSIDAKDF HLYTGGIYDG ENCTSPYGIN  300
HFVLLVGYGS ADGVDYWIAK NSWGEDWGED GYIWIQRNTG NLLGVCGMNY FASYPTKEES  360
ETLVSARVKG HRRVDHSPL                                               379

SEQ ID NO: 857      moltype = DNA  length = 1026
FEATURE             Location/Qualifiers
```

```
source                  1..1026
                        mol_type = genomic DNA
                        organism = Glycine max
SEQUENCE: 857
atgagttcat ttagccaaaa tccctatgtt ttagttctgt tcctcgttct cactgtgtgg    60
atatcccgtg taatgtctcg cgggctcatt acatctgaga gacatgagaa atggatggca   120
caatatggta aggtttacaa ggatgctgca gagaaggaga aacgtttcca agtattcaaa   180
aacaatgtgc agttcattga gtcattcaat gctgctgggg acaaaccttt caaccttagc   240
attaaccaat ttgcggacct tcatgatgaa gaatttaagc ttttactaaa caatgttcag   300
aaaaaggcaa gtagggtgga gacagcaaca gaaacatcgt ttaggtatga gaatgtaact   360
aagattcctt ctaccatgga ctggaggaaa agaggtgctg tcactccaat caaggaccaa   420
ggctacacat gtggaagttg ttgggcattt gcaactgtgg ctactgtcga gagtctccat   480
caaataacta caggtgaatt ggtgtcccta tcagagcaag aactagtaga ttgtgttaga   540
ggtgacagtg aaggttgccg tggtggttat gtggaaaatg cctttgaatt tattgctaat   600
aaaggtggaa taacaagtga agcatactat ccttacaaag gaaagatag aagttgtaag   660
gttaagaagg agactcatgg tgtggcacgg attatagggt atgagagtgt tccttctaat   720
agtgaaaagg cactcctaaa agctgtggca atcaaccag tttcagttta tattgatgca   780
ggagcaattg ctttcaaatt ttactcaagt gggattttg aagcaagaaa ttgtggaact   840
catctagacc atgctgttgc agttgttggt tatggtaaac ttcgtgatgg tacaaagtat   900
tggctagtaa aaaattcatg gagcactgca tggggtgaga agggtacat gaggatcaag   960
cgagacatac gtgccaagaa aggcttatgt ggaattgctt caaatgcctc ttatccaatc  1020
gcttaa                                                             1026

SEQ ID NO: 858           moltype = AA    length = 341
FEATURE                  Location/Qualifiers
source                   1..341
                         mol_type = protein
                         organism = Glycine max
SEQUENCE: 858
MSSFSQNPYV LVLFLVLTVW ISRVMSRGLI TSERHEKWMA QYGKVYKDAA EKEKRFQVFK    60
NNVQFIESFN AAGDKPFNLS INQFADLHDE EFKALLNNVQ KKASRVETAT ETSFRYENVT   120
KIPSTMDWRK RGAVTPIKDQ GYTCGSCWAF ATVAVESLH QITTGELVSL SEQELVDCVR   180
GDSEGCRGGY VENAFEFIAN KGGITSEAYY PYKGKDRSCK VKKETHGVAR IIGYESVPSN   240
SEKALLKAVA NQPVSVYIDA GAIAFKFYSS GIFEARNCGT HLDHAVAVVG YGKLRDGTKY   300
WLVKNSWSTA WGEKGYMRIK RDIRAKKGLC GIASNASYPI A                      341

SEQ ID NO: 859           moltype = DNA   length = 2283
FEATURE                  Location/Qualifiers
source                   1..2283
                         mol_type = genomic DNA
                         organism = Glycine max
SEQUENCE: 859
atgggtccgt ttcgtaaacc cttccttgca tttctctcgg ttgttctatt tctgggtctc    60
tatgaggcag cagcagaaca gactcagact cacaagagta cttacattgt acacgtggcg   120
aaatcggaga tgcccgagag cttcgagcac acgctgtgt ggtatgagtc gtcactgaag   180
accgtgtctg actcggcgga gatgattac acctacgaca acgccatcca cggctacgcg   240
acgagattaa ccgctgagga agcgcgtttg ctccagcgca aaacggggat tctggctgtt   300
ttgccggaga cgaggtacga gcttttcacg acgcgaacgc ctttgttct cggacttgac   360
aagagcgccg acttgttccc cgagtcgagt tcgggaagtg acgtcatcgt cggagtcctc   420
gacaccggcg tctggccgga gagcaagagc ttcgacgaca ccggactcgg acccgttccg   480
agcacggtgga aaggcgcgtg cgagacggga acgaatttca ccgcgtcgaa ctgcaacgag   540
aagttgatcg gagcaagatt ctttgctaaa ggtgtagaag ccatgcttgg tccaattaac   600
gaaaccgagg agtccagatc cgcgcgcgag gacgacggcc acggcaccca cacgtccagc   660
accgccgctg atcagttgt ttccggcgcg agcctcctcg gttacgcctc cggaacagcg   720
cgtgactggc ccacgcgcgc tagagttgct gcatacaagg tatgctggaa aggagggtgt   780
ttcagctctg acattcttgc cgcaattgaa aaggcaatat ggacaacgt gaatgttctt   840
tctttatctc tcggtggtgg catttctgat tattacagag acagtgtcgc tattggagct   900
ttttcagcga tggagaaagg gattttggtt tcatgctccg ctgggaactc gggtccgggt   960
ccctacagtc tctccaatgt ggctccatgg atcactaccg taggcgctgg tacactggat  1020
cgtgacttcc ccgcatacgt ggcgctcgga aatggactca acttctccgg cgtttcgctt  1080
taccgcggta acgctttgcc ggattcttct ttgcctttgg tttatgcagg aatgtcgagt  1140
aatggtgcta tgaatgggaa cttgtgtatc acgggaacgt tgtctcctga aaagttgct  1200
gggaagatcg tgttgtgtga ccgtgggttg accgctaggg ttcagaaagg ctcggtggtg  1260
aaatccgccg gagcgttggg gatgtgctg tccaacaccg cggtggagct acaggagctc  1320
gtggcggatg ctcattttat accggccacc gcagttgggc agaaagccgg tgacgctatt  1380
aagaagtatt tggtttccga tgcgaaaccg acggtgaaga tttttttga gggaaccaag  1440
gtggggatc agccatcgcc ggtggttgct gcgtttagct caagaggtcc caactcgatc  1500
acgccacaga tcctgaagcc tcatcatc gcgcaggtg tcaacatcct agcggggtgg  1560
tctaaagccg tggggcccac cgggttgccc gttgataaa ggcgcgtgga tttcaacatc  1620
atctctggca cctccatgtc gtgccctcac gtgagcggct tagccgcgct gatcaaatcg  1680
gctcaccctg attggagccc agccgcgtg agatcggct tgatgacaac ggcttacaca  1740
gtttacaaaa ctggtgagaa gttgcaagac agcgcaacgg aaaaccatc acgccgttc  1800
gatcacggtt cgggacacgt ggacccagtc gctgccctca atccaggact ggtctacgat  1860
ctaagctggg atgattactt aggttttctc tgccgcgttaa actactcagg tggggaaatc  1920
agcactttag ccaagagaaa attccagtgc gacgcgggca agcagtacag tgtgaccgac  1980
ctcaactacc cttcgtttgc ggtgttgttt gaatcatcag ggagcgtggt taagcacacg  2040
aggactctca ctaacgtggg gcccgcggga acttacaaag cttccgtgac gtcagacact  2100
gcgtccgtta aaatctcggt agaaccgcaa gtgttgagtt caaggagaa cgagaagaaa  2160
acgttcaccg tcacgttttc gtcatcgggt tcgccacagc atacagaaaa cgcttttgga  2220
```

-continued

```
agggtagaat ggtccgatgg gaagcacctg gttggatccc caatttcggt taattggggt  2280
tga                                                                2283

SEQ ID NO: 860        moltype = AA  length = 760
FEATURE               Location/Qualifiers
source                1..760
                      mol_type = protein
                      organism = Glycine max
SEQUENCE: 860
MGPFRKPFLA FLSVVLFLGL YEAAAEQTQT HKSTYIVHVA KSEMPESFEH HAVWYESSLK   60
TVSDSAEMIY TYDNAIHGYA TRLTAEEARL LQRQTGILAV LPETRYELFT TRTPLFLGLD  120
KSADLFPESS SGSDVIVGVL DTGVWPESKS FDDTGLGPVP STWKGACETG TNFTASNCNR  180
KLIGARFFAK GVEAMLGPIN ETEESRSARD DDGHGTHTSS TAAGSVVSGA SLLGYASGTA  240
RGMATRARVA AYKVCWKGGC FSSDILAAIE RAILDNVNVL SLSLGGGISD YYRDSVAIGA  300
FSAMEKGILV SCSAGNSGPG PYSLSNVAPW ITTVGAGTLD RDFPAYVALG NGLNFSGVSL  360
YRGNALPDSS LPLVYAGNVS NGAMNGNLCI TGTLSPEKVA GKIVLCDRGL TARVQKGSVV  420
KSAGALGMVL SNTAANGEEL VADAHLLPAT AVGQKAGDAI KKYLVSDAKP TVKIFFEGTK  480
VGIQPSPVVA AFSSRGPNSI TPQILKPDLI APGVNILAGW SKAVGPTGLP VDNRRVDFNI  540
ISGTSMSCPH VSGLAALIKS AHPDWSPAAV RSALMTTAYT VYKTGEKLQD SATGKPSTPF  600
DHGSGHVDPV AALNPGLVYD LTVDDYLGFL CALNYSAAEI STLAKRKFQC DAGKQYSVTD  660
LNYPSFAVLF ESSGSVVKHT RTLTNVGPAG TYKASVTSDT ASVKISVEPQ VLSFKENEKK  720
TPTVTFSSSG SPQHTENAFG RVEWSDGKHL VGSPISVNWG                        760
```